(12) United States Patent
Butler et al.

(10) Patent No.: US 11,572,374 B2
(45) Date of Patent: Feb. 7, 2023

(54) N-CYANO-7-AZANORBORNANE DERIVATIVES AND USES THEREOF

(71) Applicants: Amgen Inc., Thousand Oaks, CA (US); Carmot Therapeutics, Inc., Berkeley, CA (US)

(72) Inventors: John R. Butler, Colton, CA (US); Daniel Erlanson, San Francisco, CA (US); Russell Graceffa, Hampton, CA (US); Jeffrey Iwig, Albany, CA (US); Joon Won Jeong, Belmont, CA (US); Ryan D. White, Somerville, MA (US); Yongwei Wu, Belmont, CA (US); Shuyan Yi, Malden, MA (US); Xiao Mei Zheng, Dover, MA (US); Jesse M. McFarland, Berkeley, CA (US); Abhisek Banerjee, Karnataka (IN)

(73) Assignee: AMGEN INC., Thousand Oaks, CA (US)

( * ) Notice: Subject to any disclaimer, the term of this patent is extended or adjusted under 35 U.S.C. 154(b) by 3 days.

(21) Appl. No.: 17/266,466

(22) PCT Filed: Aug. 13, 2019

(86) PCT No.: PCT/US2019/046319
§ 371 (c)(1),
(2) Date: Feb. 5, 2021

(87) PCT Pub. No.: WO2020/036940
PCT Pub. Date: Feb. 20, 2020

(65) Prior Publication Data
US 2022/0363694 A1    Nov. 17, 2022

Related U.S. Application Data

(60) Provisional application No. 62/880,577, filed on Jul. 30, 2019, provisional application No. 62/718,471, filed on Aug. 14, 2018.

(51) Int. Cl.
C07D 519/00    (2006.01)
C07D 487/18    (2006.01)

(52) U.S. Cl.
CPC ......... *C07D 519/00* (2013.01); *C07D 487/18* (2013.01)

(58) Field of Classification Search
None
See application file for complete search history.

(56) References Cited

FOREIGN PATENT DOCUMENTS

| WO | WO 03/022856 A1 | 3/2003 | |
|---|---|---|---|
| WO | WO 2012/024615 A1 | 2/2012 | |
| WO | WO 2014/041111 A1 | 3/2014 | |
| WO | WO 2016/046530 A1 | 3/2016 | |
| WO | WO 2016/156816 | * 10/2016 | ........... C07D 403/12 |
| WO | WO 2016/156816 A1 | 10/2016 | |
| WO | WO 2017/009650 A1 | 1/2017 | |
| WO | WO 2017/093718 A1 | 6/2017 | |
| WO | WO 2017/103614 A1 | 6/2017 | |
| WO | WO 2017/109488 A1 | 6/2017 | |
| WO | WO 2017/141036 A1 | 8/2017 | |
| WO | WO 2017/149313 A1 | 9/2017 | |
| WO | WO 2017/158381 A1 | 9/2017 | |
| WO | WO 2017/158388 A1 | 9/2017 | |
| WO | WO 2017/163078 A1 | 9/2017 | |
| WO | WO 2018/060689 A1 | 4/2018 | |
| WO | WO 2018/060691 A1 | 4/2018 | |
| WO | WO 2018/060742 A1 | 4/2018 | |

OTHER PUBLICATIONS

CAS RN 64471-77-8 (entered into STN Nov. 16, 1984) (Year: 1984).*
CAS RN 36769-21-8 (entered into STN on Nov. 16, 1984) (Year: 1984).*

* cited by examiner

*Primary Examiner* — Craig D Ricci
(74) *Attorney, Agent, or Firm* — Bernard P. Friedrichsen

(57) ABSTRACT

The present invention provides a compound of formula (I) or a pharmaceutically acceptable salt thereof, pharmaceutical compositions comprising a compound of the invention, a method for manufacturing compounds of the invention and therapeutic uses thereof.

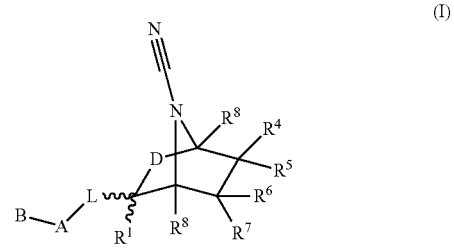

(I)

6 Claims, No Drawings

N-CYANO-7-AZANORBORNANE DERIVATIVES AND USES THEREOF

CROSS-REFERENCE TO RELATED APPLICATIONS

This application is a National Stage application under 35 U.S.C. § 371 of International Application No. PCT/US2019/046319, having an international filing date of Aug. 13, 2019, which claims the benefit of U.S. Provisional Patent Application No. 62/880.577, filed Jul. 30, 2019, and U.S. Provisional Patent Application No. 62/718,471, filed Aug. 14, 2018, and all of which are incorporated herein by reference in their entirety for all purposes.

The present invention relates generally to a class of substituted N-cyano-7-azanorbornanes with activity as inhibitors of deubiquitinating enzymes, in particular, ubiquitin C-terminal hydrolase 30 or ubiquitin specific peptidase 30 (USP30), uses thereof, processes for the preparation thereof and compositions comprising said inhibitors. These inhibitors have utility in a variety of therapeutic areas including cancer, conditions involving mitochondrial dysfunction and neurodegenerative diseases.

BACKGROUND OF THE INVENTION

Ubiquitin is a small protein consisting of 76 amino acids that is important for the regulation of protein function in a cell. Ubiquitylation and deubiquitylation are enzymatically mediated processes by which ubiquitin is covalently bound or cleaved from a target protein by deubiquitylating enzymes (DUBs), of which there are approximately 95 DUBs in human cells, divided into sub-families based on sequence homology. The USP family are characterized by their common Cys and His boxes which contain Cys and His residues critical for their DUB activities. The ubiquitylation and deubiquitylation processes have been implicated in the regulation of many cellular functions including cell cycle progression, apoptosis, modification of cell surface receptors, regulation of DNA transcription and DNA repair. Thus, the ubiquitin system has been implicated in the pathogenesis of numerous disease states including inflammation, viral infection, metabolic dysfunction, CNS disorders and oncogenesis.

Ubiquitin is a master regulator of mitochondrial dynamics. Mitochondria are dynamic organelles whose biogenesis, fusion and fission events are regulated by the post-translational regulation via ubiquitylation of many key factors such as mitofusins. While ubiquitin ligases such as parkin are known to ubiquitylate a number of mitochondrial proteins, until recently deubiquitylating enzymes remained elusive. USP30 is a 517 amino acid protein which is found on the mitochondrial outer membrane (Nakamura et al., Mol Biol (2008)$_{19}$:1903-11). It is the sole deubiquitylating enzyme bearing a mitochondrial localization signal and has been shown to debuiquitylate a number of mitochondrial proteins. It has been demonstrated that USP30 opposes parkin-mediated mitophagy and that reduction of USP30 activity can rescue parkin-mediated defects in mitophagy.

Mitochondrial dysfunction may be defined as diminished mitochondrial content (mitophagy or mitochondrial biogenesis), as a decrease in mitochondrial activity and oxidative phosphorylation, but also as modulation of reactive oxygen species (ROS) generation. Hence a role for mitochondrial dysfunction has been ascribed to a very large number of aging processes and pathologies including but not limited to neurodegenerative diseases, cancer, diabetes, metabolic disorders, cardiovascular disease, psychiatric disease and osteoarthritis.

Mitochondrial dysfunction has been implicated in the etiology of Parkinson's disease. Human genetic evidence for mitochondrial dysfunction has come from studies of familial forms of Parkinson's disease, which have identified the autosomal recessive genes PARK2 and PINK1 encoding Parkin ubiquitin ligase and phosphatase and tensin homolog-induced putative kinase 1 (PINK1) protein kinase (Hauser, D. N., and Hastings, T. G. (2013). Neurobiol Dis 51, 35-42). These genes have been linked to regulation of mitochondrial quality control by a process called mitophagy (Misgeld, T., and Schwarz, T. L. (2017) Neuron 96, 651-66; Pickrell and Youle, (2015) Neuron 85, 257-273; Trinh and Farrer, (2013) Nat Rev Neurol 9, 445-454). In healthy mitochondria PINK1 is imported and degraded by mitochondrial proteases. However, on mitochondrial damage, PINK1 accumulates on the surface of the outer mitochondrial membrane, where it recruits Parkin. Relocated Parkin subsequently ubiquitylates several mitochondrial proteins, creating a signal for the removal of the damaged mitochondrion by mitophagy. Parkinson's disease-associated mutations in PINK1 or PARK2 impair recruitment of parkin, mitochondrial ubiquitination and mitophagy (Archer, S. L. (2013). N Engl J Med 369, 2236-2251).

Enhancing mitophagy via the PINK1-Parkin pathway is proposed to be a therapeutic target for disease modification in Parkinson's disease. An additional role for the PINK1-Parkin pathway in suppressing mitochondrial antigen presentation and T-cell mediated immune responses has recently been discovered and may also play a role in Parkinson's disease pathology (Matheoud et al., (2016) Cell 166, 314-327).

From a library of 100 deubiquitinating enzymes (DUBs), Genentech identified USP30 as one of two DUBS significantly preventing mitochondrial loss after administration of the protonophore carbonyl cyanide 3-chlorophenylhydrazone (CCCP) to Parkin overexpressing HEK293 cells (Bingol et al., (2014) Nature 510, 370-375). USP30 is the only mitochondria-anchored DUB and was further validated as counter player in Parkin-mediated mitophagy in *drosophila* (Bingol et al., 2014). USP30 hinders the build-up of ubiquitin chains on mitochondrial proteins, thereby preventing inappropriate mitophagy in healthy conditions (Cunningham et al., (2015) Nat Cell Biol 17, 160-169). When mitochondria are damaged, Parkin is recruited to the membrane and highly activated, overwhelming USP30 and shifting the equilibrium to a buildup of ubiquitin chains that activate mitophagic pathways. In the case of pathogenic PARK2 mutations or otherwise compromised Parkin activity, the ligase is unable to overcome USP30 mediated deubiquitination and thus cannot properly activate mitophagy. Therefore, inhibition of USP30 could be a therapeutic treatment for Parkinson's patients that have reduced function of the PINK1-Parkin mitophagy pathway.

A series of cyano-substituted heterocycles are disclosed as deubiquitinating enzyme inhibitors in WO2016/046530, WO2016/156816, WO2017/009650, WO2017/093718, WO2017/103614 and WO2018/060742. It remains desirable to provide additional deubiquitinating enzyme inhibitors which provide selectivity for USP30 over other cysteine proteases such as other DUBs and/or Cathepsins.

Thus, new approaches are needed to modulate USP30 activity in the prevention and/or treatment of mitochondrial dysfunction and neurodegenerative diseases. There remains a need for agents that exploit different mechanisms of action and may have better outcomes in terms of relief of symptoms, safety, and patient mortality, both short-term and long-term.

SUMMARY OF THE INVENTION

The present invention provides compounds which modulate USP30 proteins, and more specifically inhibit USP30. The present invention provides, in one aspect, substituted N-cyano-7-azanorbornane compounds which inhibit USP30 activity. Certain compounds provided herein provide selective inhibition of USP30 activity compared to inhibition of Cathepsin K or S and/or other DUB enzymes. Certain compounds provided by the specification at least 10-fold greater USP30 inhibition compared to Cathepsin K or S or other DUB enzymes as measured by IC50. In certain aspects, the compounds of the invention are at least 20-fold or 50-fold selective inhibitors of USP30 compared to Cathepsin K or S or other DUB enzymes. Inhibition of USP30 activity may be particularly desirable in the treatment or prevention of a variety of diseases including mitochondrial dysfunction and neurodegenerative diseases.

The invention provides, in one aspect, substituted N-cyano-7-azanorbornane compounds which modulate USP30 enzyme activity. Preferably, the substituted N-cyano-7-azanorbornane compounds of the invention are USP30 inhibitors.

The substituted benzimidazole compounds of the invention are compounds and salts according to Formula (I):

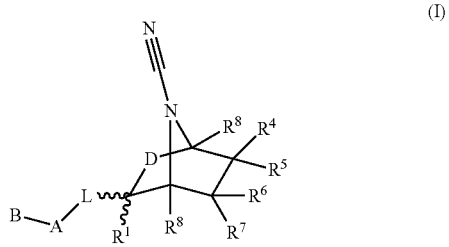

(I)

Also provided is a pharmaceutical composition comprising a pharmaceutically acceptable excipient, carrier or adjuvant and at least one compound of Formula (I) or subformulae thereof. Pharmaceutical compositions provided by the invention are suitable for use in the treatment of disease modulated by USP30 activity. In certain aspects the pharmaceutical compositions of the invention are suitable for use in the treatment of diseases associated with mitochondrial dysregulation, e.g., treatment of a disease or disorder mediated by USP30 is selected from the group consisting of a CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl-CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength.

Also provided is a packaged pharmaceutical composition, comprising a pharmaceutical composition comprising a pharmaceutically acceptable excipient, carrier or adjuvant and at least one compound of formula (I) or subformulae thereof, and instructions for using the composition to treat a patient suffering from a disease mediated by USP30 activity. In certain instances, the patient is suffering from mitochondrial dysregulation, e.g., treatment of a disease or disorder mediated by USP30 is selected from the group consisting of a CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl-CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength.

Also provided is a method of treating or preventing disease in a mammal which method comprises administering to a mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof.

Also provided is a method for modulating USP30 activity in a mammal, which method comprises administering to the mammal in need thereof a therapeutically effective amount of at least one compound of formula (I) or subformulae thereof or a pharmaceutical composition comprising a pharmaceutically acceptable excipient, carrier or adjuvant and at least one compound of formula (I) or subformulae thereof. Another aspect of the invention relates to a method of treating a mitochondrial dysregulation mediated disease or disorder, the method comprising administering a USP30 inhibitor of the invention to a patient in need of therapy. In certain embodiments, the mitochondrial dysregulations mediated disease or disorder is selected from CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl-CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastrointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength.

Also provided is the use, in the manufacture of a medicament for treating or preventing disease mediated by USP30 activity, of at least one compound of formula I or subformulae thereof.

Also provided are methods of preparing compounds formula I or subformulae thereof.

Other aspects and embodiments will be apparent to those skilled in the art form the following detailed description.

DETAILED DESCRIPTION OF THE INVENTION

The invention related generally to compounds of Formula I and salts and tautomers thereof which modulate USP30 protein activity and more particularly inhibit USP30 protein activity. In particular, the invention relates to compounds which selectively inhibit USP30 protein activity. Certain compounds provided herein selectively inhibit USP30 in comparison to activity against other cysteine proteases such as DUB proteins (including USP45) and/or Cathepsin K or S. Certain compounds provided herein offer at least 10-fold selectivity for USP30 inhibition compared to other cysteine proteases. Other compounds provided herein offer at least 20-fold, 50-fold or 100-fold selectivity for USP30 inhibition compared to other cysteine proteases. While not wishing to be bound by theory, it is believed that selective inhibition of USP30 activity may be particularly desirable for the treatment of diseases or disorders associated with mitochondrial dysfunction.

In a first embodiment, the disclosure provides a compound or salt thereof, the compound according to the Formula (I):

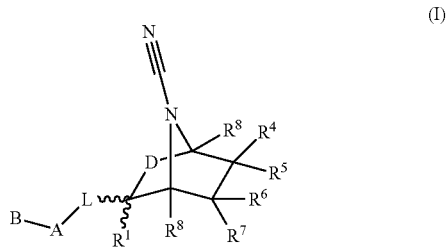

Wherein
D is $(CR^1R^2)_r$;
r is 1 or 2;
Each of $R^1$, $R^2$, $R^3$, $R^4$, $R^5$, $R^6$ and $R^7$ is independently selected at each occurrence from hydrogen, halogen, $C_1$-$C_4$alkyl, $C_1$-$C_4$alkoxy or $C_3$-$C_5$cycloalkyl; or
$R^4$ and $R^6$ taken in combination form a fused three to six-member cycloalkyl ring; or
$R^4$ and $R^5$ taken in combination form a spirocyclic three to six-member cycloalkyl ring;
$R^6$ and $R^7$ taken in combination form a spirocyclic three to six-member cycloalkyl ring;
$R^8$ is independently selected from hydrogen or $C_1$-$C_4$alkyl;
L is a bond or a divalent linker selected from —C(O)—, —C(O)N($R^B$)—, —N($R^B$)C(O)—, —N($R^B$)C(O)N($R^B$)—, —N($R^B$)S(O)$_p$—, —S(O)$_p$N($R^B$)—, —[C($R^A$)$_2$]$_q$C(O)N($R^B$)—, —C(O)N($R^B$)[C($R^A$)$_2$]$_q$—, —N($R^B$)C(O)N($R^B$)[C($R^A$)$_2$]$_q$—, —[C($R^A$)$_2$]$_q$ N($R^B$)C(O)N($R^B$)—, —C($R^A$)$_2$N($R^C$)C($R^A$)$_2$C(O)N($R^B$)—, —N($R^C$)C($R^A$)$_2$C(O)N($R^B$)—, —C(O)N($R^C$)C($R^A$)$_2$C(O)N($R^B$)—, —N($R^C$)C(O)C(O)N($R^B$)—, —OC($R^A$)$_2$C(O)N($R^B$)— or —SC($R^A$)$_2$C(O)N($R^B$)—, wherein L is attached to the azanorbornane by the right most atom;
p is selected at each occurrence from 0, 1 or 2;
q is 1, 2 or 3;
$R^A$ is independently, at each occurrence, hydrogen, $C_1$-$C_4$alkyl, halo$C_1$-$C_4$alkyl and halo$C_1$-$C_4$alkoxy, or $C(R^A)_2$, taken in combination forms —C(O)— or 1,1-cyclopropandiyl;
$R^B$ is hydrogen or $C_1$-$C_4$alkyl;
$R^C$ is hydrogen, $C_1$-$C_4$alkyl or —C($R^A$)$_2$-A-B;
A is a divalent moiety selected from $C_2$-$C_6$alkenylene, phenylene, naphthylene, 5 to 13 member heteroarylene comprising one ring N, O or S atom and 0 or 1 additional ring nitrogen atom, or saturated or partially unsaturated 4 to 13 member monocyclic, bicyclic or tricyclic carbocycle or heterocycle comprising one ring N, O or S atom and 0, 1 or 2 additional ring nitrogen atoms S, each of which is optionally substituted with 0 to 4 substituents selected from halogen, hydroxy, oxo, amino, $C_1$-$C_6$alkyl, $C_2$-$C_6$alkenyl, $C_2$-$C_6$alkynyl, $C_1$-$C_6$alkoxy, $C_3$-$C_7$cycloalkyl, $C_3$-$C_7$cycloalkoxy, $C_3$-$C_7$cycloalkyl$C_1$-$C_4$alkyl, $C_3$-$C_7$cycloalkyl$C_1$-$C_4$alkoxy, halo$C_1$-$C_6$alkyl, halo$C_1$-$C_6$alkoxy;
B is hydrogen, halogen, hydroxy, amino, $C_1$-$C_6$alkyl, halo$C_1$-$C_6$alkyl, hydroxy$C_1$-$C_6$alkyl, cyano$C_1$-$C_6$alkyl, $C_2$-$C_6$alkenyl, $C_2$-$C_6$alkynyl, $C_1$-$C_6$alkoxy, halo$C_1$-

$C_6$alkoxy, $C_3$-$C_7$cycloalkyl, halo $C_3$-$C_7$cycloalkyl, cyano$C_3$-$C_7$cycloalkyl, $C_3$-$C_7$cycloalkyl$C_1$-$C_6$alkyl, cyano$C_3$-$C_7$cycloalkyl$C_1$-$C_6$alkyl, C(O)$C_1$-$C_6$alkyl, C(O)$C_3$-$C_7$cycloalkyl, C(O)$C_1$-$C_6$alkyl, C(O)$C_3$-$C_7$cycloalkyl, $NR^9R^{10}$, $OR^{11}$, C(O)$NR^9R^{10}$, $N(R^{10})$C(O)$R^{12}$, phenyl, aralkyl, heteroaralkyl, 5, 6, 9 or 10 member heteroaryl or 4 to 8 member monocyclic or bicyclic heterocycle, wherein each heteroaryl or heterocycle has one ring N, O or S atom and 0, 1 or 2 additional ring nitrogen atoms, which phenyl, aralkyl, heteroaralkyl, heteroaryl or heterocycle is optionally substituted with 0 to 4 groups independently selected from the group consisting of halogen, hydroxy, amino, mono- and di-$C_1$-$C_6$alkylamino, cyano, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl, phenyl, 5 or 6 member heteroaryl having one ring N, O or S atom and 0, 1 or 2 additional ring nitrogen atoms, —C(O)$NR^9R^{10}$, C(O)$R^9$, $CO_2R^9$, and S(O)$_nR^9$, and where each heterocycle is optionally substituted with oxo;

$R^9$ is hydrogen, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl, aralkyl which aralkyl is substituted with 1 to 4 substituents independently selected from halogen, $C_1$-$C_4$alkyl, $C_3$-$C_6$cycloalkyl or 1,1-cyclopropandiyl;

$R^{10}$ is hydrogen or $C_1$-$C_6$alkyl;

$R^{11}$ is $C_3$-$C_6$cycloalkyl, phenyl or 5 or 6-member heteroaryl having one ring nitrogen atom and 0 or 1 additional ring heteroatoms selected from N, O or S, which phenyl or heteroaryl is optionally substituted with 0, 1, 2, or 3 groups independently selected from halogen, cyano, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl; and $R^{12}$ is selected from $C_1$-$C_6$alkyl, $C_1$-$C_6$alkoxy, halo $C_1$-$C_6$alkyl, halo $C_1$-$C_6$alkoxy, $C_3$-$C_6$cycloalkyl, phenyl or 5 or 6 member heteroaryl having one ring nitrogen atom and 0 or 1 additional ring heteroatoms selected from N, O or S, which phenyl or heteroaryl is optionally substituted with 0, 1, 2, or 3 groups independently selected from halogen, hydroxy, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl.

In certain aspects of first embodiment, the disclosure provides a compound or salt thereof, the compound according to the Formula (I):

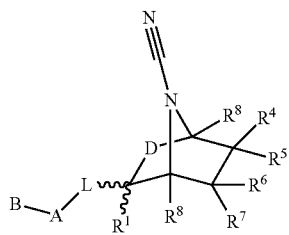

(I)

Wherein

D is (CR$^1$R$^2$)$_r$;

r is 1 or 2;

Each of $R^1$, $R^2$, $R^3$, $R^4$, $R^5$, $R^6$ and $R^7$ is independently selected at each occurrence from hydrogen, halogen, $C_1$-$C_4$alkyl, $C_1$-$C_4$alkoxy or $C_3$-$C_6$cycloalkyl; or $R^4$ and $R^6$ taken in combination form a fused three to six-member cycloalkyl ring; or $R^4$ and $R^5$ taken in combination form a spirocyclic three to six-member cycloalkyl ring;

$R^6$ and $R^7$ taken in combination form a spirocyclic three to six-member cycloalkyl ring;

$R^8$ is independently selected from hydrogen or $C_1$-$C_4$alkyl;

L is a bond or a divalent linker selected from —C(O)—, —C(O)N($R^B$)—, —N($R^B$)C(O)—, —N($R^B$)C(O)N($R^B$)—, —N($R^B$)S(O)$_p$—, —S(O)$_p$N($R^B$)—, —[C($R^A$)$_2$]$_q$C(O)N($R^B$)—, —C(O)N($R^B$)[C($R^A$)$_2$]$_q$—, C(O)N($R^B$)—[C($R^A$)$_2$]$_q$—, —C($R^A$)$_2$N($R^C$)C($R^A$)$_2$C(O)N($R^B$)—, —N($R^C$)C($R^A$)$_2$C(O)N($R^B$)—, —C(O)N($R^C$)C($R^A$)$_2$C(O)N($R^B$)—, —N($R^C$)C(O)C(O)N($R^B$)—, —OC($R^A$)$_2$C(O)N($R^B$)— or —SC($R^A$)$_2$C(O)N($R^B$)—, wherein L is attached to the azanorbornane by the right most atom;

p is selected at each occurrence from 0, 1 or 2;

q is 1, 2 or 3;

$R^A$ is independently, at each occurrence, hydrogen or $C_1$-$C_4$alkyl, or C($R^A$)$_2$, taken in combination forms —C(O)—;

$R^B$ is hydrogen or $C_1$-$C_4$alkyl;

$R^C$ is hydrogen, $C_1$-$C_4$alkyl or —C($R^A$)$_2$-A-B;

A is a divalent moiety selected from phenylene, naphthylene, 5, 6, 9 or 10 member heteroarylene comprising one ring nitrogen atom and 0 or 1 additional ring heteroatoms selected from N, O or S, or saturated or partially unsaturated 5 to 11 member monocyclic or bicyclic carbocycle or heterocycle comprising one or two ring nitrogen atoms and 0 or 1 additional ring heteroatoms selected from N, O or S, each of which is optionally substituted with 0 to 4 substituents selected from halogen, hydroxy, oxo, amino, $C_1$-$C_6$alkyl, $C_2$-$C_6$alkenyl, $C_2$-$C_6$alkynyl, $C_1$-$C_6$alkoxy, $C_3$-$C_7$cycloalkyl, $C_3$-$C_7$cycloalkoxy, $C_3$-$C_7$cycloalkyl$C_1$-$C_4$alkyl, $C_3$-$C_7$cycloalkyl$C_1$-$C_4$alkoxy, halo$C_1$-$C_6$alkyl and halo$C_1$-$C_6$alkoxy;

B is hydrogen, halogen, hydroxy, amino, $C_1$-$C_6$alkyl, halo$C_1$-$C_6$alkyl $C_2$-$C_6$alkenyl, $C_2$-$C_6$alkynyl, $C_1$-$C_6$alkoxy, halo$C_1$-$C_6$alkoxy, $C_3$-$C_7$cycloalkyl, C(O)$C_1$-$C_6$alkyl, C(O)$C_3$-$C_7$cycloalkyl, $NR^9R^{10}$, $OR^{11}$, C(O)$NR^9R^{10}$, $N(R^{10})$C(O)$R^{12}$, phenyl, 5, 6, 9 or 10 member heteroaryl or 4 to 7 member heterocycle, wherein each heteroaryl or heterocycle has one ring N, O or S atom and 0, 1 or 2 additional ring nitrogen atom, which phenyl, heteroaryl or heterocycle is optionally substituted with 0 to 4 groups independently selected from the group consisting of halogen, hydroxy, amino, mono- and di-$C_1$-$C_6$alkylamino, cyano, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl, —C(O)$NR^9R^{10}$, C(O)$R^9$, $CO_2R^9$, S(O)~$R^9$;

$R^9$ is hydrogen, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl;

$R^{10}$ is hydrogen or $C_1$-$C_6$alkyl;

$R^{11}$ is phenyl or 5 or 6-member heteroaryl having one ring nitrogen atom and 0 or 1 additional ring heteroatoms selected from N, O or S, which phenyl or heteroaryl is optionally substituted with 0, 1, 2, or 3 groups independently selected from $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl; and $R^{12}$ is selected from $C_1$-$C_6$alkyl, $C_1$-$C_6$alkoxy, halo $C_1$-$C_6$alkyl, halo $C_1$-$C_6$alkoxy, $C_3$-$C_6$cycloalkyl, phenyl or 5 or 6 member heteroaryl having one ring nitrogen atom and 0 or 1 additional ring heteroatoms selected from N, O or S, which phenyl or heteroaryl is optionally substituted with 0, 1, 2, or 3 groups independently selected from halogen, hydroxy, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl.

In a second embodiment, the disclosure provides a compound of the first embodiment which compound is represented by Formula Ia:

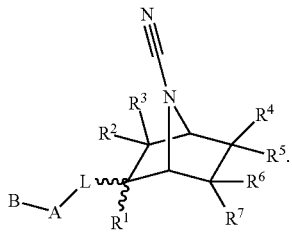

In a third embodiment, the disclosure provides a compound of the first or second embodiment, wherein L is —C(O)N(R$^B$)— and R$^B$ is hydrogen, methyl or ethyl.

In a fourth embodiment, the disclosure provides a compound of the third embodiment which represented by Formula II:

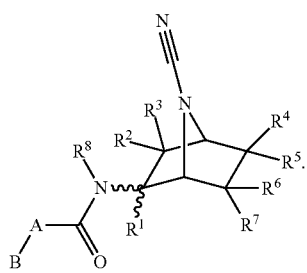

(II)

In a fifth embodiment, the disclosure provides a compound of any one of the first to fourth embodiments in which the azanorbornane is in endo orientation.

In a sixth embodiment, the disclosure provides a compound of any one of the first to fifth embodiments which compound is represented by Formula II-a or II-b:

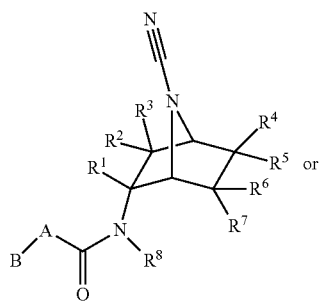

(II-a) or

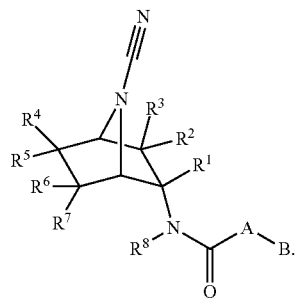

(II-b)

In a seventh embodiment, the disclosure provides a compound of any one of the first to sixth embodiments in which -A-B is selected from the group consisting of

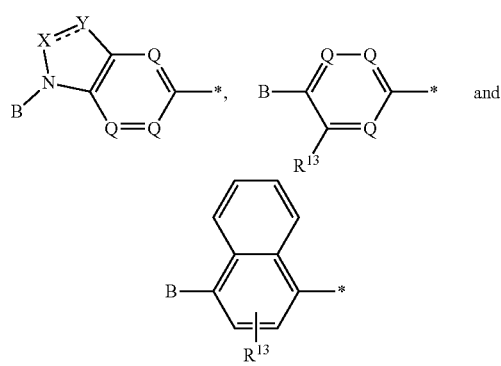

and

Wherein * represents point of attachment to L; Each occurrence of Q is independently selected from CR$^{13}$ or N;

R$^{11}$ is 0, 1, 2 or 3 independently selected from hydrogen, halogen, C$_1$-C$_6$alkyl, C$_1$-C$_6$alkoxy, haloC$_1$-C$_6$alkyl, haloC$_1$-C$_6$alkoxy, C$_3$-C$_6$cycloalkyl, C$_3$-C$_6$cycloalkyC$_1$-C$_4$alkoxy, or C$_3$-C$_6$cycloalkylC$_1$-C$_4$alkyl.

In an eighth embodiment, the disclosure provides a compound of seventh embodiment which is a compound represented by Formula III:

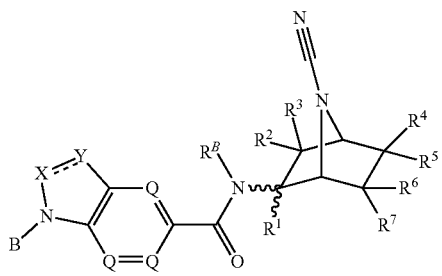

(III)

Wherein
R$^{13}$ is 0, 1, 2 or 3 independently selected from hydrogen, halogen, hydroxy, amino, C$_1$-C$_6$alkyl, and C$_1$-C$_6$alkoxy;
X is CH, CH$_2$, CH$_2$CH$_2$ or N;
Y is CH, CH$_2$, CH$_2$CH$_2$, N or O;
B is hydrogen, halogen, hydroxy, amino, C$_1$-C$_6$alkyl, C$_2$-C$_6$alkenyl, C$_2$-C$_6$alkynyl, C$_3$-C$_6$cycloalkyl, C(O)C$_1$-C$_4$alkyl, C(O)C$_3$-C$_5$cycloalkyl, C(O)OC$_1$-C$_4$alkyl, C(O)NHC$_1$-C$_4$alkyl or C(O)NHC$_3$-C$_6$cycloalkyl phenyl, 5 or 6 member heteroaryl or 5 or 6 member heterocycle, wherein each heteroaryl or heterocycle has one ring N, O or S atom and 0, 1 or 2 additional ring nitrogen atom, which phenyl, heteroaryl or heterocycle is optionally substituted with 0 to 4 groups independently selected from the group consisting of halogen, hydroxy, amino, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl, cyano$C_1$-$C_4$alkyl, cyano$C_3$-$C_5$cycloalkyl, —C(O)NR$^9$R$^{10}$, C(O)R$^9$, CO$_2$R$^9$, S(O)$_n$R$^9$;

R$^9$ is hydrogen, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl; and R$^{10}$ is hydrogen or $C_1$-$C_6$alkyl.

In certain aspects of the eighth embodiment B is phenyl, 5 or 6 member heteroaryl or 5 or 6 member heterocycle, wherein each heteroaryl or heterocycle one ring N, O or S atom and 0, 1 or 2 additional ring nitrogen atom, which phenyl, heteroaryl or heterocycle is optionally substituted with 0 to 4 groups independently selected from the group consisting of halogen, hydroxy, amino, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl, cyano$C_1$-$C_4$alkyl, cyano$C_3$-$C_5$cycloalkyl, —C(O)NR$^9$R$^{10}$, C(O)R$^9$, CO$_2$R$^9$ and S(O)~R$^9$.

In certain other aspects of the eighth embodiment, B is phenyl, 5 or 6 member heteroaryl or 5 or 6 member heterocycle, wherein each heteroaryl or heterocycle one ring N, O or S atom and 0, 1 or 2 additional ring nitrogen atom, which phenyl, heteroaryl or heterocycle is optionally substituted with 0 to 3 groups independently selected from the group consisting of halogen, $C_1$-$C_6$alkyl, $C_1$-$C_6$alkoxy, halo $C_1$-$C_6$alkyl, halo$C_1$-$C_6$alkoxy, $C_3$-$C_6$cycloalkyl, cyano$C_1$-$C_4$alkyl and cyano$C_3$-$C_5$cycloalkyl.

In certain other aspects of the eighth embodiment, B is phenyl, 5 or 6 member heteroaryl or 5 or 6 member heterocycle, wherein each heteroaryl or heterocycle one ring N, O or S atom and 0, 1 or 2 additional ring nitrogen atom, which phenyl, heteroaryl or heterocycle is optionally substituted with 0 to 4 groups independently selected from the group consisting of halogen, hydroxy, amino, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl, —C(O)NR$^9$R$^{10}$, C(O)R$^9$, CO$_2$R$^9$ and S(O)$_n$R$^9$.

In a ninth embodiment, the disclosure provides a compound of eighth embodiment which is a compound represented by Formula III-a or Formula III-b:

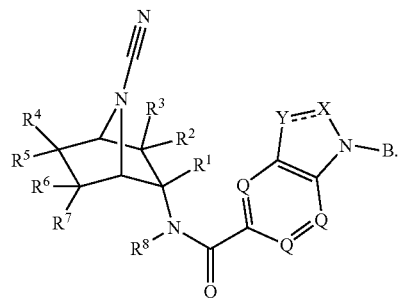

(III-a)

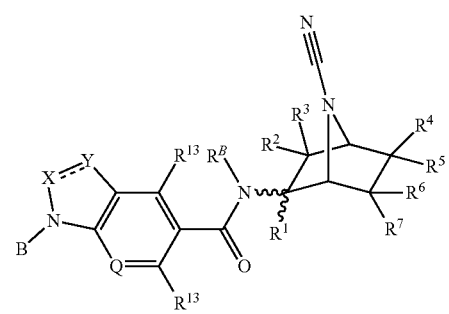

(III-b)

In a tenth embodiment, the disclosure provides a compound of eighth embodiment which is a compound represented by Formula (III-c):

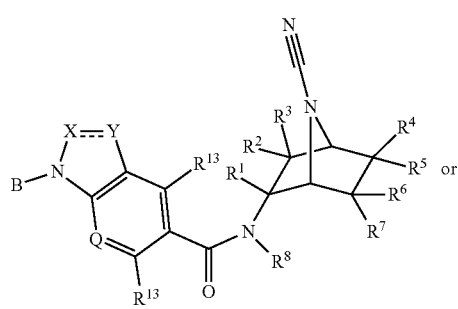

(III-c)

Wherein

R$^{13}$ is selected at each occurrence from the group consisting of hydrogen, $C_1$-$C_4$alkyl, halogen, $C_1$-$C_4$alkoxy.

In an eleventh embodiment, the disclosure provides a compound of eighth embodiment which is a compound represented by Formula III-d or Formula III-e:

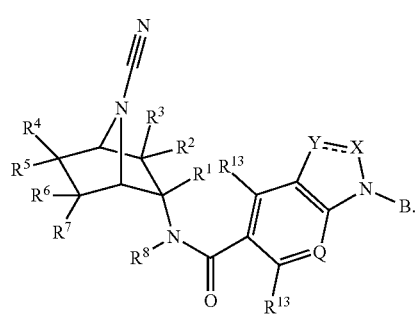

(III-d)

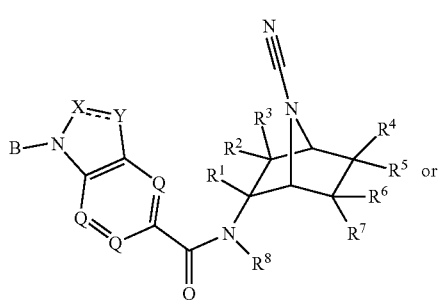

(III-e)

In a twelfth embodiment, the disclosure provides a compound of any one of the sixth to eleventh embodiment in which compound B is phenyl, pyridyl, pyrimidinyl or pyrazinyl each of which is optionally substituted with 0, 1, or 2 independently selected from $C_1$-$C_4$alkyl or $C_3$-$C_5$cycloalkyl; or B is $C_1$-$C_6$alkyl, $C_3$-$C_6$cycloalkyl, C(O)$C_1$-$C_4$alkyl, C(O)$C_3$-$C_5$cycloalkyl, C(O)O$C_1$-$C_4$alkyl, C(O)NH$C_1$-$C_4$alkyl or C(O)NH$C_3$-$C_6$cycloalkyl.

In a thirteenth embodiment, the disclosure provides a compound of the sixth embodiment, which compound is represented by Formula IV:

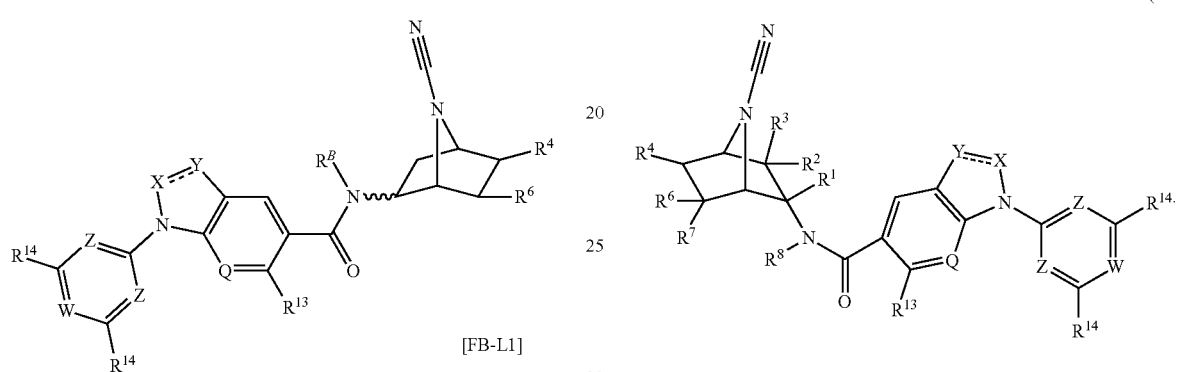

(IV)

[FB-L1]

Wherein $R^4$ and $R^6$ are each independently hydrogen or methyl;

or $R^4$ and $R^6$, taken in combination form a fused cyclopropyl ring;

$R^B$ is hydrogen or methyl;

Z is independently selected at each occurrence from CH or N;

W is $CR^{14}$ or N, wherein 0, 1, or 2 occurrences of W and Z is N and remainder is C;

$R^{13}$ is hydrogen, $C_1$-$C_4$alkyl or $C_3$-$C_5$cycloalkyl;

$R^{14}$ is independently selected at each occurrence from hydrogen, $C_1$-$C_4$alkyl, $C_3$-$C_5$cycloalkyl, cyano$C_1$-$C_4$alkyl and cyano$C_3$-$C_5$cycloalkyl;

X and Y are each $CH_2$; or

X and Y are each selected from CH or N such that at least one of X and Y is CH.

In a fourteenth embodiment, the disclosure provides a compound of the thirteenth embodiment in which at least one occurrence of either $R^3$ or $R^{14}$ is not hydrogen.

In certain aspects of the fourteenth embodiment, one occurrence of $R^{14}$ is hydrogen and one occurrence of $R^{14}$ is cyano$C_1$-$C_4$alkyl or cyano$C_3$-$C_5$cycloalkyl.

In certain other aspects of the fourteenth embodiment, $R^{11}$ is independently selected at each occurrence from hydrogen, $C_1$-$C_4$alkyl, or $C_3$-$C_5$cycloalkyl.

In a fifteenth embodiment, the disclosure provides a compound of the thirteenth or fourteenth embodiment wherein the azanorbornane is in the endo conformation.

In a sixteenth embodiment, the disclosure provides a compound of any one of the thirteenth to fifteenth embodiment, which compound is represented by Formula IV-a or Formula IV-b:

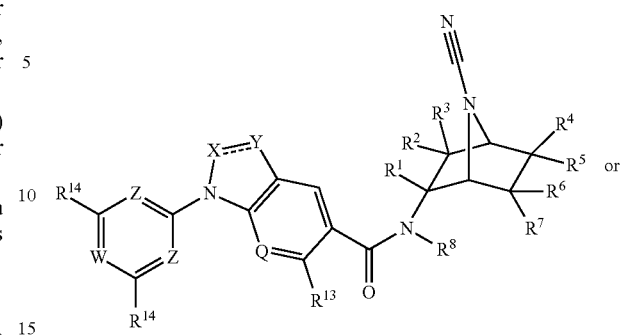

(IV-a)

(IV-b)

In a seventeenth embodiment, the disclosure provides a compound of any one of the fifth to eighth embodiment, which compound is represented by Formula V:

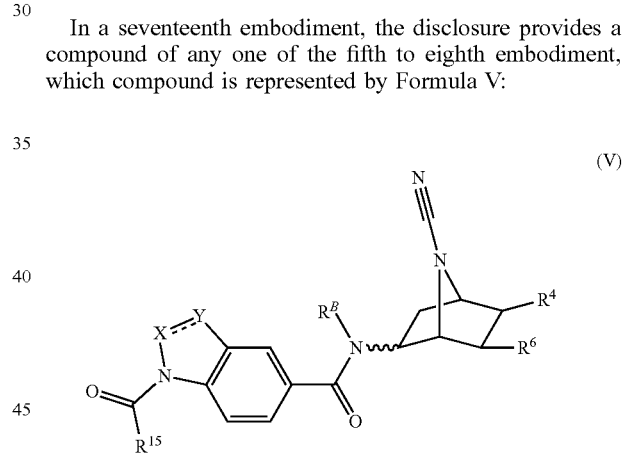

(V)

Wherein R and R are each independently hydrogen or methyl;

or $R^4$ and $R^6$, taken in combination form a fused cyclopropyl ring;

$R^8$ is hydrogen or methyl;

$R^{15}$ is $C_1$-$C_4$alkyl, $C_1$-$C_4$alkoxy, $C_3$-$C_5$cycloalkyl, $C_3$-$C_5$cycloalkyloxy, $C_3$-$C_5$cycloalkyl$C_1$-$C_4$alkyl, $C_3$-$C_5$cycloalkyl$C_1$-$C_4$alkoxy;

X and Y are each $CH_2$; or

X and Y are each selected from CH or N such that at least one of X and Y is CH.

In an eighteenth embodiment, the disclosure provides a compound of the seventeenth embodiment wherein the azanorbornane is in the endo conformation.

In a nineteenth embodiment, the disclosure provides a compound of the seventeenth or eighteenth embodiment, wherein the compound is represented by Formula V-a or Formula V-b:

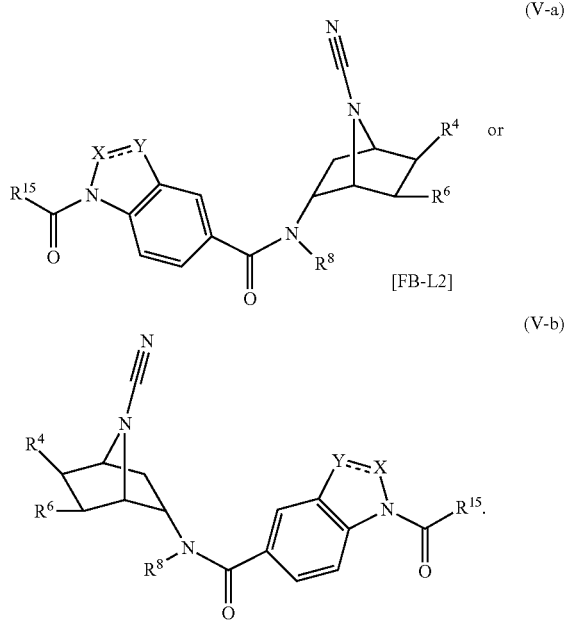

[FB-L2]

[FB-L3]

In a twentieth embodiment, the disclosure provides a compound of the first or second embodiment wherein the compound according to the formula: (VI)

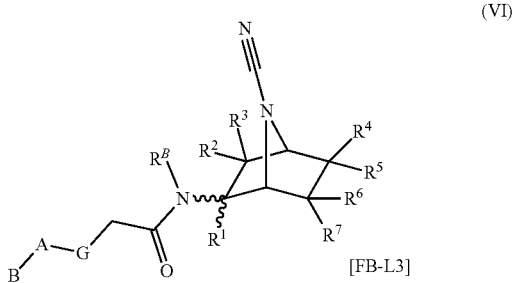

[FB-L3]

Wherein

G is O, S, N($R^C$), *—C(O)N($R^C$) or *—(CH$_2$)N($R^C$), wherein the *represents attachment to B-A-;

$R^C$ is hydrogen, $C_1$-$C_4$alkyl or —CH$_2$-A-B;

A is phenyl, naphthylene, 5 or 6-member heteroaryl comprising one ring nitrogen atom and 0 or 1 additional ring heteroatoms selected from N, O or S, each of which is optionally substituted with 0 to 4 substituents selected from halogen, hydroxy, amino, $C_1$-$C_6$alkyl, $C_2$-$C_6$alkenyl, $C_2$-$C_6$alkynyl, $C_1$-$C_6$alkoxy, halo $C_1$-$C_6$alkyl, and halo $C_1$-$C_6$alkoxy;

B is hydrogen, halogen, hydroxy, amino, $C_1$-$C_6$alkyl, $C_2$-$C_6$alkenyl, $C_2$-$C_6$alkynyl, $C_1$-$C_6$alkoxy, $C_3$-$C_6$cycloalkyl, C(O)$C_1$-$C_6$alkyl, C(O)$C_3$-$C_6$cycloakyl, C(O)NR$^9$R$^{10}$, phenyl, 5 or 6 member heteroaryl or 5 or 6 member heterocycle, wherein each heteroaryl or heterocycle has one ring N, O or S atom and 0 1 or 2 additional ring nitrogen atom, which phenyl, heteroaryl or heterocycle is optionally substituted with 0 to 4 groups independently selected from the group consisting of halogen, hydroxy, amino, $C_1$-$C_6$alkyl, $C_2$-$C_6$alkenyl, $C_2$-$C_6$alkynyl, $C_1$-$C_6$alkoxy, halo $C_1$-$C_6$alkyl, halo $C_1$-$C_6$alkoxy, $C_3$-$C_6$cycloalkyl, —C(O)NR$^9$R$^{10}$, C(O)R$^9$, CO$_2$R$^9$, S(O)$_n$R$^9$.

In a twenty-first embodiment, the disclosure provides compounds of the twentieth embodiment in which G is O, S, N(H) or *C(O)N(H), wherein the *represents attachment to B-A-; A is phenyl, naphthyl or 5 or 6-member heteroaryl, each of which is optionally substituted with 0, 1, 2, 3, or 4 groups independently selected from the group consisting of halogen, hydroxy, amino, $C_1$-$C_6$alkyl, $C_2$-$C_6$alkenyl, $C_2$-$C_6$alkynyl, $C_1$-$C_6$alkoxy, halo $C_1$-$C_6$alkyl, and halo $C_1$-$C_6$alkoxy.

In a twenty second embodiment, the disclosure provides compounds of the twentieth or twenty-first embodiment in which the compound is represented by Formula VII:

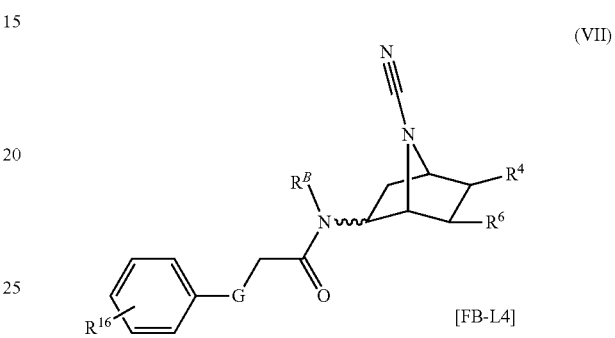

[FB-L4]

Wherein $R^B$ is H or methyl;

$R^4$ and $R^6$ are each independently hydrogen or methyl; or $R^4$ and $R^6$, taken in combination form a fused cyclopropyl ring;

G is O, S, or N(H);

$R^{16}$ is halogen, hydroxy, amino, $C_1$-$C_6$alkyl, $C_2$-$C_6$alkenyl, $C_2$-$C_6$alkynyl, $C_1$-$C_6$alkoxy, halo $C_1$-$C_6$alkyl, and halo $C_1$-$C_6$alkoxy.

In a twenty third embodiment, the invention provides compounds of the first or second embodiment and pharmaceutically acceptable salts thereof in which the compound is recited in the below Table A.

Table A

N-((1R,2R,4S)-7-cyano-7-azabicyclo[2.2.1]heptan-2-yl)-2-(1H-pyrrol-1-yl)-1,3-benzothiazole-6-carboxamide;

racemic-endo 2-methyl-2-propanyl 7-(7-cyano-7-azabicyclo [2.2.1]heptan-2-yl)carbamoyl)-3,4-dihydro-2(1H)-isoquinolinecarboxylate;

racemic-endo 2-methyl-2-propanyl 6-(7-cyano-7-azabicyclo [2.2.1]heptan-2-yl)carbamoyl)-3,4-dihydro-2(1H)-isoquinolinecarboxylate;

N-((1R,2R,4S)-7-cyano-7-azabicyclo[2.2.1]heptan-2-yl)-4-((4-cyclopropyl-2-pyrimidinyl)amino)-2,5-difluorobenzamide;

N-((1R,2R,4S)-7-cyano-7-azabicyclo[2.2.1]heptan-2-yl)-4-((4-cyclopropyl-2-pyrimidinyl)amino)-2,3-difluorobenzamide;

N-((1R,2R,4S)-7-cyano-7-azabicyclo[2.2.1]heptan-2-yl)-3-phenyl-1H-indazole-6-carboxamide;

2-methyl-2-propanyl (4-(((1R,2R,4S)-7-cyano-7-azabicyclo [2.2.1]heptan-2-yl)carbamoyl)-2-methylphenyl)carbamate;

N-((1R,2R,4S)-7-cyano-7-azabicyclo[2.2.1]heptan-2-yl)-1-(2,2-dimethylpropanoyl)-2,3-dihydro-1H-indole-5-carboxamide;

N-((1R,2R,4S)-7-cyano-7-azabicyclo[2.2.1]heptan-2-yl)-4-(1,3-thiazol-4-yl)benzamide;

4-benzamido-N-((1R,2R,4S)-7-cyano-7-azabicyclo[2.2.1] heptan-2-yl)benzamide;

N-(4-(((1R,2R,4S)-7-cyano-7-azabicyclo[2.2.1]heptan-2-yl)carbamoyl)phenyl)-2-pyridinecarboxamide;
N-((1R,2R,4S)-7-cyano-7-azabicyclo[2.2.1]heptan-2-yl)-4-(phenylethynyl)benzamide;
6-(1H-benzimidazol-1-yl)-N-((1R,2R,4S)-7-cyano-7-azabicyclo[2.2.1]heptan-2-yl)-3-pyridinecarboxamide;
4-((5-chloro-2-pyridinyl)oxy)-N-((1R,2R,4S)-7-cyano-7-azabicyclo[2.2.1]heptan-2-yl)benzamide;
N-((1R,2R,4S)-7-cyano-7-azabicyclo[2.2.1]heptan-2-yl)-4-(3,5-dimethyl-1H-pyrazol-1-yl)-3-fluorobenzamide;
2-chloro-N-((1R,2R,4S)-7-cyano-7-azabicyclo[2.2.1]heptan-2-yl)-4-(1,1-dioxido-1,2-thiazolidin-2-yl)benzamide;
2-methyl-2-propanyl (3-chloro-4-(((1R,2R,4S)-7-cyano-7-azabicyclo[2.2.1]heptan-2-yl)carbamoyl)phenyl)carbamate;
N-((1R,2R,4S)-7-cyano-7-azabicyclo[2.2.1]heptan-2-yl)-3-methyl-4-(3-methylbutanamido)benzamide;
N-((1R,2R,4S)-7-cyano-7-azabicyclo[2.2.1]heptan-2-yl)-4-(4-methyl-1H-pyrazol-1-yl)benzamide;
4-(1H-benzotriazol-1-yl)-N-((1R,2R,4S)-7-cyano-7-azabicyclo[2.2.1]heptan-2-yl)benzamide;
N-((1R,2R,4S)-7-cyano-7-azabicyclo[2.2.1]heptan-2-yl)-3-(4-pyridinyl)benzamide;
N-((1R,2R,4S)-7-cyano-7-azabicyclo[2.2.1]heptan-2-yl)-6-(cyclopropylmethoxy)-3-pyridinecarboxamide;
4-(3-chloro-2-pyridinyl)-N-((1R,2R,4S)-7-cyano-7-azabicyclo[2.2.1]heptan-2-yl)benzamide;
N-((1R,2R,4S)-7-cyano-7-azabicyclo[2.2.1]heptan-2-yl)-4-(3-pyridinyl)benzamide;
N-((1R,2R,4S)-7-cyano-7-azabicyclo[2.2.1]heptan-2-yl)-4-(3-methyl-1H-pyrazol-1-yl)benzamide;
N-((1R,2R,4S)-7-cyano-7-azabicyclo[2.2.1]heptan-2-yl)-4-(4-(trifluoromethyl)-1H-pyrazol-1-yl)benzamide;
N-((1R,2R,4S)-7-cyano-7-azabicyclo[2.2.1]heptan-2-yl)-4-(3-methyl-1H-pyrazolo[3,4-b]pyridin-1-yl)benzamide;
2-chloro-N-((1R,2R,4S)-7-cyano-7-azabicyclo[2.2.1]heptan-2-yl)-4-(4-methyl-1H-pyrazol-1-yl)benzamide;
N-((1R,2R,4S)-7-cyano-7-azabicyclo[2.2.1]heptan-2-yl)-2-fluoro-4-(4-methyl-1H-imidazol-1-yl)benzamide;
N-((1R,2R,4S)-7-cyano-7-azabicyclo[2.2.1]heptan-2-yl)-2-methyl-4-(4-methyl-1H-pyrazol-1-yl)benzamide;
N-((1R,2R,4S)-7-cyano-7-azabicyclo[2.2.1]heptan-2-yl)-3-fluoro-4-(4-methyl-1H-pyrazol-1-yl)benzamide;
racemic-endo N-(7-cyano-7-azabicyclo[2.2.1]heptan-2-yl)-5-(4-fluorophenyl)-2-pyridinecarboxamide;
racemic-endo 6-(4-chlorophenyl)-N-(7-cyano-7-azabicyclo[2.2.1]heptan-2-yl)-3-pyridinecarboxamide;
6-(4-chlorophenyl)-N-((1R,2R,4S)-7-cyano-7-azabicyclo[2.2.1]heptan-2-yl)-3-pyridinecarboxamide;
racemic-endo N-(7-cyano-7-azabicyclo[2.2.1]heptan-2-yl)-2-(3-methylanilino)-5-pyrimidinecarboxamide;
N-((1R,2R,4S)-7-cyano-7-azabicyclo[2.2.1]heptan-2-yl)-1-(6-cyclopropyl-2-pyridinyl)-6-fluoro-1H-indazole-5-carboxamide;
N-((1R,2R,4S)-7-cyano-7-azabicyclo[2.2.1]heptan-2-yl)-1-(4-cyano-6-methyl-2-pyridinyl)-1H-indazole-5-carboxamide;
N-((1R,2R,4S)-7-cyano-7-azabicyclo[2.2.1]heptan-2-yl)-1-(4-methyl-2-pyridinyl)-1H-pyrrolo[2,3-b]pyridine-5-carboxamide;
N-((1R,2R,4S)-7-cyano-7-azabicyclo[2.2.1]heptan-2-yl)-1-(4-methyl-1,3-thiazol-2-yl)-1H-indazole-5-carboxamide;
Mixture of two diastereomers: (S)—N-(7-cyano-7-azabicyclo[2.2.1]heptan-2-yl)-1-(6-methyl-2-pyridinyl)-4,5,6,7-tetrahydro-1H-indazole-5-carboxamide and (R)—N-(7-cyano-7-azabicyclo[2.2.1]heptan-2-yl)-1-(6-methyl-2-pyridinyl)-4,5,6,7-tetrahydro-1H-indazole-5-carboxamide;
N-((1R,2R,4S)-7-cyano-7-azabicyclo[2.2.1]heptan-2-yl)-3-(4-methyl-2-pyrimidinyl)-1H-indole-6-carboxamide;
N-((1R,2R,4S)-7-cyano-7-azabicyclo[2.2.1]heptan-2-yl)-6-methoxy-1-(4-methyl-2-pyrimidinyl)-1H-indole-5-carboxamide;
N-((1R,2R,4S)-7-cyano-7-azabicyclo[2.2.1]heptan-2-yl)-1-methyl-3-(6-methyl-2-pyridinyl)-1H-indazole-6-carboxamide;
N-((1R,2R,4S)-7-cyano-7-azabicyclo[2.2.1]heptan-2-yl)-1-methyl-3-(6-(trifluoromethyl)-2-pyridinyl)-1H-indazole-6-carboxamide;
N-((1R,2R,4S)-7-cyano-7-azabicyclo[2.2.1]heptan-2-yl)-1-methyl-3-phenyl-1H-indazole-6-carboxamide;
N-((1R,2R,4S)-7-cyano-7-azabicyclo[2.2.1]heptan-2-yl)-3-((3-fluorophenoxy)methyl)benzamide;
N-((1R,2R,4S)-7-cyano-7-azabicyclo[2.2.1]heptan-2-yl)-4-(2-thiophenylmethoxy)benzamide;
N-((1R,2R,4S)-7-cyano-7-azabicyclo[2.2.1]heptan-2-yl)-4-((2-methylphenyl)sulfanyl)benzamide;
N-((1R,2R,4S)-7-cyano-7-azabicyclo[2.2.1]heptan-2-yl)-4-(3-methylbutoxy)benzamide;
N-((1R,2R,4S)-7-cyano-7-azabicyclo[2.2.1]heptan-2-yl)-4-((2-cyanophenyl)sulfanyl)benzamide;
N-((1R,2R,4S)-7-cyano-7-azabicyclo[2.2.1]heptan-2-yl)-1-(6-cyclopropyl-2-pyridinyl)-3-methyl-1H-indazole-5-carboxamide;
6-chloro-N-((1R,2R,4S)-7-cyano-7-azabicyclo[2.2.1]heptan-2-yl)-1-(6-cyclopropyl-2-pyridinyl)-1H-indazole-5-carboxamide;
N-((1R,2R,4S)-7-cyano-7-azabicyclo[2.2.1]heptan-2-yl)-1-(6-cyclopropyl-2-pyridinyl)-6-methyl-1H-indazole-5-carboxamide;
5-bromo-3-chloro-N-((1R,2R,4S)-7-cyano-7-azabicyclo[2.2.1]heptan-2-yl)-1-methyl-1H-indole-2-carboxamide;
Mixture of two diastereomers: (2R)-5-bromo-N-(7-cyano-7-azabicyclo[2.2.1]heptan-2-yl)-2,3-dihydro-1H-indene-2-carboxamide, and (2S)-5-bromo-N-(7-cyano-7-azabicyclo[2.2.1]heptan-2-yl)-2,3-dihydro-1H-indene-2-carboxamide;
5-bromo-N-((1R,2R,4S)-7-cyano-7-azabicyclo[2.2.1]heptan-2-yl)-3-methyl-1-benzothiophene-2-carboxamide;
N-benzyl-3-bromo-N-(2-(((1R,2R,4S)-7-cyano-7-azabicyclo[2.2.1]heptan-2-yl)amino)-2-oxoethyl)benzamide;
N-benzyl-3-chloro-N-(2-(((1R,2R,4S)-7-cyano-7-azabicyclo[2.2.1]heptan-2-yl)amino)-2-oxoethyl)benzamide;
3-bromo-N-(2-(((1R,2R,4S)-7-cyano-7-azabicyclo[2.2.1]heptan-2-yl)amino)-2-oxoethyl)benzamide;
3-chloro-N-(2-(((1R,2R,4S)-7-cyano-7-azabicyclo[2.2.1]heptan-2-yl)amino)-2-oxoethyl)benzamide;
Mixture of two diastereomers: (3R)-1-(3-chlorophenyl)-N-(7-cyano-7-azabicyclo[2.2.1]heptan-2-yl)-5-oxo-3-pyrrolidinecarboxamide, and (3S)-1-(3-chlorophenyl)-N-(7-cyano-7-azabicyclo[2.2.1]heptan-2-yl)-5-oxo-3-pyrrolidinecarboxamide;
Mixture of two diastereomers: (3R)-1-(3-bromophenyl)-N-(7-cyano-7-azabicyclo[2.2.1]heptan-2-yl)-5-oxo-3-pyrrolidinecarboxamide, and (3S)-1-(3-bromophenyl)-N-(7-cyano-7-azabicyclo[2.2.1]heptan-2-yl)-5-oxo-3-pyrrolidinecarboxamide;
Mixture of two diastereomers: (3R)-1-(3-chlorophenyl)-N-(7-cyano-7-azabicyclo[2.2.1]heptan-2-yl)-2-oxo-3-pyrrolidinecarboxamide, and (3S)-1-(3-chlorophenyl)-N-(7-cyano-7-azabicyclo[2.2.1]heptan-2-yl)-2-oxo-3-pyrrolidinecarboxamide;

2-(3-chlorophenyl)-N-((1R,2R,4S)-7-cyano-7-azabicyclo[2.2.1]heptan-2-yl)-1,3-thiazole-4-carboxamide;
2-(4-chloro-3-(trifluoromethyl)phenoxy)-N-((endo)-7-cyano-7-azabicyclo[2.2.1]heptan-2-yl)acetamide enantiomer 1;
2-(4-chloro-3-(trifluoromethyl)phenoxy)-N-((endo)-7-cyano-7-azabicyclo[2.2.1]heptan-2-yl)acetamide enantiomer 2;
3-(3-chlorophenyl)-N-((endo)-7-cyano-7-azabicyclo[2.2.1]heptan-2-yl)-1,2-oxazole-5-carboxamide enantiomer 1;
3-(3-chlorophenyl)-N-((endo)-7-cyano-7-azabicyclo[2.2.1]heptan-2-yl)-1,2-oxazole-5-carboxamide enantiomer 2;
Racemic, endo 2-((4-chloro-3-(trifluoromethyl)phenyl)amino)-N-(7-cyano-7-azabicyclo[2.2.1]heptan-2-yl)acetamide;
Racemic, endo 3-bromo-N-(1-(7-cyano-7-azabicyclo[2.2.1]heptan-2-yl)amino)-1-oxopropan-2-yl)benzamide;
Racemic, endo 3-bromo-N-(1-7-cyano-7-azabicyclo[2.2.1]heptan-2-yl)amino)-2-methyl-1-oxopropan-2-yl)benzamide;
(endo)-7-cyano-N-(4-(3-(trifluoromethyl)phenyl)-1,3-thiazol-2-yl)-7-azabicyclo[2.2.1]heptane-2-carboxamide;
(endo)-7-cyano-N-(4-(3-(trifluoromethyl)phenyl)-1,3-thiazol-2-yl)-7-azabicyclo[2.2.1]heptane-2-carboxamide;
(exo)-7-cyano-N-(4-(3-(trifluoromethyl)phenyl)-1,3-thiazol-2-yl)-7-azabicyclo[2.2.1]heptane-2-carboxamide;
(exo)-7-cyano-N-(4-(3-(trifluoromethyl)phenyl)-1,3-thiazol-2-yl)-7-azabicyclo[2.2.1]heptane-2-carboxamide;
(endo)-2-((5-(2-fluoro-5-methylphenyl)-2,3-dihydro-1H-indol-1-yl)carbonyl)-7-azabicyclo[2.2.1]heptane-7-carbonitrile;
(endo)-2-((5-(2-fluoro-5-methylphenyl)-2,3-dihydro-1H-indol-1-yl)carbonyl)-7-azabicyclo[2.2.1]heptane-7-carbonitrile;
(exo)-2-((5-(2-fluoro-5-methylphenyl)-2,3-dihydro-1H-indol-1-yl)carbonyl)-7-azabicyclo[2.2.1]heptane-7-carbonitrile;
(exo)-2-((5-(2-fluoro-5-methylphenyl)-2,3-dihydro-1H-indol-1-yl)carbonyl)-7-azabicyclo[2.2.1]heptane-7-carbonitrile;
Racemic, endo N-(7-cyano-7-azabicyclo[2.2.1]heptan-2-yl)-1-(4,6-dimethyl-2-pyrimidinyl)-2,3-dihydro-1H-indole-5-carboxamide;
Racemic, endo N-(7-cyano-7-azabicyclo[2.2.1]heptan-2-yl)-1-(6-cyclopropyl-2-pyridinyl)-2,3-dihydro-1H-indole-5-carboxamide;
Racemic, endo N-(7-cyano-7-azabicyclo[2.2.1]heptan-2-yl)-1-(6-cyclopropyl-2-pyrazinyl)-2,3-dihydro-1H-indole-5-carboxamide;
Racemic, endo N-(7-cyano-7-azabicyclo[2.2.1]heptan-2-yl)-1-(3-cyclopropylphenyl)-2,3-dihydro-1H-indole-5-carboxamide;
Racemic, endo N-(7-cyano-7-azabicyclo[2.2.1]heptan-2-yl)-1-(4-cyclopropyl-2-pyridinyl)-2,3-dihydro-1H-indole-5-carboxamide;
Racemic, endo N-(7-cyano-7-azabicyclo[2.2.1]heptan-2-yl)-1-(4-methoxy-2-pyrimidinyl)-2,3-dihydro-1H-indole-5-carboxamide;
Racemic, endo N-(7-cyano-7-azabicyclo[2.2.1]heptan-2-yl)-1-(4-(trifluoromethyl)-2-pyrimidinyl)-2,3-dihydro-1H-indole-5-carboxamide;
Racemic, endo N-(7-cyano-7-azabicyclo[2.2.1]heptan-2-yl)-1-(4-(2-methyl-2-propanyl)-2-pyrimidinyl)-2,3-dihydro-1H-indole-5-carboxamide;
Racemic, endo N-(7-cyano-7-azabicyclo[2.2.1]heptan-2-yl)-1-(4-(2-propanyl)-2-pyrimidinyl)-2,3-dihydro-1H-indole-5-carboxamide;
N-((1R,2R,4S)-7-cyano-7-azabicyclo[2.2.1]heptan-2-yl)-1-(4-ethyl-2-pyrimidinyl)-2,3-dihydro-1H-indole-5-carboxamide;
N-((1R,2R,4S)-7-cyano-7-azabicyclo[2.2.1]heptan-2-yl)-1-(4-cyano-2-pyrimidinyl)-2,3-dihydro-1H-indole-5-carboxamide;
N-((1R,2R,4S)-7-cyano-7-azabicyclo[2.2.1]heptan-2-yl)-1-(4-cyano-6-methyl-2-pyrimidinyl)-2,3-dihydro-1H-indole-5-carboxamide;
N-((1R,2R,4S)-7-cyano-7-azabicyclo[2.2.1]heptan-2-yl)-1-(4-(difluoromethyl)-2-pyrimidinyl)-2,3-dihydro-1H-indole-5-carboxamide;
N-((1R,2R,4S)-7-cyano-7-azabicyclo[2.2.1]heptan-2-yl)-1-(4-methyl-6-(trifluoromethyl)-2-pyrimidinyl)-2,3-dihydro-1H-indole-5-carboxamide;
N-((1R,2R,4S)-7-cyano-7-azabicyclo[2.2.1]heptan-2-yl)-1-(3-fluoro-6-methyl-2-pyridinyl)-2,3-dihydro-1H-indole-5-carboxamide;
Racemic, endo N-(7-cyano-7-azabicyclo[2.2.1]heptan-2-yl)-1-(4-methyl-2-pyrimidinyl)-1H-indole-5-carboxamide;
Racemic, endo N-(7-cyano-7-azabicyclo[2.2.1]heptan-2-yl)-1-(2-pyrimidinyl)-2,3-dihydro-1H-indole-5-carboxamide;
Racemic, endo N-(7-cyano-7-azabicyclo[2.2.1]heptan-2-yl)-1-(5-methyl-2-pyrimidinyl)-2,3-dihydro-1H-indole-5-carboxamide;
N-((1R,2R,4S)-7-cyano-7-azabicyclo[2.2.1]heptan-2-yl)-1-(4-cyclopropyl-2-pyrimidinyl)-N-methyl-2,3-dihydro-1H-indole-5-carboxamide;
N-((1S,2S,4R)-7-cyano-7-azabicyclo[2.2.1]heptan-2-yl)-1-(4-cyclopropyl-2-pyrimidinyl)-N-methyl-2,3-dihydro-1H-indole-5-carboxamide (peak 2 derived);
Racemic, endo N~5~-(7-cyano-7-azabicyclo[2.2.1]heptan-2-yl)-N~1~-cyclopropyl-2,3-dihydro-1H-indole-1,5-dicarboxamide;
Racemic, endo 1-(7-cyano-7-azabicyclo[2.2.1]heptan-2-yl)-3-(4-(trifluoromethyl)phenyl)urea;
N-((1R,2R,4S)-7-cyano-7-azabicyclo[2.2.1]heptan-2-yl)-3-methyl-4-(1-methyl-1H-pyrazol-4-yl)benzamide;
N-((1R,2R,4S)-7-cyano-7-azabicyclo[2.2.1]heptan-2-yl)-3-(cyclopropylmethoxy)-4-(1-methyl-1H-pyrazol-4-yl)benzamide;
N-((1R,2R,4S)-7-cyano-7-azabicyclo[2.2.1]heptan-2-yl)-4-(1-methyl-1H-pyrazol-4-yl)-3-propoxybenzamide;
N-((1R,2R,4S)-7-cyano-7-azabicyclo[2.2.1]heptan-2-yl)-3-ethoxy-4-(1-methyl-1H-pyrazol-4-yl)benzamide;
N-((1R,2R,4S)-7-cyano-7-azabicyclo[2.2.1]heptan-2-yl)-4-(1-methyl-1H-pyrazol-4-yl)-3-(2-propanyloxy)benzamide;
N-((1R,2R,4S)-7-cyano-7-azabicyclo[2.2.1]heptan-2-yl)-3-methoxy-4-(1-methyl-1H-pyrazol-4-yl)benzamide;
N-((1R,2R,4S)-7-cyano-7-azabicyclo[2.2.1]heptan-2-yl)-4-(1-methyl-1H-pyrazol-4-yl)-3-(trifluoromethoxy)benzamide;
N-((1R,2R,4S)-7-cyano-7-azabicyclo[2.2.1]heptan-2-yl)-4-(1-methyl-1H-pyrazol-4-yl)-3-(trifluoromethyl)benzamide;
N-((1R,2R,4S)-7-cyano-7-azabicyclo[2.2.1]heptan-2-yl)-3-(6-(trifluoromethyl)-2-pyridinyl)-1H-indazole-6-carboxamide;
Racemic, endo 2-((3-bromobenzyl)(methyl)amino)-N-(7-cyano-7-azabicyclo[2.2.1]heptan-2-yl)acetamide;
Racemic, endo 2-(4-chloro-2-cyclohexylphenoxy)-N-(7-cyano-7-azabicyclo[2.2.1]heptan-2-yl)acetamide;
N~2~-benzyl-N-2~-(3-bromobenzyl)-N-((1R,2R,4S)-7-cyano-7-azabicyclo[2.2.1]heptan-2-yl)glycinamide;

N~2~-benzyl-N-2~-(3-chlorobenzyl)-N-((1R,2R,4S)-7-cyano-7-azabicyclo[2.2.1]heptan-2-yl)glycinamide;

N-((1R,2R,4S)-7-cyano-7-azabicyclo[2.2.1]heptan-2-yl)-2-(5,6,7,8-tetrahydro[1]benzothieno[2,3-d]pyrimidin-4-ylsulfanyl)acetamide;

N-2~-(3-bromobenzyl)-N-((1R,2R,4S)-7-cyano-7-azabicyclo[2.2.1]heptan-2-yl)-N-2~-(2-methylpropyl)glycinamide;

N-2~-(3-chlorobenzyl)-N-((1R,2R,4S)-7-cyano-7-azabicyclo[2.2.1]heptan-2-yl)-N-2~-(4-methoxybenzyl)glycinamide;

N-((1R,2R,4S)-7-cyano-7-azabicyclo[2.2.1]heptan-2-yl)-2-(5,7-dichloro-3,4-dihydro-2(1H)-isoquinolinyl)acetamide;

Racemic, endo N-(7-cyano-7-azabicyclo[2.2.1]heptan-2-yl)-2-(2,4-dichloro-5-ethyl-3-methylphenoxy)acetamide;

Racemic, endo 2-((5-chlorobenzo[d]thiazol-2-yl)thio)-N-(7-cyano-7-azabicyclo[2.2.1]heptan-2-yl)acetamide;

Racemic, endo 2-(4-((4-chlorophenyl)thio)piperidine-1-carbonyl)-7-azabicyclo[2.2.1]heptane-7-carbonitrile;

Racemic, endo N-(7-cyano-7-azabicyclo[2.2.1]heptan-2-yl)-1-(4-methyl-2-pyrimidinyl)-2,3-dihydro-1H-indole-5-carboxamide;

Racemic, endo N-(7-cyano-7-azabicyclo[2.2.1]heptan-2-yl)-1-(cyclopropylcarbonyl)-2,3-dihydro-1H-indole-5-carboxamide;

6-chloro-N-((1R,2R,4S)-7-cyano-7-azabicyclo[2.2.1]heptan-2-yl)-1-(6-methyl-2-pyridinyl)-1H-indazole-5-carboxamide;

N-((1R,2R,4S)-7-cyano-7-azabicyclo[2.2.1]heptan-2-yl)-1-(6-methyl-2-pyridinyl)-1H-indazole-5-carboxamide;

N-((1R,2R,4S)-7-cyano-7-azabicyclo[2.2.1]heptan-2-yl)-6-fluoro-1-(6-methyl-2-pyridinyl)-1H-indazole-5-carboxamide;

Racemic, endo N-(7-cyano-7-azabicyclo[2.2.1]heptan-2-yl)-4-(4-cyclopropyl-2-pyrimidinyl)-3,4-dihydro-2H-1,4-benzoxazine-7-carboxamide;

2-((4-chloro-1-naphthalenyl)oxy)-N-((1R,2R,4S)-7-cyano-7-azabicyclo[2.2.1]heptan-2-yl)acetamide;

2-((4-chloro-1-naphthalenyl)oxy)-N-((1R,2R,4S)-7-cyano-7-azabicyclo[2.2.1]heptan-2-yl)acetamide (peak 2 derived);

Racemic, endo 2-methyl-2-propanyl 5-((7-cyano-7-azabicyclo[2.2.1]heptan-2-yl)carbamoyl)-2,3-dihydro-1H-indole-1-carboxylate;

Racemic, endo N-(7-cyano-7-azabicyclo[2.2.1]heptan-2-yl)-1-(4-methyl-2-pyrimidinyl)-1H-indazole-5-carboxamide;

Racemic, endo N-(7-cyano-7-azabicyclo[2.2.1]heptan-2-yl)-1-(4-methyl-2-pyrimidinyl)-1H-benzimidazole-5-carboxamide;

Racemic, endo N-(7-cyano-7-azabicyclo[2.2.1]heptan-2-yl)-1-(4-cyclopropyl-2-pyridinyl)-1H-indazole-5-carboxamide;

Racemic, endo N-(7-cyano-7-azabicyclo[2.2.1]heptan-2-yl)-1-(6-cyclopropyl-2-pyridinyl)-1H-indazole-5-carboxamide;

N-((1R,2R,4S)-7-cyano-7-azabicyclo[2.2.1]heptan-2-yl)-1-(6-cyclopropyl-2-pyridinyl)-1H-indazole-5-carboxamide;

3-(4-chloro-3-(trifluoromethyl)phenyl)-N-((1R,2R,4S)-7-cyano-7-azabicyclo[2.2.1]heptan-2-yl)propanamide;

N-((1R,2R,4S)-7-cyano-7-azabicyclo[2.2.1]heptan-2-yl)-1-(6-ethyl-2-pyridinyl)-1H-indazole-5-carboxamide;

N-((1R,2R,4S)-7-cyano-7-azabicyclo[2.2.1]heptan-2-yl)-1-(4-methyl-2-pyrimidinyl)-1H-pyrrolo[3,2-b]pyridine-5-carboxamide;

N-((1R,2R,4S)-7-cyano-7-azabicyclo[2.2.1]heptan-2-yl)-4-fluoro-1-(4-methyl-2-pyrimidinyl)-1H-indole-5-carboxamide;

N-((1R,2R,4S)-7-cyano-7-azabicyclo[2.2.1]heptan-2-yl)-4-(methyl(4-methyl-2-pyrimidinyl)amino)benzamide;

N-((1R,2R,4S)-7-cyano-7-azabicyclo[2.2.1]heptan-2-yl)-4-methyl-1-(4-methyl-2-pyrimidinyl)-1H-indole-5-carboxamide;

Racemic, endo N-(7-cyano-7-azabicyclo[2.2.1]heptan-2-yl)-4-(2-pyrimidinylamino)benzamide;

N-((1R,2R,4S)-7-cyano-7-azabicyclo[2.2.1]heptan-2-yl)-6-(3,5-dimethyl-1,2-oxazol-4-yl)-1H-indole-2-carboxamide;

N-((1R,2R,4S)-7-cyano-7-azabicyclo[2.2.1]heptan-2-yl)-1-(4-cyclopropyl-2-pyrimidinyl)-2,3-dihydro-1H-indole-5-carboxamide;

N-((1R,2R,4S)-7-cyano-7-azabicyclo[2.2.1]heptan-2-yl)-1-(4-cyclopropyl-2-pyrimidinyl)-2,3-dihydro-1H-indole-5-carboxamide;

N-((1R,2R,4S)-7-cyano-7-azabicyclo[2.2.1]heptan-2-yl)-4-(1-methyl-1H-pyrazol-4-yl)benzamide;

6-chloro-N-((1R,2R,4S)-7-cyano-7-azabicyclo[2.2.1]heptan-2-yl)-1-(4-methyl-2-pyrimidinyl)-2,3-dihydro-1H-indole-5-carboxamide;

5-(3-chlorophenyl)-N-((1R,2R,4S)-7-cyano-7-azabicyclo[2.2.1]heptan-2-yl)-4-methyl-1,3-thiazole-2-carboxamide; and 5-(3-chlorophenyl)-N-((1R,2R,4S)-7-cyano-7-azabicyclo[2.2.1]heptan-2-yl)-1,3-thiazole-2-carboxamide.

In a twenty fourth embodiment, the invention provides compounds of the first embodiment and pharmaceutically acceptable salts thereof in which the compound is recited in the below Table B.

TABLE B 2-chloro-N-((1R,2R,4S)-7-cyano-7-azabicyclo[2.2.1]heptan-2-yl)-4-((cyclopropylcarbonyl)amino)benzamide;

2-chloro-N-((1R,2R,4S)-7-cyano-7-azabicyclo[2.2.1]heptan-2-yl)-4-(1H-indazol-1-yl)benzamide;

(3R)-6-chloro-N-((1R,2R,4S)-7-cyano-7-azabicyclo[2.2.1]heptan-2-yl)-2,3,4,9-tetrahydro-1H-carbazole-3-carboxamide;

(3S)-6-chloro-N-((1R,2R,4S)-7-cyano-7-azabicyclo[2.2.1]heptan-2-yl)-2,3,4,9-tetrahydro-1H-carbazole-3-carboxamide;

(4R)-7-chloro-N-((1R,2R,4S)-7-cyano-7-azabicyclo[2.2.1]heptan-2-yl)-2,3,4,5-tetrahydro-1-benzoxepine-4-carboxamide;

5-chloro-N-((1R,2R,4S)-7-cyano-7-azabicyclo[2.2.1]heptan-2-yl)-1-methyl-3-(6-methyl-2-pyridinyl)-1H-indazole-6-carboxamide;

N-((1R,2R,4S)-7-cyano-7-azabicyclo[2.2.1]heptan-2-yl)-1-(cyclopropylmethyl)-3-(6-methyl-2-pyridinyl)-1H-indazole-6-carboxamide;

N-((1R,2R,4S)-7-cyano-7-azabicyclo[2.2.1]heptan-2-yl)-1-(2-methylpropyl)-3-(6-methyl-2-pyridinyl)-1H-indazole-6-carboxamide;

N-((1R,2R,4S)-7-cyano-7-azabicyclo[2.2.1]heptan-2-yl)-3-(6-methyl-2-pyridinyl)-1-(4,4,4-trifluorobutyl)-1H-indazole-6-carboxamide;

N-((1R,2R,4S)-7-cyano-7-azabicyclo[2.2.1]heptan-2-yl)-3-(6-methyl-2-pyridinyl)-1-propyl-1H-indazole-6-carboxamide;

6-chloro-N-((1R,2R,4S)-7-cyano-7-azabicyclo[2.2.1]heptan-2-yl)-1-(6-(2,2,2-trifluoroethoxy)-2-pyridinyl)-1H-indazole-5-carboxamide;

6-chloro-N-((1R,2R,4S)-7-cyano-7-azabicyclo[2.2.1]heptan-2-yl)-1-(1,7-naphthyridin-2-yl)-1H-indazole-5-carboxamide;

6-chloro-N-((1R,2R,4S)-7-cyano-7-azabicyclo[2.2.1]heptan-2-yl)-1-(6-(cyanomethyl)-2-pyridinyl)-1H-indazole-5-carboxamide;

6-chloro-N-((1R,2R,4S)-7-cyano-7-azabicyclo[2.2.1]heptan-2-yl)-1-(1,8-naphthyridin-2-yl)-1H-indazole-5-carboxamide;

4-(3-chlorophenyl)-N-((1R,2R,4S)-7-cyano-7-azabicyclo[2.2.1]heptan-2-yl)-1,3-thiazole-2-carboxamide;

N-((1R,2R,4S)-7-cyano-7-azabicyclo[2.2.1]heptan-2-yl)-2-(3-thiophenyl)-1,3-thiazole-4-carboxamide;

1-(3-chlorophenyl)-N-((1R,2R,4S)-7-cyano-7-azabicyclo[2.2.1]heptan-2-yl)-1H-pyrazole-3-carboxamide;

1-(3-chlorophenyl)-N-((1R,2R,4S)-7-cyano-7-azabicyclo[2.2.1]heptan-2-yl)-5-methyl-1H-pyrazole-3-carboxamide;

N-((1R,2R,4S)-7-cyano-7-azabicyclo[2.2.1]heptan-2-yl)-3-(2-methyl-1,3-thiazol-4-yl)benzamide;

7-bromo-N-((1R,2R,4S)-7-cyano-7-azabicyclo[2.2.1]heptan-2-yl)-1-oxo-1,2-dihydro-3-isoquinolinecarboxamide;

(3S)—N-((1R,2R,4S)-7-cyano-7-azabicyclo[2.2.1]heptan-2-yl)-1-phenyl-3-pyrrolidinecarboxamide;

(2S,3S)—N-((1R,2R,4S)-7-cyano-7-azabicyclo[2.2.1]heptan-2-yl)-2-methyl-1-phenyl-3-pyrrolidinecarboxamide;

(3S)—N-((1R,2R,4S)-7-cyano-7-azabicyclo[2.2.1]heptan-2-yl)-1-(4-cyano-2-fluorophenyl)-3-pyrrolidinecarboxamide;

(3S)-1-(3-chlorophenyl)-N-((1R,2R,4S)-7-cyano-7-azabicyclo[2.2.1]heptan-2-yl)-3-pyrrolidinecarboxamide;

N-((1R,2R,4S)-7-cyano-7-azabicyclo[2.2.1]heptan-2-yl)-5-phenyl-2-furancarboxamide;

N-((1R,2R,4S)-7-cyano-7-azabicyclo[2.2.1]heptan-2-yl)-5-(3-(2-propanyl)phenyl)-2-furancarboxamide;

N-((1R,2R,4S)-7-cyano-7-azabicyclo[2.2.1]heptan-2-yl)-5-(3-(trifluoromethyl)phenyl)-2-furancarboxamide;

(3R)-1-(3-chlorophenyl)-N-((1R,2R,4S)-7-cyano-7-azabicyclo[2.2.1]heptan-2-yl)-3-piperidinecarboxamide;

N-((1R,2R,4S)-7-cyano-7-azabicyclo[2.2.1]heptan-2-yl)-1-(4-(trifluoromethyl)-2-pyrimidinyl)-4-piperidinecarboxamide;

(3S)-1-(3-bromophenyl)-N-((1R,2R,4S)-7-cyano-7-azabicyclo[2.2.1]heptan-2-yl)-3-pyrrolidinecarboxamide;

(3S)-1-(3-chloro-4-(trifluoromethyl)phenyl)-N-((1R,2R,4S)-7-cyano-7-azabicyclo[2.2.1]heptan-2-yl)-3-pyrrolidinecarboxamide;

(3S)-6-chloro-N-((1R,2R,4S)-7-cyano-7-azabicyclo[2.2.1]heptan-2-yl)-3,4-dihydro-2H-chromene-3-carboxamide;

2-chloro-N-((1R,2R,4S)-7-cyano-7-azabicyclo[2.2.1]heptan-2-yl)-4-(6-cyclopropyl-2-pyridinyl)benzamide;

1-(3-chlorophenyl)-N-((1R,2R,4S)-7-cyano-7-azabicyclo[2.2.1]heptan-2-yl)-4-piperidinecarboxamide;

N-((1R,2R,4S)-7-cyano-7-azabicyclo[2.2.1]heptan-2-yl)-1-(3,5-dichlorophenyl)-4-piperidinecarboxamide;

(3S)—N-((1R,2R,4S)-7-cyano-7-azabicyclo[2.2.1]heptan-2-yl)-1-(4-methyl-2-pyridinyl)-3-pyrrolidinecarboxamide;

(3S)—N-((1R,2R,4S)-7-cyano-7-azabicyclo[2.2.1]heptan-2-yl)-1-(5-cyano-3-pyridinyl)-3-pyrrolidinecarboxamide;

(3S)—N-((1R,2R,4S)-7-cyano-7-azabicyclo[2.2.1]heptan-2-yl)-1-(2-methoxy-4-pyridinyl)-3-pyrrolidinecarboxamide;

(3S)—N-((1R,2R,4S)-7-cyano-7-azabicyclo[2.2.1]heptan-2-yl)-1-(6-methyl-2-pyridinyl)-3-pyrrolidinecarboxamide;

(3S)—N-((1R,2R,4S)-7-cyano-7-azabicyclo[2.2.1]heptan-2-yl)-1-(6-methyl-2-pyrazinyl)-3-pyrrolidinecarboxamide;

(3R)—N-((1R,2R,4S)-7-cyano-7-azabicyclo[2.2.1]heptan-2-yl)-1-(3,5-dichlorophenyl)-3-methyl-3-pyrrolidinecarboxamide;

(3S)—N-((1R,2R,4S)-7-cyano-7-azabicyclo[2.2.1]heptan-2-yl)-1-(3,5-dichlorophenyl)-3-fluoro-3-pyrrolidinecarboxamide;

(1S,4R,5R)—N-((1R,2R,4S)-7-cyano-7-azabicyclo[2.2.1]heptan-2-yl)-2-(3,5-dichlorophenyl)-2-azabicyclo[3.1.0]hexane-4-carboxamide;

2-(3-chlorophenyl)-N-((1R,2R,4S)-7-cyano-7-azabicyclo[2.2.1]heptan-2-yl)-1,3-oxazole-5-carboxamide;

(3S)—N-((1R,2R,4S)-7-cyano-7-azabicyclo[2.2.1]heptan-2-yl)-1-(3-(cyanomethyl)phenyl)-3-pyrrolidinecarboxamide;

(3S)-1-(3-chloro-5-methoxyphenyl)-N-((1R,2R,4S)-7-cyano-7-azabicyclo[2.2.1]heptan-2-yl)-3-pyrrolidinecarboxamide;

N-((1R,2R,4S)-7-cyano-7-azabicyclo[2.2.1]heptan-2-yl)-1-(3,5-dichlorophenyl)-L-prolinamide;

3'-chloro-N-((1R,2R,4S)-7-cyano-7-azabicyclo[2.2.1]heptan-2-yl)[biphenyl]-3-carboxamide;

N-((1R,2R,4S)-7-cyano-7-azabicyclo[2.2.1]heptan-2-yl)-4-(2,5-dichlorophenyl)-5-methyl-2-pyridinecarboxamide;

4-(3-chlorophenyl)-N-((1R,2R,4S)-7-cyano-7-azabicyclo[2.2.1]heptan-2-yl)-5-methyl-2-pyridinecarboxamide;

N-((1R,2R,4S)-7-cyano-7-azabicyclo[2.2.1]heptan-2-yl)-1-(6-(1-cyanocyclopropyl)-2-pyridinyl)-4-piperidinecarboxamide;

N-((1R,2R,4S)-7-cyano-7-azabicyclo[2.2.1]heptan-2-yl)-6-(3-(1-cyanocyclopropyl)phenyl)-3-pyridinecarboxamide;

3-chloro-N-((1R,2R,4S)-7-cyano-7-azabicyclo[2.2.1]heptan-2-yl)-3'-cyclopropyl-5'-fluoro[biphenyl]-4-carboxamide;

N-((1R,2R,4S)-7-cyano-7-azabicyclo[2.2.1]heptan-2-yl)-6-(1-cyanocyclopropyl)[2,3'-bipyridine]-6'-carboxamide;

2-chloro-N-((1R,2R,4S)-7-cyano-7-azabicyclo[2.2.1]heptan-2-yl)-4-(6-(1-ethynylcyclopropyl)-2-pyridinyl)benzamide;

2-chloro-N-((1R,2R,4S)-7-cyano-7-azabicyclo[2.2.1]heptan-2-yl)-4-((3R)-3-cyano-3-methyl-2,3-dihydro-1H-inden-5-yl)benzamide;

2-chloro-N-((1R,2R,4S)-7-cyano-7-azabicyclo[2.2.1]heptan-2-yl)-4-((3S)-3-cyano-3-methyl-2,3-dihydro-1H-inden-5-yl)benzamide;

2-chloro-N-((1R,2R,4S)-7-cyano-7-azabicyclo[2.2.1]heptan-2-yl)-4-(6-(2-methyl-2-propanyl)-2-pyridinyl)benzamide;

(1S,6R,7R)—N-((1R,2R,4S)-7-cyano-7-azabicyclo[2.2.1]heptan-2-yl)-3-(3,5-dichlorophenyl)-3-azabicyclo[4.1.0]heptane-7-carboxamide;

(1R,6S,7R)—N-((1R,2R,4S)-7-cyano-7-azabicyclo[2.2.1]heptan-2-yl)-3-(3,5-dichlorophenyl)-3-azabicyclo[4.1.0]heptane-7-carboxamide;

(1S,6R,7R)—N-((1R,2R,4S)-7-cyano-7-azabicyclo[2.2.1]heptan-2-yl)-3-(3,5-dichlorophenyl)-3-azabicyclo[4.1.0]heptane-7-carboxamide;

(3S)—N-((1R,2R,4S)-7-cyano-7-azabicyclo[2.2.1]heptan-2-yl)-1-(6-cyclopropyl-2-pyridinyl)-3-piperidinecarboxamide;

(1S,5S)—N-((1R,2R,4S)-7-cyano-7-azabicyclo[2.2.1]heptan-2-yl)-3-(3,5-dichlorophenyl)-3-azabicyclo[3.1.0]hexane-1-carboxamide;

(1R,5R)—N-((1R,2S,4S)-7-cyano-7-azabicyclo[2.2.1]heptan-2-yl)-3-(3,5-dichlorophenyl)-3-azabicyclo[3.1.0]hexane-1-carboxamide;
(1R,5S)—N-((1R,2R,4S)-7-cyano-7-azabicyclo[2.2.1]heptan-2-yl)-3-(3,5-dichlorophenyl)-3-azabicyclo[3.1.0]hexane-1-carboxamide;
(3S)—N-((1R,2R,4S)-7-cyano-7-azabicyclo[2.2.1]heptan-2-yl)-1-(6-(1-cyanocyclopropyl)-2-pyridinyl)-3-piperidinecarboxamide;
N-((1R,2R,4S)-7-cyano-7-azabicyclo[2.2.1]heptan-2-yl)-1-cyclopentyl-1H-indazole-3-carboxamide;
N-((1R,2R,4S)-7-cyano-7-azabicyclo[2.2.1]heptan-2-yl)-1-(6-cyclopropyl-2-pyridinyl)-4-piperidinecarboxamide;
N-((1R,2R,4S)-7-cyano-7-azabicyclo[2.2.1]heptan-2-yl)-1-(3,5-dichlorophenyl)-1H-1,2,4-triazole-3-carboxamide;
2-chloro-N-((1R,2R,4S)-7-cyano-7-azabicyclo[2.2.1]heptan-2-yl)-4-(6-(2-cyano-2-propanyl)-2-pyrazinyl)benzamide;
2-chloro-N-((1R,2R,4S)-7-cyano-7-azabicyclo[2.2.1]heptan-2-yl)-4-((3S)-3-cyano-1-pipendinyl)benzamide;
2-chloro-N-((1R,2R,4S)-7-cyano-7-azabicyclo[2.2.1]heptan-2-yl)-4-((3R)-3-cyano-1-piperidinyl)benzamide;
2-chloro-N-((1R,2R,4S)-7-cyano-7-azabicyclo[2.2.1]heptan-2-yl)-4-((3S)-3-cyano-1-piperidinyl)benzamide;
2-chloro-N-((1R,2R,4S)-7-cyano-7-azabicyclo[2.2.1]heptan-2-yl)-4-((3R)-3-cyano-3-methyl-2,3-dihydro-1H-inden-5-yl)benzamide;
2-chloro-N-((1R,2R,4S)-7-cyano-7-azabicyclo[2.2.1]heptan-2-yl)-4-((1S,2S,5R)-2-cyano-6-azabicyclo[3.2.1]octan-6-yl)benzamide;
N-((1R,2R,4S)-7-cyano-7-azabicyclo[2.2.1]heptan-2-yl)-1-(3-cyanophenyl)-1H-pyrazole-3-carboxamide;
2-chloro-N-((1R,2R,4S)-7-cyano-7-azabicyclo[2.2.1]heptan-2-yl)-4-(6-(1-cyanocyclobutyl)-2-pyridinyl)benzamide;
(2S)—N-((1R,2R,4S)-7-cyano-7-azabicyclo[2.2.1]heptan-2-yl)-1-(3,5-dichlorobenzyl)-2-azetidinecarboxamide;
(2R)—N-((1R,2R,4S)-7-cyano-7-azabicyclo[2.2.1]heptan-2-yl)-1-(3,5-dichlorobenzyl)-2-azetidinecarboxamide;
2-chloro-N-((1R,2R,4S)-7-cyano-7-azabicyclo[2.2.1]heptan-2-yl)-4-((3S)-3-(cyanomethyl)-1-pyrrolidinyl)benzamide;
2-chloro-N-((1R,2R,4S)-7-cyano-7-azabicyclo[2.2.1]heptan-2-yl)-4-((3R)-3-(cyanomethyl)-1-pyrrolidinyl)benzamide;
N-((1R,2R,4S)-7-cyano-7-azabicyclo[2.2.1]heptan-2-yl)-1-(3-cyanophenyl)-1H-indazole-3-carboxamide;
(3R)—N-((1R,2R,4S)-7-cyano-7-azabicyclo[2.2.1]heptan-2-yl)-1-(3,5-dichlorobenzyl)-3-pyrrolidinecarboxamide;
(3S)—N-((1R,2R,4S)-7-cyano-7-azabicyclo[2.2.1]heptan-2-yl)-1-(6-(1-cyanocyclopropyl)-2-pyridinyl)-3-pyrrolidinecarboxamide;
2-chloro-N-((1R,2R,4S)-7-cyano-7-azabicyclo[2.2.1]heptan-2-yl)-4-((1S,2R,5R)-2-cyano-6-azabicyclo[3.2.1]octan-6-yl)benzamide;
2-chloro-N-((1R,2R,4S)-7-cyano-7-azabicyclo[2.2.1]heptan-2-yl)-4-((1-cyanocyclopropyl)methoxy)benzamide;
N-((1R,2R,4S)-7-cyano-7-azabicyclo[2.2.1]heptan-2-yl)-4-(6-(1-cyanocyclopropyl)-2-pyridinyl)-2-cyclopropylbenzamide;
2-chloro-N-((1R,2R,4S)-7-cyano-7-azabicyclo[2.2.1]heptan-2-yl)-3-((cis-3-cyanocyclobutyl)oxy)benzamide;
2-chloro-N-((1S,2R,4R)-7-cyano-7-azabicyclo[2.2.1]heptan-2-yl)-4-((3R)-3-(cyanomethyl)-1-pyrrolidinyl)benzamide;
2-chloro-N-((1R,2R,4S)-7-cyano-7-azabicyclo[2.2.1]heptan-2-yl)-4-((cis-3-cyanocyclobutyl)oxy)benzamide;
2-chloro-N-((1R,2R,4S)-7-cyano-7-azabicyclo[2.2.1]heptan-2-yl)-4-(6-(1-cyano-3,3-difluorocyclobutyl)-3-pyridinyl)benzamide;
2-chloro-N-((1R,2R,4S)-7-cyano-7-azabicyclo[2.2.1]heptan-2-yl)-3'-(1-cyanocyclopropyl)[biphenyl]-3-carboxamide;
2-chloro-N-((1R,2R,4S)-7-cyano-7-azabicyclo[2.2.1]heptan-2-yl)-4-((3S)-3-(cyanomethyl)-1-piperidinyl)benzamide;
2-chloro-N-((1R,2R,4S)-7-cyano-7-azabicyclo[2.2.1]heptan-2-yl)-4-((3R)-3-(cyanomethyl)-1-piperidinyl)benzamide;
3-chloro-N-((1R,2R,4S)-7-cyano-7-azabicyclo[2.2.1]heptan-2-yl)-3'-(1-cyanocyclopropyl)-5'-fluoro[biphenyl]-4-carboxamide;
2-chloro-N-((1R,2R,4S)-7-cyano-7-azabicyclo[2.2.1]heptan-2-yl)-4-(4,5,6,7-tetrahydro-1H-indazol-1-yl)benzamide;
2-chloro-N-((1R,2R,4S)-7-cyano-7-azabicyclo[2.2.1]heptan-2-yl)-4-(5,6-dihydrocyclopenta[c]pyrazol-1(4H)-yl)benzamide;
2-chloro-N-((1R,2R,4S)-7-cyano-7-azabicyclo[2.2.1]heptan-2-yl)-4-(5,6-dihydrocyclopenta[c]pyrazol-2(4H)-yl)benzamide;
2-chloro-N-((1R,2R,4S)-7-cyano-7-azabicyclo[2.2.1]heptan-2-yl)-4-((3S)-3-(cyanomethyl)-1-piperidinyl)benzamide;
(3S)-6-chloro-N-((1R,2R,4S)-7-cyano-7-azabicyclo[2.2.1]heptan-2-yl)-N,9-dimethyl-2,3,4,9-tetrahydro-1H-carbazole-3-carboxamide;
N-((1R,2R,4S)-7-cyano-7-azabicyclo[2.2.1]heptan-2-yl)-1-(6-cyclopropyl-2-pyridinyl)-6-fluoro-N-methyl-1H-indazole-5-carboxamide;
6-chloro-N-((1R,2R,4S)-7-cyano-7-azabicyclo[2.2.1]heptan-2-yl)-N-methyl-1-(6-methyl-2-pyridinyl)-1H-indazole-5-carboxamide;
N-((1R,2R,4S)-7-cyano-7-azabicyclo[2.2.1]heptan-2-yl)-6-fluoro-N-methyl-1-(6-methyl-2-pyridinyl)-1H-indazole-5-carboxamide;
N-((1R,2R,4S)-7-cyano-7-azabicyclo[2.2.1]heptan-2-yl)-N,1-dimethyl-3-(6-methyl-2-pyridinyl)-1H-indazole-6-carboxamide;
(3R)-1-(3-chlorophenyl)-N-((1R,2R,4S)-7-cyano-7-azabicyclo[2.2.1]heptan-2-yl)-N-methyl-3-pyrrolidinecarboxamide;
(3S)-1-(3-chlorophenyl)-N-((1R,2R,4S)-7-cyano-7-azabicyclo[2.2.1]heptan-2-yl)-N-methyl-3-pyrrolidinecarboxamide;
(3R)-1-(3-chlorophenyl)-N-((1R,2R,4S)-7-cyano-7-azabicyclo[2.2.1]heptan-2-yl)-N-methyl-5-oxo-3-pyrrolidinecarboxamide;
(3S)—N-((1R,2R,4S)-7-cyano-7-azabicyclo[2.2.1]heptan-2-yl)-1-(3,5-dichlorophenyl)-N-methyl-3-pyrrolidinecarboxamide;
(3S)—N-((1R,2R,4S)-7-cyano-7-azabicyclo[2.2.1]heptan-2-yl)-1-(3-cyano-6-(trifluoromethyl)-2-pyridinyl)-N-methyl-3-pyrrolidinecarboxamide;
N-((1R,2R,4S)-7-cyano-7-azabicyclo[2.2.1]heptan-2-yl)-N-methyl-1-(2,3,5-trichlorophenyl)-L-prolinamide;
N-((1R,2R,4S)-7-cyano-7-azabicyclo[2.2.1]heptan-2-yl)-N-methyl-1-(2,3,5-trichlorophenyl)-D-prolinamide;
N-((1R,2R,4S)-7-cyano-7-azabicyclo[2.2.1]heptan-2-yl)-6-(4-methyl-2-pyrimidinyl)-1H-indole-2-carboxamide;
5-(3-chlorophenyl)-N-((1R,2R,4S)-7-cyano-7-azabicyclo[2.2.1]heptan-2-yl)-2-furancarboxamide;

(3R)—N-((1R,2R,4S)-7-cyano-7-azabicyclo[2.2.1]heptan-2-yl)-1-(4-cyclopropyl-2-pyrimidinyl)-3-pyrrolidinecarboxamide;
(3R)—N-((1R,2R,4S)-7-cyano-7-azabicyclo[2.2.1]heptan-2-yl)-1-(3-(trifluoromethyl)phenyl)-3-pyrrolidinecarboxamide;
(3R)—N-((1R,2R,4S)-7-cyano-7-azabicyclo[2.2.1]heptan-2-yl)-1-(3,5-dichlorophenyl)-3-pyrrolidinecarboxamide;
(3R)—N-((1R,2R,4S)-7-cyano-7-azabicyclo[2.2.1]heptan-2-yl)-1-(6-(trifluoromethyl)-2-pyridinyl)-3-pyrrolidinecarboxamide;
N-((1R,2R,4S)-7-cyano-7-azabicyclo[2.2.1]heptan-2-yl)-1-(2-quinolinyl)-1H-indazole-5-carboxamide;
N-((1R,2R,4S)-7-cyano-7-azabicyclo[2.2.1]heptan-2-yl)-1-(6-(1H-imidazol-1-yl)-2-pyridinyl)-1H-indazole-5-carboxamide;
N-((1R,2R,4S)-7-cyano-7-azabicyclo[2.2.1]heptan-2-yl)-1-(6-phenyl-2-pyridinyl)-1H-indazole-5-carboxamide;
N-((1R,2R,4S)-7-cyano-7-azabicyclo[2.2.1]heptan-2-yl)-1-(6-(1H-pyrazol-1-yl)-2-pyridinyl)-1H-indazole-5-carboxamide;
N-((1R,2R,4S)-7-cyano-7-azabicyclo[2.2.1]heptan-2-yl)-1-(6-(1,1-difluoroethyl)-2-pyridinyl)-1H-indazole-5-carboxamide;
N-((1R,2R,4S)-7-cyano-7-azabicyclo[2.2.1]heptan-2-yl)-1-(6-(difluoromethoxy)-2-pyridinyl)-1H-indazole-5-carboxamide;
N-((1R,2R,4S)-7-cyano-7-azabicyclo[2.2.1]heptan-2-yl)-1-(6-(difluoromethyl)-2-pyridinyl)-1H-indazole-5-carboxamide;
1-([2,2'-bipyridin]-6-yl)-N-((1R,2R,4S)-7-cyano-7-azabicyclo[2.2.1]heptan-2-yl)-1H-indazole-5-carboxamide;
(1R,5R)-3-(3-chlorophenyl)-N-((1R,2R,4S)-7-cyano-7-azabicyclo[2.2.1]heptan-2-yl)-3-azabicyclo[3.1.0]hexane-1-carboxamide;
N-((1R,2R,4S)-7-cyano-7-azabicyclo[2.2.1]heptan-2-yl)-1-(3,5-dichlorophenyl)-1H-pyrazole-3-carboxamide;
(1S,4R,5S)—N-((1R,2R,4S)-7-cyano-7-azabicyclo[2.2.1]heptan-2-yl)-2-(3,5-dichlorophenyl)-2-azabicyclo[3.1.0]hexane-4-carboxamide;
(1S,4S,5S)—N-((1R,2R,4S)-7-cyano-7-azabicyclo[2.2.1]heptan-2-yl)-2-(3,5-dichlorophenyl)-2-azabicyclo[3.1.0]hexane-4-carboxamide;
(1S,4S,5S)—N-((1R,2R,4S)-7-cyano-7-azabicyclo[2.2.1]heptan-2-yl)-2-(3,5-dichlorophenyl)-2-azabicyclo[3.1.0]hexane-4-carboxamide;
(4S)—N-((1S,2R,4S)-7-cyano-7-azabicyclo[2.2.1]heptan-2-yl)-1-(3,5-dichlorophenyl)-4-azepanecarboxamide;
N-((1R,2R,4S)-7-cyano-7-azabicyclo[2.2.1]heptan-2-yl)-5-(1-methyl-1H-pyrazol-4-yl)-1,3-thiazole-2-carboxamide;
N-((1R,2R,4S)-7-cyano-7-azabicyclo[2.2.1]heptan-2-yl)-2-(3-cyanophenyl)-1,3-thiazole-4-carboxamide;
N-((1R,2R,4S)-7-cyano-7-azabicyclo[2.2.1]heptan-2-yl)-2-(3-cyclopropylphenyl)-1,3-thiazole-4-carboxamide;
N-((1R,2R,4S)-7-cyano-7-azabicyclo[2.2.1]heptan-2-yl)-7-(4-methyl-2-pyrimidinyl)-1H-indole-3-carboxamide;
N-((1R,2R,4S)-7-cyano-7-azabicyclo[2.2.1]heptan-2-yl)-7-(6-methyl-2-pyridinyl)-1H-indole-3-carboxamide;
N-((1R,2R,4S)-7-cyano-7-azabicyclo[2.2.1]heptan-2-yl)-1-(6-methyl-2-pyridinyl)-7-(trifluoromethyl)-1H-indazole-5-carboxamide;
(3R)-1-(3-chlorophenyl)-N-((1R,2R,4S)-7-cyano-7-azabicyclo[2.2.1]heptan-2-yl)-5-oxo-3-pyrrolidinecarboxamide;
(3S)-1-(3-chlorophenyl)-N-((1R,2R,4S)-7-cyano-7-azabicyclo[2.2.1]heptan-2-yl)-5-oxo-3-pyrrolidinecarboxamide;
(3S)-1-(3-chlorophenyl)-N-((1R,2R,4S)-7-cyano-7-azabicyclo[2.2.1]heptan-2-yl)-3-pyrrolidinecarboxamide;
(3R)-1-(3-chlorophenyl)-N-((1R,2R,4S)-7-cyano-7-azabicyclo[2.2.1]heptan-2-yl)-3-pyrrolidinecarboxamide;
(2S)-5-bromo-N-((1R,2R,4S)-7-cyano-7-azabicyclo[2.2.1]heptan-2-yl)-2,3-dihydro-1H-indene-2-carboxamide;
(2R)-5-bromo-N-((1R,2R,4S)-7-cyano-7-azabicyclo[2.2.1]heptan-2-yl)-2,3-dihydro-1H-indene-2-carboxamide;
(3R)—N-((1R,2R,4S)-7-cyano-7-azabicyclo[2.2.1]heptan-2-yl)-1-(4-cyclopropyl-2-pyrimidinyl)-3-pyrrolidinecarboxamide;
(3R)—N-((1R,2R,4S)-7-cyano-7-azabicyclo[2.2.1]heptan-2-yl)-1-(6-(trifluoromethyl)-2-pyridinyl)-3-pyrrolidinecarboxamide;
(3S)—N-((1R,2R,4S)-7-cyano-7-azabicyclo[2.2.1]heptan-2-yl)-1-(6-(trifluoromethyl)-2-pyridinyl)-3-pyrrolidinecarboxamide;
(3S)—N-((1R,2R,4S)-7-cyano-7-azabicyclo[2.2.1]heptan-2-yl)-1-(3,5-dichlorophenyl)-3-pyrrolidinecarboxamide;
(3S)-1-(5-chloro-2-cyanophenyl)-N-((1R,2R,4S)-7-cyano-7-azabicyclo[2.2.1]heptan-2-yl)-3-pyrrolidinecarboxamide;
(3S)—N-((1R,2R,4S)-7-cyano-7-azabicyclo[2.2.1]heptan-2-yl)-1-(6-cyano-4-(trifluoromethyl)-2-pyridinyl)-3-pyrrolidinecarboxamide;
(3S)—N-((1R,2R,4S)-7-cyano-7-azabicyclo[2.2.1]heptan-2-yl)-1-(6-cyano-4-methyl-2-pyridinyl)-3-pyrrolidinecarboxamide;
(3S)—N-((1R,2R,4S)-7-cyano-7-azabicyclo[2.2.1]heptan-2-yl)-1-(4-methyl-6-(trifluoromethyl)-2-pyridinyl)-3-pyrrolidinecarboxamide;
(3S)—N-((1R,2R,4S)-7-cyano-7-azabicyclo[2.2.1]heptan-2-yl)-1-(4-cyano-6-(trifluoromethyl)-2-pyridinyl)-3-pyrrolidinecarboxamide;
(3S)—N-((1R,2R,4S)-7-cyano-7-azabicyclo[2.2.1]heptan-2-yl)-1-(3-cyano-6-(trifluoromethyl)-2-pyridinyl)-3-pyrrolidinecarboxamide;
(3S)—N-((1R,2R,4S)-7-cyano-7-azabicyclo[2.2.1]heptan-2-yl)-1-(6-(trifluoromethyl)-2-pyrazinyl)-3-pyrrolidinecarboxamide;
(3S)-1-(3-chloro-6-(trifluoromethyl)-2-pyridinyl)-N-((1R,2R,4S)-7-cyano-7-azabicyclo[2.2.1]heptan-2-yl)-3-pyrrolidinecarboxamide;
(3S)—N-((1R,2R,4S)-7-cyano-7-azabicyclo[2.2.1]heptan-2-yl)-1-(3-methylphenyl)-3-pyrrolidinecarboxamide;
(3S)—N-((1R,2R,4S)-7-cyano-7-azabicyclo[2.2.1]heptan-2-yl)-1-(3-methoxyphenyl)-3-pyrrolidinecarboxamide;
7-chloro-N-((1R,2R,4S)-7-cyano-7-azabicyclo[2.2.1]heptan-2-yl)-2,3-dihydro-1-benzoxepine-4-carboxamide;
(3S)—N-((1R,2R,4S)-7-cyano-7-azabicyclo[2.2.1]heptan-2-yl)-1-(2,5-dichlorophenyl)-3-pyrrolidinecarboxamide;
(3S)—N-((1R,2R,4S)-7-cyano-7-azabicyclo[2.2.1]heptan-2-yl)-1-(3,5-dichloro-4-(trifluoromethoxy)phenyl)-3-pyrrolidinecarboxamide;
(3S)-1-(3-chloro-5-(trifluoromethyl)phenyl)-N-((1R,2R,4S)-7-cyano-7-azabicyclo[2.2.1]heptan-2-yl)-3-pyrrolidinecarboxamide;
(3S)-1-(3-chloro-5-methylphenyl)-N-((1R,2R,4S)-7-cyano-7-azabicyclo[2.2.1]heptan-2-yl)-3-pyrrolidinecarboxamide;
(3S)-1-(5-chloro-2-methylphenyl)-N-((1R,2R,4S)-7-cyano-7-azabicyclo[2.2.1]heptan-2-yl)-3-pyrrolidinecarboxamide;
6-(3-chlorophenyl)-N-((1R,2R,4S)-7-cyano-7-azabicyclo[2.2.1]heptan-2-yl)-2-pyridinecarboxamide;
N-((1R,2R,4S)-7-cyano-7-azabicyclo[2.2.1]heptan-2-yl)-4-(2,5-dichlorophenyl)-2-pyridinecarboxamide;

N-((1R,2R,4S)-7-cyano-7-azabicyclo[2.2.1]heptan-2-yl)-4-(3,5-dichlorophenyl)-2-pyridinecarboxamide;

4-(3-chlorophenyl)-N-((1R,2R,4S)-7-cyano-7-azabicyclo[2.2.1]heptan-2-yl)-2-pyridinecarboxamide;

(3S)—N-((1R,2R,4S)-7-cyano-7-azabicyclo[2.2.1]heptan-2-yl)-1-(3,5-dichloro-4-methoxyphenyl)-3-pyrrolidinecarboxamide;

(3S)—N-((1R,2R,4S)-7-cyano-7-azabicyclo[2.2.1]heptan-2-yl)-1-(3,5-dichloro-4-fluorophenyl)-3-pyrrolidinecarboxamide;

(3S)—N-((1R,2R,4S)-7-cyano-7-azabicyclo[2.2.1]heptan-2-yl)-1-(3-cyclopropylphenyl)-3-pyrrolidinecarboxamide;

(2S)—N-((1R,2R,4S)-7-cyano-7-azabicyclo[2.2.1]heptan-2-yl)-4-(3,5-dichlorophenyl)-2-morpholinecarboxamide;

(3S)—N-((1R,2R,4S)-7-cyano-7-azabicyclo[2.2.1]heptan-2-yl)-1-(2,3,5-trichlorophenyl)-3-pyrrolidinecarboxamide;

N-((1R,2R,4S)-7-cyano-7-azabicyclo[2.2.1]heptan-2-yl)-1-(3,5-dichlorophenyl)-1H-pyrazole-4-carboxamide;

3-chloro-N-((1R,2R,4S)-7-cyano-7-azabicyclo[2.2.1]heptan-2-yl)-1-(3,5-dichlorophenyl)-1H-pyrazole-4-carboxamide;

(3S)-1-(3-chloro-5-cyanophenyl)-N-((1R,2R,4S)-7-cyano-7-azabicyclo[2.2.1]heptan-2-yl)-3-pyrrolidinecarboxamide;

(3S)-1-(2-chloro-5-cyanophenyl)-N-((1R,2R,4S)-7-cyano-7-azabicyclo[2.2.1]heptan-2-yl)-3-pyrrolidinecarboxamide;

(3S)—N-((1R,2R,4S)-7-cyano-7-azabicyclo[2.2.1]heptan-2-yl)-1-(2-oxo-1-(2-propanyl)-5-(trifluoromethyl)-1,2-dihydro-3-pyridinyl)-3-pyrrolidinecarboxamide;

(3S)—N-((1R,2R,4S)-7-cyano-7-azabicyclo[2.2.1]heptan-2-yl)-1-(3,4-dichlorophenyl)-3-pyrrolidinecarboxamide;

(3S)—N-((1R,2R,4S)-7-cyano-7-azabicyclo[2.2.1]heptan-2-yl)-1-(2,3-dichlorophenyl)-3-pyrrolidinecarboxamide;

(3S)-1-(2-chloro-5-(trifluoromethyl)phenyl)-N-((1R,2R,4S)-7-cyano-7-azabicyclo[2.2.1]heptan-2-yl)-3-pyrrolidinecarboxamide;

(1R,4R,5R)—N-((1R,2R,4S)-7-cyano-7-azabicyclo[2.2.1]heptan-2-yl)-2-(3,5-dichlorophenyl)-2-azabicyclo[3.1.0]hexane-4-carboxamide;

(1S,3S)—N-((1R,2R,4S)-7-cyano-7-azabicyclo[2.2.1]heptan-2-yl)-3-(2,5-dichlorophenyl)cyclopentanecarboxamide;

(1R,3R)—N-((1R,2R,4S)-7-cyano-7-azabicyclo[2.2.1]heptan-2-yl)-3-(2,5-dichlorophenyl)cyclopentanecarboxamide;

(1S,3R)—N-((1R,2R,4S)-7-cyano-7-azabicyclo[2.2.1]heptan-2-yl)-3-(2,5-dichlorophenyl)cyclopentanecarboxamide;

(5R)—N-((1R,2R,4S)-7-cyano-7-azabicyclo[2.2.1]heptan-2-yl)-1-(6-(1,1-difluoroethyl)-2-pyridinyl)-4,5,6,7-tetrahydro-1H-indazole-5-carboxamide;

(5R)—N-((1R,2R,4S)-7-cyano-7-azabicyclo[2.2.1]heptan-2-yl)-1-(6-(difluoromethoxy)-2-pyridinyl)-4,5,6,7-tetrahydro-1H-indazole-5-carboxamide;

(5S)—N-((1R,2R,4S)-7-cyano-7-azabicyclo[2.2.1]heptan-2-yl)-2-(6-(1-cyanocyclopropyl)-2-pyridinyl)-4,5,6,7-tetrahydro-2H-indazole-5-carboxamide;

(5S)—N-((1R,2R,4S)-7-cyano-7-azabicyclo[2.2.1]heptan-2-yl)-2-(6-(1,1-difluoroethyl)-2-pyridinyl)-4,5,6,7-tetrahydro-2H-indazole-5-carboxamide;

(5S)—N-((1R,2R,4S)-7-cyano-7-azabicyclo[2.2.1]heptan-2-yl)-2-(6-(difluoromethoxy)-2-pyridinyl)-4,5,6,7-tetrahydro-2H-indazole-5-carboxamide;

(5R)—N-((1R,2R,4S)-7-cyano-7-azabicyclo[2.2.1]heptan-2-yl)-2-(6-(1,1-difluoroethyl)-2-pyridinyl)-4,5,6,7-tetrahydro-2H-indazole-5-carboxamide;

(5R)—N-((1R,2R,4S)-7-cyano-7-azabicyclo[2.2.1]heptan-2-yl)-2-(6-(difluoromethoxy)-2-pyridinyl)-4,5,6,7-tetrahydro-2H-indazole-5-carboxamide;

(5R)—N-((1R,2R,4S)-7-cyano-7-azabicyclo[2.2.1]heptan-2-yl)-2-(6-(difluoromethyl)-2-pyridinyl)-4,5,6,7-tetrahydro-2H-indazole-5-carboxamide;

(3S)—N-((1R,2R,4S)-7-cyano-7-azabicyclo[2.2.1]heptan-2-yl)-1-(3,5-dichlorophenyl)-3-azepanecarboxamide;

7-chloro-N-((1R,2R,4S)-7-cyano-7-azabicyclo[2.2.1]heptan-2-yl)-2,3-dihydrobenzo[f][1,4]oxazepine-4(5H)-carboxamide;

7-chloro-N-((1R,2R,4S)-7-cyano-7-azabicyclo[2.2.1]heptan-2-yl)-1,2,3,5-tetrahydro-4H-1,4-benzodiazepine-4-carboxamide;

1-(6-acetamido-2-pyridinyl)-6-chloro-N-((1R,2R,4S)-7-cyano-7-azabicyclo[2.2.1]heptan-2-yl)-1H-indazole-5-carboxamide;

(5R)—N-((1R,2R,4S)-7-cyano-7-azabicyclo[2.2.1]heptan-2-yl)-1-(6-methyl-2-pyridinyl)-4,5,6,7-tetrahydro-1H-indazole-5-carboxamide;

(5S)—N-((1R,2R,4S)-7-cyano-7-azabicyclo[2.2.1]heptan-2-yl)-1-(6-methyl-2-pyridinyl)-4,5,6,7-tetrahydro-1H-indazole-5-carboxamide;

(5R)—N-((1R,2R,4S)-7-cyano-7-azabicyclo[2.2.1]heptan-2-yl)-2-(6-methyl-2-pyridinyl)-4,5,6,7-tetrahydro-2H-indazole-5-carboxamide;

(5S)—N-((1R,2R,4S)-7-cyano-7-azabicyclo[2.2.1]heptan-2-yl)-2-(6-methyl-2-pyridinyl)-4,5,6,7-tetrahydro-2H-indazole-5-carboxamide;

(5S)—N-((1R,2R,4S)-7-cyano-7-azabicyclo[2.2.1]heptan-2-yl)-2-(6-cyclopropyl-2-pyridinyl)-4,5,6,7-tetrahydro-2H-indazole-5-carboxamide;

(5R)—N-((1R,2R,4S)-7-cyano-7-azabicyclo[2.2.1]heptan-2-yl)-2-(6-cyclopropyl-2-pyridinyl)-4,5,6,7-tetrahydro-2H-indazole-5-carboxamide;

6-(5-azaspiro[2.5]octan-5-yl)-N-((1R,2R,4S)-7-cyano-7-azabicyclo[2.2.1]heptan-2-yl)-4-pyrimidinecarboxamide;

(2S)—N-((1R,2R,4S)-7-cyano-7-azabicyclo[2.2.1]heptan-2-yl)-2-(2,3-dichlorophenyl)-1-pyrrolidinecarboxamide;

N-((1R,2R,4S)-7-cyano-7-azabicyclo[2.2.1]heptan-2-yl)-6-((2R)-2-methyl-2-phenyl-4-morpholinyl)-4-pyrimidinecarboxamide;

6-((2R)-2-(4-chlorophenyl)-2-methyl-4-morpholinyl)-N-((1R,2R,4S)-7-cyano-7-azabicyclo[2.2.1]heptan-2-yl)-4-pyrimidinecarboxamide;

6-(((1-(4-bromophenyl)cyclopropyl)methyl)(methyl)amino)-N-((1R,2R,4S)-7-cyano-7-azabicyclo[2.2.1]heptan-2-yl)-4-pyrimidinecarboxamide;

2-chloro-N-((1S,2R,5S)-8-cyano-8-azabicyclo[3.2.1]octan-2-yl)-4-(4-methyl-1H-pyrazol-1-yl)benzamide;

3-(6-chloro-2,3-dihydro-1H-indol-1-yl)-N-((1R,2R,4S)-7-cyano-7-azabicyclo[2.2.1]heptan-2-yl)propanamide;

(2S)-2-(3-bromo-2-methylphenyl)-N-((1R,2R,4S)-7-cyano-7-azabicyclo[2.2.1]heptan-2-yl)-1-pyrrolidinecarboxamide;

(2S)—N-((1R,2R,4S)-7-cyano-7-azabicyclo[2.2.1]heptan-2-yl)-2-(2,3-dichlorophenyl)-1-azetidinecarboxamide;

1-((1R,2R,4S)-7-cyano-7-azabicyclo[2.2.1]heptan-2-yl)-3-(((1S,3S)-3-(2-propanyl)-2,3-dihydro-1H-inden-1-yl)methyl)urea;

1-((1R,2R,4S)-7-cyano-7-azabicyclo[2.2.1]heptan-2-yl)-3-((1R)-1-(2,3-dichlorophenyl)ethyl)urea;

(2E)-N-((1R,2R,4S)-7-cyano-7-azabicyclo[2.2.1]heptan-2-yl)-4-(2,5-dichlorophenyl)-2-methyl-2-butenamide;

N-((1R,2R,4S)-7-cyano-7-azabicyclo[2.2.1]heptan-2-yl)-4-(2,5-dichlorophenyl)butanamide;
(1R,3S)—N-((1R,2R,4S)-7-cyano-7-azabicyclo[2.2.1]heptan-2-yl)-3-(2,5-dichlorophenyl)cyclopentanecarboxamide;
N-((1R,2R,4S)-7-cyano-7-azabicyclo[2.2.1]heptan-2-yl)-3-(4-fluorophenoxy)benzamide;
N-((1R,2R,4S)-7-cyano-7-azabicyclo[2.2.1]heptan-2-yl)-3-(4-fluorobenzyl)benzamide;
3-(4-chlorophenoxy)-N-((1R,2R,4S)-7-cyano-7-azabicyclo[2.2.1]heptan-2-yl)benzamide;
(1S,2S)—N-((1R,2R,4S)-7-cyano-7-azabicyclo[2.2.1]heptan-2-yl)-2-(2,5-dichlorobenzyl)cyclopropanecarboxamide;
1-(((1R)-7-chloro-1,2,3,4-tetrahydro-1-naphthalenyl)methyl)-3-((1R,2R,4S)-7-cyano-7-azabicyclo[2.2.1]heptan-2-yl)urea;
N-((1R,2R,4S)-7-cyano-7-azabicyclo[2.2.1]heptan-2-yl)-3-(4-cyanophenoxy)benzamide;
N-((1R,2R,4S)-7-cyano-7-azabicyclo[2.2.1]heptan-2-yl)dibenzo[b,d]furan-3-carboxamide;
(2E)-3-(5-chloro-1-ethyl-1H-pyrrolo[2,3-b]pyridin-3-yl)-N-((1R,2R,4S)-7-cyano-7-azabicyclo[2.2.1]heptan-2-yl)-2-propenamide;
2-(3-bromo-2-cyanophenoxy)-N-((1R,2R,4S)-7-cyano-7-azabicyclo[2.2.1]heptan-2-yl)acetamide;
N-(2-(((1R,2R,4S)-7-cyano-7-azabicyclo[2.2.1]heptan-2-yl)amino)-2-oxoethyl)-4,5,6,7-tetrahydro-1-benzothiophene-2-carboxamide;
(2S,3E)-N-((1R,2R,4S)-7-cyano-7-azabicyclo[2.2.1]heptan-2-yl)-4-(2,5-dichlorophenyl)-2-methoxy-3-butenamide;
(3E)-N-((1R,2R,4S)-7-cyano-7-azabicyclo[2.2.1]heptan-2-yl)-4-(2,5-dichlorophenyl)-N-methyl-3-butenamide;
2',5'-dichloro-N-((1R,2R,4S)-7-cyano-7-azabicyclo[2.2.1]heptan-2-yl)[biphenyl]-3-carboxamide;
(3E)-4-(3-chlorophenyl)-N-((1R,2R,4S)-7-cyano-7-azabicyclo[2.2.1]heptan-2-yl)-3-butenamide;
(2E)-3-(5-chloro-1-ethyl-1H-indol-3-yl)-N-((1R,2R,4S)-7-cyano-7-azabicyclo[2.2.1]heptan-2-yl)-2-methyl-2-propenamide;
(3E)-N-((1R,2R,4S)-7-cyano-7-azabicyclo[2.2.1]heptan-2-yl)-4-(2,5-dichlorophenyl)-3-butenamide;
1-((1R,2R,4S)-7-cyano-7-azabicyclo[2.2.1]heptan-2-yl)-3-(2-(2,5-dichlorophenyl)ethyl)-1,3-dimethylurea;
(3R)—N-((1R,2R,4S)-7-cyano-7-azabicyclo[2.2.1]heptan-2-yl)-2,3,4,9-tetrahydro-1H-carbazole-3-carboxamide;
1-((1R,2R,4S)-7-cyano-7-azabicyclo[2.2.1]heptan-2-yl)-3-(2-(2,5-dichlorophenyl)ethyl)urea;
(2E)-3-(5-chloro-1-benzothiophen-3-yl)-N-((1R,2R,4S)-7-cyano-7-azabicyclo[2.2.1]heptan-2-yl)-2-methyl-2-propenamide;
3'-bromo-N-((1R,2R,4S)-7-cyano-7-azabicyclo[2.2.1]heptan-2-yl)[biphenyl]-3-carboxamide;
(2E)-3-(5-chloro-1H-indazol-3-yl)-N-((1R,2R,4S)-7-cyano-7-azabicyclo[2.2.1]heptan-2-yl)-2-methyl-2-propenamide;
1-(2-(2-bromo-5-chlorophenyl)ethyl)-3-((1R,2R,4S)-7-cyano-7-azabicyclo[2.2.1]heptan-2-yl)-1,3-dimethylurea;
N'-((1R,2R,4S)-7-cyano-7-azabicyclo[2.2.1]heptan-2-yl)-N-(2-hydroxyethyl)-N-((1R,3R,5S,7r)-tricyclo[3.3.1.1~3,7~]decan-1-ylmethyl)ethanediamide;
7-chloro-N-((1R,2R,4S)-7-cyano-7-azabicyclo[2.2.1]heptan-2-yl)-2,3-dihydro-1,4-benzoxazepine-4(5H)-carboxamide;
8-chloro-N-((1R,2R,4S)-7-cyano-7-azabicyclo[2.2.1]heptan-2-yl)-1,3,4,5-tetrahydro-2H-pyrido[4,3-b]indole-2-carboxamide;
2',3-dichloro-N-((1R,2R,4S)-7-cyano-7-azabicyclo[2.2.1]heptan-2-yl)-3'-(cyanomethyl)[biphenyl]-4-carboxamide;
3,3'-dichloro-N-((1R,2R,4S)-7-cyano-7-azabicyclo[2.2.1]heptan-2-yl)-5'-(cyanomethyl)[biphenyl]-4-carboxamide;
2',3-dichloro-N-((1R,2R,4S)-7-cyano-7-azabicyclo[2.2.1]heptan-2-yl)-5'-(cyanomethyl)[biphenyl]-4-carboxamide;
3,4'-dichloro-N-((1R,2R,4S)-7-cyano-7-azabicyclo[2.2.1]heptan-2-yl)-3'-(cyanomethyl)[biphenyl]-4-carboxamide;
3-chloro-N-((1R,2R,4S)-7-cyano-7-azabicyclo[2.2.1]heptan-2-yl)-3'-(2-cyano-2-propanyl)[biphenyl]-4-carboxamide;
3-chloro-N-((1R,2R,4S)-7-cyano-7-azabicyclo[2.2.1]heptan-2-yl)-3'-(cyanomethyl)-5'-fluoro[biphenyl]-4-carboxamide;
3-chloro-N-((1R,2R,4S)-7-cyano-7-azabicyclo[2.2.1]heptan-2-yl)-3'-(cyanomethyl)-4'-fluoro[biphenyl]-4-carboxamide;
3-chloro-N-((1R,2R,4S)-7-cyano-7-azabicyclo[2.2.1]heptan-2-yl)-3'-(cyanomethyl)-2'-fluoro[biphenyl]-4-carboxamide;
3-chloro-N-((1R,2R,4S)-7-cyano-7-azabicyclo[2.2.1]heptan-2-yl)-5'-(cyanomethyl)-2'-fluoro[biphenyl]-4-carboxamide;
2-chloro-N-((1R,2R,4S)-7-cyano-7-azabicyclo[2.2.1]heptan-2-yl)-4-(6-(2-cyano-2-propanyl)-2-pyridinyl)benzamide;
3-chloro-N-((1R,2R,4S)-7-cyano-7-azabicyclo[2.2.1]heptan-2-yl)-5'-(cyanomethyl)-2'-methyl[biphenyl]-4-carboxamide;
3-chloro-N-((1R,2R,4S)-7-cyano-7-azabicyclo[2.2.1]heptan-2-yl)-3'-(cyanomethyl)-4'-methyl[biphenyl]-4-carboxamide;
3-chloro-N-((1R,2R,4S)-7-cyano-7-azabicyclo[2.2.1]heptan-2-yl)-3'-(cyanomethyl)-5'-methyl[biphenyl]-4-carboxamide;
3-chloro-N-((1R,2R,4S)-7-cyano-7-azabicyclo[2.2.1]heptan-2-yl)-3'-(cyanomethyl)[biphenyl]-4-carboxamide;
3-chloro-N-((1R,2R,4S)-7-cyano-7-azabicyclo[2.2.1]heptan-2-yl)-3'-(1-cyanocyclobutyl)[biphenyl]-4-carboxamide;
2-chloro-N-((1R,2R,4S)-7-cyano-7-azabicyclo[2.2.1]heptan-2-yl)-4-(6-(methoxymethyl)-2-pyridinyl)benzamide;
3-chloro-N-((1R,2R,4S)-7-cyano-7-azabicyclo[2.2.1]heptan-2-yl)-4'-(cyanomethyl)[biphenyl]-4-carboxamide;
2-chloro-N-((1R,2R,4S)-7-cyano-7-azabicyclo[2.2.1]heptan-2-yl)-4-(6-(1-cyanocyclopropyl)-2-pyridinyl)-N-methylbenzamide;
2-chloro-N-((1R,2R,4S)-7-cyano-7-azabicyclo[2.2.1]heptan-2-yl)-4-(5-(1-cyanocyclopropyl)-3-pyridinyl)benzamide;
4-(6-(acetyl(methyl)amino)-2-pyridinyl)-2-chloro-N-((1R,2R,4S)-7-cyano-7-azabicyclo[2.2.1]heptan-2-yl)benzamide;
2-chloro-N-((1R,2R,4S)-7-cyano-7-azabicyclo[2.2.1]heptan-2-yl)-4-(5-(cyanomethyl)-3-pyridinyl)benzamide;
2-chloro-N-((1R,2R,4S)-7-cyano-7-azabicyclo[2.2.1]heptan-2-yl)-4-(4-(cyanomethyl)-2-pyridinyl)benzamide;
N-((1R,2R,4S)-7-cyano-7-azabicyclo[2.2.1]heptan-2-yl)-4-(6-(1-cyanocyclopropyl)-2-pyridinyl)-2-methylbenzamide;
3-chloro-N-((1R,2R,4S)-7-cyano-7-azabicyclo[2.2.1]heptan-2-yl)-3'-(1-cyanocyclopropyl)[biphenyl]-4-carboxamide;

2-chloro-N-((1R,2R,4S)-7-cyano-7-azabicyclo[2.2.1]heptan-2-yl)-4-(2-(cyanomethyl)-3-pyridinyl)benzamide;
N-((1R,2R,4S)-7-cyano-7-azabicyclo[2.2.1]heptan-2-yl)-4-(6-(1-cyanocyclopropyl)-2-pyridinyl)-2-(trifluoromethyl)benzamide;
N-((1R,2R,4S)-7-cyano-7-azabicyclo[2.2.1]heptan-2-yl)-4-(6-(1-cyanocyclopropyl)-2-pyridinyl)-2-fluorobenzamide;
N-((1R,2R,4S)-7-cyano-7-azabicyclo[2.2.1]heptan-2-yl)-4-(1-methyl-1H-pyrazol-3-yl)-2-(trifluoromethyl)benzamide;
N-((1R,2R,4S)-7-cyano-7-azabicyclo[2.2.1]heptan-2-yl)-4-(imidazo[1,5-a]pyridin-6-yl)-2-(trifluoromethyl)benzamide;
N-((1R,2R,4S)-7-cyano-7-azabicyclo[2.2.1]heptan-2-yl)-2-fluoro-4-(1-methyl-1H-pyrazol-3-yl)benzamide;
N-((1R,2R,4S)-7-cyano-7-azabicyclo[2.2.1]heptan-2-yl)-2-fluoro-4-(imidazo[1,5-a]pyridin-6-yl)benzamide;
2,6-dichloro-N-((1R,2R,4S)-7-cyano-7-azabicyclo[2.2.1]heptan-2-yl)-4-(1-methyl-1H-pyrazol-3-yl)benzamide;
2,6-dichloro-N-((1R,2R,4S)-7-cyano-7-azabicyclo[2.2.1]heptan-2-yl)-4-(imidazo[1,5-a]pyridin-6-yl)benzamide;
2-chloro-N-((1R,2R,4S)-7-cyano-7-azabicyclo[2.2.1]heptan-2-yl)-4-(5-cyano-2-pyrimidinyl)benzamide;
2-chloro-N-((1R,2R,4S)-7-cyano-7-azabicyclo[2.2.1]heptan-2-yl)-4-(4-cyano-2-pyrimidinyl)benzamide;
2-chloro-N-((1R,2R,4S)-7-cyano-7-azabicyclo[2.2.1]heptan-2-yl)-4-(6-methyl-2-pyrazinyl)benzamide;
2-chloro-N-((1R,2R,4S)-7-cyano-7-azabicyclo[2.2.1]heptan-2-yl)-4-(5-methyl-2-pyrazinyl)benzamide;
2-chloro-N-((1R,2R,4S)-7-cyano-7-azabicyclo[2.2.1]heptan-2-yl)-4-(4-cyano-2-pyridinyl)benzamide;
2-chloro-N-((1R,2R,4S)-7-cyano-7-azabicyclo[2.2.1]heptan-2-yl)-4-(6-methyl-2-pyridinyl)benzamide;
2-chloro-N-((1R,2R,4S)-7-cyano-7-azabicyclo[2.2.1]heptan-2-yl)-4-(2-methyl-4-pyrimidinyl)benzamide;
2-chloro-N-((1R,2R,4S)-7-cyano-7-azabicyclo[2.2.1]heptan-2-yl)-4-(6-methyl-3-pyridazinyl)benzamide;
2-chloro-N-((1R,2R,4S)-7-cyano-7-azabicyclo[2.2.1]heptan-2-yl)-4-(6-(difluoromethyl)-2-pyridinyl)benzamide;
2-chloro-N-((1R,2R,4S)-7-cyano-7-azabicyclo[2.2.1]heptan-2-yl)-4-(6-(cyanomethyl)-2-pyridinyl)benzamide;
2-chloro-N-((1R,2R,4S)-7-cyano-7-azabicyclo[2.2.1]heptan-2-yl)-4-(6-(difluoromethoxy)-2-pyridinyl)benzamide;
2-chloro-N-((1R,2R,4S)-7-cyano-7-azabicyclo[2.2.1]heptan-2-yl)-4-(6-(1,1-difluoroethyl)-2-pyridinyl)benzamide;
2-chloro-N-((1R,2R,4S)-7-cyano-7-azabicyclo[2.2.1]heptan-2-yl)-4-(6-cyclopropyl-2-pyrazinyl)benzamide;
2-chloro-N-((1R,2R,4S)-7-cyano-7-azabicyclo[2.2.1]heptan-2-yl)-4-(6-cyano-2-pyridinyl)benzamide;
2-chloro-N-((1R,2R,4S)-7-cyano-7-azabicyclo[2.2.1]heptan-2-yl)-4-(6-(1-cyanocyclopropyl)-2-pyridinyl)benzamide;
2-chloro-N-((1R,2R,4S)-7-cyano-7-azabicyclo[2.2.1]heptan-2-yl)-4-(6-(2,2,2-trifluoroethoxy)-2-pyridinyl)benzamide;
2-chloro-N-((1R,2R,4S)-7-cyano-7-azabicyclo[2.2.1]heptan-2-yl)-4-(4-(trifluoromethyl)-1H-pyrazol-1-yl)benzamide;
2-chloro-N-((1R,2R,4S)-7-cyano-7-azabicyclo[2.2.1]heptan-2-yl)-4-(4-(cyanomethyl)-1H-pyrazol-1-yl)benzamide;
2-chloro-N-((1R,2R,4S)-7-cyano-7-azabicyclo[2.2.1]heptan-2-yl)-4-(4-ethyl-1H-pyrazol-1-yl)benzamide;
2-chloro-N-((1R,2R,4S)-7-cyano-7-azabicyclo[2.2.1]heptan-2-yl)-4-(imidazo[1,2-a]pyridin-6-yl)benzamide;
2-chloro-N-((1R,2R,4S)-7-cyano-7-azabicyclo[2.2.1]heptan-2-yl)-4-(1-methyl-1H-indazol-7-yl)benzamide;
2-chloro-N-((1R,2R,4S)-7-cyano-7-azabicyclo[2.2.1]heptan-2-yl)-4-(7-methylimidazo[1,2-a]pyridin-6-yl)benzamide;
2-chloro-N-((1R,2R,4S)-7-cyano-7-azabicyclo[2.2.1]heptan-2-yl)-4-(2-methylimidazo[1,2-a]pyridin-6-yl)benzamide;
2-chloro-N-((1R,2R,4S)-7-cyano-7-azabicyclo[2.2.1]heptan-2-yl)-4-(imidazo[1,2-a]pyridin-7-yl)benzamide;
2-chloro-N-((1R,2R,4S)-7-cyano-7-azabicyclo[2.2.1]heptan-2-yl)-4-(imidazo[1,5-a]pyridin-6-yl)benzamide;
2-chloro-N-((1R,2R,4S)-7-cyano-7-azabicyclo[2.2.1]heptan-2-yl)-4-(1-methyl-1H-pyrazol-3-yl)benzamide;
2-chloro-N-((1R,2R,4S)-7-cyano-7-azabicyclo[2.2.1]heptan-2-yl)-4-(1-methyl-1H-pyrazol-5-yl)benzamide;
2-chloro-N-((1R,2R,4S)-7-cyano-7-azabicyclo[2.2.1]heptan-2-yl)-4-(1-cyclopropyl-1H-pyrazol-4-yl)benzamide;
2-chloro-N-((1R,2R,4S)-7-cyano-7-azabicyclo[2.2.1]heptan-2-yl)-4-(1-(cyanomethyl)-1H-pyrazol-4-yl)benzamide;
2-chloro-N-((1R,2R,4S)-7-cyano-7-azabicyclo[2.2.1]heptan-2-yl)-4-(1-methyl-1H-imidazol-4-yl)benzamide;
2-chloro-N-((1R,2R,4S)-7-cyano-7-azabicyclo[2.2.1]heptan-2-yl)-4-(1-methyl-1H-pyrazol-4-yl)benzamide;
N-((1R,2R,4S)-7-cyano-7-azabicyclo[2.2.1]heptan-2-yl)-3-(2-methylpropoxy)-4-(3-methyl-1H-pyrazol-1-yl)benzamide;
N-((1R,2R,4S)-7-cyano-7-azabicyclo[2.2.1]heptan-2-yl)-4-(4-cyano-2-pyridinyl)-3-(2-methylpropoxy)benzamide;
N-((1R,2R,4S)-7-cyano-7-azabicyclo[2.2.1]heptan-2-yl)-3-(2-methylpropoxy)-4-(5-methyl-2-pyrazinyl)benzamide;
N-((1R,2R,4S)-7-cyano-7-azabicyclo[2.2.1]heptan-2-yl)-3-(2-methylpropoxy)-4-(6-methyl-2-pyridinyl)benzamide;
N-((1R,2R,4S)-7-cyano-7-azabicyclo[2.2.1]heptan-2-yl)-3-(2-methylpropoxy)-4-(4-methyl-2-pyrimidinyl)benzamide;
N-((1R,2R,4S)-7-cyano-7-azabicyclo[2.2.1]heptan-2-yl)-4-(6-(cyanomethyl)-2-pyridinyl)-3-(2-methylpropoxy)benzamide;
N-((1R,2R,4S)-7-cyano-7-azabicyclo[2.2.1]heptan-2-yl)-3-(2-methylpropoxy)-4-(1-methyl-1H-pyrazol-3-yl)benzamide;
N-((1R,2R,4S)-7-cyano-7-azabicyclo[2.2.1]heptan-2-yl)-3-(2-methylpropoxy)-4-(1-methyl-1H-pyrazol-5-yl)benzamide;
N-((1R,2R,4S)-7-cyano-7-azabicyclo[2.2.1]heptan-2-yl)-4-(1-methyl-1H-imidazol-4-yl)-3-(2-methylpropoxy)benzamide;
N-((1R,2R,4S)-7-cyano-7-azabicyclo[2.2.1]heptan-2-yl)-4-(6-cyano-2-pyridinyl)-3-(2-methylpropoxy)benzamide;
N-((1R,2R,4S)-7-cyano-7-azabicyclo[2.2.1]heptan-2-yl)-3-(2-methylpropoxy)-4-(6-methyl-3-pyridazinyl)benzamide;
N-((1R,2R,4S)-7-cyano-7-azabicyclo[2.2.1]heptan-2-yl)-3-(2-methylpropoxy)-4-(2-methyl-4-pyrimidinyl)benzamide;
N-((1R,2R,4S)-7-cyano-7-azabicyclo[2.2.1]heptan-2-yl)-3-((2R)-2-methylbutoxy)-4-(1-methyl-1H-pyrazol-4-yl)benzamide;
N-((1R,2R,4S)-7-cyano-7-azabicyclo[2.2.1]heptan-2-yl)-4-(1-ethyl-1H-pyrazol-4-yl)-3-(2-methylpropoxy)benzamide;
N-((1R,2R,4S)-7-cyano-7-azabicyclo[2.2.1]heptan-2-yl)-4-(1-cyclopropyl-1H-pyrazol-4-yl)-3-(2-methylpropoxy)benzamide;

N-((1R,2R,4S)-7-cyano-7-azabicyclo[2.2.1]heptan-2-yl)-2-methyl-4-(1-methyl-1H-pyrazol-4-yl)-1,3-benzothiazole-7-carboxamide;

N-((1R,2R,4S)-7-cyano-7-azabicyclo[2.2.1]heptan-2-yl)-5-(2-methylpropoxy)-2,4-bis(1-methyl-1H-pyrazol-4-yl)benzamide;

2-chloro-N-((1R,2R,4S)-7-cyano-7-azabicyclo[2.2.1]heptan-2-yl)-5-(2-methylpropoxy)-4-(1-methyl-1H-pyrazol-4-yl)benzamide;

2-chloro-N-((1R,2R,4S)-7-cyano-7-azabicyclo[2.2.1]heptan-2-yl)-3-(2-methylpropoxy)-4-(1-methyl-1H-pyrazol-4-yl)benzamide;

2-chloro-N-((1R,2R,4S)-7-cyano-7-azabicyclo[2.2.1]heptan-2-yl)-3-(2-methylpropoxy)-4-(4-methyl-1H-pyrazol-1-yl)benzamide;

N-((1R,2R,4S)-7-cyano-7-azabicyclo[2.2.1]heptan-2-yl)-3-(2-methylpropoxy)-4-(4-methyl-1H-pyrazol-1-yl)benzamide;

N-((1R,2R,4S)-7-cyano-7-azabicyclo[2.2.1]heptan-2-yl)-7-methyl-1-(6-methyl-2-pyridinyl)-1H-indazole-5-carboxamide;

N-((1R,2R,4S)-7-cyano-7-azabicyclo[2.2.1]heptan-2-yl)-N-methyl-3-(2-methylpropoxy)-4-(1-methyl-1H-pyrazol-4-yl)benzamide;

3-butoxy-N-((1R,2R,4S)-7-cyano-7-azabicyclo[2.2.1]heptan-2-yl)-4-(1-methyl-1H-pyrazol-4-yl)benzamide;

N-((1R,2R,4S)-7-cyano-7-azabicyclo[2.2.1]heptan-2-yl)-3-(cyclobutylmethoxy)-4-(1-methyl-1H-pyrazol-4-yl)benzamide;

N-((1R,2R,4S)-7-cyano-7-azabicyclo[2.2.1]heptan-2-yl)-3-(2-methylpropoxy)-4-(1-methyl-1H-pyrazol-4-yl)benzamide;

6-chloro-N-((1R,2R,4S)-7-cyano-7-azabicyclo[2.2.1]heptan-2-yl)-1-(6-cyano-2-pyridinyl)-1H-indazole-5-carboxamide; and 6-chloro-N-((1R,2R,4S)-7-cyano-7-azabicyclo[2.2.1]heptan-2-yl)-1-(4-cyano-2-pyridinyl)-1H-indazole-5-carboxamide.

In another embodiment synthetic intermediates are provided, which intermediates are useful for the preparation of compounds of Formula (I) and subformulac thereof. Preferred synthetic intermediates provided in the specification include racemates and enantiomerically enriched forms of compounds selected from:

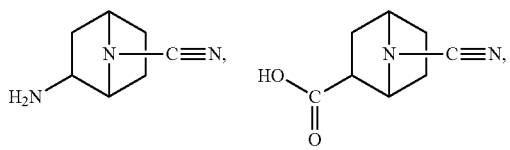

-continued

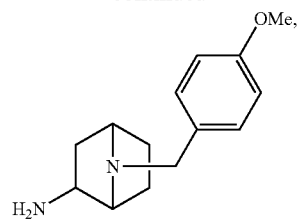

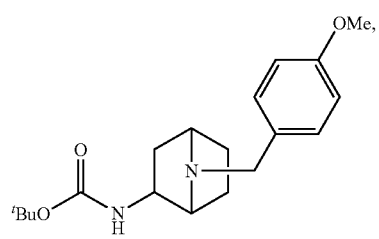

and salts thereof. Wherein each of the above compounds may be racemic, a mixture of diastereomers or enantiomerically enriched in a single stereoisomer. The synthetic intermediates provided may be prepared in either endo or exo relative orientation. In certain aspects, the endo geometry is preferred for preparation of compounds provided by the disclosure. Synthetic intermediates may be prepared in free base/acid form or as an acid or base addition salt. In certain embodiments hydrochloride salts are provided for primary amine synthetic intermediates.

Certain preferred synthetic intermediates provided by the disclosure include endo azanorbornane cores selected from:

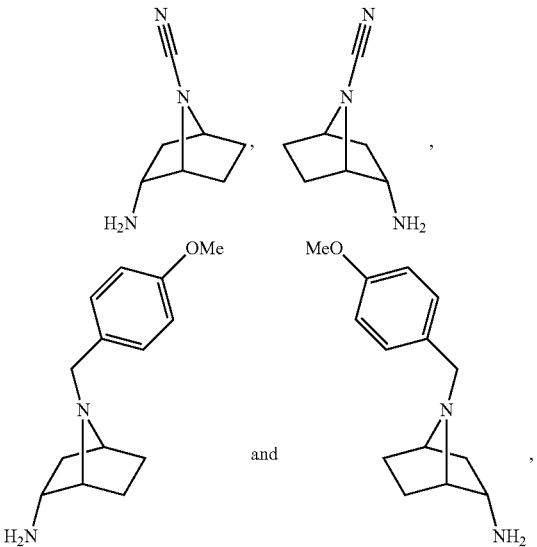

each of which may be a free base or an acid addition salt (such as a hydrochloride salt, an trifluoroacetic acid salt or the like).

Certain preferred synthetic intermediates provided by the disclosure include endo azanorbornane cores selected from:

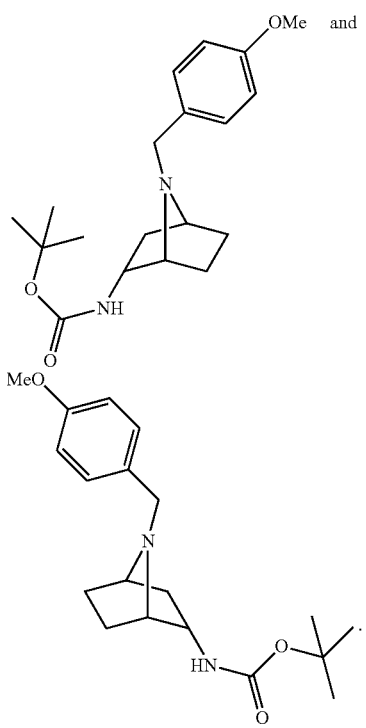

In another embodiment, pharmaceutical compositions are provided which comprise one or more pharmaceutically acceptable carriers and a therapeutically effective amount of a compound of any one of formulae I or a subformulae thereof. In some aspects, the composition is formulated in a form selected from the group consisting of an injectable fluid, an aerosol, a tablet, a pill, a capsule, a syrup, a cream, a gel and a transdermal patch.

In another embodiment, combinations, in particular pharmaceutical combinations, are provided which comprise a therapeutically effective amount of the compound any one of formulae I or a subformulae thereof.

In another embodiment, methods of modulating USP30 protein activity in a subject are provided which comprise administering to the subject a therapeutically effective amount of Formula I or a subformulae thereof. In preferred aspects of the embodiment, methods of inhibiting USP30 activity in a subject are provided, which comprise administering to the subject a therapeutically effective amount of a compound of Formula I or subformulae thereof. In certain aspects of the embodiment, method of inhibiting USP30 activity in a subject are provided, which comprise administering to the subject a therapeutically effective amount of a compound of Formula I or subformulae thereof.

In yet other embodiments, methods of treating a disorder or a disease in a subject mediated by USP30 protein activity are provided, in particular methods of treating a disease or disorder mediated by USP30 protein activity are provided. The methods comprise administering to the subject a therapeutically effective amount of the compound of Formula I or a subformulae thereof.

In another embodiment, methods of treating or preventing a disease or disorder are provided where the disease or disorder is mediated by mitochondrial dysfunction. In certain aspects of the embodiment the disease or disorder is selected from neurodegenerative diseases, cancer, diabetes, metabolic disorders, cardiovascular disease, psychiatric disease and osteoarthritis. In certain specific aspects of the embodiment, the disease or disorder is selected from the group consisting of CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl-CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength which method comprises the step of administering to a subject in need of therapy a therapeutically effective amount of a compound or salt of Formula I or a subformulae thereof. In certain aspects of this embodiment, the method comprises treating a disease or disorder selected from Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1. In certain instances, the treatment methods and/or the prevention methods are suitable for the treatment and or prevention of Parkinson's Disease.

In another aspect, the invention provides for the use of compounds of Formula I or a subformulae thereof for use in the preparation of a medicament or for use in the manufacture of a medicament for the treatment of a disorder or disease in a subject mediated by USP30 activity. In certain other aspects, the invention provides for the use of a compound according to formula I or a subformulae thereof in the treatment of a disease or disorder mediated by mitochondrial dysfunction.

In certain uses of the embodiment, the disease or disorder is selected from neurodegenerative diseases, cancer, diabetes, metabolic disorders, cardiovascular disease, psychiatric disease and osteoarthritis.

More particularly, the use of compounds of Formula I in the preparation of a medicament or in use in the manufacture of a medicament for treatment of a disease or disorder selected from CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl-CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength. In certain instances, the invention provides for the use of compounds of Formula I or a subformulae thereof for use in the preparation of a medicament or for use in the manufacture of a medicament or the treatment of a disease or disorder in a subject selected from Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1. In certain instances, the invention provides for the use of compounds of Formula I or a subformulae thereof for use in the preparation of a medicament or for use in the manufacture of a medicament or the treatment of Parkinson's disease.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 20 carbon atoms, 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. Unless otherwise provided, alkylene refers to moieties having 1 to 20 carbon atoms, 1 to 16 carbon atoms, 1 to 10 carbon atoms, 1 to 7 carbon atoms, or 1 to 4 carbon atoms.

Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein, which is substituted with one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "hydroxy alkyl" refers to an alkyl as defined herein which is substituted with one or more hydroxy groups. The term "hydroxy cycloalkyl-alkyl" refers to an alkyl group that is substituted with a cycloalkyl group, as defined herein, and further substituted with a hydroxy group. The hydroxy group can be on the alkyl group, the cycloalkyl group, or on each of the alkyl and cycloalkyl groups.

The term "aryl" refers to an aromatic hydrocarbon group having 6-20 carbon atoms in the ring portion. Typically, aryl is monocyclic, bicyclic or tricyclic aryl having 6-20 carbon atoms.

Furthermore, the term "aryl" as used herein, refers to an aromatic substituent which can be a single aromatic ring, or multiple aromatic rings that are fused together. Non-limiting examples include phenyl, naphthyl or tetrahydronaphthyl, each of which may optionally be substituted with 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S-nitro, cyano, carboxy, alkyl-O—C(O)—, carbamoyl, alkyl-S(O)—, sulfonyl, sulfonamido, phenyl, and heterocyclyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-7, more preferably about 1-4 carbons.

As used herein, the term "heterocycle," "heterocycloalkyl" or "heterocyclo" refers to a saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spirocyclic rings. Examples of heterocycles include tetrahydrofuran, dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, azetidine, thiazolidine, morpholine, and the like.

As used herein, the term "cycloalkyl" refers to saturated or partially unsaturated monocyclic, bicyclic or tricyclic hydrocarbon groups of 3-12 carbon atoms. For the avoidance of doubt, cycloalkyl is not intended to include aromatic groups such as naphthylene or phenyl. Unless otherwise provided, cycloalkyl refers to cyclic hydrocarbon groups having between 3 and 9 ring carbon atoms or between 3 and 7 ring carbon atoms, each of which can be optionally substituted with one, or two, or three, or more substituents independently selected from the group consisting of alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like. The term "hydroxy cycloalkyl" refers specifically to a cycloalkyl group substituted with one or more hydroxy groups.

As used herein, the term "heteroaryl" refers to a 5-14 membered monocyclic- or bicyclic- or tricyclic-aromatic ring system, having 1 to 8 heteroatoms selected from N, O and S. In certain preferred aspects, the heteroaryl is a 5-10 membered ring system (e.g., 5-7 membered monocycle or an 8-10 membered bicycle) or a 5-7 membered ring system. Exemplary monocyclic heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, and 2-, 4-, and 5-pyrimidinyl. Exemplary bicyclic heteroaryl groups include 1-, 3-, 4-, 5-, 6-, 7-, or 8-isoquinolinyl, 2-, 3-, 4-, 5-, 6-, 7-, or 8-quinolinyl, 1-, 3-, 4-, 5-, 6-, 7-, or 8-isoquinolinyl, 1-, 2-, 4-, 5-, 6-, 7-, or 8-benzimidazolyl and 1-, 2-, 3-, 4-, 5-, 6-, 7-, or 8-indolyl.

The term "heteroaryl" also refers to a group in which a heteroaromatic ring is fused to one or more aryl, cycloaliphatic, or heterocyclyl rings, where the radical or point of attachment is on the heteroaromatic ring As used herein, the term "halogen" or "halo" refers to fluoro, chloro, bromo, and iodo.

As used herein, the term "optionally substituted" unless otherwise specified refers to a group that is unsubstituted or is substituted with one or more, typically 1, 2, 3 or 4, suitable non-hydrogen substituents. If the identity of the "optional substituent" is not clearly defined in context of the optionally substituted group, then each optional substituent is independently selected from the group consisting of: alkyl, hydroxy, halogen, oxo, amino, alkylamino, dialkylamino, alkoxy, cycloalkyl, CO$_2$H, heterocycloalkyloxy (which denotes a heterocyclic group bonded through an oxygen bridge), —CO$_2$alkyl, mercapto, nitro, cyano, sulfamoyl, sulfonamide, aryl, —OC(O)alkyl, —OC(O)aryl, aryl-S—, aryloxy; alkylthio, formyl (i.e., HC(O)—), —C(O)NH$_2$, aralkyl (alkyl substituted with aryl), aryl and aryl substituted with alkyl, cycloalkyl, alkoxy, hydroxy, amino, alkyl-C(O)—NH—, alkylamino, dialkylamino or halogen. It is understood that where a group is indicated to be optionally substituted, the disclosure includes embodiments in which the group is unsubstituted as well as embodiments in which the group is substituted.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. The use of "rel" indicates that the diastereomeric orientation is known but the absolute stereochemistry is not. In cases where the absolute stereochemistry has not been determined the optical rotation and/or chiral chromatography conditions will indicate which isomer is present. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line or retention time on chiral chromatography separation. Certain of the compounds described herein contain one or more asymmetric centers or axes and may thus give rise to enantiomers, diastereomers, and other stereoisomeric forms that may be defined, in terms of absolute stereochemistry, as (R)- or (S)-, or with the (+) or (−) sign. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. Certain compounds provided in the disclosure comprise a fused bicyclic ring system, e.g., 2-substituted-N-cyano-7-azanorbornane also known as 2-substituted-7-azabicyclo[2.2.1]heptane-7-carbonitrile. Fused bicyclic ring systems may be present in endo or exo configuration. In certain aspects, the disclosure provides compounds comprising an endo-N-cyano-7-azanorbornane moiety.

It is understood that for any compound provided herein, including any compound of Formula (I), or any embodiment thereof, or any compound of Table A, or a salt of any of the foregoing, the compound may exist in any stereochemical form, such as a single enantiomer, diastereomer, or tautomer or a mixture of one or more enantiomers, diastereomers, and tautomers in any ratio.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, benzenesuflonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper. In certain other embodiments, the salts are selected from ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds as disclosed herein in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form. In yet another aspect, the present invention provides compounds as disclosed herein in $C_1$-$C_4$alkyl sufonic acid, benzenesulfonic acid or mono-, di- or tri-$C_1$-$C_4$alkyl substituted benzene sulfonic acid addition salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{124}$I, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an F or labeled compound may be particularly desirable for PET or SPECT studies. Isotopically labeled compounds of this invention and salts thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has at least 50% deuterium incorporation at each designated deuterium atom, 60% deuterium incorporation, at least 75% deuterium incorporation, at least 90% deuterium incorporation, at least 95% deuterium incorporation, at least 99% deuterium incorporation, or at least 99.5% deuterium incorporation.

The compounds of the present invention may inherently or by design form solvates with solvents (including water). Therefore, it is intended that the invention embrace both solvated and unsolvated forms. The term "solvate" refers to a molecular complex of a compound of the present invention (including salts thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder, or a disease or biological process (i) mediated by USP30 activity, or (ii) associated with USP30 activity; or (2) inhibiting the activity of USP30. In another non-limiting embodiment, the term "a therapeutically effective amount" refers to the amount of the compound of the present invention that, when administered to a cell, or a tissue, or a non-cellular biological material, or a medium, is effective to at least partially inhibit USP30 activity.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like.

In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevent," "preventing" or "prevention" of any disease or disorder refers in one embodiment, to delay or avoidance of onset of the disease or disorder (i.e., slowing or preventing the onset of the disease or disorder in a patient susceptible to development of the disease or disorder).

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high performance liquid chromatography (HPLC) or supercritical fluid chromatography (SFC) using a chiral adsorbent.

Mixtures of isomers obtainable according to the invention can be separated in a manner known to those skilled in the art into the individual isomers; diastereoisomers can be separated, for example, by partitioning between polyphasic solvent mixtures, recrystallization and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Intermediates and final products can be worked up and/or purified according to standard methods, e.g. using chromatographic methods, distribution methods, (re-) crystallization, and the like.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any process steps disclosed herein can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H* form, depending on the nature of the reaction and/or of the reactants at reduced, normal or elevated temperature, for example in a temperature range of from about −100° C. to about 250° C., including, for example, from approximately −80° C. to approximately 250° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

Typically, the pharmaceutical compositions are tablets or gelatin capsules comprising the active ingredient together with one or more of: a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners. Tablets may be either film coated or enteric coated according to methods known in the art. Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distcarate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient. Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin. Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives. As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atom/zer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions.

An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

Prophylactic and Therapeutic Uses

The compounds disclosed herein in free form or in pharmaceutically acceptable salt form, exhibit valuable pharmacological properties, e.g. USP30 protein modulating properties and more particularly inhibition of USP30 protein activity, e.g. as indicated in in vitro and in vivo tests as provided in the next sections and are therefore indicated for therapy.

The present invention provides methods of treating a disease or disorder associated with USP30 protein activity by administering to a subject in need thereof an effective amount of a compound disclosed herein. In certain aspects, diseases and disorders associated with mitochondrial dysregulation are suitable for therapy by administration of a compound of the invention. In certain aspects, the disease or disorder suitable for therapy by administration of the compound of the invention include, but are not limited to, neurodegenerative diseases, cancer, diabetes, metabolic disorders, cardiovascular disease, psychiatric disease and osteoarthritis. In certain instances, the patient is suffering from CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl-CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength. In certain embodiments, the disease or disorder suitable for therapy by administration of a compound of the invention include Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in-α synuclein, parkin and PINK1. In certain aspects, methods of treating Parkinson's disease by administration of a compound of the invention to a patient are provided.

In a specific embodiment, the present invention provides a method of treating or preventing a neurodegenerative disease by administering to a subject in need thereof an effective amount of a compound disclosed herein. In certain embodiments, patients who are currently asymptomatic but are at risk of developing neurodegenerative disease are suitable for administration with a compound of the invention. The methods of treating or preventing neurodegenerative disease include, but are not limited to, methods of treating or preventing Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1. In certain aspects, the methods of treating or preventing neurodegenerative diseases provided include methods of treating Parkinson's disease.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients.

The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10' molar and 10' molar concentrations. A therapeutically effective amount in vivo may range depending on the route of administration, between about 0.1-500 mg/kg, or between about 1-100 mg/kg.

The activity of a compound according to the present invention can be assessed by in vitro & in vivo methods, such as those described in the examples below.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound disclosed herein and at least one other therapeutic agent as a combined preparation for simultaneous, separate or sequential use in therapy. In one embodiment, the therapy is the treatment of a disease or condition mediated by USP30 protein activity. In preferred aspects, the therapy is a treatment for a neurodegenerative disease, including, but not limited to, Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1.

Products provided as a combined preparation include a composition comprising the compound disclosed herein and the other therapeutic agent(s) together in the same pharmaceutical composition, or the compound disclosed herein and the other therapeutic agent(s) in separate form, e.g. in the form of a kit.

In one embodiment, the invention provides a pharmaceutical composition comprising a compound as disclosed herein and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers.

Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound as disclosed herein for treating a disease or condition mediated by USP30 protein activity wherein the medicament is prepared for administration with another therapeutic agent. The invention also provides the use of another therapeutic agent for treating a disease or condition mediated by USP30 protein activity, wherein the medicament is administered with a compound as disclosed herein. In another aspect, the invention provides the use of a compound as disclosed herein for treating a neurodegenerative disease or disorder selected from Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α synuclein, parkin and PINK1, wherein the medicament is prepared for administration with another therapeutic agent. The invention also provides the use of another therapeutic agent for treating a disease or disorder selected from Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α synuclein, parkin and PINK1, wherein the medicament is administered with a compound as disclosed herein.

The invention also provides a compound as disclosed herein for use in a method of treating a disease or condition mediated by USP30 protein activity wherein the compound is prepared for administration with another therapeutic agent. The invention also provides another therapeutic agent for use in a method of treating a disease or condition mediated by USP30 protein activity, wherein the other therapeutic agent is prepared for administration with a compound as disclosed herein. The invention also provides a compound as disclosed herein for use in a method of treating a disease or condition mediated by USP30 protein activity, wherein the compound is administered with another therapeutic agent. The invention also provides another therapeutic agent for use in a method of treating a disease or condition mediated by USP30 protein activity, wherein the other therapeutic agent is administered with a compound as disclosed herein.

The invention also provides the use of a compound as disclosed herein for treating a disease or condition mediated by USP30 protein activity wherein the patient has previously (e.g. within 24 hours) been treated with another therapeutic agent. The invention also provides the use of another therapeutic agent for treating a disease or condition mediated by USP30 protein activity wherein the patient has previously (e.g. within 24 hours) been treated with a compound as disclosed herein.

The pharmaceutical compositions can be administered alone or in combination with other molecules known to have a beneficial effect in treatment of USP30 mediated disease or more particularly in the treatment of diseases associated with mitochondrial dysfunction and/or neurodegenerative disease. In certain aspects, the pharmaceutical compositions provided may be administered alone or in combination with other molecules known to have a beneficial effect in treatment of a disease or disorder selected from CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl-CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength. In certain aspects, the pharmaceutical composition has a beneficial effect in the treatment of a neurodegenerative disease selected from Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1. A combination therapy regimen may be additive, or it may produce synergistic results (e.g., improvement in mitochondrial function which is more than expected for the combined use of the two agents). In some embodiments, the present invention provide a combination therapy for preventing and/or treating USP30 mediated disease or more particularly Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1 with a compound of the invention and a second therapeutic agent. In some aspects, the second therapeutic agent is selected from dopamine agonists (such as levodopa), dopamine receptor agonists (such as pramipexole), Mao-B inhibitors (such as rasagiline), catechol-O-methyltransferase (COMT) inhibitors (such as entacapone), glucosylceramide synthase inhibitors (such as Genzvme—GZ/SAR402671), and glucosylcerebrosidase chaperones (such as Lysosomal Therapeutics-LTI 291).

In one embodiment, the invention provides a method of inhibiting the activity of USP30, in a subject, wherein the method comprises administering to the subject a therapeutically effective amount of the compound according to the definition of Formula (I). The invention further provides methods of inhibiting the activity of USP30 protein in a subject by administering a compound as disclosed herein, wherein the method comprises administering to the subject a therapeutically effective amount of the compound as disclosed herein.

In one embodiment, the invention provides a compound as disclosed herein, for use as a medicament.

In one embodiment, the invention provides the use of a compound as disclosed herein for the treatment of a disorder or disease in a subject characterized by the activity of USP30. In particular, the invention provides the use of a compound as disclosed herein for the treatment of a disorder or disease mediated by the activity of USP30, e.g., a disorder or disease mediated by mitochondrial dysfunction such as Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1. In certain preferred aspects, the invention provides for the use of a compound as disclosed herein for the treatment of Parkinson's disease.

In one embodiment, the invention provides the use of a compound as disclosed herein in the manufacture of a medicament for the treatment of a disorder or disease in a subject characterized by activity of USP30. More particularly in the manufacture of a medicament for the treatment of a disease or disorder in a subject characterized by activity of USP30, e.g., a disorder or disease mediated by mitochondrial dysfunction such as Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1. In certain preferred aspects, the invention provides the use of a compound as disclosed herein in the manufacture of a medicament for the treatment of Parkinson's disease.

In one embodiment, the invention provides the use of a compound as disclosed herein for the treatment of a disorder or disease in a subject characterized by activity of USP30. More particularly, the invention provides uses of the compounds provided herein in the treatment of a disease or disorder characterized by activity of USP30, e.g., a disorder or disease mediated by mitochondrial dysfunction such as Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1. In certain embodiments, the uses of the compounds provided herein is for the treatment of Parkinson's disease.

In a specific embodiment, the present invention provides use of the compounds of the invention for treating or preventing CNS disorder, neurodegenerative disease, multiple sclerosis, mitochondrial myopathy, encephalopathy, lactic acidosis, stroke-like episodes, Leber's hereditary optic neuropathy, cancer, neuropathy, ataxia, retinitis pigmentosa, maternally inherited Leigh syndrome, Danon disease, diabetes, diabetic nephropathy, metabolic disorders, heart failure, ischemic heart disease leading to myocardial infarction, psychiatric disease, schizophrenia, multiple sulfatase deficiency, mucolipidosis II, mucolipidosis III, mucolipidosis IV, GMI-gangliosidosis, neuronal ceroid-lipofuscinoses, Alpers disease, Barth syndrome, Beta-oxidation defects, carnitine-acyl-carnitine deficiency, carnitine deficiency, creatine deficiency syndromes, co-enzyme Q10 deficiency, complex I deficiency, complex II deficiency, complex III deficiency, complex IV deficiency, complex V deficiency, COX deficiency, chronic progressive external ophthalmoplegia syndrome, CPT I deficiency, CPT II deficiency, glutaric aciduria type II, Kearns-Sayre syndrome, lactic acidosis, long-chain acyl-CoA dehydrogenase deficiency, Leigh disease or syndrome, lethal infantile cardiomyopathy, Luft disease, glutaric aciduria type II, medium-chain acyl- CoA dehydrogenase deficiency, myoclonic epilepsy and ragged-red fiber syndrome, mitochondrial cytopathy, mitochondrial recessive ataxia syndrome, mitochondrial DNA depletion syndrome, myoneurogastointestinal disorder and encephalopathy, Stiff Person syndrome, pyruvate dehydrogenase deficiency, pyruvate carboxylase deficiency, POLG mutations, medium/short-chain 3-hydroxyacyl-CoA dehydrogenase deficiency, very long-chain acyl-CoA dehydrogenase deficiency, and age-dependent decline in cognitive function and muscle strength. In certain embodiments, patients who are currently asymptomatic but are at risk of developing a disorder or disease mediated by mitochondrial dysfunction such as Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α synuclein, parkin and PINK1 are suitable for administration with a compound of the invention. The use in treating or preventing a disorder or disease mediated by mitochondrial dysfunction such as Parkinson's disease, Alzheimer's disease, amyotrophic lateral sclerosis, Huntington's disease, ischemia, stroke, dementia with Lewy bodies, frontotemporal dementia, autosomal recessive juvenile Parkinson's disease where parkin is mutated and Parkinson's disease related to mutations in α-synuclein, parkin and PINK1 include, but are not limited to, uses in treating or preventing one or more symptoms or aspects of disorder or disease mediated by mitochondrial dysfunction.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure materials.

The following examples are intended to illustrate the invention and are not to be construed as being limitations thereon. Temperatures are given in degrees centigrade (° C.). If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art.

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Biotage. Mass spectral data was determined by electrospray ionization technique. Unless otherwise stated, reactions were run at room temperature.

Commercially available materials were purchased from Millipore-Sigma, HDH Pharma, Pharmablock, Alfa Aesar, Enovation Chemicals, Combi-Blocks, and other suppliers as stated.

Compound names, i.e., IUPAC names, for compounds described in the instant application were generated using ChemDraw compound naming software.

The following abbreviations are used: The following abbreviations are used:
ACN—Acctonitrile
CDI—1,1'-carbonyldiimidazole
DCM—dichloromethane
DMSO—dimethyl sulfoxide
DMF—N.N-dimethylformamide
THF—tetrahydrofuran
Et$_2$O—diethyl ether
EiOAc—ethyl acetate
EtOH—ethyl alcohol
HATU—1-[Bis(dimethylamino)methylene]-1H-1,2,3-triazolo[4,5-b]pyridinium 3-oxid hexafluorophosphate, N-[(Dimethylamino)-1H-1,2,3-triazolo-[4,5-b]pyridin -1-ylmethylene]-N-methylmethanaminium hexafluorophosphate N-oxide
Hunig's base or
DIEA—N,N-Diisopropylethylamine
LiOH—lithium hydroxide
Ms—mesylate
McCN—acctonitrile
MeOH—methyl alcohol
NaOH—sodium hydroxide
ppt—precipitate
Rbf —round bottom flask
rt —room temperature
RuPhos Pd Gl—Chloro-(2-Dicyclohexylphosphino-2',6'-diisopropoxy-1,1'-biphenyl)[2-(2-aminoethyl)phenyl)palladium(II)-methyl-t-butyl ether adduct
SFC—supercritical fluid chromatography
sm—starting material
T3P—Propylphosphonic anhydride solution
TFA—trifluoroacetic acid
tmp—2,2,6,6-tetramcthylpiperidine
h—hour
min—min
rt—room temperature (22-25° C.)
mL milliliters
μL microliters
g grams
μg micrograms
mg milligrams
μmoL micromoles
μW microwave (heating)

General Method of Preparation

The compounds described herein are prepared using techniques known to one skilled in the art through the reaction sequences depicted in General Methods 1-3 as well as by other methods. Furthermore, in the following schemes, where specific acids, bases, reagents, coupling agents, solvents, etc. are mentioned, it is understood that other suitable acids, bases, reagents, coupling agents, solvents, etc. may be used and are included within the scope of the present invention.

Compounds can be prepared using general method 1 in which an amino-cyanamide derivative was treated with a carboxylic acid and coupling reagent such as T3P in the presence of an amine base such as triethylamine and pyridine. Alternatively the compounds could be prepared by treating the amino-cyanamide with base such as triethylamine and an acid chloride as depicted in general method 2.

General method 3 depicts an alternative preparation that utilizes a protected diamine derivative in coupling conditions as described in general method 1. Deprotection of the resulting amide followed by cyanation with cyanogen bromide in the presence of an inorganic base such as potassium carbonate provides the cyanamide.

Analogous amides can be prepared via the method depicted in general method 4 by treatment of a protected amino acid derivative with an amine and a coupling reagent such as T3P in the presence of pyridine. The resulting protected derivative can then be deprotected and treated with cyanogen bromide and base as in general method 3.

In another general method bromo-acetamide Intermediate B can be reacted with a heteroatom substituted moiety (R-AH) in the presence of a base such as cesium carbonate in a polar aprotic solvent such as DMF as depicted in General Method 5.

Compounds can also be synthesized via General Method 6 in which a cyanamide containing aryl or heteroaryl amine participates in a C—N coupling reaction with a heteroaryl-halide and a transition metal catalyst such as palladium, in complex with supporting ligands such as RuPhos, and a base such as cesium carbonate in polar solvent at elevated temperature in a microwave reactor.

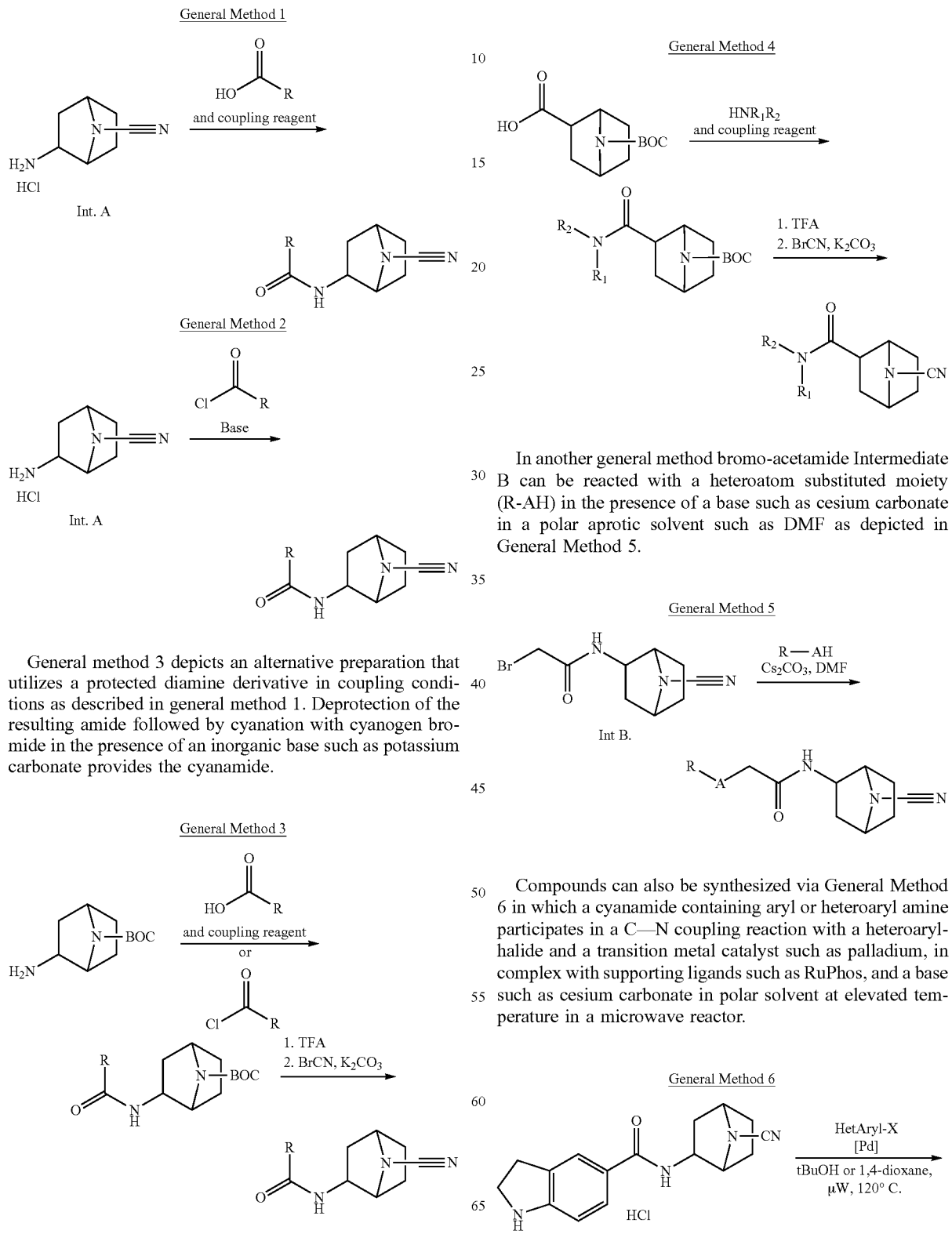

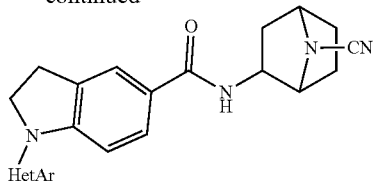

Synthetic Intermediates

Intermediate A: (1R, 2R, 4S)-2-amino-7-azabicyclo[2.2.1]heptane-7-carbonitrile hydrochloride

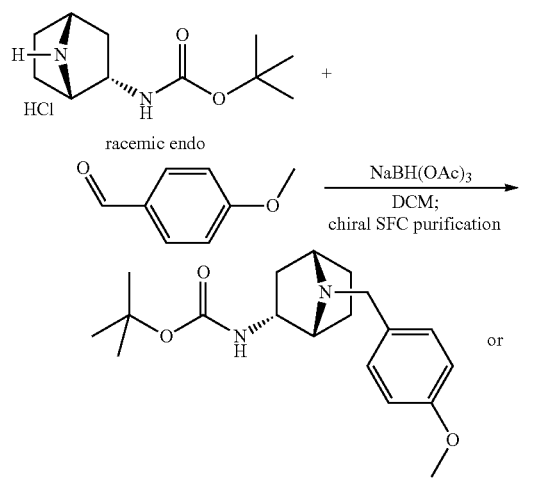

peak 1

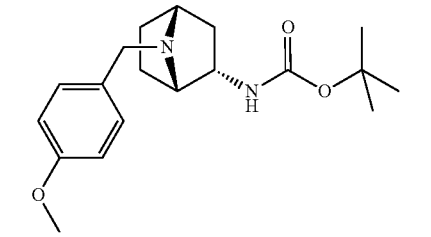

or

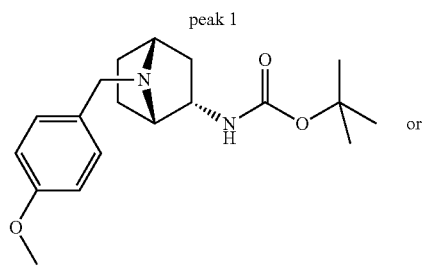

Peak 2

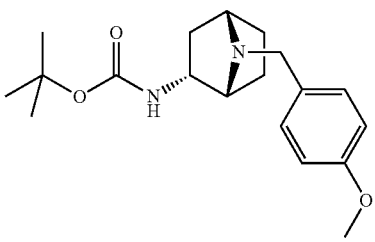

Step 1: To a red cap vial was added tert-butyl racemic-(1S,2S,4R)-7-azabicyclo[2.2.1]hept-2-ylcarbamate hydrochloride (0.7 g, 2.81 mmol, CAS #2098589-06-9) and 4-methoxybenzaldehyde (0.621 ml, 5.07 mmol) in dichloromethane (5.63 ml) followed by addition of sodium triacetoxyborohydride (1.074 g, 5.07 mmol). It was stirred at rt for 3.5 h. Another 1.5 h later, LCMS showed partial conversion. Then another 0.2 g of sodium triacetoxyborohydride was added, and the reaction mixture was stirred at rt for 18 hr. LC/MS showed >90% conversion to desired product. Then water and 10 mL of 1N NaOH was added and the reaction was extracted with DCM. The organic extract was washed with brine and dried over $MgSO_4$. The solution was filtered and concentrated in vacuo to give the crude material as a light-yellow oil. The crude material was absorbed onto a plug of silica gel and purified by chromatography through a 25 g biotage ultra column, eluting with a gradient of 10% to 40% EtOAc in EtOH (3/1 with 0.5% $Et_3N$ as additive) in Heptane, to provide tert-butyl racemic-(1S,2S,4R)-7-(4-methoxybenzyl)-7-azabicyclo[2.2.1]heptan-2-yl)carbamate (0.8 g, 2.406 mmol, 86% yield) as clear oil. m/z: 333.3 [M+1] The sample was purified by SFC using a Chiralpak AD-H 2×25 cm, 5 micron column, a mobile phase of 15% methanol w/ 0.2% diethylamine using a flowrate of 80 mL/min. to generate peak 1 with an ee of >99% and peak 2 with an ee of >97%. Peak assignment determined by SFC: Chiralpak AD-H, 15% methanol w/ 0.2% diethylamine. The absolute stereochemistry of the peak 1 intermediate was established by X-ray crystallography and peak 1 derived material was found to have (1R,2R,4S) stereochemistry.

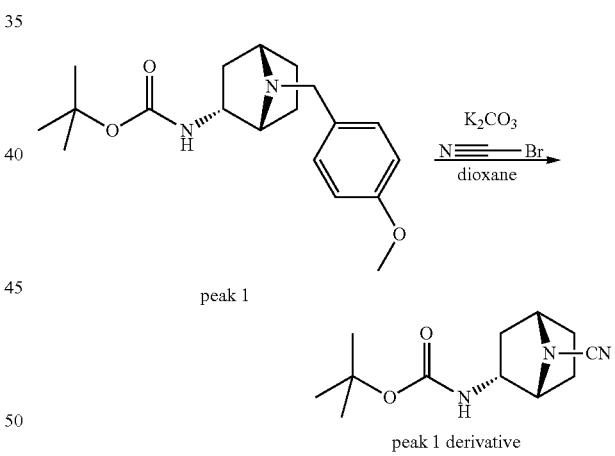

Step 2: To a 25-mL round-bottomed flask was added peak 1 derived tert-butyl ((1R,2R,4S)-7-(4-methoxybenzyl)-7-azabicyclo[2.2.1]heptan-2-yl)carbamate (0.108 g, 0.325 mmol) and $K_2CO_3$ (0.103 g, 0.747 mmol) in 1,4-dioxane (1.477 ml) followed by addition of cyanogen bromide solution, 5.0 m in acetonitrile (0.130 ml, 0.650 mmol). The reaction mixture was allowed to stir at rt overnight before being quenched with a saturated aqueous solution of $NaHCO_3$. The reaction mixture was diluted in $CH_2Cl_2$ and water and the layers were separated. The aqueous phase was extracted with $CH_2Cl_2$. The organic extracts were combined and dried over $Na_2SO_4$, filtered, and concentrated under reduced pressure. The product was used directly in the next step. m/z: 260.2 [M+23]

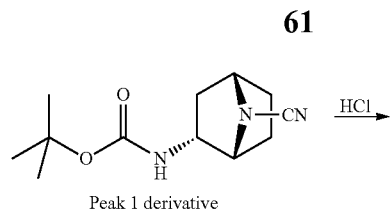

Peak 1 derivative

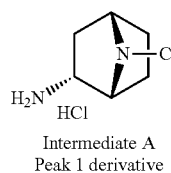

Intermediate A
Peak 1 derivative

Step 3: To a 50 mL round bottom flask was added crude tert-butyl ((1S,2S,4R)-7-cyano-7-azabicyclo[2.2.1]heptan-2-yl)carbamate (0.414 g, 1.745 mmol) and hydrogen chloride solution, 4.0 m in dioxane (6.54 ml, 26.2 mmol) in 1,4-dioxane (4.36 ml) at 0° C. It was warmed to rt and stirred for 1 h. LC/MS showed incomplete conversion. Then another 2 mL of 4.0 M HCl in dioxane was added and the reaction stirred for another 25 min. The precipitate was collected by filtration, to yield peak 1 derived (1S,2S,4R)-2-amino-7-azabicyclo[2.2.1]heptane-7-carbonitrile hydrochloride (0.4 g, 2.304 mmol, 132% yield) as a white solid. m/z: 138.2 [M+1] $^1$H NMR (500 MHz, DMSO-d$_6$) δ 8.48 (br s, 3H), 4.25-4.28 (m, 1H), 4.20 (t, J=4.74 Hz, 1H), 3.57-3.64 (m, 1H), 2.14-2.21 (m, 1H), 1.96 (br d, J=11.16 Hz, 1H), 1.78-1.88 (m, 2H), 1.72-1.78 (m, 1H), 1.41 (br d, J=13.49 Hz, 1H)

An identical procedure for steps 2 and 3 above were used to obtain racemic material from racemic endo-tert-butyl (7-azabicyclo[2.2.1]heptan-2-yl)carbamate (CAS 2098589-06-9) to provide Racemic Intermediate A Intermediate B: 2-bromo-N-((1R,2R,4S)-7-cyano-7-azabicyclo[2.2.1]heptan-2-yl)acetamide

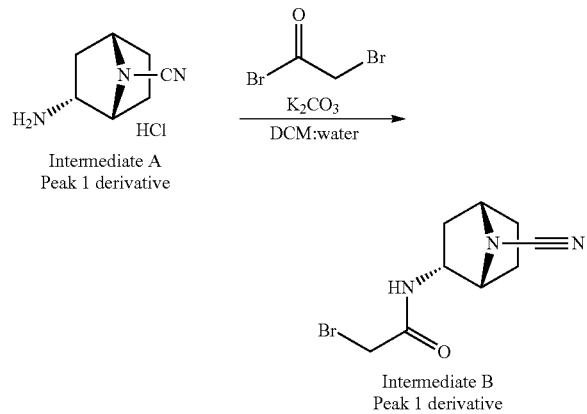

Intermediate A (1 g, 2.99 mmol; 52% by weight) was dissolved in dichloromethane (14.97 ml). Water (14.97 ml) and K$_2$CO$_3$ (0.828 g, 5.99 mmol) were added and with vigorous stirring 2-bromoacetyl bromide (0.339 ml, 3.89 mmol) was added. After 45 min full conv. was observed and the aq. was separated, extracted 2× with DCM. The combined organics were washed with brine, dried over Na$_2$SO$_4$, and concentrated to provide 2-bromo-N-((1R,2R,4S)-7-cyano-7-azabicyclo[2.2.1]heptan-2-yl)acetamide (0.9 g, 3.49 mmol, 116% yield) as a viscous oil which was used directly. m/z: 258.0, 261.0 [M+1]

Intermediate C: N-((1R,2R,4S)-7-cyano-7-azabicyclo[2.2.1]heptan-2-yl)indoline-5-carboxamide hydrochloride

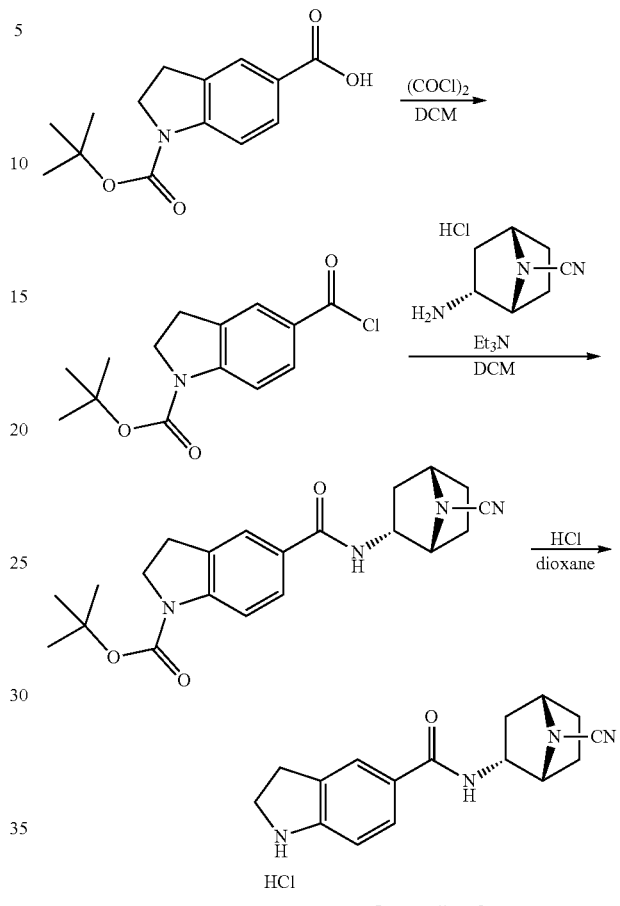

Intermediate C
peak 1 derived

Step 1:

To a glass reaction vial were added 1-(tert-butoxycarbonyl)-5-indolinecarboxylic acid (2.3 g, 8.74 mmol) and oxalyl chloride (1.0 ml, 11.36 mmol) in dichloromethane (17.5 ml) followed by 3 drops of DMF at 0° C. It was stirred at rt for 0.5 h. LCMS proved desired product formation by quenched with MeOH. It was concentrated and dried on high vacuum to yield tert-butyl 5-(chlorocarbonyl)indoline-1-carboxylate (2.46 g, 8.74 mmol, 100% yield) as brown solid. It was used for next step directly.

Step 2:

To a glass vial were added Intermediate A (0.641 g, 3.69 mmol) and tert-butyl 5-(chlorocarbonyl)indoline-1-carboxylate (0.8 g, 2.84 mmol) in DCM (9.5 ml) followed by triethylamine (1.4 ml, 9.94 mmol) at 0° C. The reaction was stirred at rt for 0.5 h when LC/MS showed desired product formation. The reaction mixture was diluted with water and extracted with DCM. The combined organics were concentrated and the crude material was adsorbed onto a plug of silica gel and purified by chromatography through a Biotage 25 g redi-sep ultra, eluting with a gradient of 10% to 70% EtOAc in Heptane, to provide tert-butyl 5-(((1R,2R,4S)-7-cyano-7-azabicyclo[2.2.1]heptan-2-yl)carbamoyl)indoline-1-carboxylate (0.55 g, 1.438 mmol, 50.6% yield) as white solid. m/z: 383.2 [M+1]

Step 3:
To a round-bottomed flask was added tert-butyl 5-(chlorocarbonyl)indoline-1-carboxylate (0.8 g, 2.84 mmol) and hydrogen chloride solution, 4.0 m in dioxane (10.7 ml, 42.6 mmol) in dioxane (5 ml) slowly. The reaction mixture was stirred at rt for 3 h. LCMS showed all sm consumed and the white ppt was collected by filtration to yield N-((1R,2R,4S)-7-cyano-7-azabicyclo[2.2]heptan-2-yl)indoline-5-carboxamide hydrochloride (0.59 g, 1.851 mmol, 65.2% yield) as a white solid. m/z: 283.2 [M+1]

The intermediates in the table below were made by identical procedures:

| Int. | Structure[FB-L7] | Name | LC/MS data |
| --- | --- | --- | --- |
| C-1 | | 4-bromo-N-((1R,2R,4S)-7-cyano-7-azabicyclo[2.2.1]heptan-2-yl)-3-methylbenzamide | m/z: 334.2 [M + 1] |
| C-2 | | 6-chloro-N-((1R,2R,4S)-7-cyano-7-azabicyclo[2.2.1]heptan-2-yl)-1H-indazole-5-carboxamide | m/z: 316.0 [M + 1] |
| C-3 | | 7-bromo-N-((1R,2R,4S)-7-cyano-7-azabicyclo[2.2.1]heptan-2-yl)-1H-indole-3-carboxamide | m/z: 359.0/361.0 [M + 1] |
| C-4 | | 4-bromo-2-chloro-N-((1R,2R,4S)-7-cyano-7-azabicyclo[2.2.1]heptan-2-yl)benzamide | m/z: 354.0/356.0 [M + 1] |
| C-5 | | 4-bromo-2,6-dichloro-N-((1R,2R,4S)-7-cyano-7-azabicyclo[2.2.1]heptan-2-yl)benzamide | m/z: 390.0 [M + 1] |
| C-6 | | 4-bromo-N-((1R,2R,4S)-7-cyano-7-azabicyclo[2.2.1]heptan-2-yl)-2-(trifluoromethyl)benzamide | m/z: 389.0 [M + 1] |
| C-7 | | 4-bromo-N-((1R,2R,4S)-7-cyano-7-azabicyclo[2.2.1]heptan-2-yl)-2-fluorobenzamide | m/z: 339.0 [M + 1] |
| C-8 | | 4-bromo-N-((1R,2R,4S)-7-cyano-7-azabicyclo[2.2.1]heptan-2-yl)-2-methylbenzo[d]thiazole-7-carboxamide | m/z: 393.0 [M + 1] |

Intermediate D: 1-(4-methylpyrimidin-2-yl)indoline-5-carboxylic acid

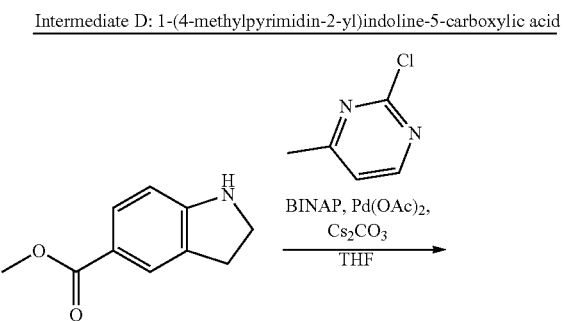

Intermediate E: 1-(4-methylpyrimidin-2-yl)-1H-indazole-5-carboxylic acid

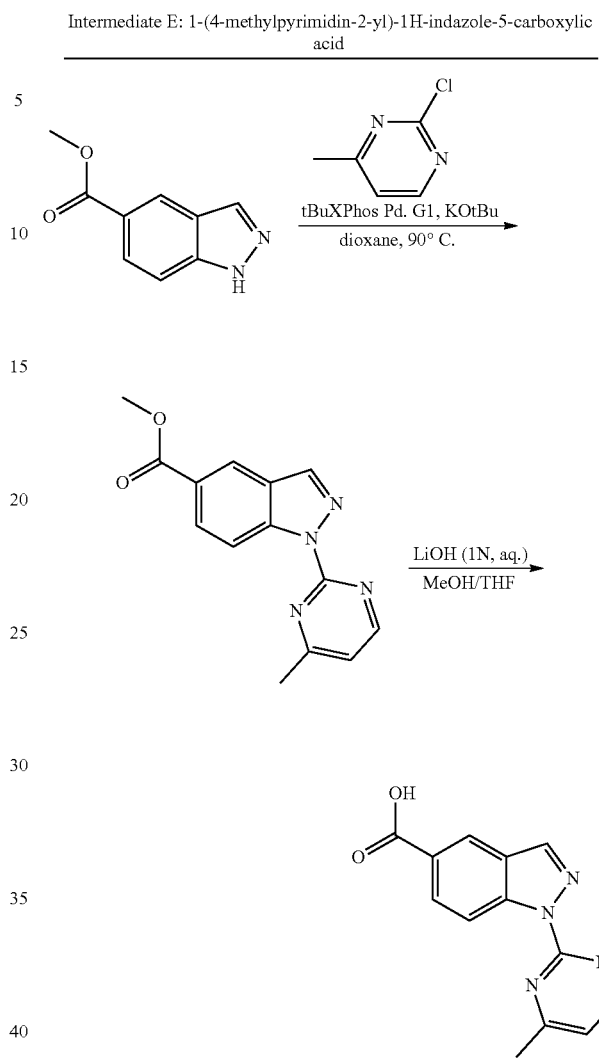

Step 1:

A glass microwave reaction vessel was charged with methyl indoline-5-carboxylate (0.06 g, 0.339 mmol), 2-chloro-4-methylpyrimidine (0.054 g, 0.423 mmol), racemic-2,2'-bis(diphenylphosphino)-1,1'-binaphthyl (0.032 g, 0.051 mmol), palladium (ii) acetate (7.60 mg, 0.034 mmol) and cesium carbonate (0.221 g, 0.677 mmol) in tetrahydrofuran (1.7 ml). The reaction mixture was purged with $N_2$ and heated in a microwave reactor at 110° C. for 10 min. LCMS showed desired product. The reaction mixture was diluted with water and extracted with DCM. The organic extract was washed with saturated NaCl and dried over $MgSO_4$. The solution was filtered and concentrated in vacuo to yield crude product which was used for next step directly. m/z: 270.2 [M+1]

Step 2:

To a glass reaction vial containing crude product from step 1 was added LiOH (1 M) (1.35 ml, 1.35 mmol) in MeOH/THF (0.5 ml/0.5 ml, 1:1) and heated to 50° C. for 2 h. It was concentrated and acidified with 2N HCl (aq.) until pH ~2. The white ppt was collected by filtration to yield 1-(4-methylpyrimidin-2-yl)indoline-5-carboxylic acid (0.08 g, 0.313 mmol, 93% yield) as white solid which was dried on high vacuum and used in the next step directly. m/z: 256.2 [M+1]

Step 1:

To a glass reaction vial were charged with 2-chloro-4-methylpyrimidine (0.095 g, 0.738 mmol), methyl indazole-5-carboxylate (0.1 g, 0.568 mmol), chloro(2-di-t-butylphosphino-2',4',6'-tri-i-propyl-1,1'-biphenyl)[2-(2-aminoethyl)phenyl] Pd(ii) (0.058 g, 0.085 mmol) with potassium tert-butoxide (0.159 g, 1.42 mmol) in dioxane (2.3 mL). The reaction mixture was purged with N2 gas and heated in heating block at 90° C. 20 min later, LCMS showed nearly full conversion to desired product as major product. The orange reaction mixture was diluted with water and extracted with DCM. The organic extract was concentrated in vacuo to give the crude material as an orange solid which was used directly in the next step. m/z: 269.2 [M+1]

Step 2:

To a glass reaction vial containing crude product from step 1 was added LiOH (1 M) (2.3 ml, 2.3 mmol) in MeOH/THF (1:1, 2.2 mL). The mixture was heated to 60° C. for 1.5 h. LCMS showed nearly full conversion to desired product. It was cooled to rt and organic solvent was reduced. To the red residue was treated with water (~1 mL), and 2N HCl aq. slowly until pH ~2. The red ppt was collected by filtration and dried on high vacuum and used directly. m/z: 255.2 [M+1]

The intermediates in the table below were made by identical procedures:

| Int. | Structure[FB-L8] | Name | LC/MS data |
| --- | --- | --- | --- |
| E-1 | | 4-((4-cyclopropylpyrimidin-2-yl)amino)-2,5-difluorobenzoic acid | m/z: 306.0 [M + 1] |
| E-2 | | 4-((4-cyclopropylpyrimidin-2-yl)amino)-2,3-difluorobenzoic acid | m/z: 306.1 [M + 1] |
| E-3 | | 1-(6-methylpyridin-2-yl)-1H-indazole-5-carboxylic acid | m/z: 254.2 [M + 1] |
| E-4 | | 6-chloro-1-(6-methylpyridin-2-yl)-1H-indazole-5-carboxylic acid | m/z: 288.0 [M + 1] |
| E-5 | | 6-fluoro-1-(6-methylpyridin-2-yl)-1H-indazole-5-carboxylic acid | m/z: 272.2 [M + 1] |

-continued

| Int. | Structure[FB-L8] | Name | LC/MS data |
|---|---|---|---|
| E-6 | | 6-chloro-1-(6-(2,2,2-trifluoroethoxy)pyridin-2-yl)-1H-indazole-5-carboxylic acid | m/z: 372.0 [M + 1] |
| E-7 | | 6-chloro-1-(1,7-naphthyridin-2-yl)-1H-indazole-5-carboxylic acid | m/z: 325.0 [M + 1] |
| E-8 | | 6-chloro-1-(6-(cyanomethyl)pyridin-2-yl)-1H-indazole-5-carboxylic acid | |
| E-9 | | 6-chloro-1-(1,8-naphthyridin-2-yl)-1H-indazole-5-carboxylic acid | m/z: 325.0 [M + 1] |
| E-10 | | 1-(6-methylpyridin-2-yl)-4,5,6,7-tetrahydro-1H-indazole-5-carboxylic acid | m/z: 258.1 [M + 1] | and

| Int. | Structure[FB-L8] | Name | LC/MS data |
|---|---|---|---|
| | 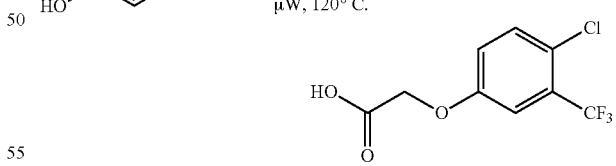 | | |

Intermediate F: N-Benzyl-N-(3-bromobenzyl)glycine

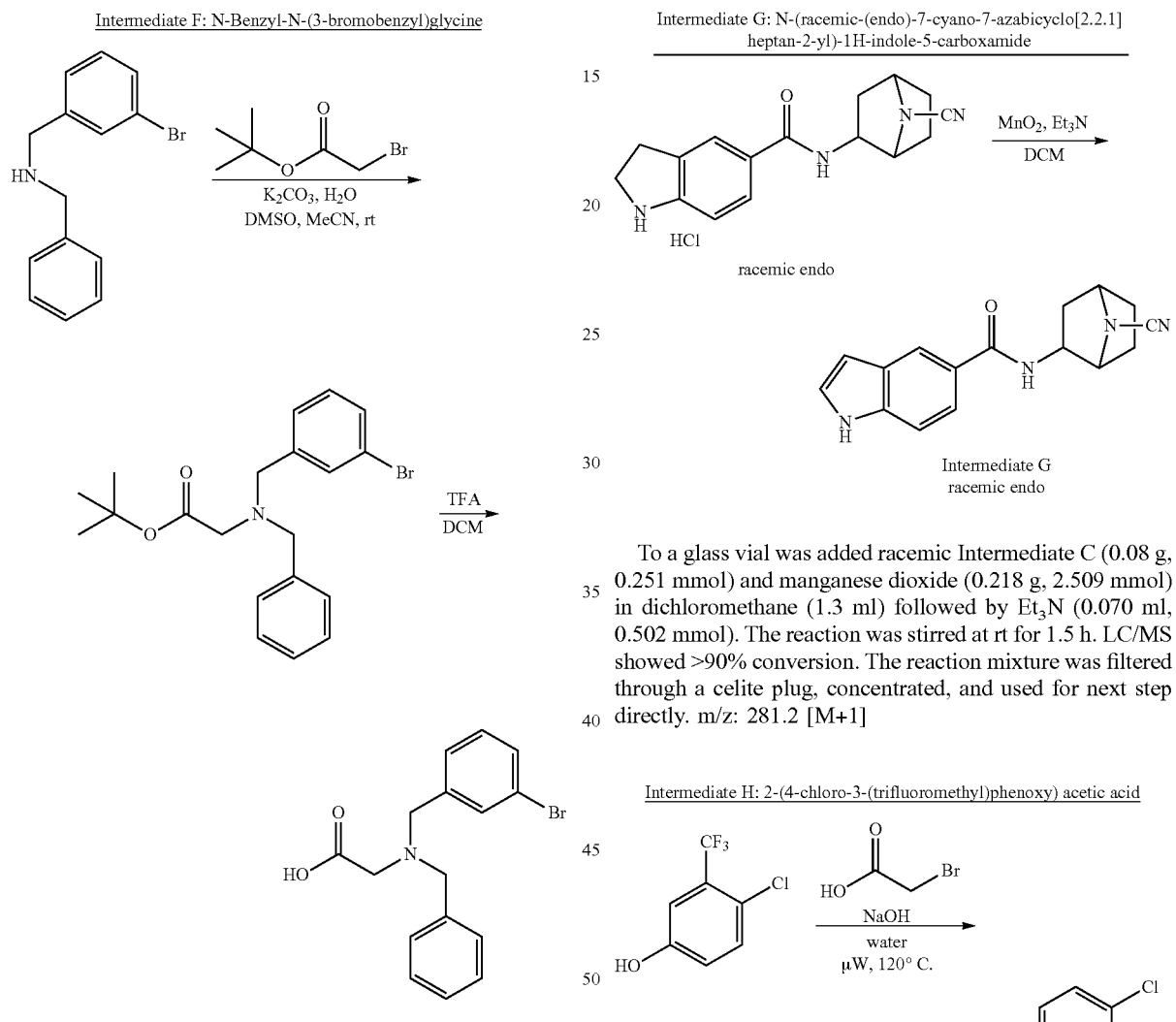

The mixture of N-benzyl-1-(3-bromophenyl)methanamine (HCl salt, 47 mg, 0.15 mmol), tert-butyl 2-bromoacetate (35 mg, 0.18 mmol), K$_2$CO$_3$ (aq 2 M, 0.15 mL, 0.30 mmol), DMSO (0.1 mL) and MeCN (0.5 mL) was stirred at room temperature for 6 h. The resulting solution was subjected to preparative HPLC (0.1% TFA) to afford tert-butyl N-benzyl-N-(3-bromobenzyl)glycinate (60 mg, quantitative). To the mixture of tert-butyl N-benzyl-N-(3-bromobenzyl)glycinate obtained in the previous reaction, trifluoroacetic acid (1.0 mL) and dichloromethane (0.5 mL) was stirred at room temperature for 5 h. The resulting mixture was concentrated, dissolved in dichloromethane (2.0 mL), then concentrated again to provide N-benzyl-N-(3-bromobenzyl)glycine. [M+H] 334.1.

Intermediate G: N-(racemic-(endo)-7-cyano-7-azabicyclo[2.2.1]heptan-2-yl)-1H-indole-5-carboxamide To a glass vial was added racemic Intermediate C (0.08 g, 0.251 mmol) and manganese dioxide (0.218 g, 2.509 mmol) in dichloromethane (1.3 ml) followed by Et$_3$N (0.070 ml, 0.502 mmol). The reaction was stirred at rt for 1.5 h. LC/MS showed >90% conversion. The reaction mixture was filtered through a celite plug, concentrated, and used for next step directly. m/z: 281.2 [M+1]

Intermediate H: 2-(4-chloro-3-(trifluoromethyl)phenoxy) acetic acid

To a 0.5-2 mL microwave vial were added 4-chloro-3-(trifluoromethyl)phenol (0.51 g, 2.59 mmol) and sodium hydroxide, pellets (0.467 g, 11.68 mmol) in water (2.2 ml). It was stirred at rt for 5 min and then bromoacetic acid (0.901 g, 6.49 mmol) was added. The mixture was heated in microwave reactor at 120° C. for 10 min. The reaction was acidified with 2 N aq. HCl until pH ~2. The white ppt was collected by filtration and dried on high vacuum overnight to yield 2-(4-chloro-3-(trifluoromethyl)phenoxy)acetic acid (0.5 g, 1.964 mmol, 76% yield) as white solid.

Intermediate I: (racemic-(endo)-7-cyano-7-azabicyclo[2.2.1]heptane-2-carboxyl acid

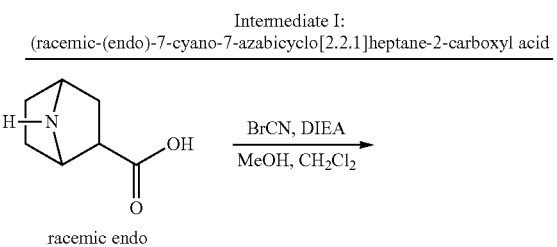

racemic endo

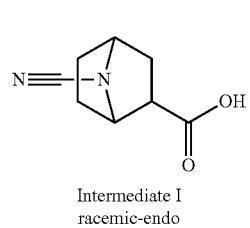

Intermediate I
racemic-endo

To a stirred solution of racemic-(1R,2R,4S)-7-azabicyclo[2.2.1]heptane-2-carboxylic acid carboxylate (HCl salt, 8.9 mg, 0.050 mmol, purchased from ChemBridge) DIEA (0.026 mL, 0.15 mmol) and methanol (0.5 mL) was added cyanogen bromide (11 mg, 0.10 mmol) in dichloromethane (0.2 mL) at room temperature. After stirring for 20 min. the mixture was concentrated to provide racemic-(1R,2R,4S)-7-cyano-7-azabicyclo[2.2.1]heptane-2-carboxylic acid which was used for the next reaction without further purification. MS (EI) for $C_8H_{10}N_2O_2$, found 167.1 (MH+).

Intermediate J: 6-chloro-N-((1R,2R,4S)-7-(4-methoxybenzyl)-7-azabicyclo[2.2.1]heptan-2-yl)-1-(4-methylpyrimdin-2-yl)indoline-5-carboxamide

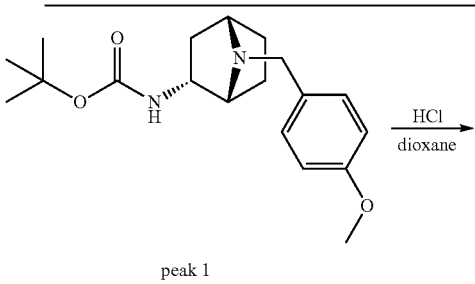

peak 1

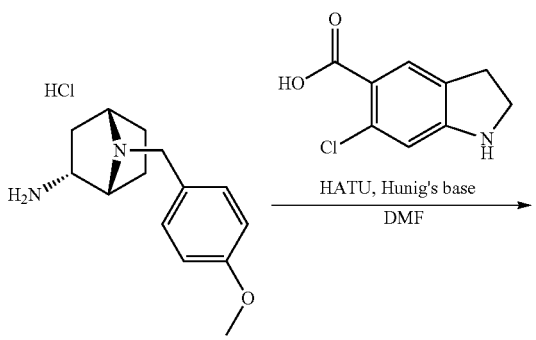

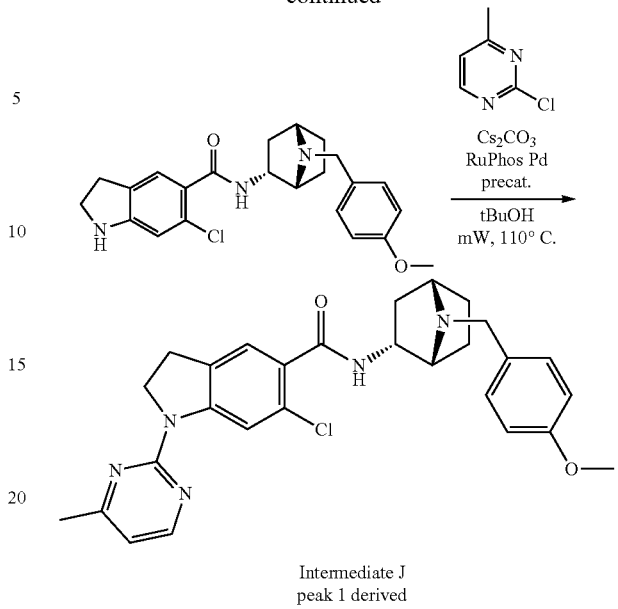

Intermediate J
peak 1 derived

Step 1:
To a red cap vial was added tert-butyl ((1R,2R,4S)-7-(4-methoxybenzyl)-7-azabicyclo[2.2.1]heptan-2-yl)carbamate (0.5 g, 1.504 mmol) (from intermediate A step 1) and HCl in dioxane (4 M) (3.01 ml, 12.03 mmol) in dioxane (3.0 ml). The slurry was stirred at rt for 4 h when LC/MS showed nearly full conversion to desired product. The reaction was concentrated and MTBE was added. The mixture was stirred at rt until white ppt formed. The white ppt was collected by quick filtration and dried on high vacuum overnight to yield the desired HCl salt (1R,2R,4S)-7-(4-methoxybenzyl)-7-azabicyclo[2.2.1]heptan-2-amine hydrochloride (0.40 g, 1.488 mmol, 99% yield) as a white solid. m/z: 233.2 [M+1]

Step 2:
To a vial containing 6-chloro-5-indolinecarboxylic acid (0.15 g, 0.759 mmol) was added HATU (0.404 g, 1.063 mmol) and Hunig's base (0.398 ml, 2.277 mmol) in DMF (2.9 ml). After stirring for 5 min, (1R,2R,4S)-7-(4-methoxybenzyl)-7-azabicyclo[2.2.1]heptan-2-amine hydrochloride (0.265 g, 0.987 mmol) was added. The orange reaction mixture was stirred at rt for 5 min when LCMS showed the desired product. The reaction mixture was treated with 6N NaOH (aq.) and extracted with DCM and the crude material was absorbed onto a plug of silica gel and purified by chromatography through a Biotage SNAP KP-NH 28 g column, eluting with a gradient of 10% to 35% EtOAc/EtOH (3/1) in Heptane, to provide 6-chloro-N-((1R,2R,4S)-7-(4-methoxybenzyl)-7-azabicyclo[2.2.1]heptan-2-yl)indoline-5-carboxamide (0.13 g, 0.316 mmol, 41.6% yield) as off-white foam. m/z: 412.2 [M+1]

Step 3:
A glass microwave reaction vessel was charged with 6-chloro-N-((1R,2R,4S)-7-(4-methoxybenzyl)-7-azabicyclo[2.2.1]heptan-2-yl)indoline-5-carboxamide (0.06 g, 0.146 mmol), 2-chloro-4-methylpyrimidine (0.028 g, 0.218 mmol), RuPhos Pd G1 methyl t-butyl ether adduct (0.024 g, 0.029 mmol) and cesium carbonate (0.119 g, 0.364 mmol). The reaction vial was purged with $N_2$ and tBuOH (0.73 ml) was added. The reaction mixture was heated in microwave reactor at 110° C. for 10 min. LCMS showed full conversion to desired product. The reaction mixture was diluted with water and extracted with DCM. The organic extract was concentrated. The crude material was absorbed onto a plug of silica gel and purified by chromatography through a 10 g biotage ultra column, eluting with a gradient of 10% to 75% EtOAc/EtOH (3/1) in Heptane to provide 6-chloro-N-((1R, 2R,4S)-7-(4-methoxybenzyl)-7-azabicyclo[2.2.1]heptan-2-yl)-1-(4-methylpyrimidin-2-yl)indoline-5-carboxamide (0.04 g, 0.079 mmol, 54.5% yield) as a yellow foam. m/z: 504.2 [M+1]

The intermediates in the table below were made by identical procedures:

| Int. | Structure | Name | LC/MS data |
|---|---|---|---|
| J-1 | 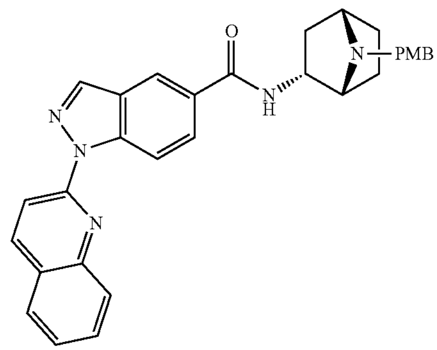 | N-((1R,2R,4S)-7-(4-methoxybenzyl)-7-azabicyclo[2.2.1]heptan-2-yl)-1-(quinolin-2-yl)-1H-indazole-5-carboxamide | m/z: 504.2 [M + 1] |
| J-2 | 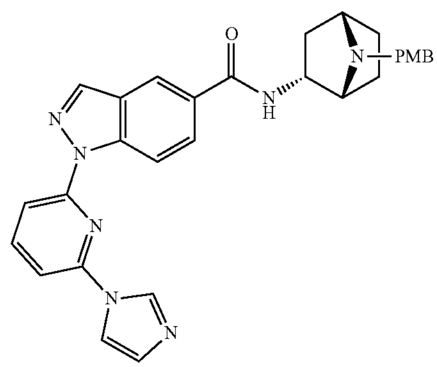 | 1-(6-(1H-imidazol-1-yl)pyridin-2-yl)-N-((1R,2R,4S)-7-(4-methoxybenzyl)-7-azabicyclo[2.2.1]heptan-2-yl)-1H-indazole-5-carboxamide | |
| J-3 | 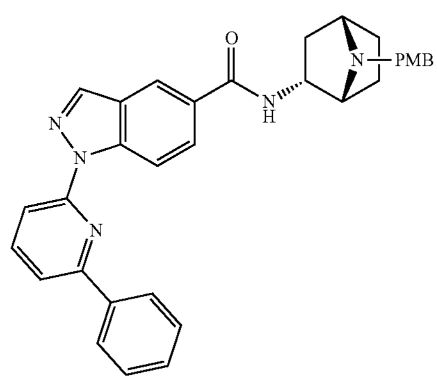 | N-((1R,2R,4S)-7-(4-methoxybenzyl)-7-azabicyclo[2.2.1]heptan-2-yl)-1-(6-phenylpyridin-2-yl)-1H-indazole-5-carboxamide | |
| J-4 | 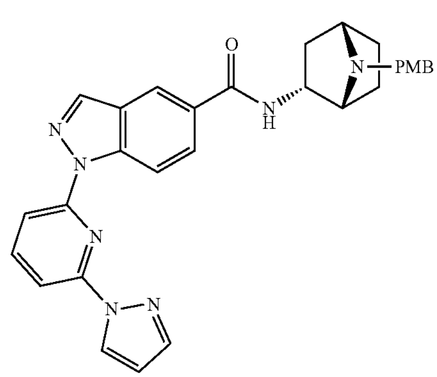 | 1-(6-(1H-pyrazol-1-yl)pyridin-2-yl)-N-((1R,2R,4S)-7-(4-methoxybenzyl)-7-azabicyclo[2.2.1]heptan-2-yl)-1H-indazole-5-carboxamide | |

-continued

| Int. | Structure | Name | LC/MS data |
|---|---|---|---|
| J-5 | 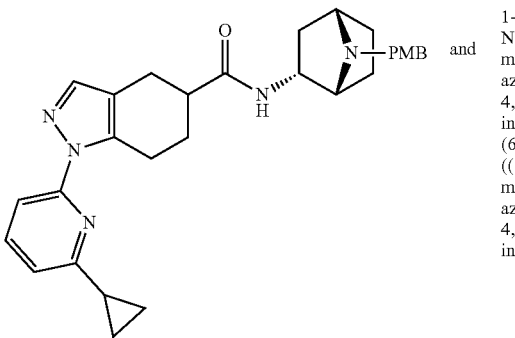 and 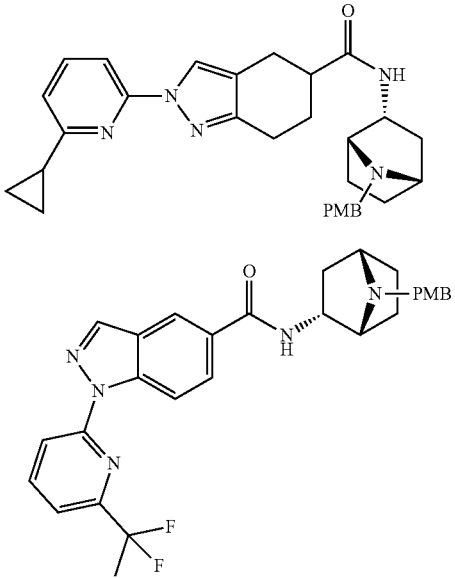 | 1-(6-cyclopropylpyridin-2-yl)-N-((1R,2R,4S)-7-(4-methoxybenzyl)-7-azabicyclo[2.2.1]heptan-2-yl)-4,5,6,7-tetrahydro-1H-indazole-5-carboxamide and 2-(6-cyclopropylpyridin-2-yl)-N-((1R,2R,4S)-7-(4-methoxybenzyl)-7-azabicyclo[2.2.1]heptan-2-yl)-4,5,6,7-tetrahydro-2H-indazole-5-carboxamide | m/z: 498.2 [M + 1] |
| J-6 | 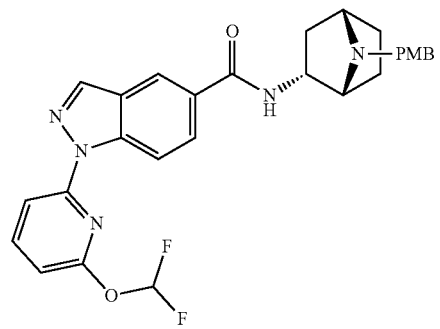 | 1-(6-(1,1-difluoroethyl)pyridin-2-yl)-N-((1R,2R,4S)-7-(4-methoxybenzyl)-7-azabicyclo[2.2.1]heptan-2-yl)-1H-indazole-5-carboxamide | m/z: 518.0 [M + 1] |
| J-7 | 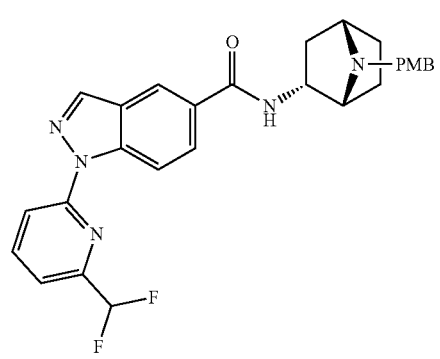 | 1-(6-(difluoromethoxy)pyridin-2-yl)-N-((1R,2R,4S)-7-(4-methoxybenzyl)-7-azabicyclo[2.2.1]heptan-2-yl)-1H-indazole-5-carboxamide | m/z: 520.0 [M + 1] |
| J-8 | 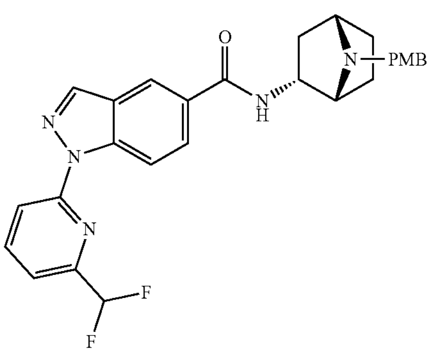 | 1-(6-(difluoromethyl)pyridin-2-yl)-N-((1R,2R,4S)-7-(4-methoxybenzyl)-7-azabicyclo[2.2.1]heptan-2-yl)-1H-indazole-5-carboxamide | m/z: 504.0 [M + 1] |

-continued
| Int. | Structure | Name | LC/MS data |
|---|---|---|---|
| J-9 | 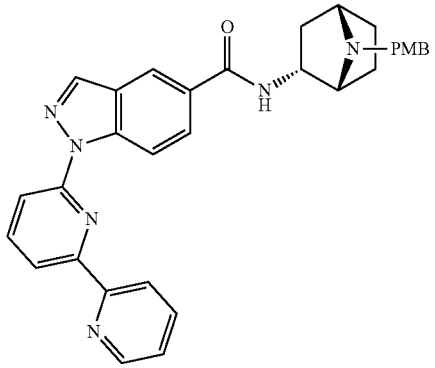 | 1-([2,2'-bipyridin]-6-yl)-N-((1R,2R,4S)-7-(4-methoxybenzyl)-7-azabicyclo[2.2.1]heptan-2-yl)-1H-indazole-5-carboxamide | m/z: 531.2 [M + 1] |
| J-10 | 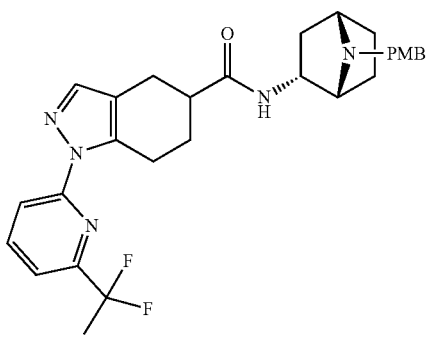<br>and<br>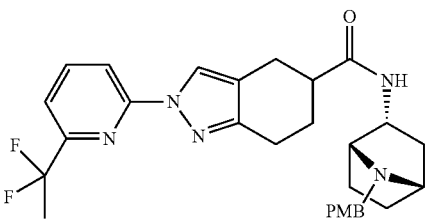 | 1-(6-(1,1-difluoroethyl)pyridin-2-yl)-N-((1R,2R,4S)-7-(4-methoxybenzyl)-7-azabicyclo[2.2.1]heptan-2-yl)-4,5,6,7-tetrahydro-1H-indazole-5-carboxamide and 2-(6-(1,1-difluoroethyl)pyridin-2-yl)-N-((1R,2R,4S)-7-(4-methoxybenzyl)-7-azabicyclo[2.2.1]heptan-2-yl)-4,5,6,7-tetrahydro-2H-indazole-5-carboxamide | |

| Int. | Structure | Name | LC/MS data |
|---|---|---|---|
| J-11 | 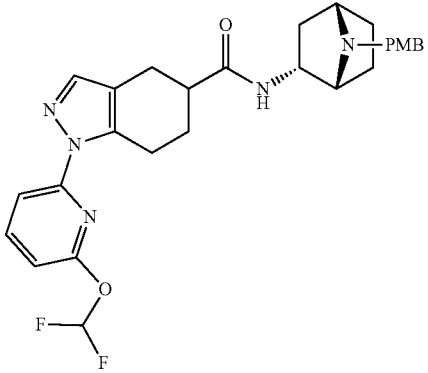 | 1-(6-(difluoromethoxy)pyridin-2-yl)-N-((1R,2R,4S)-7-(4-methoxybenzyl)-7-azabicyclo[2.2.1]heptan-2-yl)-4,5,6,7-tetrahydro-1H-indazole-5-carboxamide and 2-(6-(difluoromethoxy)pyridin-2-yl)-N-((1R,2R,4S)-7-(4-methoxybenzyl)-7-azabicyclo[2.2.1]heptan-2-yl)-4,5,6,7-tetrahydro-2H-indazole-5-carboxamide | |
| J-12 | 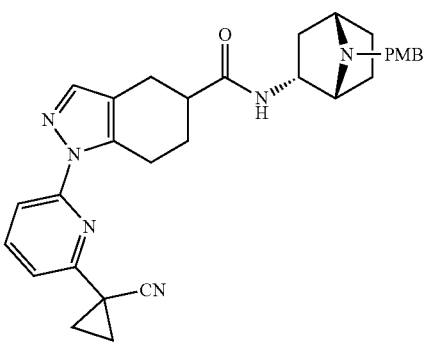 | 1-(6-(1-cyanocyclopropyl)pyridin-2-yl)-N-((1R,2R,4S)-7-(4-methoxybenzyl)-7-azabicyclo[2.2.1]heptan-2-yl)-4,5,6,7-tetrahydro-1H-indazole-5-carboxamide and 2-(6-(1-cyanocyclopropyl)pyridin-2-yl)-N-((1R,2R,4S)-7-(4-methoxybenzyl)-7-azabicyclo[2.2.1]heptan-2-yl)-4,5,6,7-tetrahydro-2H-indazole-5-carboxamide | |

Intermediate K: 3-(4-methylpyrimidin-2-yl)-1H-indole-6-carboxylic acid

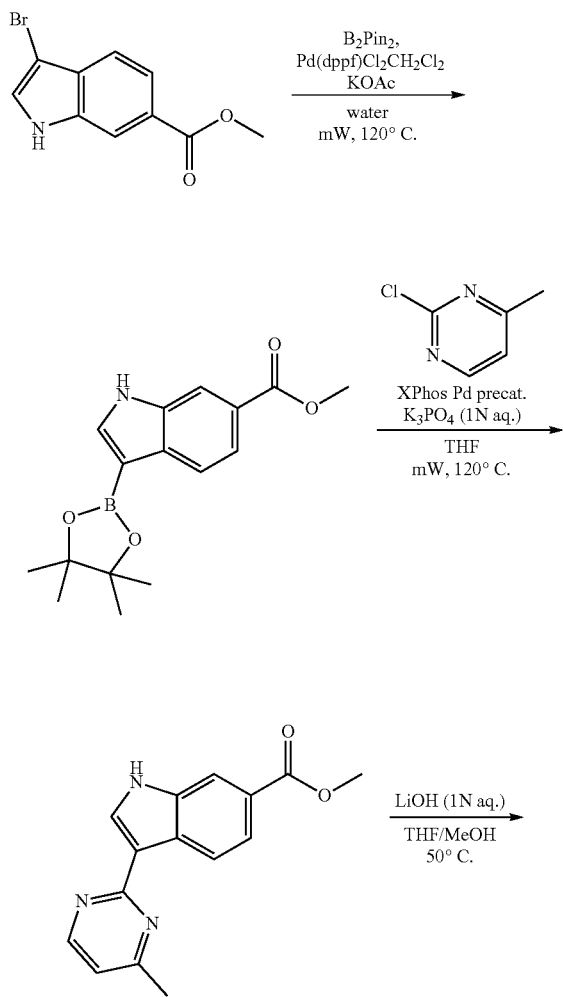

Step 1: A glass microwave reaction vessel was charged with methyl 3-bromo-1H-indole-6-carboxylate (0.15 g, 0.590 mmol), 1,3,2-dioxaborolane (0.225 g, 0.886 mmol) and [1,1'-bis(diphenylphosphino)ferrocene]-dichloropalladium(II), complex with dichloromethane (0.072 g, 0.089 mmol) in potassium acetate (0.098 g, 1.004 mmol) and THF (3 ml). The reaction mixture was stirred and heated in a microwave reactor at 120° C. for 20 min. LCMS showed full conversion. The reaction mixture was diluted with water and extracted with DCM. The organic extract was concentrated in vacuo to give the crude material as a dark brown oil which was used for next step directly.

Step 2: A glass microwave reaction vessel was charged with methyl 3-(4,4,5,5-tetramethyl-1,3,2-dioxaborolan-2-yl)-1H-indole-6-carboxylate (crude product from step 1), 2-chloro-4-methylpyrimidine (0.091 g, 0.708 mmol), chloro (2-dicyclohexylphosphino-2',4',6'-tri-i-propyl-1,1'-biphenyl)[2-(2-aminoethyl)phenyl]pd(ii) me-t-butylether (0.087 g, 0.118 mmol) in THF (2.95 ml) followed by K3PO4 (1N) (1.2 ml, 1.2 mmol). The reaction mixture was purged with $N_2$, stirred and heated in a microwave reactor at 120° C. for 6 min. LCMS showed desired product. The organic extract was diluted with water and extracted with DCM. The organic phase was washed with water and concentrated. The solution was filtered and concentrated in vacuo to give the crude material as an orange oil. The crude material was absorbed onto a plug of silica gel and purified by chromatography through a 10 g biotage ultra column, eluting with a gradient of 10% to 60% EtOAc/EtOH (3/1) in Heptane, to provide methyl 3-(4-methylpyrimidin-2-yl)-1H-indole-6-carboxylate (0.06 g, 0.224 mmol, 38% yield) as orange foam. m/z: 268.2 [M+1]

Step 3: Refer to intermediate E step 2 to provide 3-(4-methylpyrimidin-2-yl)-1H-indole-6-carboxylic acid (0.025 g, 0.1 mmol, 42.2% yield). m/z: 254.2 [M+1]

The intermediates in the table below were made by identical procedures:

| Int. | Structure[FB-L9] | Name | LC/MS data |
|---|---|---|---|
| K-1 | | 6-(4-methylpyrimidin-2-yl)-1H-indole-2-carboxylic acid | m/z: 254.2 [M + 1] |

Intermediate L:

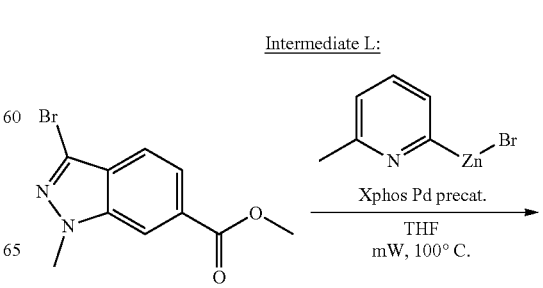

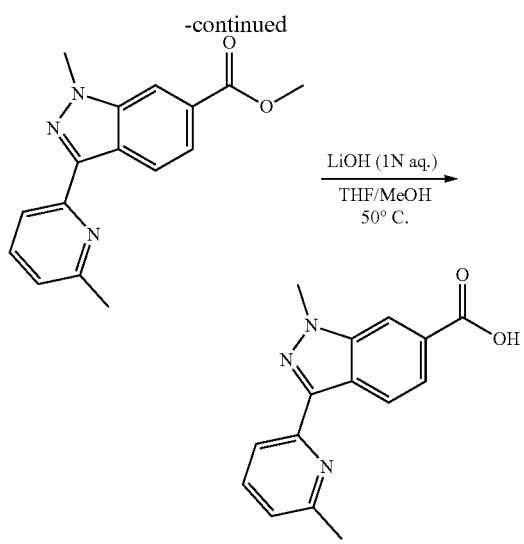

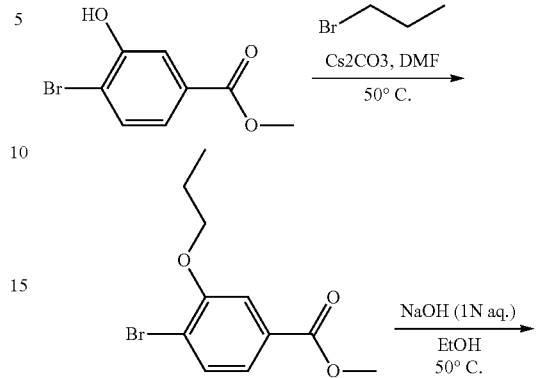

Intermediate M: 4-bromo-N-((1R,2R,4S)-7-cyano-7-azabicyclo[2.2.1]heptan-2-yl)-3-propoxybenzamide

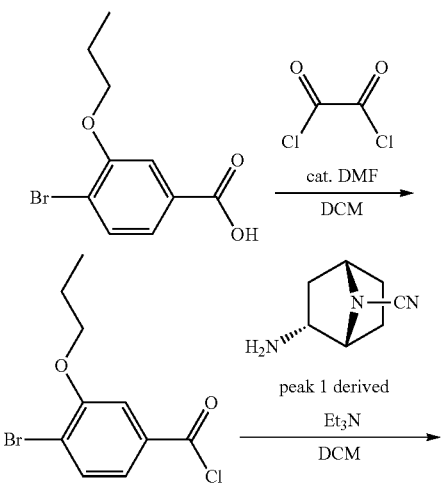

Step 1:
A glass microwave reaction vessel was charged with 6-methyl-2-pyridylzinc bromide (0.5 M) (1.19 ml, 0.595 mmol), methyl 3-bromo-1-methyl-1 h-indazole-6-carboxylate (0.1 g, 0.372 mmol) and chloro(2-dicyclohexylphosphino-2',4',6'-tri-i-propyl-1,1'-biphenyl)[2-(2-aminoethyl)phenyl]pd(ii) Me-tert-butylether (0.041 g, 0.056 mmol) in THF (0.74 ml). The reaction mixture was stirred and heated in a microwave reactor at 100° C. for 5 min. LC/MS showed full conversion to desired product. The reaction mixture was diluted with water and extracted with DCM. It was concentrated and used for next step directly. m/z: 282.2 [M+1]

Step 2:
Refer to intermediate E step 2 to provide 1-methyl-3-(6-methylpyridin-2-yl)-1H-indazole-6-carboxylic acid (0.12 g, 0.449 mmol, 121% yield) as off-white solid. m/z: 268.2 [M+1]

The intermediates in the table below were made by identical procedures:

| Int. | Structure[FB-L10] | Name | LC/MS data |
|---|---|---|---|
| L-1 | | 5-chloro-1-methyl-3-(6-methylpyridin-2-yl)-1H-indazole-6-carboxylic acid | m/z: 302.0 [M + 1] |
| L-2 | | methyl 3-(6-methylpyridin-2-yl)-1H-indazole-6-carboxylate | m/z: 268.2 [M + 1] |

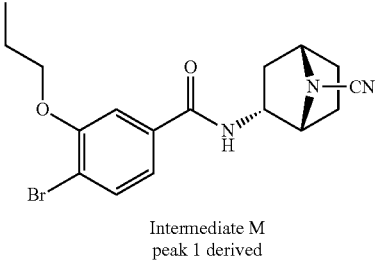

Intermediate M
peak 1 derived

Step 1:

To a reaction vial was added, 1-bromopropane (0.149 g, 1.212 mmol), cesium carbonate (0.282 g, 0.866 mmol), methyl 4-bromo-3-hydroxybenzoate (0.200 g, 0.866 mmol), and N, N-dimethylformamide (2.164 ml). The vial was capped and heated to 50° C. for 1 hour. The reaction was complete as determined by LCMS. The reaction was diluted with DCM (10 mL) and filtered.

The filtrate was removed in vacuo and the remaining crude material was used directly in the next step. m/z: 274.8 [M+1]

Step 2:

The crude material from Step 1, was take up in EtOH (5 mL). To this, NaOH (1 M) (2.0 ml, 2.0 mmol) was added and the reaction stirred at 50° C. for 1 hour. The solvent was removed in vacuo and the remaining crude material was taken up in 5 mL of water. The solution was acidified with 1N HCl aq. slowly until pH ~2. The resulting white solid was filtered and dried in vacuo, to give 4-bromo-3-propoxybenzoic acid (0.186 g, 0.718 mmol, 83% yield). m/z: 256.0 [M−1]

Step 3:

To a red cap vial containing 4-bromo-3-propoxybenzoic acid (0.149 g, 0.576 mmol) and oxalyl chloride (0.101 ml, 1.152 mmol) in DCM (2.88 ml) was added 3 drops of DMF. The reaction was stirred for 30 minutes and then concentrated under reduced pressure and dried on the high vacuum. The crude material was used directly in the next step.

Step 4:

To red cap vial containing 4-bromo-3-propoxybenzoyl chloride and (1R,2R,4S)-2-amino-7-azabicyclo[2.2.1]heptane-7-carbonitrile hydrochloride (Intermediate A, Peak 1 derived) (0.100 g, 0.576 mmol) in DCM (2.88 ml) followed by triethylamine (0.401 ml, 2.88 mmol) at 0C. It was stirred at rt for 1 hour. LCMS confirms reaction complete. The reaction mixture was diluted with water and extracted with DCM. It was concentrated and the crude material was absorbed onto a plug of silica gel and purified by chromatography through a 10 g biotage ultra, eluting with a gradient of 0% to 75% EtOAc in Heptane, to provide 4-bromo-N-((1R,2R,4S)-7-cyano-7-azabicyclo[2.2.1]heptan-2-yl)-3-propoxybenzamide (0.156 g, 0.412 mmol, 71.6% yield) as off-white solid. m/z: 379.8 [M+1]

The intermediates in the table below were made by identical procedures:

| Int. | Structure[FB-L11] | Name | LC/MS data |
|---|---|---|---|
| M-1 | | 4-bromo-N-((1R,2R,4S)-7-cyano-7-azabicyclo[2.2.1]heptan-2-yl)-3-ethoxybenzamide | m/z: 365.0 [M + 1] |
| M-2 | | 4-bromo-N-((1R,2R,4S)-7-cyano-7-azabicyclo[2.2.1]heptan-2-yl)-3-(cyclopropylmethoxy)benzamide | m/z: 391.0 [M + 1] |
| M-3 | | 4-bromo-N-((1R,2R,4S)-7-cyano-7-azabicyclo[2.2.1]heptan-2-yl)-3-(2-methylbutoxy)benzamide | m/z: 406.0 [M + 1] |
| M-4 | | 4-bromo-2-chloro-N-((1R,2R,4S)-7-cyano-7-azabicyclo[2.2.1]heptan-2-yl)-5-isobutoxybenzamide | m/z: 428.0 [M + 1] |

| Int. | Structure[FB-L11] | Name | LC/MS data |
|---|---|---|---|
| M-5 | | 4-bromo-3-butoxy-N-((1R,2R,4S)-7-cyano-7-azabicyclo[2.2.1]heptan-2-yl)benzamide | m/z: 393.2 [M + 1] |
| M-6 | | 4-bromo-N-((1R,2R,4S)-7-cyano-7-azabicyclo[2.2.1]heptan-2-yl)-3-(cyclobutylmethoxy)benzamide | m/z: 405.2 [M + 1] |

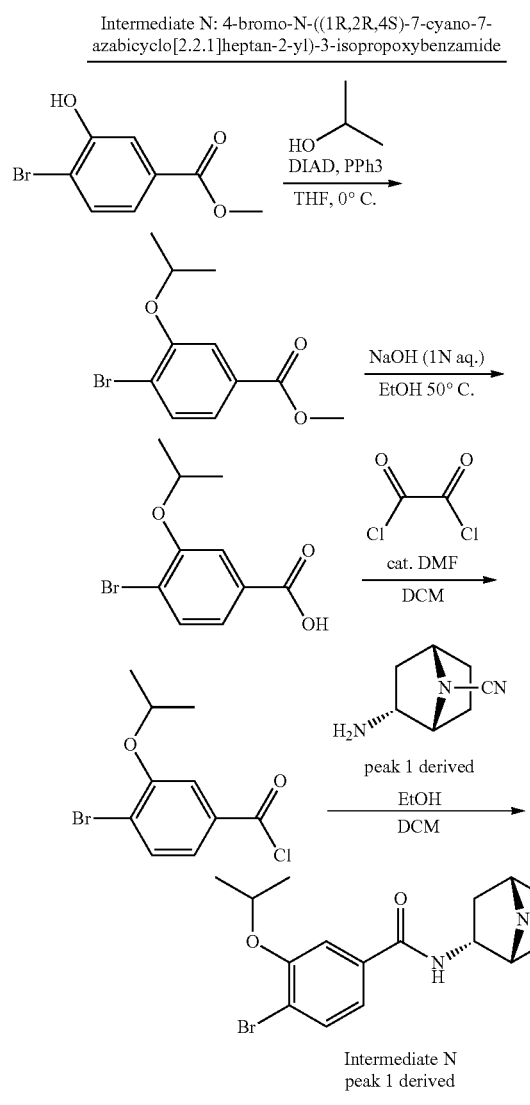

Intermediate N: 4-bromo-N-((1R,2R,4S)-7-cyano-7-azabicyclo[2.2.1]heptan-2-yl)-3-isopropoxybenzamide Step 1:

To a reaction vial was added, methyl 4-bromo-3-hydroxybenzoate (0.200 g, 0.866 mmol), triphenylphosphine (0.386 g, 1.472 mmol), propan-2-ol (0.073 g, 1.212 mmol), and tetrahydrofuran (2.164 ml). The reaction vial was cooled to 0° C. and diisopropyl azodicarboxylate (0.290 ml, 1.472 mmol) was added. The ice bath was removed and the reaction allowed to warm up to room temperature. After 3 hours, the reaction was complete as determined by LCMS. The reaction was quenched with water and extracted with DCM. The organics were dried over $MgSO_4$ and filtered. The solvent was removed in vaccuo and the crude material was absorbed onto a plug of silica gel and purified by chromatography through a 10 g biotage ultra column, eluting with a gradient of 10% to 60% EtOAc/Heptane, to provide methyl 4-bromo-3-isopropoxybenzoate (0.189 g, 0.692 mmol, 80% yield). m/z: 274.0 [M+1]

Step 2, Step 3, and Step 4:

Refer to intermediate M step 2, step 3, and step 4 to provide 4-bromo-N-((1R,2R,4S)-7-cyano-7-azabicyclo[2.2.1]heptan-2-yl)-3-isopropoxybenzamide (derived from peak 1 azanorbornane) (0.123 g, 0.325 mmol, 56.5% yield). m/z: 379.0 [M+1]

Intermediate O: 1-(cyclopropylmethyl)-3-(6-methylpyridin-2-yl)-1H-indazole-6-carboxylic acid

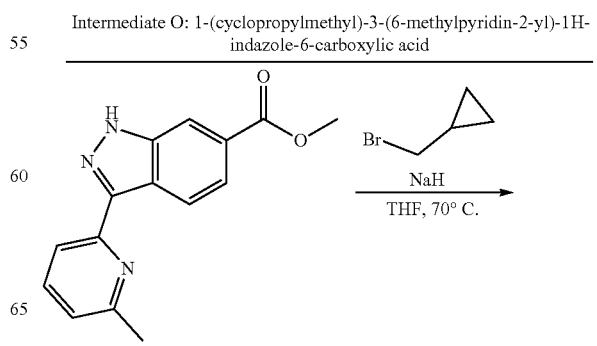

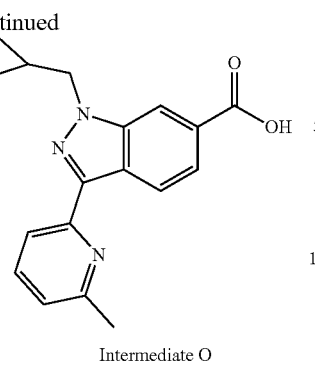

Intermediate O

To a red cap vial containing Intermediate L-2 (0.12 g, 0.449 mmol) in tetrahydrofuran (1.796 ml) was added NaH (60%) (0.032 g, 0.808 mmol). This was stirred at rt for 5 min then (bromomethyl)cyclopropane (0.085 g, 0.629 mmol) was added. The reaction mixture was stirred at rt for 3 h when LC/MS showed no conversion. Additional 30 mg of NaH. was added followed by 3 equiv. of (bromomethyl)cyclopropane and the reaction was heated to 70° C. for 1 hour to provide the desired product. After quenching with water a precipitate formed which was filtered to provide the acid which was used crude for amidation. m/z: 308.2 [M+1]. Alternatively, potassium tert-butoxide could also be used as base to provide better conversion with other electrophiles.

The intermedia in the table below were made by identical procedures:

| Int. | Structure[FB-L12] | Name | LC/MS data |
|---|---|---|---|
| O-1 | | 1-isobutyl-3-(6-methylpyridin-2-yl)-1H-indazole-6-carboxylic acid | m/z: 310.2 [M + 1] |
| O-2 | | 3-(6-methylpyridin-2-yl)-1-(4,4,4-triflurobutyl)-1H-indazole-6-carboxylic acid | m/z: 364.2 [M + 1] |
| O-3 | | 3-(6-methylpyridin-2-yl)-1-propyl-1H-indazole-6-carboxylic acid | m/z: 296.2 [M + 1] |

Intermediate P:
3-(3,5-dichlorophenyl)-3-azabicyclo[4.1.0]heptan-7-carboxylic acid

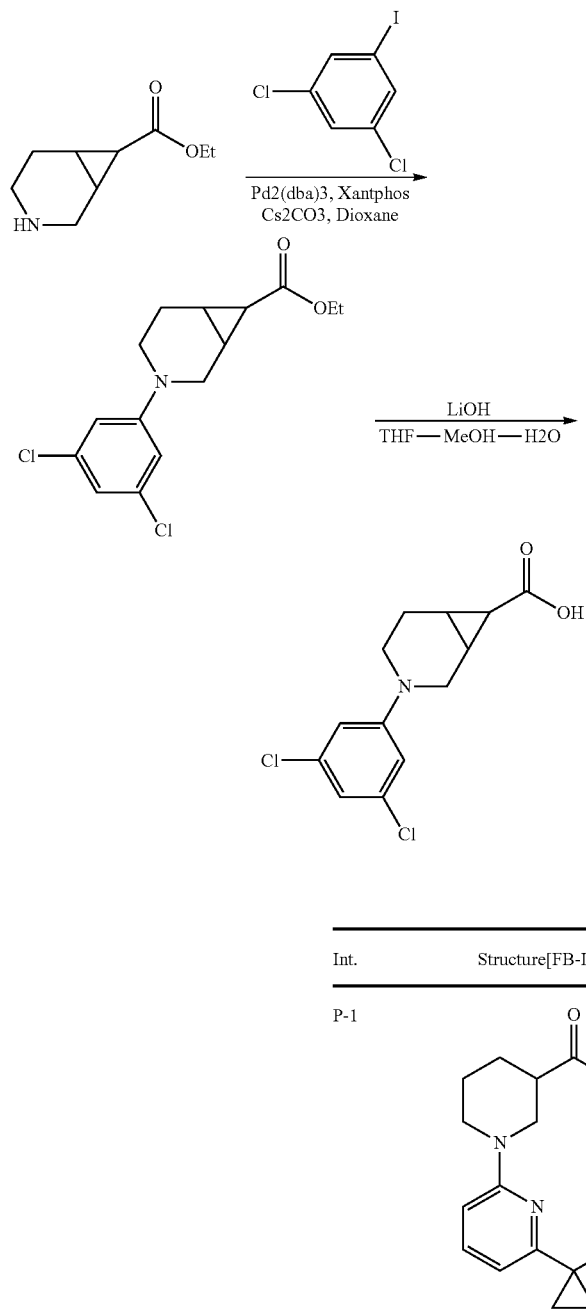

Step 1: A solution of ethyl 3-azabicyclo[4.1.0]heptane-7-carboxylate hydrochloride (0.250 g, 1.215 mmol), 1,3-dichloro-5-iodobenzene (0.398 g, 1.459 mmol), cesium carbonate (0.990 g, 3.04 mmol), xantphos (0.070 g, 0.122 mmol) in 1,4-dioxane (10 mL) was added $Pd_2(dba)_3$ (0.056 g, 0.061 mmol). The reaction mixture was heated at 85° C. for 16 h before it was filtered through a celite pad and washed with ethyl acetate (20 mL). The filtrate was evaporated under vacuum and purified by column chromatography using 10% to 12% ethyl acetate in petroleum ether to provide ethyl 3-(3,5-dichlorophenyl)-3-azabicyclo[4.1.0]heptane-7-carboxylate (0.200 g, 0.637 mmol, 52.4% yield) as light-yellow solid. $^1$H NMR (400 MHz, Chloroform-d): δ ppm 6.75 (t, J=1.7 Hz, 1H), 6.62 (d, J=1.8 Hz, 2H), 4.15 (q, J=7.1 Hz, 2H), 3.64 (d, J=12.6 Hz, 1H), 3.46-3.51 (m, 1H), 3.17-3.23 (m, 1H), 3.02 (m, 1H), 2.10-2.25 (m, 1H), 1.95-2.06 (m, 1H), 1.77-1.88 (m, 2H), 1.66 (t, J=4.2 Hz, 1H), 1.28 (t, J=7.1 Hz, 3H); m/z (ESI): 314.0 (M+H)+.

Step-2: To a solution of ethyl 3-(3,5-dichlorophenyl)-3-azabicyclo[4.1.0]heptane-7-carboxylate (0.200 g, 0.637 mmol) in tetrahydrofuran (1 mL), methanol (1 mL) and water (1 mL) was added Lithium Hydroxide mono hydrate (0.080 g, 1.910 mmol) and the reaction mixture was stirred for 16 h. The solvents were evaporated under vacuum and the reaction mixture was neutralized with 1.5N HCl (2 mL). The precipitated solid was filtered and washed with water (1 mL) to get 3-(3,5-dichlorophenyl)-3-azabicyclo[4.1.0]heptane-7-carboxylic acid (0.075 g, 41.2% yield). $^1$H NMR (400 MHz, DMSO-$d_6$): δ ppm 12.12 (s, 1H), 6.80 (s, 2H), 6.76 (s, 1H), 3.47-3.64 (m, 2H), 3.03-3.29 (m, 2H), 1.94-2.12 (m, 1H), 1.84 (m, 1H), 1.54-1.71 (m, 2H), 1.46 (t, J=4.1 Hz, 1H); m/z (ESI): 288.2 (M−H)+.

The intermediates in the table below were made following similar procedures:

| Int. | Structure[FB-L13] | Name | $^1$H NMR | MS Data |
|---|---|---|---|---|
| P-1 | | 1-(6-(1-cyanocyclopropyl)pyridin-2-yl)piperidine-3-carboxylic acid | | m/z (ESI): 272.2 (M + H)+ |
| P-2 | | 1-(6-cyclopropylpyridin-2-yl)piperidine-4-carboxylic acid | $^1$H NMR (400 MHz, DMSO-$d_6$): δ ppm 7.72 (t, J = 8.1 Hz, 1 H), 6.97 (d, J = 9.0 Hz, 1 H), 6.47 (d, J = 7.5 Hz, 1 H), 4.15 (dt, J = 13.4, 4.1 Hz, 2 H), 3.09-3.25 (m, 2 H), 2.60 (m, 1 H), 2.39 (m, 1 H), 1.83-2.00 (m, 2 H), 1.51-1.68 (m, 2 H), 1.08 (m, 2 H), 0.74-0.97 (m, 2 H). | m/z (ESI): 247.3 (M + H)+ |

-continued

| Int. | Structure[FB-L13] | Name | ¹H NMR | MS Data |
|---|---|---|---|---|
| P-3 | 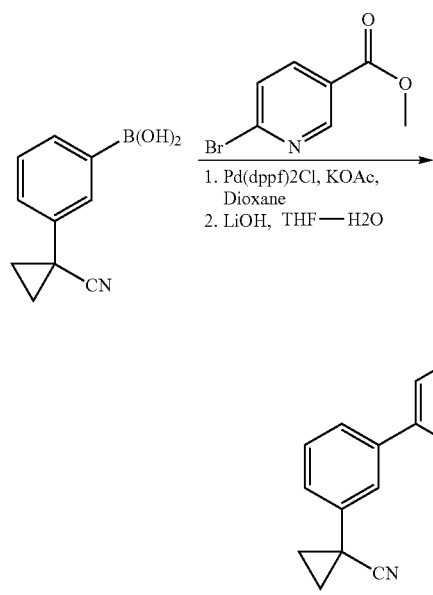 | 1-(6-(1-cyanocyclo-propyl)pyridin-2-yl)pyrrolidine-3-carboxylic acid | | m/z (ESI): 258.3 (M + H)⁺ |

Intermediate Q: 6-(3-(1-cyanocyclopropyl)phenyl)nicotinic acid

Step 1: A solution of methyl 6-bromonicotinate (1.5 g, 6.94 mmol), (3-(1-cyanocyclopropyl)phenyl)boronic acid (1.948 g, 10.42 mmol) and potassium acetate (2.044 g, 20.83 mmol) in 1,4-dioxane (20.0 mL) was added Pd(dppf)Cl₂ (0.508 g, 0.694 mmol). The reaction mixture was stirred at 80° C. for 16 h before it was diluted with water and extracted with EtOAc (3×150 mL). The organic extracts were dried over Na₂SO₄, filtered and concentrated in vacuo. The concentrate was purified by column chromatography using a gradient of 0% to 20% EtOAc in pet ether, to provide methyl 6-(3-(1-cyanocyclopropyl)phenyl)nicotinate (1.2 g, 4.31 mmol, 62.1% yield) as white solid.

¹H NMR (400 MHz, DMSO-d₆): δ ppm 9.12-9.22 (m, 1H), 8.38 (dd, J=8.4, 2.2 Hz, 1H), 8.21 (dd, J=8.4, 0.9 Hz, 1H), 8.01-8.21 (m, 2H), 7.57 (td, J=7.7, 0.8 Hz, 1H), 7.45-7.55 (m, 1H), 7.34-7.49 (m, 1H), 3.92 (s, 3H), 1.74-1.89 (m, 4H); m/z (ESI): 279.3 (M+H)+.

Step-2: To a solution of methyl 6-(3-(1-cyanocyclopropyl)phenyl)nicotinate (1.2 g, 4.31 mmol) in tetrahydrofuran (3 mL) and water (1 mL) was added Lithium Hydroxide mono hydrate (0.516 g, 21.56 mmol) and the reaction mixture was stirred for 16 h. The solvents were evaporated under vacuum and the reaction mixture was neutralized with 1.5N HCl (2 mL). The precipitated solid was filtered and washed with water (1 mL) to obtain 6-(3-(1-cyanocyclopropyl)phenyl)nicotinic acid (1 g, 3.78 mmol, 88% yield). ¹H NMR (400 MHz, DMSO-d₄): δ ppm 9.17 (d, J=2.2 Hz, 1H), 8.35 (dd, J=8.3, 2.3 Hz, 1H), 8.17 (d, J=8.3 Hz, 1H), 8.01-8.15 (m, 2H), 7.56 (t, J=7.7 Hz, 1H), 7.47 (d, J=7.9 Hz, 1H), 1.82 (m, 2H), 1.63 (m, 2H); m/z (ESI): 265.1 (M+H)⁺.

The intermediates in the table below were made following similar procedures:

| Int. | Structure[FB-L14] | Name | ¹H NMR | MS Data |
|---|---|---|---|---|
| Q-1 | | 3-chloro-3'-cyclopropyl-5'-fluoro-[1,1'-biphenyl]-4-carboxylic acid | ¹H NMR (400 MHz, DMSO-d₆): δ ppm 13.44 (s, 1 H), 7.90 (d, J = 1.8 Hz, 1 H), 7.86 (s, 1 H), 7.77 (dd, J = 8.2, 1.8 Hz, 1 H), 7.34-7.42 (m, 1 H), 7.30-7.37 (m, 1 H), 6.97 (dt, J = 10.1, 1.9 Hz, 1 H), 2.04 (m, 1 H), 0.95-1.06 (m, 2 H), 0.78-0.95 (m, 2 H). | m/z (ESI): 289.1 (M − H)⁺ |

| Int. | Structure[FB-L14] | Name | ¹H NMR | MS Data |
|---|---|---|---|---|
| Q-2 | | 6-(1-cyanocyclopropyl)-[2,3'-bipyridine]-6'-carboxylic acid | ¹H NMR (400 MHz, DMSO-d₆): δ ppm 9.36 (d, J = 2.3 Hz, 1 H), 8.60 (dd, J = 8.2, 2.3 Hz, 1 H), 8.15 (d, = 8.2 Hz, 1 H), 8.09 (d, J = 7.8 Hz, 1 H), 8.02 (t, J = 7.8 Hz, 1 H), 7.63 (d, J = 7.7 Hz, 1 H), 1.88 (t, J = 3.3 Hz, 4H). | m/z (ESI): 266.1 (M + H)⁺ |
| Q-3 | | 2-chloro-4-(6-(1-ethynylcyclopropyl)pyridin-2-yl)benzoic acid | ¹H NMR (400 MHz, DMSO-d₆): δ ppm 8.14 (d, J = 1.7 Hz, 1 H), 8.06 (dd, J = 8.1, 1.7 Hz, 1H), 7.91 (d, J = 4.4 Hz, 2 H), 7.78-7.87 (m, 2 H), 3.26 (br s, 1 H), 1.70 (m, 2 H), 1.46 (m, 2 H). | m/z (ESI): 298.1 (M + H)⁺ |
| Q-4 | | 2-chloro-4-(3-cyano-3-methyl-2,3-dihydro-1H-inden-5-yl)benzoic acid | ¹H NMR (400 MHz, DMSO-d₆): δ ppm 13.40 (s, 1 H), 7.87-7.93 (m, 3 H), 7.78 (dd, J = 8.1, 1.9 Hz, 1 H), 7.72 (dd, J = 7.9, 1.8 Hz, 1 H), 7.45 (d, J = 7.9 Hz, 1 H), 3.05 (t, J = 7.1 Hz, 2 H), 2.58-2.67 (m, 1 H), 2.23 (dt, J = 13.0, 7.5 Hz, 1 H), 1.72 (s, 3 H). | m/z (ESI): 310.0 (M − H)⁺ |
| Q-5 | | 4-(6-(tert-butyl)pyridin-2-yl)-2-chlorobenzoic acid | ¹H NMR (400 MHz, DMSO-d₆): δ ppm 13.46 (s, 1 H), 8.27 (d, J = 1.7 Hz, 1 H), 8.17 (dd, J = 8.1, 1.8 Hz, 1 H), 7.88-7.98 (m, 2 H), 7.87 (t, J = 7.7 Hz, 1 H), 7.50 (dd, J = 7.6, 1.1 Hz, 1 H), 1.39 (s, 9H). | m/z (ESI): 290.1 (M + H)⁺ |
| Q-6 | | 2-chloro-4-(6-(2-cyanopropan-2-yl)pyrazin-2-yl)benzoic acid | | m/z (ESI): 302.1 (M + H)⁺ |

-continued

| Int. | Name | ¹H NMR | MS Data |
|---|---|---|---|
| Q-7 | 2-chloro-4-(6-(1-cyanocyclobutyl)pyridin-2-yl)benzoic acid | | m/z (ESI): 313.1 (M + H)⁺ |
| Q-8 | 2-chloro-4-(6-(1-cyano-3,3-difluorocyclobutyl)pyridin-2-yl)benzoic acid | ¹H NMR (400 MHz, DMSO-$d_6$): δ ppm 13.54 (s, 1 H), 8.31 (d, J = 1.8 Hz, 1 H), 8.19 (td, J = 7.8, 7.3, 1.3 Hz, 2 H), 8.10 (t, J = 7.8 Hz, 1 H), 7.95 (d, J = 8.2 Hz, 1 H), 7.75 (dd, J = 7.7, 0.8 Hz, 1 H), 3.51-3.71 (m, 4 H). | m/z (ESI): 348.9 (M)⁺ |
| Q-9 | 2-chloro-3'-(1-cyanocyclopropyl)-[1,1'-biphenyl]-3-carboxylic acid | ¹H NMR (400 MHz, DMSO-$d_6$): δ ppm 7.68 (dd, J = 5.9, 3.7 Hz, 1 H), 7.50 (m, 3 H), 7.27-7.40 (m, 3 H), 1.77 (m, 2H), 1.54 (m, 2H). | m/z (ESI): 296.1 (M − H)⁻ |
| Q-10 | 2-chloro-4-(6-cyclopropyl-pyridin-2-yl)benzoic acid | ¹H NMR (400 MHz, DMSO-$d_6$): δ ppm 13.46 (s, 1 H), 8.18 (d, J = 1.7 Hz, 1 H), 8.09 (dd, J = 8.2, 1.7 Hz, 1 H), 7.90 (d, J = 8.1 Hz, 1 H), 7.84 (dd, J = 7.9, 1.1 Hz, 1 H), 7.78 (t, J = 7.7 Hz, 1 H), 7.35 (dd, J = 7.6, 1.0 Hz, 1 H), 2.19 (m, 1H), 0.98-1.07 (m, 4 H). | |
| Q-11 | 3-chloro-3'-(1-cyanocyclopropyl)-5'-fluoro-[1,1'-biphenyl]-4-carboxylic acid | ¹H NMR (400 MHz, DMSO-$d_6$): δ ppm 13.48 (s, 1 H), 7.95 (d, J = 1.7 Hz, 1 H), 7.89 (d, J = 8.1 Hz, 1 H), 7.80 (dd, J = 8.2, 1.8 Hz, 1 H), 7.57-7.66 (m, 1 H), 7.48 (t, J = 1.6 Hz, 1H), 1.79-1.89 (m, 2 H), 1.65-1.79 (m, 2 H). | m/z (ESI): 314.1 (M + H)⁺ |

-continued

| Int. | Structure[FB-L14] | Name | $^1$H NMR | MS Data |
|---|---|---|---|---|
| Q-12 | | 4-(6-(1-cyanocyclopropyl)pyridin-2-yl)-2-cyclopropylbenzoic acid | $^1$H NMR (400 MHz, Chloroform-d): δ ppm 8.08 (d, J = 8.2 Hz, 1 H), 7.79-7.86 (m, 2 H), 7.69-7.83 (m, 1 H), 7.63-7.69 (m, 2 H), 2.87 (m, 1 H), 1.97 (m, 2 H), 1.80 (m, 2 H), 1.04-1.17 (m, 2 H), 1.27 (m, 2 H), 1.09 (m, 2 H) | m/z (ESI): 305.2 (M + H)$^+$ |

Intermediate R: 1-cyclopentyl-1H-indazole-3-carboxylic acid

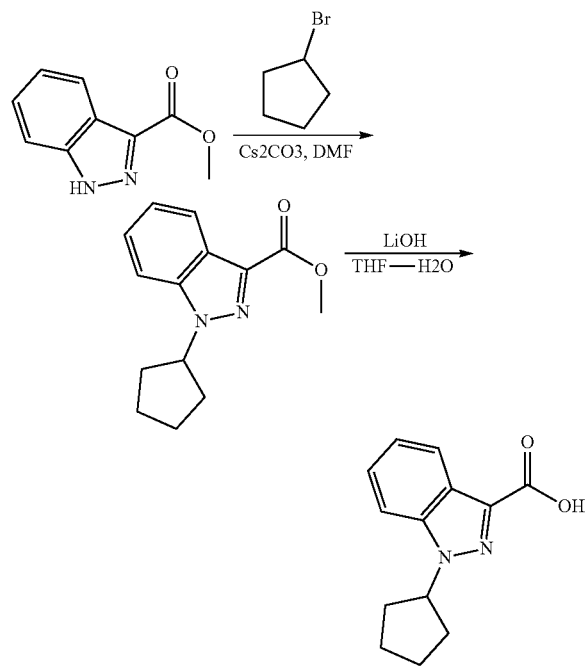

Step 1: To a solution of methyl 1H-indazole-3-carboxylate (1.0 g, 5.68 mmol) in N, N-dimethylformamide (10.0 mL) were added cesium carbonate (4.07 g, 12.49 mmol) and bromocyclopentane (0.931 g, 6.24 mmol). The reaction mixture was stirred at 90° C. for 16 h before it was diluted with ice water (2×100 mL) and extracted with ethyl acetate (100 mL). The organic extracts were dried over Na$_2$SO$_4$, filtered and concentrated in vacuo. The concentrate was purified by column chromatography using a gradient of 0% to 15% ethyl acetate in pet ether, to provide methyl 1-cyclopentyl-1H-indazole-3-carboxylate (0.7 g, 2.87 mmol, 50.5% yield) as a light brown oil. $^1$H NMR (400 MHz, DMSO-d$_6$): δ ppm 8.09 (dt, J=8.1, 1.1 Hz, 1H), 7.87 (dt, J=8.6, 1.0 Hz, 1H), 7.48-7.52 (m, 1H), 7.33-7.38 (m, 1H), 5.26-5.36 (m, 1H), 3.92 (s, 3H), 2.18 (m, 2H), 2.02-2.08 (m, 2H), 1.90 (m, 2H), 1.68-1.78 (m, 2H); m/z (ESI): 245.2 (M+H)$^+$.

Step 2: To a solution of methyl 1-cyclopentyl-1H-indazole-3-carboxylate (0.7 g, 2.87 mmol) in tetrahydrofuran (1 mL), methanol (1 mL) and water (1 mL) was added lithium hydroxide mono hydrate (0.274 g, 11.46 mmol) and the reaction mixture was stirred for 16 h. The solvents were evaporated under vacuum and the reaction mixture was neutralized with 1.5N HCL. The precipitated solid was filtered and washed with water (1 mL) to get 1-cyclopentyl-1H-indazole-3-carboxylic acid (0.6 g, 2.61 mmol, 91% yield) as white solid. $^1$H NMR (400 MHz, DMSO-do): δ ppm 12.97 (s, 1H), 8.08 (dd, J=8.2, 1.2 Hz, 1H), 7.83 (d, J=8.5 Hz, 1H), 7.47 (m, 1H), 7.29-7.34 (m, 1H), 5.24-5.32 (m, 1H), 2.15-2.22 (m, 2H), 2.05 (m, 2H), 1.90 (m, 2H), 1.73 (m, 2H); m/z (ESI): 231.3 (M+H)$^+$.

The intermediates in the table below were made following similar procedures:

| Int. | Structure[FB-L15] | Name | 1H NMR | MS Data |
|---|---|---|---|---|
| R-1 | | 1-(3,5-dichlorobenzyl)azetidine-2-carboxylic acid | $^1$H NMR (400 MHz, DMSO-d$_6$): δ ppm 7.47 (t, J = 2.0 Hz, 1 H), 7.36 (d, J = 2.0 Hz, 2 H), 3.87 (d, J = 13.9 Hz, 1 H), 3.72 (t, J = 8.5 Hz, 1 H), 3.56 (d, J = 13.9 Hz, 1H), 3.19 (td, J = 7.2, 3.3 Hz, 1 H), 2.89 (td, J = 8.5, 6.7 Hz, 1 H), 2.06-2.23 (m, 2 H). | m/z (ESI): 260.0 (M + H)$^+$ |

| Int. | Structure[FB-L15] | Name | 1H NMR | MS Data |
|---|---|---|---|---|
| R-2 | | 1-(3,5-dichloro-benzyl)pyrrolidine-3-carboxylic acid | | m/z (ESI): 274.1 (M + H)+ |

Intermediate S: 2-chloro-4-((1-cyanocyclopropyl)methoxy)benzoic acid

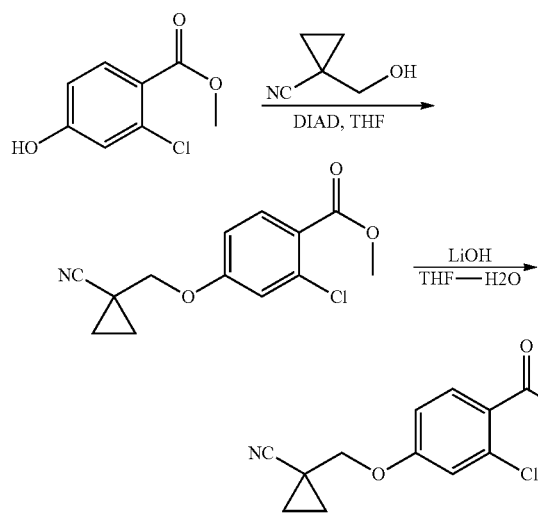

Step 1: To a solution of methyl 2-chloro-3-hydroxybenzoate (1.0 g, 5.36 mmol), 1-(hydroxymethyl)cyclopropyl-1-carbonitrile (0.596 g, 5.36 mmol), triphenylphosphine (2.81 g, 10.72 mmol) in THF (10 mL) was added DIAD (2.084 mL, 10.72 mmol) at 0° C. The reaction mixture was stirred at ambient temperature for 16 h before it was diluted with water (30 mL) and extracted with EtOAc (2×30 mL). The organic extracts were washed with brine, dried over Na$_2$SO$_4$, filtered and concentrated in vacuo. The concentrate was purified by column chromatography using 0% to 30% EtOAc in petroleum ether, to provide methyl 2-chloro-3-((1-cyanocyclopropyl)methoxy)benzoate (1.5 g, 5.65 mmol, 105% yield) as light-yellow sticky liquid. m/z (ESI): 264.9 (M−H)−.

Step 2: To a solution of methyl 2-chloro-3-((1-cyanocyclopropyl)methoxy)benzoate (1.5 g, 5.65 mmol) in tetrahydrofuran (10 mL), methanol (2 mL) and water (5 mL) was added Lithium Hydroxide mono hydrate (0.811 g, 33.9 mmol) and the reaction mixture was stirred for 16 h. The solvents were evaporated under vacuum and the reaction mixture was neutralized with 1.5 N HCl. The precipitated solid was filtered and washed with water (1 mL) to get 2-chloro-4-((1-cyanocyclopropyl)methoxy)benzoic acid (0.9 g, 3.58 mmol, 63.3% yield) as light-yellow oil. m/z (ESI): 249.1 (M−H)−.

The intermediates in the table below were made following similar procedures:

| Int. | Structure[FB-L16] | Name | 1H NMR | MS Data |
|---|---|---|---|---|
| S-1 | | 2-chloro-3-(3-cyanocyclobutoxy)benzoic acid | | m/z (ESI): 252.1 (M − H)+ |
| S-2 | | 2-chloro-4-(3-cyanocyclobutoxy)benzoic acid | 1H NMR(400 MHz, DMSO-d$_6$): δ ppm 13.1 (s, 1 H), 7.87-7.78 (m, 1H), 7.02 (d, J = 2.5 Hz, 1H), 7.00-6.89 (m, 1 H), 5.15-5.04 (m, 1 H), 3.46 (m, 1 H), 2.89-2.78 (m, 2H), , 2.51-2.43 (m, 2 H). | m/z (ESI): 250.1 (M − H)+ |

Intermediate T: 2-chloro-4-(3-cyanopiperidin-1-yl)benzoic acid

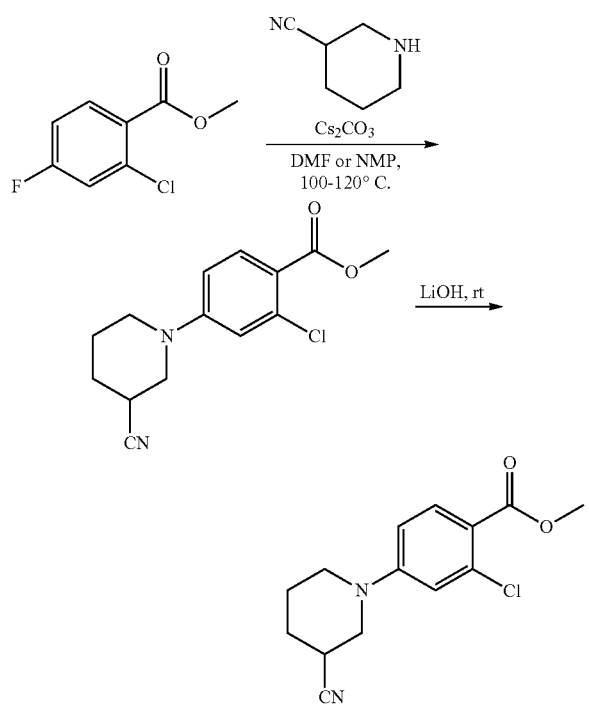

Step 1: To a mixture of methyl 2-chloro-4-fluorobenzoate (1.0 g, 5.30 mmol) and piperidine-3-carbonitrile (0.584 g, 5.30 mmol) in N-methyl-2-pyrrolidinone (10 mL) was added K$_2$CO$_3$ (0.733 g, 5.30 mmol) and the reaction mixture was heated at 135° C. for 16 h. The reaction mixture was quenched with ice cubes and stirred for 5 min to get solid. The solid was filtered and washed with water and dried under suction to get methyl 2-chloro-4-(3-cyanopiperidin-1-yl)benzoate (0.85 g, 57.5% Yield). $^1$H NMR (400 MHz, Chloroform-d): δ ppm 7.87 (d, J=8.9 Hz, 1H), 6.91 (d, J=2.6 Hz, 1H), 6.79 (dd, J=8.9, 2.6 Hz, 1H), 3.92 (s, 3H), 3.69 (ddt, J=12.9, 3.6, 1.3 Hz, 2H), 3.37-3.51 (m, 2H), 3.26 (ddd, J=12.7, 8.8, 3.3 Hz, 2H), 2.79-2.92 (m, 2H), 2.40 (t, J=8.1 Hz, 1H). m/z (ESI): 279.1 (M+H)$^+$.

Step 2: To a solution of methyl 2-chloro-4-(3-cyanopiperidin-1-yl)benzoate (0.850 g, 3.05 mmol) in a mixture tetrahydrofuran (2 mL), methanol (2 mL) and water (2 mL) was added lithium hydroxide mono hydrate (0.384 g, 9.15 mmol) at rt which was stirred for 16 h. The solvent was evaporated under vacuum and neutralized with 1.5 N HCl to obtain a solid that was washed with water and dried under suction to provide 2-chloro-4-(3-cyanopiperidin-1-yl)benzoic acid (0.60 g, 74.3% yield). $^1$H NMR (400 MHz, DMSO-d$_6$): δ ppm 7.70-7.80 (m, 1H), 7.03 (d, J=2.6 Hz, 1H), 6.97 (dd, 0.1=8.9, 2.6 Hz, 1H), 3.58-3.74 (m, 2H), 3.30-3.50 (m, 2H), 3.02-3.18 (m, 1H), 1.80-2.06 (m, 2H), 1.54-1.74 (m, 2H). m/z (ESI): 265.1 (M+H)$^+$.

The intermediates in the table below were made following similar procedures:

| Int. | Structure | Name | 1HNMR | MS Data |
|---|---|---|---|---|
| T-1 | 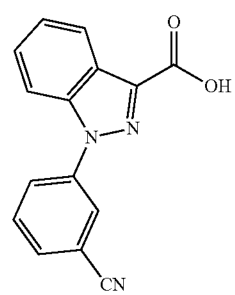 [SMILES: N#Cc1cccc(-n2nc(C(=O)O)c3ccccc32)c1] | 1-(3-cyanophenyl)-1H-indazole-3-carboxylic acid | $^1$H NMR(400 MHz, DMSO-d$_6$): δ ppm 13.45 (s, 1 H), 8.16-8.30 (m, 2H), 7.95-8.16 (m, 2H), 7.70-7.95 (m, 1 H), 7.55-7.66 (m, 1 H), 7.42-7.51 (m, 1 H), 7.12-7.36 (m, 1 H). | m/z (ESI): 264.1 (M + H)$^+$ |
| T-2 | 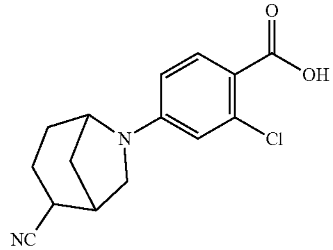 [SMILES: N#CC1CCC2CC1CN2c1ccc(C(=O)O)c(Cl)c1] | 2-chloro-4-(2-cyano-6-azabicyclo[3.2.1]octan-6-yl)benzoic acid | $^1$H NMR(400 MHz, DMSO-d$_6$): δ ppm 12.36 (br s, 1 H), 7.72-7.80 (m, 1 H), 6.56-6.70 (m, 2 H), 3.22-3.35 (m, 4 H), 2.18 (t, J = 8.1 Hz, 3 H), 1.90-2.02 (m, 4 H). | m/z (ESI): 291.1 (M + H)$^+$ |

| Int. | Structure | Name | 1HNMR | MS Data |
|---|---|---|---|---|
| T-3 | 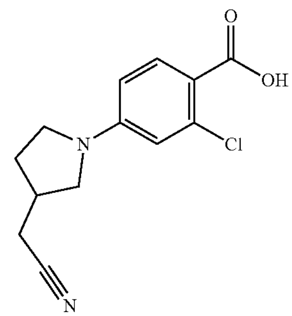 [SMILES: N#CCC1CCN(c2ccc(C(=O)O)c(Cl)c2)C1] | 2-chloro-4-(3-(cyanomethyl)pyrrolidin-1-yl)benzoic acid | $^1$H NMR (400 MHz, DMSO-$d_6$): δ ppm 7.76 (d, J = 8.6 Hz, 1 H), 6.41-6.59 (m, 2H), 3.50 (dd, J = 10.2, 7.0 Hz, 1 H), 3.37-3.45 (m, 1 H), 3.27-3.34 (m, 1 H), 3.03 (dd, J = 10.2, 6.7 Hz, 1 H), 2.64-2.77 (m, 2 H), 2.59-2.64 (m, 1 H), 2.15-2.22 (m, 1 H), 1.77-1.88 (m, 1 H). | m/z (ESI): 265.1 (M + H)$^+$ |
| T-4 | 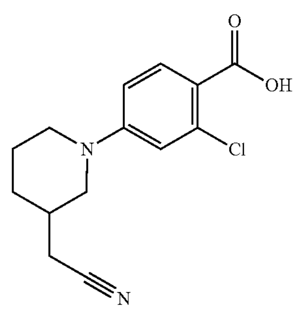 [SMILES: N#CCC1CCCN(c2ccc(C(=O)O)c(Cl)c2)C1] | 2-chloro-4-(3-(cyanomethyl)piperidin-1-yl)benzoic acid | $^1$H NMR (400 MHz, DMSO-$d_6$): δ ppm 12.57, (s, 1 H), 7.73 (d, J = 8.9 Hz, 1 H), 6.61-7.06 (m, 2 H), 3.76 (t, J = 15.5 Hz, 2H), 2.84 (ddd, J = 13.2, 11.4, 3.0 Hz, 1 H), 2.70 (dd, J = 12.9, 10.1 Hz, 3H), 1.78-1.92 (m, 2 H), 1.61-1.77 (m, 1 H), 1.33-1.56 (m, 1 H), 1.15-1.39 (m, 1 H). | m/z (ESI): 279.1 (M + H)$^+$ |
| T-5 | 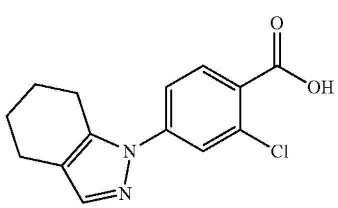 [SMILES: O=C(O)c1ccc(-n2ncc3c2CCCC3)cc1Cl] | 2-chloro-4-(4,5,6,7-tetrahydro-1H-indazol-1-yl)benzoic acid | | m/z (ESI): 277.1 (M + H)$^+$ |
| T-6 | 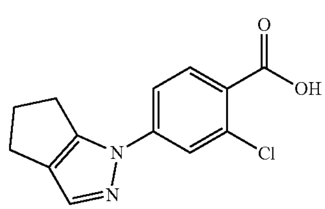 [SMILES: O=C(O)c1ccc(-n2ncc3c2CCC3)cc1Cl] | 2-chloro-4-(5,6-dihydrocyclopenta[c]pyrazol-1(4H)-yl)benzoic acid | $^1$H NMR (400 MHz, DMSO-$d_6$): δ ppm 8.24 (d, J = 1.2 Hz, 1 H), 7.82-7.93 (m, 2 H), 7.72-7.82 (m, 1 H), 2.59-2.73 (m, 4 H), 2.31-2.51 (m, 2 H). | m/z (ESI): 263.1 (M + H)$^+$ |
| T-7 | 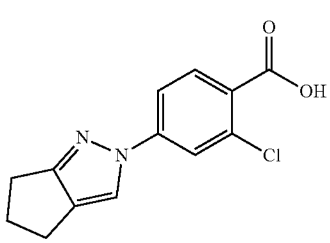 [SMILES: O=C(O)c1ccc(-n2cc3c(n2)CCC3)cc1Cl] | 2-chloro-4-(5,6-dihydrocyclopenta[c]pyrazol-2(4H)-yl)benzoic acid | $^1$H NMR (400 MHz, DMSO-$d_6$): δ ppm 8.26 (d, J = 1.2 Hz, 1 Hz, 1 H), 7.91 (d, J = 8.6 Hz, 1 H), 7.81 (dd, J = 8.6, 2.2 Hz, 1 H), 2.60-2.76 (m, 4 H), 2.32-2.42 (m, 2 H). | |

-continued

| Int. | Structure | Name | 1HNMR | MS Data |
|------|-----------|------|-------|---------|
| S-8 | 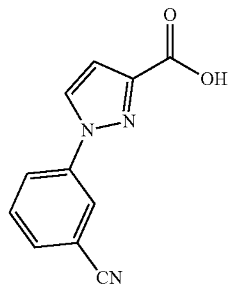 [SMILES: N#Cc1cccc(-n2ccc(C(=O)O)n2)c1] | 1-(3-cyanophenyl)-1H-pyrazole-3-carboxylic acid | | m/z (ESI): 214.1 (M + H)+ |

Intermediate U: 1-(3,5-dichlorophenyl)-1H-1,2,4-triazole-3-carboxylic acid

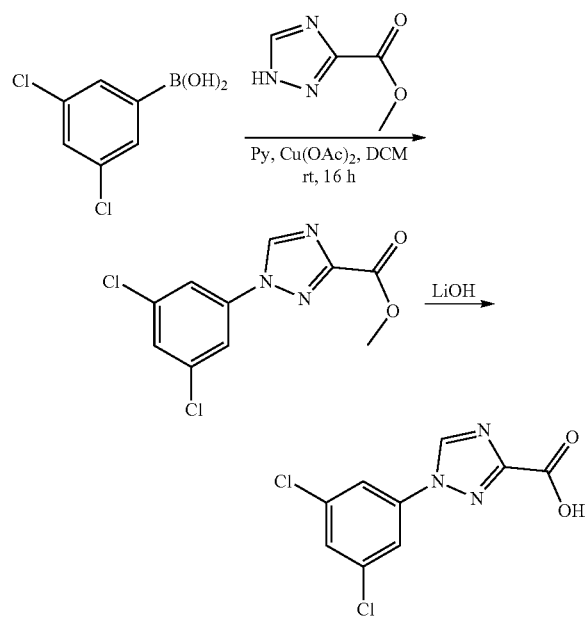

Step 1: To a mixture of methyl 4H-1,2,4-triazole-3-carboxylate (0.599 g, 4.72 mmol) and (3,5-dichlorophenyl) boronic acid (0.9 g, 4.72 mmol) in dichloromethane (9 mL) was added pyridine (0.763 mL, 9.43 mmol) followed by copper (II) acetate (0.600 g, 3.30 mmol) and stirred rt for 16 h under open air. The reaction mixture was filtered through a bed of celite and washed with EtOAc. The EtOAc layer was washed with water, brine, dried over $Na_2SO_4$, filtered and concentrated in vacuo to provide the crude material as a green oil. The crude material was absorbed onto a plug of silica gel and purified by flash column chromatography eluting with a gradient of 0% to 5% EtOAc in petroleum ether to provide methyl 1-(3,5-dichlorophenyl)-1H-1,2,4-triazole-3-carboxylate (0.8 g, 2.94 mmol, 62.3% yield) as grey solid. $^1$H NMR (400 MHz, DMSO-$d_6$): δ ppm 9.55 (s, 1H), 8.05 (d, J=1.8 Hz, 2H), 7.78 (t, J=1.8 Hz, 1H), 3.92 (s, 3H).

Step 2: To a solution of methyl 1-(3,5-dichlorophenyl)-1H-1,2,4-triazole-3-carboxylate (0.8 g, 2.94 mmol) in tetrahydrofuran (8 mL), water (2 mL) was added LiOH (0.176 g, 7.35 mmol) at rt and was stirred for 4 h. The residual solvent was evaporated under reduced pressure and then neutralized with 1.5 N HCl solution. It was extracted with ethyl acetate, dried over $Na_2SO_4$, concentrated in vacuo to give the product 1-(3,5-dichlorophenyl)-1H-1,2,4-triazole-3-carboxylic acid (0.6 g, 2.325 mmol, 79% yield) as a off-white solid. $^1$H NMR (400 MHz, DMSO-$d_6$): δ ppm 13.74, (br s, 1H), 9.50 (s, 1H), 8.04 (d, J=1.8 Hz, 2H), 7.78 (s, 1H).

Intermediate V: 1-(3,5-dichlorophenyl)-N-((1R,2R,4S)-7-(4-methoxybenzyl)-7-azabicyclo[2.2.1]heptan-2-yl)azepane-4-carboxamide

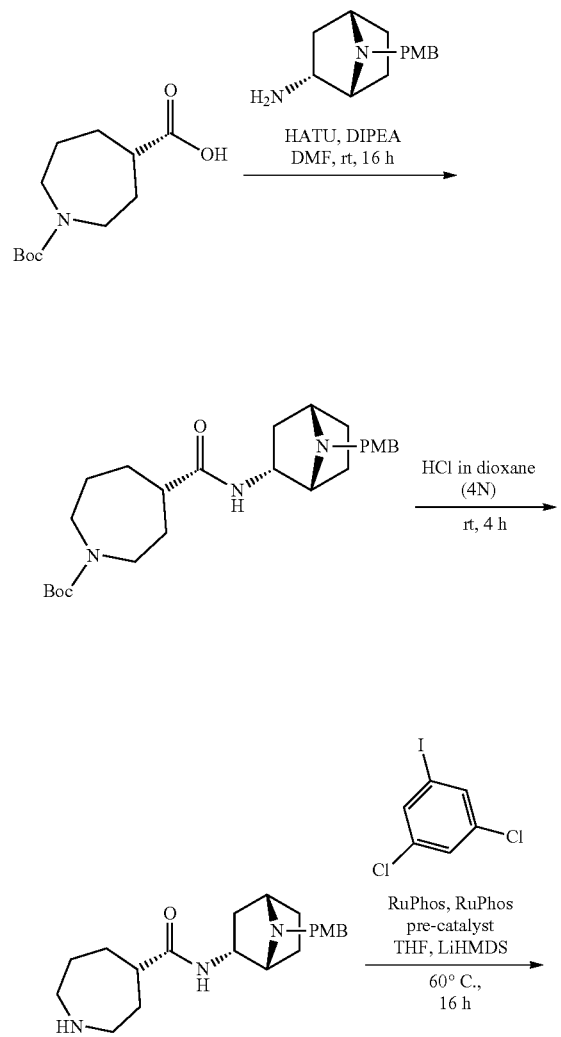

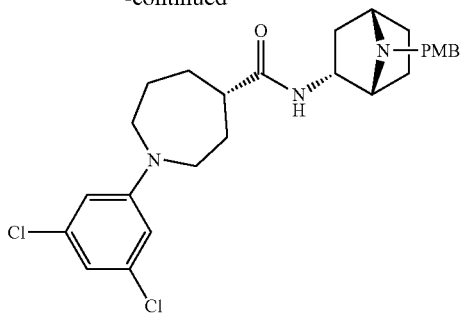

Step 1: To a solution of (1R,2R,4S)-7-(4-methoxybenzyl)-7-azabicyclo[2.2.1]heptan-2-amine (0.900 g, 3.87 mmol) in N, N-dimethylformamide (20 mL) were added 1-(tert-butoxycarbonyl)azepane-4-carboxylic acid (0.943 g, 3.87 mmol), DIPEA (1.353 mL, 7.75 mmol) followed by HATU (2.209 g, 5.81 mmol) at rt and was stirred for 16 h. The reaction mixture was diluted with water and extracted with EtOAc. The organic extracts were washed with brine, dried over Na$_2$SO$_4$, filtered and concentrated in vacuo to give the crude material as a light-yellow oil. The crude product was purified by reverse-phase preparative HPLC (0.1% TFA in CH$_3$CN/H$_2$O, gradient 40% to 45%) to provide tert-butyl 4-(((1R,2R,4S)-7-(4-methoxybenzyl)-7-azabicyclo[2.2.1]heptan-2-yl)carbamoyl)azepane-1-carboxylate (0.500 g, 1.093 mmol, 28.2% yield) as a light-yellow oil. $^1$H NMR (400 MHz, DMSO-d$_6$): δ ppm 9.62 (s, 1H), 8.25 (s, 1H), 7.46 (d, J=8.1 Hz, 2H), 7.03 (d, J=8.1 Hz, 2H), 4.62 (s, 1H), 4.26 (d, J=56.3 Hz, 2H), 3.94 (s, 2H), 3.79 (s, 2H), 3.12-3.30 (m, 2H), 2.24 (s, 2H), 1.89-2.05 (m, 2H), 1.62-1.86 (m, 6H), 1.40 (s, 12H). m/z (ESI): 458.4 (M+H)$^+$.

Step 2: To a solution of tert-butyl 4-(((1R,2R,4S)-7-(4-methoxybenzyl)-7-azabicyclo[2.2.1]heptan-2-yl)carbamoyl)azepane-1-carboxylate (0.500 g, 1.093 mmol) in 1,4-dioxane (5 mL) was added HCl in dioxane (1 mL, 5.46 mmol) dropwise at rt and stirred for 4 h. The solvent was evaporated under vacuum to get N-((1R,2R,4S)-7-(4-methoxybenzyl)-7 azabicyclo[2.2.1]heptan-2-yl)azepane-4-carboxamide hydrochloride (0.500 g, 116% yield) as crude which was directly used for the next step without purification.

Step 3: To a solution of N-((1R,2R,4S)-7-(4-methoxybenzyl)-7-azabicyclo[2.2.1]heptan-2-yl)azepane-4-carboxamide hydrochloride (0.500 g, 1.269 mmol) in THF (5 mL) was added LHMDS (1.0 M solution in THF, 2.54 mL, 2.54 mmol) dropwise at 0° C. and then stirred for 30 min at rt. To it 1,3-dichloro-5-iodobenzene (0.346 g, 1.269 mmol), Ruphos precatalyst (0.023 g, 0.032 mmol) followed by Ruphos (0.015 g, 0.032 mmol) was added and the reaction mixture was degassed with nitrogen for 5 min. After heating at 70° C. for 16 h, the reaction mixture was diluted with water and extracted with EtOAc. The organic extracts were washed with brine, dried over Na$_2$SO$_4$, filtered and concentrated in vacuo to give the crude material as a light-yellow oil. The crude product was purified by reverse-phase preparative HPLC (0.1% TFA in CH$_3$CN/H$_2$O, gradient 65% to 70% over 30 min) to provide 1-(3,5-dichlorophenyl)-N-((1R,2R,4S)-7-(4-methoxybenzyl)-7-azabicyclo[2.2.1]heptan-2-yl)azepane-4-carboxamide (0.150 g, 0.164 mmol, 12.94% yield) as a light-yellow solid. $^1$H NMR (400 MHz, DMSO-d$_6$): δ ppm 7.73-7.81 (m, 1H), 7.12-7.31 (m, 4H), 6.81-6.90 (m, 1H), 6.65 (dt, J=4.6, 1.7 Hz, 2H), 3.73 (s, 3H), 3.47-3.61 (m, 2H), 3.42 (dd, J=4.1, 1.8 Hz, 3H), 3.06-3.21 (m, 3H), 2.59 (d, J=7.2 Hz, 2H), 2.20 (d, J=6.0 Hz, 2H), 1.92 (d, J=38.7 Hz, 4H), 1.58 (p, J=4.0 Hz, 4H), 1.36 (s, 2H). m/z (ESI): 502.1, 504.1 (M+1)$^+$.

The intermediates in the table below were made following similar procedures.

| Int. No. | Structure[FB-L17] | Name | 1H NMR | MS Data |
|---|---|---|---|---|
| U-1 | 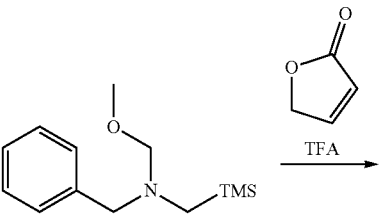 | (1S,5S)-2-(3,5-dichlorophenyl)-N-((1R,2R,4S)-7-(4-methoxybenzyl)-7-azabicyclo[2.2.1]heptan-2-yl)-2-azabicyclo[3.1.0]hexane-4-carboxamide | | m/z (ESI): 486.1, 488.1 (M + H)$^+$. |

Intermediate V:
3-(3,5-dichlorophenyl)-3-azabicyclo[3.1.0]hexane-1-carboxylic acid

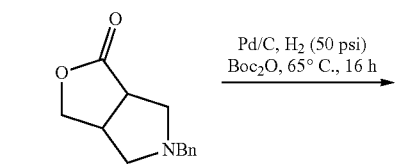

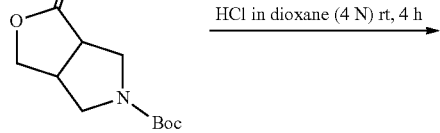

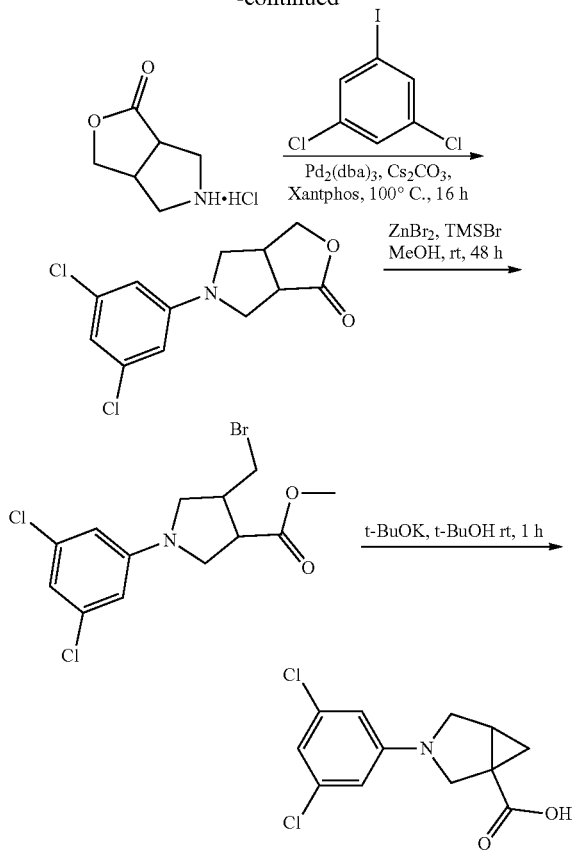

Step 1: A mixture of furan-2(5H)-one (3.0 g, 35.7 mmol) and N-benzyl-1-methoxy-N-((trimethylsilyl)methyl)methanamine (10.34 g, 43.5 mmol) in dichloromethane (30 mL) was cooled to 0'° C. and was treated with TFA (0.591 mL, 7.67 mmol) drop wise. It was stirred for 16 h at rt. The reaction mixture was quenched with saturated NaHCO₃ and extracted with DCM. The organic extracts were washed with brine, dried over Na₂SO₄, filtered and concentrated in vacuo to give the crude material as a yellow oil. The crude material was absorbed onto a plug of silica gel and purified by flash column chromatography eluting with a gradient of 30% to 40% Ethyl acetate in petroleum ether to provide 5-benzylhexahydro-1H-furo[3,4-c]pyrrol-1-one (3.2 g, 14.73 mmol, 41.3% yield) as light-yellow oil. $^1$H NMR (400 MHz, DMSO-d₆): δ ppm 7.12-7.40 (m, 5H), 4.43 (t, J=8.7 Hz, 1H), 3.87-4.09 (m, 1H), 3.56 (d, J=2.0 Hz, 2H), 3.12 (ddd, J=9.5, 7.1, 1.2 Hz, 1H), 2.90-3.06 (m, 2H), 2.75-2.86 (m, 1H), 2.33 (dt, J=9.1, 7.2 Hz, 2H). m/z (ESI): 218.2 (M+H)⁺.

Step 2: A mixture of 5-benzylhexahydro-1H-furo[3,4-c]pyrrol-1-one (5.0 g, 23.01 mmol) and Boc-anhydride (8.01 mL, 34.5 mmol) in methanol (100 mL) was purged with nitrogen for 2 min and then changed with Pd—C(1.225 g, 0.050 mmol) at rt. The reaction mixture was heated at 65° C. under 50 psi pressure of Hydrogen gas for 16 h. The reaction mixture was filtered through celite pad and washed with methanol. The filtrate was evaporated to obtain crude material which was purified by silica gel chromatography eluting with 25% to 30% Ethyl acetate in Petroleum ether to provide tert-butyl-1-oxotetrahydro-1H-furo[3,4-c]pyrrole-5(3H)-carboxylate (5.0 g, 22.00 mmol, 96% yield) as a light-yellow oil. $^1$H NMR (400 MHz, Chloroform-d): d ppm 4.47 (dd, J=9.6, 5.9 Hz, 1H), 4.22 (d, J=9.6 H z, 1H), 3.89 (d, J=11.5 H z, 1H), 3.71-3.84 (m, 1H), 3.64 (s, 1H), 3.33 (s, 1H), 3.16-3.26 (m, 2H), 1.48 (s, 9H).

Step 3: To a solution of tert-butyl-1-oxotetrahydro-1H-furo[3,4-c]pyrrole-5(3H)-carboxylate (5.0 g, 22.00 mmol) in 1,4-dioxane (10 mL) was added HCl in Dioxane (4.0 M solution, 27.5 mL, 110.0 mmol) dropwise at rt and was stirred for 4 h. The solvent was evaporated under vacuum to get crude hexahydro-1H-furo[3,4-c]pyrrol-1-one hydrochloride (2.5 g, 69%) which was directly used for the next step. $^1$H NMR (400 MHz, DMSO-D₂0): S ppm 4.46 (dd, J=9.6, 7.5 Hz, 1H), 4.21 (dd, J=9.6, 2.7 Hz, 1H), 3.53-3.57 (m, 1H), 3.41-3.49 (m, 5H), 3.31-3.37 (m, 1H), 3.19 (dd, J=12.0, 5.5 Hz, 1H); m/z (ESI): 128.2 (M+H)⁺.

Step 4: To a mixture of hexahydro-1H-furo[3,4-c]pyrrol-1-one hydrochloride (2.0 g, 15.73 mmol) and 1,3-dichloro-5-iodobenzene (4.29 g, 15.73 mmol) in toluene (20 mL) was added Cs₂CO₃ (10.25 g, 31.5 mmol), Xantphos (0.45 g, 0.787 mmol) followed by tris(dibenzylideneacetone)dipalladium(0) (0.360 g, 0.393 mmol) at rt and then degassed with nitrogen for 2 mins. It was heated at 100° C. for 16 h. The reaction mixture was filtered through celite pad and washed with Ethyl acetate. The solvent was evaporated under vacuum to get crude which was purified by flash column chromatography eluting with a gradient of 30% to 40% EtOAc in petroleum ether to provide 5-(3,5-dichlorophenyl)hexahydro-1H-furo[3,4-c]pyrrol-1-one (02.5 g, 9.19 mmol, 58.4% yield) as light-yellow solid. $^1$H NMR (400 MHz, DMSO-d₆): δ ppm 6.79 (t, J=1.8 Hz, 1H), 6.64 (d, J=1.8 Hz, 2H), 4.48 (dd, J=9.3, 6.0 Hz, 1H), 4.25 (dd, J=9.2, 1.7 Hz, 1H), 3.56-3.76 (m, 1H), 3.43-3.55 (m, 3H), 3.38 (d, J=14.5 Hz, 1H), 3.29-3.33 (m, 1H). m/z (ESI): 272.2, 274.2 (M+H)⁺.

Step 5: To a solution of 5-(3,5-dichlorophenyl)hexahydro-1H-furo[3,4-c]pyrrol-1-one (1.70 g, 6.25 mmol) in methanol (20 mL) was added TMS-Br (8.11 mL, 62.5 mmol) at 0° C. dropwise and stirred for 5 min. Zinc bromide (0.422 g, 1.874 mmol) was added and the resultant reaction mixture was stirred for 48 h at rt. The reaction was diluted with water and EtOAc. The organic extract was separated and washed with brine, dried over Na₂SO₄, filtered and concentrated to provide yellow oil that was purified by column chromatography eluting with a gradient of 10% to 15% EtOAc in petroleum ether to provide methyl 4-(bromomethyl)-1-(3,5-dichlorophenyl)pyrrolidine-3-carboxylate (1.20 g, 3.27 mmol, 52.3% yield) as light-yellow solid. $^1$H NMR (400 MHz, DMSO-d₆): δ ppm 6.71 (t, J=1.8 Hz, 1H), 6.53 (d, J=1.8 Hz, 2H), 3.51-3.63 (m, 5H), 3.45 (td, J=6.8, 5.2 Hz, 1H), 3.34 (s, 3H), 3.24 (dd, J=9.7, 7.0 Hz, 1H), 2.95-3.02 (m, 1H).

Step 6: To a solution of methyl 4-(bromomethyl)-1-(3,5-dichlorophenyl)pyrrolidine-3-carboxylate (0.200 g, 0.545 mmol) in tert-butanol (2 mL).was added potassium tert-butoxide (0.092 g, 0.817 mmol) at rt and was stirred for 1 h. The reaction mixture was filtered through celite pad and washed with Ethyl acetate (10 mL). The filtrate was washed with H₂O, brine, dried over Na₂SO₄, filtered and evaporated under vacuum. The crude product was purified by reverse-phase preparative HPLC (CH₃CN/H₂O, gradient 20% to 25% over 60 min) to provide 3-(3,5-dichlorophenyl)-3-azabicyclo[3.1.0]hexane-1-carboxylic acid (0.080 g, 0.294 mmol, 54.0% yield) as off-white solid. $^1$H NMR (400 MHz, DMSO-d₆): δ ppm 6.65 (t, J=1.8 Hz, 1H), 6.46 (d, J=1.8 Hz, 2H), 3.62 (d, J=9.7 Hz, 1H), 3.39-3.44 (m, 2H), 3.25 (dd, J=9.6, 4.5 Hz, 1H), 1.70 (dt, J=8.5, 4.4 Hz, 1H), 1.30 (dd, J=7.9, 3.2 Hz, 1H), 0.37 (dd, J=4.6, 3.3 Hz, 1H). m/z (ESI): 271.1 (M−H)⁺.

Intermediate W: N-((1R,2R,4S)-7-cyano-7-azabicyclo[2.2.1]heptan-2-yl)-1-(3,5-dichlorophenyl)azepane-3-carboxamide

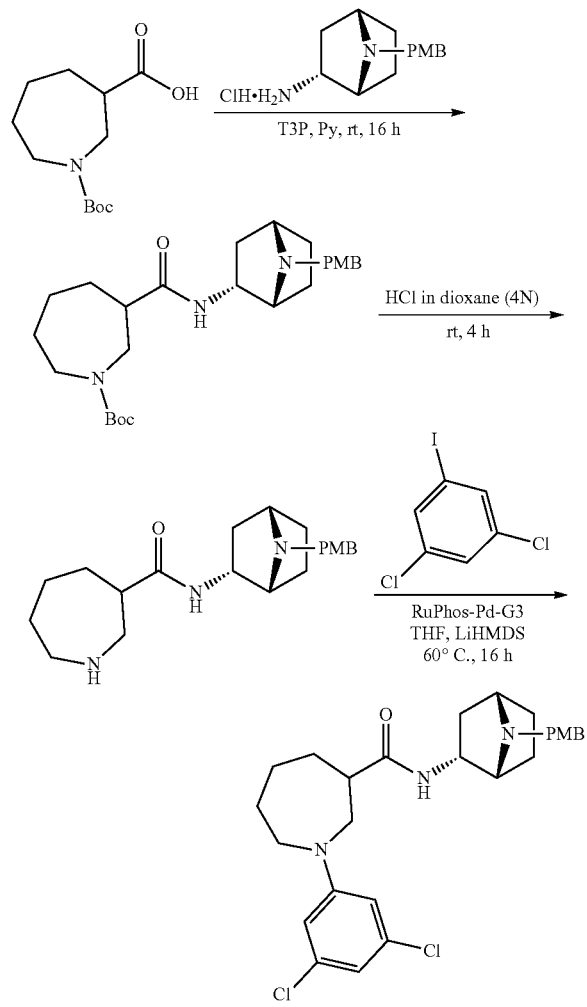

Step 1: To a solution of 1-(tert-butoxycarbonyl)azepane-3-carboxylic acid (0.5 g, 2.055 mmol) in CH$_2$Cl$_2$ was added Pyridine (0.499 mL, 6.17 mmol), T$_3$P (0.981 g, 3.08 mmol) at 0° C. and stirred for 5 min. Then (1R,2R,4S)-7-(4-methoxybenzyl)-7-azabicyclo[2.2.1]heptan-2-amine hydrochloride (0.428 g, 2.466 mmol) was added and stirred at room temperature for 16 h. The reaction was quenched with ice water, extracted with EtOAc, dried over Na$_2$SO$_4$, filtered and evaporated in vacuo.

This material was purified by silica gel chromatography using a gradient of 80% ethyl acetate in petroleum ether to provide tert-butyl-3-(((1R,2R,4S)-7-(4-methoxybenzyl)-7-azabicyclo[2.2.1]heptan-2-yl)carbamoyl)azepane-1-carboxylate (0.49 g, 1.352 mmol, 65.8% yield) as pale yellow viscous liquid. $^1$H NMR (400 MHz, DMSO-d$_6$): δ ppm 8.00-8.26 (m, 1H), 4.04-4.12 (m, 2H), 3.52-3.72 (m, 2H), 2.95-3.15 (m, 2H), 2.40-2.61 (m, 2H), 2.07-2.23 (m, 1H), 1.62-1.54 (m, 9H), 1.32-1.47 (m, 9H), 1.13-1.27 (m, 2H). m/z (ESI): 361.3 (M–H)$^+$.

Step 2: To a 25-mL round-bottomed flask was added tert-butyl-3-(((1R,2R,4S)-7-(4-methoxybenzyl)-7-azabicyclo[2.2.1]heptan-2-yl)carbamoyl)azepane-1-carboxylate (0.3 g, 0.793 mmol) in 1,4-dioxane (4 mL) was treated with HCl (4 M in Dioxane, 0.594 mL, 2.378 mmol) drop wise at ambient temperature and stirred for 4 h. The reaction mixture was concentrated under reduced pressure and the crude material was washed with hexane twice to get N-((1R,2R,4S)-7-(4-methoxybenzyl)-7-azabicyclo[2.2.1]heptan-2-yl)azepane-3-carboxamide (0.2 g, 0.633 mmol, 80% yield) as a tan solid.

Step 4: To a solution of N-((1R,2R,4S)-7-(4-methoxybenzyl)-7-azabicyclo[2.2.1]heptan-2-yl)azepane-3-carboxamide (0.116 g, 0.366 mmol) in tetrahydrofuran (4 mL) was added LiHMDS (0.184 g, 1.099 mmol) under nitrogen atmosphere at 0° C. and was stirred at RT for 5 min. Another flask was charged with 1,3-dichloro-5-iodobenzene (0.1 g, 0.366 mmol) in tetrahydrofuran (4 mL) followed by Ruphos precatalyst (5.34 mg, 7.33 µmol), Ruphos (3.42 mg, 7.33 µmol) and was degassed with N$_2$ gas for 5 min. This resultant reaction mixture was added to the first one and was stirred at 60° C. for 16 h. The reaction mixture was filtered through celite, and washed with H$_2$O and EtOAc. The organic layer was separated, washed with brine, dried over Na$_2$SO$_4$, filtered and concentrated in vacuo. The crude material was purified by Prep-HPLC to provide 1-(3,5-dichlorophenyl)-N-((1R,2R,4S)-7-(4-methoxybenzyl)-7-azabicyclo[2.2.1]heptan-2-yl)azepane-3-carboxamide (0.02 g, 0.049 mmol, 13.40% yield) as an off white solid. $^1$H NMR (400 MHz, DMSO-d$_6$): δ ppm 8.24 (t, J=5.3 Hz, 1H), 6.54-6.87 (m, 3H), 4.10 (dt, J=19.7, 5.1 Hz, 3H), 3.61-3.84 (m, 2H), 3.38-3.44 (m, 2H), 3.24 (dd, J=14.2, 8.7 Hz, 1H), 2.71-2.81 (m, 1H), 2.18 (q, J=13.1, 10.5 Hz, 1H), 1.73-1.98 (m, 4H), 1.45-1.72 (m, 4H), 1.20-1.38 (m, 2H). m/z (ESI): 407.2 (M+H)$^+$.

Intermediate X: 3-(2,5-Dichlorophenyl)cyclopentane-1-carboxylic acid

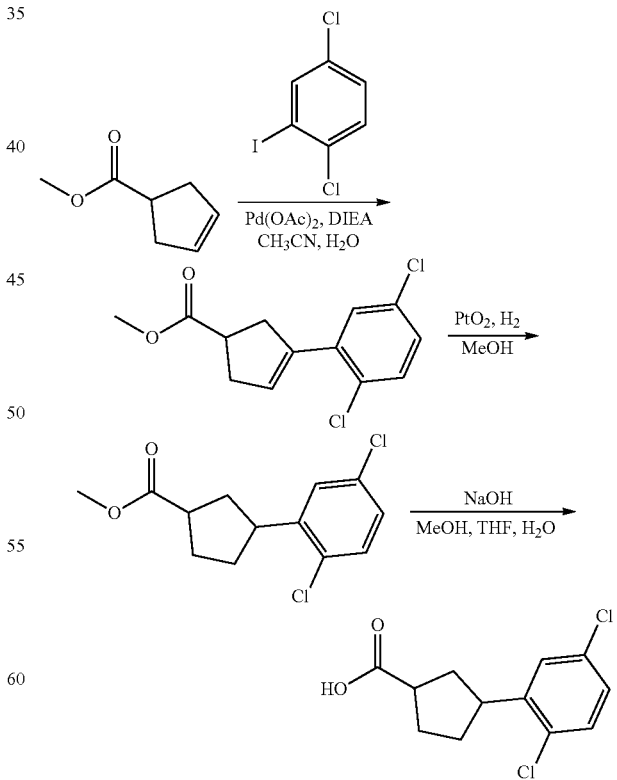

The mixture of methyl cyclopent-3-ene-1-carboxylate (0.25 mL, 2.0 mmol), 1,4-dichloro-2-iodobenzene (0.27 mL, 2.0 mmol), palladium acetate (0.2 mmol), DIEA (0.36 mL, 2.0 mmol), water (1 mL) and acetonitrile (5.0 mL) was degassed and flushed with nitrogen. After stirring at 85° C. for 3 h, the resulting mixture was cooled and diluted with EtOAc and brine. The organic layer was dried over $Na_2SO_4$, concentrated under reduced pressure and purified by silica gel column chromatography (15-20% EtOAc/Hex) to afford methyl 3-(2,5-dichlorophenyl)cyclopent-3-ene-1-carboxylate (432 mg, 80%) as an oil.

Methyl 3-(2,5-dichlorophenyl)cyclopent-3-ene-1-carboxylate (44 mg, 0.16 mmol), $PtO_2$ (10 mg, 0.044 mmol), and methanol (2.0 mL) were stirred at room temperature for 2 h under 1 atm hydrogen pressure (balloon). The resulting mixture was filtered through celite and concentrated under reduced pressure to provide crude methyl 3-(2,5-dichlorophenyl)cyclopentane-1-carboxylate.

Methyl 3-(2,5-dichlorophenyl)cyclopentane-1-carboxylate (crude from the previous reaction, 0.16 mmol), NaOH (aq IN, 1.0 mL, 1.0 mmol), THF (1.0 mL) and methanol (1.0 mL) were stirred at room temperature for 1 h. The resulting mixture was diluted with water and washed with EtOAc twice. The resulting aqueous layer was acidified with 1N aq. HCl and extracted with EtOAc. The organic layer was dried over $Na_2SO_4$, concentrated under reduced pressure to afford the desired product (31 mg, 75%) which was used in the next step without further purification. MS (ED) for $C_1H_{12}Cl_2$, found 257.0 [M−1].

Intermediate Y: 2-chloro-N-((1R,2R,4S)-7-cyano-7-azabicyclo[2.2.1]heptan-2-yl)-4-(4,4,5,5-tetramethyl-1,3,2-dioxaborolan-2-yl)benzamide

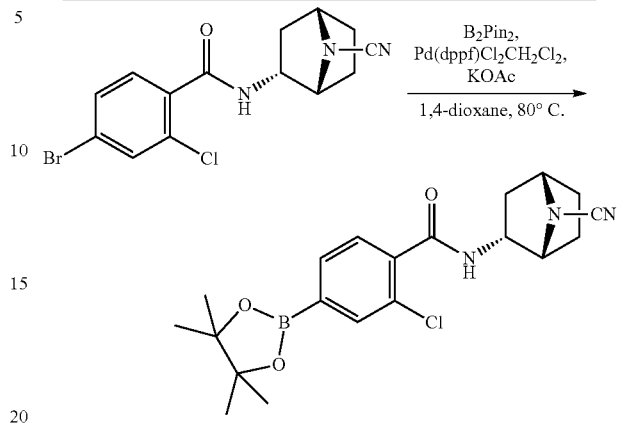

To a reaction vial was added, potassium acetate (0.747 g, 7.61 mmol), $PdCl_2$(dppf)-DCM adduct (0.207 g, 0.254 mmol), bis(pinacolato)diboron (0.967 g, 3.81 mmol), 4-bromo-2-chloro-N-((1R,2R,4S)-7-cyano-7-azabicyclo[2.2.1]heptan-2-yl)benzamide (0.900 g, 2.54 mmol), and 1,4-dioxane (12.69 ml). The vial was purged with nitrogen and sealed. The vial was heated to 80° C. for 3 hours. The reaction mixture was poured directly onto an ISCO loading cartridge and purified by chromatography, eluting with a gradient of 0% to 50% EtOAc in Heptane to provide 2-chloro-N-((1R,2R,4S)-7-cyano-7-azabicyclo[2.2.1]heptan-2-yl)-4-(4,4,5,5-tetramethyl-1,3,2-dioxaborolan-2-yl)benzamide (0.659 g, 0.412 mmol, 81.0% yield) as off-white solid. m/z: 320.0 [M+1]

The intermediates below were made by identical procedures

| Int. | Structure[FB-L20] | Name | LC/MS data |
|---|---|---|---|
| Y-1 | | N-((1R,2R,4S)-7-cyano-7-azabicyclo[2.2.1]heptan-2-yl)-2-methyl-4-(4,4,5,5-tetramethyl-1,3,2-dioxaborolan-2-yl)benzamide | m/z: 382.0 [M + 1] |
| Y-2 | | N-((1R,2R,4S)-7-cyano-7-azabicyclo[2.2.1]heptan-2-yl)-2-fluoro-4-(4,4,5,5-tetramethyl-1,3,2-dioxaborolan-2-yl)benzamide | m/z: 386.0 [M + 1] |

-continued

| Int. | Structure[FB-L20] | Name | LC/MS data |
|---|---|---|---|
| Y-3 | 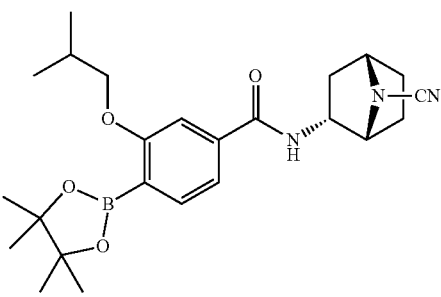 | N-((1R,2R,4S)-7-cyano-7-azabicyclo[2.2.1]heptan-2-yl)-4-(4,4,5,5-tetramethyl-1,3,2-dioxaborolan-2-yl)-2-(trifluoromethyl)benzamide | m/z: 436.0 [M + 1] |

Intermediate Z: N-((1R,2R,4S)-7-cyano-7-azabicyclo[2.2.1]heptan-2-yl)-3-isobutoxy-4-(4,4,5,5-tetramethyl-1,3,2-dioxaborolan-2-yl)benzamide

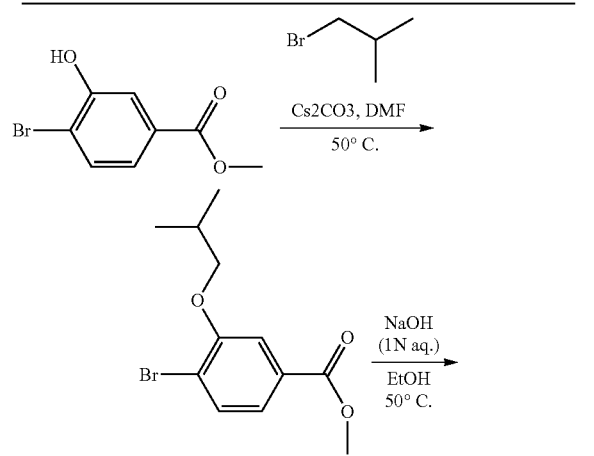

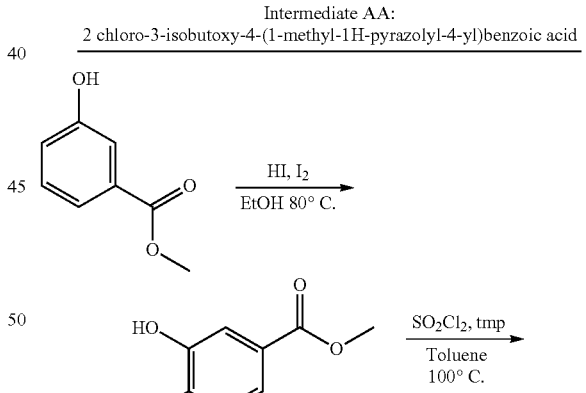

Intermediate Z was prepared in an identical way to Intermediate M followed borylation as described for intermediate Y. N-((1R,2R,4S)-7-cyano-7-azabicyclo[2.2.1]heptan-2-yl)-3-isobutoxy-4-(4,4,5,5-tetramethyl-1,3,2-dioxaborolan-2-yl)benzamide (1.02 g, 2.32 mmol, 70.1% yield) was obtained as an off-white solid. m/z: 440.0 [M+1]

Intermediate AA:
2 chloro-3-isobutoxy-4-(1-methyl-1H-pyrazolyl-4-yl)benzoic acid

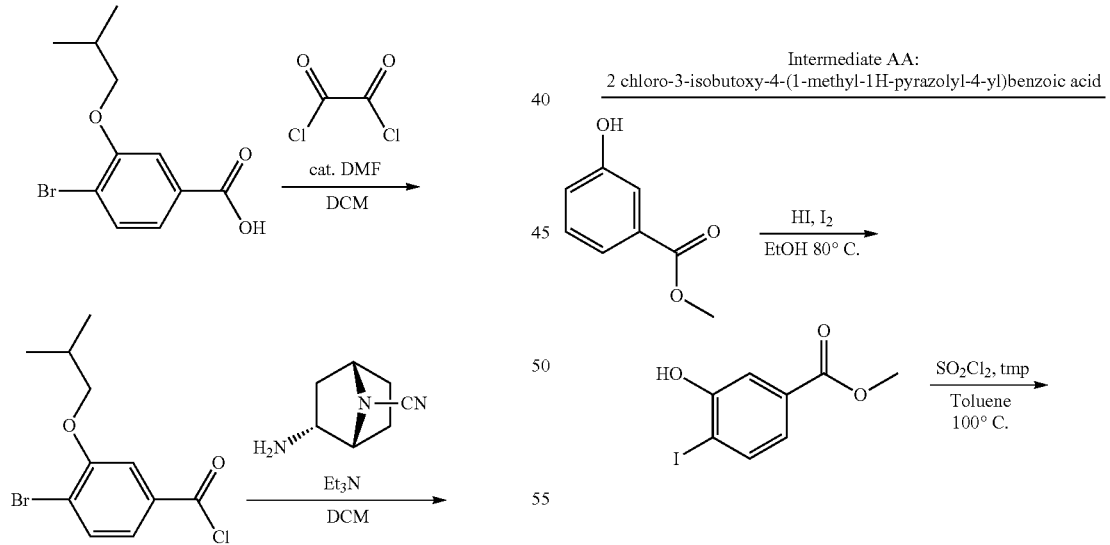

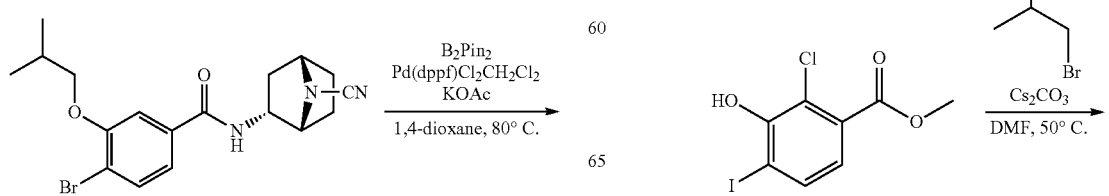

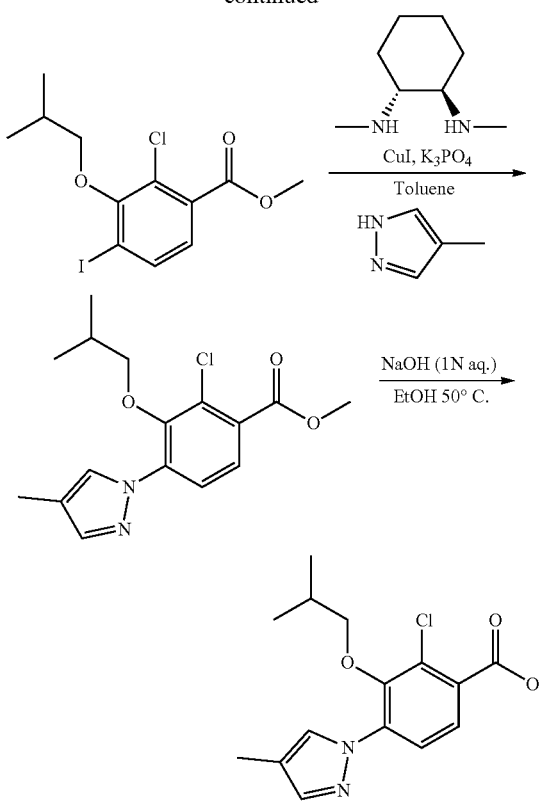

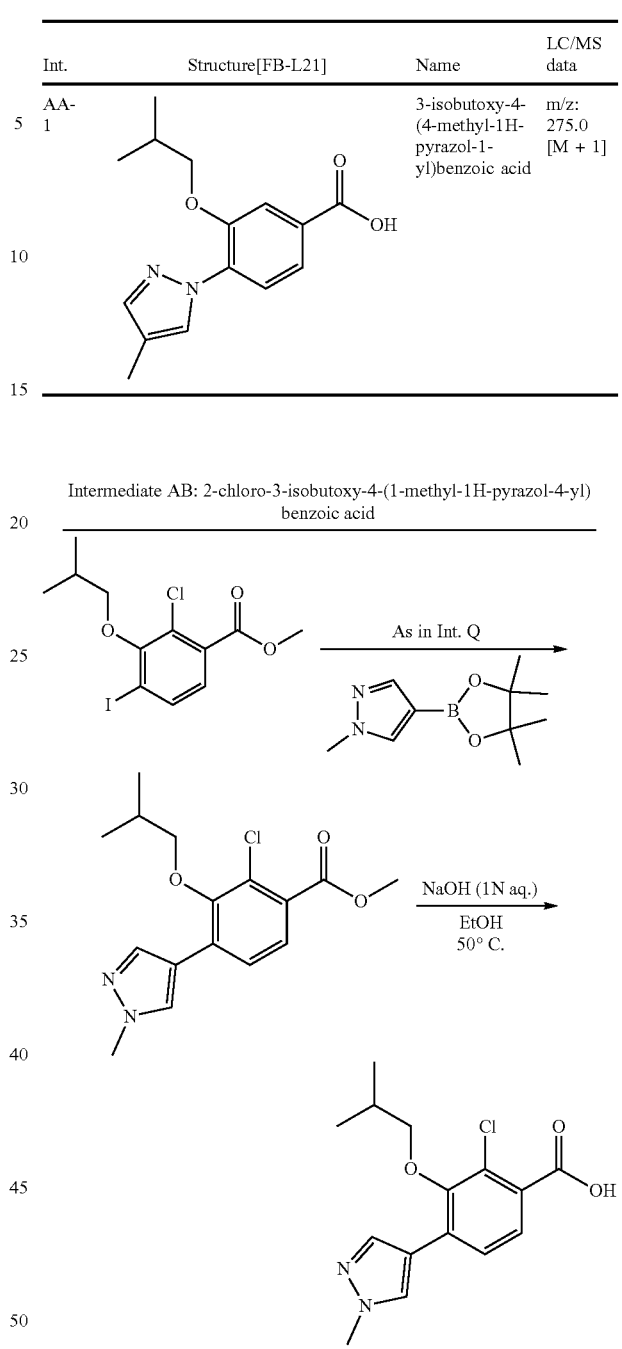

Step 1: To a stirred solution of methyl 3-hydroxybenzoate (2.00 g, 13.15 mmol) in ethanol (6.57 ml) was added iodine (1.335 g, 5.26 mmol) in one portion. The reaction was heated to reflux before an aqueous solution (2 mL) of iodic acid (0.462 g, 2.63 mmol) was added. The mixture was refluxed for 1 hour before it was cooled to room temperature. The product was recovered by filtration and washed with water to give methyl 3-hydroxy-4-iodobenzoate (2.78 g, 10.00 mmol, 76% yield) as a white solid (m/z: 279.0 [M+1]) and was used for the next step directly.

Step 2: A mixture of methyl 3-hydroxy-4-iodobenzoate (1.39 g, 5.00 mmol) and 2,2,6,6-tetramethylpiperidine (7.06 mg, 0.050 mmol) in toluene (50.0 ml) was heated to 100° C. Then, sulfuryl chloride (0.675 g, 5.00 mmol) dissolved in toluene (50 ml) was added dropwise. The mixture was stirred at 100° C. for 1 hour. Upon completion. the reaction was cooled to room temperature and the product was recovered by filtration and washed with toluene to give methyl 2-chloro-3-hydroxy-4-iodobenzoate (1.30 g, 4.16 mmol, 83% yield) as a white solid. m/z: 313.2 [M+1]

Step 3: Performed as in Intermediate M, Step 1. methyl 2-chloro-4-iodo-3-isobutoxybenzoate (0.423 g, 1.148 mmol, 71.7% yield). m/z: 369.2 [M+1]

Step 4: Performed as in Method 19 to provide methyl 2-chloro-3-isobutoxy-4-(4-methyl-1H-pyrazol-1-yl)benzoate (0.046 g, 0.143 mmol, 52.5% yield). m/z: 323.2 [M+1]

Step 5: Performed as in Intermediate M step 2. 2-chloro-3-isobutoxy-4-(4-methyl-1H-pyrazol-1-yl)benzoic acid (0.042 g, 0.136 mmol, 50% yield). m/z: 309.0 [M+1]

The intermediates below were made by identical procedures

| Int. | Structure[FB-L21] | Name | LC/MS data |
|---|---|---|---|
| AA-1 | (structure) | 3-isobutoxy-4-(4-methyl-1H-pyrazol-1-yl)benzoic acid | m/z: 275.0 [M + 1] |

Intermediate AB: 2-chloro-3-isobutoxy-4-(1-methyl-1H-pyrazol-4-yl)benzoic acid

Methyl 2-chloro-3-hydroxy-4-iodobenzoate was converted to 2-chloro-3-isobutoxy-4-(1-methyl-1H-pyrazol-4-yl)benzoic acid (0.055 g, 0.178 mmol, 65.7% yield) using the procedure for Intermediate Q. m/z: 309.0 [M+1]

Synthetic Examples

The following examples are labeled using a classification system in which the first number refers to the method used to synthesize the compound, the second number is an identifying number, and the third number, if present, refers to the compound's order of elution in a chromatographic separation process where stereochemistry if shown is arbitrarily defined. If the third number is absent, the compound is a single compound or mixture of isomers. The sequential numbering of the Examples is interrupted and certain Example numbers are intentionally omitted due to formatting considerations.

Method 1

Example 1-1: N-((1R,2R,4S)-7-cyano-7-azabicyclo[2.2.1]heptan-2-yl)-2-(1H-pyrrol-1-yl)benzo[d]thiazole-6-carboxamide

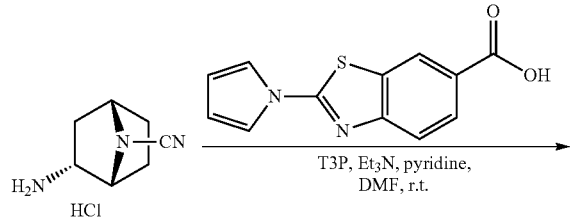

Intermediate A

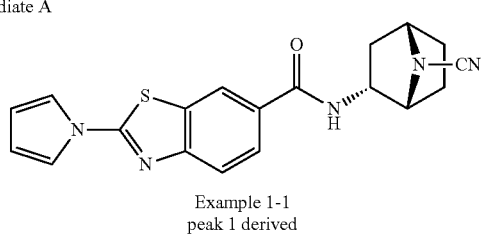

Example 1-1
peak 1 derived

A 4 ml vial containing 2-(1H-pyrrol-1-yl)benzo[d]thiazole-6-carboxylic acid (0.2 mmol) was treated with a solution of Intermediate A in DMF (0.25 mmol). A solution of T3P in DMF (0.255 ml, 0.400 mmol) was added. Followed by a solution of pyridine and triethylamine. The vial was sealed and agitated on a shaker plate for 18 hrs. The reaction was quenched with 1 ml of a 10% 1M NaOH solution in wet DMF and purified by RP-HPLC (Purification performed with 0.1% NH4OH in H2O (A) and ACN (B) as mobile phase, XSelect column (19×100 mm, 10 um), MS mode: ESI+). Fractions containing the product were concentrated to provide the title compound: LC/MS

Method 2

Example 2-1-1 and 2-1-2: 2-(4-chloro-3-(trifluoromethyl)phenoxy)-N-(-7-cyano-7-azabicyclo[2.2.1]heptan-2-yl)acetamide endo enantiomer 1 and 2-(4-chloro-3-(trifluoromethyl)phenoxy)-N-((1S,2S,4R)-7-cyano-7-azabicyclo[2.2.1]heptan-2-yl)acetamide endo enantiomer 2

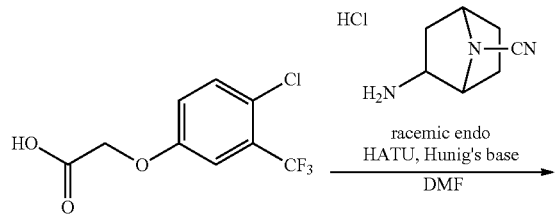

racemic endo
HATU, Hunig's base
DMF

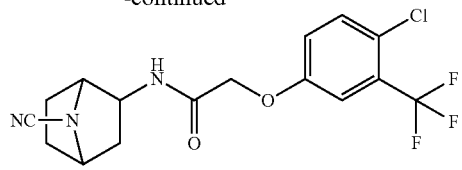

Example 2-1-1
enantiomer 1

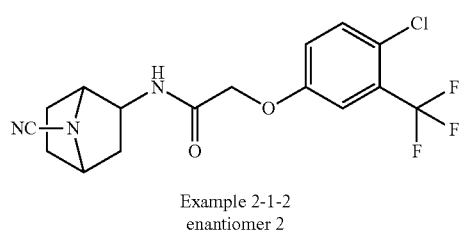

Example 2-1-2
enantiomer 2

To red cap vials were added 2-(4-chloro-3-(trifluoromethyl)phenoxy)acetic acid (0.12 g, 0.471 mmol) and HATU (0.358 g, 0.943 mmol) in DMF (2.5 ml) followed by Hunig's base (0.41 ml, 2.357 mmol). They were stirred at rt for 5 min and racemic Intermediate A (0.131 g, 0.754 mmol) was added. They were stirred at rt for 10 min. LCMS showed conversion to desired product. The crude material was absorbed onto a plug of silica gel and purified by chromatography through a 10 g×2 biotage ultra column, eluting with a gradient of 10% to 50% EtOAc:EtOH (3:1) in Heptane, to provide racemic 2-(4-chloro-3-(trifluoromethyl)phenoxy)-N-((1S,2S,4R)-7-cyano-7-azabicyclo[2.2.1]heptan-2-yl)acetamide (0.05 g, 0.134 mmol, 28.4% yield) product as yellow solid. m/z: 374.0 [M+1] $^1$H NMR (500 MHz, DMSO-$d_6$) δ 8.42 (br d, J=5.58 Hz, 1H), 7.65 (d, J=8.82 Hz, 1H), 7.38 (d, J=2.98 Hz, 1H), 7.28 (dd, J=3.05, 8.89 Hz, 1H), 4.64-4.71 (m, 2H), 4.10-4.16 (m, 3H), 2.13-2.20 (m, 1H), 1.74-1.83 (m, 2H), 1.55-1.67 (m, 2H), 1.36 (dd, J=4.15, 12.85 Hz, 1H) The sample was purified by SFC using an Whelk-01-S,S, 21×250 mm, 5 micron column, a mobile phase of 30% isopropanol using a flow rate of 110 mL/min to generate 11 mg of 2-1-1 with ee >99% and 8 mg of 2-1-2 with ee >96%.

Method 3

Example 3-1-1 and 3-1-2: 3-(3-chlorophenyl)-N-((1S,2S,4R)-7-cyano-7-azabicyclo[2.2.1]heptan-2-yl)isoxazole-5-carboxamide and 3-(3-chlorophenyl)-N-((1R,2R,4S)-7-cyano-7-azabicyclo[2.2.1]heptan-2-yl)isoxazole-5-carboxamide

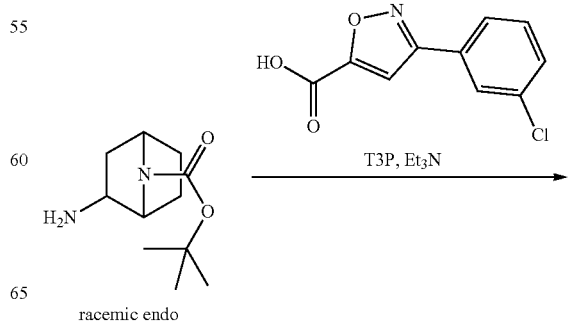

racemic endo

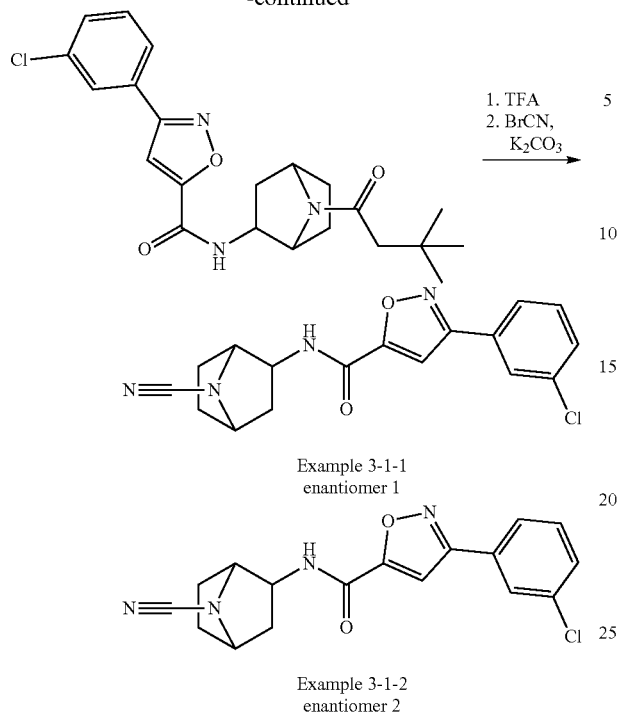

Example 3-1-1
enantiomer 1

Example 3-1-2
enantiomer 2

Step 1: To a mixture of 3-(3-chlorophenyl)-1,2-oxazole-5-carboxylic acid (0.619 ml, 2.77 mmol), and racemic-endo-tert-butyl (1R,2R,4S)-2-amino-7-azabicyclo[2.2.1]heptane-7-carboxylate (0.263 g, 1.597 mmol) in dichloromethane (5.89 ml) was added triethylamine, anhydrous (0.809 ml, 5.76 mmol) and T3P in DMF (2.427 ml, 4.16 mmol). The reaction mixture was stirred at 20° C. for 12 h. LC/MS showed completion conversion to the amide. Saturated NaHCO₃ solution was added and the mixture was stirred for 5 min. The mixture was partitioned in a phase separator. The organic layer was collected and concentrated. The crude material was absorbed onto a plug of silica gel and purified by chromatography through a 40 g Redi-Sep GOLD pre-packed silica gel column, eluting with a gradient of 0% to 60% EtOAc in heptane, to provide rac-tert-butyl (1R,2R,4S)-2-(3-(3-chlorophenyl)isoxazole-5-carboxamido)-7-azabicyclo[2.2.1]heptane-7-carboxylate (0.401 g, 0.960 mmol, 81% yield) as a white solid.

Step 2: To a solution of rac-tert-butyl (1R,2R,4S)-2-(3-(3-chlorophenyl)isoxazole-5-carboxamido)-7-azabicyclo[2.2.1]heptane-7-carboxylate (0.071 g, 0.170 mmol) in dichloromethane (0.850 ml) was added 2,2,2-trifluoroacetic acid (0.484 ml, 4.25 mmol). The mixture was stirred at rt for 12 h. LC/MS showed complete Boc deprotection. The mixture was passed through a 5 g SCX-2 Column with the aid of MeOH. The basic components were eluted with 2 M NH₃ in MeOH and concentrated to provide rac-N-((1R,2R,4S)-7-azabicyclo[2.2.1]heptan-2-yl)-3-(3-chlorophenyl)isoxazole-5-carboxamide Step 3: The solid obtained in step 2 was dissolved in tetrahydrofuran (0.850 ml). Potassium carbonate (0.070 g, 0.510 mmol) was added followed by cyanic bromide, 5 M solution in acetonitrile (0.037 ml, 0.187 mmol). The mixture was stirred at rt for 12 h. LC/MS showed completion of the reaction. The mixture was partitioned between water and DCM. The organic layer was collected and concentrated.

The crude material was absorbed onto a plug of silica gel and purified by chromatography through a Biotage Ultra 10 g pre-packed silica gel column, eluting with a gradient of 0% to 50% EtOAc in heptane, to provide a white solid. chiral purification was performed via preparative SFC, to give 3-1-1 (>99% ee, >99% chemical purity) and 3-1-2 (95.22% ee, 96.49% chemical purity) which were arbitrarily assigned stereochemistry. m/z: 343.16 [M+1] ¹H NMR (500 MHz, DMSO-d₆) δ 9.30 (d, J=6.23 Hz, 1H), 8.01 (t, J=1.69 Hz, 1H), 7.92 (d, J=7.41 Hz, 1H), 7.77 (s, 1H), 7.56-7.64 (m, 2H), 4.22-4.33 (m, 2H), 4.18 (t, J=4.80 Hz, 1H), 3.32 (s, 15H), 2.17-2.25 (m, 1H), 1.85-1.92 (m, 1H), 1.77-1.85 (m, 1H), 1.64-1.74 (m, 2H), 1.62 (dd, J=4.67, 12.85 Hz, 1H)

Method 4

Example 4-1-1, 4-1-2, 4-1-3, and 4-1-4: (1S,2S,4R)-7-cyano-N-(4-(3-(trifluoromethyl)phenyl)thiazol-2-yl)-7-azabicyclo[2.2.1]heptane-2-carboxamide; (1S,2R,4R)-7-cyano-N-(4-(3-(trifluoromethyl)phenyl)thiazol-2-yl)-7-azabicyclo[2.2.1]heptane-2-carboxamide; (1R,2S,4S)-7-cyano-N-(4-(3-(trifluoromethyl)phenyl)thiazol-2-yl)-7-azabicyclo[2.2.1]heptane-2-carboxamide; and (1R,2R,4S)-7-cyano-N-(4-(3-(trifluoromethyl)phenyl)thiazol-2-yl)-7-azabicyclo[2.2.1]heptane-2-carboxamide

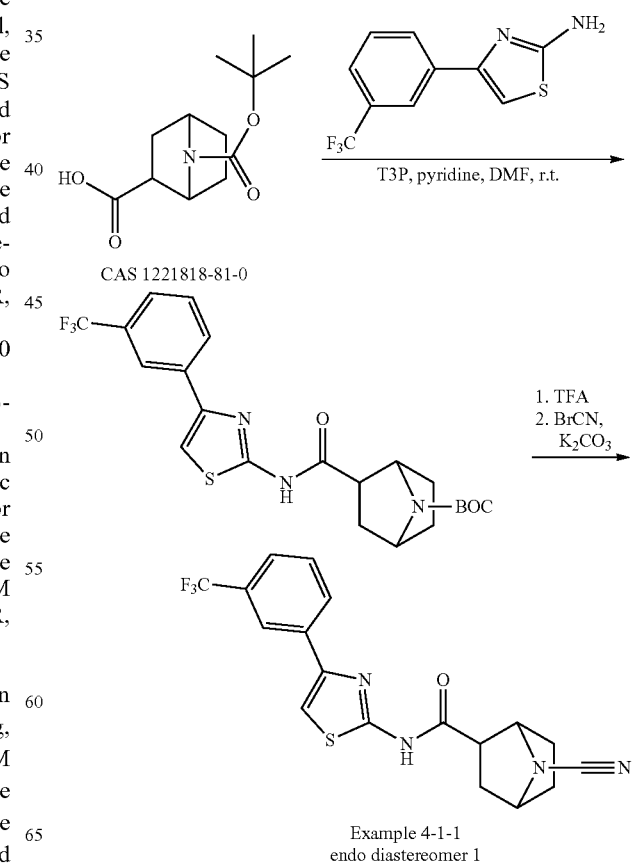

Example 4-1-1
endo diastereomer 1

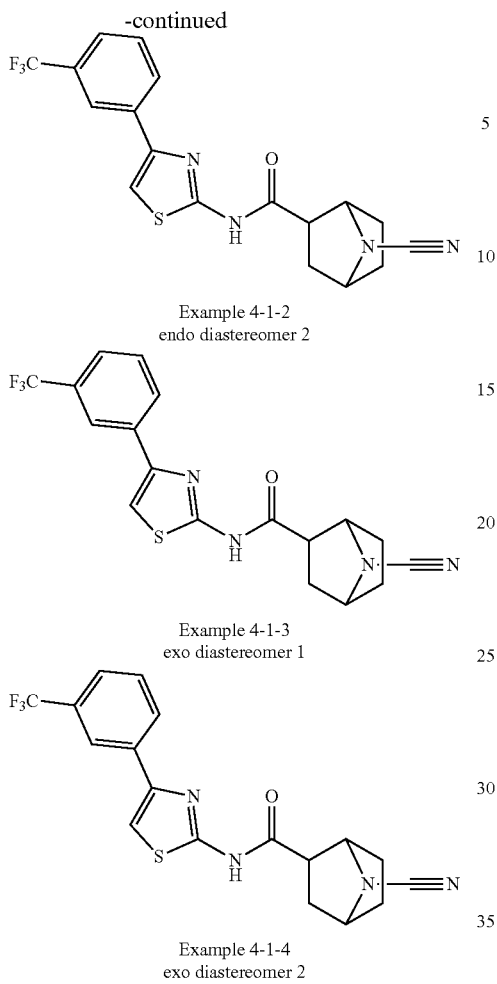

Example 4-1-2
endo diastereomer 2

Example 4-1-3
exo diastereomer 1

Example 4-1-4
exo diastereomer 2

7-(tert-butoxycarbonyl)-7-azabicyclo[2.2.1]heptane-2-carboxylic acid (0.5 g 1.05 equiv.) and 4-(3-(trifluoromethyl)phenyl)thiazol-2-amine (1.0 equiv.) were weighed to an 8 ml vial. 1-propanephosphonic acid cyclic anhydride, 50 wt. % solution in ethyl acetate (2.51 ml, 3.95 mmol) was added followed by pyridine and the reaction was stirred at r.t. for 3 hr when full consumption of the acid was observed. Saturated NaHCO$_3$ was added and the reaction was extracted with EtOAc 3×. The combined organics were washed with 1N HCl, brine, dried over Na$_2$SO$_4$, filtered and concentrated. The orange foam obtained was brought up in ~0.5 ml of DCM and treated with ~1 ml of TFA and allowed to stand o/n. After concentrating the crude oil was azeotroped 1× with heptane, was brought up in tetrahydrofuran (9.87 ml) and treated with K$_2$CO$_3$ (1.1 g 4 equiv.) for a few minutes before cyanic bromide (5M acetonitrile, 0.434 ml, 2.171 mmol) was added. After 1 hour the reaction was quenched with water, extracted 3× with EtOAc, and the combined organics were washed with sat NaHCO$_3$. The organics were separated, concentrated and purified by SFC: Chiralpak IC 3×15 cm, 5 micron column, a mobile phase of 20% methanol using a flowrate of 80 mL/min. to generate 137 mg of 4-1-1 with an ee of >99%, 135 mg of 4-1-2 with an ee of >98%, m/z=393.0 (M+H), $^1$H NMR (500 MHz, DMSO-d$_6$) δ 8.23 (s, 1H), 8.19 (br t, J=3.57 Hz, 1H), 7.86 (s, 1H), 7.63-7.69 (m, 2H), 4.47 (t, J=4.74 Hz, 1H), 4.22 (t, J=4.28 Hz, 1H), 3.30-3.49 (m, 1H), 1.93-2.05 (m, 2H), 1.76-1.85 (m, 1H), 1.64-1.76 (m, 1H), 1.46-1.57 (m, 2H) 118 mg of 4-1-3 with an ee of >96% and 124 mg of 4-1-4 with an ee of >98%. m/z=393.0 (M+H) $^1$H NMR (500 MHz, DMSO-d$_6$) δ 8.24 (s, 1H), 8.17-8.22 (m, 1H), 7.83 (s, 1H), 7.66 (d, J=4.89 Hz, 2H), 4.44 (d, J=4.54 Hz, 1H), 4.22 (t, J=4.48 Hz, 1H), 2.89 (dd, J=5.13, 9.02 Hz, 1H), 2.15-2.26 (m, 1H), 1.72-1.90 (m, 3H), 1.62-1.71 (m, 1H), 1.51-1.62 (m, 1H). Peak assignment determined by SFC: Chiralpak IC, 15% methanol.

Method 5

Example 5-1: N-((1S,2S,4R)-7-cyano-7-azabicyclo[2.2.1]heptan-2-yl)-1-(4,6-dimethylpyrimidin-2-yl)indoline-5-carboxamide

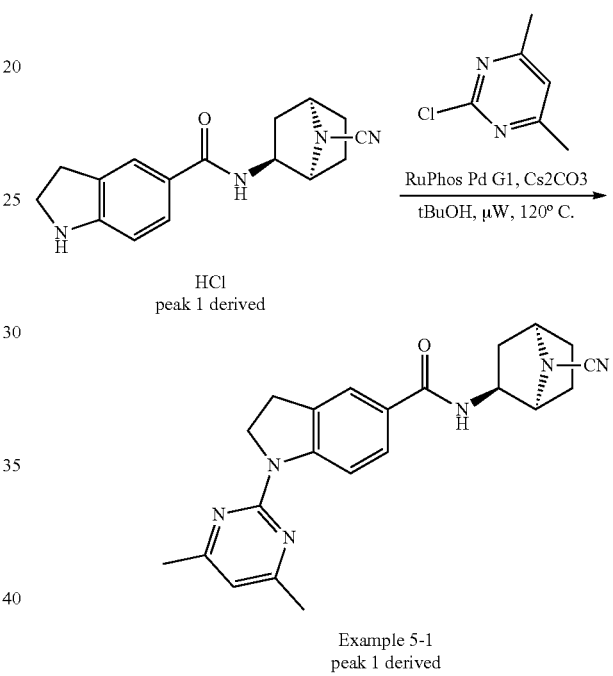

HCl
peak 1 derived

Example 5-1
peak 1 derived

A glass microwave reaction vessel was charged with 2-chloro-4,6-dimethyl-1,3-diazine (0.023 g, 0.163 mmol), N-((1S,2S,4R)-7-cyano-7-azabicyclo[2.2.1]heptan-2-yl)indoline-5-carboxamide hydrochloride (0.04 g, 0.125 mmol), Ruphos pd G1 methyl t-butyl ether adduct (0.020 g, 0.025 mmol) and cesium carbonate (0.143 g, 0.439 mmol). The reaction vial was purged with N$_2$ and tBuOH (0.6 ml) was added. The reaction mixture was heated in a microwave reactor at 120° C. for 10 min. LCMS showed desired product formation. The reaction mixture were diluted with water and extracted with DCM. The organic extracts were concentrated. The crude material was absorbed onto a plug of silica gel and purified by chromatography through a 10 g Biotage ultra column, eluting with a gradient of 10% to 60% EtOAc/EtOH (3/1) in heptane, to N-((1S,2S,4R)-7-cyano-7-azabicyclo[2.2.1]heptan-2-yl)-1-(4,6-dimethylpyrimidin-2-yl)indoline-5-carboxamide as off-whitesolid. m/z: 389.0 [M+1] $^1$H NMR (500 MHz, DMSO-d$_6$) δ 8.42 (d, J=9.08 Hz, 1H), 8.36 (d, J=6.10 Hz, 1H), 7.74 (s, 1H), 7.75 (d, J=6.32 Hz, 1H), 6.74 (s, 1H), 4.26-4.32 (m, 1H), 4.20-4.25 (m, 3H), 4.13-4.19 (m, 1H), 3.18 (t, J=8.69 Hz, 2H), 2.36-2.43 (m, 6H), 2.19 (br s, 1H), 1.77-1.89 (m, 2H), 1.62-1.72 (m, 2H), 1.56 (dd, J=4.80, 12.85 Hz, 1H)

Method 6

Example 6-1: N-(racemic-(endo)-7-cyano-7-azabicyclo[2.2.1]heptan-2-yl)-1-(4-methylpyrimidin-2-yl)-1H-indole-5-carboxamide

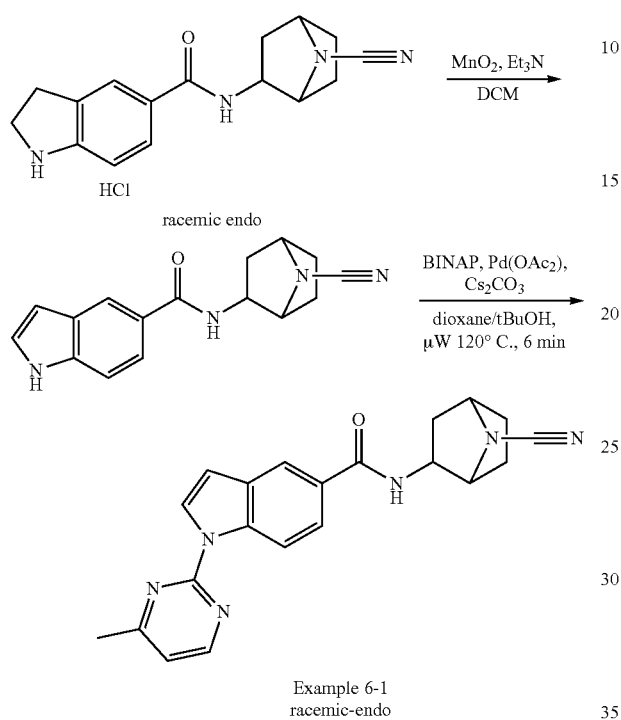

Example 6-1
racemic-endo

A glass microwave reaction vessel was charged with N-((1S,2S,4R)-7-cyano-7-azabicyclo[2.2.1]heptan-2-yl)-1H-indole-5-carboxamide (0.04 g, 0.143 mmol), 2-chloro-4-methylpyrimidine (0.024 g, 0.185 mmol), cesium carbonate (0.093 g, 0.285 mmol), palladium (ii) acetate (9.61 mg, 0.043 mmol), and racemic-2,2'-bis(diphenylphosphino)-1,1'-binaphthyl (0.027 g, 0.043 mmol) in a mixture of 1,4-dioxane (0.7 ml) and tert-butanol (0.7 ml). The reaction mixture was purged with $N_2$, stirred and heated in an Initiator microwave reactor at 120° C. for 6 min. LCMS showed nearly full conversion to desired product. Then the orange reaction mixture was diluted with water and extracted with DCM. The organic extract was concentrated in vacuo to give the crude material as an orange solid. The crude material was absorbed onto a plug of silica gel and purified by chromatography through a 10 g biotage ultra column, eluting with a gradient of 10% to 60% EtOAc/EtOH in Heptane, to provide a racemic mixture of N-((1S,2S,4R)-7-cyano-7-azabicyclo[2.2.1]heptan-2-yl)-1-(4-methylpyrimidin-2-yl)-1H-indole-5-carboxamide (0.013 g, 0.035 mmol, 24% yield) as a light-yellow solid. m/z: 373.2 [M+1] $^1$H NMR (400 MHz, DMSO-$d_6$) δ 8.81 (d, J=8.81 Hz, 1H), 8.74 (d, J=5.08 Hz, 1H), 8.57 (d, J=5.91 Hz, 1H), 8.36 (d, J=3.63 Hz, 1H), 8.21 (d, J=1.66 Hz, 1H), 7.84 (dd, J=1.76, 8.81 Hz, 1H), 7.28 (d, J=4.98 Hz, 1H), 6.90 (d, J=3.63 Hz, 1H), 4.34 (br dd, J=4.72, 11.14 Hz, 1H), 4.26 (t, J=4.51 Hz, 1H), 4.17 (t, J=4.72 Hz, 1H), 2.59 (s, 3H), 2.23 (br s, 1H), 1.87-1.96 (m, 1H), 1.78-1.86 (m, 1H), 1.66-1.75 (m, 2H), 1.60 (dd, J=4.72, 12.80 Hz, 1H)

Method 7

Example 7-1: N-((1R,2R,4S)-7-cyano-7-azabicyclo[2.2.1]heptan-2-yl)-1-(4-cyclopropylpyrimidin-2-yl)-N-methylindoline-5-carboxamide

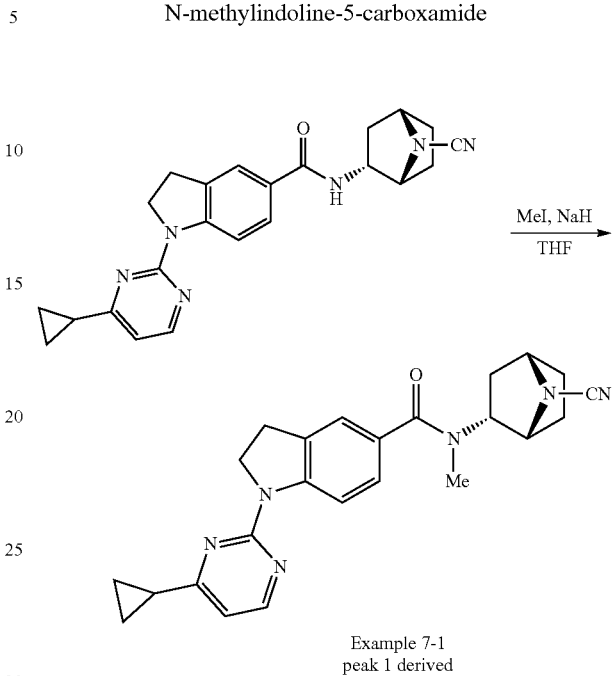

Example 7-1
peak 1 derived

To a glass reaction vial were added Intermediate A, peak 1 derived N-((1S,2S,4R)-7-cyano-7-azabicyclo[2.2.1]heptan-2-yl)-1-(4-cyclopropylpyrimidin-2-yl)indoline-5-carboxamide (0.03 g, 0.075 mmol) in tetrahydrofuran (0.5 ml) followed by NaH (60% in mineral oil) (5.4 mg, 0.135 mmol). It was stirred at rt for 5 min, then MeI (0.012 ml, 0.187 mmol) was added. The reaction mixture was stirred at rt for 0.5 h. LCMS showed full conversion to desired product. The reaction mixture was diluted with water and extracted with DCM. The organic extract was washed with saturated NaCl and dried over $MgSO_4$. The solution was filtered and concentrated in vacuo to give the crude material as a light-yellow solid. m/z: 415.3 [M+1] $^1$H NMR (400 MHz, DMSO-$d_6$) δ 8.37 (d, J=5.08 Hz, 1H), 8.24 (d, J=8.19 Hz, 1H), 7.34 (s, 1H), 7.33 (d, J=9.57 Hz, 1H), 6.89 (d, J=5.08 Hz, 1H), 4.46 (t, J=4.30 Hz, 1H), 4.14-4.23 (m, 4H), 3.17 (t, J=8.81 Hz, 2H), 2.96 (s, 3H), 2.04-2.22 (m, 2H), 1.81-1.90 (m, 2H), 1.66-1.75 (m, 2H), 1.05-1.14 (m, 4H)

Method 8

Example 8-1: N5-((1S,2S,4R)-7-cyano-7-azabicyclo[2.2.1]heptan-2-yl)-N1-cyclopropylindoline-1,5-dicarboxamide

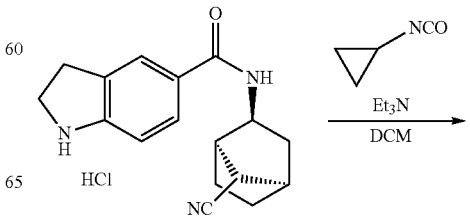

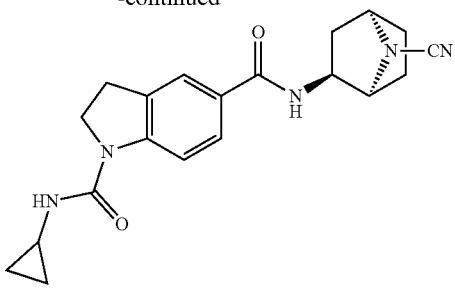

Example 8-1
peak 1 derived

To a glass vial was added Intermediate A, peak 1 derived N-((1S,2S,4R)-7-cyano-7-azabicyclo[2.2.1]heptan-2-yl)indoline-5-carboxamide hydrochloride (0.05 g, 0.157 mmol) and cyclopropyl isocyanate (0.013 g, 0.157 mmol) in dichloromethane (0.627 ml) followed by Et$_3$N (0.057 ml, 0.408 mmol). It was stirred at rt for 6 h. and LCMS showed nearly full conversion to desired product. The reaction was quenched with water and extracted with DCM. The organics were concentrated and the purification was done using HPLC with 0.1% NH40H in ACN and water as mobile phase. m/z: 366.2 [M+1] $^1$H NMR (600 MHz, DMSO-d$_6$) δ 8.32 (d, J=6.07 Hz, 1H), 7.86 (d, J=8.33 Hz, 1H), 7.66 (s, 1H), 7.65 (d, J=7.10 Hz, 1H), 6.84 (d, J=2.65 Hz, 1H), 4.23-4.29 (m, 1H), 4.20 (t, J=4.48 Hz, 1H), 4.14 (t, J=4.79 Hz, 1H), 3.87 (t, J=8.80 Hz, 21H), 3.12 (t, J=8.76 Hz, 2H), 2.59 (tdd, J=3.56, 6.99, 10.41 Hz, 1H), 2.14-2.20 (m, 1H), 1.76-1.87 (m, 2H), 1.61-1.71 (m, 2H), 1.55 (dd, J=4.67, 12.69 Hz, 1H), 0.58-0.64 (m, 2H), 0.47-0.53 (m, 2H)

Method 9

Example 9-1: N-((1R,2R,4S)-7-cyano-7-azabicyclo[2.2.1]heptan-2-yl)-3-methyl-4-(1-methyl-1H-pyrazol-4-yl)benzamide

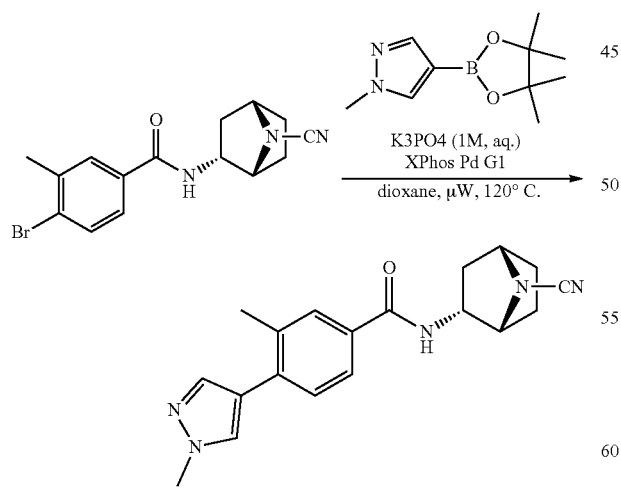

Example 9-1
peak 1 derived

A glass microwave reaction vessel was charged with Intermediate A, peak 1 derived 4-bromo-N-((1R,2R,4S)-7-cyano-7-azabicyclo[2.2.1]heptan-2-yl)-3-methylbenzamide (0.083 g, 0.247 mmol), 1-methylpyrazole-4-boronic acid pinacol ester (0.077 g, 0.371 mmol) and chloro(2-dicyclohexylphosphino-2',4',6'-tri-i-propyl-1,1'-biphenyl)[2-(2-aminoethyl)phenyl]pd(II) methyl-tert-butylether (0.037 g, 0.049 mmol) in K$_3$PO$_4$ (1 M, aq.) (0.50 ml, 0.50 mmol) and dioxane (1.3 ml). The reaction mixture was stirred and heated in a microwave reactor at 120° C. for 12 min. LC/MS showed full conversion to desired product. The reaction mixture was diluted with water and extracted with DCM. The organic extract was washed with saturated NaCl and concentrated to give the crude material as an orange oil. The crude material was absorbed onto a plug of silica gel and purified by chromatography through a 10 g biotage ultra column, eluting with a gradient of 10% to 70% EtOAc/EtOH (3/1) in Heptane, to provide N-((1R,2R,4S)-7-cyano-7-azabicyclo[2.2.1]heptan-2-yl)-3-methyl-4-(1-methyl-1H-pyrazol-4-yl)benzamide (0.067 g, 0.200 mmol, 81% yield) as an off white solid. m/z: 366.2 [M+1] $^1$H NMR (500 MHz, DMSO-d$_6$) δ 8.49 (d, J=5.97 Hz, 1H), 8.04 (s, 1H), 7.76 (s, 1H), 7.74 (s, 1H), 7.69 (dd, J=1.62, 7.98 Hz, 1H), 7.49 (d, J=8.04 Hz, 1H), 4.22-4.33 (m, 2H), 4.16 (t, J=4.74 Hz, 1H), 3.90 (s, 3H), 2.44 (s, 3H), 2.17-2.24 (m, 1H), 1.77-1.90 (m, 2H), 1.63-1.73 (m, 2H), 1.57 (dd, J=4.67, 12.72 Hz, 1H)

Method 10

Example 10-1: 2-((3-Bromobenzyl)(methyl)amino)-N-(racemic-(endo)-7-cyano-7-azabicyclo[2.2.1]heptan-2-yl)acetamide

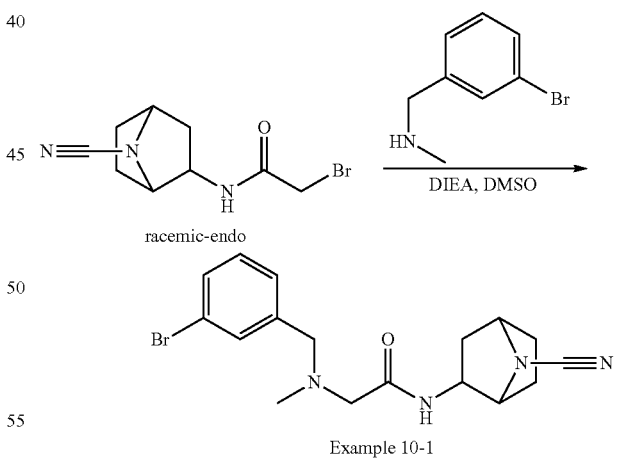

Example 10-1

The mixture of 2-bromo-N-(racemic-(endo)-7-cyano-7-azabicyclo[2.2.1]heptan-2-yl)acetamide 3 (4.0 mg, 0.015 mmol), 1-(3-bromophenyl)-N-methylmethanamine (3.1 mg, 0.015 mmol), DIEA (5.0 μL, 0.03 mmol) and DMSO (0.3 mL) was stirred at room temperature for 2 h. The resulting mixture was purified by preparative HPLC (NH$_4$OAc) to afford the product (racemic, AcOH salt, 6.3 mg, 82%) as a white solid after lyophilization. MS (EI) for C$_{17}$H$_{21}$BrN$_4$O, found 377.0 (M+1).

Method 11

Example 11-1: 2-(4-Chloro-2-cyclohexylphenoxy)-N-(racemic-(endo)-7-cyano-7-azabicyclo[2.2.1]heptan-2-yl)acetamide

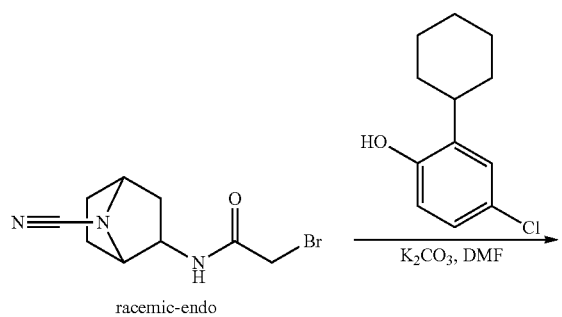

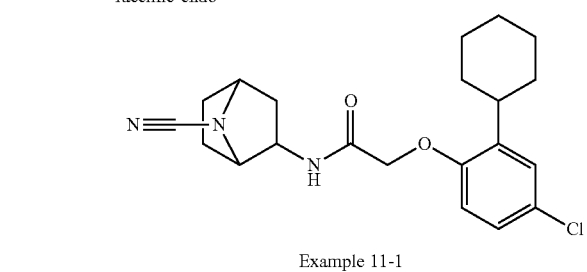

Example 11-1

The mixture of 2-bromo-N-((1R,2R,4S)-7-cyano-7-azabicyclo[2.2.1]heptan-2-yl)acetamide (racemate, 5.0 mg, 0.019 mmol), 4-chloro-2-cyclohexylphenol (4.0 mg, 0.019 mmol), potassium carbonate (3.9 mg, 0.029 mmol) and DMF (0.4 mL) was stirred at room temperature for 1 h. The resulting mixture was purified by preparative HPLC (0.1% AcOH) to afford the product (racemic, 4.7 mg, 82%) as a white solid after lyophilization. MS (EI) for $C_{21}H_{26}ClN_3O_2$, found 388.0 (M+1).

Method 12

Example 12-1: racemic-(endo)-2-(4-((4-Chlorophenyl)thio)piperidine-1-carbonyl)-7-azabicyclo[2.2.1]heptane-7-carbonitrile (racemic)

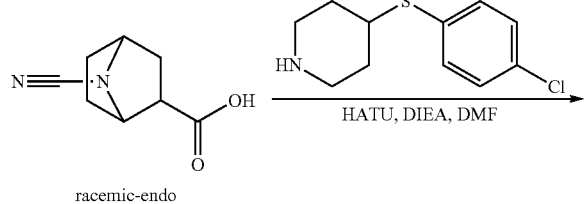

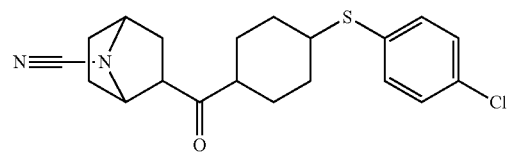

Example 12-1

To a stirred solution of crude racemic-(endo)-7-cyano-7-azabicyclo[2.2.1]heptane-2-carboxylic acid (Intermediate 1) 4-((4-chlorophenyl)thio)piperidine (11 mg, 0.050 mmol), HATU (29 mg, 0.075 mmol) and DMF (0.5 mL) was added DIEA (0.026 mL, 0.15 mmol) at room temperature. After stirring for 20 min, the mixture was purified by preparative HPLC (0.1% AcOH) to afford racemic-(endo)-2-(4-((4-chlorophenyl)thio)piperidine-1-carbonyl)-7-azabicyclo[2.2.1] heptane-7-carbonitrile (5.0 mg, 27%, 2 steps) as a white solid after lyophilization MS (EI) for $C_{19}H_{22}C_1N_3OS$, found 453.1 (M+1).

Method 13

Example 13-1: N-(racemic-(endo)-7-cyano-7-azabicyclo[2.2.1]heptan-2-yl)-1-(4-methylpyrimidin-2-yl)indoline-5-carboxamide

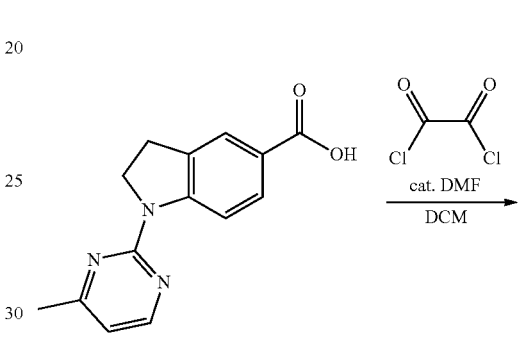

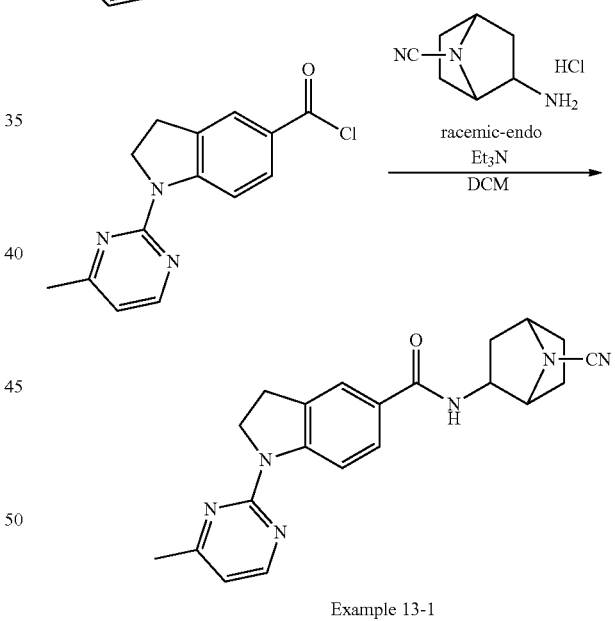

Example 13-1

Step 1: To a glass reaction vial containing 1-(4-methylpyrimidin-2-yl)indoline-5-carboxylic acid (0.087 g, 0.340 mmol) was added oxalyl chloride (0.049 ml, 0.557 mmol) in dichloromethane (0.619 ml) followed by 2 drops of DMF at rt. The reaction was stirred at rt for 0.5 h. when LC/MS showed starting material was consumed. The reaction was concentrated and used in the next step directly.

Step 2: To a glass reaction vial containing crude product from step 1 was added racemic Intermediate A (0.064 g, 0.371 mmol) and triethylamine (0.216 ml, 1.547 mmol) in dichloromethane (0.619 ml). The reaction mixture were stirred at rt for 15 min, LC/MS showed desired product formation. The reaction mixture was quenched with water and extracted with DCM. The crude material was absorbed onto a plug of silica gel and purified by chromatography through a 10 g biotage ultra column, eluting with a gradient of 10% to 55% EtOAc/EtOH (3/1) in Heptane, to provide N-(racemic-(endo)-7-cyano-7-azabicyclo[2.2.1]heptan-2-yl)-1-(4-methylpyrimidin-2-yl)indoline-5-carboxamide (38.7 mg, 0.103 mmol, 33% yield) as a white solid.

Method 14

Example 14-1: N-(racemic-(endo)-7-cyano-7-azabicyclo[2.2.1]heptan-2-yl)-4-(pyrimidin-2-ylamino)benzamide (racemic)

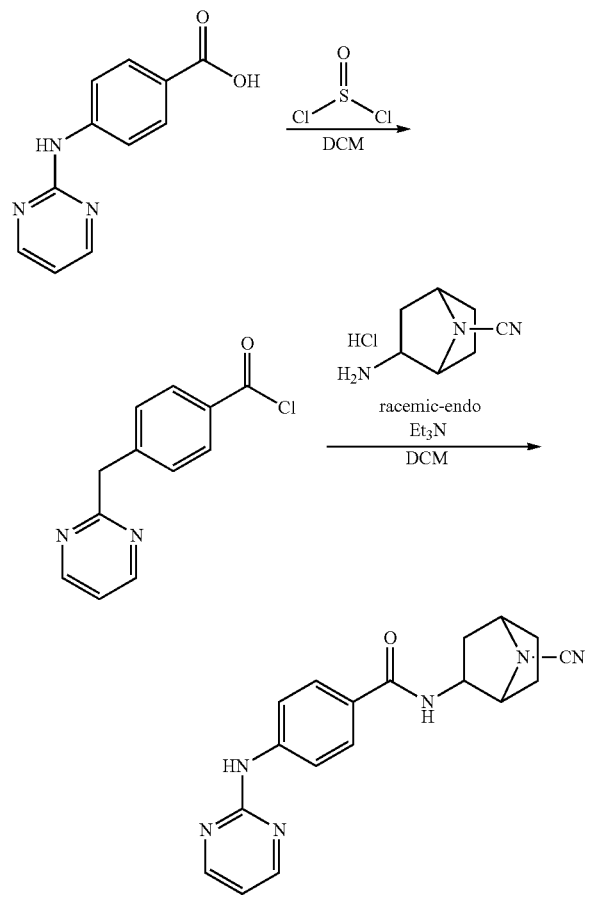

Example 14-1

Step 1: To a glass reaction vial were added 4-(pyrimidin-2-ylamino)benzoic acid (100 mg, 0.465 mmol) and thionyl chloride (237 µl, 3.25 mmol) in dichloromethane (1.2 ml) followed by 2 drops of DMF under rt. It was stirred at rt for 0.5 h. LCMS proved desired product formation by quenched LCMS sample with MeOH. It was concentrated and dried on high vacuum to yield 4-(pyrimidin-2-ylamino)benzoyl chloride (0.12 g, 0.514 mmol, 111% yield) as off white solid.

Step 2: Performed as in Method 13, step 2 to provide 29 mg of racemic N-(racemic-(endo)-7-cyano-7-azabicyclo[2.2.1]heptan-2-yl)-4-(pyrimidin-2-ylamino)benzamide m/z: 335.2 [M+1].

Method 15

Example 15-1: 6-chloro-N-((1R,2R,4S)-7-cyano-7-azabicyclo[2.2.1]heptan-2-yl)-1-(4-methylpyrimidin-2-yl)indoline-5-carboxamide

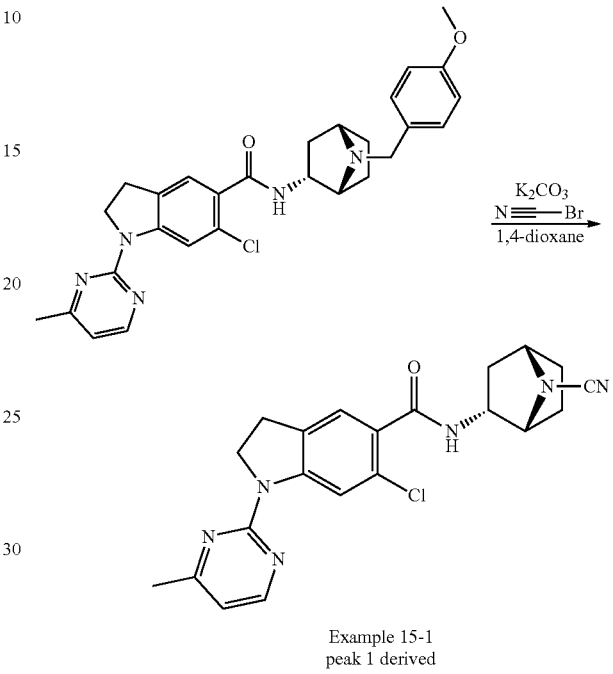

Example 15-1
peak 1 derived

To a red cap vial was added 6-chloro-N-((1R,2R,4S)-7-(4-methoxybenzyl)-7-azabicyclo[2.2.1]heptan-2-yl)-1-(4-methylpyrimidin-2-yl)indoline-5-carboxamide (0.04 g, 0.079 mmol) and $K_2CO_3$ (0.025 g, 0.183 mmol) in 1,4-dioxane (0.36 ml) followed by cyanogen bromide solution, 5.0 m in acetonitrile (0.032 ml, 0.159 mmol). The heterogeneous mixture was stirred at rt for 1 h. LC/MS showed full conversion to the desired product. The reaction mixture was quenched with sat. $NaHCO_3$ aq. and extracted with DCM. The organic extract was concentrated and purified under reverse phase column with 0.1% NH4OH in ACN and water as mobile phase to yield 20 mg of desired product. m/z: 409.0 [M+1]. $^1$H NMR (600 MHz, DMSO-$d_6$) δ 8.64 (br d, J=5.60 Hz, 1H), 8.50 (d, J=4.98 Hz, 1H), 8.41 (s, 1H), 7.31 (s, 1H), 6.88 (d, J=4.98 Hz, 1H), 4.21-4.26 (m, 4H), 4.09-4.19 (m, 1H), 3.20 (br s, 1H), 3.16 (t, J=8.68 Hz, 2H), 2.44 (s, 3H), 2.15-2.24 (m, 1H), 1.99 (ddd, J=4.17, 8.99, 12.85 Hz, 1H), 1.75-1.86 (m, 1H), 1.66-1.74 (m, 1H), 1.56-1.65 (m, 1H), 1.40 (dd, J=4.01, 12.81 Hz, 1H)

Method 16

Example 16-1: 5-(3-chlorophenyl)-N-((1R,2R,4S)-7-cyano-7-azabicyclo[2.2.1]heptan-2-yl)thiazole-2-carboxamide

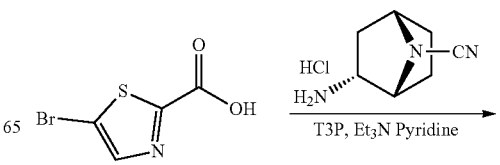

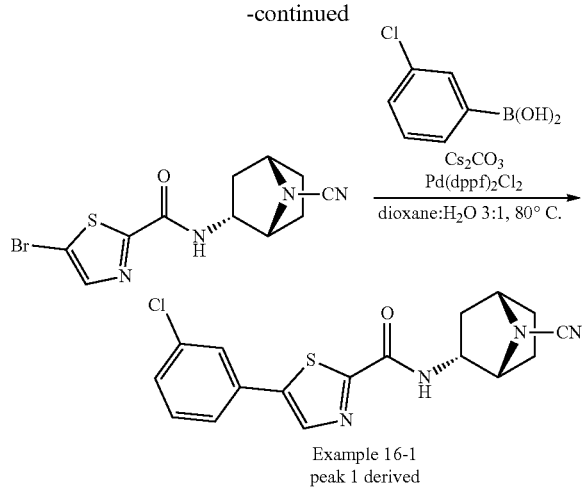

Example 16-1
peak 1 derived

Step 1

Performed as in Method 1, 5-bromo-N-((1R,2R,4S)-7-cyano-7-azabicyclo[2.2.1]heptan-2-yl)thiazole-2-carboxamide was obtained in 74% yield.

Step 2

To a 8 mL vial was added 5-bromo-N-((1R,2R,4S)-7-cyano-7-azabicyclo[2.2.1]heptan-2-yl)thiazole-2-carboxamide (21 mg, 0.064 mmol), 3-chlorophenylboronic acid (15.05 mg, 0.096 mmol), (1,1'-bis(diphenylphosphino)ferrocene) dichloropalladium (4.70 mg, 6.42 µmol) and cesium carbonate (62.7 mg, 0.193 mmol). 1,4-dioxane (160 µl) and water (53.5 µl) was then added and the solution was sparged with Ar for 1 min before sealed and heated to 80° C. LC-MS at 1 h showed completion of the reaction to the desired product. Water (1 mL) was added and the aqueous layer was extracted with DCM (5 mL×3). The organic extracts were combined and concentrated under vacuum. The yellow residue was applied to silica column chromatography (4 g Biotage column, eluting with a gradient of 0%-80% EA in Heptane) to afford 5-(3-chlorophenyl)-N-((1R,2R,4S)-7-cyano-7-azabicyclo[2.2.1]heptan-2-yl)thiazole-2-carboxamide (16.0 mg, 0.045 mmol, 70% yield) as an off-white solid. m/z: 359.0 [M+1] $^1$H NMR (500 MHz, CHLOROFORM-d) δ 8.00-8.02 (m, 1H), 7.61 (td, J=1.17, 1.82 Hz, 1H), 7.45-7.53 (m, 1H), 7.38-7.43 (m, 2H), 7.23-7.28 (m, 1H), 4.51-4.57 (m, 1H), 4.41-4.45 (m, 1H), 4.14 (t, J=5.13 Hz, 1H), 2.57 (dddd, J=2.98, 5.16, 11.13, 13.04 Hz, 1H), 2.07-2.16 (m, 1H), 1.94-2.02 (m, 2H), 1.66-1.72 (m, 1H), 1.24-1.31 (m, 1H).

Method 17

Example 17-1: 7-chloro-N-((1R,2R,4S)-7-cyano-7-azabicyclo[2.2.1]heptan-2-yl)-2,3-dihydrobenzo[f][1,4]oxazepine-4(5H)-carboxamide

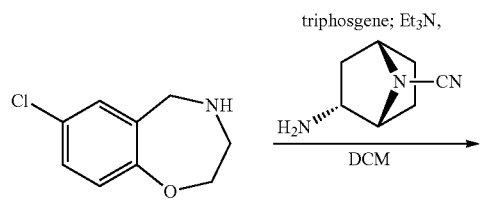

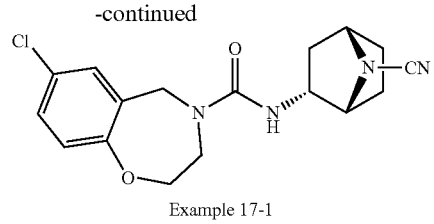

Example 17-1

Triphosgene (0.145 g, 0.490 mmol, aldrich) was dissolved in DCM and treated with 3 drops of DMF. 7-chloro-2,3,4,5-tetrahydrobenzo[f][1,4]oxazepine (0.15 g, 0.817 mmol, enamine) was added and the reaction was stirred at r.t. for 2 hours before being concentrated. The crude chloro-formamide was dissolved in DCM and Intermediate A (0.142 g, 0.817 mmol) was added followed by triethylamine. After 1 hour complete conversion was observed and the reaction was diluted with water and extracted with EtOAc 3×. The combined organics were combined, dried over Na2SO4, filtered, concentrated and purified via mass-directed reverse phase purification to provide 17-1 as a white solid (0.103 g, 36% yield). m/z: 347.0 [M+1] $^1$H NMR (DMSO-d6) δ: 7.41 (d, J=2.4 Hz, 1H), 7.22 (dd, J=8.5, 2.6 Hz, 1H), 6.98 (d, J=8.6 Hz, 1H), 6.56 (br d, J=5.1 Hz, 1H), 4.54 (d, J=15.7 Hz, 1H), 4.46 (d, J=15.7 Hz, 1H), 4.03-4.11 (m, 2H), 3.89-4.03 (m, 3H), 3.76-3.84 (m, 1H), 3.61-3.69 (m, 1H), 2.04-2.12 (m, 1H), 1.69-1.78 (m, 1H), 1.52-1.61 (m, 2H), 1.45-1.52 (m, 1H), 1.36 (dd, J=12.6, 4.7 Hz, 1H)

Method 18

Example 18-1: 7-chloro-N-((1R,2R,4S)-7-cyano-7-azabicyclo[2.2.1]heptan-2-yl)-1,2,3,5-tetrahydro-4H-benzo[c][1,4]diazepine-4-carboxamide

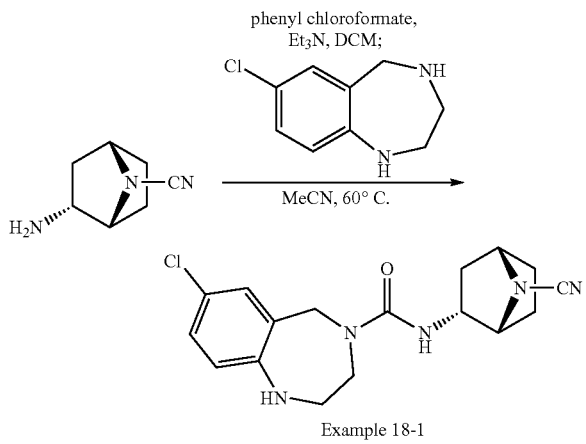

Example 18-1

Intermediate A (0.2 g, 1.152 mmol) was dissolved in DCM and treated with phenyl chloroformate (0.180 g, 0.144 ml, 1.152 mmol) at rt for 2 hours before being quenched with water. The reaction was diluted with EtOAc, the organics were separated and the aq. layer was re-extracted 2× with EtOAc. The combined organics were washed with brine, dried over Na2SO4, filtered and concentrated. The crude was dissolved in acetonitrile and 7-chloro-2,3,4,5-tetrahydro-1H-benzo[e][1,4]diazepine (0.210 g, 1.152 mmol, combi-blocks) was added followed by pyridine and the reaction was allowed to stir for 12 hrs when a mixture of phenol-carbamate of both amines was observed along with benzodiazepine starting material and product. The reaction was heated to 65° C. for 4 hours, concentrated and purified via mass-directed, reverse phase purification to provide 18-1 in low yield (0.004 g, 1% yield). m/z: 346.0 [M+1] $^1$H NMR (DMSO-d6) δ: 7.25 (br s, 1H), 7.03 (dd, J=8.5, 1.7 Hz, 1H), 6.80 (d, J=8.1 Hz, 1H), 6.40 (br d, J=5.2 Hz, 1H), 5.71 (br s, 1H), 4.41 (d, J=15.6 Hz, 1H), 4.32 (d, J=15.6 Hz, 1H), 4.03-4.08 (m, 1H), 4.01 (t, J=4.5 Hz, 1H), 3.94 (br dd, J=10.5, 4.8 Hz, 1H), 3.61 (td, J=6.7, 4.2 Hz, 1H), 3.39-3.48 (m, 1H), 3.04-3.11 (m, 1H), 2.97-3.04 (m, 1H), 2.05-2.12 (m, 1H), 1.70-1.77 (m, 1H), 1.59-1.66 (m, 1H), 1.52-1.58 (m, 1H), 1.46-1.52 (m, 1H), 1.37 (dd, J=12.6, 4.6 Hz, 1H)

Method 19

Example 19-1: 1-(6-acctamidopyridin-2-yl)-6-chloro-N-((1R,2R,4S)-7-cyano-7-azabicyclo[2.2.1]heptan-2-yl)-1H-indazole-5-carboxamide

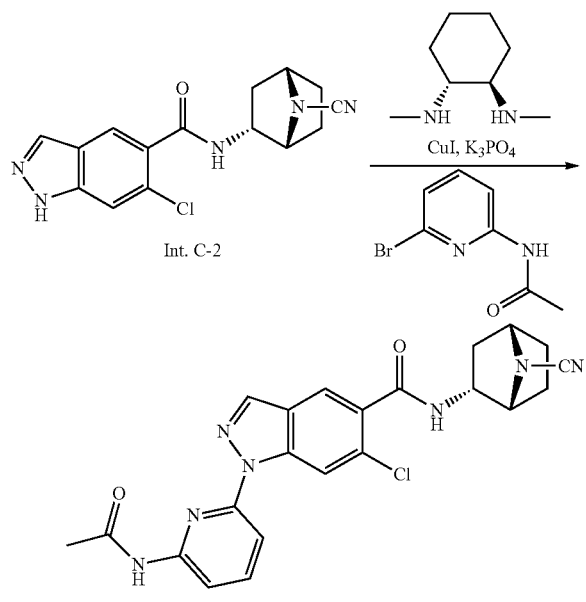

Example 19-1

A glass microwave reaction vessel was charged with 2-(acetylamino)-3-bromopyridine (0.082 g, 0.380 mmol, Combi-Blocks Inc.), Intermediate C-2 (0.06 g, 0.190 mmol), copper(i) iodide (14 mg, 0.08 mmol, Sigma-Aldrich Corporation) and trans-n,n'-dimethylcyclohexane-1,2-diamine (10.81 mg, 0.012 ml, 0.076 mmol, Sigma-Aldrich Corporation) in 1,4-dioxane (0.950 ml). The reaction mixture was stirred and irradiated in a Biotage microwave reactor at a set temperature of 130° C. for 5 min when LC/MS showed nearly full conversion to desired product. The crude material was absorbed onto a plug of silica gel and purified by chromatography via a 10 g biotage column ultra (gradient of 10% to 25% to 40% [3:1 EtOAc:EtOH]/Heptane with 0.5% Et3N) to provide 20 mg of impure material which was further purified by RP-HPLC (PREP LC/MS-2 System Column: XBridge Shield RP18 19×100 mm 10 um Mobile phase: 0.1% NH40H in water/acetonitrile Flow rate: 40 ml/min Gradient: 10 min 20-50%) to provide 19-1. m/z: 450.0 [M+1]. $^1$H NMR (DMSO-d6) δ:10.68-10.74 (m, 1H), 9.14 (s, 1H), 8.82-8.87 (m, 1H), 8.53 (s, 1H), 8.02 (s, 1H), 7.93-8.00 (m, 2H), 7.67-7.71 (m, 1H), 4.26-4.33 (m, 2H), 4.17 (t, J=4.8 Hz, 1H), 2.11-2.36 (m, 4H), 2.00-2.10 (m, 1H), 1.80-1.87 (m, 1H), 1.70-1.79 (m, 1H), 1.61 (ddd, J=12.1, 8.9, 3.6 Hz, 1H), 1.41 (dd, J=12.7, 4.0 Hz, 1H)

Method 20

Example 20-1: N-((1R,2R,4S)-7-cyano-7-azabicyclo[2.2.1]heptan-2-yl)-7-(4-methylpyrimidin-2-yl)-1H-indole-3-carboxamide

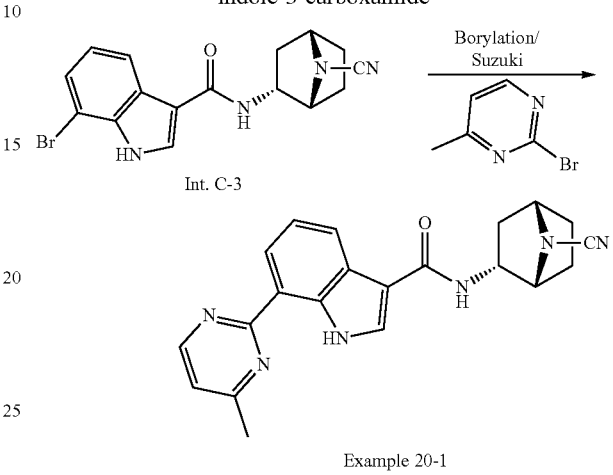

Example 20-1

Intermediate C-3 (0.1 g, 0.28 mmol) was treated with borylation and Suzuki reaction conditions used for the synthesis of Intermediate K and purified via RP-HPLC (PREP LC/MS-2 System Column: XBridge Shield RP18 19×100 mm 10 um Mobile phase: 0.1% NH40H in water/acetonitrile Flow rate: 40 ml/min Gradient: 10 min 20-50%) to provide 20-1 as a white solid (0.006 g, 5% yield). m/z: 373.0 [M+1] $^1$H NMR (DMSO-d6) δ: 8.83 (d, J=5.1 Hz, 1H), 8.35 (br t, J=6.6 Hz, 2H), 8.23 (br d, J=2.8 Hz, 1H), 8.14-8.21 (m, 111), 7.34 (d, J=5.0 Hz, 1H), 7.28 (t, J=7.7 Hz, 1H), 4.31-4.40 (m, 111), 4.27 (s, 1H), 4.16 (s, 1H), 4.03-4.12 (m, 111), 2.65 (s, 3H), 2.17-2.30 (m, 1H), 1.90-2.00 (m, 111), 1.78-1.88 (m, 111), 1.70 (br s, 2H), 1.53 (br dd, J=12.7, 4.7 Hz, 11H)

Method 21

Example 21-1-1-21-1-4

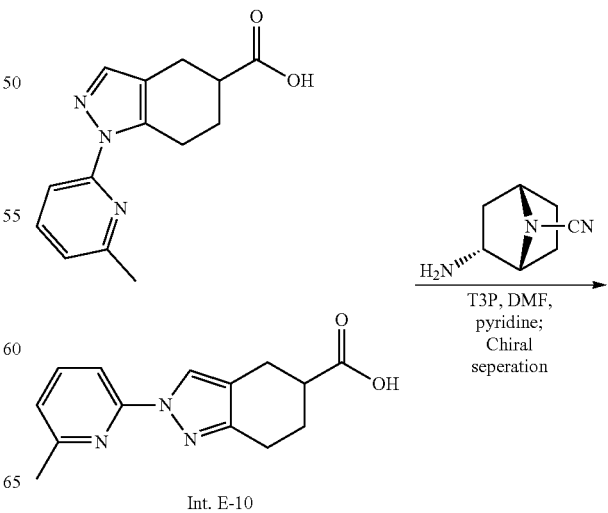

Int. E-10

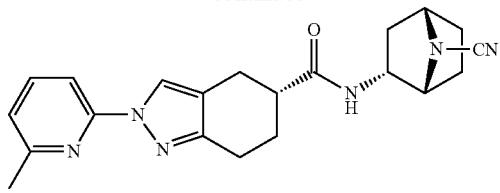

Example JB-21-1-1

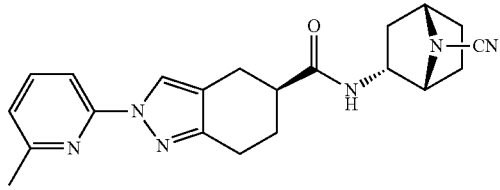

Example JB-21-1-2

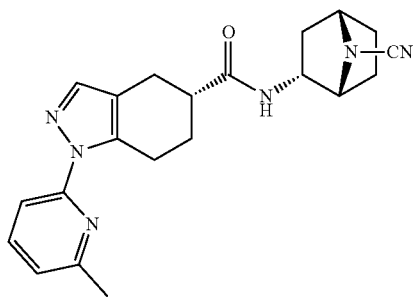

Example JB-21-1-3

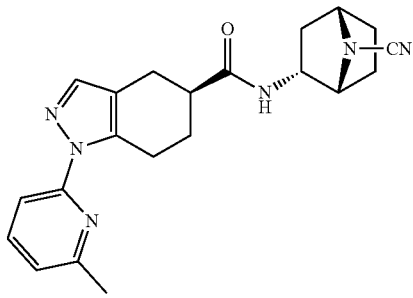

Example JB-21-1-4

Intermediate E-10 (0.15 g, 0.58 mmol) was treated with amidation conditions described in Method 1. The sample was purified by SFC using a Chiralpak AD-H 2×15 cm, 5um column, a mobile phase of 50% methanol using a flowrate of 80 mL/min. to generate 12 mg of peak 1 and 2 and 23 mg of peak 3 with an ee of >99% and 19 mg of peak 4 with an ee of >99%. Peak 1 and 2 was purified by SFC using a Chiralpak AD-H 2×25 cm 5 um column, a mobile phase of 30% methanol using a flowrate of 80 mL/min to generate 3 mg of peak 1 with an ee of >99% and 1 mg of peak 2 with an ee of >98%. Peak assignment determined by SFC: Chiralpak AD-H, 30% and 50% methanol and stereochemistry was arbitrarily assigned. m/z: 377.0 [M+1] $^1$H NMR: see analytical data table.

Method 22

Example 22-1: N-((1R,2R,4S)-7-cyano-7-azabicyclo[2.2.1]heptan-2-yl)-1-(6-methyl-2-pyridinyl)-7-(trifluoromethyl)-1H-indazole-5-carboxamide

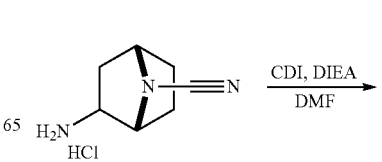

Methyl 7-(trifluoromethyl)-1H-indazole-5-carboxylate (0.08 g, 0.328 mmol, synnovator) was treated with conditions described in Method 19 to obtain methyl 1-(6-methylpyridin-2-yl)-7-(trifluoromethyl)-1H-indazole-5-carboxylate (0.1 g, 91% yield) after silica gel chromatography (10 g biotage ultra column, 10%-60% [EtOAc/EtOH (3/1)]: Heptane. This material was treated with conditions described in method 13 to obtain the final compound. m/z: 441.0 [M+1]. $^1$H NMR (DMSO-d6) δ: 9.61 (s, 1H), 8.85 (d, J=5.8 Hz, 1H), 8.74 (s, 1H), 8.19 (s, 1H), 8.01-8.08 (m, 2H), 7.46 (d, J=7.3 Hz, 1H), 4.31-4.36 (m, 1H), 4.29 (t, J=4.4 Hz, 1H), 4.19 (t, J=4.9 Hz, 1H), 2.62 (s, 3H), 2.21-2.30 (m, 11H), 1.89-1.96 (m, 1H), 1.80-1.89 (m, 1H), 1.66-1.76 (m, 2H), 1.59 (dd, J=12.7, 4.6 Hz, 1H)

Method 23

Example 23-1: 1-((1R,2R,4S)-7-Cyano-7-azabicyclo[2.2.1]heptan-2-yl)-3-(2,5-dichlorophenethyl)urea

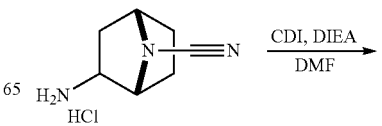

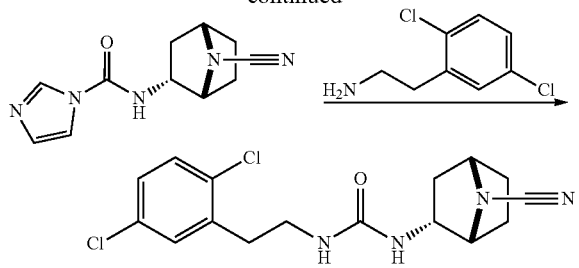

The mixture of Intermediate A (8.1 mg, 0.047 mmol), CDI (11 mg, 0.068 mmol), DIEA (0.030 mL, 0.17 mmol) DMF (0.3 mL) was stirred at room temperature for 30 min. After adding 2-(2,5-dichlorophenyl)ethan-1-amine (19 mg, 0.10 mmol) at room temperature, the mixture was stirred for 16 h and purified by preparative HPLC (0.1% AcOH) to afford the desired product (15 mg, 90%) as a white solid after lyophilization. MS (EI) for $C_{16}H_{18}C_2N_4O$, found 353.3 [M+1].

Method 24

Example 24-1: N1-(((3R,5R,7R)-Adamantan-1-yl)methyl)-N2-((1R,2R,4S)-7-cyano-7-azabicyclo[2.2.1]heptan-2-yl)-N1-(2-hydroxyethyl)oxalamide

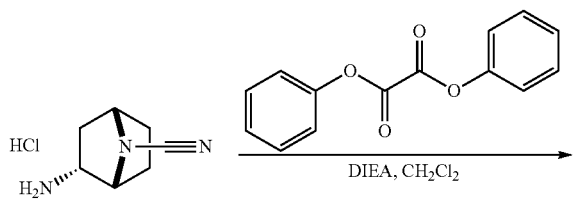

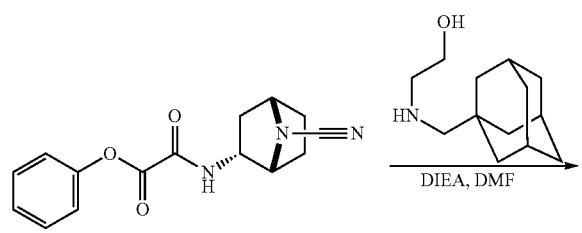

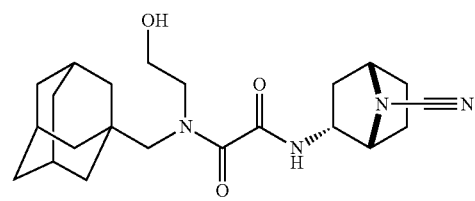

To a stirred solution of Intermediate A (9.0 mg, 0.052 mmol), diphenyl oxalate (15 mg, 0.062 mmol) and dichloromethane (0.5 mL) was added DIEA (0.030 mL, 0.17 mmol) at room temperature. After stirring for 1 h, the resulting mixture was concentrated and brought up in DMF (0.5 mL). After adding 2-((((3r,5r,7r)-adamantan-1-yl)methyl)amino)ethan-1-ol (HCl salt, 27 mg, 0.11 mmol) and DIPEA (0.030 mL, 0.17 mmol) at room temperature, the mixture was stirred for 3 h and purified by preparative HPLC (0.1% AcOH) to afford the desired product (13 mg, 62%) as a white solid after lyophilization. MS (ESI)=401.3 [M+1].

Method 25

Example 25-1: 2-chloro-N-((1R,2R,4S)-7-cyano-7-azabicyclo[2.2.1]heptan-2-yl)-4-(4-ethyl-1H-pyrazol-1-yl)benzamide

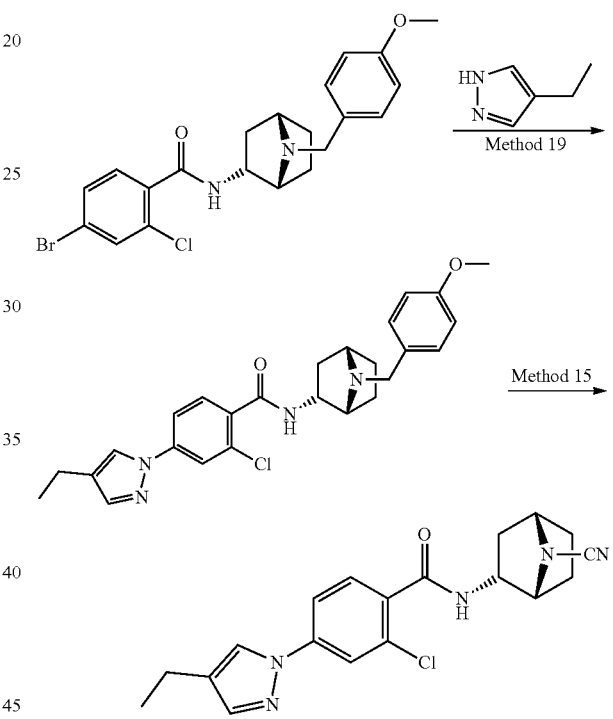

4-bromo-2-chloro-N-((1R,2R,4S)-7-(4-methoxybenzyl)-7-azabicyclo[2.2.1]heptan-2-yl)benzamide (0.100 g, 0.222 mmol) was treated with conditions described in Method 19 to obtain 2-chloro-4-(4-ethyl-1H-pyrazol-1-yl)-N-((1R,2R,4S)-7-(4-methoxybenzyl)-7-azabicyclo[2.2.1]heptan-2-yl)benzamide after silica gel chromatography (10 g biotage ultra column, 10%-50% [EtOAc/Heptane]. This material was treated with conditions of method 15 to obtain the final compound. m/z: 410.0 [M+1]. $^1$H NMR (500 MHz, CHLOROFORM-d) δ ppm 0.90 (t, J=6.94 Hz, 4H) 1.18 (dd, J=12.98, 4.41 Hz, 5H) 1.25-1.34 (m, 9H) 1.60-1.66 (m, 5H) 1.96-2.15 (m, 15H) 2.55-2.61 (m, 5H) 4.11-4.14 (m, 5H) 4.49-4.52 (m, 4H) 4.53-4.59 (m, 5H) 4.89 (q, J=8.56 Hz, 9H) 6.53 (br d, J=5.71 Hz, 4H) 6.92 (d, J=8.30 Hz, 4H) 7.27 (s, 1H) 7.46 (d, J=7.53 Hz, 5H) 7.77 (t, J=7.85 Hz, 5H) 7.86 (d, J=8.17 Hz, 4H) 7.96 (dd, J=8.17, 1.69 Hz, 4H) 8.06 (d, J=1.69 Hz, 4H).

Method 26

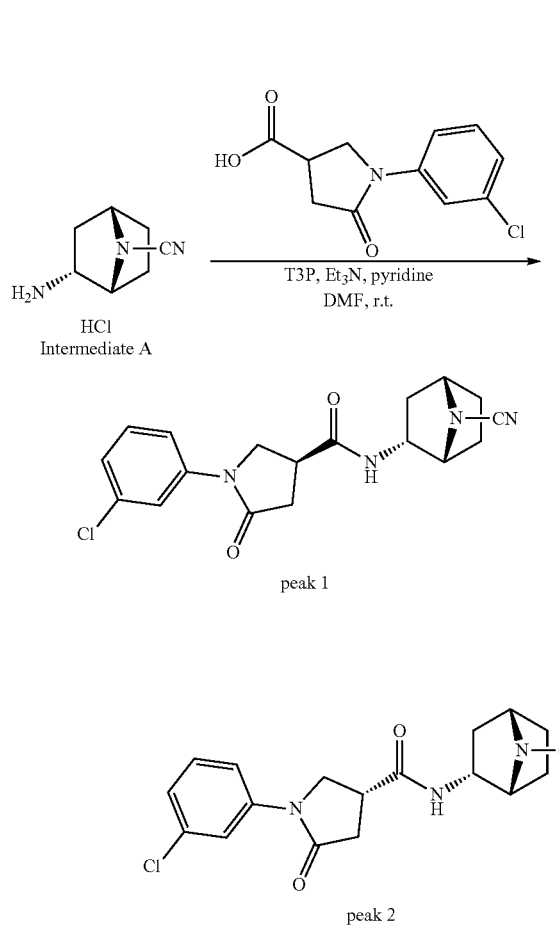

peak 1 peak 2

The synthesis was performed with Method 1, 1-(3-chlorophenyl)-N-((1R,2R,4S)-7-cyano-7-azabicyclo[2.2.1]heptan-2-yl)-5-oxopyrrolidine-3-carboxamide was obtained in 70% yield.

The chiral separation was performed as follows: The sample was purified by SFC Chiralpak AD-H 2×15 cm 5 mic column, a mobile phase of 40% methanol using a flowrate of 80 mL/min. to generate 19.71 mg of Enantiomer 1 peak 1 with an ee >99% and Enantiomer 2 17.52 mg of peak 2 with an ee >99%. Peak assignment determined by SFC: Chiralpak AD-H analytical column. 40% methanol and stereochemistry was arbitrarily assigned.

Method 27

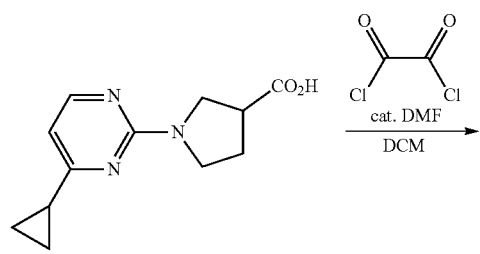

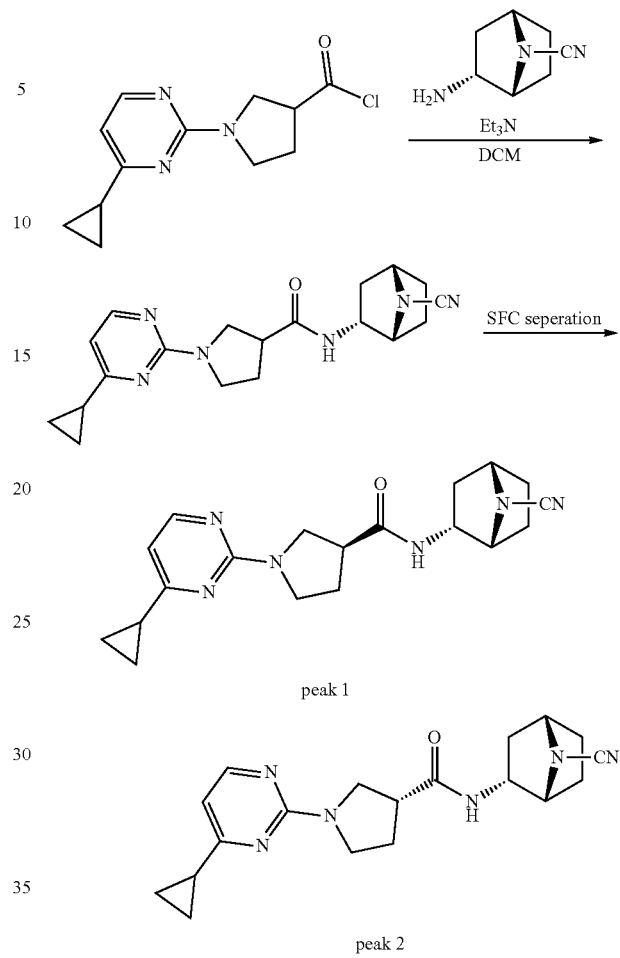

peak 1 peak 2

The synthesis was performed with Method 13. N-((1R,2R,4S)-7-cyano-7-azabicyclo[2.2.1]heptan-2-yl)-1-(4-cyclopropylpyrimidin-2-yl)pyrrolidine-3-carboxamide was obtained in 54% yield (45 mg).

The chiral separation was performed as followed. The sample was purified by SFC using a Chiralpak AD-H 2×25 cm, 5um column, a mobile phase of 35% methanol using a flowrate of 80 mL/min. to generate 6.9 mg of peak 1 with an ee >99% and 7.89 mg of peak 2 with an ee >99%. Peak assignment determined by SFC: Chiralpak AD-H analytical column, 35% methanol and stereochemistry was arbitrarily assigned.

Method 28

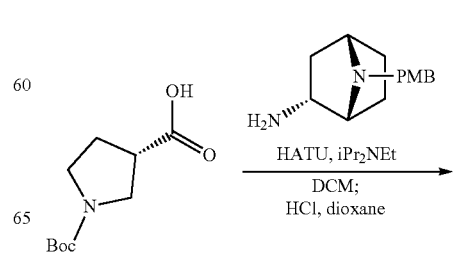

-continued

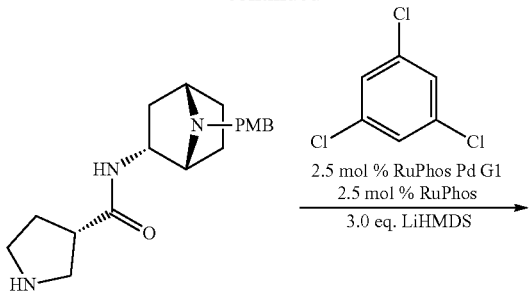

2.5 mol % RuPhos Pd G1
2.5 mol % RuPhos
3.0 eq. LiHMDS

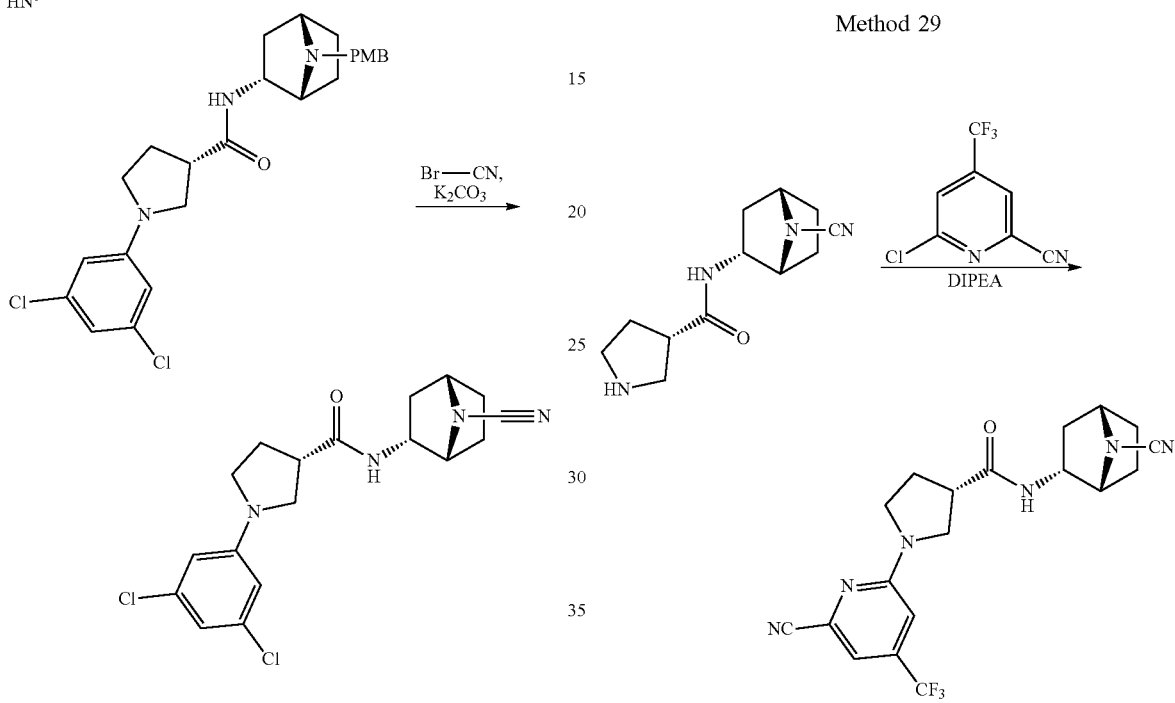

Step 1: To the solution of (S)-1-boc-pyrrolidine-3-carboxylic acid (215 mg, 1 mmol, Combi-Blocks) and hatu (418 mg, 1.100 mmol, Combi-Blocks Inc.) in N, N-dimethylformamide (2500 µl) was added n,n-diisopropylethylamine (646 mg, 5.00 mmol) dropwise at room temperature. The solution turned yellow. LS-MS at 1 h showed the completion of the reaction. The solution was poured into sat. NaHCO3 (10 mL) (lots of white precipitates) and extracted with EtOAc (30 mL×2). The organic extracts were combined and washed with water (20 mL×2), brine, dried over Na2SO4 and concentrated. To the crude mixture was added HCl in Dioxane (2.5 mL, 4N) and the mixture was stirred for 1 h. LC-MS showed the completion of the reaction. The solvent was removed, and the material was brought up in MeOH, passed through an SCX-2 column (5 g) washing with MeOH (3 CV). The column was washed with ammonia in MeOH to elute the pure amine product which was used directly in the C—N coupling step.

Step 2: To a 2 dram vial containing (S)—N-((1R,2R,4S)-7-(4-methoxybenzyl)-7-azabicyclo[2.2.1]heptan-2-yl)pyrrolidine-3-carboxamide (61.5 mg, 0.187 mmol, 125374-7-2) was added ruphos, 95% (2.178 mg, 4.67 µmol) and Ruphos Pd G1 (3.40 mg, 4.67 µmol). The mixture was degassed and filled with N2 three times before 1,1,1,3,3,3-hexamethyldisilazane lithium salt (560 µl, 0.560 mmol) in THF (1 M) was added, followed by 1,3,5-trichlorobenzene (102 mg, 0.560 mmol). The mixture was sonicated and heated at 70° C. LC-MS after 1 h showed complete conversion to the product. The crude mixture was used directly in the following step.

Step 3: Water (8.41 mg, 8.41 µl, 0.467 mmol, Lab) was added dropwise to quench the reaction. potassium carbonate (77 mg, 0.560 mmol) was then added followed by cyanogen bromide solution, 5.0 m in acetonitrile (74.7 µl, 0.373 mmol). The mixture was then stirred at room temperature overnight. After the reaction, the mixture was quenched with water, extracted with DCM, concentrated and applied to a column (0%-80% EA in Heptane) to afford (S)—N-((1R, 2R,4S)-7-cyano-7-azabicyclo[2.2.1]heptan-2-yl)-1-(3,5-dichlorophenyl)pyrrolidine-3-carboxamide in 11% yield.

Method 29

A 2 dram vial containing (S)—N-((1R,2R,4S)-7-cyano-7-azabicyclo[2.2.1]heptan-2-yl)pyrrolidine-3-carboxamide hydrochloride (0.2 mmol) was added 6-chloro-4-(trifluoromethyl)picolinonitrile (62.0 mg, 0.300 mmol), acetonitrile (667 µl) and DIPEA (140 µl, 0.800 mmol). The suspension was stirred at 60° C. for 2 h when LC-MS showed good conversion (80%). The reaction was purified via RP-HPLC with 0.1% NH4OH in ACN and water as mobile phase to afford (S)-1-(6-cyano-4-(trifluoromethyl)pyridin-2-yl)-N-((1R,2R,4S)-7-cyano-7-azabicyclo[2.2.1]heptan-2-yl)pyrrolidine-3-carboxamide in 41% yield.

Method 30

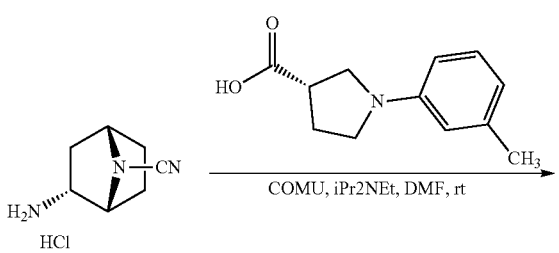

-continued

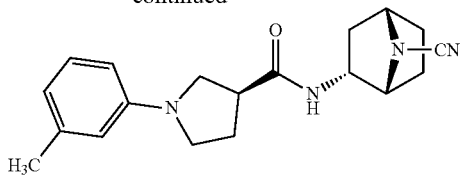

To a mixture of (S)-1-(m-tolyl)pyrrolidine-3-carboxylic acid (0.19 mmol) and n,n-diisopropylethylamine (98 mg, 133 μl, 0.759 mmol) in N, N-dimethylformamide (667 μl) was added COMU (89 mg, 0.209 mmol). Then (1R,2R,4S)-2-amino-7-azabicyclo[2.2.1]heptane-7-carbonitrile hydrochloride (65.9 mg, 0.190 mmol) was added. The mixture was stirred at room temperature. After 1 h, the reaction was complete. The mixture was poured into NaHCO₃ (sat), extracted with EA (30 mL×2) and the EA layers were combined, washed with water and brine, dried over Na2SO4 and concentrated. The residue was purified by silica gel chromatography (0%-75% EA in Heptane) to afford (S)—N-((1R,2R,4S)-7-cyano-7-azabicyclo[2.2.1]heptan-2-yl)-1-(m-tolyl)pyrrolidine-3-carboxamide in 29% yield.

Method 31

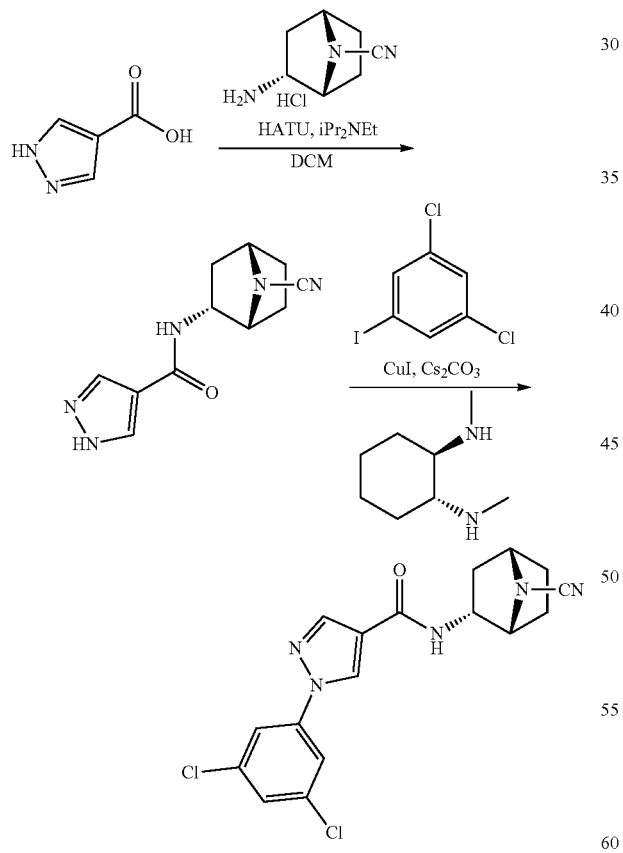

Step 1: To the 8 mL vial containing 1H-pyrazole-4-carboxylic acid (0.3 mmol) was added hatu (0.125 g, 0.330 mmol) and (1R,2R,4S)-2-amino-7-azabicyclo[2.2.1]heptane-7-carbonitrile hydrochloride (0.104 g, 0.300 mmol) in N, N-dimethylformamide (1.200 ml). Then DIPEA (0.155 g, 0.210 ml, 1.200 mmol) was added. The mixture was stirred at room temperature. After 2 h the compound was purified by RP-HPLC (5%-50% ACN in water+0.1% formic acid) to afford the product, which was used directly in the Cu catalyzed C—N coupling step.

Step 2: To a 2 dram vial was added N-((1R,2R,4S)-7-cyano-7-azabicyclo[2.2.1]heptan-2-yl)-1H-pyrazole-4-carboxamide (0.3 mmol), copper(i) iodide, (0.03 mmol), cesium carbonate (0.6 mmol), 3,5-dichloroiodobenzene (0.45 mmol), (1r,2r)-(–)-n,n''-dimethylcyclohexane-1,2-diamine (8.53 mg, 9.46 μl, 0.060 mmol) and DMF (600 μl). The mixture was stirred at 100° C. for 1 h, was purified directly via RP-HPLC with 0.1% NH4OH in ACN and water as mobile phase to afford N-((1R,2R,4S)-7-cyano-7-azabicyclo[2.2.1]heptan-2-yl)-1-(3,5-dichlorophenyl)-1H-pyrazole-4-carboxamide in 4% yield.

Method 32

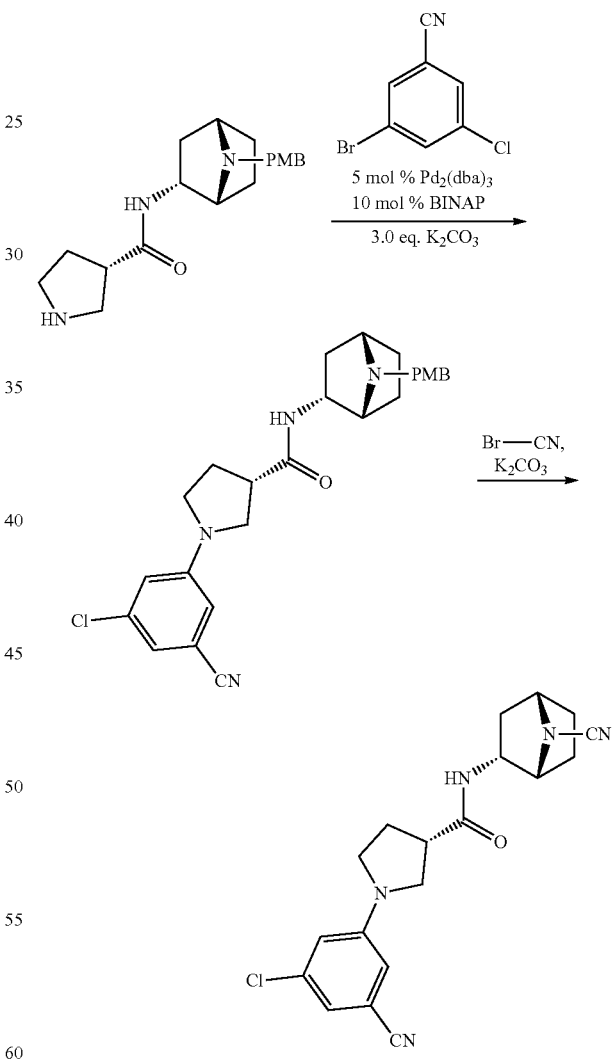

Step 1: To a 2 dram vial was added 3-bromo-5-chlorobenzonitrile (0.25 mmol), potassium carbonate (111 mg, 0.800 mmol), tris (dibenzylideneacetone) dipalladium (0) (0.013 mmol) and 2,2'-bis(diphenylphosphaneyl)-1,1'-binaphthalene (0.026 mmol). The vial was evacuated and back filled with N2 two times. Then (S)—N-((1R,2R,4S)-7-(4- methoxybenzyl)-7-azabicyclo[2.2.1]heptan-2-yl)pyrrolidine-3-carboxamide (500 μl, 0.25 mmol) in THF was added. The dark red solution was stirred at 70° C. for 20 h. LC-MS showed good conversion to the product.

Step 2: Cyanogen bromide solution, 5.0 m in acetonitrile (150 μl, 0.750 mmol) was directly added to the reaction mixture. The mixture was further stirred for 30 min. LC-MS showed full conversion to the cyanamide. The reaction was quenched with water and extracted with DCM (5 mL×3). The combined DCM layers were concentrated and the residue was purified by silica gel chromatography (0-100% EA in Heptane) to afford the product (S)-1-(3-chloro-5-cyanophenyl)-N-((1R,2R,4S)-7-cyano-7-azabicyclo[2.2.1]heptan-2-yl)pyrrolidine-3-carboxamide in 30% yield.

Method 33

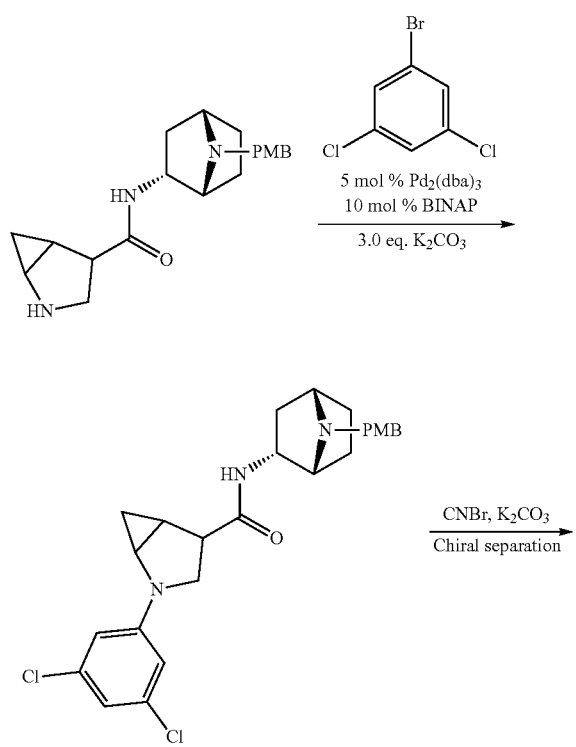

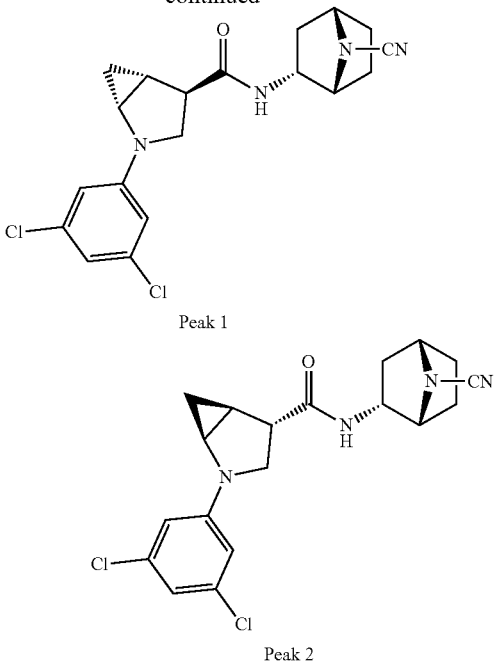

Peak 1

Peak 2

The synthesis followed the procedure in Method 23 followed by SFC purification Column: Zorbax Eclipse Plus C18 5 um 21.2×100 mm Mobile Phase: Solvent A=0.1% Formic Acid in 100% Water. Solvent B=Acetonitrile Gradient: Start % B=47.3 Final % B=67.3 Gradient. Time=7 min, then a 2 min hold at 98% B. Wavelength=215 and 254 nm. ESI+Range: 150 to 1500 dalton. Sample was loaded at 25% B. Flow Rate: 40.0 mL/min Sample: 500 mg of sample was dissolved in 4 mL DMSO Inj: 0.5 mL Peak 1, 8.2 mg Peak 2, 19.2 mg Step 2: Peak 2, the major diastereomer, was further separated into two enantiomers: Sample was purified via preparative SFC using a Chiral Technologies IC (250×21 mm, 5 mm) with a mobile phase of 75% Liquid CO2 and 75% MeCOH using a flowrate of 90 mL/min. to generate 7 mg of peak 1 with an ee of >99% and 4 mg of peak 2 with an ee of >99%. Peak assignment determined by SFC with IC column with 25% MeCOH and stereochemistry was arbitrarily assigned.

Table of Examples and Analytical Data

The compounds below were synthesized using the methods above and are classified using the numbering convention detailed in the synthetic example section.

| Ex # | Name[FB-L22] | Structure |
|---|---|---|
| 1-1 | N-((1R,2R,4S)-7-cyano-7-azabicyclo[2.2.1]heptan-2-yl)-2-(1H-pyrrol-1-yl)-1,3-benzothiazole-6-carboxamide | 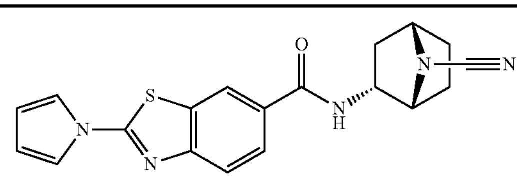 |
| 1-2 | racemic-endo 2-methyl-2-propanyl 7-(7-cyano-7-azabicyclo[2.2.1]heptan-2-yl)carbamoyl)-3,4-dihydro-2(1H)-isoquinolinecarboxylate | 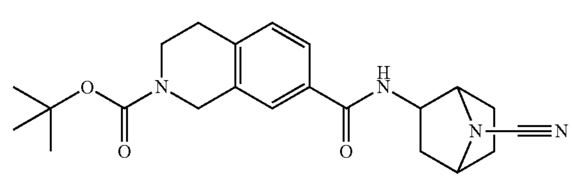 [SMILES: CC(C)(C)OC(=O)N1CCc2ccc(C(=O)NC3CC4CCC3N4C#N)cc2C1] |

| Ex # | Name[FB-L22] | Structure |
|---|---|---|
| 1-3 | racemic-endo 2-methyl-2-propanyl 6-(7-cyano-7-azabicyclo[2.2.1]heptan-2-yl)carbamoyl)-3,4-dihydro-2(1H)-isoquinolinecarboxylate | 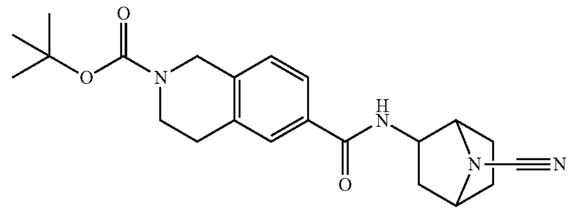 [SMILES: CC(C)(C)OC(=O)N1CCc2cc(C(=O)NC3CC4CCC3N4C#N)ccc2C1] |
| 1-4 | N-((1R,2R,4S)-7-cyano-7-azabicyclo[2.2.1]heptan-2-yl)-4-((4-cyclopropyl-2-pyrimidinyl)amino)-2,5-difluorobenzamide | 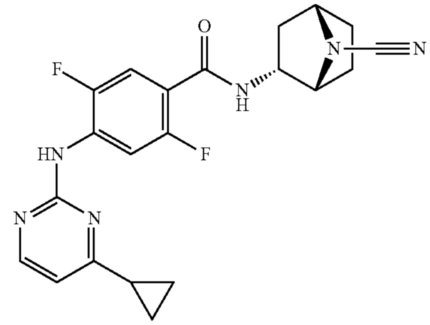 [SMILES: N#CN1[C@H]2CC[C@@H]1[C@H](NC(=O)c1cc(F)c(Nc3nccc(C4CC4)n3)cc1F)C2] |
| 1-5 | N-((1R,2R,4S)-7-cyano-7-azabicyclo[2.2.1]heptan-2-yl)-4-((4-cyclopropyl-2-pyrimidinyl)amino)-2,3-difluorobenzamide | 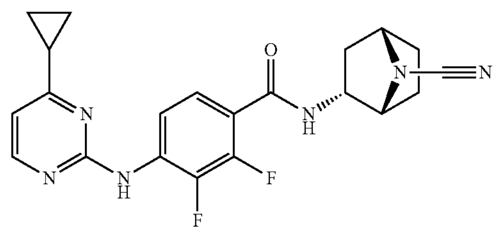 [SMILES: N#CN1[C@H]2CC[C@@H]1[C@H](NC(=O)c1ccc(Nc3nccc(C4CC4)n3)c(F)c1F)C2] |
| 1-6 | N-((1R,2R,4S)-7-cyano-7-azabicyclo[2.2.1]heptan-2-yl)-3-phenyl-1H-indazole-6-carboxamide | 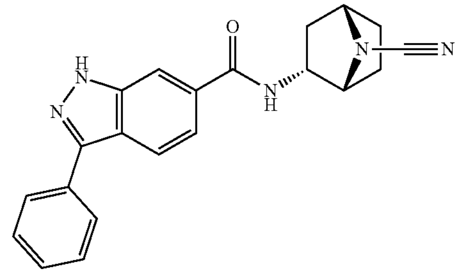 [SMILES: N#CN1[C@H]2CC[C@@H]1[C@H](NC(=O)c1ccc3c(-c4ccccc4)n[nH]c3c1)C2] |
| 1-7 | 2-methyl-2-propanyl (4-(((1R,2R,4S)-7-cyano-7-azabicyclo[2.2.1]heptan-2-yl)carbamoyl)-2-methylphenyl)carbamate | 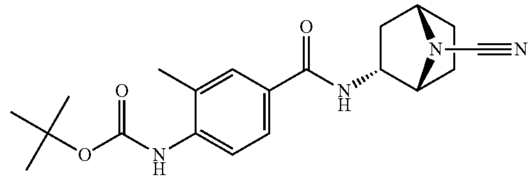 [SMILES: Cc1cc(C(=O)N[C@@H]2C[C@@H]3CC[C@H]2N3C#N)ccc1NC(=O)OC(C)(C)C] |
| 1-8 | N-((1R,2R,4S)-7-cyano-7-azabicyclo[2.2.1]heptan-2-yl)-1-(2,2-dimethylpropanoyl)-2,3-dihydro-1H-indole-5-carboxamide | 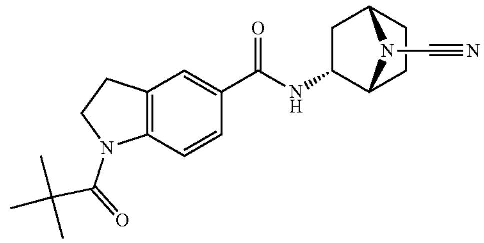 [SMILES: CC(C)(C)C(=O)N1CCc2cc(C(=O)N[C@@H]3C[C@@H]4CC[C@H]3N4C#N)ccc21] |

-continued

| Ex # | Name[FB-L22] | Structure |
|---|---|---|
| 1-9 | N-((1R,2R,4S)-7-cyano-7-azabicyclo[2.2.1]heptan-2-yl)-4-(1,3-thiazol-4-yl)benzamide | 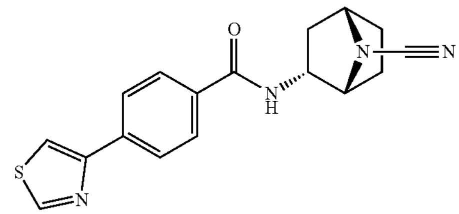 [SMILES: N#CN1[C@H]2CC[C@@H]1[C@H](NC(=O)c1ccc(-c3cscn3)cc1)C2] |
| 1-10 | 4-benzamido-N-((1R,2R,4S)-7-cyano-7-azabicyclo[2.2.1]heptan-2-yl)benzamide | 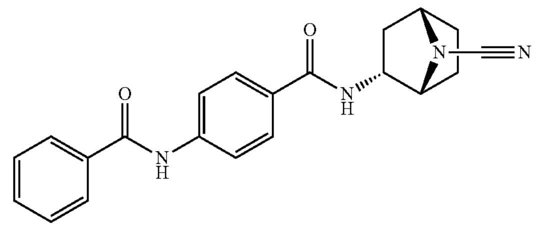 [SMILES: N#CN1[C@H]2CC[C@@H]1[C@H](NC(=O)c1ccc(NC(=O)c3ccccc3)cc1)C2] |
| 1-11 | N-(4-(((1R,2R,4S)-7-cyano-7-azabicyclo[2.2.1]heptan-2-yl)carbamoyl)phenyl)-2-pyridinecarboxamide | 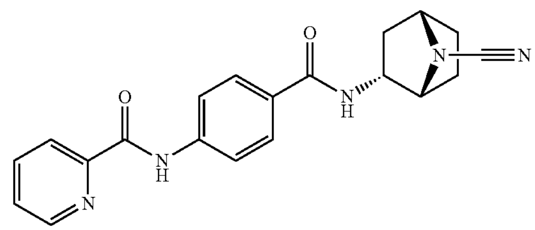 [SMILES: N#CN1[C@H]2CC[C@@H]1[C@H](NC(=O)c1ccc(NC(=O)c3ccccn3)cc1)C2] |
| 1-12 | N-((1R,2R,4S)-7-cyano-7-azabicyclo[2.2.1]heptan-2-yl)-4-(phenylethynyl)benzamide | 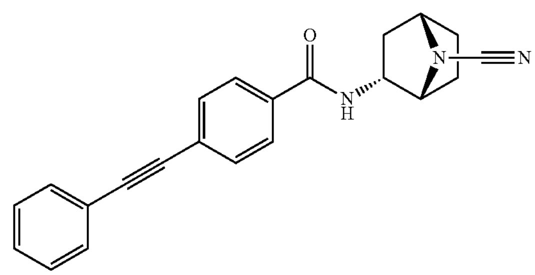 [SMILES: N#CN1[C@H]2CC[C@@H]1[C@H](NC(=O)c1ccc(C#Cc3ccccc3)cc1)C2] |
| 1-13 | 6-(1H-benzimidazol-1-yl)-N-((1R,2R,4S)-7-cyano-7-azabicyclo[2.2.1]heptan-2-yl)-3-pyridinecarboxamide | 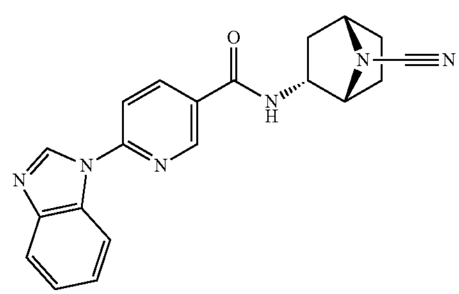 [SMILES: N#CN1[C@H]2CC[C@@H]1[C@H](NC(=O)c1ccc(-n3cnc4ccccc43)nc1)C2] |
| 1-14 | 4-((5-chloro-2-pyridinyl)oxy)-N-((1R,2R,4S)-7-cyano-7-azabicyclo[2.2.1]heptan-2-yl)benzamide | 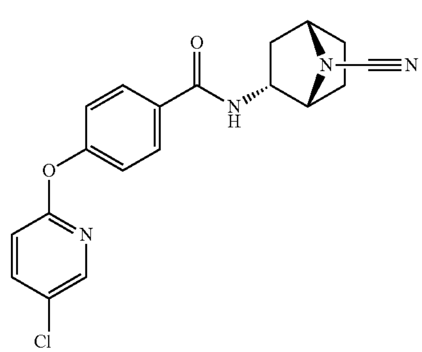 [SMILES: N#CN1[C@H]2CC[C@@H]1[C@H](NC(=O)c1ccc(Oc3ccc(Cl)cn3)cc1)C2] |

-continued

| Ex # | Name[FB-L22] | Structure |
|---|---|---|
| 1-15 | N-((1R,2R,4S)-7-cyano-7-azabicyclo[2.2.1]heptan-2-yl)-4-(3,5-dimethyl-1H-pyrazol-1-yl)-3-fluorobenzamide | 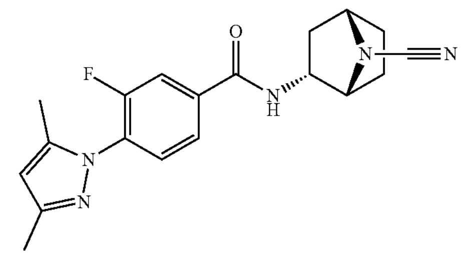 [SMILES: Cc1cc(C)n(-c2ccc(C(=O)N[C@@H]3C[C@@H]4CC[C@H]3N4C#N)cc2F)n1] |
| 1-16 | 2-chloro-N-((1R,2R,4S)-7-cyano-7-azabicyclo[2.2.1]heptan-2-yl)-4-(1,1-dioxido-1,2-thiazolidin-2-yl)benzamide | 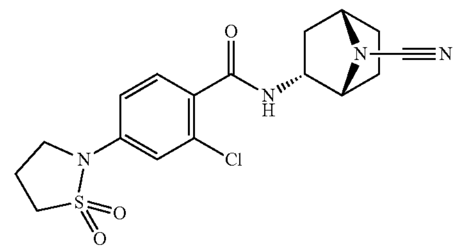 [SMILES: N#CN1[C@H]2CC[C@@H]1[C@H](NC(=O)c1ccc(N3CCCS3(=O)=O)cc1Cl)C2] |
| 1-17 | 2-methyl-2-propanyl (3-chloro-4-(((1R,2R,4S)-7-cyano-7-azabicyclo[2.2.1]heptan-2-yl)carbamoyl)phenyl)carbamate | 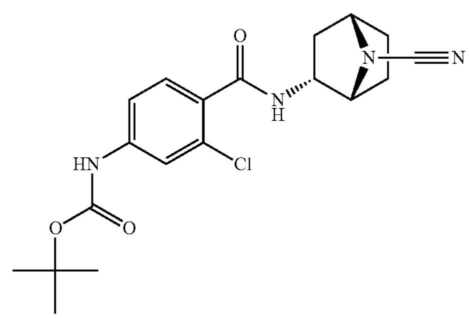 [SMILES: CC(C)(C)OC(=O)Nc1ccc(C(=O)N[C@@H]2C[C@@H]3CC[C@H]2N3C#N)c(Cl)c1] |
| 1-18 | N-((1R,2R,4S)-7-cyano-7-azabicyclo[2.2.1]heptan-2-yl)-3-methyl-4-(3-methylbutanamido)benzamide | 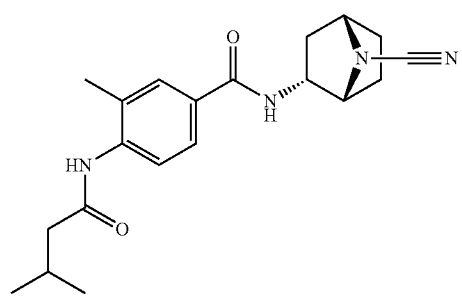 [SMILES: Cc1cc(C(=O)N[C@@H]2C[C@@H]3CC[C@H]2N3C#N)ccc1NC(=O)CC(C)C] |
| 1-19 | N-((1R,2R,4S)-7-cyano-7-azabicyclo[2.2.1]heptan-2-yl)-4-(4-methyl-1H-pyrazol-1-yl)benzamide | 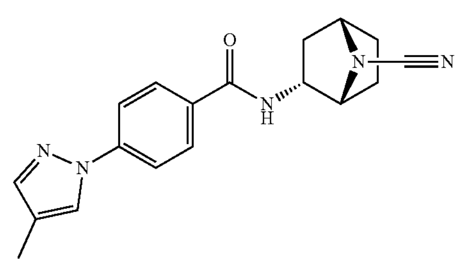 [SMILES: Cc1cnn(-c2ccc(C(=O)N[C@@H]3C[C@@H]4CC[C@H]3N4C#N)cc2)c1] |

-continued

| Ex # | Name[FB-L22] | Structure |
|---|---|---|
| 1-20 | 4-(1H-benzotriazol-1-yl)-N-((1R,2R,4S)-7-cyano-7-azabicyclo[2.2.1]heptan-2-yl)benzamide | 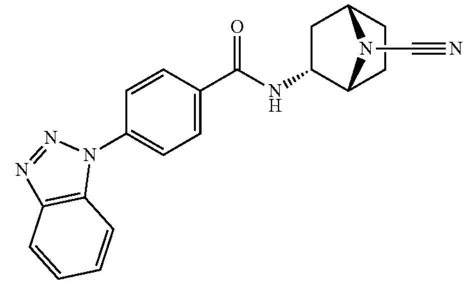 [SMILES: N#CN1[C@H]2CC[C@@H]1[C@H](NC(=O)c1ccc(-n3nnc4ccccc43)cc1)C2] |
| 1-21 | N-((1R,2R,4S)-7-cyano-7-azabicyclo[2.2.1]heptan-2-yl)-3-(4-pyridinyl)benzamide | 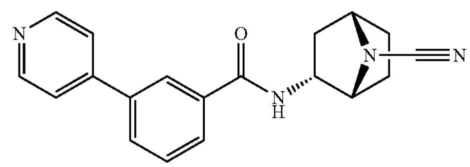 [SMILES: N#CN1[C@H]2CC[C@@H]1[C@H](NC(=O)c1cccc(-c3ccncc3)c1)C2] |
| 1-22 | N-((1R,2R,4S)-7-cyano-7-azabicyclo[2.2.1]heptan-2-yl)-6-(cyclopropylmethoxy)-3-pyridinecarboxamide | 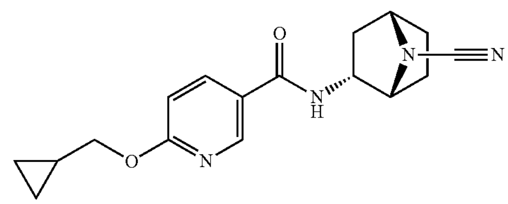 [SMILES: N#CN1[C@H]2CC[C@@H]1[C@H](NC(=O)c1ccc(OCC3CC3)nc1)C2] |
| 1-23 | 4-(3-chloro-2-pyridinyl)-N-((1R,2R,4S)-7-cyano-7-azabicyclo[2.2.1]heptan-2-yl)benzamide | 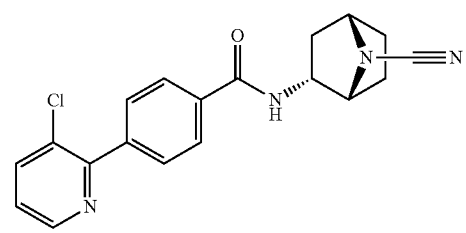 [SMILES: N#CN1[C@H]2CC[C@@H]1[C@H](NC(=O)c1ccc(-c3ncccc3Cl)cc1)C2] |
| 1-24 | N-((1R,2R,4S)-7-cyano-7-azabicyclo[2.2.1]heptan-2-yl)-4-(3-pyridinyl)benzamide | 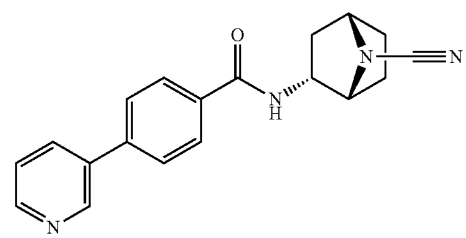 [SMILES: N#CN1[C@H]2CC[C@@H]1[C@H](NC(=O)c1ccc(-c3cccnc3)cc1)C2] |
| 1-25 | N-((1R,2R,4S)-7-cyano-7-azabicyclo[2.2.1]heptan-2-yl)-4-(3-methyl-1H-pyrazol-1-yl)benzamide | 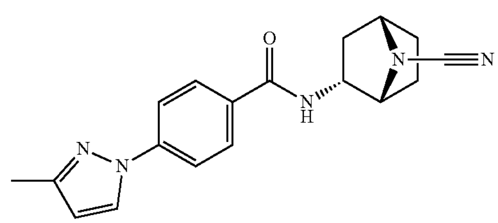 [SMILES: Cc1ccn(-c2ccc(C(=O)N[C@@H]3C[C@@H]4CC[C@H]3N4C#N)cc2)n1] |
| 1-26 | N-((1R,2R,4S)-7-cyano-7-azabicyclo[2.2.1]heptan-2-yl)-4-(4-(trifluoromethyl)-1H-pyrazol-1-yl)benzamide | 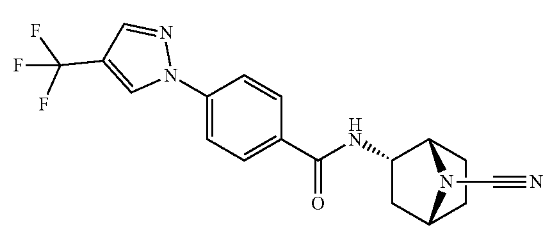 [SMILES: N#CN1[C@@H]2CC[C@H]1[C@@H](NC(=O)c1ccc(-n3cc(C(F)(F)F)cn3)cc1)C2] |

-continued

| Ex # | Name[FB-L22] | Structure |
|---|---|---|
| 1-27 | N-((1R,2R,4S)-7-cyano-7-azabicyclo[2.2.1]heptan-2-yl)-4-(3-methyl-1H-pyrazolo[3,4-b]pyridin-1-yl)benzamide | 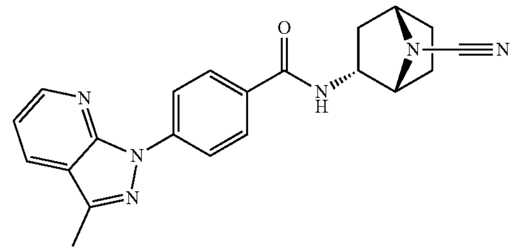 [SMILES: Cc1nn(-c2ccc(C(=O)N[C@@H]3C[C@@H]4CC[C@H]3N4C#N)cc2)c2ncccc12] |
| 1-28 | 2-chloro-N-((1R,2R,4S)-7-cyano-7-azabicyclo[2.2.1]heptan-2-yl)-4-(4-methyl-1H-pyrazol-1-yl)benzamide | 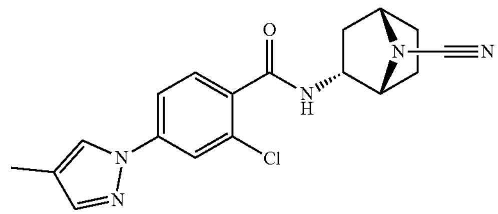 [SMILES: Cc1cnn(-c2ccc(C(=O)N[C@@H]3C[C@@H]4CC[C@H]3N4C#N)c(Cl)c2)c1] |
| 1-29 | N-((1R,2R,4S)-7-cyano-7-azabicyclo[2.2.1]heptan-2-yl)-2-fluoro-4-(4-methyl-1H-imidazol-1-yl)benzamide | 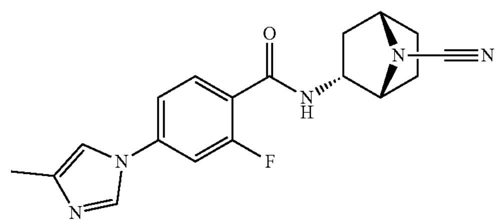 [SMILES: Cc1cn(-c2ccc(C(=O)N[C@@H]3C[C@@H]4CC[C@H]3N4C#N)c(F)c2)cn1] |
| 1-30 | N-((1R,2R,4S)-7-cyano-7-azabicyclo[2.2.1]heptan-2-yl)-2-methyl-4-(4-methyl-1H-pyrazol-1-yl)benzamide | 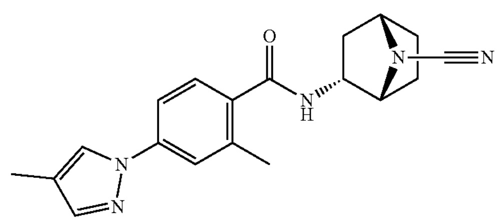 [SMILES: Cc1cnn(-c2ccc(C(=O)N[C@@H]3C[C@@H]4CC[C@H]3N4C#N)c(C)c2)c1] |
| 1-31 | N-((1R,2R,4S)-7-cyano-7-azabicyclo[2.2.1]heptan-2-yl)-3-fluoro-4-(4-methyl-1H-pyrazol-1-yl)benzamide | 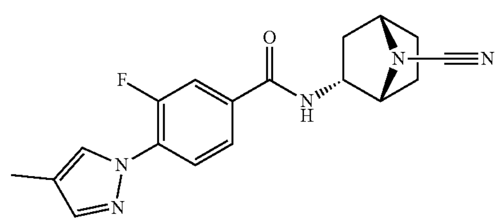 [SMILES: Cc1cnn(-c2ccc(C(=O)N[C@@H]3C[C@@H]4CC[C@H]3N4C#N)cc2F)c1] |
| 1-32 | racemic-endo N-(7-cyano-7-azabicyclo[2.2.1]heptan-2-yl)-5-(4-fluorophenyl)-2-pyridinecarboxamide | 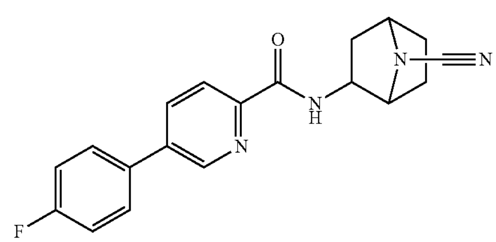 [SMILES: N#CN1C2CCC1C(NC(=O)c1ccc(-c3ccc(F)cc3)cn1)C2] |

-continued

| Ex # | Name[FB-L22] | Structure |
|---|---|---|
| 1-33 | racemic-endo 6-(4-chlorophenyl)-N-(7-cyano-7-azabicyclo[2.2.1]heptan-2-yl)-3-pyridinecarboxamide | 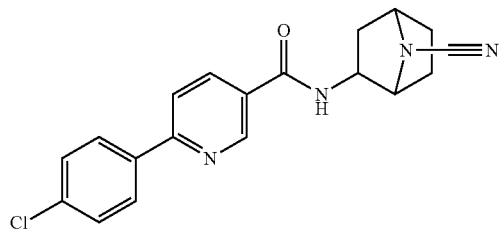 [SMILES: N#CN1C2CCC1C(NC(=O)c1ccc(-c3ccc(Cl)cc3)nc1)C2] |
| 1-34 | 6-(4-chlorophenyl)-N-((1R,2R,4S)-7-cyano-7-azabicyclo[2.2.1]heptan-2-yl)-3-pyridinecarboxamide | 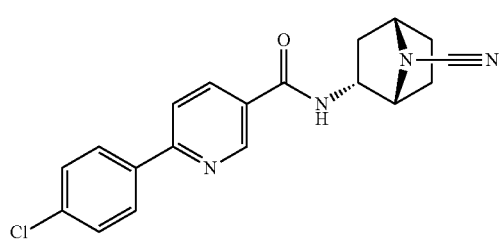 [SMILES: N#CN1[C@H]2CC[C@@H]1[C@H](NC(=O)c1ccc(-c3ccc(Cl)cc3)nc1)C2] |
| 1-35 | racemic-endo N-(7-cyano-7-azabicyclo[2.2.1]heptan-2-yl)-2-(3-methylanilino)-5-pyrimidinecarboxamide | 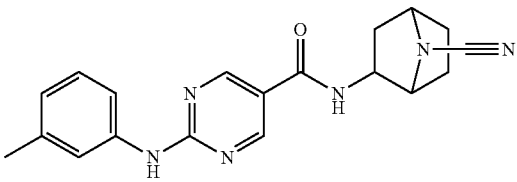 [SMILES: Cc1cccc(Nc2ncc(C(=O)NC3CC4CCC3N4C#N)cn2)c1] |
| 1-36 | N-((1R,2R,4S)-7-cyano-7-azabicyclo[2.2.1]heptan-2-yl)-1-(6-cyclopropyl-2-pyridinyl)-6-fluoro-1H-indazole-5-carboxamide | 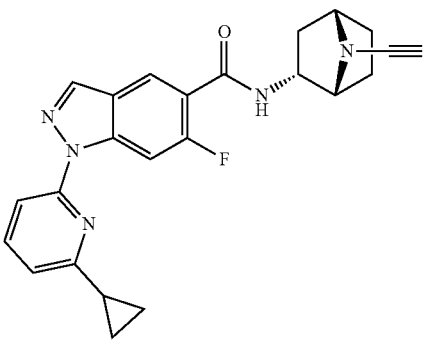 |
| 1-37 | N-((1R,2R,4S)-7-cyano-7-azabicyclo[2.2.1]heptan-2-yl)-1-(4-cyano-6-methyl-2-pyridinyl)-1H-indazole-5-carboxamide | 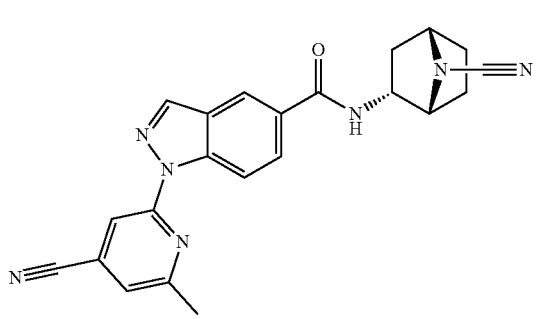 [SMILES: Cc1cc(C#N)cc(-n2ncc3cc(C(=O)N[C@@H]4C[C@@H]5CC[C@H]4N5C#N)ccc32)n1] |

| Ex # | Name[FB-L22] | Structure |
|---|---|---|
| 1-38 | N-((1R,2R,4S)-7-cyano-7-azabicyclo[2.2.1]heptan-2-yl)-1-(4-methyl-2-pyridinyl)-1H-pyrrolo[2,3-b]pyridine-5-carboxamide | 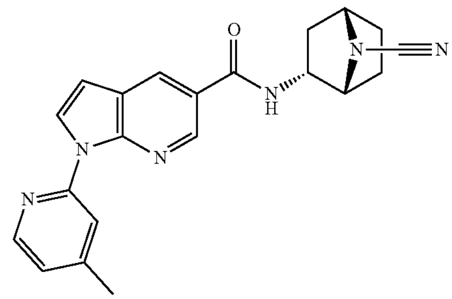 [SMILES: Cc1ccnc(-n2ccc3cc(C(=O)N[C@@H]4C[C@@H]5CC[C@H]4N5C#N)cnc32)c1] |
| 1-39 | N-((1R,2R,4S)-7-cyano-7-azabicyclo[2.2.1]heptan-2-yl)-1-(4-methyl-1,3-thiazol-2-yl)-1H-indazole-5-carboxamide | 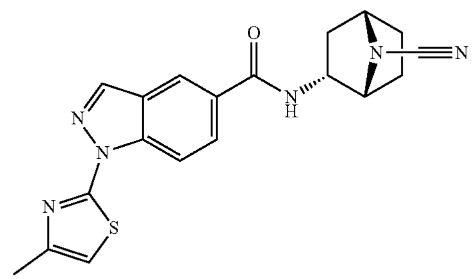 [SMILES: Cc1csc(-n2ncc3cc(C(=O)N[C@@H]4C[C@@H]5CC[C@H]4N5C#N)ccc32)n1] |
| 1-40 | Mixture of two diastereomers: (S)-N-(7-cyano-7-azabicyclo[2.2.1]heptan-2-yl)-1-(6-methyl-2-pyridinyl)-4,5,6,7-tetrahydro-1H-indazole-5-carboxamide and (R)-N-(7-cyano-7-azabicyclo[2.2.1]heptan-2-yl)-1-(6-methyl-2-pyridinyl)-4,5,6,7-tetrahydro-1H-indazole-5-carboxamide | and |
| 1-41 | N-((1R,2R,4S)-7-cyano-7-azabicyclo[2.2.1]heptan-2-yl)-3-(4-methyl-2-pyrimidinyl)-1H-indole-6-carboxamide | 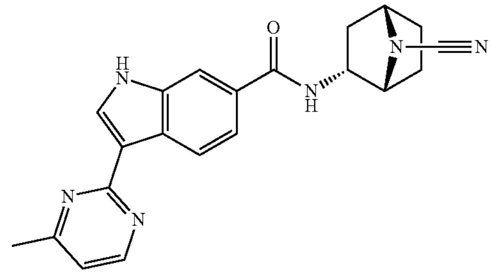 [SMILES: Cc1ccnc(-c2c[nH]c3cc(C(=O)N[C@@H]4C[C@@H]5CC[C@H]4N5C#N)ccc23)n1] |

-continued

| Ex # | Name[FB-L22] | Structure |
|---|---|---|
| 1-42 | N-((1R,2R,4S)-7-cyano-7-azabicyclo[2.2.1]heptan-2-yl)-6-methoxy-1-(4-methyl-2-pyrimidinyl)-1H-indole-5-carboxamide | 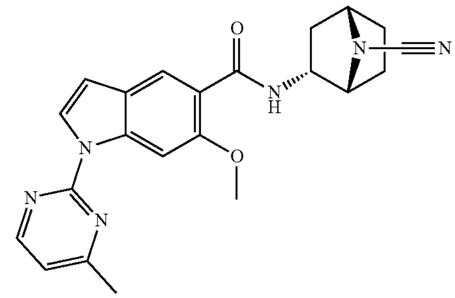 [SMILES: COc1cc2c(ccn2-c2nccc(C)n2)cc1C(=O)N[C@@H]1C[C@@H]2CC[C@H]1N2C#N] |
| 1-43 | N-((1R,2R,4S)-7-cyano-7-azabicyclo[2.2.1]heptan-2-yl)-1-methyl-3-(6-methyl-2-pyridinyl)-1H-indazole-6-carboxamide | 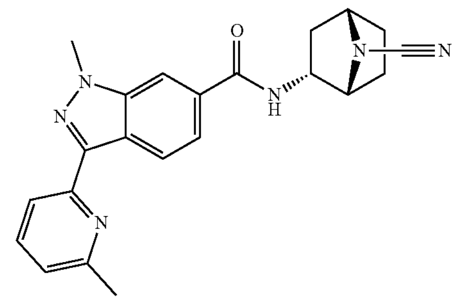 [SMILES: Cc1cccc(-c2nn(C)c3cc(C(=O)N[C@@H]4C[C@@H]5CC[C@H]4N5C#N)ccc23)n1] |
| 1-44 | N-((1R,2R,4S)-7-cyano-7-azabicyclo[2.2.1]heptan-2-yl)-1-methyl-3-(6-(trifluoromethyl)-2-pyridinyl)-1H-indazole-6-carboxamide | 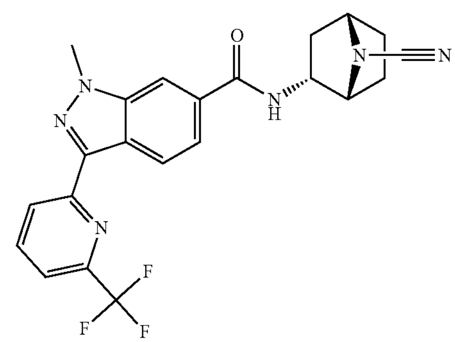 [SMILES: Cn1nc(-c2cccc(C(F)(F)F)n2)c2ccc(C(=O)N[C@@H]3C[C@@H]4CC[C@H]3N4C#N)cc21] |
| 1-45 | N-((1R,2R,4S)-7-cyano-7-azabicyclo[2.2.1]heptan-2-yl)-1-methyl-3-phenyl-1H-indazole-6-carboxamide | 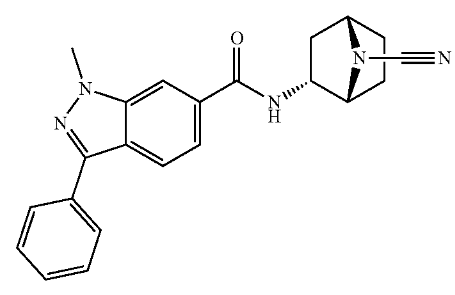 [SMILES: Cn1nc(-c2ccccc2)c2ccc(C(=O)N[C@@H]3C[C@@H]4CC[C@H]3N4C#N)cc21] |
| 1-46 | N-((1R,2R,4S)-7-cyano-7-azabicyclo[2.2.1]heptan-2-yl)-3-((3-fluorophenoxy)methyl)benzamide | 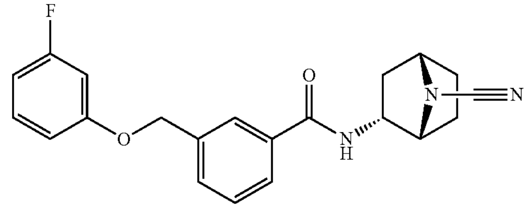 [SMILES: N#CN1[C@H]2CC[C@@H]1[C@H](NC(=O)c1cccc(COc3cccc(F)c3)c1)C2] |

-continued

| Ex # | Name[FB-L22] | Structure |
|---|---|---|
| 1-47 | N-((1R,2R,4S)-7-cyano-7-azabicyclo[2.2.1]heptan-2-yl)-4-(2-thiophenylmethoxy)benzamide | 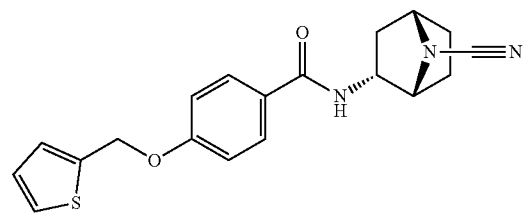 [SMILES: N#CN1[C@H]2CC[C@@H]1[C@H](NC(=O)c1ccc(OCc3cccs3)cc1)C2] |
| 1-48 | N-((1R,2R,4S)-7-cyano-7-azabicyclo[2.2.1]heptan-2-yl)-4-((2-methylphenyl)sulfanyl)benzamide | 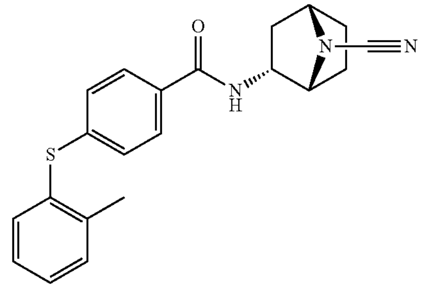 [SMILES: Cc1ccccc1Sc1ccc(C(=O)N[C@@H]2C[C@@H]3CC[C@H]2N3C#N)cc1] |
| 1-49 | N-((1R,2R,4S)-7-cyano-7-azabicyclo[2.2.1]heptan-2-yl)-4-(3-methylbutoxy)benzamide | 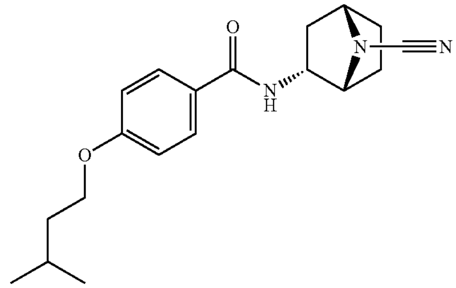 [SMILES: CC(C)CCOc1ccc(C(=O)N[C@@H]2C[C@@H]3CC[C@H]2N3C#N)cc1] |
| 1-50 | N-((1R,2R,4S)-7-cyano-7-azabicyclo[2.2.1]heptan-2-yl)-4-((2-cyanophenyl)sulfanyl)benzamide | 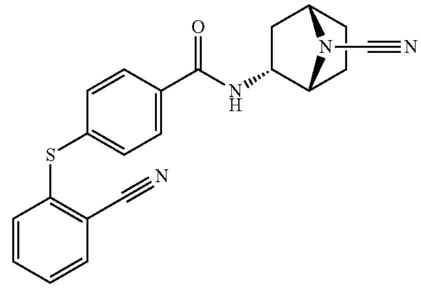 [SMILES: N#Cc1ccccc1Sc1ccc(C(=O)N[C@@H]2C[C@@H]3CC[C@H]2N3C#N)cc1] |
| 1-51 | N-((1R,2R,4S)-7-cyano-7-azabicyclo[2.2.1]heptan-2-yl)-1-(6-cyclopropyl-2-pyridinyl)-3-methyl-1H-indazole-5-carboxamide | 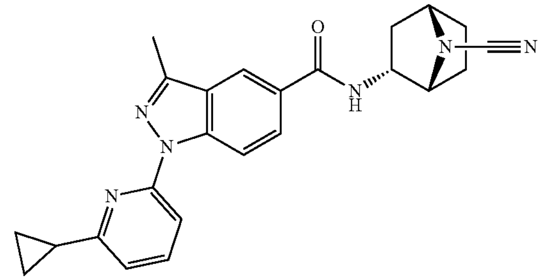 [SMILES: Cc1nn(-c2cccc(C3CC3)n2)c2ccc(C(=O)N[C@@H]3C[C@@H]4CC[C@H]3N4C#N)cc12] |

-continued

| Ex # | Name[FB-L22] | Structure |
|---|---|---|
| 1-52 | 6-chloro-N-((1R,2R,4S)-7-cyano-7-azabicyclo[2.2.1]heptan-2-yl)-1-(6-cyclopropyl-2-pyridinyl)-1H-indazole-5-carboxamide | 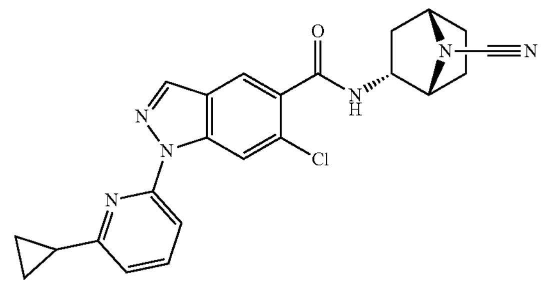 [SMILES: N#CN1[C@H]2CC[C@@H]1[C@H](NC(=O)c1cc3cnn(-c4cccc(C5CC5)n4)c3cc1Cl)C2] |
| 1-53 | N-((1R,2R,4S)-7-cyano-7-azabicyclo[2.2.1]heptan-2-yl)-1-(6-cyclopropyl-2-pyridinyl)-6-methyl-1H-indazole-5-carboxamide | 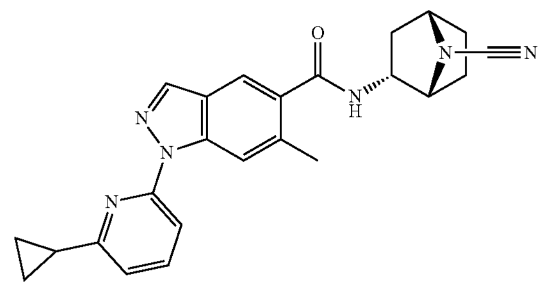 [SMILES: Cc1cc2c(cnn2-c2cccc(C3CC3)n2)cc1C(=O)N[C@@H]1C[C@@H]2CC[C@H]1N2C#N] |
| 1-54 | 5-bromo-3-chloro-N-((1R,2R,4S)-7-cyano-7-azabicyclo[2.2.1]heptan-2-yl)-1-methyl-1H-indole-2-carboxamide | 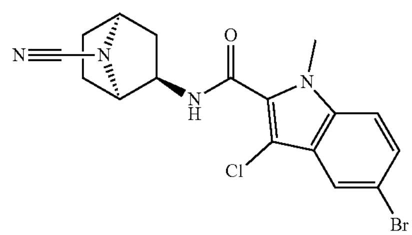 [SMILES: Cn1c(C(=O)N[C@@H]2C[C@@H]3CC[C@H]2N3C#N)c(Cl)c2cc(Br)ccc21] |
| 1-55 | Mixture of two diastereomers: (2R)-5-bromo-N-(7-cyano-7-azabicyclo[2.2.1]heptan-2-yl)-2,3-dihydro-1H-indene-2-carboxamide, and (2S)-5-bromo-N-(7-cyano-7-azabicyclo[2.2.1]heptan-2-yl)-2,3-dihydro-1H-indene-2-carboxamide | |

-continued

| Ex # | Name[FB-L22] | Structure |
|---|---|---|
| 1-56 | 5-bromo-N-((1R,2R,4S)-7-cyano-7-azabicyclo[2.2.1]heptan-2-yl)-3-methyl-1-benzothiophene-2-carboxamide | 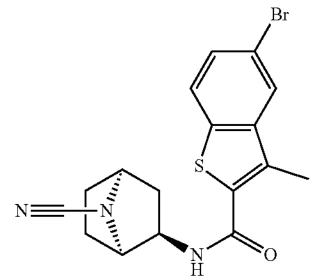 [SMILES: Cc1c(C(=O)N[C@@H]2C[C@@H]3CC[C@H]2N3C#N)sc2ccc(Br)cc12] |
| 1-57 | N-benzyl-3-bromo-N-(2-(((1R,2R,4S)-7-cyano-7-azabicyclo[2.2.1]heptan-2-yl)amino)-2-oxoethyl)benzamide | 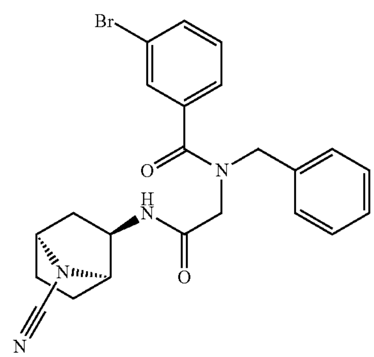 [SMILES: N#CN1[C@H]2CC[C@@H]1[C@H](NC(=O)CN(Cc1ccccc1)C(=O)c1cccc(Br)c1)C2] |
| 1-58 | N-benzyl-3-chloro-N-(2-(((1R,2R,4S)-7-cyano-7-azabicyclo[2.2.1]heptan-2-yl)amino)-2-oxoethyl)benzamide | 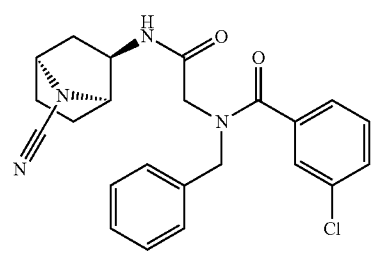 [SMILES: N#CN1[C@H]2CC[C@@H]1[C@H](NC(=O)CN(Cc1ccccc1)C(=O)c1cccc(Cl)c1)C2] |
| 1-59 | 3-bromo-N-(2-(((1R,2R,4S)-7-cyano-7-azabicyclo[2.2.1]heptan-2-yl)amino)-2-oxoethyl)benzamide | 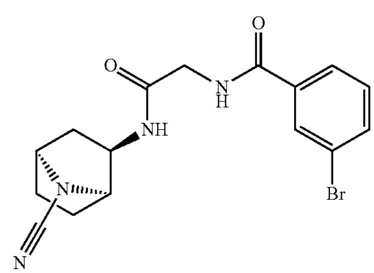 [SMILES: N#CN1[C@H]2CC[C@@H]1[C@H](NC(=O)CNC(=O)c1cccc(Br)c1)C2] |
| 1-60 | 3-chloro-N-(2-(((1R,2R,4S)-7-cyano-7-azabicyclo[2.2.1]heptan-2-yl)amino)-2-oxoethyl)benzamide | 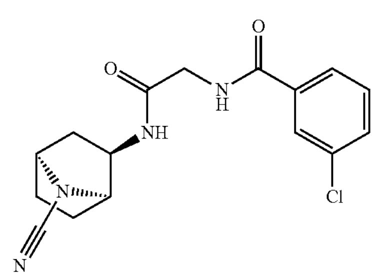 [SMILES: N#CN1[C@H]2CC[C@@H]1[C@H](NC(=O)CNC(=O)c1cccc(Cl)c1)C2] |

-continued

| Ex # | Name[FB-L22] | Structure |
|---|---|---|
| 1-61 | Mixture of two diastereomers: (3R)-1-(3-chlorophenyl)-N-(7-cyano-7-azabicyclo[2.2.1]heptan-2-yl)-5-oxo-3-pyrrolidinecarboxamide, and (3S)-1-(3-chlorophenyl)-N-(7-cyano-7-azabicyclo[2.2.1]heptan-2-yl)-5-oxo-3-pyrrolidinecarboxamide | 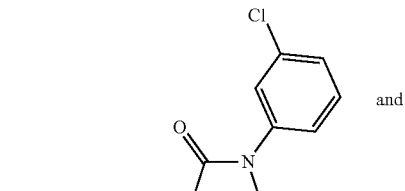 and 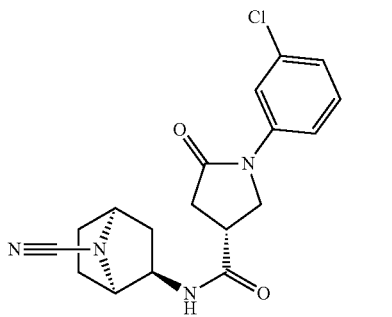 |
| 1-62 | Mixture of two diastereomers: (3R)-1-(3-bromophenyl)-N-(7-cyano-7-azabicyclo[2.2.1]heptan-2-yl)-5-oxo-3-pyrrolidinecarboxamide, and (3S)-1-(3-bromophenyl)-N-(7-cyano-7-azabicyclo[2.2.1]heptan-2-yl)-5-oxo-3-pyrrolidinecarboxamide | [FB-L24] 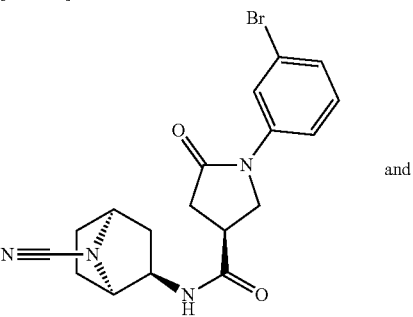 and 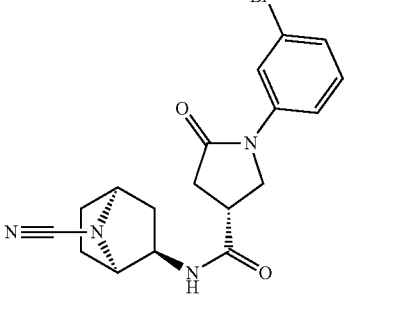 |
| 1-63 | Mixture of two diastereomers: (3R)-1-(3-chlorophenyl)-N-(7-cyano-7-azabicyclo[2.2.1]heptan-2-yl)-2-oxo-3-pyrrolidinecarboxamide, and (3S)-1-(3-chlorophenyl)-N-(7-cyano-7-azabicyclo[2.2.1]heptan-2-yl)-2-oxo-3-pyrrolidinecarboxamide | 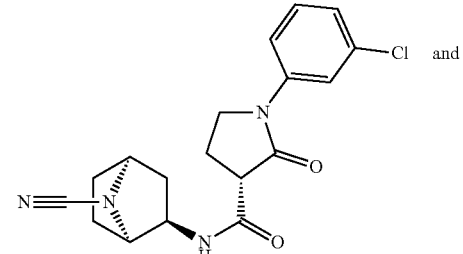 and 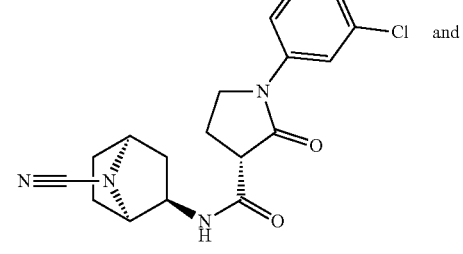 |

| Ex # | Name[FB-L22] | Structure |
|---|---|---|
| | |  |
| 1-64 | 2-(3-chlorophenyl)-N-((1R,2R,4S)-7-cyano-7-azabicyclo[2.2.1]heptan-2-yl)-1,3-thiazole-4-carboxamide | 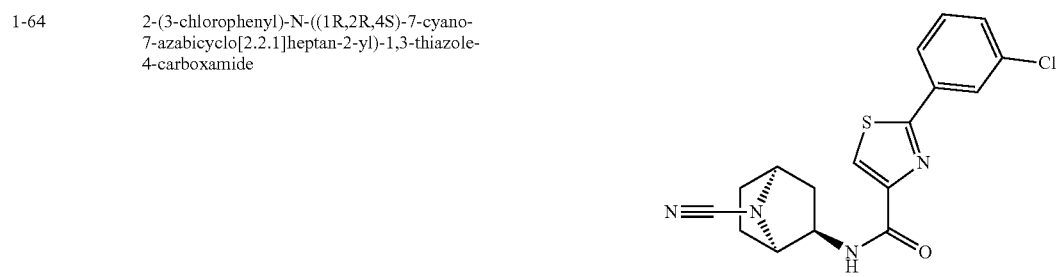 |
| 2-1-1 | 2-(4-chloro-3-(trifluoromethyl)phenoxy)-N-((endo)-7-cyano-7-azabicyclo[2.2.1]heptan-2-yl)acetamide enantiomer 1 | 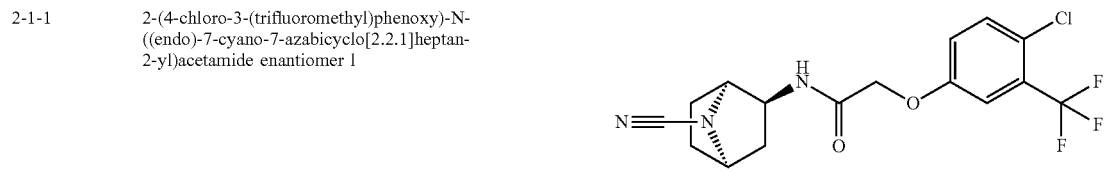 |
| 2-1-2 | 2-(4-chloro-3-(trifluoromethyl)phenoxy)-N-((endo)-7-cyano-7-azabicyclo[2.2.1]heptan-2-yl)acetamide enantiomer 2 | 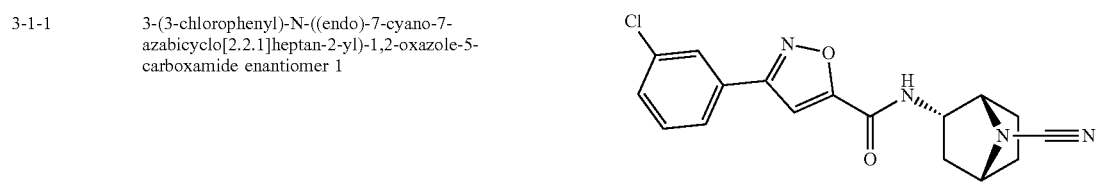 |
| 3-1-1 | 3-(3-chlorophenyl)-N-((endo)-7-cyano-7-azabicyclo[2.2.1]heptan-2-yl)-1,2-oxazole-5-carboxamide enantiomer 1 | 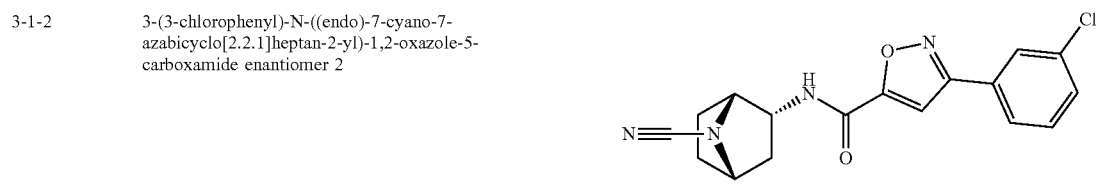 |
| 3-1-2 | 3-(3-chlorophenyl)-N-((endo)-7-cyano-7-azabicyclo[2.2.1]heptan-2-yl)-1,2-oxazole-5-carboxamide enantiomer 2 | 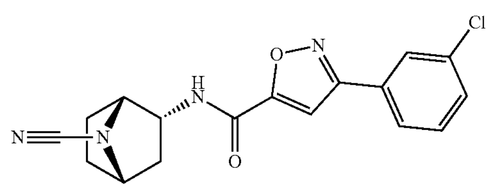 [SMILES: N#CN1[C@H]2CC[C@@H]1[C@H](NC(=O)c1cc(-c3cccc(Cl)c3)no1)C2] |
| 3-3 | Racemic, endo 2-((4-chloro-3-(trifluoromethyl)phenyl)amino)-N-(7-cyano-7-azabicyclo[2.2.1]heptan-2-yl)acetamide | 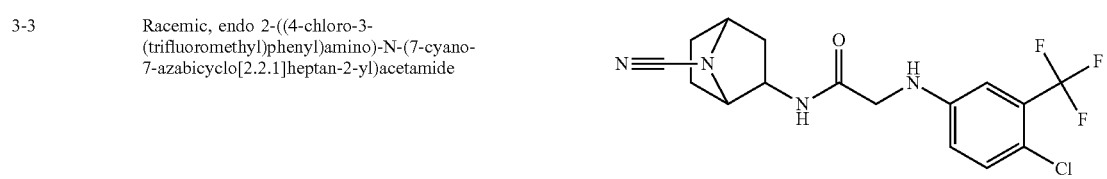 |

| Ex # | Name[FB-L22] | Structure |
|---|---|---|
| 3-7 | Racemic, endo 3-bromo-N-(1-(7-cyano-7-azabicyclo[2.2.1]heptan-2-yl)amino)-1-oxopropan-2-yl)benzamide | 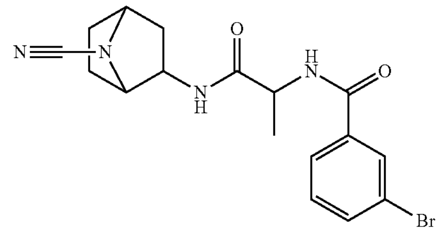 [SMILES: CC(NC(=O)c1cccc(Br)c1)C(=O)NC1CC2CCC1N2C#N] |
| 3-8 | Racemic, endo 3-bromo-N-(1-7-cyano-7-azabicyclo[2.2.1]heptan-2-yl)amino)-2-methyl-1-oxopropan-2-yl)benzamide | 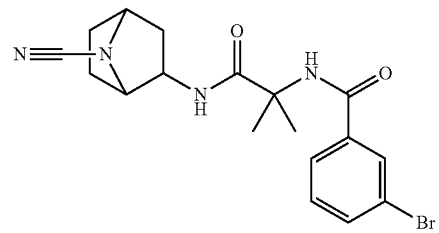 [SMILES: CC(C)(NC(=O)c1cccc(Br)c1)C(=O)NC1CC2CCC1N2C#N] |
| 4-1-1 | (endo)-7-cyano-N-(4-(3-(trifluoromethyl)phenyl)-1,3-thiazol-2-yl)-7-azabicyclo[2.2.1]heptane-2-carboxamide | 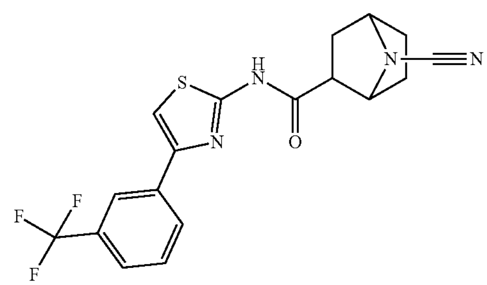 [SMILES: N#CN1C2CCC1C(C(=O)Nc1nc(-c3cccc(C(F)(F)F)c3)cs1)C2] |
| 4-1-2 | (endo)-7-cyano-N-(4-(3-(trifluoromethyl)phenyl)-1,3-thiazol-2-yl)-7-azabicyclo[2.2.1]heptane-2-carboxamide | 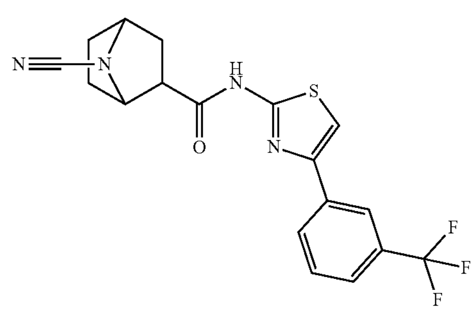 [SMILES: N#CN1C2CCC1C(C(=O)Nc1nc(-c3cccc(C(F)(F)F)c3)cs1)C2] |
| 4-1-3 | (exo)-7-cyano-N-(4-(3-(trifluoromethyl)phenyl)-1,3-thiazol-2-yl)-7-azabicyclo[2.2.1]heptane-2-carboxamide | 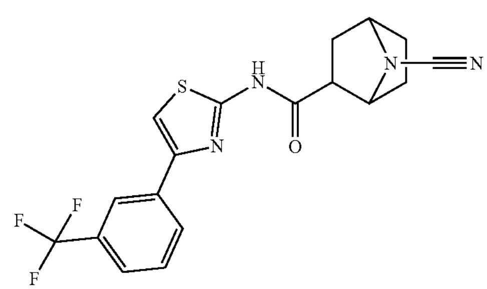 [SMILES: N#CN1C2CCC1C(C(=O)Nc1nc(-c3cccc(C(F)(F)F)c3)cs1)C2] |

-continued

| Ex # | Name[FB-L22] | Structure |
|---|---|---|
| 4-1-4 | (exo)-7-cyano-N-(4-(3-(trifluoromethyl)phenyl)-1,3-thiazol-2-yl)-7-azabicyclo[2.2.1]heptane-2-carboxamide | 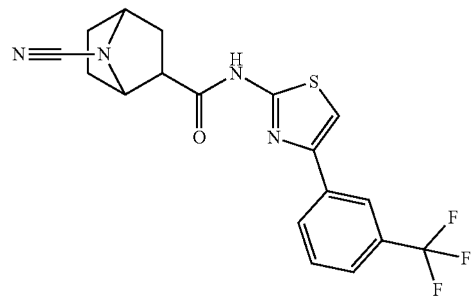 [SMILES: N#CN1C2CCC1C(C(=O)Nc1nc(-c3cccc(C(F)(F)F)c3)cs1)C2] |
| 4-2-1 | (endo)-2-((5-(2-fluoro-5-methylphenyl)-2,3-dihydro-1H-indol-1-yl)carbonyl)-7-azabicyclo[2.2.1]heptane-7-carbonitrile | 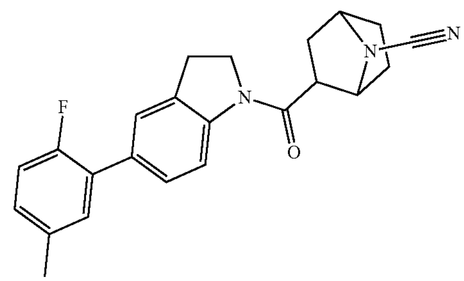 [SMILES: Cc1ccc(F)c(-c2ccc3c(c2)CCN3C(=O)C2CC3CCC2N3C#N)c1] |
| 4-2-2 | (endo)-2-((5-(2-fluoro-5-methylphenyl)-2,3-dihydro-1H-indol-1-yl)carbonyl)-7-azabicyclo[2.2.1]heptane-7-carbonitrile | 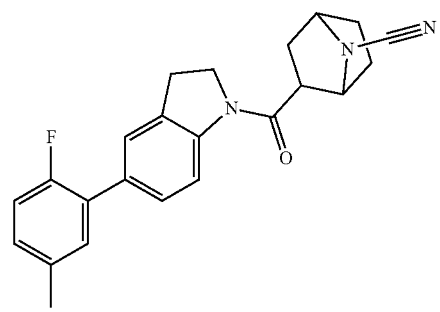 [SMILES: Cc1ccc(F)c(-c2ccc3c(c2)CCN3C(=O)C2CC3CCC2N3C#N)c1] |
| 4-2-3 | (exo)-2-((5-(2-fluoro-5-methylphenyl)-2,3-dihydro-1H-indol-1-yl)carbonyl)-7-azabicyclo[2.2.1]heptane-7-carbonitrile | 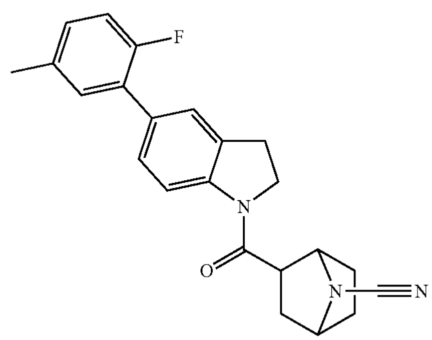 [SMILES: Cc1ccc(F)c(-c2ccc3c(c2)CCN3C(=O)C2CC3CCC2N3C#N)c1] |
| 4-2-4 | (exo)-2-((5-(2-fluoro-5-methylphenyl)-2,3-dihydro-1H-indol-1-yl)carbonyl)-7-azabicyclo[2.2.1]heptane-7-carbonitrile | 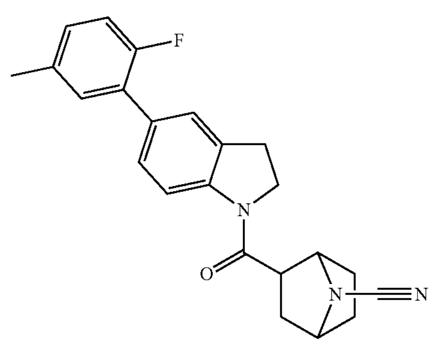 [SMILES: Cc1ccc(F)c(-c2ccc3c(c2)CCN3C(=O)C2CC3CCC2N3C#N)c1] |

-continued

| Ex # | Name[FB-L22] | Structure |
|---|---|---|
| 5-1 | Racemic, endo N-(7-cyano-7-azabicyclo[2.2.1]heptan-2-yl)-1-(4,6-dimethyl-2-pyrimidinyl)-2,3-dihydro-1H-indole-5-carboxamide | 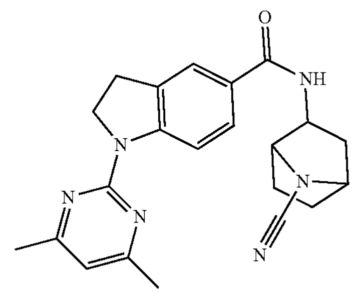 [SMILES: Cc1cc(C)nc(N2CCc3cc(C(=O)NC4CC5CCC4N5C#N)ccc32)n1] |
| 5-2 | Racemic, endo N-(7-cyano-7-azabicyclo[2.2.1]heptan-2-yl)-1-(6-cyclopropyl-2-pyridinyl)-2,3-dihydro-1H-indole-5-carboxamide | 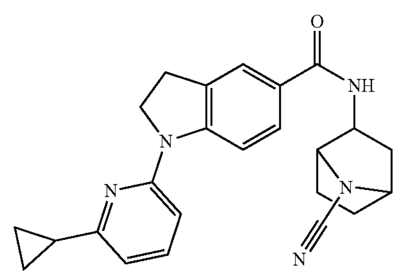 [SMILES: N#CN1C2CCC1C(NC(=O)c1ccc3c(c1)CCN3c1cccc(C3CC3)n1)C2] |
| 5-3 | Racemic, endo N-(7-cyano-7-azabicyclo[2.2.1]heptan-2-yl)-1-(6-cyclopropyl-2-pyrazinyl)-2,3-dihydro-1H-indole-5-carboxamide | 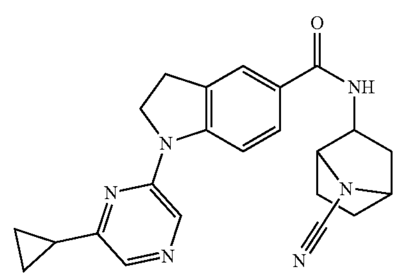 [SMILES: N#CN1C2CCC1C(NC(=O)c1ccc3c(c1)CCN3c1cncc(C3CC3)n1)C2] |
| 5-4 | Racemic, endo N-(7-cyano-7-azabicyclo[2.2.1]heptan-2-yl)-1-(3-cyclopropylphenyl)-2,3-dihydro-1H-indole-5-carboxamide | 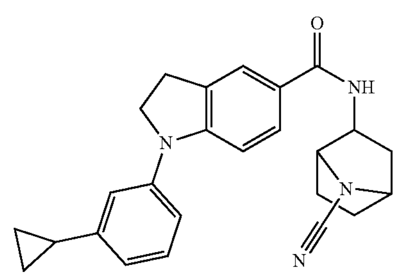 [SMILES: N#CN1C2CCC1C(NC(=O)c1ccc3c(c1)CCN3c1cccc(C3CC3)c1)C2] |
| 5-5 | Racemic, endo N-(7-cyano-7-azabicyclo[2.2.1]heptan-2-yl)-1-(4-cyclopropyl-2-pyridinyl)-2,3-dihydro-1H-indole-5-carboxamide | 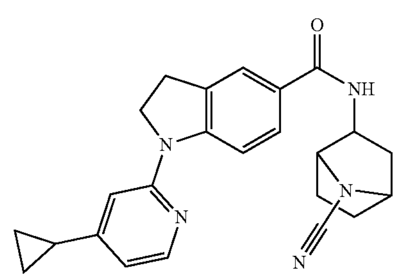 [SMILES: N#CN1C2CCC1C(NC(=O)c1ccc3c(c1)CCN3c1cc(C3CC3)ccn1)C2] |

| Ex # | Name[FB-L22] | Structure |
|---|---|---|
| 5-6 | Racemic, endo N-(7-cyano-7-azabicyclo[2.2.1]heptan-2-yl)-1-(4-methoxy-2-pyrimidinyl)-2,3-dihydro-1H-indole-5-carboxamide | 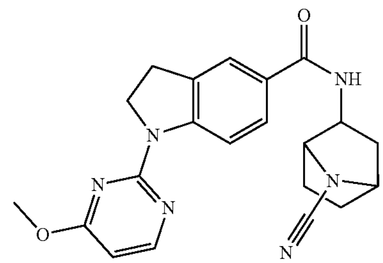 [SMILES: COc1ccnc(N2CCc3cc(C(=O)NC4CC5CCC4N5C#N)ccc32)n1] |
| 5-7 | Racemic, endo N-(7-cyano-7-azabicyclo[2.2.1]heptan-2-yl)-1-(4-(trifluoromethyl)-2-pyrimidinyl)-2,3-dihydro-1H-indole-5-carboxamide | 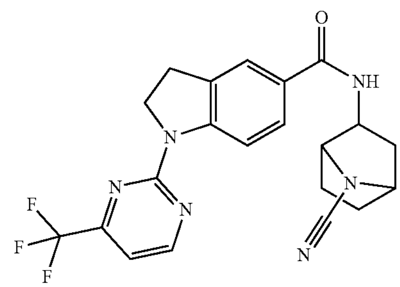 [SMILES: N#CN1C2CCC1C(NC(=O)c1ccc3c(c1)CCN3c1nccc(C(F)(F)F)n1)C2] |
| 5-8 | Racemic, endo N-(7-cyano-7-azabicyclo[2.2.1]heptan-2-yl)-1-(4-(2-methyl-2-propanyl)-2-pyrimidinyl)-2,3-dihydro-1H-indole-5-carboxamide | 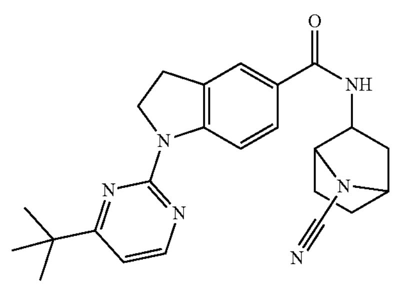 [SMILES: CC(C)(C)c1ccnc(N2CCc3cc(C(=O)NC4CC5CCC4N5C#N)ccc32)n1] |
| 5-9 | Racemic, endo N-(7-cyano-7-azabicyclo[2.2.1]heptan-2-yl)-1-(4-(2-propanyl)-2-pyrimidinyl)-2,3-dihydro-1H-indole-5-carboxamide | 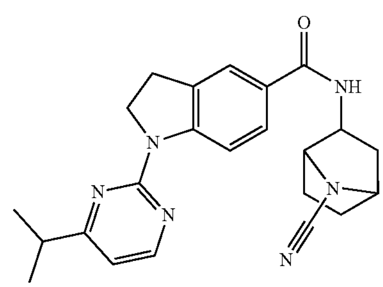 [SMILES: CC(C)c1ccnc(N2CCc3cc(C(=O)NC4CC5CCC4N5C#N)ccc32)n1] |
| 5-10 | N-((1R,2R,4S)-7-cyano-7-azabicyclo[2.2.1]heptan-2-yl)-1-(4-ethyl-2-pyrimidinyl)-2,3-dihydro-1H-indole-5-carboxamide | 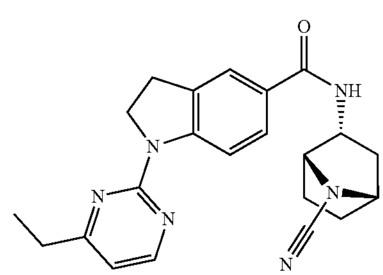 [SMILES: CCc1ccnc(N2CCc3cc(C(=O)N[C@@H]4C[C@@H]5CC[C@H]4N5C#N)ccc32)n1] |

| Ex # | Name[FB-L22] | Structure |
|---|---|---|
| 5-11 | N-((1R,2R,4S)-7-cyano-7-azabicyclo[2.2.1]heptan-2-yl)-1-(4-cyano-2-pyrimidinyl)-2,3-dihydro-1H-indole-5-carboxamide | 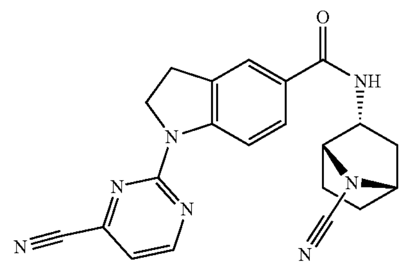 [SMILES: N#Cc1ccnc(N2CCc3cc(C(=O)N[C@@H]4C[C@@H]5CC[C@H]4N5C#N)ccc32)n1] |
| 5-12 | N-((1R,2R,4S)-7-cyano-7-azabicyclo[2.2.1]heptan-2-yl)-1-(4-cyano-6-methyl-2-pyrimidinyl)-2,3-dihydro-1H-indole-5-carboxamide | 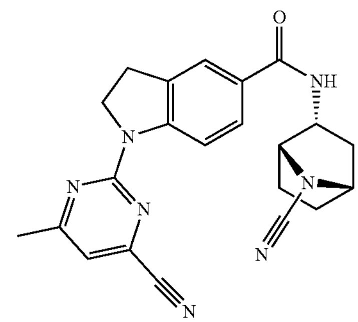 [SMILES: Cc1cc(C#N)nc(N2CCc3cc(C(=O)N[C@@H]4C[C@@H]5CC[C@H]4N5C#N)ccc32)n1] |
| 5-13 | N-((1R,2R,4S)-7-cyano-7-azabicyclo[2.2.1]heptan-2-yl)-1-(4-(difluoromethyl)-2-pyrimidinyl)-2,3-dihydro-1H-indole-5-carboxamide | 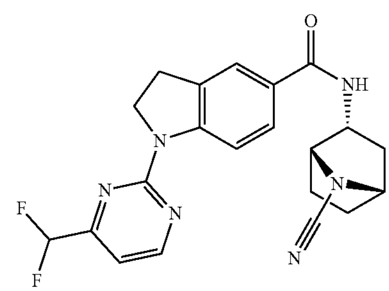 [SMILES: N#CN1[C@H]2CC[C@@H]1[C@H](NC(=O)c1ccc3c(c1)CCN3c1nccc(C(F)F)n1)C2] |
| 5-14 | N-((1R,2R,4S)-7-cyano-7-azabicyclo[2.2.1]heptan-2-yl)-1-(4-methyl-6-(trifluoromethyl)-2-pyrimidinyl)-2,3-dihydro-1H-indole-5-carboxamide | 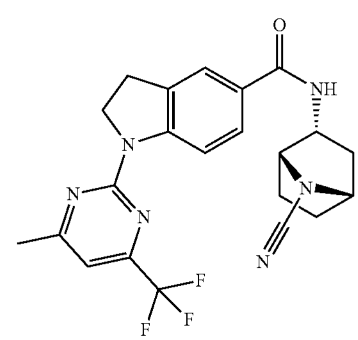 [SMILES: Cc1cc(C(F)(F)F)nc(N2CCc3cc(C(=O)N[C@@H]4C[C@@H]5CC[C@H]4N5C#N)ccc32)n1] |
| 5-15 | N-((1R,2R,4S)-7-cyano-7-azabicyclo[2.2.1]heptan-2-yl)-1-(3-fluoro-6-methyl-2-pyridinyl)-2,3-dihydro-1H-indole-5-carboxamide | 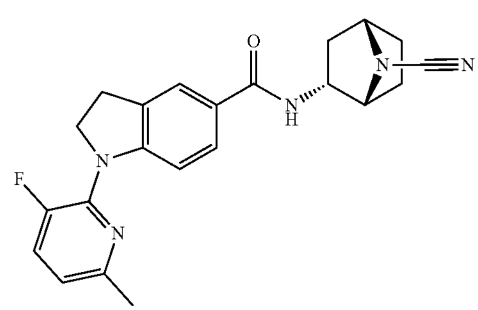 [SMILES: Cc1ccc(F)c(N2CCc3cc(C(=O)N[C@@H]4C[C@@H]5CC[C@H]4N5C#N)ccc32)n1] |

-continued

| Ex # | Name[FB-L22] | Structure |
|---|---|---|
| 6-1 | Racemic, endo N-(7-cyano-7-azabicyclo[2.2.1]heptan-2-yl)-1-(4-methyl-2-pyrimidinyl)-1H-indole-5-carboxamide | 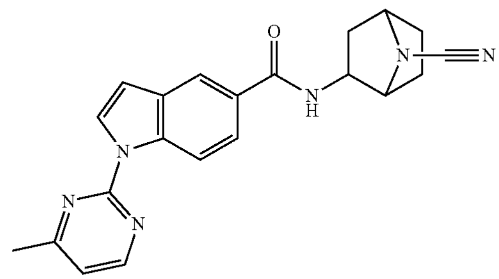 [SMILES: Cc1ccnc(-n2ccc3cc(C(=O)NC4CC5CCC4N5C#N)ccc32)n1] |
| 6-2 | Racemic, endo N-(7-cyano-7-azabicyclo[2.2.1]heptan-2-yl)-1-(2-pyrimidinyl)-2,3-dihydro-1H-indole-5-carboxamide | 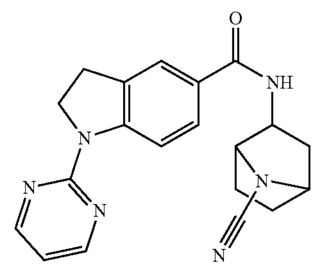 [SMILES: N#CN1C2CCC1C(NC(=O)c1ccc3c(c1)CCN3c1ncccn1)C2] |
| 6-3 | Racemic, endo N-(7-cyano-7-azabicyclo[2.2.1]heptan-2-yl)-1-(5-methyl-2-pyrimidinyl)-2,3-dihydro-1H-indole-5-carboxamide | 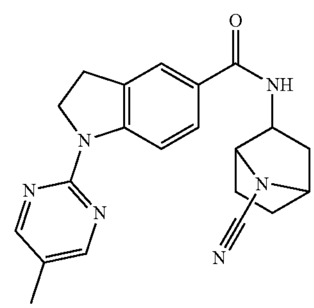 [SMILES: Cc1cnc(N2CCc3cc(C(=O)NC4CC5CCC4N5C#N)ccc32)nc1] |
| 7-1 | N-((1R,2R,4S)-7-cyano-7-azabicyclo[2.2.1]heptan-2-yl)-1-(4-cyclopropyl-2-pyrimidinyl)-N-methyl-2,3-dihydro-1H-indole-5-carboxamide | 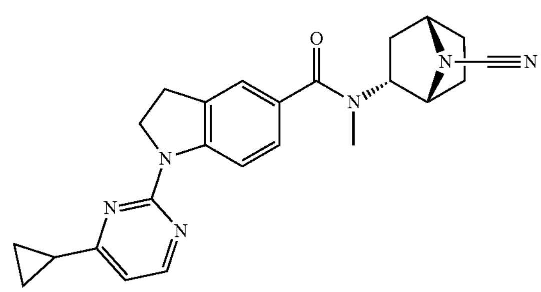 [SMILES: CN(C(=O)c1ccc2c(c1)CCN2c1nccc(C2CC2)n1)[C@@H]1C[C@@H]2CC[C@H]1N2C#N] |
| 7-2 | N-((1S,2S,4R)-7-cyano-7-azabicyclo[2.2.1]heptan-2-yl)-1-(4-cyclopropyl-2-pyrimidinyl)-N-methyl-2,3-dihydro-1H-indole-5-carboxamide (peak 2 derived) | 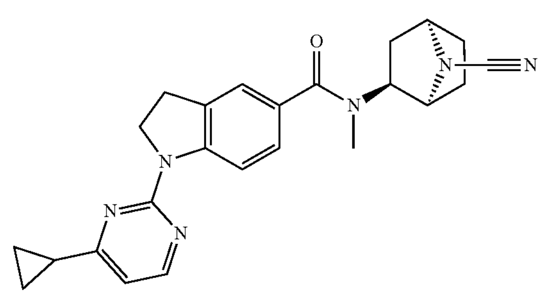 [SMILES: CN(C(=O)c1ccc2c(c1)CCN2c1nccc(C2CC2)n1)[C@H]1C[C@H]2CC[C@@H]1N2C#N] |

-continued

| Ex # | Name[FB-L22] | Structure |
|---|---|---|
| 8-1 | Racemic, endo N~5~-(7-cyano-7-azabicyclo[2.2.1]heptan-2-yl)-N~1~-cyclopropyl-2,3-dihydro-1H-indole-1,5-dicarboxamide | 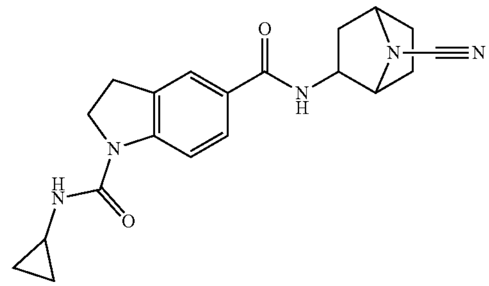 [SMILES: N#CN1C2CCC1C(NC(=O)c1ccc3c(c1)CCN3C(=O)NC1CC1)C2] |
| 8-2 | Racemic, endo 1-(7-cyano-7-azabicyclo[2.2.1]heptan-2-yl)-3-(4-(trifluoromethyl)phenyl)urea | 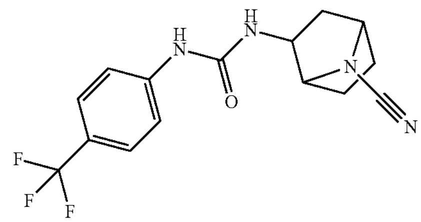 [SMILES: N#CN1C2CCC1C(NC(=O)Nc1ccc(C(F)(F)F)cc1)C2] |
| 9-1 | N-((1R,2R,4S)-7-cyano-7-azabicyclo[2.2.1]heptan-2-yl)-3-methyl-4-(1-methyl-1H-pyrazol-4-yl)benzamide | 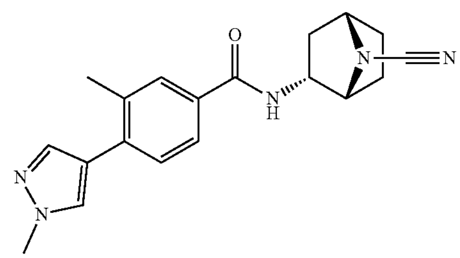 [SMILES: Cc1cc(C(=O)N[C@@H]2C[C@@H]3CC[C@H]2N3C#N)ccc1-c1cnn(C)c1] |
| 9-2 | N-((1R,2R,4S)-7-cyano-7-azabicyclo[2.2.1]heptan-2-yl)-3-(cyclopropylmethoxy)-4-(1-methyl-1H-pyrazol-4-yl)benzamide | 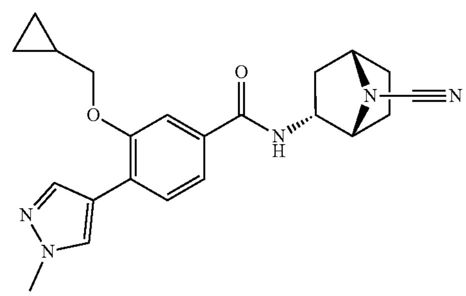 [SMILES: Cn1cc(-c2ccc(C(=O)N[C@@H]3C[C@@H]4CC[C@H]3N4C#N)cc2OCC2CC2)cn1] |
| 9-3 | N-((1R,2R,4S)-7-cyano-7-azabicyclo[2.2.1]heptan-2-yl)-4-(1-methyl-1H-pyrazol-4-yl)-3-propoxybenzamide | 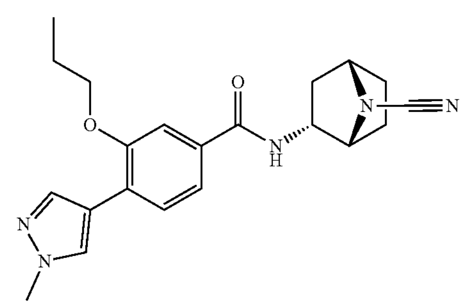 [SMILES: CCCOc1cc(C(=O)N[C@@H]2C[C@@H]3CC[C@H]2N3C#N)ccc1-c1cnn(C)c1] |

-continued

| Ex # | Name[FB-L22] | Structure |
|---|---|---|
| 9-4 | N-((1R,2R,4S)-7-cyano-7-azabicyclo[2.2.1]heptan-2-yl)-3-ethoxy-4-(1-methyl-1H-pyrazol-4-yl)benzamide | 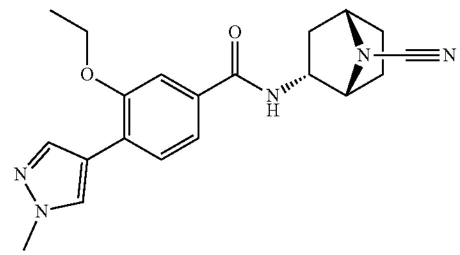 [SMILES: CCOc1cc(C(=O)N[C@@H]2C[C@@H]3CC[C@H]2N3C#N)ccc1-c1cnn(C)c1] |
| 9-5 | N-((1R,2R,4S)-7-cyano-7-azabicyclo[2.2.1]heptan-2-yl)-4-(1-methyl-1H-pyrazol-4-yl)-3-(2-propanyloxy)benzamide | 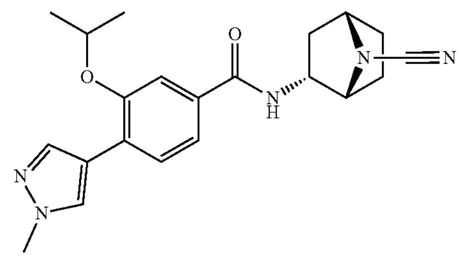 [SMILES: CC(C)Oc1cc(C(=O)N[C@@H]2C[C@@H]3CC[C@H]2N3C#N)ccc1-c1cnn(C)c1] |
| 9-6 | N-((1R,2R,4S)-7-cyano-7-azabicyclo[2.2.1]heptan-2-yl)-3-methoxy-4-(1-methyl-1H-pyrazol-4-yl)benzamide | 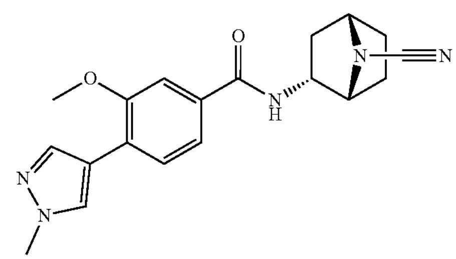 [SMILES: COc1cc(C(=O)N[C@@H]2C[C@@H]3CC[C@H]2N3C#N)ccc1-c1cnn(C)c1] |
| 9-7 | N-((1R,2R,4S)-7-cyano-7-azabicyclo[2.2.1]heptan-2-yl)-4-(1-methyl-1H-pyrazol-4-yl)-3-(trifluoromethoxy)benzamide | 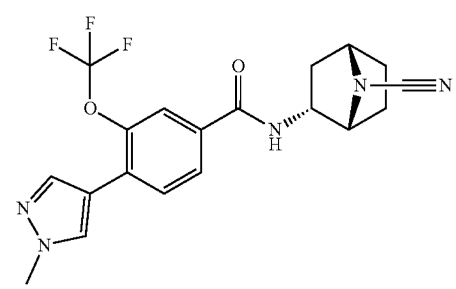 [SMILES: Cn1cc(-c2ccc(C(=O)N[C@@H]3C[C@@H]4CC[C@H]3N4C#N)cc2OC(F)(F)F)cn1] |
| 9-8 | N-((1R,2R,4S)-7-cyano-7-azabicyclo[2.2.1]heptan-2-yl)-4-(1-methyl-1H-pyrazol-4-yl)-3-(trifluoromethyl)benzamide | 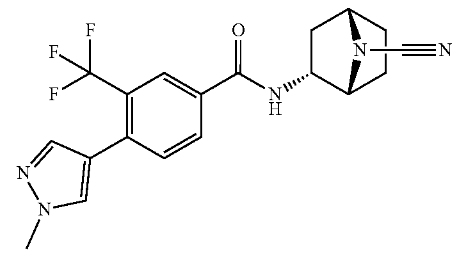 [SMILES: Cn1cc(-c2ccc(C(=O)N[C@@H]3C[C@@H]4CC[C@H]3N4C#N)cc2C(F)(F)F)cn1] |

-continued

| Ex # | Name[FB-L22] | Structure |
|---|---|---|
| 9-9 | N-((1R,2R,4S)-7-cyano-7-azabicyclo[2.2.1]heptan-2-yl)-3-(6-(trifluoromethyl)-2-pyridinyl)-1H-indazole-6-carboxamide | 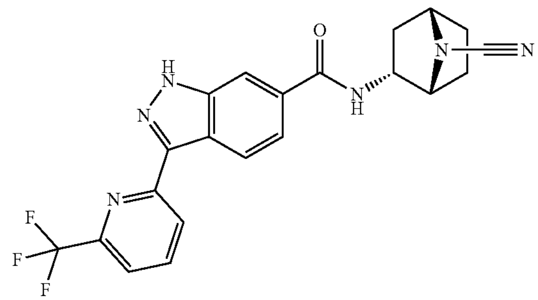 [SMILES: N#CN1[C@H]2CC[C@@H]1[C@H](NC(=O)c1ccc3c(-c4cccc(C(F)(F)F)n4)n[nH]c3c1)C2] |
| 10-1 | Racemic, endo 2-((3-bromobenzyl)(methyl)amino)-N-(7-cyano-7-azabicyclo[2.2.1]heptan-2-yl)acetamide | 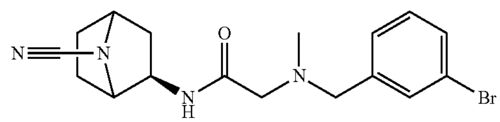 [SMILES: CN(CC(=O)N[C@@H]1CC2CCC1N2C#N)Cc1cccc(Br)c1] |
| 11-1 | Racemic, endo 2-(4-chloro-2-cyclohexylphenoxy)-N-(7-cyano-7-azabicyclo[2.2.1]heptan-2-yl)acetamide | 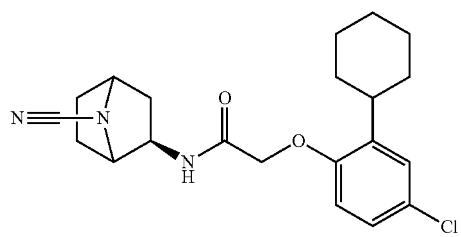 [SMILES: N#CN1C2CCC1[C@H](NC(=O)COc1ccc(Cl)cc1C1CCCCC1)C2] |
| 11-2 | N~2~-benzyl-N~2~-(3-bromobenzyl)-N-((1R,2R,4S)-7-cyano-7-azabicyclo[2.2.1]heptan-2-yl)glycinamide | 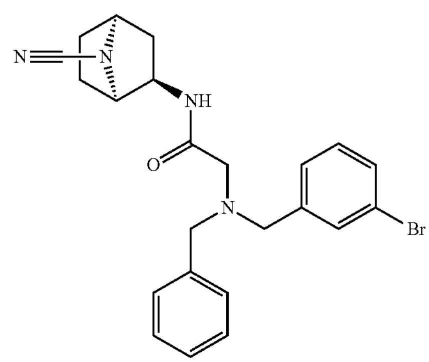 [SMILES: N#CN1[C@H]2CC[C@@H]1[C@H](NC(=O)CN(Cc1ccccc1)Cc1cccc(Br)c1)C2] |
| 11-3 | N~2~-benzyl-N~2~-(3-chlorobenzyl)-N-((1R,2R,4S)-7-cyano-7-azabicyclo[2.2.1]heptan-2-yl)glycinamide | 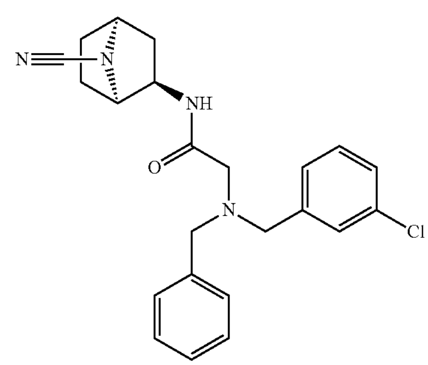 [SMILES: N#CN1[C@H]2CC[C@@H]1[C@H](NC(=O)CN(Cc1ccccc1)Cc1cccc(Cl)c1)C2] |

-continued

| Ex # | Name[FB-L22] | Structure |
|---|---|---|
| 11-4 | N-((1R,2R,4S)-7-cyano-7-azabicyclo[2.2.1]heptan-2-yl)-2-(5,6,7,8-tetrahydro[1]benzothieno[2,3-d]pyrimidin-4-ylsulfanyl)acetamide | 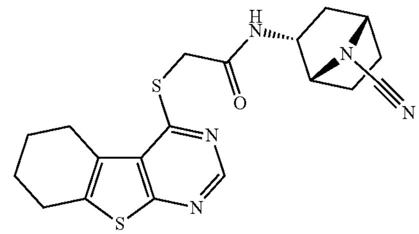 [SMILES: N#CN1[C@H]2CC[C@@H]1[C@H](NC(=O)CSc1ncnc3sc4c(c13)CCCC4)C2] |
| 11-5 | N~2~-(3-bromobenzyl)-N-((1R,2R,4S)-7-cyano-7-azabicyclo[2.2.1]heptan-2-yl)-N~2~-(2-methylpropyl)glycinamide | 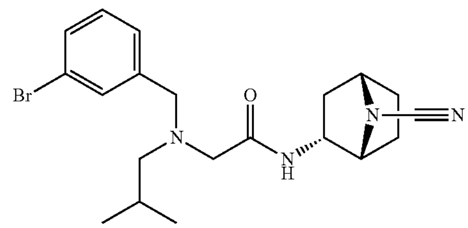 [SMILES: CC(C)CN(CC(=O)N[C@@H]1C[C@@H]2CC[C@H]1N2C#N)Cc1cccc(Br)c1] |
| 11-6 | N~2~-(3-chlorobenzyl)-N-((1R,2R,4S)-7-cyano-7-azabicyclo[2.2.1]heptan-2-yl)-N~2~-(4-methoxybenzyl)glycinamide | 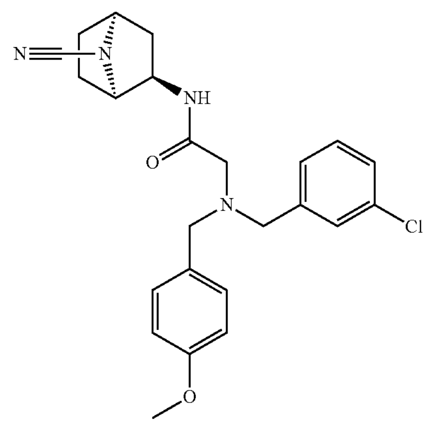 [SMILES: COc1ccc(CN(CC(=O)N[C@@H]2C[C@@H]3CC[C@H]2N3C#N)Cc2cccc(Cl)c2)cc1] |
| 11-7 | N-((1R,2R,4S)-7-cyano-7-azabicyclo[2.2.1]heptan-2-yl)-2-(5,7-dichloro-3,4-dihydro-2(1H)-isoquinolinyl)acetamide | 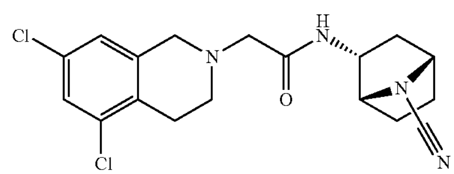 [SMILES: N#CN1[C@H]2CC[C@@H]1[C@H](NC(=O)CN1CCc3c(Cl)cc(Cl)cc3C1)C2] |
| 11-8 | Racemic, endo N-(7-cyano-7-azabicyclo[2.2.1]heptan-2-yl)-2-(2,4-dichloro-5-ethyl-3-methylphenoxy)acetamide | 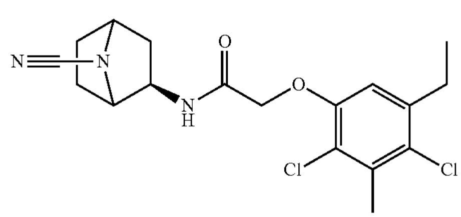 [SMILES: CCc1cc(OCC(=O)N[C@@H]2CC3CCC2N3C#N)c(Cl)c(C)c1Cl] |
| 11-9 | Racemic, endo 2-((5-chlorobenzo[d]thiazol-2-yl)thio)-N-(7-cyano-7-azabicyclo[2.2.1]heptan-2-yl)acetamide | 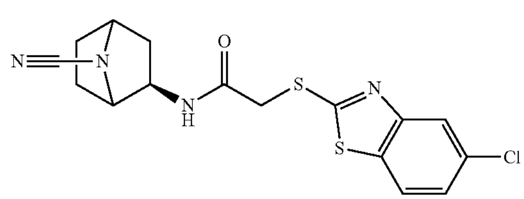 [SMILES: N#CN1C2CCC1[C@H](NC(=O)CSc1nc3cc(Cl)ccc3s1)C2] |

-continued

| Ex # | Name[FB-L22] | Structure |
|---|---|---|
| 12-1 | Racemic, endo 2-(4-((4-chlorophenyl)thio)piperidine-1-carbonyl)-7-azabicyclo[2.2.1]heptane-7-carbonitrile | 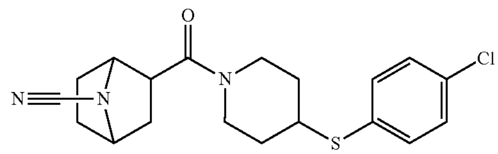 [SMILES: N#CN1C2CCC1C(C(=O)N1CCC(Sc3ccc(Cl)cc3)CC1)C2] |
| 13-1 | Racemic, endo N-(7-cyano-7-azabicyclo[2.2.1]heptan-2-yl)-1-(4-methyl-2-pyrimidinyl)-2,3-dihydro-1H-indole-5-carboxamide | 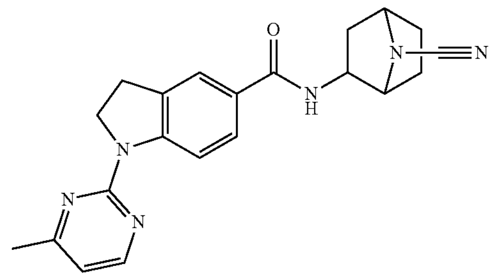 [SMILES: Cc1ccnc(N2CCc3cc(C(=O)NC4CC5CCC4N5C#N)ccc32)n1] |
| 13-2 | Racemic, endo N-(7-cyano-7-azabicyclo[2.2.1]heptan-2-yl)-1-(cyclopropylcarbonyl)-2,3-dihydro-1H-indole-5-carboxamide | 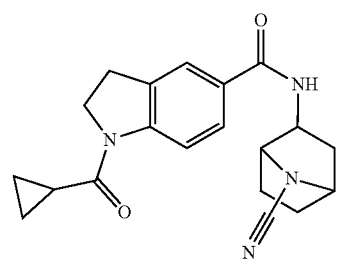 [SMILES: N#CN1C2CCC1C(NC(=O)c1ccc3c(c1)CCN3C(=O)C1CC1)C2] |
| 13-3 | 6-chloro-N-((1R,2R,4S)-7-cyano-7-azabicyclo[2.2.1]heptan-2-yl)-1-(6-methyl-2-pyridinyl)-1H-indazole-5-carboxamide | 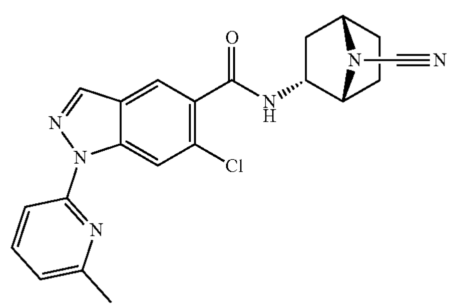 [SMILES: Cc1cccc(-n2ncc3cc(C(=O)N[C@@H]4C[C@@H]5CC[C@H]4N5C#N)c(Cl)cc32)n1] |
| 13-4 | N-((1R,2R,4S)-7-cyano-7-azabicyclo[2.2.1]heptan-2-yl)-1-(6-methyl-2-pyridinyl)-1H-indazole-5-carboxamide | 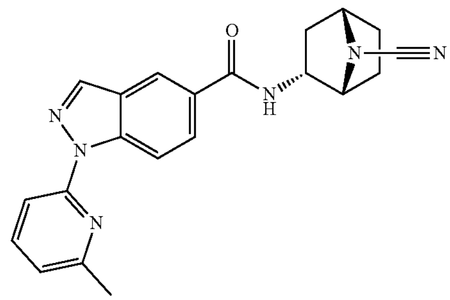 [SMILES: Cc1cccc(-n2ncc3cc(C(=O)N[C@@H]4C[C@@H]5CC[C@H]4N5C#N)ccc32)n1] |

-continued

| Ex # | Name[FB-L22] | Structure |
|---|---|---|
| 13-5 | N-((1R,2R,4S)-7-cyano-7-azabicyclo[2.2.1]heptan-2-yl)-6-fluoro-1-(6-methyl-2-pyridinyl)-1H-indazole-5-carboxamide | 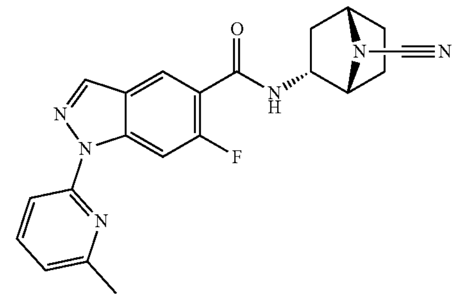 [SMILES: Cc1cccc(-n2ncc3cc(C(=O)N[C@@H]4C[C@@H]5CC[C@H]4N5C#N)c(F)cc32)n1] |
| 13-6 | Racemic, endo N-(7-cyano-7-azabicyclo[2.2.1]heptan-2-yl)-4-(4-cyclopropyl-2-pyrimidinyl)-3,4-dihydro-2H-1,4-benzoxazine-7-carboxamide | 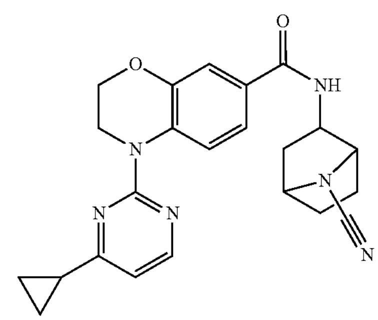 [SMILES: N#CN1C2CCC1C(NC(=O)c1ccc3c(c1)OCCN3c1nccc(C3CC3)n1)C2] |
| 13-7 | 2-((4-chloro-1-naphthalenyl)oxy)-N-((1R,2R,4S)-7-cyano-7-azabicyclo[2.2.1]heptan-2-yl)acetamide | 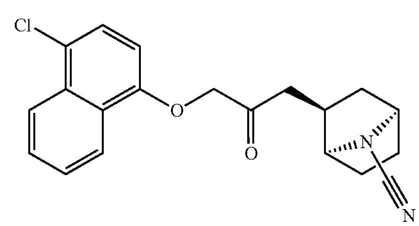 [SMILES: N#CN1[C@@H]2CC[C@H]1[C@@H](CC(=O)COc1ccc(Cl)c3ccccc13)C2] |
| 13-8 | 2-((4-chloro-1-naphthalenyl)oxy)-N-((1R,2R,4S)-7-cyano-7-azabicyclo[2.2.1]heptan-2-yl)acetamide (peak 2 derived) | 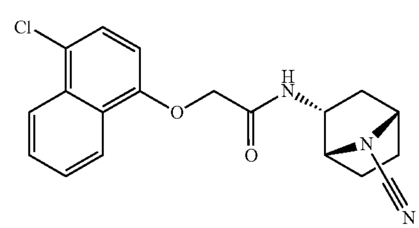 [SMILES: N#CN1[C@H]2CC[C@@H]1[C@H](NC(=O)COc1ccc(Cl)c3ccccc13)C2] |
| 13-9 | Racemic, endo 2-methyl-2-propanyl 5-((7-cyano-7-azabicyclo[2.2.1]heptan-2-yl)carbamoyl)-2,3-dihydro-1H-indole-1-carboxylate | 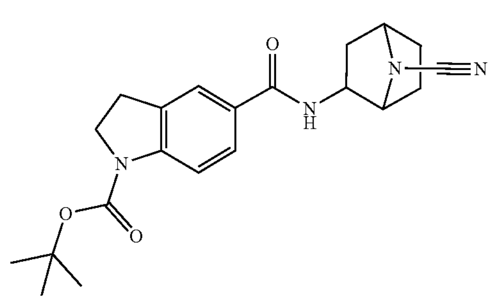 [SMILES: CC(C)(C)OC(=O)N1CCc2cc(C(=O)NC3CC4CCC3N4C#N)ccc21] |

-continued

| Ex # | Name[FB-L22] | Structure |
|---|---|---|
| 13-10 | Racemic, endo N-(7-cyano-7-azabicyclo[2.2.1]heptan-2-yl)-1-(4-methyl-2-pyrimidinyl)-1H-indazole-5-carboxamide | 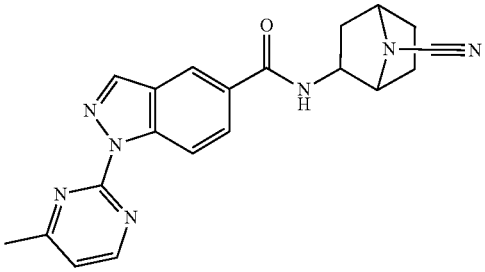 [SMILES: Cc1ccnc(-n2ncc3cc(C(=O)NC4CC5CCC4N5C#N)ccc32)n1] |
| 13-11 | Racemic, endo N-(7-cyano-7-azabicyclo[2.2.1]heptan-2-yl)-1-(4-methyl-2-pyrimidinyl)-1H-benzimidazole-5-carboxamide | 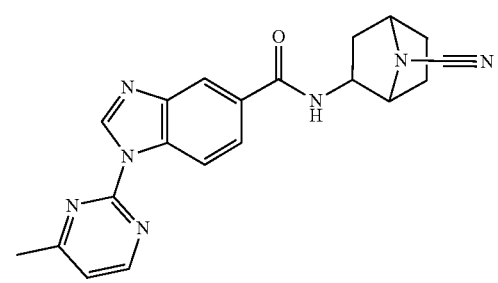 [SMILES: Cc1ccnc(-n2cnc3cc(C(=O)NC4CC5CCC4N5C#N)ccc32)n1] |
| 13-12 | Racemic, endo N-(7-cyano-7-azabicyclo[2.2.1]heptan-2-yl)-1-(4-cyclopropyl-2-pyridinyl)-1H-indazole-5-carboxamide | 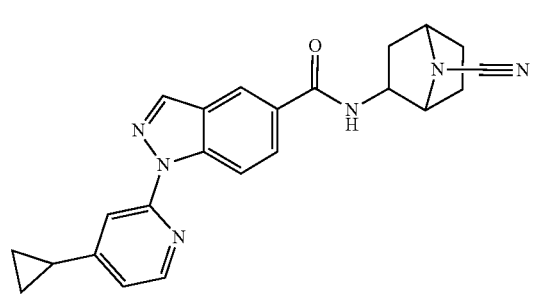 [SMILES: N#CN1C2CCC1C(NC(=O)c1ccc3c(cnn3-c3cc(C4CC4)ccn3)c1)C2] |
| 13-13 | Racemic, endo N-(7-cyano-7-azabicyclo[2.2.1]heptan-2-yl)-1-(6-cyclopropyl-2-pyridinyl)-1H-indazole-5-carboxamide | 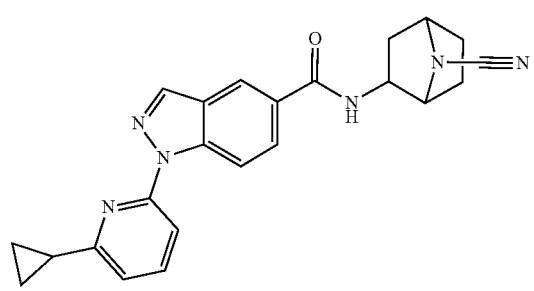 [SMILES: N#CN1C2CCC1C(NC(=O)c1ccc3c(cnn3-c3cccc(C4CC4)n3)c1)C2] |
| 13-14 | N-((1R,2R,4S)-7-cyano-7-azabicyclo[2.2.1]heptan-2-yl)-1-(6-cyclopropyl-2-pyridinyl)-1H-indazole-5-carboxamide | 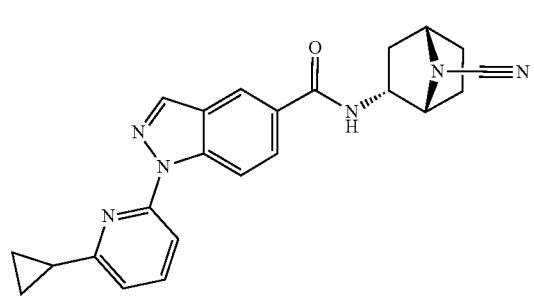 [SMILES: N#CN1[C@H]2CC[C@@H]1[C@H](NC(=O)c1ccc3c(cnn3-c3cccc(C4CC4)n3)c1)C2] |
| 13-15 | 3-(4-chloro-3-(trifluoromethyl)phenyl)-N-((1R,2R,4S)-7-cyano-7-azabicyclo[2.2.1]heptan-2-yl)propanamide | 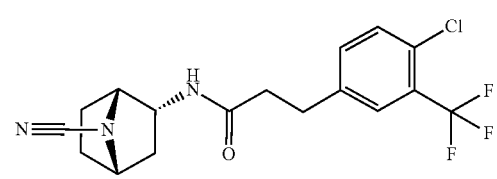 [SMILES: N#CN1[C@H]2CC[C@@H]1[C@H](NC(=O)CCc1ccc(Cl)c(C(F)(F)F)c1)C2] |

| Ex # | Name[FB-L22] | Structure |
|---|---|---|
| 13-16 | N-((1R,2R,4S)-7-cyano-7-azabicyclo[2.2.1]heptan-2-yl)-1-(6-ethyl-2-pyridinyl)-1H-indazole-5-carboxamide | 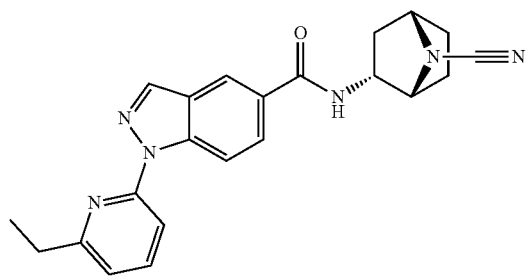 [SMILES: CCc1cccc(-n2ncc3cc(C(=O)N[C@@H]4C[C@@H]5CC[C@H]4N5C#N)ccc32)n1] |
| 13-17 | N-((1R,2R,4S)-7-cyano-7-azabicyclo[2.2.1]heptan-2-yl)-1-(4-methyl-2-pyrimidinyl)-1H-pyrrolo[3,2-b]pyridine-5-carboxamide | 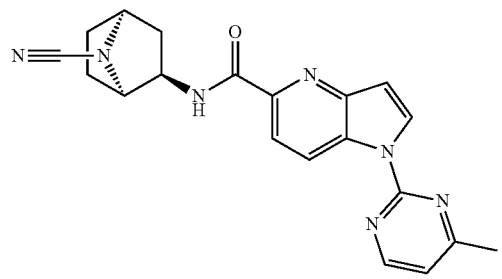 [SMILES: Cc1ccnc(-n2ccc3nc(C(=O)N[C@@H]4C[C@@H]5CC[C@H]4N5C#N)ccc32)n1] |
| 13-18 | N-((1R,2R,4S)-7-cyano-7-azabicyclo[2.2.1]heptan-2-yl)-4-fluoro-1-(4-methyl-2-pyrimidinyl)-1H-indole-5-carboxamide | 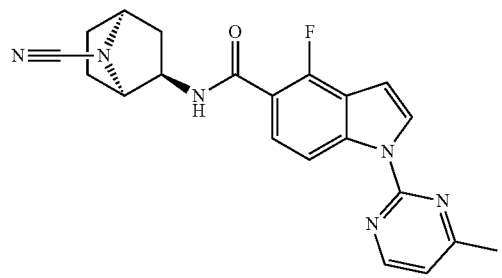 [SMILES: Cc1ccnc(-n2ccc3c(F)c(C(=O)N[C@@H]4C[C@@H]5CC[C@H]4N5C#N)ccc32)n1] |
| 13-19 | N-((1R,2R,4S)-7-cyano-7-azabicyclo[2.2.1]heptan-2-yl)-4-(methyl(4-methyl-2-pyrimidinyl)amino)benzamide | 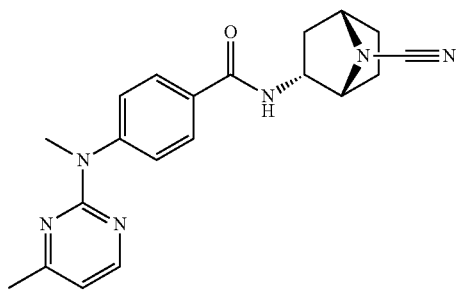 [SMILES: Cc1ccnc(N(C)c2ccc(C(=O)N[C@@H]3C[C@@H]4CC[C@H]3N4C#N)cc2)n1] |
| 13-20 | N-((1R,2R,4S)-7-cyano-7-azabicyclo[2.2.1]heptan-2-yl)-4-methyl-1-(4-methyl-2-pyrimidinyl)-1H-indole-5-carboxamide | 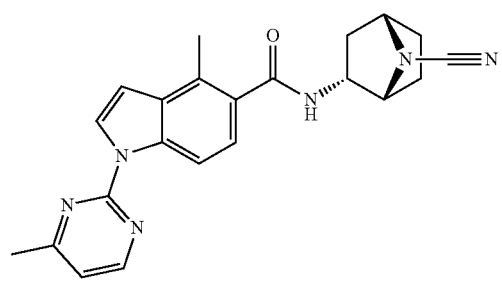 [SMILES: Cc1ccnc(-n2ccc3c(C)c(C(=O)N[C@@H]4C[C@@H]5CC[C@H]4N5C#N)ccc32)n1] |

-continued

| Ex # | Name[FB-L22] | Structure |
|---|---|---|
| 14-1 | Racemic, endo N-(7-cyano-7-azabicyclo[2.2.1]heptan-2-yl)-4-(2-pyrimidinylamino)benzamide | 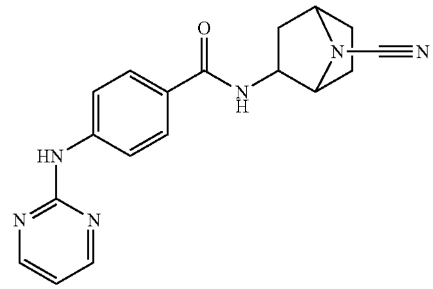 [SMILES: N#CN1C2CCC1C(NC(=O)c1ccc(Nc3ncccn3)cc1)C2] |
| 14-2 | N-((1R,2R,4S)-7-cyano-7-azabicyclo[2.2.1]heptan-2-yl)-6-(3,5-dimethyl-1,2-oxazol-4-yl)-1H-indole-2-carboxamide | 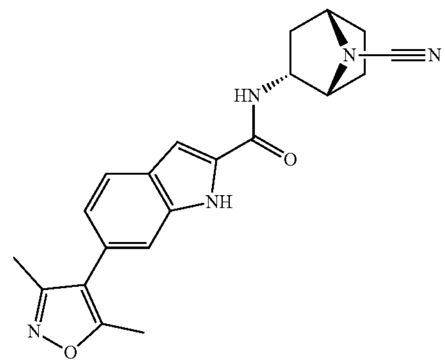 [SMILES: Cc1noc(C)c1-c1ccc2cc(C(=O)N[C@@H]3C[C@@H]4CC[C@H]3N4C#N)[nH]c2c1] |
| 14-3 | N-((1R,2R,4S)-7-cyano-7-azabicyclo[2.2.1]heptan-2-yl)-1-(4-cyclopropyl-2-pyrimidinyl)-2,3-dihydro-1H-indole-5-carboxamide | 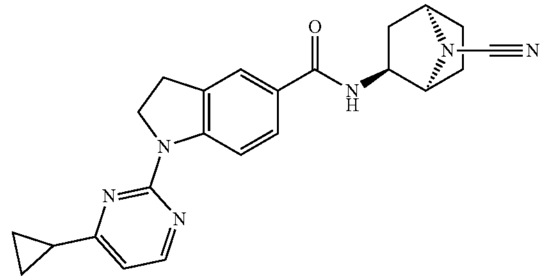 [SMILES: N#CN1[C@@H]2CC[C@H]1[C@@H](NC(=O)c1ccc3c(c1)CCN3c1nccc(C3CC3)n1)C2] |
| 14-4 | N-((1R,2R,4S)-7-cyano-7-azabicyclo[2.2.1]heptan-2-yl)-1-(4-cyclopropyl-2-pyrimidinyl)-2,3-dihydro-1H-indole-5-carboxamide | 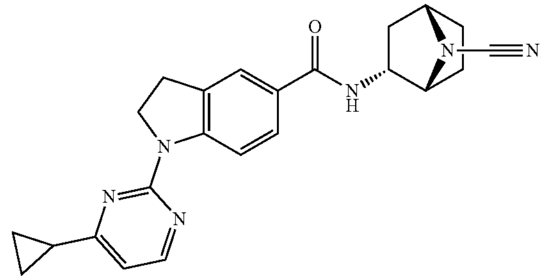 [SMILES: N#CN1[C@H]2CC[C@@H]1[C@H](NC(=O)c1ccc3c(c1)CCN3c1nccc(C3CC3)n1)C2] |
| 14-5 | N-((1R,2R,4S)-7-cyano-7-azabicyclo[2.2.1]heptan-2-yl)-4-(1-methyl-1H-pyrazol-4-yl)benzamide | 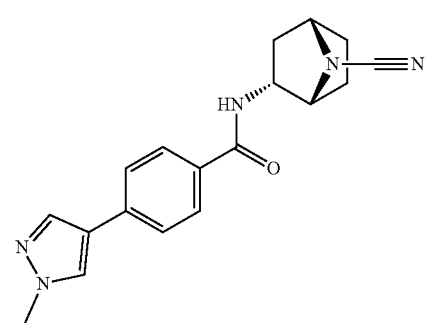 [SMILES: Cn1cc(-c2ccc(C(=O)N[C@@H]3C[C@@H]4CC[C@H]3N4C#N)cc2)cn1] |

-continued

| Ex # | Name[FB-L22] | Structure |
|---|---|---|
| 15-1 | 6-chloro-N-((1R,2R,4S)-7-cyano-7-azabicyclo[2.2.1]heptan-2-yl)-1-(4-methyl-2-pyrimidinyl)-2,3-dihydro-1H-indole-5-carboxamide | 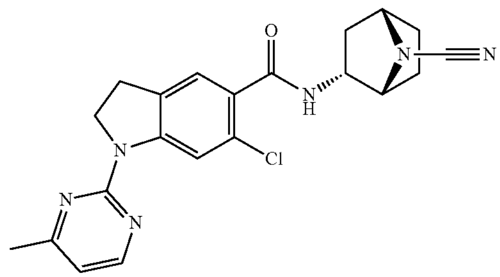 [SMILES: Cc1ccnc(N2CCc3cc(C(=O)N[C@@H]4C[C@@H]5CC[C@H]4N5C#N)c(Cl)cc32)n1] |
| 16-1 | 5-(3-chlorophenyl)-N-((1R,2R,4S)-7-cyano-7-azabicyclo[2.2.1]heptan-2-yl)-4-methyl-1,3-thiazole-2-carboxamide | 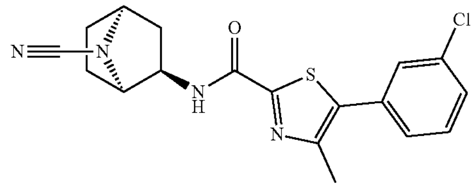 [SMILES: Cc1nc(C(=O)N[C@@H]2C[C@@H]3CC[C@H]2N3C#N)sc1-c1cccc(Cl)c1] |
| 16-2 | 5-(3-chlorophenyl)-N-((1R,2R,4S)-7-cyano-7-azabicyclo[2.2.1]heptan-2-yl)-1,3-thiazole-2-carboxamide | 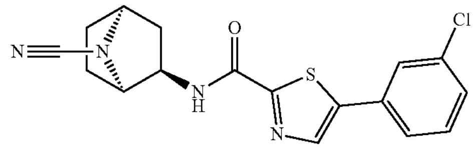 [SMILES: N#CN1[C@H]2CC[C@@H]1[C@H](NC(=O)c1ncc(-c3cccc(Cl)c3)s1)C2] |
| 1-65 | 2-chloro-N-((1R,2R,4S)-7-cyano-7-azabicyclo[2.2.1]heptan-2-yl)-4-((cyclopropylcarbonyl)amino)benzamide | 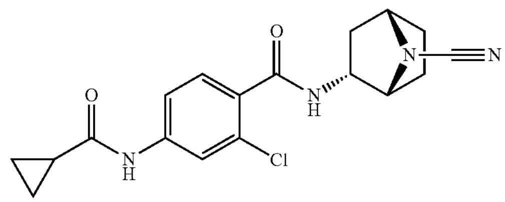 [SMILES: N#CN1[C@H]2CC[C@@H]1[C@H](NC(=O)c1ccc(NC(=O)C3CC3)cc1Cl)C2] |
| 1-66 | 2-chloro-N-((1R,2R,4S)-7-cyano-7-azabicyclo[2.2.1]heptan-2-yl)-4-(1H-indazol-1-yl)benzamide | 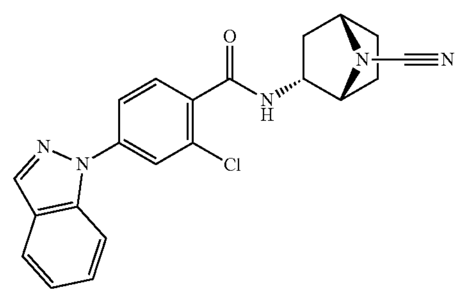 [SMILES: N#CN1[C@H]2CC[C@@H]1[C@H](NC(=O)c1ccc(-n3ncc4ccccc43)cc1Cl)C2] |
| 1-68-2 | (3S)-6-chloro-N-((1R,2R,4S)-7-cyano-7-azabicyclo[2.2.1]heptan-2-yl)-2,3,4,9-tetrahydro-1H-carbazole-3-carboxamide | 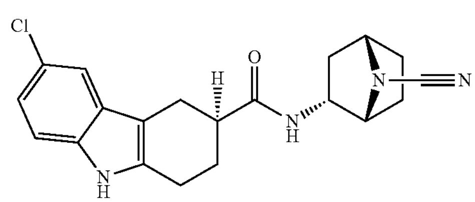 [SMILES: N#CN1[C@H]2CC[C@@H]1[C@H](NC(=O)[C@H]1CCc3[nH]c4ccc(Cl)cc4c3C1)C2] |
| 1-69 | (4R)-7-chloro-N-((1R,2R,4S)-7-cyano-7-azabicyclo[2.2.1]heptan-2-yl)-2,3,4,5-tetrahydro-1-benzoxepine-4-carboxamide | 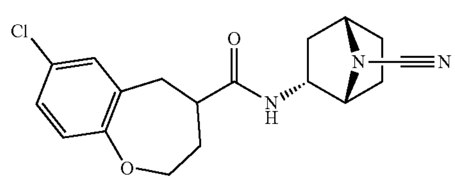 [SMILES: N#CN1[C@H]2CC[C@@H]1[C@H](NC(=O)C1CCOc3ccc(Cl)cc3C1)C2] |

| Ex # | Name[FB-L22] | Structure |
|---|---|---|
| 1-70 | 5-chloro-N-((1R,2R,4S)-7-cyano-7-azabicyclo[2.2.1]heptan-2-yl)-1-methyl-3-(6-methyl-2-pyridinyl)-1H-indazole-6-carboxamide | 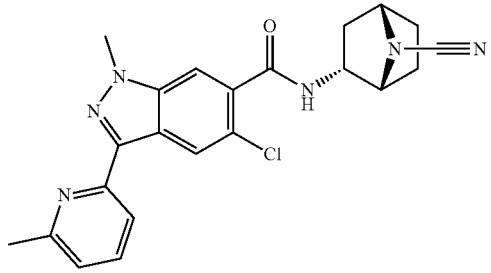 [SMILES: Cc1cccc(-c2nn(C)c3cc(C(=O)N[C@@H]4C[C@@H]5CC[C@H]4N5C#N)c(Cl)cc23)n1] |
| 1-71 | N-((1R,2R,4S)-7-cyano-7-azabicyclo[2.2.1]heptan-2-yl)-1-(cyclopropylmethyl)-3-(6-methyl-2-pyridinyl)-1H-indazole-6-carboxamide | 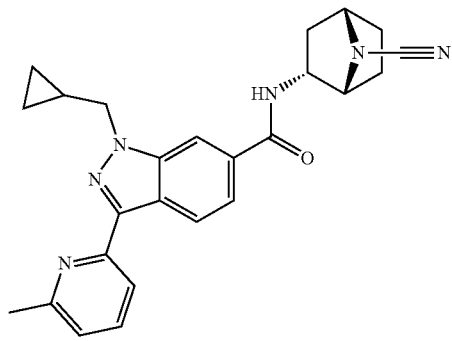 [SMILES: Cc1cccc(-c2nn(CC3CC3)c3cc(C(=O)N[C@@H]4C[C@@H]5CC[C@H]4N5C#N)ccc23)n1] |
| 1-72 | N-((1R,2R,4S)-7-cyano-7-azabicyclo[2.2.1]heptan-2-yl)-1-(2-methylpropyl)-3-(6-methyl-2-pyridinyl)-1H-indazole-6-carboxamide | 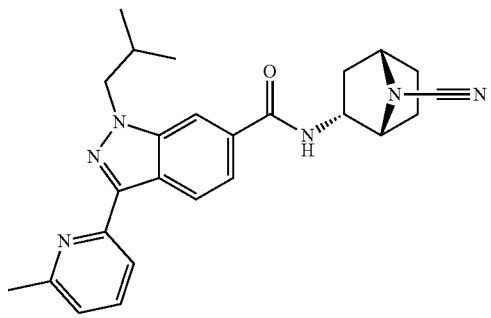 [SMILES: Cc1cccc(-c2nn(CC(C)C)c3cc(C(=O)N[C@@H]4C[C@@H]5CC[C@H]4N5C#N)ccc23)n1] |
| 1-73 | N-((1R,2R,4S)-7-cyano-7-azabicyclo[2.2.1]heptan-2-yl)-3-(6-methyl-2-pyridinyl)-1-(4,4,4-trifluorobutyl)-1H-indazole-6-carboxamide | 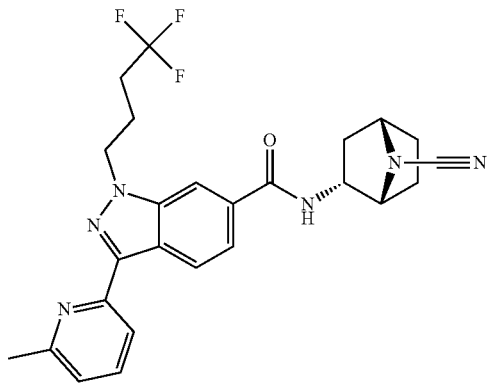 [SMILES: Cc1cccc(-c2nn(CCCC(F)(F)F)c3cc(C(=O)N[C@@H]4C[C@@H]5CC[C@H]4N5C#N)ccc23)n1] |

| Ex # | Name[FB-L22] | Structure |
|---|---|---|
| 1-74 | N-((1R,2R,4S)-7-cyano-7-azabicyclo[2.2.1]heptan-2-yl)-3-(6-methyl-2-pyridinyl)-1-propyl-1H-indazole-6-carboxamide | 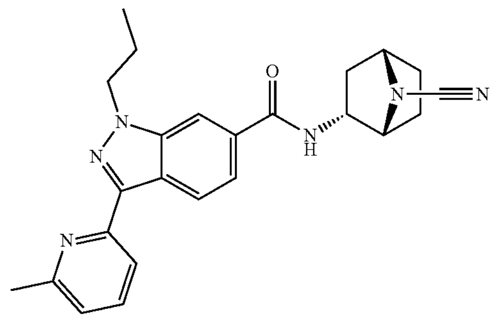 [SMILES: CCCn1nc(-c2cccc(C)n2)c2ccc(C(=O)N[C@@H]3C[C@@H]4CC[C@H]3N4C#N)cc21] |
| 1-75 | 6-chloro-N-((1R,2R,4S)-7-cyano-7-azabicyclo[2.2.1]heptan-2-yl)-1-(6-(2,2,2-trifluoroethoxy)-2-pyridinyl)-1H-indazole-5-carboxamide | 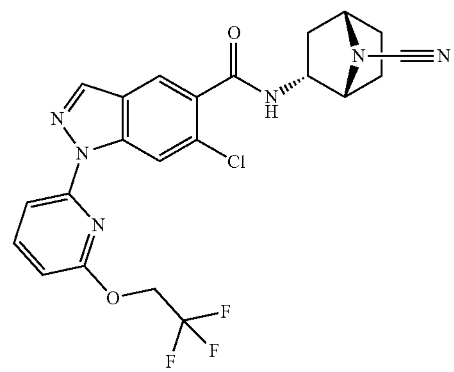 [SMILES: N#CN1[C@H]2CC[C@@H]1[C@H](NC(=O)c1cc3cnn(-c4cccc(OCC(F)(F)F)n4)c3cc1Cl)C2] |
| 1-76 | 6-chloro-N-((1R,2R,4S)-7-cyano-7-azabicyclo[2.2.1]heptan-2-yl)-1-(1,7-naphthyridin-2-yl)-1H-indazole-5-carboxamide | 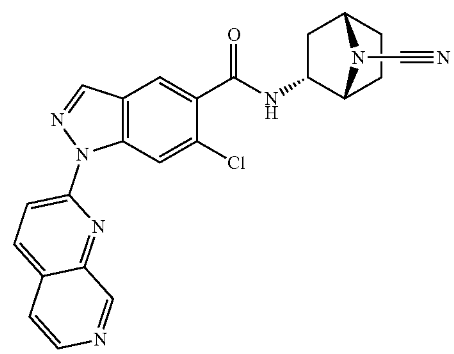 [SMILES: N#CN1[C@H]2CC[C@@H]1[C@H](NC(=O)c1cc3cnn(-c4ccc5ccncc5n4)c3cc1Cl)C2] |
| 1-77 | 6-chloro-N-((1R,2R,4S)-7-cyano-7-azabicyclo[2.2.1]heptan-2-yl)-1-(6-(cyanomethyl)-2-pyridinyl)-1H-indazole-5-carboxamide | 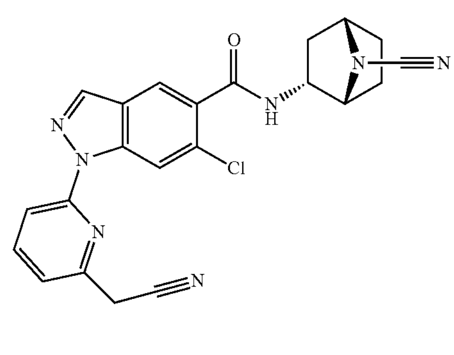 [SMILES: N#CCc1cccc(-n2ncc3cc(C(=O)N[C@@H]4C[C@@H]5CC[C@H]4N5C#N)c(Cl)cc32)n1] |

-continued

| Ex # | Name[FB-L22] | Structure |
|---|---|---|
| 1-78 | 6-chloro-N-((1R,2R,4S)-7-cyano-7-azabicyclo[2.2.1]heptan-2-yl)-1-(1,8-naphthyridin-2-yl)-1H-indazole-5-carboxamide | 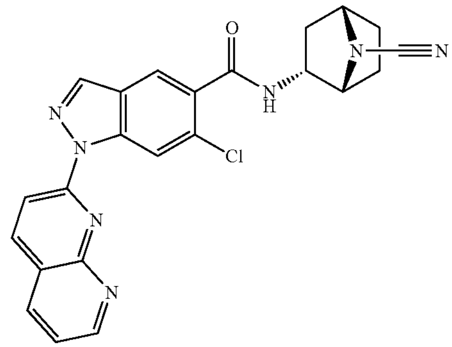 [SMILES: N#CN1[C@H]2CC[C@@H]1[C@H](NC(=O)c1cc3cnn(-c4ccc5cccnc5n4)c3cc1Cl)C2] |
| 1-79 | 4-(3-chlorophenyl)-N-((1R,2R,4S)-7-cyano-7-azabicyclo[2.2.1]heptan-2-yl)-1,3-thiazole-2-carboxamide | 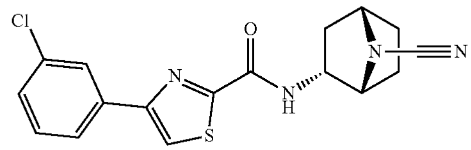 [SMILES: N#CN1[C@H]2CC[C@@H]1[C@H](NC(=O)c1nc(-c3cccc(Cl)c3)cs1)C2] |
| 1-80 | N-((1R,2R,4S)-7-cyano-7-azabicyclo[2.2.1]heptan-2-yl)-2-(3-thiophenyl)-1,3-thiazole-4-carboxamide | 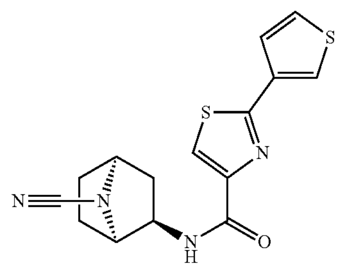 [SMILES: N#CN1[C@H]2CC[C@@H]1[C@H](NC(=O)c1csc(-c3ccsc3)n1)C2] |
| 1-81 | 1-(3-chlorophenyl)-N-((1R,2R,4S)-7-cyano-7-azabicyclo[2.2.1]heptan-2-yl)-1H-pyrazole-3-carboxamide | 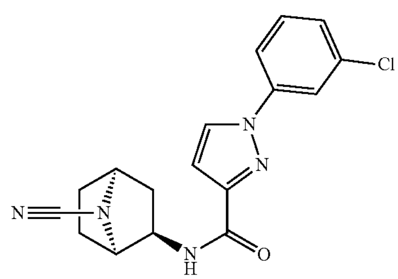 [SMILES: N#CN1[C@H]2CC[C@@H]1[C@H](NC(=O)c1ccn(-c3cccc(Cl)c3)n1)C2] |
| 1-82 | 1-(3-chlorophenyl)-N-((1R,2R,4S)-7-cyano-7-azabicyclo[2.2.1]heptan-2-yl)-5-methyl-1H-pyrazole-3-carboxamide | 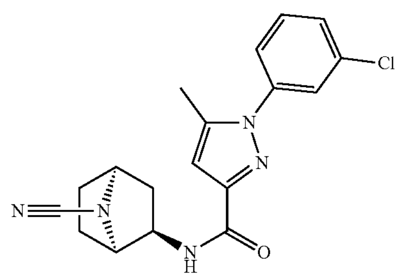 [SMILES: Cc1cc(C(=O)N[C@@H]2C[C@@H]3CC[C@H]2N3C#N)nn1-c1cccc(Cl)c1] |
| 1-83 | N-((1R,2R,4S)-7-cyano-7-azabicyclo[2.2.1]heptan-2-yl)-3-(2-methyl-1,3-thiazol-4-yl)benzamide | 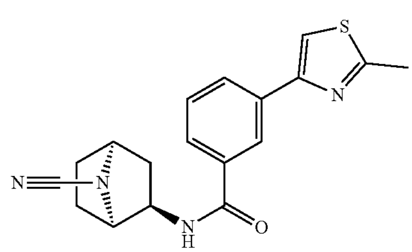 [SMILES: Cc1nc(-c2cccc(C(=O)N[C@@H]3C[C@@H]4CC[C@H]3N4C#N)c2)cs1] |

| Ex # | Name[FB-L22] | Structure |
|---|---|---|
| 1-84 | 7-bromo-N-((1R,2R,4S)-7-cyano-7-azabicyclo[2.2.1]heptan-2-yl)-1-oxo-1,2-dihydro-3-isoquinolinecarboxamide | 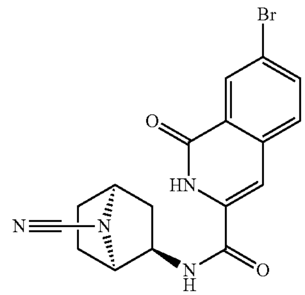 [SMILES: N#CN1[C@H]2CC[C@@H]1[C@H](NC(=O)c1cc3ccc(Br)cc3c(=O)[nH]1)C2] |
| 1-85 | N-((1R,2R,4S)-7-cyano-7-azabicyclo[2.2.1]heptan-2-yl)-1-phenyl-3-pyrrolidinecarboxamide | 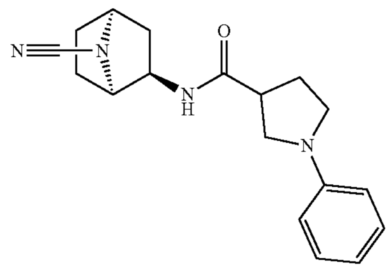 [SMILES: N#CN1[C@H]2CC[C@@H]1[C@H](NC(=O)C1CCN(c3ccccc3)C1)C2] |
| 1-86 | N-((1R,2R,4S)-7-cyano-7-azabicyclo[2.2.1]heptan-2-yl)-2-methyl-1-phenyl-3-pyrrolidinecarboxamide | 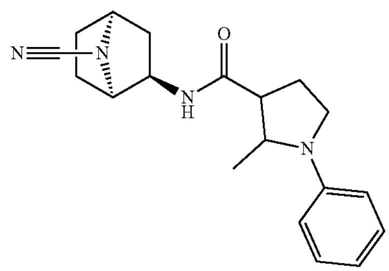 [SMILES: CC1C(C(=O)N[C@@H]2C[C@@H]3CC[C@H]2N3C#N)CCN1c1ccccc1] |
| 1-87 | (3S)-N-(1R,2R,4S)-7-cyano-7-azabicyclo[2.2.1]heptan-2-yl)-1-(4-cyano-2-fluorophenyl)-3-pyrrolidinecarboxamide | 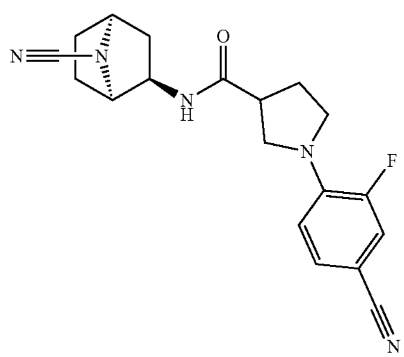 [SMILES: N#Cc1ccc(N2CCC(C(=O)N[C@@H]3C[C@@H]4CC[C@H]3N4C#N)C2)c(F)c1] |
| 1-88 | 1-(3-chlorophenyl)-N-((1R,2R,4S)-7-cyano-7-azabicyclo[2.2.1]heptan-2-yl)-3-pyrrolidinecarboxamide | 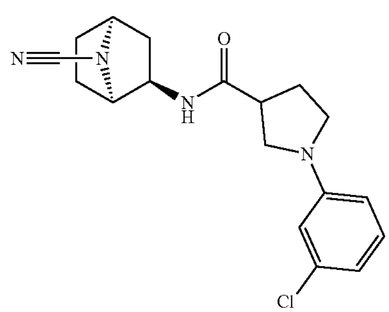 |

-continued

| Ex # | Name[FB-L22] | Structure |
|---|---|---|
| 1-89 | N-((1R,2R,4S)-7-cyano-7-azabicyclo[2.2.1]heptan-2-yl)-5-phenyl-2-furancarboxamide | 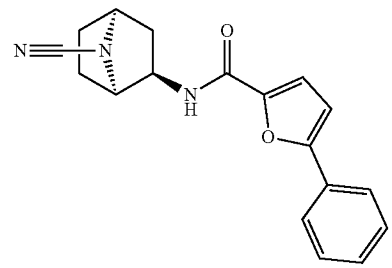 [SMILES: N#CN1[C@H]2CC[C@@H]1[C@H](NC(=O)c1ccc(-c3ccccc3)o1)C2] |
| 1-90 | N-((1R,2R,4S)-7-cyano-7-azabicyclo[2.2.1]heptan-2-yl)-5-(3-(2-propanyl)phenyl)-2-furancarboxamide | 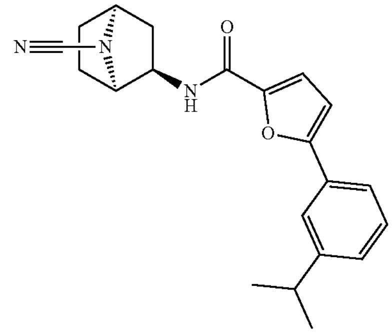 [SMILES: CC(C)c1cccc(-c2ccc(C(=O)N[C@@H]3C[C@@H]4CC[C@H]3N4C#N)o2)c1] |
| 1-91 | N-((1R,2R,4S)-7-cyano-7-azabicyclo[2.2.1]heptan-2-yl)-5-(3-(trifluoromethyl)phenyl)-2-furancarboxamide | 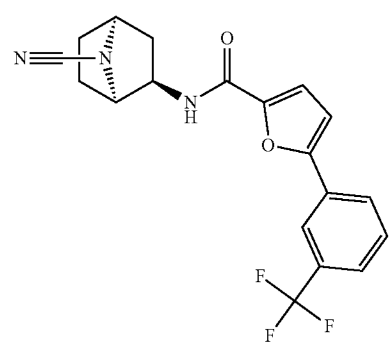 [SMILES: N#CN1[C@H]2CC[C@@H]1[C@H](NC(=O)c1ccc(-c3cccc(C(F)(F)F)c3)o1)C2] |
| 1-92 | 1-(3-chlorophenyl)-N-((1R,2R,4S)-7-cyano-7-azabicyclo[2.2.1]heptan-2-yl)-3-piperidinecarboxamide | 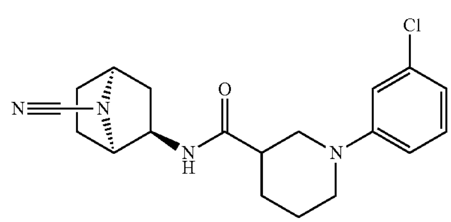 [SMILES: N#CN1[C@H]2CC[C@@H]1[C@H](NC(=O)C1CCCN(c3cccc(Cl)c3)C1)C2] |
| 1-93 | N-((1R,2R,4S)-7-cyano-7-azabicyclo[2.2.1]heptan-2-yl)-1-(4-(trifluoromethyl)-2-pyrimidinyl)-4-piperidinecarboxamide | 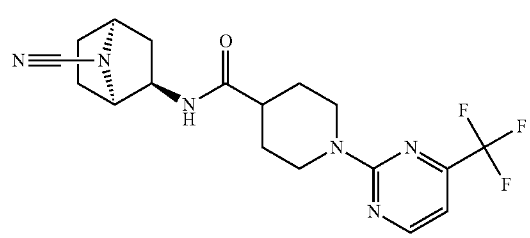 [SMILES: N#CN1[C@H]2CC[C@@H]1[C@H](NC(=O)C1CCN(c3nccc(C(F)(F)F)n3)CC1)C2] |

| Ex # | Name[FB-L22] | Structure |
|---|---|---|
| 1-94 | 1-(3-bromophenyl)-N-((1R,2R,4S)-7-cyano-7-azabicyclo[2.2.1]heptan-2-yl)-3-pyrrolidinecarboxamide | 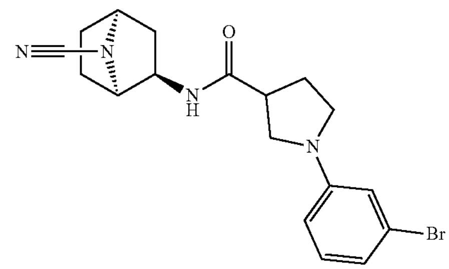 [SMILES: N#CN1[C@H]2CC[C@@H]1[C@H](NC(=O)C1CCN(c3cccc(Br)c3)C1)C2] |
| 1-95 | 1-(3-chloro-4-(trifluoromethyl)phenyl)-N-((1R,2R,4S)-7-cyano-7-azabicyclo[2.2.1]heptan-2-yl)-3-pyrrolidinecarboxamide | 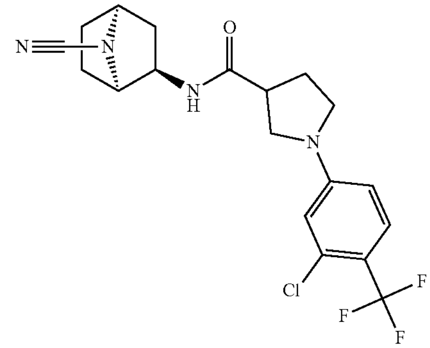 [SMILES: N#CN1[C@H]2CC[C@@H]1[C@H](NC(=O)C1CCN(c3ccc(C(F)(F)F)c(Cl)c3)C1)C2] |
| 1-96 | 6-chloro-N-((1R,2R,4S)-7-cyano-7-azabicyclo[2.2.1]heptan-2-yl)-3,4-dihydro-2H-chromene-3-carboxamide | 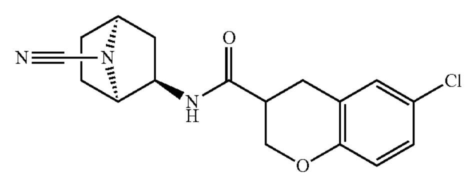 [SMILES: N#CN1[C@H]2CC[C@@H]1[C@H](NC(=O)C1COc3ccc(Cl)cc3C1)C2] |
| 1-97 | 2-chloro-N-((1R,2R,4S)-7-cyano-7-azabicyclo[2.2.1]heptan-2-yl)-4-(6-cyclopropyl-2-pyridinyl)benzamide | 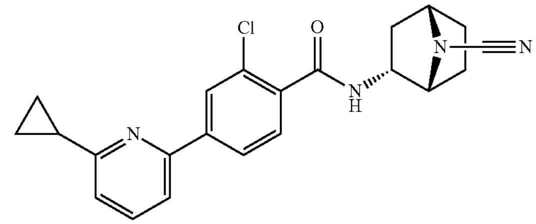 [SMILES: N#CN1[C@H]2CC[C@@H]1[C@H](NC(=O)c1ccc(-c3cccc(C4CC4)n3)cc1Cl)C2] |
| 2-2 | 1-(3-chlorophenyl)-N-((1R,2R,4S)-7-cyano-7-azabicyclo[2.2.1]heptan-2-yl)-4-piperidinecarboxamide | 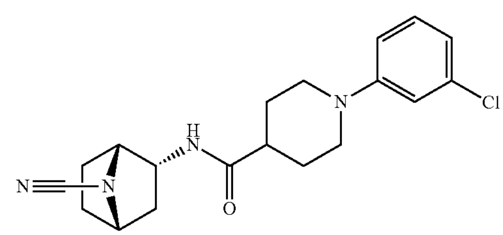 [SMILES: N#CN1[C@H]2CC[C@@H]1[C@H](NC(=O)C1CCN(c3cccc(Cl)c3)CC1)C2] |
| 2-3 | N-((1R,2R,4S)-7-cyano-7-azabicyclo[2.2.1]heptan-2-yl)-1-(3,5-dichlorophenyl)-4-piperidinecarboxamide | 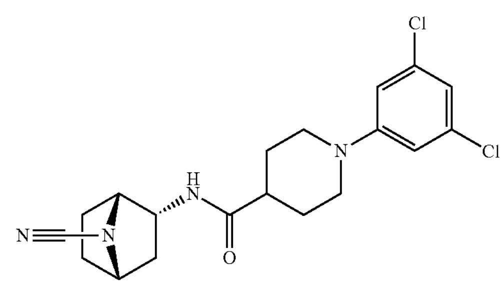 [SMILES: N#CN1[C@H]2CC[C@@H]1[C@H](NC(=O)C1CCN(c3cc(Cl)cc(Cl)c3)CC1)C2] |

-continued

| Ex # | Name[FB-L22] | Structure |
|---|---|---|
| 2-4 | (3S)-N-((1R,2R,4S)-7-cyano-7-azabicyclo[2.2.1]heptan-2-yl)-1-(4-methyl-2-pyridinyl)-3-pyrrolidinecarboxamide | 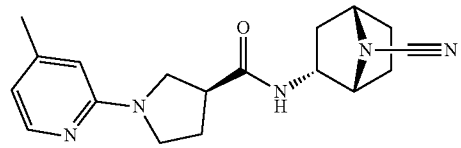 [SMILES: Cc1ccnc(N2CC[C@H](C(=O)N[C@@H]3C[C@@H]4CC[C@H]3N4C#N)C2)c1] |
| 2-5 | (3S)-N-((1R,2R,4S)-7-cyano-7-azabicyclo[2.2.1]heptan-2-yl)-1-(5-cyano-3-pyridinyl)-3-pyrrolidinecarboxamide | 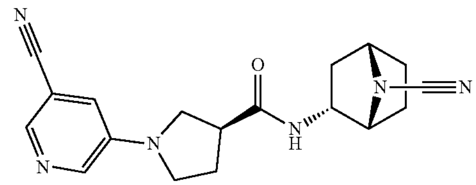 [SMILES: N#Cc1cncc(N2CC[C@H](C(=O)N[C@@H]3C[C@@H]4CC[C@H]3N4C#N)C2)c1] |
| 2-6 | (3S)-N-((1R,2R,4S)-7-cyano-7-azabicyclo[2.2.1]heptan-2-yl)-1-(2-methoxy-4-pyridinyl)-3-pyrrolidinecarboxamide | 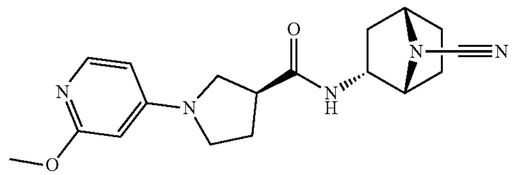 [SMILES: COc1cc(N2CC[C@H](C(=O)N[C@@H]3C[C@@H]4CC[C@H]3N4C#N)C2)ccn1] |
| 2-7 | (3S)-N-((1R,2R,4S)-7-cyano-7-azabicyclo[2.2.1]heptan-2-yl)-1-(6-methyl-2-pyridinyl)-3-pyrrolidinecarboxamide | 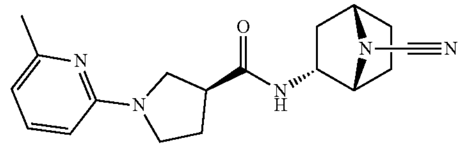 [SMILES: Cc1cccc(N2CC[C@H](C(=O)N[C@@H]3C[C@@H]4CC[C@H]3N4C#N)C2)n1] |
| 2-8 | (3S)-N-((1R,2R,4S)-7-cyano-7-azabicyclo[2.2.1]heptan-2-yl)-1-(6-methyl-2-pyrazinyl)-3-pyrrolidinecarboxamide | 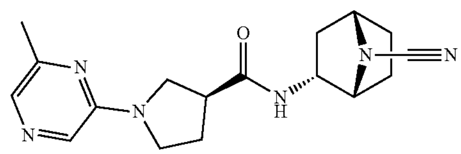 [SMILES: Cc1cncc(N2CC[C@H](C(=O)N[C@@H]3C[C@@H]4CC[C@H]3N4C#N)C2)n1] |
| 2-9 | N-((1R,2R,4S)-7-cyano-7-azabicyclo[2.2.1]heptan-2-yl)-1-(3,5-dichlorophenyl)-3-methyl-3-pyrrolidinecarboxamide | 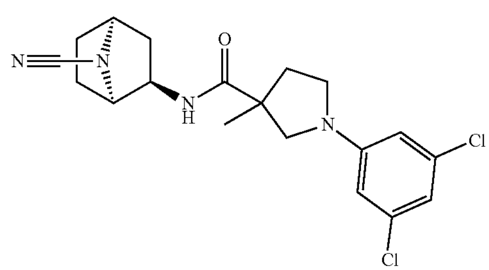 [SMILES: CC1(C(=O)N[C@@H]2C[C@@H]3CC[C@H]2N3C#N)CCN(c2cc(Cl)cc(Cl)c2)C1] |
| 2-10 | N-((1R,2R,4S)-7-cyano-7-azabicyclo[2.2.1]heptan-2-yl)-1-(3,5-dichlorophenyl)-3-fluoro-3-pyrrolidinecarboxamide | 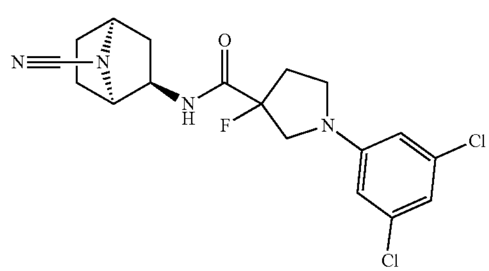 [SMILES: N#CN1[C@H]2CC[C@@H]1[C@H](NC(=O)C1(F)CCN(c3cc(Cl)cc(Cl)c3)C1)C2] |

-continued

| Ex # | Name[FB-L22] | Structure |
|---|---|---|
| 2-11 | N-((1R,2R,4S)-7-cyano-7-azabicyclo[2.2.1]heptan-2-yl)-2-(3,5-dichlorophenyl)-2-azabicyclo[3.1.0]hexane-4-carboxamide | 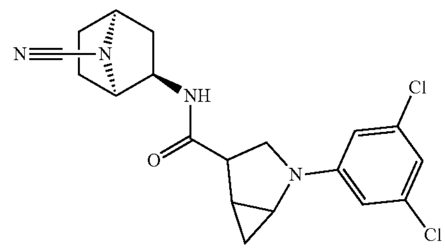 [SMILES: N#CN1[C@H]2CC[C@@H]1[C@H](NC(=O)C1CN(c3cc(Cl)cc(Cl)c3)C3CC13)C2] |
| 2-12 | 2-(3-chlorophenyl)-N-((1R,2R,4S)-7-cyano-7-azabicyclo[2.2.1]heptan-2-yl)-1,3-oxazole-5-carboxamide | 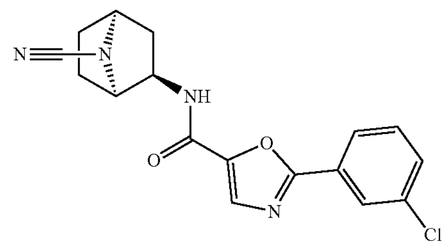 [SMILES: N#CN1[C@H]2CC[C@@H]1[C@H](NC(=O)c1cnc(-c3cccc(Cl)c3)o1)C2] |
| 2-13 | (3S)-N-((1R,2R,4S)-7-cyano-7-azabicyclo[2.2.1]heptan-2-yl)-1-(3-(cyanomethyl)phenyl)-3-pyrrolidinecarboxamide | 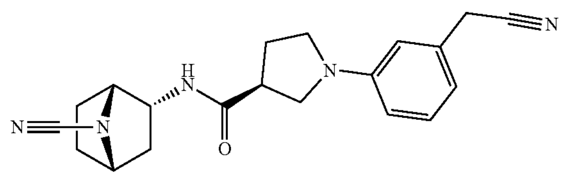 [SMILES: N#CCc1cccc(N2CC[C@H](C(=O)N[C@@H]3C[C@@H]4CC[C@H]3N4C#N)C2)c1] |
| 2-14 | (3S)-1-(3-chloro-5-methoxyphenyl)-N-((1R,2R,4S)-7-cyano-7-azabicyclo[2.2.1]heptan-2-yl)-3-pyrrolidinecarboxamide | 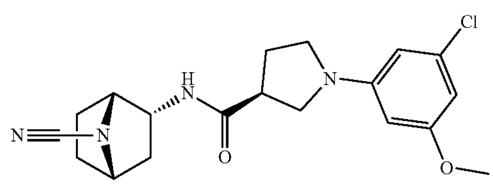 [SMILES: COc1cc(Cl)cc(N2CC[C@H](C(=O)N[C@@H]3C[C@@H]4CC[C@H]3N4C#N)C2)c1] |
| 2-15 | N-((1R,2R,4S)-7-cyano-7-azabicyclo[2.2.1]heptan-2-yl)-1-(3,5-dichlorophenyl)-L-prolinamide | 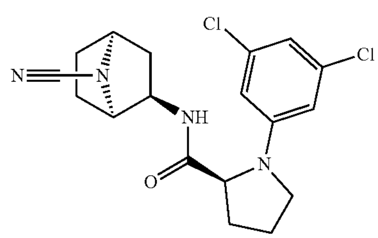 [SMILES: N#CN1[C@H]2CC[C@@H]1[C@H](NC(=O)[C@@H]1CCCN1c1cc(Cl)cc(Cl)c1)C2] |
| 2-16 | 3'-chloro-N-((1R,2R,4S)-7-cyano-7-azabicyclo[2.2.1]heptan-2-yl)[biphenyl]-3-carboxamide | 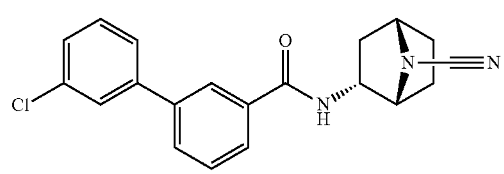 [SMILES: N#CN1[C@H]2CC[C@@H]1[C@H](NC(=O)c1cccc(-c3cccc(Cl)c3)c1)C2] |
| 2-17 | N-((1R,2R,4S)-7-cyano-7-azabicyclo[2.2.1]heptan-2-yl)-4-(2,5-dichlorophenyl)-5-methyl-2-pyridinecarboxamide | 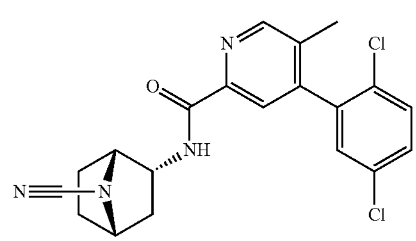 [SMILES: Cc1cnc(C(=O)N[C@@H]2C[C@@H]3CC[C@H]2N3C#N)cc1-c1cc(Cl)ccc1Cl] |

-continued

| Ex # | Name[FB-L22] | Structure |
|---|---|---|
| 2-18 | 4-(3-chlorophenyl)-N-((1R,2R,4S)-7-cyano-7-azabicyclo[2.2.1]heptan-2-yl)-5-methyl-2-pyridinecarboxamide | 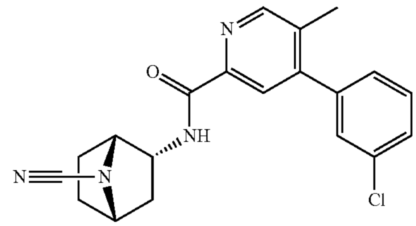 [SMILES: Cc1cnc(C(=O)N[C@@H]2C[C@@H]3CC[C@H]2N3C#N)cc1-c1cccc(Cl)c1] |
| 2-19 | N-((1R,2R,4S)-7-cyano-7-azabicyclo[2.2.1]heptan-2-yl)-1-(6-(1-cyanocyclopropyl)-2-pyridinyl)-4-piperidinecarboxamide | 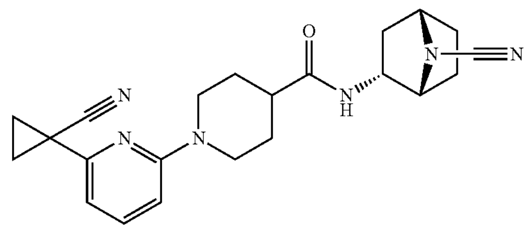 [SMILES: N#CN1[C@H]2CC[C@@H]1[C@H](NC(=O)C1CCN(c3cccc(C4(C#N)CC4)n3)CC1)C2] |
| 2-20 | N-((1R,2R,4S)-7-cyano-7-azabicyclo[2.2.1]heptan-2-yl)-6-(3-(1-cyanocyclopropyl)phenyl)-3-pyridinecarboxamide | 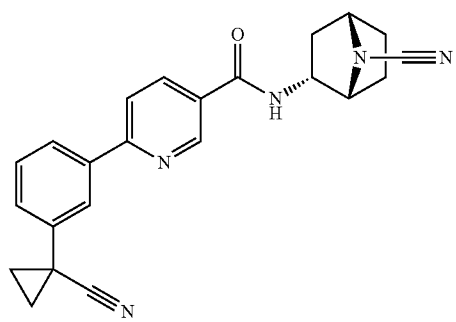 [SMILES: N#CN1[C@H]2CC[C@@H]1[C@H](NC(=O)c1ccc(-c3cccc(C4(C#N)CC4)c3)nc1)C2] |
| 2-21 | 3-chloro-N-((1R,2R,4S)-7-cyano-7-azabicyclo[2.2.1]heptan-2-yl)-3'-cyclopropyl-5'-fluoro[biphenyl]-4-carboxamide | 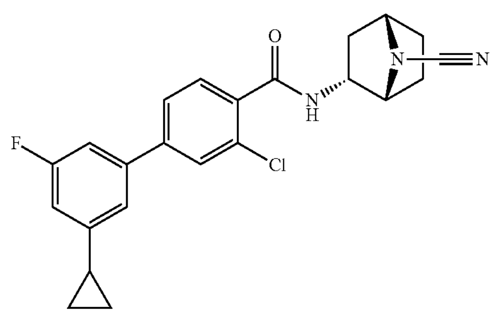 [SMILES: N#CN1[C@H]2CC[C@@H]1[C@H](NC(=O)c1ccc(-c3cc(F)cc(C4CC4)c3)cc1Cl)C2] |
| 2-22 | N-((1R,2R,4S)-7-cyano-7-azabicyclo[2.2.1]heptan-2-yl)-6-(1-cyanocyclopropyl)[2,3'-bipyridine]-6'-carboxamide | 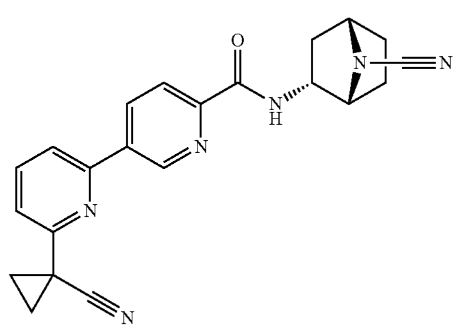 [SMILES: N#CN1[C@H]2CC[C@@H]1[C@H](NC(=O)c1ccc(-c3cccc(C4(C#N)CC4)n3)cn1)C2] |

-continued

| Ex # | Name[FB-L22] | Structure |
|---|---|---|
| 2-23 | 2-chloro-N-((1R,2R,4S)-7-cyano-7-azabicyclo[2.2.1]heptan-2-yl)-4-(6-(1-ethynylcyclopropyl)-2-pyridinyl)benzamide | 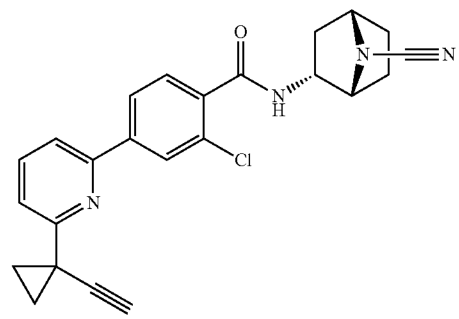 [SMILES: C#CC1(c2cccc(-c3ccc(C(=O)N[C@@H]4C[C@@H]5CC[C@H]4N5C#N)c(Cl)c3)n2)CC1] |
| 2-24-1 | 2-chloro-N-((1R,2R,4S)-7-cyano-7-azabicyclo[2.2.1]heptan-2-yl)-4-((3R)-3-cyano-3-methyl-2,3-dihydro-1H-inden-5-yl)benzamide | 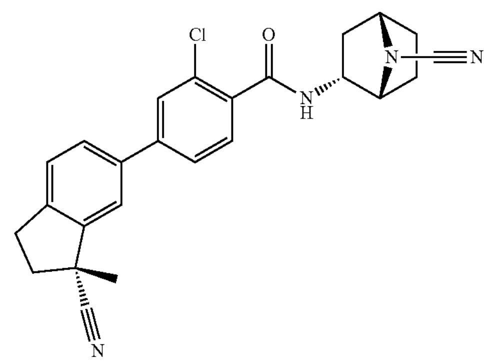 [SMILES: C[C@@]1(C#N)CCc2ccc(-c3ccc(C(=O)N[C@@H]4C[C@@H]5CC[C@H]4N5C#N)c(Cl)c3)cc21] |
| 2-24-2 | 2-chloro-N-((1R,2R,4S)-7-cyano-7-azabicyclo[2.2.1]heptan-2-yl)-4-((3S)-3-cyano-3-methyl-2,3-dihydro-1H-inden-5-yl)benzamide | 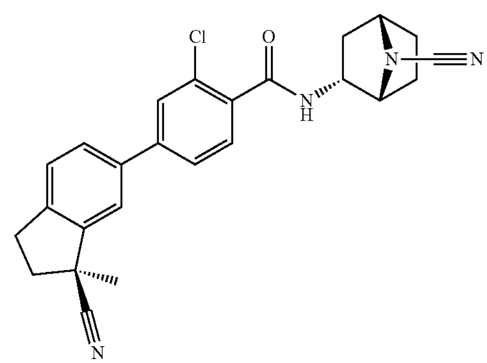 [SMILES: C[C@]1(C#N)CCc2ccc(-c3ccc(C(=O)N[C@@H]4C[C@@H]5CC[C@H]4N5C#N)c(Cl)c3)cc21] |
| 2-26 | 2-chloro-N-((1R,2R,4S)-7-cyano-7-azabicyclo[2.2.1]heptan-2-yl)-4-(6-(2-methyl-2-propanyl)-2-pyridinyl)benzamide | 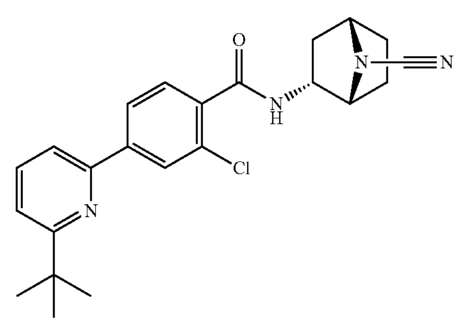 [SMILES: CC(C)(C)c1cccc(-c2ccc(C(=O)N[C@@H]3C[C@@H]4CC[C@H]3N4C#N)c(Cl)c2)n1] |

-continued

| Ex # | Name[FB-L22] | Structure |
|---|---|---|
| 2-27-2 | (1S,6R,7R)-N-((1R,2R,4S)-7-cyano-7-azabicyclo[2.2.1]heptan-2-yl)-3-(3,5-dichlorophenyl)-3-azabicyclo[4.1.0]heptane-7-carboxamide | 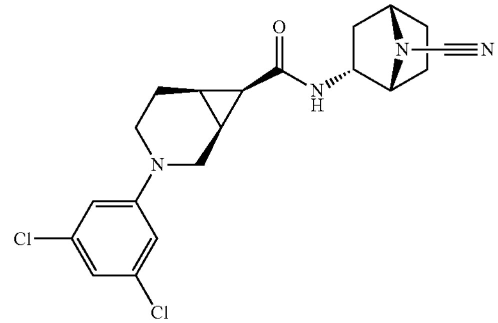 [SMILES: N#CN1[C@H]2CC[C@@H]1[C@H](NC(=O)[C@@H]1[C@@H]3CCN(c4cc(Cl)cc(Cl)c4)C[C@@H]31)C2] |
| 2-27-1 | (1R,6S,7R)-N-((1R,2R,4S)-7-cyano-7-azabicyclo[2.2.1]heptan-2-yl)-3-(3,5-dichlorophenyl)-3-azabicyclo[4.1.0]heptane-7-carboxamide | 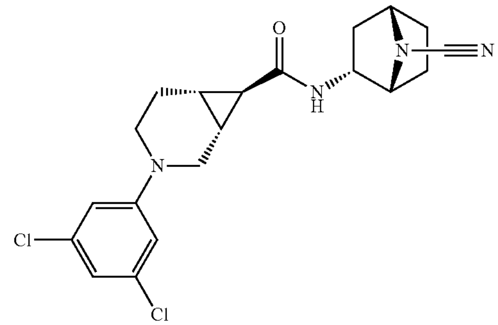 [SMILES: N#CN1[C@H]2CC[C@@H]1[C@H](NC(=O)[C@H]1[C@@H]3CN(c4cc(Cl)cc(Cl)c4)CC[C@@H]31)C2] |
| 2-29 | N-((1R,2R,4S)-7-cyano-7-azabicyclo[2.2.1]heptan-2-yl)-3-(3,5-dichlorophenyl)-3-azabicyclo[4.1.0]heptane-7-carboxamide | 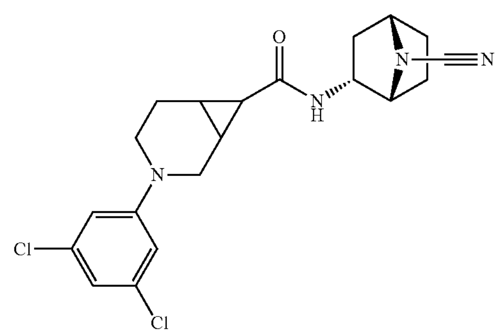 [SMILES: N#CN1[C@H]2CC[C@@H]1[C@H](NC(=O)C1C3CCN(c4cc(Cl)cc(Cl)c4)CC31)C2] |
| 2-30 | N-((1R,2R,4S)-7-cyano-7-azabicyclo[2.2.1]heptan-2-yl)-1-(6-cyclopropyl-2-pyridinyl)-3-piperidinecarboxamide | 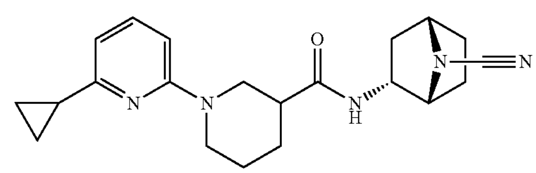 [SMILES: N#CN1[C@H]2CC[C@@H]1[C@H](NC(=O)C1CCCN(c3cccc(C4CC4)n3)C1)C2] |
| 2-31-2 | (1S,5S)-N-((1R,2R,4S)-7-cyano-7-azabicyclo[2.2.1]heptan-2-yl)-3-(3,5-dichlorophenyl)-3-azabicyclo[3.1.0]hexane-1-carboxamide | 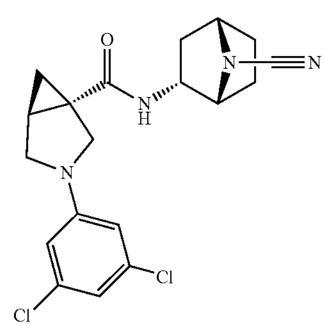 [SMILES: N#CN1[C@H]2CC[C@@H]1[C@H](NC(=O)[C@@]13C[C@@H]1CN(c1cc(Cl)cc(Cl)c1)C3)C2] |

-continued

| Ex # | Name[FB-L22] | Structure |
|---|---|---|
| 2-31-2 | (1R,5R)-N-((1R,2S,4S)-7-cyano-7-azabicyclo[2.2.1]heptan-2-yl)-3-(3,5-dichlorophenyl)-3-azabicyclo[3.1.0]hexane-1-carboxamide | 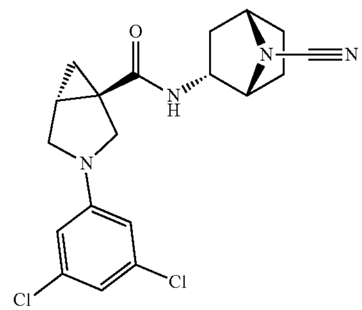 [SMILES: N#CN1[C@H]2CC[C@@H]1[C@H](NC(=O)[C@]13C[C@H]1CN(c1cc(Cl)cc(Cl)c1)C3)C2] |
| 2-33 | (1R,5S)-N-((1R,2R,4S)-7-cyano-7-azabicyclo[2.2.1]heptan-2-yl)-3-(3,5-dichlorophenyl)-3-azabicyclo[3.1.0]hexane-1-carboxamide | 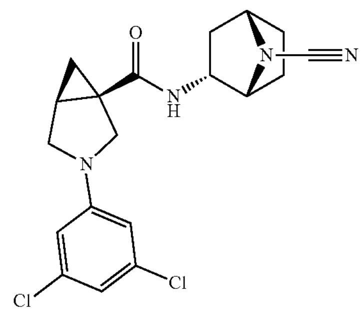 [SMILES: N#CN1[C@H]2CC[C@@H]1[C@H](NC(=O)[C@]13C[C@@H]1CN(c1cc(Cl)cc(Cl)c1)C3)C2] |
| 2-34 | (3S)-N-((1R,2R,4S)-7-cyano-7-azabicyclo[2.2.1]heptan-2-yl)-1-(6-(1-cyanocyclopropyl)-2-pyridinyl)-3-piperidinecarboxamide | 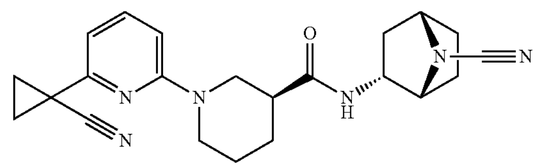 [SMILES: N#CN1[C@H]2CC[C@@H]1[C@H](NC(=O)[C@H]1CCCN(c3cccc(C4(C#N)CC4)n3)C1)C2] |
| 2-35 | N-((1R,2R,4S)-7-cyano-7-azabicyclo[2.2.1]heptan-2-yl)-1-cyclopentyl-1H-indazole-3-carboxamide | 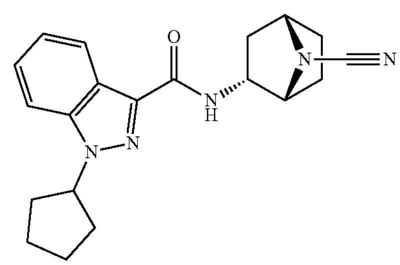 [SMILES: N#CN1[C@H]2CC[C@@H]1[C@H](NC(=O)c1nn(C3CCCC3)c3ccccc13)C2] |
| 2-36 | N-((1R,2R,4S)-7-cyano-7-azabicyclo[2.2.1]heptan-2-yl)-1-(6-cyclopropyl-2-pyridinyl)-4-piperidinecarboxamide | 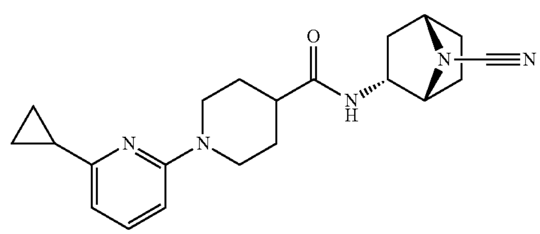 [SMILES: N#CN1[C@H]2CC[C@@H]1[C@H](NC(=O)C1CCN(c3cccc(C4CC4)n3)CC1)C2] |
| 2-37 | N-((1R,2R,4S)-7-cyano-7-azabicyclo[2.2.1]heptan-2-yl)-1-(3,5-dichlorophenyl)-1H-1,2,4-triazole-3-carboxamide | 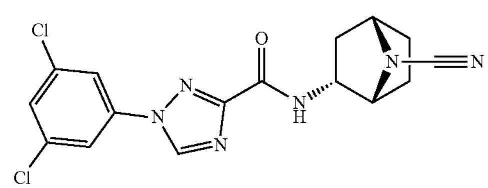 [SMILES: N#CN1[C@H]2CC[C@@H]1[C@H](NC(=O)c1ncn(-c3cc(Cl)cc(Cl)c3)n1)C2] |

-continued

| Ex # | Name[FB-L22] | Structure |
|---|---|---|
| 2-38 | 2-chloro-N-((1R,2R,4S)-7-cyano-7-azabicyclo[2.2.1]heptan-2-yl)-4-(6-(2-cyano-2-propanyl)-2-pyrazinyl)benzamide | 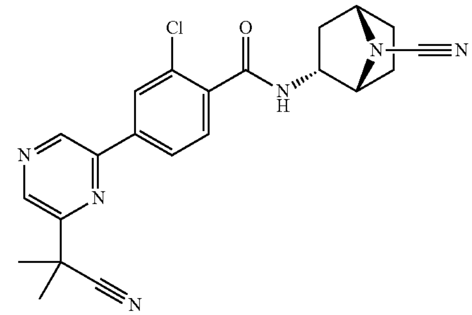 [SMILES: CC(C)(C#N)c1cncc(-c2ccc(C(=O)N[C@@H]3C[C@@H]4CC[C@H]3N4C#N)c(Cl)c2)n1] |
| 2-39-1 | 2-chloro-N-((1R,2R,4S)-7-cyano-7-azabicyclo[2.2.1]heptan-2-yl)-4-((3S)-3-cyano-1-piperidinyl)benzamide | 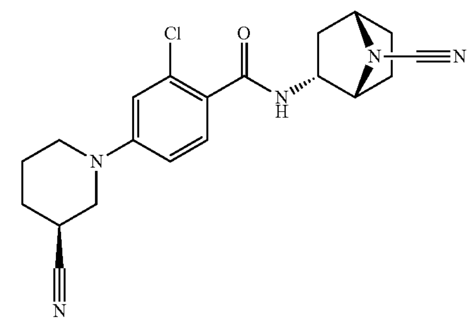 [SMILES: N#C[C@H]1CCCN(c2ccc(C(=O)N[C@@H]3C[C@@H]4CC[C@H]3N4C#N)c(Cl)c2)C1] |
| 2-39-2 | 2-chloro-N-((1R,2R,4S)-7-cyano-7-azabicyclo[2.2.1]heptan-2-yl)-4-((3R)-3-cyano-1-piperidinyl)benzamide | 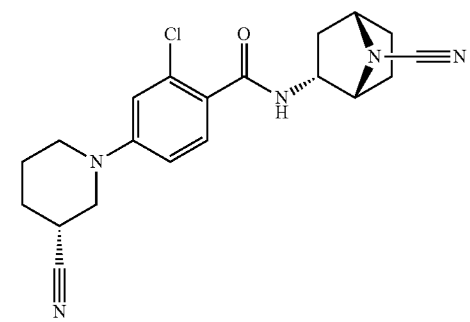 [SMILES: N#C[C@@H]1CCCN(c2ccc(C(=O)N[C@@H]3C[C@@H]4CC[C@H]3N4C#N)c(Cl)c2)C1] |
| 2-41 | 2-chloro-N-((1R,2R,4S)-7-cyano-7-azabicyclo[2.2.1]heptan-2-yl)-4-((3S)-3-cyano-1-piperidinyl)benzamide | 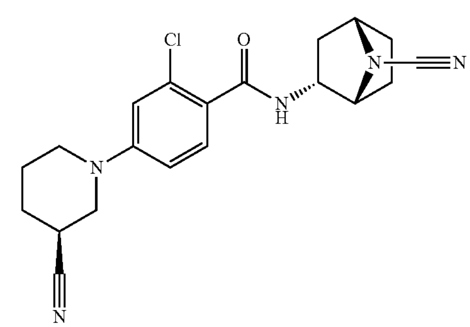 [SMILES: N#C[C@H]1CCCN(c2ccc(C(=O)N[C@@H]3C[C@@H]4CC[C@H]3N4C#N)c(Cl)c2)C1] |
| 2-42 | 2-chloro-N-((1R,2R,4S)-7-cyano-7-azabicyclo[2.2.1]heptan-2-yl)-4-((3R)-3-cyano-3-methyl-2,3-dihydro-1H-inden-5-yl)benzamide | 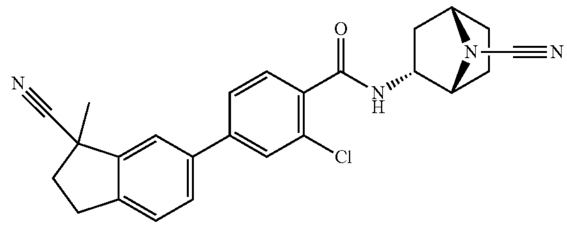 [SMILES: CC1(C#N)CCc2ccc(-c3ccc(C(=O)N[C@@H]4C[C@@H]5CC[C@H]4N5C#N)c(Cl)c3)cc21] |

| Ex # | Name[FB-L22] | Structure |
|---|---|---|
| 2-43-1 | 2-chloro-N-((1R,2R,4S)-7-cyano-7-azabicyclo[2.2.1]heptan-2-yl)-4-((1S,2S,5R)-2-cyano-6-azabicyclo[3.2.1]octan-6-yl)benzamide | 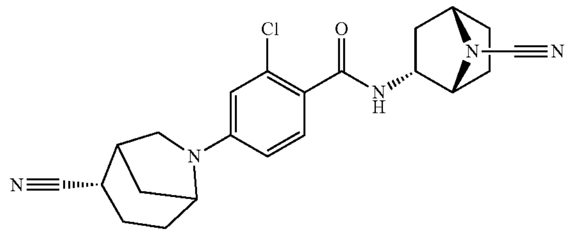 [SMILES: N#C[C@H]1CCC2CC1CN2c1ccc(C(=O)N[C@@H]2C[C@@H]3CC[C@H]2N3C#N)c(Cl)c1] |
| 2-44 | N-((1R,2R,4S)-7-cyano-7-azabicyclo[2.2.1]heptan-2-yl)-1-(3-cyanophenyl)-1H-pyrazole-3-carboxamide | 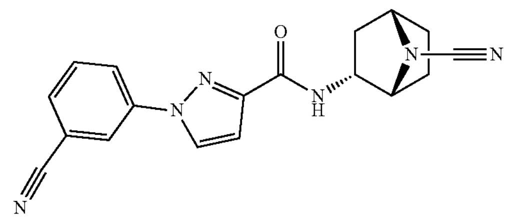 [SMILES: N#Cc1cccc(-n2ccc(C(=O)N[C@@H]3C[C@@H]4CC[C@H]3N4C#N)n2)c1] |
| 2-45 | 2-chloro-N-((1R,2R,4S)-7-cyano-7-azabicyclo[2.2.1]heptan-2-yl)-4-(6-(1-cyanocyclobutyl)-2-pyridinyl)benzamide | 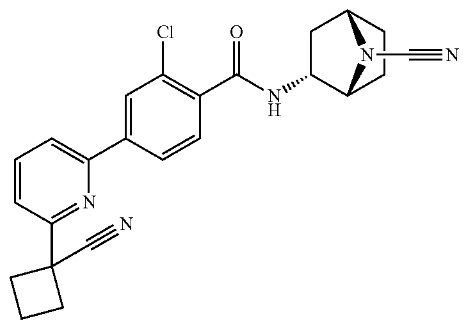 [SMILES: N#CN1[C@H]2CC[C@@H]1[C@H](NC(=O)c1ccc(-c3cccc(C4(C#N)CCC4)n3)cc1Cl)C2] |
| 2-46-2 | (2S)-N-((1R,2R,4S)-7-cyano-7-azabicyclo[2.2.1]heptan-2-yl)-1-(3,5-dichlorobenzyl)-2-azetidinecarboxamide | 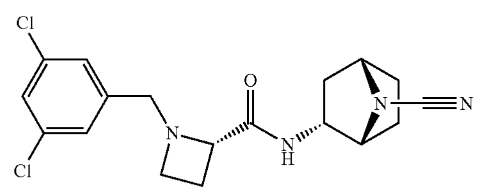 [SMILES: N#CN1[C@H]2CC[C@@H]1[C@H](NC(=O)[C@@H]1CCN1Cc1cc(Cl)cc(Cl)c1)C2] |
| 2-46-3 | (2R)-N-((1R,2R,4S)-7-cyano-7-azabicyclo[2.2.1]heptan-2-yl)-1-(3,5-dichlorobenzyl)-2-azetidinecarboxamide | 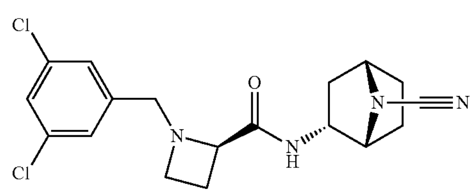 [SMILES: N#CN1[C@H]2CC[C@@H]1[C@H](NC(=O)[C@H]1CCN1Cc1cc(Cl)cc(Cl)c1)C2] |
| 2-48-1 | 2-chloro-N-((1R,2R,4S)-7-cyano-7-azabicyclo[2.2.1]heptan-2-yl)-4-((3S)-3-(cyanomethyl)-1-pyrrolidinyl)benzamide | 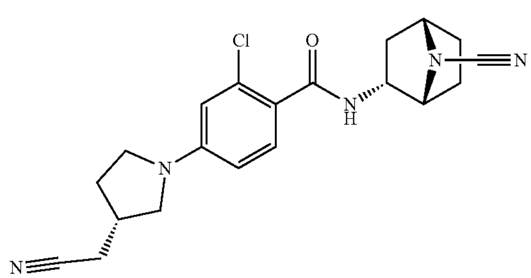 [SMILES: N#CC[C@@H]1CCN(c2ccc(C(=O)N[C@@H]3C[C@@H]4CC[C@H]3N4C#N)c(Cl)c2)C1] |

-continued

| Ex # | Name[FB-L22] | Structure |
|---|---|---|
| 2-48-2 | 2-chloro-N-((1R,2R,4S)-7-cyano-7-azabicyclo[2.2.1]heptan-2-yl)-4-((3R)-3-(cyanomethy))-1-pyrrolidinyl)benzamide | 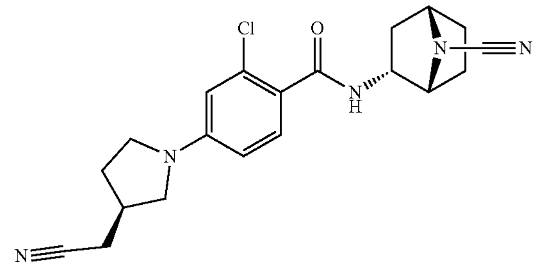 [SMILES: N#CC[C@H]1CCN(c2ccc(C(=O)N[C@@H]3C[C@@H]4CC[C@H]3N4C#N)c(Cl)c2)C1] |
| 2-50 | N-((1R,2R,4S)-7-cyano-7-azabicyclo[2.2.1]heptan-2-yl)-1-(3-cyanophenyl)-1H-indazole-3-carboxamide | 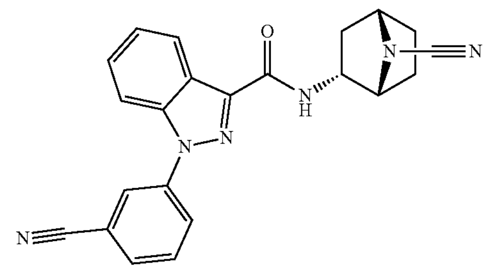 [SMILES: N#Cc1cccc(-n2nc(C(=O)N[C@@H]3C[C@@H]4CC[C@H]3N4C#N)c3ccccc32)c1] |
| 2-51 | (3R)-N-((1R,2R,4S)-7-cyano-7-azabicyclo[2.2.1]heptan-2-yl)-1-(3,5-dichlorobenzyl)-3-pyrrolidinecarboxamide | 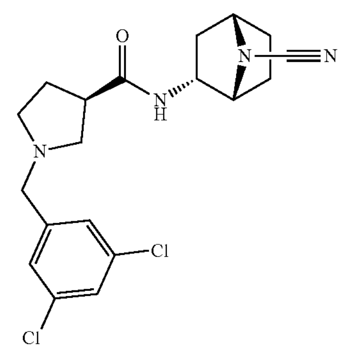 [SMILES: N#CN1[C@H]2CC[C@@H]1[C@H](NC(=O)[C@@H]1CCN(Cc3cc(Cl)cc(Cl)c3)C1)C2] |
| 2-52 | (3S)-N-((1R,2R,4S)-7-cyano-7-azabicyclo[2.2.1]heptan-2-yl)-1-(6-(1-cyanocyclopropyl)-2-pyridinyl)-3-pyrrolidinecarboxamide | 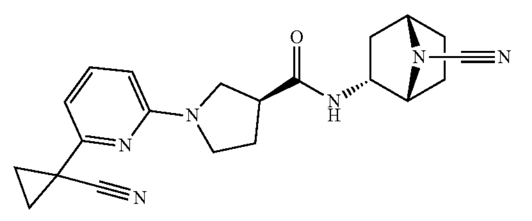 [SMILES: N#CN1[C@H]2CC[C@@H]1[C@H](NC(=O)[C@H]1CCN(c3cccc(C4(C#N)CC4)n3)C1)C2] |
| 2-43-2 | 2-chloro-N-((1R,2R,4S)-7-cyano-7-azabicyclo[2.2.1]heptan-2-yl)-4-((2R)-2-cyano-6-azabicyclo[3.2.1]octan-6-yl)benzamide | 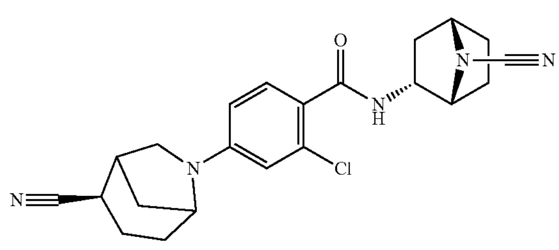 [SMILES: N#C[C@@H]1CCC2CC1CN2c1ccc(C(=O)N[C@@H]2C[C@@H]3CC[C@H]2N3C#N)c(Cl)c1] |

-continued

| Ex # | Name[FB-L22] | Structure |
|---|---|---|
| 2-54 | 2-chloro-N-((1R,2R,4S)-7-cyano-7-azabicyclo[2.2.1]heptan-2-yl)-4-((1-cyanocyclopropyl)methoxy)benzamide | 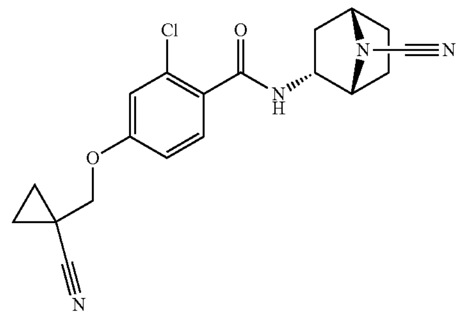 [SMILES: N#CN1[C@H]2CC[C@@H]1[C@H](NC(=O)c1ccc(OCC3(C#N)CC3)cc1Cl)C2] |
| 2-55 | N-((1R,2R,4S)-7-cyano-7-azabicyclo[2.2.1]heptan-2-yl)-4-(6-(1-cyanocyclopropyl)-2-pyridinyl)-2-cyclopropylbenzamide | 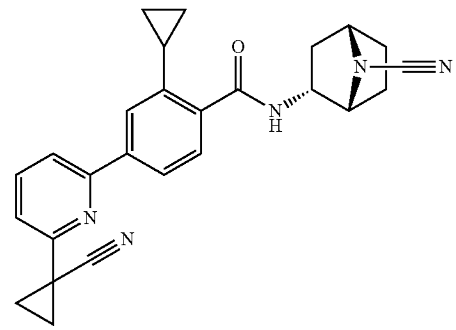 [SMILES: N#CN1[C@H]2CC[C@@H]1[C@H](NC(=O)c1ccc(-c3cccc(C4(C#N)CC4)n3)cc1C1CC1)C2] |
| 2-56 | 2-chloro-N-((1R,2R,4S)-7-cyano-7-azabicyclo[2.2.1]heptan-2-yl)-3-((cis-3-cyanocyclobutyl)oxy)benzamide | 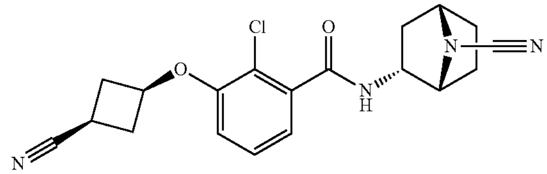 [SMILES: N#CN1[C@H]2CC[C@@H]1[C@H](NC(=O)c1cccc(O[C@H]3C[C@@H](C#N)C3)c1Cl)C2] |
| 2-57 | 2-chloro-N-((1S,2R,4R)-7-cyano-7-azabicyclo[2.2.1]heptan-2-yl)-4-((3R)-3-(cyanomethyl)-1-pyrrolidinyl)benzamide | 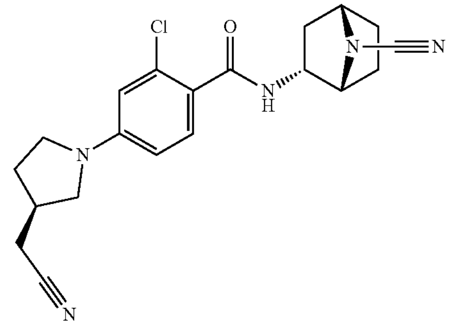 [SMILES: N#CC[C@H]1CCN(c2ccc(C(=O)N[C@@H]3C[C@@H]4CC[C@H]3N4C#N)c(Cl)c2)C1] |
| 2-58 | 2-chloro-N-((1R,2R,4S)-7-cyano-7-azabicyclo[2.2.1]heptan-2-yl)-4-((cis-3-cyanocyclobutyl)oxy)benzamide | 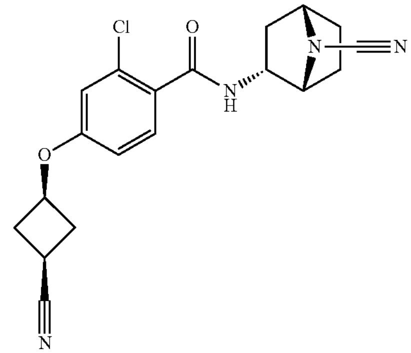 [SMILES: N#CN1[C@H]2CC[C@@H]1[C@H](NC(=O)c1ccc(O[C@H]3C[C@@H](C#N)C3)cc1Cl)C2] |

-continued

| Ex # | Name[FB-L22] | Structure |
|---|---|---|
| 2-59 | 2-chloro-N-((1R,2R,4S)-7-cyano-7-azabicyclo[2.2.1]heptan-2-yl)-4-(6-(1-cyano-3,3-difluorocyclobutyl)-3-pyridinyl)benzamide | 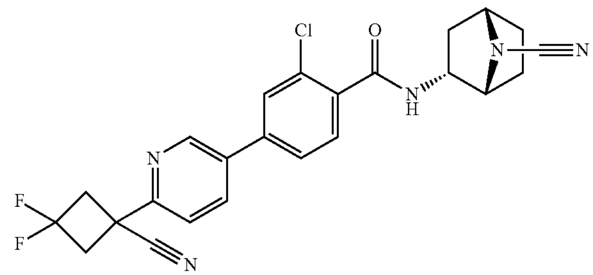 [SMILES: N#CN1[C@H]2CC[C@@H]1[C@H](NC(=O)c1ccc(-c3ccc(C4(C#N)CC(F)(F)C4)nc3)cc1Cl)C2] |
| 2-60 | 2-chloro-N-((1R,2R,4S)-7-cyano-7-azabicyclo[2.2.1]heptan-2-yl)-3'-(1-cyanocyclopropyl)[biphenyl]-3-carboxamide | 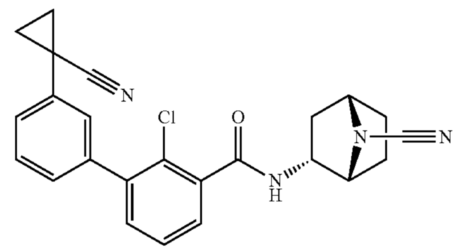 [SMILES: N#CN1[C@H]2CC[C@@H]1[C@H](NC(=O)c1cccc(-c3cccc(C4(C#N)CC4)c3)c1Cl)C2] |
| 2-61-2 | 2-chloro-N-((1R,2R,4S)-7-cyano-7-azabicyclo[2.2.1]heptan-2-yl)-4-((3S)-3-(cyanomethyl)-1-piperidinyl)benzamide | 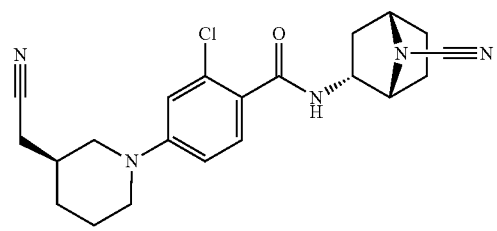 [SMILES: N#CC[C@@H]1CCCN(c2ccc(C(=O)N[C@@H]3C[C@@H]4CC[C@H]3N4C#N)c(Cl)c2)C1] |
| 2-61-1 | 2-chloro-N-((1R,2R,4S)-7-cyano-7-azabicyclo[2.2.1]heptan-2-yl)-4-((3R)-3-(cyanomethyl)-1-piperidinyl)benzamide | 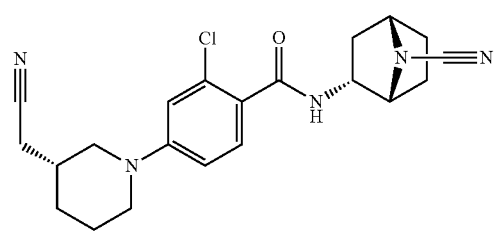 [SMILES: N#CC[C@H]1CCCN(c2ccc(C(=O)N[C@@H]3C[C@@H]4CC[C@H]3N4C#N)c(Cl)c2)C1] |
| 2-63 | 3-chloro-N-((1R,2R,4S)-7-cyano-7-azabicyclo[2.2.1]heptan-2-yl)-3'-(1-cyanocyclopropyl)-5'-fluoro[biphenyl]-4-carboxamide | 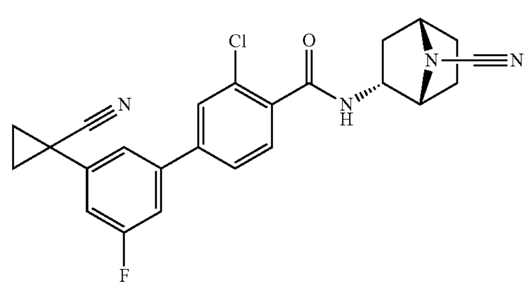 [SMILES: N#CN1[C@H]2CC[C@@H]1[C@H](NC(=O)c1ccc(-c3cc(F)cc(C4(C#N)CC4)c3)cc1Cl)C2] |
| 2-64 | 2-chloro-N-((1R,2R,4S)-7-cyano-7-azabicyclo[2.2.1]heptan-2-yl)-4-(4,5,6,7-tetrahydro-1H-indazol-1-yl)benzamide | 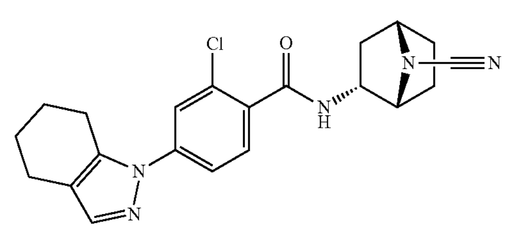 [SMILES: N#CN1[C@H]2CC[C@@H]1[C@H](NC(=O)c1ccc(-n3ncc4c3CCCC4)cc1Cl)C2] |

-continued

| Ex # | Name[FB-L22] | Structure |
|---|---|---|
| 2-65 | 2-chloro-N-((1R,2R,4S)-7-cyano-7-azabicyclo[2.2.1]heptan-2-yl)-4-(5,6-dihydrocyclopenta[c]pyrazol-1(4H)-yl)benzamide | 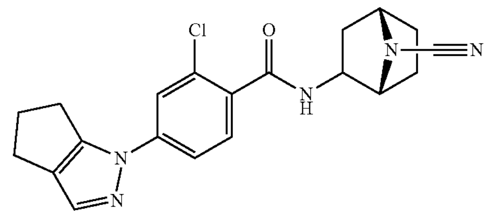 [SMILES: N#CN1[C@H]2CC[C@@H]1C(NC(=O)c1ccc(-n3ncc4c3CCC4)cc1Cl)C2] |
| 2-66 | 2-chloro-N-((1R,2R,4S)-7-cyano-7-azabicyclo[2.2.1]heptan-2-yl)-4-(5,6-dihydrocyclopenta[c]pyrazol-2(4H)-yl)benzamide | 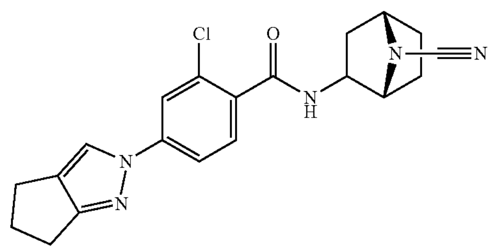 [SMILES: N#CN1[C@H]2CC[C@@H]1C(NC(=O)c1ccc(-n3cc4c(n3)CCC4)cc1Cl)C2] |
| 2-67 | 2-chloro-N-((1R,2R,4S)-7-cyano-7-azabicyclo[2.2.1]heptan-2-yl)-4-((3S)-3-(cyanomethyl)-1-piperidinyl)benzamide | 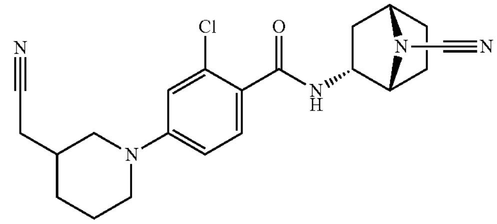 |
| 5-16 | N-((1R,2R,4S)-7-cyano-7-azabicyclo[2.2.1]heptan-2-yl)-1-(3,5-dichlorophenyl)-3-azepanecarboxamide | 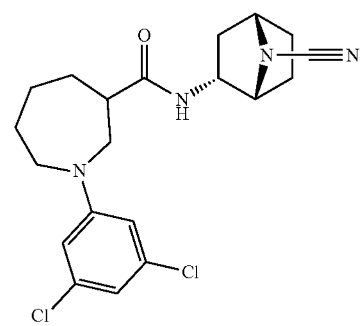 [SMILES: N#CN1[C@H]2CC[C@@H]1[C@H](NC(=O)C1CCCCN(c3cc(Cl)cc(Cl)c3)C1)C2] |
| 7-3 | (3S)-6-chloro-N-((1R,2R,4S)-7-cyano-7-azabicyclo[2.2.1]heptan-2-yl)-N,9-dimethyl-2,3,4,9-tetrahydro-1H-carbazole-3-carboxamide | 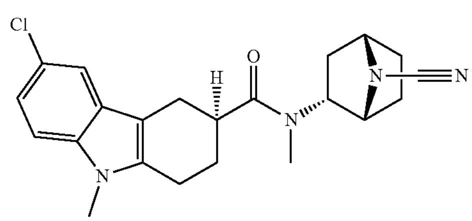 [SMILES: CN(C(=O)[C@H]1CCc2c(c3cc(Cl)ccc3n2C)C1)[C@@H]1C[C@@H]2CC[C@H]1N2C#N] |
| 7-4 | N-((1R,2R,4S)-7-cyano-7-azabicyclo[2.2.1]heptan-2-yl)-1-(6-cyclopropyl-2-pyridinyl)-6-fluoro-N-methyl-1H-indazole-5-carboxamide | 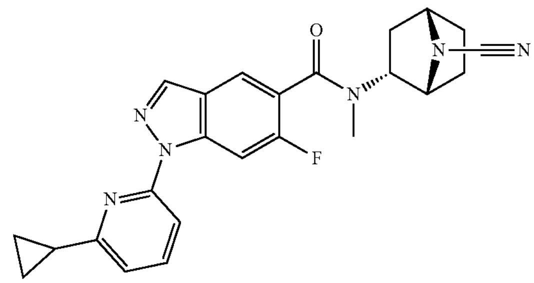 [SMILES: CN(C(=O)c1cc2cnn(-c3cccc(C4CC4)n3)c2cc1F)[C@@H]1C[C@@H]2CC[C@H]1N2C#N] |

-continued

| Ex # | Name[FB-L22] | Structure |
|---|---|---|
| 7-5 | 6-chloro-N-((1R,2R,4S)-7-cyano-7-azabicyclo[2.2.1]heptan-2-yl)-N-methyl-1-(6-methyl-2-pyridinyl)-1H-indazole-5-carboxamide | 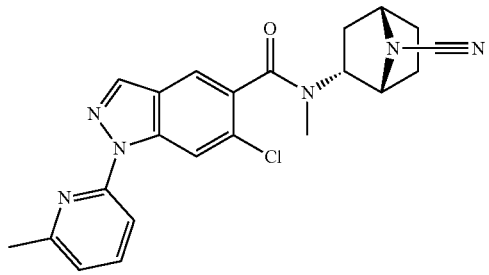 [SMILES: Cc1cccc(-n2ncc3cc(C(=O)N(C)[C@@H]4C[C@@H]5CC[C@H]4N5C#N)c(Cl)cc32)n1] |
| 7-6 | N-((1R,2R,4S)-7-cyano-7-azabicyclo[2.2.1]heptan-2-yl)-6-fluoro-N-methyl-1-(6-methyl-2-pyridinyl)-1H-indazole-5-carboxamide | 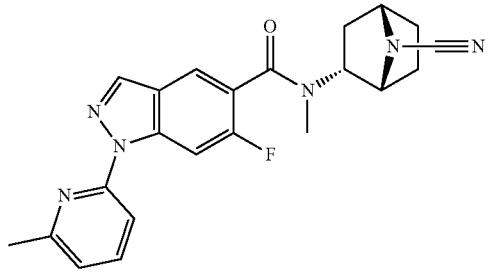 [SMILES: Cc1cccc(-n2ncc3cc(C(=O)N(C)[C@@H]4C[C@@H]5CC[C@H]4N5C#N)c(F)cc32)n1] |
| 7-7 | N-((1R,2R,4S)-7-cyano-7-azabicyclo[2.2.1]heptan-2-yl)-N,1-dimethyl-3-(6-methyl-2-pyridinyl)-1H-indazole-6-carboxamide | 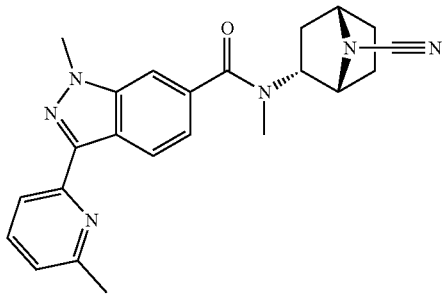 [SMILES: Cc1cccc(-c2nn(C)c3cc(C(=O)N(C)[C@@H]4C[C@@H]5CC[C@H]4N5C#N)ccc23)n1] |
| 7-8 | (3R)-1-(3-chlorophenyl)-N-((1R,2R,4S)-7-cyano-7-azabicyclo[2.2.1]heptan-2-yl)-N-methyl-3-pyrrolidinecarboxamide | 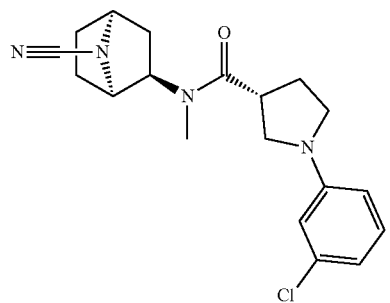 [SMILES: CN(C(=O)[C@@H]1CCN(c2cccc(Cl)c2)C1)[C@@H]1C[C@@H]2CC[C@H]1N2C#N] |
| 7-9 | (3S)-1-(3-chlorophenyl)-N-((1R,2R,4S)-7-cyano-7-azabicyclo[2.2.1]heptan-2-yl)-N-methyl-3-pyrrolidinecarboxamide | 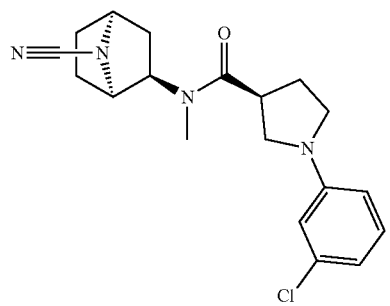 [SMILES: CN(C(=O)[C@H]1CCN(c2cccc(Cl)c2)C1)[C@@H]1C[C@@H]2CC[C@H]1N2C#N] |

-continued

| Ex # | Name[FB-L22] | Structure |
|---|---|---|
| 7-10 | (3R)-1-(3-chlorophenyl)-N-((1R,2R,4S)-7-cyano-7-azabicyclo[2.2.1]heptan-2-yl)-N-methyl-5-oxo-3-pyrrolidinecarboxamide | 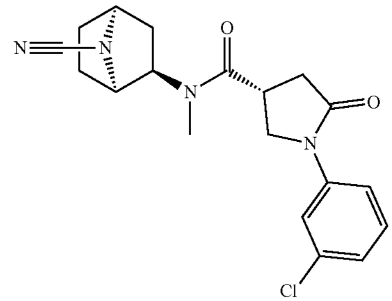 [SMILES: CN(C(=O)[C@@H]1CC(=O)N(c2cccc(Cl)c2)C1)[C@@H]1C[C@@H]2CC[C@H]1N2C#N] |
| 7-11 | (3S)-N-((1R,2R,4S)-7-cyano-7-azabicyclo[2.2.1]heptan-2-yl)-1-(3,5-dichlorophenyl)-N-methyl-3-pyrrolidinecarboxamide | 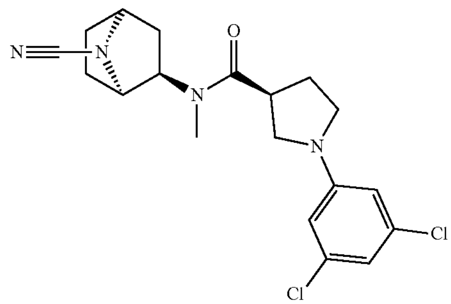 |
| 7-12 | (3S)-N-((1R,2R,4S)-7-cyano-7-azabicyclo[2.2.1]heptan-2-yl)-1-(3-cyano-6-(trifluoromethyl)-2-pyridinyl)-N-methyl-3-pyrrolidinecarboxamide | 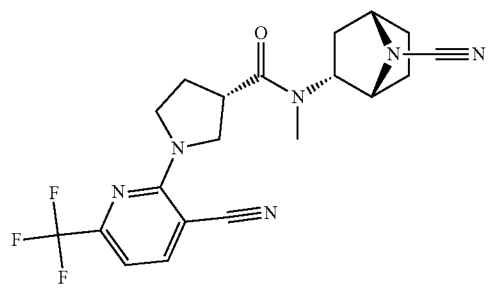 [SMILES: CN(C(=O)[C@H]1CCN(c2nc(C(F)(F)F)ccc2C#N)C1)[C@@H]1C[C@@H]2CC[C@H]1N2C#N] |
| 7-13-2 | N-((1R,2R,4S)-7-cyano-7-azabicyclo[2.2.1]heptan-2-yl)-N-methyl-1-(2,3,5-trichlorophenyl)-L-prolinamide | 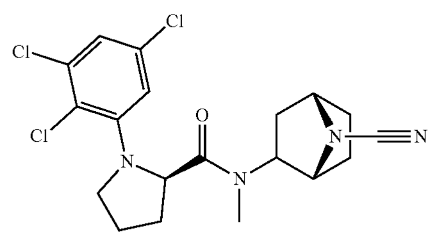 [SMILES: CN(C(=O)[C@H]1CCCN1c1cc(Cl)cc(Cl)c1Cl)C1C[C@@H]2CC[C@H]1N2C#N] |
| 7-13-1 | N-((1R,2R,4S)-7-cyano-7-azabicyclo[2.2.1]heptan-2-yl)-N-methyl-1-(2,3,5-trichlorophenyl)-D-prolinamide | 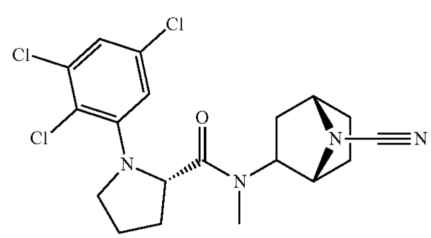 [SMILES: CN(C(=O)[C@@H]1CCCN1c1cc(Cl)cc(Cl)c1Cl)C1C[C@@H]2CC[C@H]1N2C#N] |
| 7-15 | 1-((1R,2R,4S)-7-cyano-7-azabicyclo[2.2.1]heptan-2-yl)-3-(2-(2,5-dichlorophenyl)ethyl)-1,3-dimethylurea | 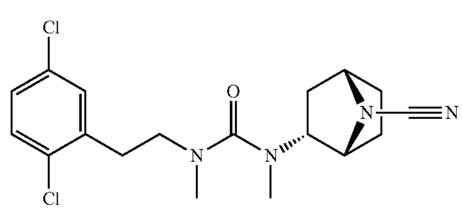 |

-continued

| Ex # | Name[FB-L22] | Structure |
|---|---|---|
| 7-16 | 1-(2-(2-bromo-5-chlorophenyl)ethyl)-3-((1R,2R,4S)-7-cyano-7-azabicyclo[2.2.1]heptan-2-yl)-1,3-dimethylurea | 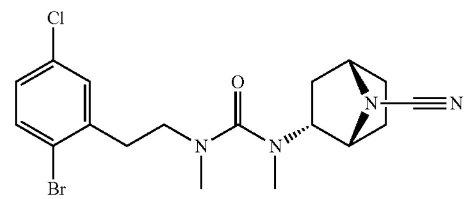 [SMILES: CN(CCc1cc(Cl)ccc1Cl)C(=O)N(C)[C@@H]1C[C@@H]2CC[C@H]1N2C#N] |
| 7-17 | 2-chloro-N-((1R,2R,4S)-7-cyano-7-azabicyclo[2.2.1]heptan-2-yl)-4-(6-(1-cyanocyclopropyl)-2-pyridinyl)-N-methylbenzamide | 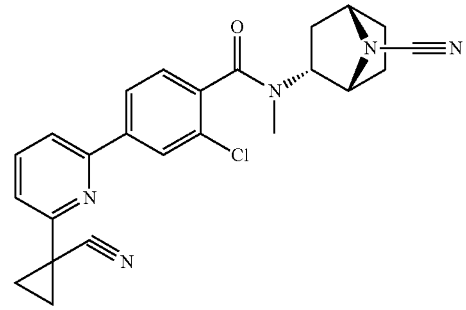 [SMILES: CN(C(=O)c1ccc(-c2cccc(C3(C#N)CC3)n2)cc1Cl)[C@@H]1C[C@@H]2CC[C@H]1N2C#N] |
| 7-18 | N-((1R,2R,4S)-7-cyano-7-azabicyclo[2.2.1]heptan-2-yl)-N-methyl-3-(2-methylpropoxy)-4-(1-methyl-1H-pyrazol-4-yl)benzamide | 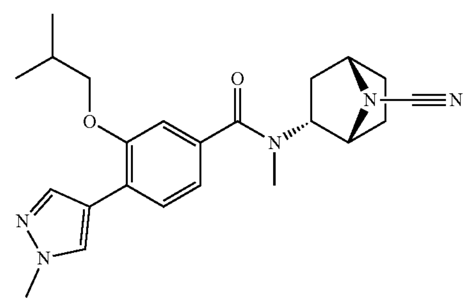 [SMILES: CC(C)COc1cc(C(=O)N(C)[C@@H]2C[C@@H]3CC[C@H]2N3C#N)ccc1-c1cnn(C)c1] |
| 9-1 | N-((1R,2R,4S)-7-cyano-7-azabicyclo[2.2.1]heptan-2-yl)-2-methyl-4-(1-methyl-1H-pyrazol-4-yl)-1,3-benzothiazole-7-carboxamide | 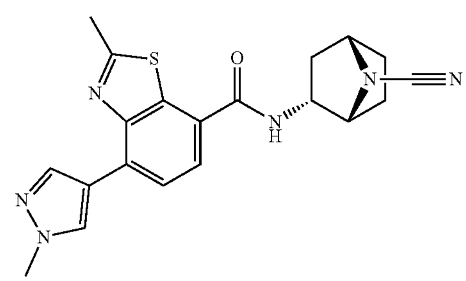 [SMILES: Cc1nc2c(-c3cnn(C)c3)ccc(C(=O)N[C@@H]3C[C@@H]4CC[C@H]3N4C#N)c2s1] |
| 9-2 | N-((1R,2R,4S)-7-cyano-7-azabicyclo[2.2.1]heptan-2-yl)-5-(2-methylpropoxy)-2,4-bis(1-methyl-1H-pyrazol-4-yl)benzamide | 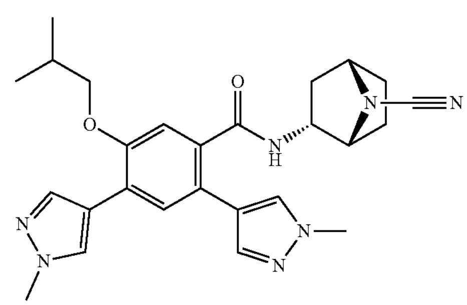 [SMILES: CC(C)COc1cc(C(=O)N[C@@H]2C[C@@H]3CC[C@H]2N3C#N)c(-c2cnn(C)c2)cc1-c1cnn(C)c1] |

-continued

| Ex # | Name[FB-L22] | Structure |
|---|---|---|
| 9-3 | 2-chloro-N-((1R,2R,4S)-7-cyano-7-azabicyclo[2.2.1]heptan-2-yl)-5-(2-methylpropoxy)-4-(1-methyl-1H-pyrazol-4-yl)benzamide | 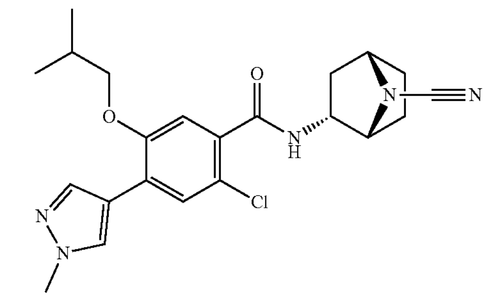 [SMILES: CC(C)COc1cc(C(=O)N[C@@H]2C[C@@H]3CC[C@H]2N3C#N)c(Cl)cc1-c1cnn(C)c1] |
| 9-4 | 3-butoxy-N-((1R,2R,4S)-7-cyano-7-azabicyclo[2.2.1]heptan-2-yl)-4-(1-methyl-1H-pyrazol-4-yl)benzamide | 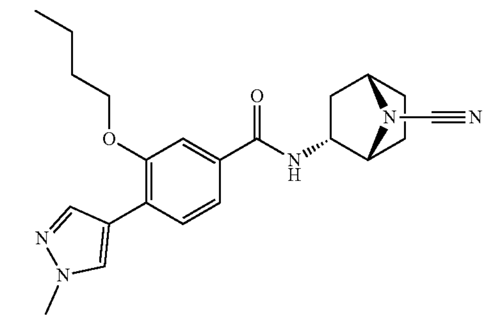 [SMILES: CCCCOc1cc(C(=O)N[C@@H]2C[C@@H]3CC[C@H]2N3C#N)ccc1-c1cnn(C)c1] |
| 9-5 | N-((1R,2R,4S)-7-cyano-7-azabicyclo[2.2.1]heptan-2-yl)-3-(cyclobutylmethoxy)-4-(1-methyl-1H-pyrazol-4-yl)benzamide | 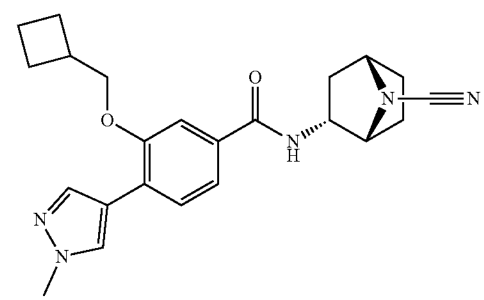 [SMILES: Cn1cc(-c2ccc(C(=O)N[C@@H]3C[C@@H]4CC[C@H]3N4C#N)cc2OCC2CCC2)cn1] |
| 9-6 | N-((1R,2R,4S)-7-cyano-7-azabicyclo[2.2.1]heptan-2-yl)-3-(2-methylpropoxy)-4-(1-methyl-1H-pyrazol-4-yl)benzamide | 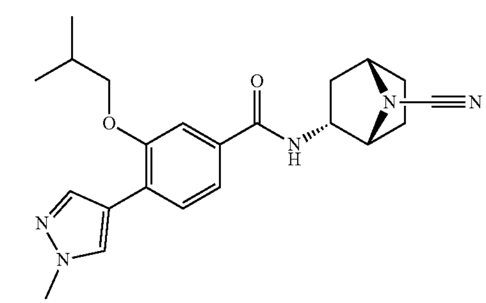 [SMILES: CC(C)COc1cc(C(=O)N[C@@H]2C[C@@H]3CC[C@H]2N3C#N)ccc1-c1cnn(C)c1] |
| 12-2 | 6-(5-azaspiro[2.5]octan-5-yl)-N-((1R,2R,4S)-7-cyano-7-azabicyclo[2.2.1]heptan-2-yl)-4-pyrimidinecarboxamide | 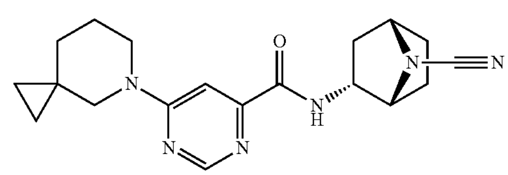 [SMILES: N#CN1[C@H]2CC[C@@H]1[C@H](NC(=O)c1cc(N3CCCC4(CC4)C3)ncn1)C2] |

-continued

| Ex # | Name[FB-L22] | Structure |
|---|---|---|
| 12-3 | N-((1R,2R,4S)-7-cyano-7-azabicyclo[2.2.1]heptan-2-yl)-6-(2-methyl-2-phenyl-4-morpholinyl)-4-pyrimidinecarboxamide | 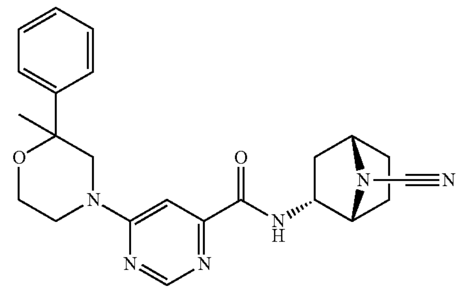 [SMILES: CC1(c2ccccc2)CN(c2cc(C(=O)N[C@@H]3C[C@@H]4CC[C@H]3N4C#N)ncn2)CCO1] |
| 12-4 | 6-(2-(4-chlorophenyl)-2-methyl-4-morpholinyl)-N-((1R,2R,4S)-7-cyano-7-azabicyclo[2.2.1]heptan-2-yl)-4-pyrimidinecarboxamide | 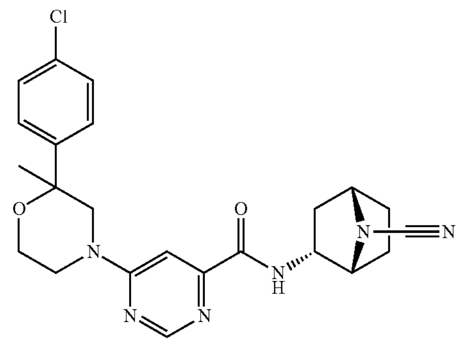 [SMILES: CC1(c2ccc(Cl)cc2)CN(c2cc(C(=O)N[C@@H]3C[C@@H]4CC[C@H]3N4C#N)ncn2)CCO1] |
| 12-5 | 6-(((1-(4-bromophenyl)cyclopropyl)methyl)(methyl)amino)-N-((1R,2R,4S)-7-cyano-7-azabicyclo[2.2.1]heptan-2-yl)-4-pyrimidinecarboxamide | 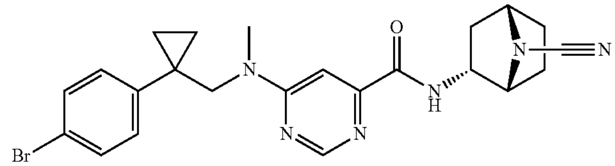 [SMILES: CN(CC1(c2ccc(Br)cc2)CC1)c1cc(C(=O)N[C@@H]2C[C@@H]3CC[C@H]2N3C#N)ncn1] |
| 12-6 | 2-chloro-N-(8-cyano-8-azabicyclo[3.2.1]octan-2-yl)-4-(4-methyl-1H-pyrazol-1-yl)benzamide | 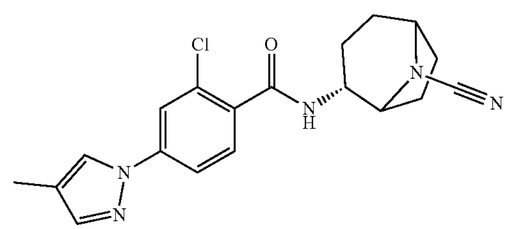 [SMILES: Cc1cnn(-c2ccc(C(=O)N[C@@H]3CCC4CCC3N4C#N)c(Cl)c2)c1] |
| 12-7 | 3-(6-chloro-2,3-dihydro-1H-indol-1-yl)-N-((1R,2R,4S)-7-cyano-7-azabicyclo[2.2.1]heptan-2-yl)propanamide | 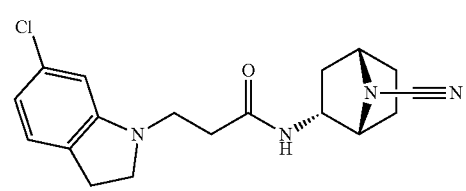 [SMILES: N#CN1[C@H]2CC[C@@H]1[C@H](NC(=O)CCN1CCc3ccc(Cl)cc31)C2] |
| 12-8 | (2E)-N-((1R,2R,4S)-7-cyano-7-azabicyclo[2.2.1]heptan-2-yl)-4-(2,5-dichlorophenyl)-2-methyl-2-butenamide | 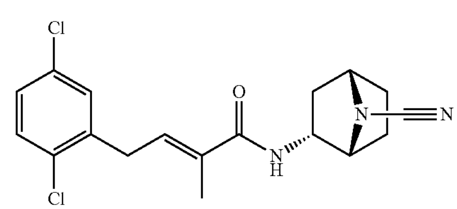 [SMILES: C/C(=C\Cc1cc(Cl)ccc1Cl)C(=O)N[C@@H]1C[C@@H]2CC[C@H]1N2C#N] |

| Ex # | Name[FB-L22] | Structure |
|---|---|---|
| 12-9 | N-((1R,2R,4S)-7-cyano-7-azabicyclo[2.2.1]heptan-2-yl)-4-(2,5-dichlorophenyl)butanamide | 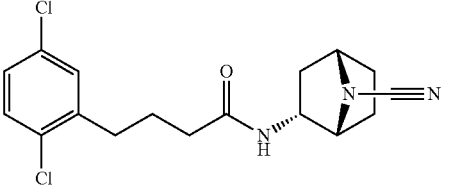 [SMILES: N#CN1[C@H]2CC[C@@H]1[C@H](NC(=O)CCCc1cc(Cl)ccc1Cl)C2] |
| 12-10 | N-((1R,2R,4S)-7-cyano-7-azabicyclo[2.2.1]heptan-2-yl)-3-(2,5-dichlorophenyl)cyclopentanecarboxamide | 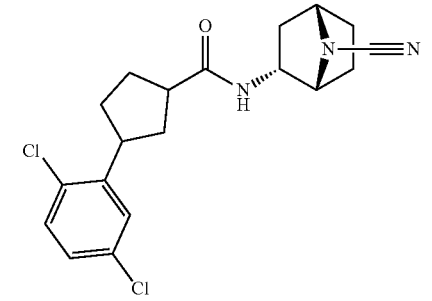 [SMILES: N#CN1[C@H]2CC[C@@H]1[C@H](NC(=O)C1CCC(c3cc(Cl)ccc3Cl)C1)C2] |
| 12-11 | N-((1R,2R,4S)-7-cyano-7-azabicyclo[2.2.1]heptan-2-yl)-3-(4-fluorophenoxy)benzamide | 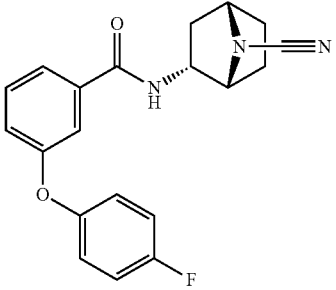 [SMILES: N#CN1[C@H]2CC[C@@H]1[C@H](NC(=O)c1cccc(Oc3ccc(F)cc3)c1)C2] |
| 12-12 | N-((1R,2R,4S)-7-cyano-7-azabicyclo[2.2.1]heptan-2-yl)-3-(4-fluorobenzyl)benzamide | 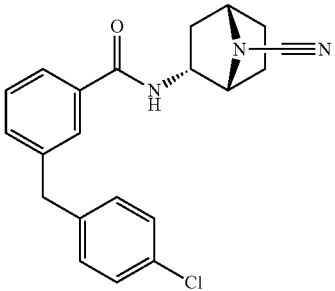 [SMILES: N#CN1[C@H]2CC[C@@H]1[C@H](NC(=O)c1cccc(Cc3ccc(Cl)cc3)c1)C2] |
| 12-13 | 3-(4-chlorophenoxy)-N-((1R,2R,4S)-7-cyano-7-azabicyclo[2.2.1]heptan-2-yl)benzamide | 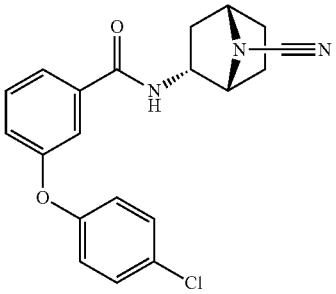 [SMILES: N#CN1[C@H]2CC[C@@H]1[C@H](NC(=O)c1cccc(Oc3ccc(Cl)cc3)c1)C2] |

| Ex # | Name[FB-L22] | Structure |
|---|---|---|
| 12-14 | N-((1R,2R,4S)-7-cyano-7-azabicyclo[2.2.1]heptan-2-yl)-2-(2,5-dichlorobenzyl)cyclopropanecarboxamide | 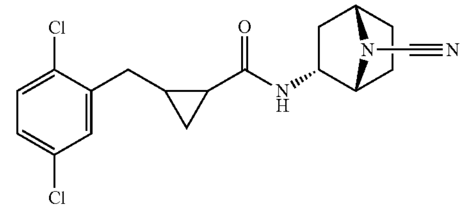 [SMILES: N#CN1[C@H]2CC[C@@H]1[C@H](NC(=O)C1CC1Cc1cc(Cl)ccc1Cl)C2] |
| 12-15 | N-((1R,2R,4S)-7-cyano-7-azabicyclo[2.2.1]heptan-2-yl)-3-(4-cyanophenoxy)benzamide | 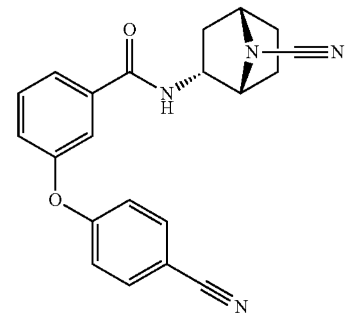 [SMILES: N#Cc1ccc(Oc2cccc(C(=O)N[C@@H]3C[C@@H]4CC[C@H]3N4C#N)c2)cc1] |
| 12-16 | N-((1R,2R,4S)-7-cyano-7-azabicyclo[2.2.1]heptan-2-yl)dibenzo[b,d]furan-3-carboxamide | 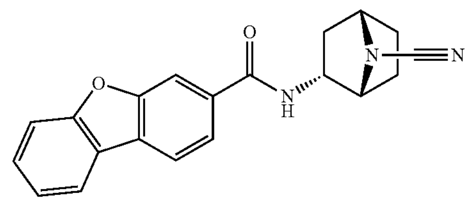 [SMILES: N#CN1[C@H]2CC[C@@H]1[C@H](NC(=O)c1ccc3c(c1)oc1ccccc13)C2] |
| 12-17 | (2E)-3-(5-chloro-1-ethyl-1H-pyrrolo[2,3-b]pyridin-3-yl)-N-((1R,2R,4S)-7-cyano-7-azabicyclo[2.2.1]heptan-2-yl)-2-propenamide | 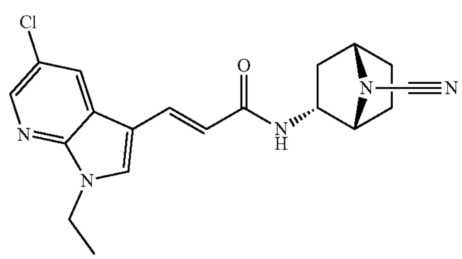 [SMILES: CCn1cc(/C=C/C(=O)N[C@@H]2C[C@@H]3CC[C@H]2N3C#N)c2cc(Cl)cnc21] |
| 12-18 | 2-(3-bromo-2-cyanophenoxy)-N-((1R,2R,4S)-7-cyano-7-azabicyclo[2.2.1]heptan-2-yl)acetamide | 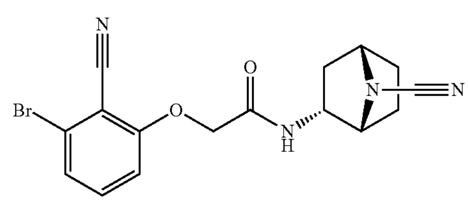 [SMILES: N#Cc1c(Br)cccc1OCC(=O)N[C@@H]1C[C@@H]2CC[C@H]1N2C#N] |
| 12-19 | N-(2-(((1R,2R,4S)-7-cyano-7-azabicyclo[2.2.1]heptan-2-yl)amino)-2-oxoethyl)-4,5,6,7-tetrahydro-1-benzothiophene-2-carboxamide | 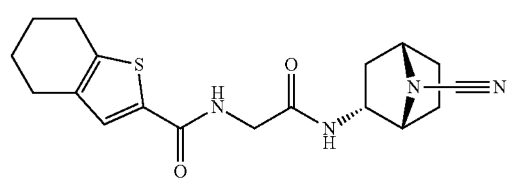 [SMILES: N#CN1[C@H]2CC[C@@H]1[C@H](NC(=O)CNC(=O)c1cc3c(s1)CCCC3)C2] |
| 12-20 | (3E)-N-((1R,2R,4S)-7-cyano-7-azabicyclo[2.2.1]heptan-2-yl)-4-(2,5-dichlorophenyl)-2-methoxy-3-butenamide | 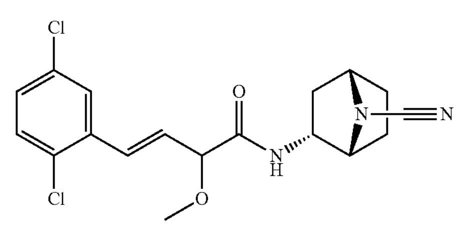 [SMILES: COC(/C=C/c1cc(Cl)ccc1Cl)C(=O)N[C@@H]1C[C@@H]2CC[C@H]1N2C#N] |

-continued

| Ex # | Name[FB-L22] | Structure |
|---|---|---|
| 12-21 | (3E)-N-((1R,2R,4S)-7-cyano-7-azabicyclo[2.2.1]heptan-2-yl)-4-(2,5-dichlorophenyl)-N-methyl-3-butenamide | 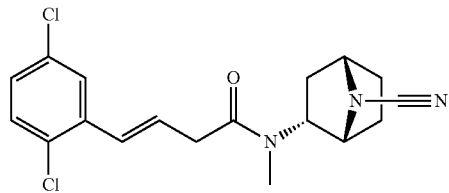 [SMILES: CN(C(=O)C/C=C/c1cc(Cl)ccc1Cl)[C@@H]1C[C@@H]2CC[C@H]1N2C#N] |
| 12-22 | 2',5'-dichloro-N-((1R,2R,4S)-7-cyano-7-azabicyclo[2.2.1]heptan-2-yl)[biphenyl]-3-carboxamide | 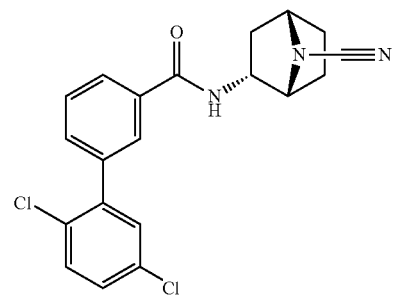 [SMILES: N#CN1[C@H]2CC[C@@H]1[C@H](NC(=O)c1cccc(-c3cc(Cl)ccc3Cl)c1)C2] |
| 12-23 | (3E)-4-(3-chlorophenyl)-N-((1R,2R,4S)-7-cyano-7-azabicyclo[2.2.1]heptan-2-yl)-3-butenamide | 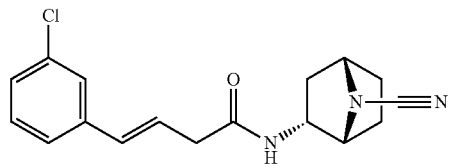 [SMILES: N#CN1[C@H]2CC[C@@H]1[C@H](NC(=O)C/C=C/c1cccc(Cl)c1)C2] |
| 12-24 | (2E)-3-(5-chloro-1-ethyl-1H-indol-3-yl)-N-((1R,2R,4S)-7-cyano-7-azabicyclo[2.2.1]heptan-2-yl)-2-methyl-2-propenamide | 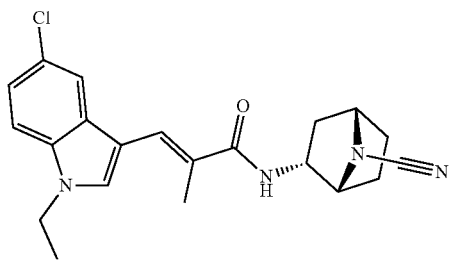 [SMILES: CCn1cc(/C=C(\C)C(=O)N[C@@H]2C[C@@H]3CC[C@H]2N3C#N)c2cc(Cl)ccc21] |
| 12-25 | (3E)-N-((1R,2R,4S)-7-cyano-7-azabicyclo[2.2.1]heptan-2-yl)-4-(2,5-dichlorophenyl)-3-butenamide | 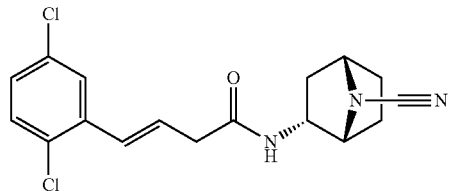 [SMILES: N#CN1[C@H]2CC[C@@H]1[C@H](NC(=O)C/C=C/c1cc(Cl)ccc1Cl)C2] |
| 12-26 | N-((1R,2R,4S)-7-cyano-7-azabicyclo[2.2.1]heptan-2-yl)-2,3,4,9-tetrahydro-1H-carbazole-3-carboxamide | 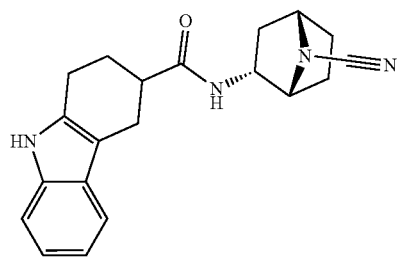 [SMILES: N#CN1[C@H]2CC[C@@H]1[C@H](NC(=O)C1CCc3[nH]c4ccccc4c3C1)C2] |

-continued

| Ex # | Name[FB-L22] | Structure |
|---|---|---|
| 12-27 | (2E)-3-(5-chloro-1-benzothiophen-3-yl)-N-((1R,2R,4S)-7-cyano-7-azabicyclo[2.2.1]heptan-2-yl)-2-methyl-2-propenamide | 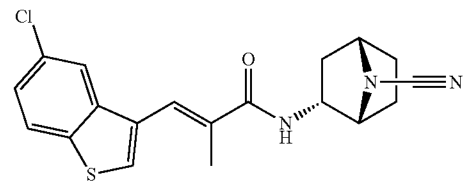 [SMILES: C/C(=C\c1csc2ccc(Cl)cc12)C(=O)N[C@@H]1C[C@@H]2CC[C@H]1N2C#N] |
| 12-28 | 3'-bromo-N-((1R,2R,4S)-7-cyano-7-azabicyclo[2.2.1]heptan-2-yl)[biphenyl]-3-carboxamide | 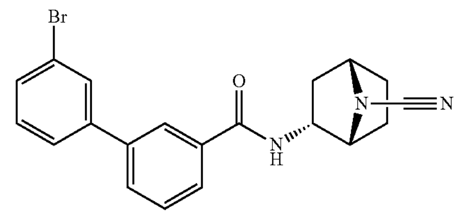 [SMILES: N#CN1[C@H]2CC[C@@H]1[C@H](NC(=O)c1cccc(-c3cccc(Br)c3)c1)C2] |
| 12-29 | (2E)-3-(5-chloro-1H-indazol-3-yl)-N-((1R,2R,4S)-7-cyano-7-azabicyclo[2.2.1]heptan-2-yl)-2-methyl-2-propenamide | 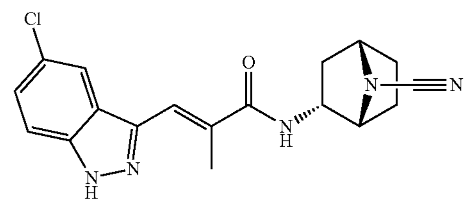 |
| 13-21 | N-((1R,2R,4S)-7-cyano-7-azabicyclo[2.2.1]heptan-2-yl)-6-(4-methyl-2-pyrimidinyl)-1H-indole-2-carboxamide | 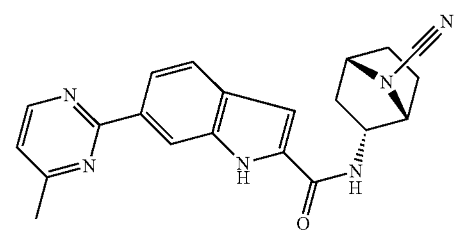 |
| 13-22 | 5-(3-chlorophenyl)-N-((1R,2R,4S)-7-cyano-7-azabicyclo[2.2.1]heptan-2-yl)-2-furancarboxamide | 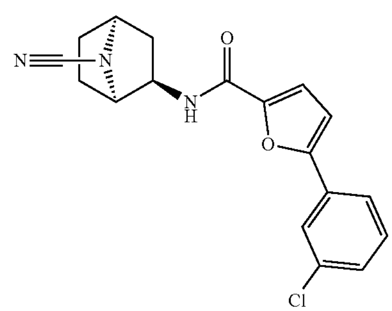 [SMILES: N#CN1[C@H]2CC[C@@H]1[C@H](NC(=O)c1ccc(-c3cccc(Cl)c3)o1)C2] |
| 13-23 | N-((1R,2R,4S)-7-cyano-7-azabicyclo[2.2.1]heptan-2-yl)-1-(4-cyclopropyl-2-pyrimidinyl)-3-pyrrolidinecarboxamide | 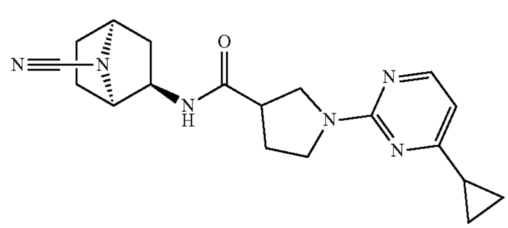 [SMILES: N#CN1[C@H]2CC[C@@H]1[C@H](NC(=O)C1CCN(c3nccc(C4CC4)n3)C1)C2] |
| 13-24 | N-((1R,2R,4S)-7-cyano-7-azabicyclo[2.2.1]heptan-2-yl)-1-(3-(trifluoromethyl)phenyl)-3-pyrrolidinecarboxamide | 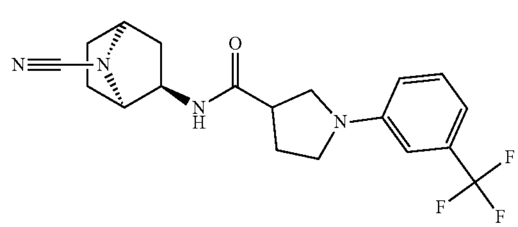 |

| Ex # | Name[FB-L22] | Structure |
|---|---|---|
| 13-25 | N-((1R,2R,4S)-7-cyano-7-azabicyclo[2.2.1]heptan-2-yl)-1-(3,5-dichlorophenyl)-3-pyrrolidinecarboxamide | 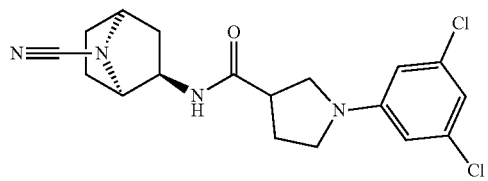 |
| 13-26 | N-((1R,2R,4S)-7-cyano-7-azabicyclo[2.2.1]heptan-2-yl)-1-(6-(trifluoromethyl)-2-pyridinyl)-3-pyrrolidinecarboxamide | 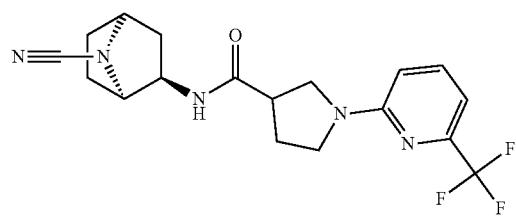 |
| 13-27 | 2-chloro-N-((1R,2R,4S)-7-cyano-7-azabicyclo[2.2.1]heptan-2-yl)-3-(2-methylpropoxy)-4-(1-methyl-1H-pyrazol-4-yl)benzamide | 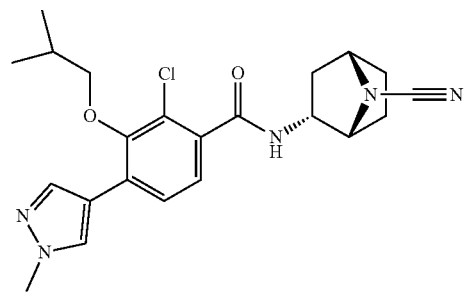 [SMILES: CC(C)COc1c(-c2cnn(C)c2)ccc(C(=O)N[C@@H]2C[C@@H]3CC[C@H]2N3C#N)c1Cl] |
| 13-28 | 2-chloro-N-((1R,2R,4S)-7-cyano-7-azabicyclo[2.2.1]heptan-2-yl)-3-(2-methylpropoxy)-4-(4-methyl-1H-pyrazol-1-yl)benzamide | 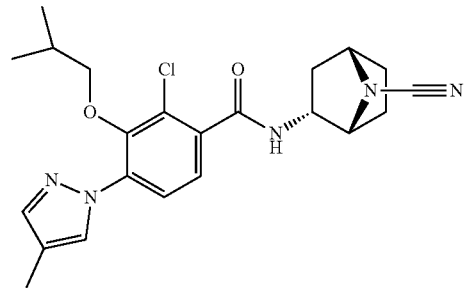 [SMILES: Cc1cnn(-c2ccc(C(=O)N[C@@H]3C[C@@H]4CC[C@H]3N4C#N)c(Cl)c2OCC(C)C)c1] |
| 13-29 | N-((1R,2R,4S)-7-cyano-7-azabicyclo[2.2.1]heptan-2-yl)-3-(2-methylpropoxy)-4-(4-methyl-1H-pyrazol-1-yl)benzamide | 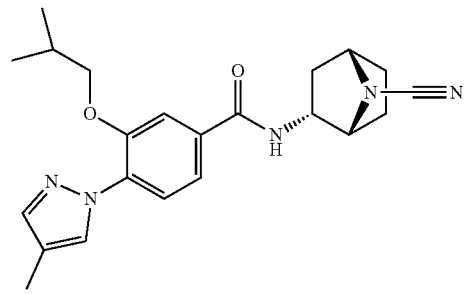 [SMILES: Cc1cnn(-c2ccc(C(=O)N[C@@H]3C[C@@H]4CC[C@H]3N4C#N)cc2OCC(C)C)c1] |

| Ex # | Name[FB-L22] | Structure |
|---|---|---|
| 13-30 | N-((1R,2R,4S)-7-cyano-7-azabicyclo[2.2.1]heptan-2-yl)-7-methyl-1-(6-methyl-2-pyridinyl)-1H-indazole-5-carboxamide | 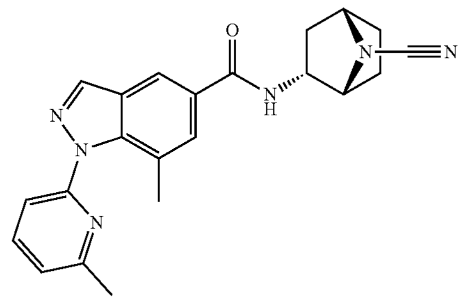 [SMILES: Cc1cccc(-n2ncc3cc(C(=O)N[C@@H]4C[C@@H]5CC[C@H]4N5C#N)cc(C)c32)n1] |
| 15-2 | N-((1R,2R,4S)-7-cyano-7-azabicyclo[2.2.1]heptan-2-yl)-1-(2-quinolinyl)-1H-indazole-5-carboxamide | 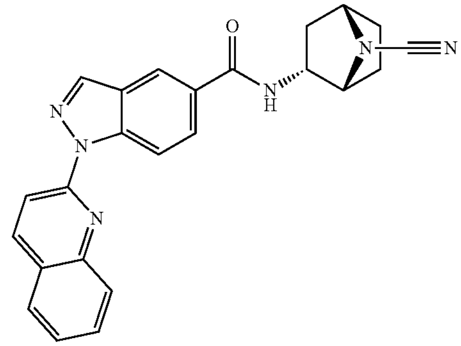 [SMILES: N#CN1[C@H]2CC[C@@H]1[C@H](NC(=O)c1ccc3c(cnn3-c3ccc4ccccc4n3)c1)C2] |
| 15-3 | N-((1R,2R,4S)-7-cyano-7-azabicyclo[2.2.1]heptan-2-yl)-1-(6-(1H-imidazol-1-yl)-2-pyridinyl)-1H-indazole-5-carboxamide | 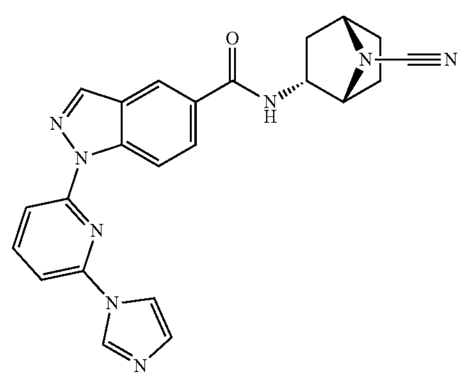 [SMILES: N#CN1[C@H]2CC[C@@H]1[C@H](NC(=O)c1ccc3c(cnn3-c3cccc(-n4ccnc4)n3)c1)C2] |
| 15-4 | N-((1R,2R,4S)-7-cyano-7-azabicyclo[2.2.1]heptan-2-yl)-1-(6-phenyl-2-pyridinyl)-1H-indazole-5-carboxamide | 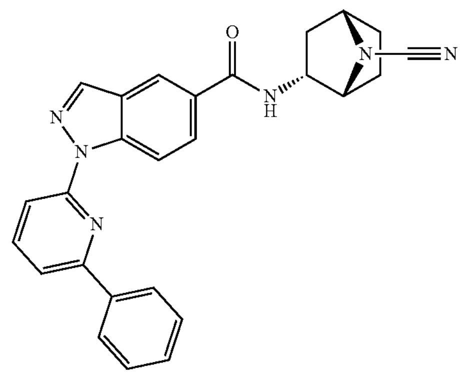 [SMILES: N#CN1[C@H]2CC[C@@H]1[C@H](NC(=O)c1ccc3c(cnn3-c3cccc(-c4ccccc4)n3)c1)C2] |

-continued

| Ex # | Name[FB-L22] | Structure |
|---|---|---|
| 15-5 | N-((1R,2R,4S)-7-cyano-7-azabicyclo[2.2.1]heptan-2-yl)-1-(6-(1H-pyrazol-1-yl)-2-pyridinyl)-1H-indazole-5-carboxamide | 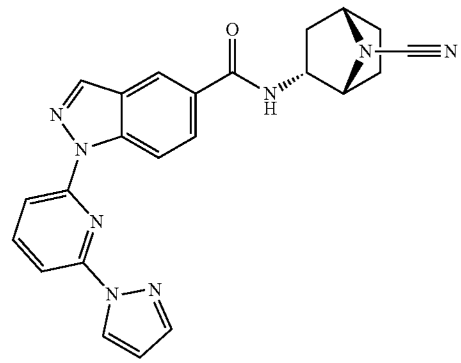 [SMILES: N#CN1[C@H]2CC[C@@H]1[C@H](NC(=O)c1ccc3c(cnn3-c3cccc(-n4cccn4)n3)c1)C2] |
| 15-6 | N-((1R,2R,4S)-7-cyano-7-azabicyclo[2.2.1]heptan-2-yl)-1-(6-(1,1-difluoroethyl)-2-pyridinyl)-1H-indazole-5-carboxamide | 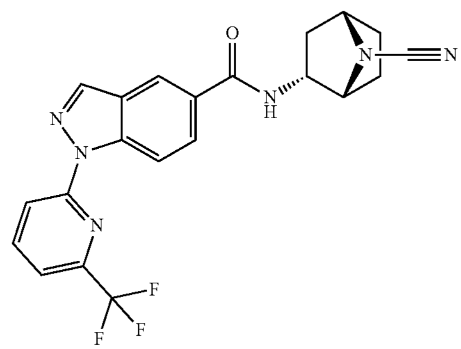 [SMILES: N#CN1[C@H]2CC[C@@H]1[C@H](NC(=O)c1ccc3c(cnn3-c3cccc(C(F)(F)F)n3)c1)C2] |
| 15-7 | N-((1R,2R,4S)-7-cyano-7-azabicyclo[2.2.1]heptan-2-yl)-1-(6-(difluoromethoxy)-2-pyridinyl)-1H-indazole-5-carboxamide | 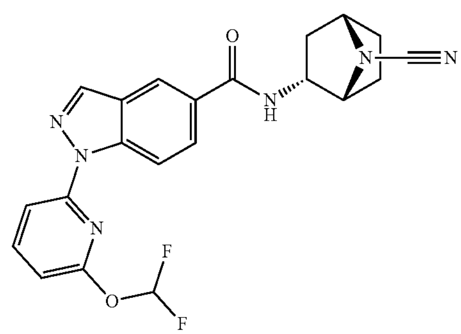 [SMILES: N#CN1[C@H]2CC[C@@H]1[C@H](NC(=O)c1ccc3c(cnn3-c3cccc(OC(F)F)n3)c1)C2] |
| 15-8 | N-((1R,2R,4S)-7-cyano-7-azabicyclo[2.2.1]heptan-2-yl)-1-(6-(difluoromethyl)-2-pyridinyl)-1H-indazole-5-carboxamide | 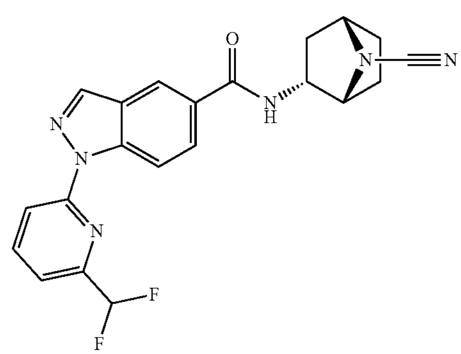 [SMILES: N#CN1[C@H]2CC[C@@H]1[C@H](NC(=O)c1ccc3c(cnn3-c3cccc(C(F)F)n3)c1)C2] |

-continued

| Ex # | Name[FB-L22] | Structure |
|---|---|---|
| 15-9 | 1-([2,2'-bipyridin]-6-yl)-N-((1R,2R,4S)-7-cyano-7-azabicyclo[2.2.1]heptan-2-yl)-1H-indazole-5-carboxamide | 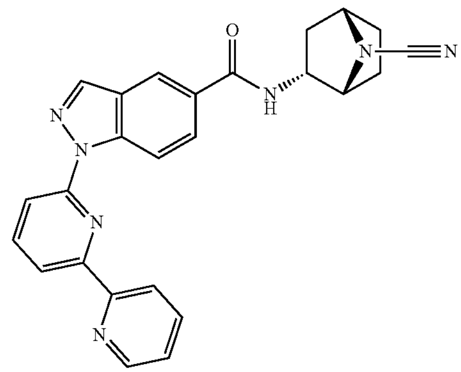 [SMILES: N#CN1[C@H]2CC[C@@H]1[C@H](NC(=O)c1ccc3c(cnn3-c3cccc(-c4ccccn4)n3)c1)C2] |
| 15-10 | 3-(3-chlorophenyl)-N-((1R,2R,4S)-7-cyano-7-azabicyclo[2.2.1]heptan-2-yl)-3-azabicyclo[3.1.0]hexane-1-carboxamide | 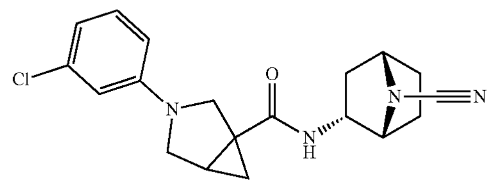 [SMILES: N#CN1[C@H]2CC[C@@H]1[C@H](NC(=O)C13CC1CN(c1cccc(Cl)c1)C3)C2] |
| 15-11 | N-((1R,2R,4S)-7-cyano-7-azabicyclo[2.2.1]heptan-2-yl)-1-(3,5-dichlorophenyl)-1H-pyrazole-3-carboxamide | 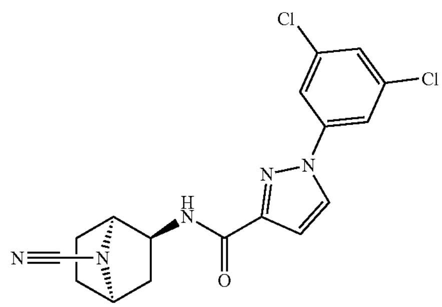 [SMILES: N#CN1[C@@H]2CC[C@H]1[C@@H](NC(=O)c1ccn(-c3cc(Cl)cc(Cl)c3)n1)C2] |
| 15-12-2 | (1S,4R,5S)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | 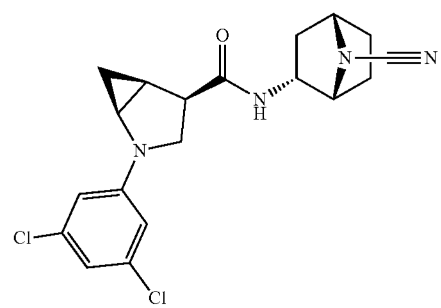 [SMILES: N#CN1[C@H]2CC[C@@H]1[C@H](NC(=O)[C@H]1CN(c3cc(Cl)cc(Cl)c3)[C@H]3C[C@@H]13)C2] |
| 15-12-1 | (1S,4S,5S)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | 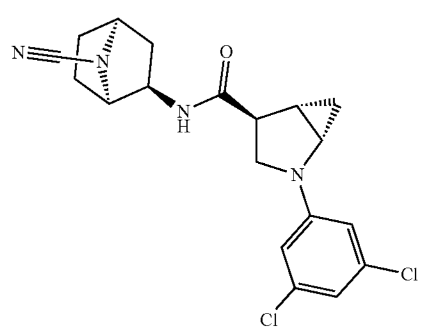 [SMILES: N#CN1[C@H]2CC[C@@H]1[C@H](NC(=O)[C@@H]1CN(c3cc(Cl)cc(Cl)c3)[C@H]3C[C@@H]13)C2] |

-continued

| Ex # | Name[FB-L22] | Structure |
|---|---|---|
| 15-14 | N-((1S,2R,4S)-7-cyano-7-azabicyclo[2.2.1]heptan-2-yl)-1-(3,5-dichlorophenyl)-4-azepanecarboxamide | 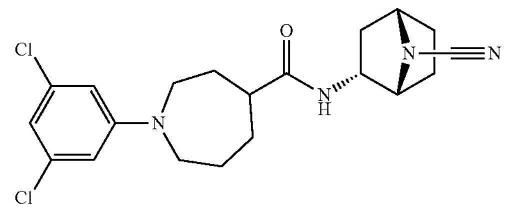 [SMILES: N#CN1[C@H]2CC[C@@H]1[C@H](NC(=O)C1CCCN(c3cc(Cl)cc(Cl)c3)CC1)C2] |
| 15-15 | 6-chloro-N-((1R,2R,4S)-7-cyano-7-azabicyclo[2.2.1]heptan-2-yl)-1-(6-cyano-2-pyridinyl)-1H-indazole-5-carboxamide | 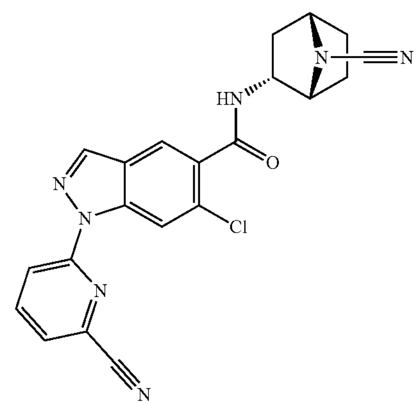 [SMILES: N#Cc1cccc(-n2ncc3cc(C(=O)N[C@@H]4C[C@@H]5CC[C@H]4N5C#N)c(Cl)cc32)n1] |
| 15-16 | 6-chloro-N-((1R,2R,4S)-7-cyano-7-azabicyclo[2.2.1]heptan-2-yl)-1-(4-cyano-2-pyridinyl)-1H-indazole-5-carboxamide | 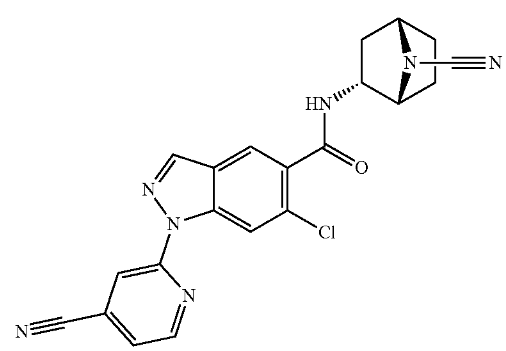 [SMILES: N#Cc1ccnc(-n2ncc3cc(C(=O)N[C@@H]4C[C@@H]5CC[C@H]4N5C#N)c(Cl)cc32)c1] |
| 16-3 | N-((1R,2R,4S)-7-cyano-7-azabicyclo[2.2.1]heptan-2-yl)-5-(1-methyl-1H-pyrazol-4-yl)-1,3-thiazole-2-carboxamide | 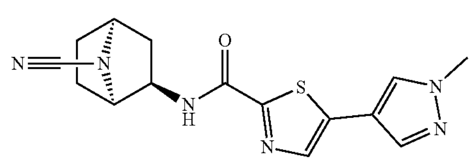 [SMILES: Cn1cc(-c2cnc(C(=O)N[C@@H]3C[C@@H]4CC[C@H]3N4C#N)s2)cn1] |
| 16-4 | N-((1R,2R,4S)-7-cyano-7-azabicyclo[2.2.1]heptan-2-yl)-2-(3-cyanophenyl)-1,3-thiazole-4-carboxamide | 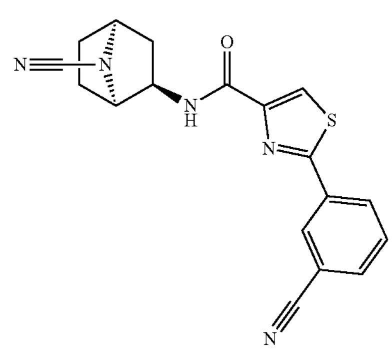 [SMILES: N#Cc1cccc(-c2nc(C(=O)N[C@@H]3C[C@@H]4CC[C@H]3N4C#N)cs2)c1] |

| Ex # | Name[FB-L22] | Structure |
|---|---|---|
| 16-5 | N-((1R,2R,4S)-7-cyano-7-azabicyclo[2.2.1]heptan-2-yl)-2-(3-cyclopropylphenyl)-1,3-thiazole-4-carboxamide | 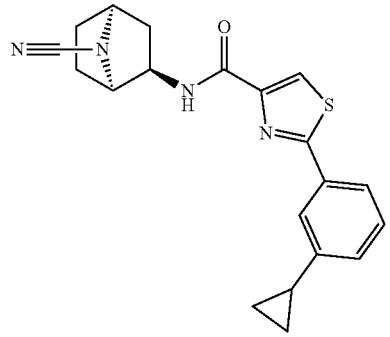 [SMILES: N#CN1[C@H]2CC[C@@H]1[C@H](NC(=O)c1csc(-c3cccc(C4CC4)c3)n1)C2] |
| 20-1 | N-((1R,2R,4S)-7-cyano-7-azabicyclo[2.2.1]heptan-2-yl)-7-(4-methyl-2-pyrimidinyl)-1H-indole-3-carboxamide | 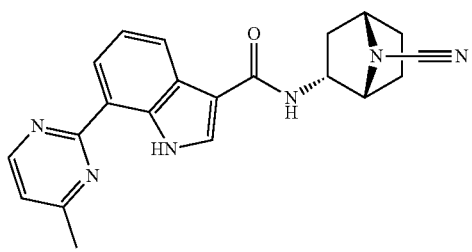 [SMILES: Cc1ccnc(-c2cccc3c(C(=O)N[C@@H]4C[C@@H]5CC[C@H]4N5C#N)c[nH]c23)n1] |
| 20-2 | N-((1R,2R,4S)-7-cyano-7-azabicyclo[2.2.1]heptan-2-yl)-7-(6-methyl-2-pyridinyl)-1H-indole-3-carboxamide | 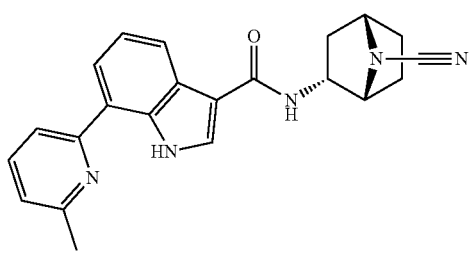 [SMILES: Cc1cccc(-c2cccc3c(C(=O)N[C@@H]4C[C@@H]5CC[C@H]4N5C#N)c[nH]c23)n1] |
| 20-3 | 2',3-dichloro-N-((1R,2R,4S)-7-cyano-7-azabicyclo[2.2.1]heptan-2-yl)-3'-(cyanomethyl)[biphenyl]-4-carboxamide | 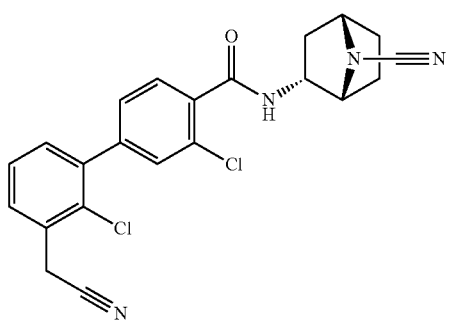 [SMILES: N#CCc1cccc(-c2ccc(C(=O)N[C@@H]3C[C@@H]4CC[C@H]3N4C#N)c(Cl)c2)c1Cl] |
| 20-4 | 3,3'-dichloro-N-((1R,2R,4S)-7-cyano-7-azabicyclo[2.2.1]heptan-2-yl)-5'-(cyanomethyl)[biphenyl]-4-carboxamide | 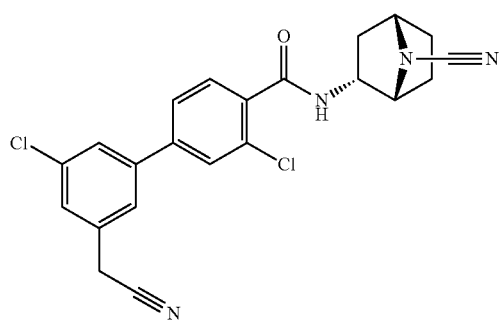 [SMILES: N#CCc1cc(Cl)cc(-c2ccc(C(=O)N[C@@H]3C[C@@H]4CC[C@H]3N4C#N)c(Cl)c2)c1] |

-continued

| Ex # | Name[FB-L22] | Structure |
|---|---|---|
| 20-5 | 2',3-dichloro-N-((1R,2R,4S)-7-cyano-7-azabicyclo[2.2.1]heptan-2-yl)-5'-(cyanomethyl)[biphenyl]-4-carboxamide | 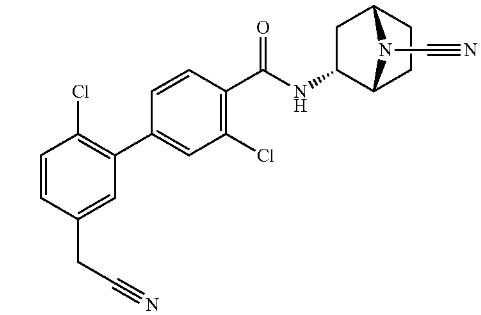 [SMILES: N#CCc1ccc(Cl)c(-c2ccc(C(=O)N[C@@H]3C[C@@H]4CC[C@H]3N4C#N)c(Cl)c2)c1] |
| 20-6 | 3,4'-dichloro-N-((1R,2R,4S)-7-cyano-7-azabicyclo[2.2.1]heptan-2-yl)-3'-(cyanomethyl)[biphenyl]-4-carboxamide | 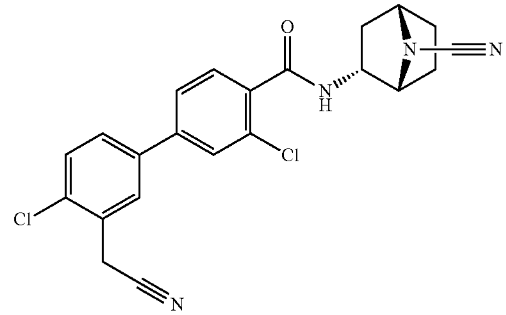 [SMILES: N#CCc1cc(-c2ccc(C(=O)N[C@@H]3C[C@@H]4CC[C@H]3N4C#N)c(Cl)c2)ccc1Cl] |
| 20-7 | 3-chloro-N-((1R,2R,4S)-7-cyano-7-azabicyclo[2.2.1]heptan-2-yl)-3'-(2-cyano-2-propanyl)[biphenyl]-4-carboxamide | 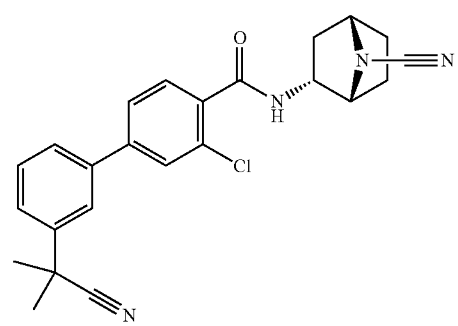 [SMILES: CC(C)(C#N)c1cccc(-c2ccc(C(=O)N[C@@H]3C[C@@H]4CC[C@H]3N4C#N)c(Cl)c2)c1] |
| 20-8 | 3-chloro-N-((1R,2R,4S)-7-cyano-7-azabicyclo[2.2.1]heptan-2-yl)-3'-(cyanomethyl)-5'-fluoro[biphenyl]-4-carboxamide | 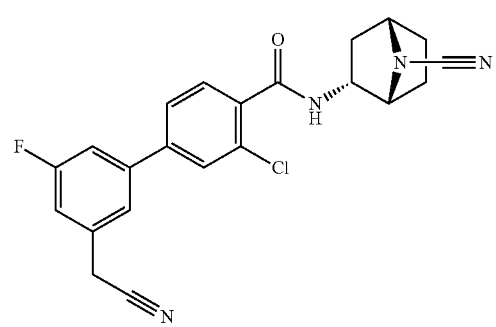 [SMILES: N#CCc1cc(F)cc(-c2ccc(C(=O)N[C@@H]3C[C@@H]4CC[C@H]3N4C#N)c(Cl)c2)c1] |
| 20-9 | 3-chloro-N-((1R,2R,4S)-7-cyano-7-azabicyclo[2.2.1]heptan-2-yl)-3'-(cyanomethyl)-4'-fluoro[biphenyl]-4-carboxamide | 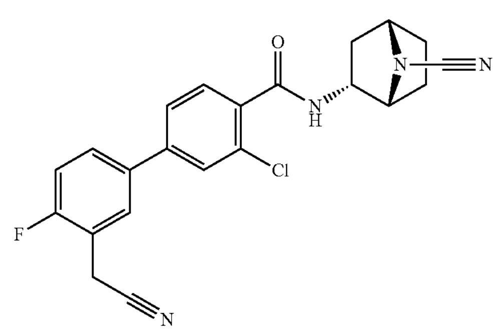 [SMILES: N#CCc1cc(-c2ccc(C(=O)N[C@@H]3C[C@@H]4CC[C@H]3N4C#N)c(Cl)c2)ccc1F] |

| Ex # | Name[FB-L22] | Structure |
|---|---|---|
| 20-10 | 3-chloro-N-((1R,2R,4S)-7-cyano-7-azabicyclo[2.2.1]heptan-2-yl)-3'-(cyanomethyl)-2'-fluoro[biphenyl]-4-carboxamide | 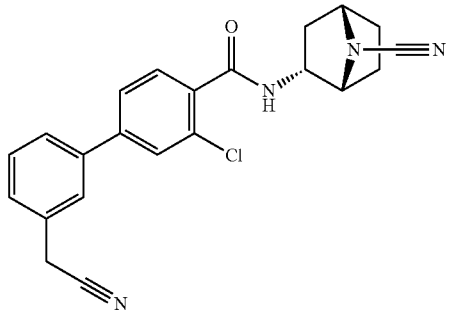 [SMILES: N#CCc1cccc(-c2ccc(C(=O)N[C@@H]3C[C@@H]4CC[C@H]3N4C#N)c(Cl)c2)c1] |
| 20-11 | 3-chloro-N-((1R,2R,4S)-7-cyano-7-azabicyclo[2.2.1]heptan-2-yl)-5'-(cyanomethyl)-2'-fluoro[biphenyl]-4-carboxamide | 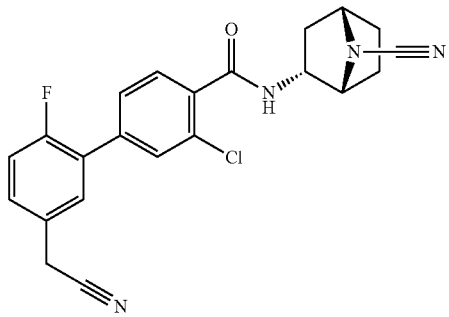 |
| 20-12 | 2-chloro-N-((1R,2R,4S)-7-cyano-7-azabicyclo[2.2.1]heptan-2-yl)-4-(6-(2-cyano-2-propanyl)-2-pyridinyl)benzamide | 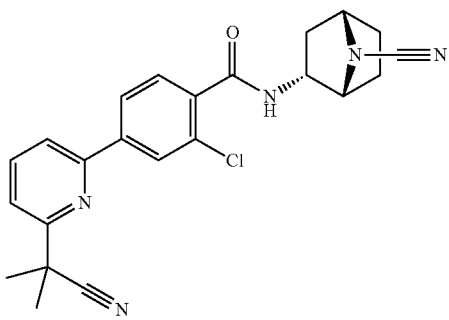 [SMILES: CC(C)(C#N)c1cccc(-c2ccc(C(=O)N[C@@H]3C[C@@H]4CC[C@H]3N4C#N)c(Cl)c2)n1] |
| 20-13 | 3-chloro-N-((1R,2R,4S)-7-cyano-7-azabicyclo[2.2.1]heptan-2-yl)-5'-(cyanomethyl)-2'-methyl[biphenyl]-4-carboxamide | 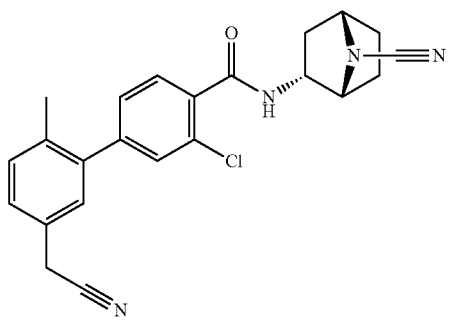 [SMILES: Cc1ccc(CC#N)cc1-c1ccc(C(=O)N[C@@H]2C[C@@H]3CC[C@H]2N3C#N)c(Cl)c1] |

-continued

| Ex # | Name[FB-L22] | Structure |
|---|---|---|
| 20-14 | 3-chloro-N-((1R,2R,4S)-7-cyano-7-azabicyclo[2.2.1]heptan-2-yl)-3'-(cyanomethyl)-4'-methyl[biphenyl]-4-carboxamide | 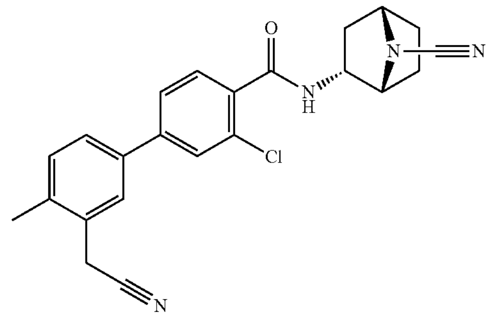 [SMILES: Cc1ccc(-c2ccc(C(=O)N[C@@H]3C[C@@H]4CC[C@H]3N4C#N)c(Cl)c2)cc1CC#N] |
| 20-15 | 3-chloro-N-((1R,2R,4S)-7-cyano-7-azabicyclo[2.2.1]heptan-2-yl)-3'-(cyanomethyl)-5'-methyl[biphenyl]-4-carboxamide | 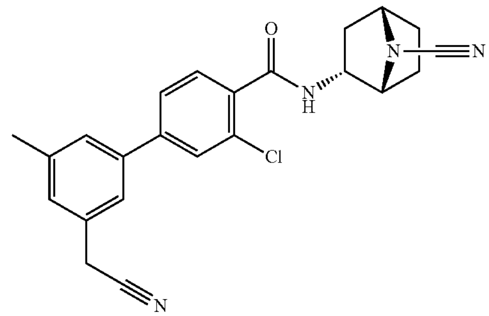 [SMILES: Cc1cc(CC#N)cc(-c2ccc(C(=O)N[C@@H]3C[C@@H]4CC[C@H]3N4C#N)c(Cl)c2)c1] |
| 20-16 | 3-chloro-N-((1R,2R,4S)-7-cyano-7-azabicyclo[2.2.1]heptan-2-yl)-3'-(cyanomethyl)[biphenyl]-4-carboxamide | 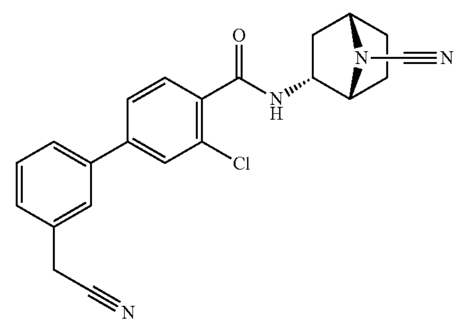 [SMILES: N#CCc1cccc(-c2ccc(C(=O)N[C@@H]3C[C@@H]4CC[C@H]3N4C#N)c(Cl)c2)c1] |
| 20-17 | 3-chloro-N-((1R,2R,4S)-7-cyano-7-azabicyclo[2.2.1]heptan-2-yl)-3'-(1-cyanocyclobutyl)[biphenyl]-4-carboxamide | 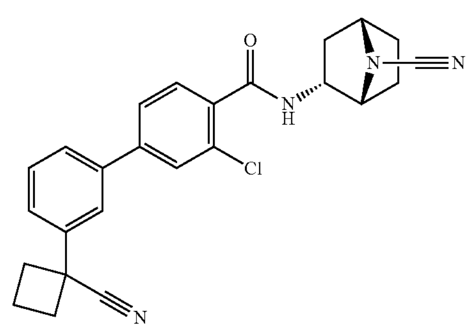 [SMILES: N#CN1[C@H]2CC[C@@H]1[C@H](NC(=O)c1ccc(-c3cccc(C4(C#N)CCC4)c3)cc1Cl)C2] |

| Ex # | Name[FB-L22] | Structure |
|---|---|---|
| 20-18 | 2-chloro-N-((1R,2R,4S)-7-cyano-7-azabicyclo[2.2.1]heptan-2-yl)-4-(6-(methoxymethyl)-2-pyridinyl)benzamide | 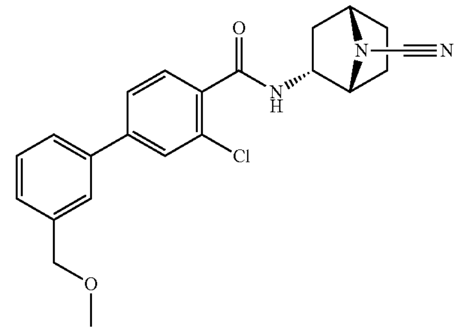 [SMILES: COCc1cccc(-c2ccc(C(=O)N[C@@H]3C[C@@H]4CC[C@H]3N4C#N)c(Cl)c2)c1] |
| 20-19 | 3-chloro-N-((1R,2R,4S)-7-cyano-7-azabicyclo[2.2.1]heptan-2-yl)-4'-(cyanomethyl)[biphenyl]-4-carboxamide | 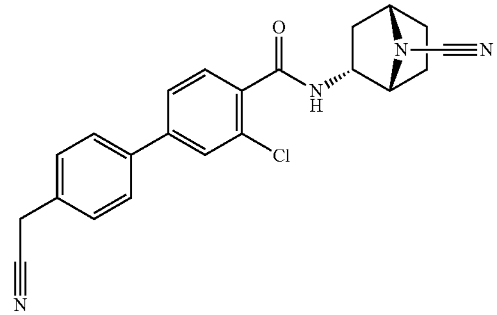 [SMILES: N#CCc1ccc(-c2ccc(C(=O)N[C@@H]3C[C@@H]4CC[C@H]3N4C#N)c(Cl)c2)cc1] |
| 20-20 | 2-chloro-N-((1R,2R,4S)-7-cyano-7-azabicyclo[2.2.1]heptan-2-yl)-4-(5-(1-cyanocyclopropyl)-3-pyridinyl)benzamide | 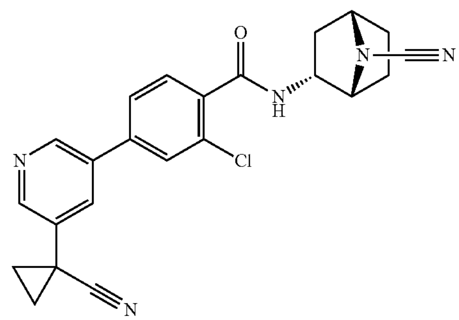 [SMILES: N#CN1[C@H]2CC[C@@H]1[C@H](NC(=O)c1ccc(-c3cncc(C4(C#N)CC4)c3)cc1Cl)C2] |
| 20-21 | 4-(6-(acetyl(methyl)amino)-2-pyridinyl)-2-chloro-N-((1R,2R,4S)-7-cyano-7-azabicyclo[2.2.1]heptan-2-yl)benzamide | 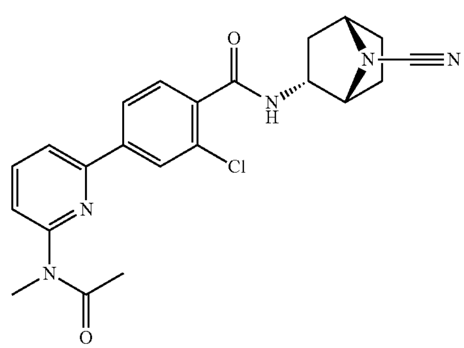 [SMILES: CC(=O)N(C)c1cccc(-c2ccc(C(=O)N[C@@H]3C[C@@H]4CC[C@H]3N4C#N)c(Cl)c2)n1] |
| 20-22 | 2-chloro-N-((1R,2R,4S)-7-cyano-7-azabicyclo[2.2.1]heptan-2-yl)-4-(5-(cyanomethyl)-3-pyridinyl)benzamide | 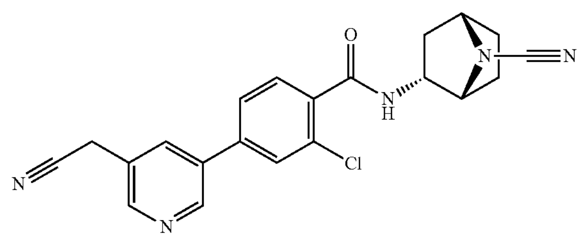 [SMILES: N#CCc1cncc(-c2ccc(C(=O)N[C@@H]3C[C@@H]4CC[C@H]3N4C#N)c(Cl)c2)c1] |

-continued

| Ex # | Name[FB-L22] | Structure |
|---|---|---|
| 20-23 | 2-chloro-N-((1R,2R,4S)-7-cyano-7-azabicyclo[2.2.1]heptan-2-yl)-4-(4-(cyanomethyl)-2-pyridinyl)benzamide | 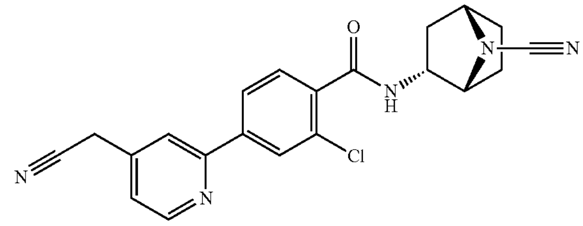 [SMILES: N#CCc1ccnc(-c2ccc(C(=O)N[C@@H]3C[C@@H]4CC[C@H]3N4C#N)c(Cl)c2)c1] |
| 20-24 | N-((1R,2R,4S)-7-cyano-7-azabicyclo[2.2.1]heptan-2-yl)-4-(6-(1-cyanocyclopropyl)-2-pyridinyl)-2-methylbenzamide | 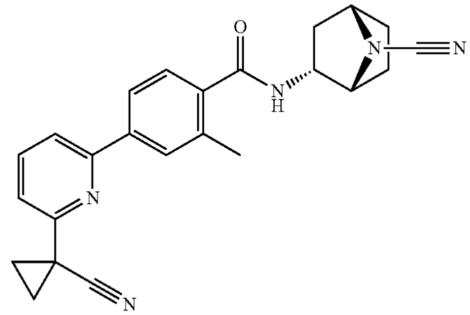 [SMILES: Cc1cc(-c2cccc(C3(C#N)CC3)n2)ccc1C(=O)N[C@@H]1C[C@@H]2CC[C@H]1N2C#N] |
| 20-25 | 3-chloro-N-((1R,2R,4S)-7-cyano-7-azabicyclo[2.2.1]heptan-2-yl)-3'-(1-cyanocyclopropyl)[biphenyl]-4-carboxamide | 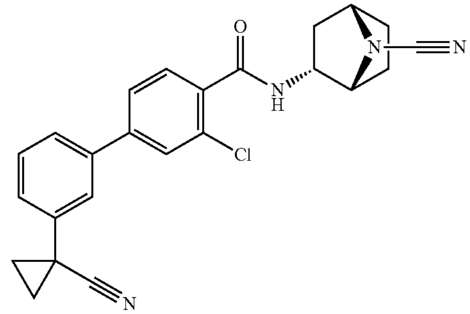 [SMILES: N#CN1[C@H]2CC[C@@H]1[C@H](NC(=O)c1ccc(-c3cccc(C4(C#N)CC4)c3)cc1Cl)C2] |
| 20-26 | 2-chloro-N-((1R,2R,4S)-7-cyano-7-azabicyclo[2.2.1]heptan-2-yl)-4-(2-(cyanomethyl)-3-pyridinyl)benzamide | 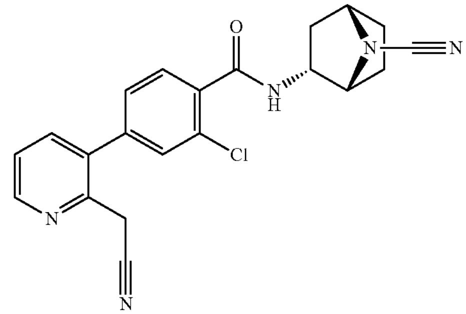 [SMILES: N#CCc1ncccc1-c1ccc(C(=O)N[C@@H]2C[C@@H]3CC[C@H]2N3C#N)c(Cl)c1] |
| 20-27 | N-((1R,2R,4S)-7-cyano-7-azabicyclo[2.2.1]heptan-2-yl)-4-(6-(1-cyanocyclopropyl)-2-pyridinyl)-2-(trifluoromethyl)benzamide | 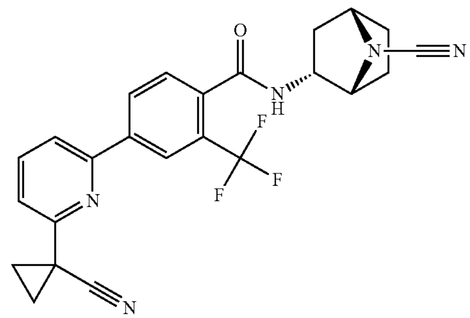 [SMILES: N#CN1[C@H]2CC[C@@H]1[C@H](NC(=O)c1ccc(-c3cccc(C4(C#N)CC4)n3)cc1C(F)(F)F)C2] |

-continued

| Ex # | Name[FB-L22] | Structure |
|---|---|---|
| 20-28 | N-((1R,2R,4S)-7-cyano-7-azabicyclo[2.2.1]heptan-2-yl)-4-(6-(1-cyanocyclopropyl)-2-pyridinyl)-2-fluorobenzamide | 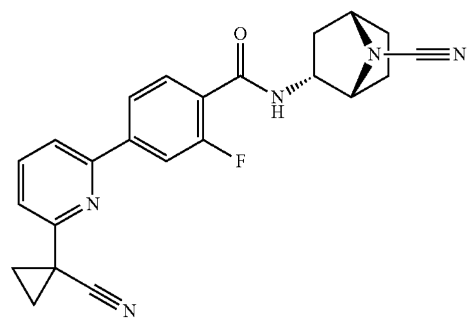 [SMILES: N#CN1[C@H]2CC[C@@H]1[C@H](NC(=O)c1ccc(-c3cccc(C4(C#N)CC4)n3)cc1F)C2] |
| 20-29 | N-((1R,2R,4S)-7-cyano-7-azabicyclo[2.2.1]heptan-2-yl)-4-(1-methyl-1H-pyrazol-3-yl)-2-(trifluoromethyl)benzamide | 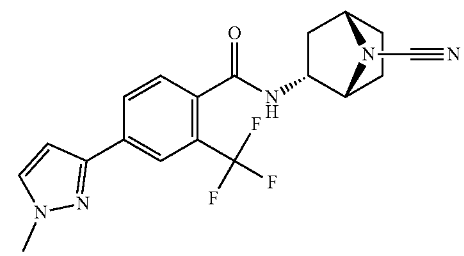 [SMILES: Cn1ccc(-c2ccc(C(=O)N[C@@H]3C[C@@H]4CC[C@H]3N4C#N)c(C(F)(F)F)c2)n1] |
| 20-30 | N-((1R,2R,4S)-7-cyano-7-azabicyclo[2.2.1]heptan-2-yl)-4-(imidazo[1,5-a]pyridin-6-yl)-2-(trifluoromethyl)benzamide | 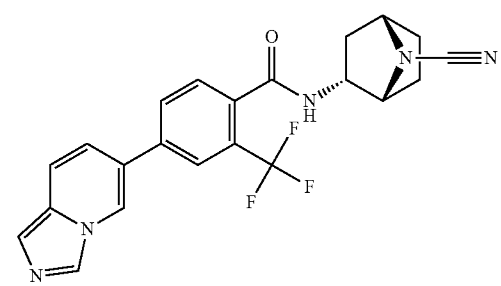 [SMILES: N#CN1[C@H]2CC[C@@H]1[C@H](NC(=O)c1ccc(-c3ccc4cncn4c3)cc1C(F)(F)F)C2] |
| 20-31 | N-((1R,2R,4S)-7-cyano-7-azabicyclo[2.2.1]heptan-2-yl)-2-fluoro-4-(1-methyl-1H-pyrazol-3-yl)benzamide | 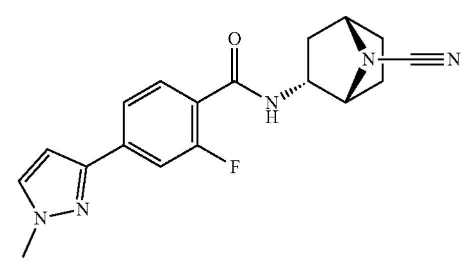 [SMILES: Cn1ccc(-c2ccc(C(=O)N[C@@H]3C[C@@H]4CC[C@H]3N4C#N)c(F)c2)n1] |
| 20-32 | N-((1R,2R,4S)-7-cyano-7-azabicyclo[2.2.1]heptan-2-yl)-2-fluoro-4-(imidazo[1,5-a]pyridin-6-yl)benzamide | 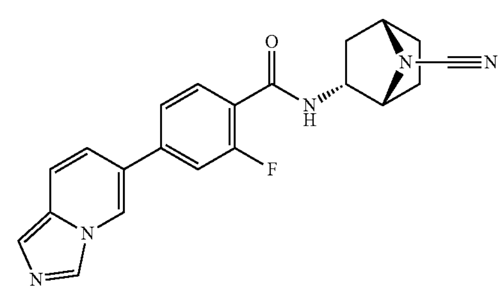 [SMILES: N#CN1[C@H]2CC[C@@H]1[C@H](NC(=O)c1ccc(-c3ccc4cncn4c3)cc1F)C2] |

-continued

| Ex # | Name[FB-L22] | Structure |
|---|---|---|
| 20-33 | 2,6-dichloro-N-((1R,2R,4S)-7-cyano-7-azabicyclo[2.2.1]heptan-2-yl)-4-(1-methyl-1H-pyrazol-3-yl)benzamide | 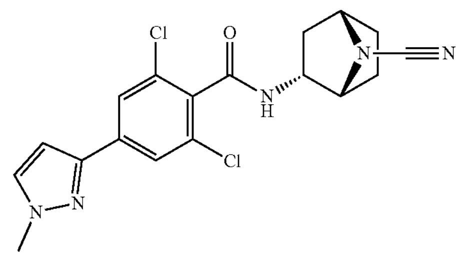 [SMILES: Cn1ccc(-c2cc(Cl)c(C(=O)N[C@@H]3C[C@@H]4CC[C@H]3N4C#N)c(Cl)c2)n1] |
| 20-34 | 2,6-dichloro-N-((1R,2R,4S)-7-cyano-7-azabicyclo[2.2.1]heptan-2-yl)-4-(imidazo[1,5-a]pyridin-6-yl)benzamide | 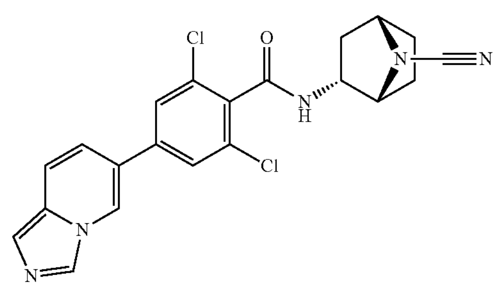 [SMILES: N#CN1[C@H]2CC[C@@H]1[C@H](NC(=O)c1c(Cl)cc(-c3ccc4cncn4c3)cc1Cl)C2] |
| 20-35 | 2-chloro-N-((1R,2R,4S)-7-cyano-7-azabicyclo[2.2.1]heptan-2-yl)-4-(5-cyano-2-pyrimidinyl)benzamide | 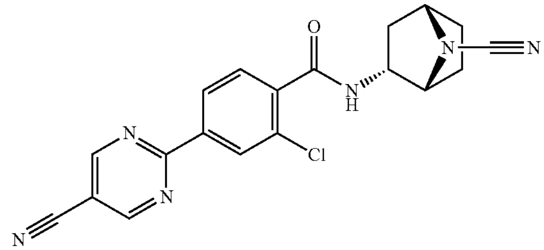 [SMILES: N#Cc1cnc(-c2ccc(C(=O)N[C@@H]3C[C@@H]4CC[C@H]3N4C#N)c(Cl)c2)nc1] |
| 20-36 | 2-chloro-N-((1R,2R,4S)-7-cyano-7-azabicyclo[2.2.1]heptan-2-yl)-4-(4-cyano-2-pyrimidinyl)benzamide | 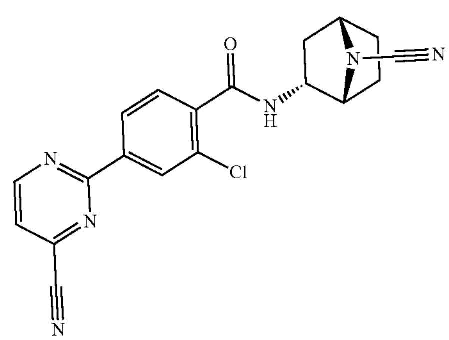 [SMILES: N#Cc1ccnc(-c2ccc(C(=O)N[C@@H]3C[C@@H]4CC[C@H]3N4C#N)c(Cl)c2)n1] |
| 20-37 | 2-chloro-N-((1R,2R,4S)-7-cyano-7-azabicyclo[2.2.1]heptan-2-yl)-4-(6-methyl-2-pyrazinyl)benzamide | 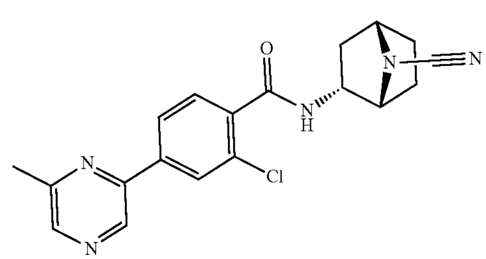 [SMILES: Cc1cncc(-c2ccc(C(=O)N[C@@H]3C[C@@H]4CC[C@H]3N4C#N)c(Cl)c2)n1] |

| Ex # | Name[FB-L22] | Structure |
|---|---|---|
| 20-38 | 2-chloro-N-((1R,2R,4S)-7-cyano-7-azabicyclo[2.2.1]heptan-2-yl)-4-(5-methyl-2-pyrazinyl)benzamide | 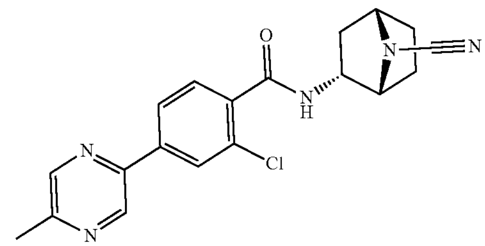 [SMILES: Cc1cnc(-c2ccc(C(=O)N[C@@H]3C[C@@H]4CC[C@H]3N4C#N)c(Cl)c2)cn1] |
| 20-39 | 2-chloro-N-((1R,2R,4S)-7-cyano-7-azabicyclo[2.2.1]heptan-2-yl)-4-(4-cyano-2-pyridinyl)benzamide | 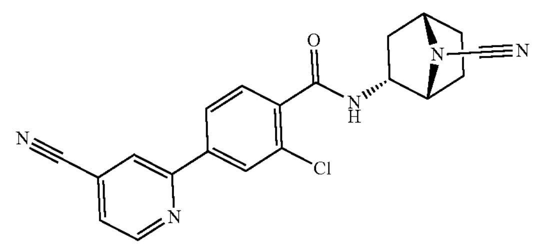 [SMILES: N#Cc1ccnc(-c2ccc(C(=O)N[C@@H]3C[C@@H]4CC[C@H]3N4C#N)c(Cl)c2)c1] |
| 20-40 | 2-chloro-N-((1R,2R,4S)-7-cyano-7-azabicyclo[2.2.1]heptan-2-yl)-4-(6-methyl-2-pyridinyl)benzamide | 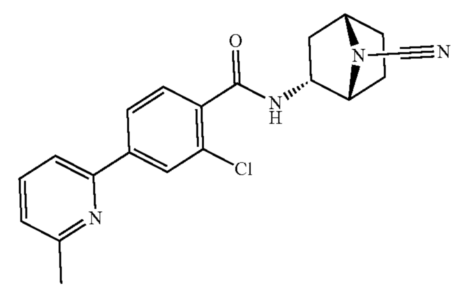 [SMILES: Cc1cccc(-c2ccc(C(=O)N[C@@H]3C[C@@H]4CC[C@H]3N4C#N)c(Cl)c2)n1] |
| 20-41 | 2-chloro-N-((1R,2R,4S)-7-cyano-7-azabicyclo[2.2.1]heptan-2-yl)-4-(2-methyl-4-pyrimidinyl)benzamide | 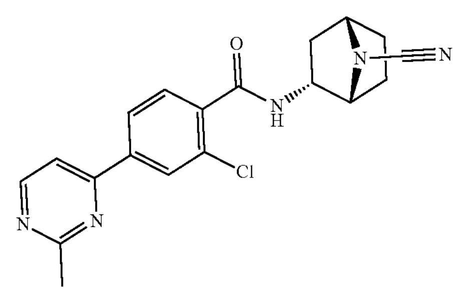 [SMILES: Cc1nccc(-c2ccc(C(=O)N[C@@H]3C[C@@H]4CC[C@H]3N4C#N)c(Cl)c2)n1] |
| 20-42 | 2-chloro-N-((1R,2R,4S)-7-cyano-7-azabicyclo[2.2.1]heptan-2-yl)-4-(6-methyl-3-pyridazinyl)benzamide | 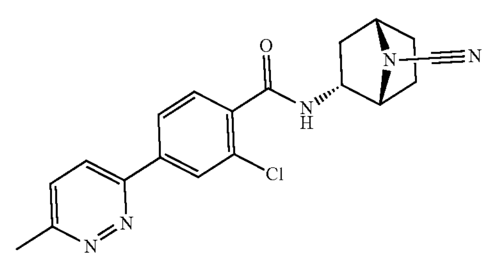 [SMILES: Cc1ccc(-c2ccc(C(=O)N[C@@H]3C[C@@H]4CC[C@H]3N4C#N)c(Cl)c2)nn1] |

| Ex # | Name[FB-L22] | Structure |
|---|---|---|
| 20-43 | 2-chloro-N-((1R,2R,4S)-7-cyano-7-azabicyclo[2.2.1]heptan-2-yl)-4-(6-(difluoromethyl)-2-pyridinyl)benzamide | 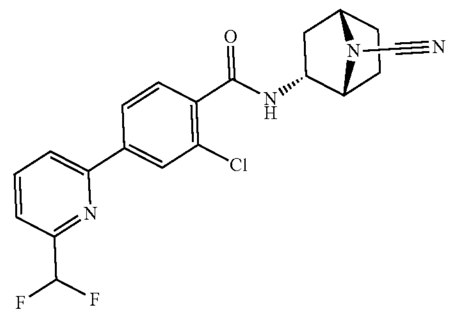 [SMILES: N#CN1[C@H]2CC[C@@H]1[C@H](NC(=O)c1ccc(-c3cccc(C(F)F)n3)cc1Cl)C2] |
| 20-44 | 2-chloro-N-((1R,2R,4S)-7-cyano-7-azabicyclo[2.2.1]heptan-2-yl)-4-(6-(cyanomethyl)-2-pyridinyl)benzamide | 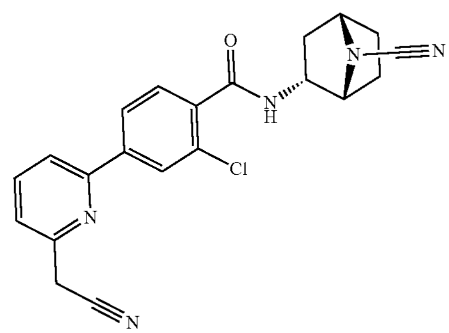 [SMILES: N#CCc1cccc(-c2ccc(C(=O)N[C@@H]3C[C@@H]4CC[C@H]3N4C#N)c(Cl)c2)n1] |
| 20-45 | 2-chloro-N-((1R,2R,4S)-7-cyano-7-azabicyclo[2.2.1]heptan-2-yl)-4-(6-(difluoromethoxy)-2-pyridinyl)benzamide | 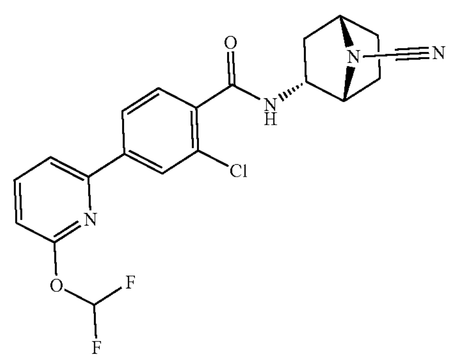 [SMILES: N#CN1[C@H]2CC[C@@H]1[C@H](NC(=O)c1ccc(-c3cccc(OC(F)F)n3)cc1Cl)C2] |
| 20-46 | 2-chloro-N-((1R,2R,4S)-7-cyano-7-azabicyclo[2.2.1]heptan-2-yl)-4-(6-(1,1-difluoroethyl)-2-pyridinyl)benzamide | 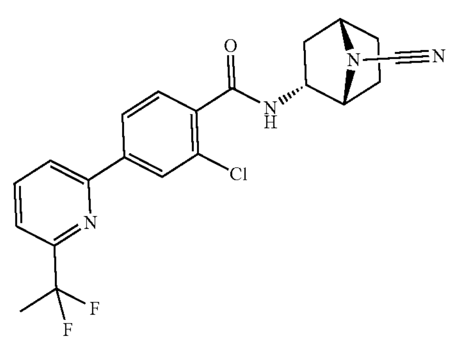 [SMILES: CC(F)(F)c1cccc(-c2ccc(C(=O)N[C@@H]3C[C@@H]4CC[C@H]3N4C#N)c(Cl)c2)n1] |

-continued

| Ex # | Name[FB-L22] | Structure |
|---|---|---|
| 20-47 | 2-chloro-N-((1R,2R,4S)-7-cyano-7-azabicyclo[2.2.1]heptan-2-yl)-4-(6-cyclopropyl-2-pyrazinyl)benzamide | 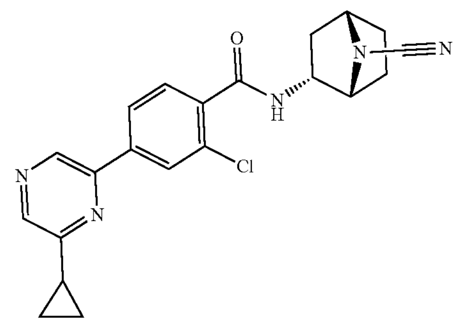 [SMILES: N#CN1[C@H]2CC[C@@H]1[C@H](NC(=O)c1ccc(-c3cncc(C4CC4)n3)cc1Cl)C2] |
| 20-48 | 2-chloro-N-((1R,2R,4S)-7-cyano-7-azabicyclo[2.2.1]heptan-2-yl)-4-(6-cyano-2-pyridinyl)benzamide | 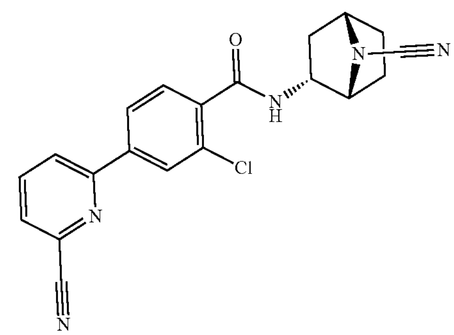 [SMILES: N#Cc1cccc(-c2ccc(C(=O)N[C@@H]3C[C@@H]4CC[C@H]3N4C#N)c(Cl)c2)n1] |
| 20-49 | 2-chloro-N-((1R,2R,4S)-7-cyano-7-azabicyclo[2.2.1]heptan-2-yl)-4-(6-(1-cyanocyclopropyl)-2-pyridinyl)benzamide | 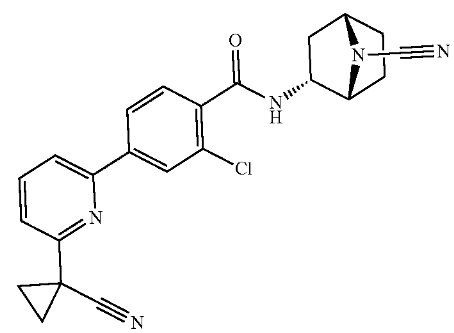 [SMILES: N#CN1[C@H]2CC[C@@H]1[C@H](NC(=O)c1ccc(-c3cccc(C4(C#N)CC4)n3)cc1Cl)C2] |
| 20-50 | 2-chloro-N-((1R,2R,4S)-7-cyano-7-azabicyclo[2.2.1]heptan-2-yl)-4-(6-(2,2,2-trifluoroethoxy)-2-pyridinyl)benzamide | 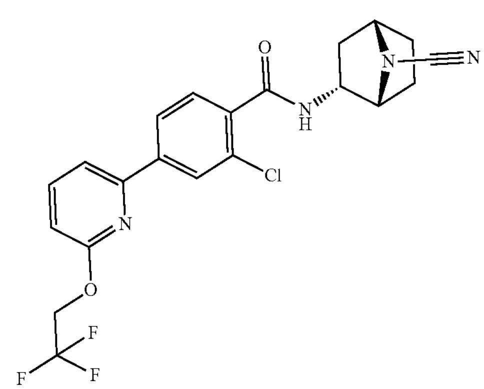 [SMILES: N#CN1[C@H]2CC[C@@H]1[C@H](NC(=O)c1ccc(-c3cccc(OCC(F)(F)F)n3)cc1Cl)C2] |

-continued

| Ex # | Name[FB-L22] | Structure |
|---|---|---|
| 20-51 | 2-chloro-N-((1R,2R,4S)-7-cyano-7-azabicyclo[2.2.1]heptan-2-yl)-4-(imidazo[1,2-a]pyridin-6-yl)benzamide | 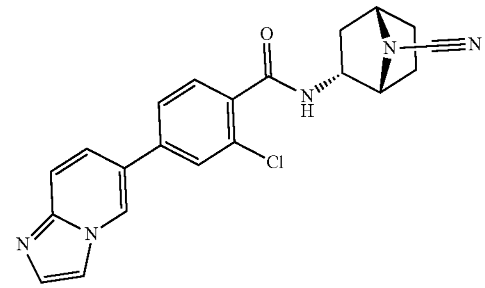 [SMILES: N#CN1[C@H]2CC[C@@H]1[C@H](NC(=O)c1ccc(-c3ccc4nccn4c3)cc1Cl)C2] |
| 20-52 | 2-chloro-N-((1R,2R,4S)-7-cyano-7-azabicyclo[2.2.1]heptan-2-yl)-4-(1-methyl-1H-indazol-7-yl)benzamide | 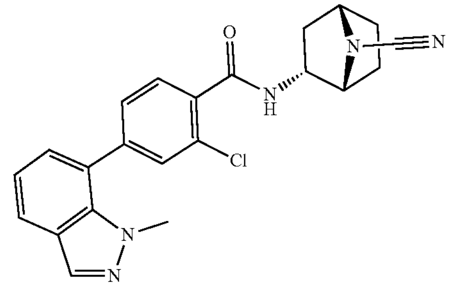 [SMILES: Cn1ncc2cccc(-c3ccc(C(=O)N[C@@H]4C[C@@H]5CC[C@H]4N5C#N)c(Cl)c3)c21] |
| 20-53 | 2-chloro-N-((1R,2R,4S)-7-cyano-7-azabicyclo[2.2.1]heptan-2-yl)-4-(7-methylimidazo[1,2-a]pyridin-6-yl)benzamide | 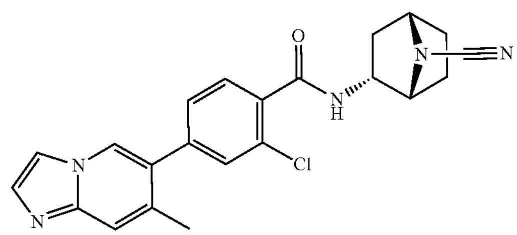 [SMILES: Cc1cc2nccn2cc1-c1ccc(C(=O)N[C@@H]2C[C@@H]3CC[C@H]2N3C#N)c(Cl)c1] |
| 20-54 | 2-chloro-N-((1R,2R,4S)-7-cyano-7-azabicyclo[2.2.1]heptan-2-yl)-4-(2-methylimidazo[1,2-a]pyridin-6-yl)benzamide | 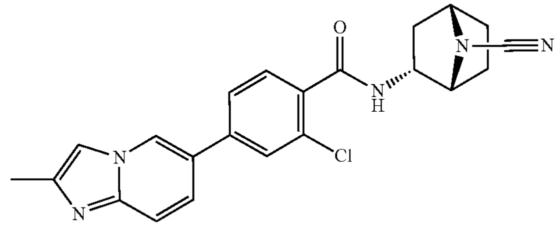 [SMILES: Cc1cn2cc(-c3ccc(C(=O)N[C@@H]4C[C@@H]5CC[C@H]4N5C#N)c(Cl)c3)ccc2n1] |
| 20-55 | 2-chloro-N-((1R,2R,4S)-7-cyano-7-azabicyclo[2.2.1]heptan-2-yl)-4-(imidazo[1,2-a]pyridin-7-yl)benzamide | 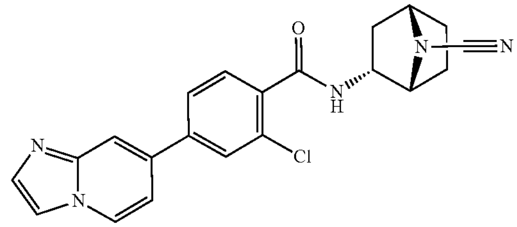 [SMILES: N#CN1[C@H]2CC[C@@H]1[C@H](NC(=O)c1ccc(-c3ccn4ccnc4c3)cc1Cl)C2] |
| 20-56 | 2-chloro-N-((1R,2R,4S)-7-cyano-7-azabicyclo[2.2.1]heptan-2-yl)-4-(imidazo[1,5-a]pyridin-6-yl)benzamide | 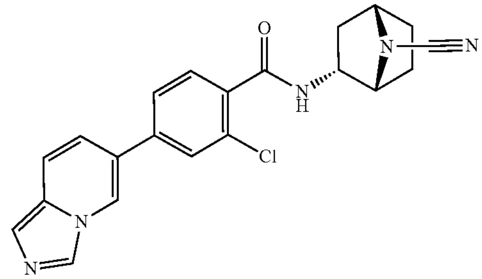 [SMILES: N#CN1[C@H]2CC[C@@H]1[C@H](NC(=O)c1ccc(-c3ccc4cncn4c3)cc1Cl)C2] |

| Ex # | Name[FB-L22] | Structure |
|---|---|---|
| 20-57 | 2-chloro-N-((1R,2R,4S)-7-cyano-7-azabicyclo[2.2.1]heptan-2-yl)-4-(1-methyl-1H-pyrazol-3-yl)benzamide | 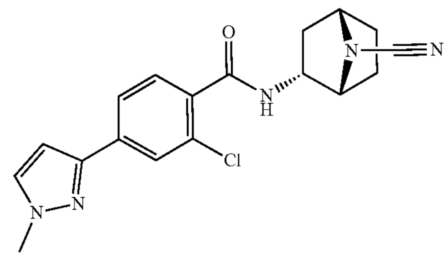 |
| 20-58 | 2-chloro-N-((1R,2R,4S)-7-cyano-7-azabicyclo[2.2.1]heptan-2-yl)-4-(1-methyl-1H-pyrazol-5-yl)benzamide | 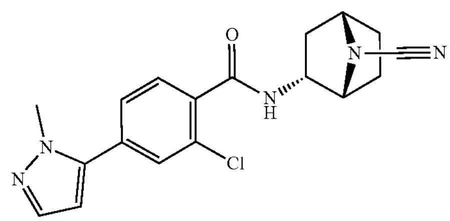 [SMILES: Cn1nccc1-c1ccc(C(=O)N[C@@H]2C[C@@H]3CC[C@H]2N3C#N)c(Cl)c1] |
| 20-59 | 2-chloro-N-((1R,2R,4S)-7-cyano-7-azabicyclo[2.2.1]heptan-2-yl)-4-(1-cyclopropyl-1H-pyrazol-4-yl)benzamide | 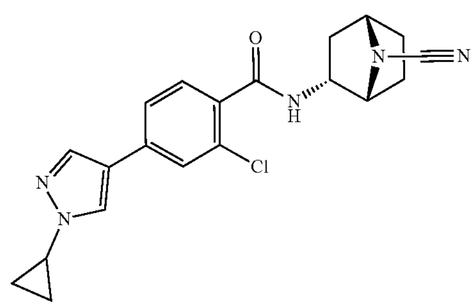 [SMILES: N#CN1[C@H]2CC[C@@H]1[C@H](NC(=O)c1ccc(-c3cnn(C4CC4)c3)cc1Cl)C2] |
| 20-60 | 2-chloro-N-((1R,2R,4S)-7-cyano-7-azabicyclo[2.2.1]heptan-2-yl)-4-(1-(cyanomethyl)-1H-pyrazol-4-yl)benzamide | 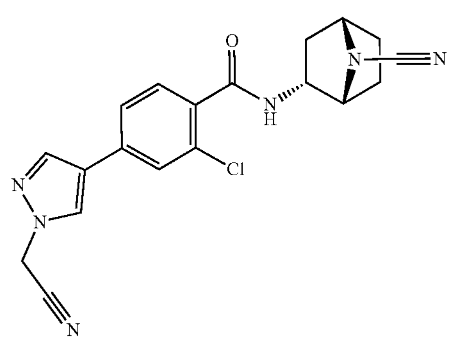 [SMILES: N#CCn1cc(-c2ccc(C(=O)N[C@@H]3C[C@@H]4CC[C@H]3N4C#N)c(Cl)c2)cn1] |
| 20-61 | 2-chloro-N-((1R,2R,4S)-7-cyano-7-azabicyclo[2.2.1]heptan-2-yl)-4-(1-methyl-1H-imidazol-4-yl)benzamide | 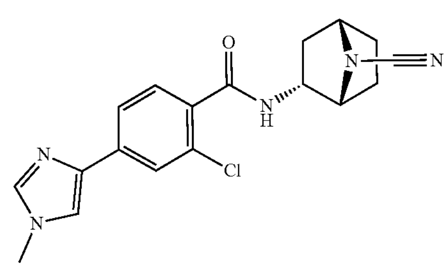 [SMILES: Cn1cnc(-c2ccc(C(=O)N[C@@H]3C[C@@H]4CC[C@H]3N4C#N)c(Cl)c2)c1] |

| Ex # | Name[FB-L22] | Structure |
|---|---|---|
| 20-62 | 2-chloro-N-((1R,2R,4S)-7-cyano-7-azabicyclo[2.2.1]heptan-2-yl)-4-(1-methyl-1H-pyrazol-4-yl)benzamide | 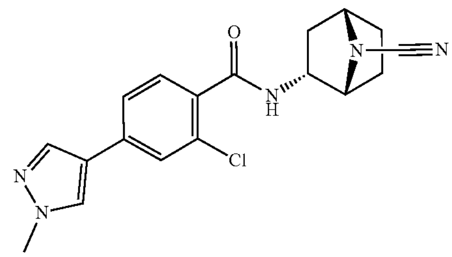 [SMILES: Cn1cc(-c2ccc(C(=O)N[C@@H]3C[C@@H]4CC[C@H]3N4C#N)c(Cl)c2)cn1] |
| 20-63 | N-((1R,2R,4S)-7-cyano-7-azabicyclo[2.2.1]heptan-2-yl)-4-(4-cyano-2-pyridinyl)-3-(2-methylpropoxy)benzamide | 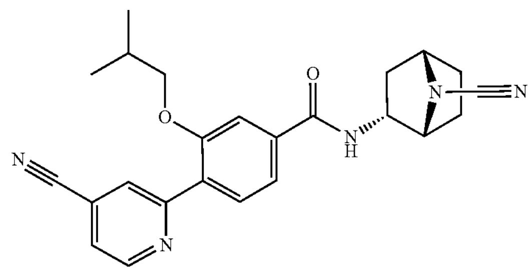 [SMILES: CC(C)COc1cc(C(=O)N[C@@H]2C[C@@H]3CC[C@H]2N3C#N)ccc1-c1cc(C#N)ccn1] |
| 20-64 | N-((1R,2R,4S)-7-cyano-7-azabicyclo[2.2.1]heptan-2-yl)-3-(2-methylpropoxy)-4-(5-methyl-2-pyrazinyl)benzamide | 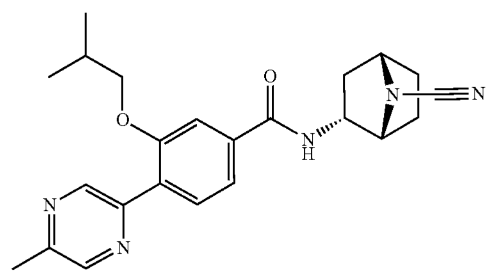 [SMILES: Cc1cnc(-c2ccc(C(=O)N[C@@H]3C[C@@H]4CC[C@H]3N4C#N)cc2OCC(C)C)cn1] |
| 20-65 | N-((1R,2R,4S)-7-cyano-7-azabicyclo[2.2.1]heptan-2-yl)-3-(2-methylpropoxy)-4-(6-methyl-2-pyridinyl)benzamide | 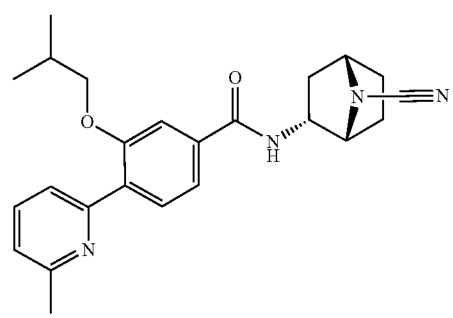 [SMILES: Cc1cccc(-c2ccc(C(=O)N[C@@H]3C[C@@H]4CC[C@H]3N4C#N)cc2OCC(C)C)n1] |
| 20-66 | N-((1R,2R,4S)-7-cyano-7-azabicyclo[2.2.1]heptan-2-yl)-3-(2-methylpropoxy)-4-(4-methyl-2-pyrimidinyl)benzamide | 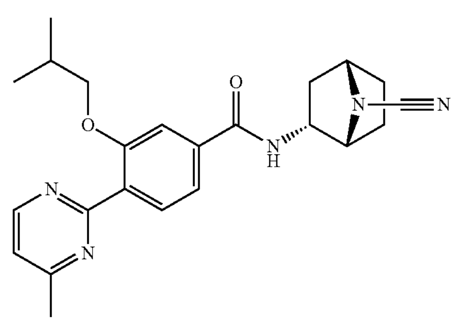 [SMILES: Cc1ccnc(-c2ccc(C(=O)N[C@@H]3C[C@@H]4CC[C@H]3N4C#N)cc2OCC(C)C)n1] |

-continued

| Ex # | Name[FB-L22] | Structure |
|---|---|---|
| 20-67 | N-((1R,2R,4S)-7-cyano-7-azabicyclo[2.2.1]heptan-2-yl)-4-(6-(cyanomethyl)-2-pyridinyl)-3-(2-methylpropoxy)benzamide | 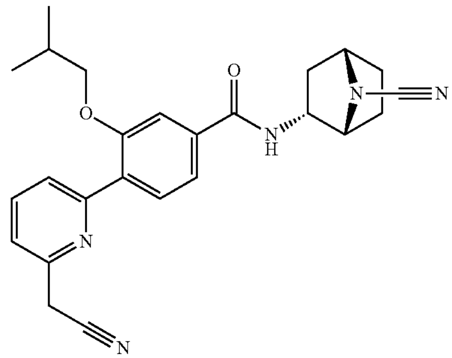 [SMILES: CC(C)COc1cc(C(=O)N[C@@H]2C[C@@H]3CC[C@H]2N3C#N)ccc1-c1cccc(CC#N)n1] |
| 20-68 | N-((1R,2R,4S)-7-cyano-7-azabicyclo[2.2.1]heptan-2-yl)-3-(2-methylpropoxy)-4-(1-methyl-1H-pyrazol-3-yl)benzamide | 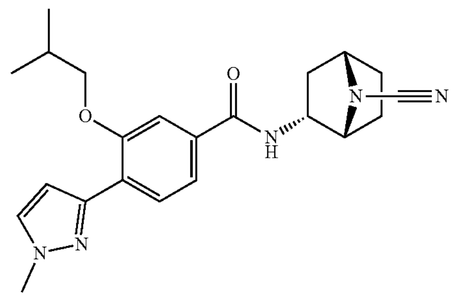 [SMILES: CC(C)COc1cc(C(=O)N[C@@H]2C[C@@H]3CC[C@H]2N3C#N)ccc1-c1ccn(C)n1] |
| 20-69 | N-((1R,2R,4S)-7-cyano-7-azabicyclo[2.2.1]heptan-2-yl)-3-(2-methylpropoxy)-4-(1-methyl-1H-pyrazol-5-yl)benzamide | 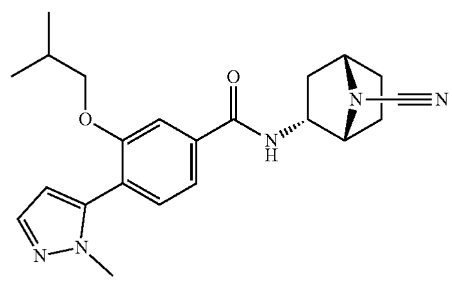 [SMILES: CC(C)COc1cc(C(=O)N[C@@H]2C[C@@H]3CC[C@H]2N3C#N)ccc1-c1ccnn1C] |
| 20-70 | N-((1R,2R,4S)-7-cyano-7-azabicyclo[2.2.1]heptan-2-yl)-4-(1-methyl-1H-imidazol-4-yl)-3-(2-methylpropoxy)benzamide | 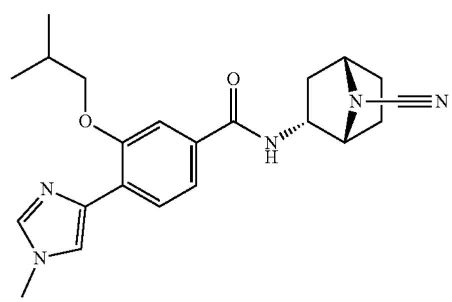 [SMILES: CC(C)COc1cc(C(=O)N[C@@H]2C[C@@H]3CC[C@H]2N3C#N)ccc1-c1cn(C)cn1] |
| 20-71 | N-((1R,2R,4S)-7-cyano-7-azabicyclo[2.2.1]heptan-2-yl)-4-(6-cyano-2-pyridinyl)-3-(2-methylpropoxy)benzamide | 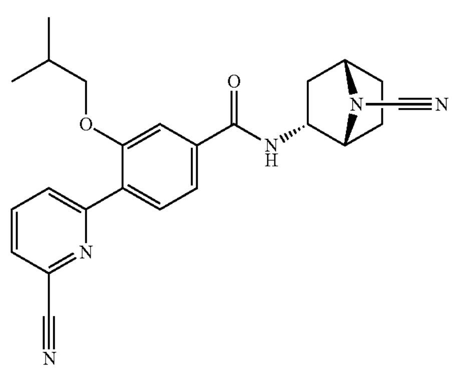 [SMILES: CC(C)COc1cc(C(=O)N[C@@H]2C[C@@H]3CC[C@H]2N3C#N)ccc1-c1cccc(C#N)n1] |

-continued

| Ex # | Name[FB-L22] | Structure |
|---|---|---|
| 20-72 | N-((1R,2R,4S)-7-cyano-7-azabicyclo[2.2.1]heptan-2-yl)-3-(2-methylpropoxy)-4-(6-methyl-3-pyridazinyl)benzamide | 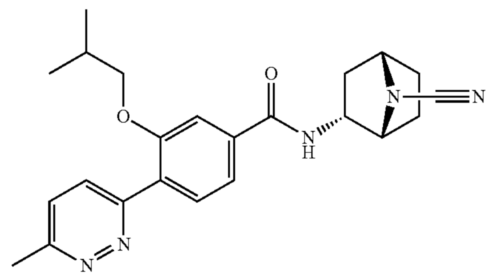 [SMILES: Cc1ccc(-c2ccc(C(=O)N[C@@H]3C[C@@H]4CC[C@H]3N4C#N)cc2OCC(C)C)nn1] |
| 20-73 | N-((1R,2R,4S)-7-cyano-7-azabicyclo[2.2.1]heptan-2-yl)-3-(2-methylpropoxy)-4-(2-methyl-4-pyrimidinyl)benzamide | 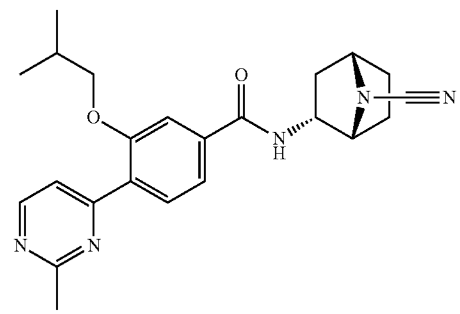 [SMILES: Cc1nccc(-c2ccc(C(=O)N[C@@H]3C[C@@H]4CC[C@H]3N4C#N)cc2OCC(C)C)n1] |
| 20-74 | N-((1R,2R,4S)-7-cyano-7-azabicyclo[2.2.1]heptan-2-yl)-3-(2-methylbutoxy)-4-(1-methyl-1H-pyrazol-4-yl)benzamide | 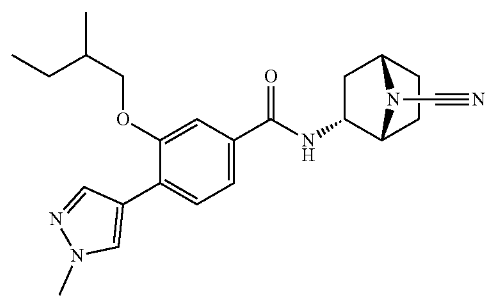 [SMILES: CCC(C)COc1cc(C(=O)N[C@@H]2C[C@@H]3CC[C@H]2N3C#N)ccc1-c1cnn(C)c1] |
| 20-75 | N-((1R,2R,4S)-7-cyano-7-azabicyclo[2.2.1]heptan-2-yl)-4-(1-ethyl-1H-pyrazol-4-yl)-3-(2-methylpropoxy)benzamide | 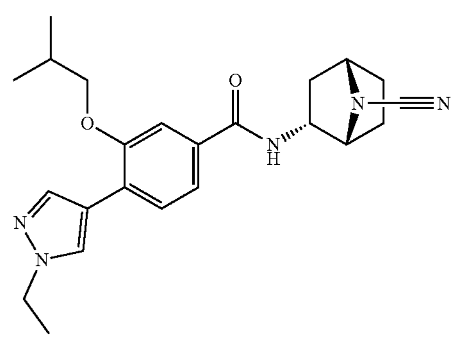 [SMILES: CCn1cc(-c2ccc(C(=O)N[C@@H]3C[C@@H]4CC[C@H]3N4C#N)cc2OCC(C)C)cn1] |
| 20-76 | N-((1R,2R,4S)-7-cyano-7-azabicyclo[2.2.1]heptan-2-yl)-4-(1-cyclopropyl-1H-pyrazol-4-yl)-3-(2-methylpropoxy)benzamide | 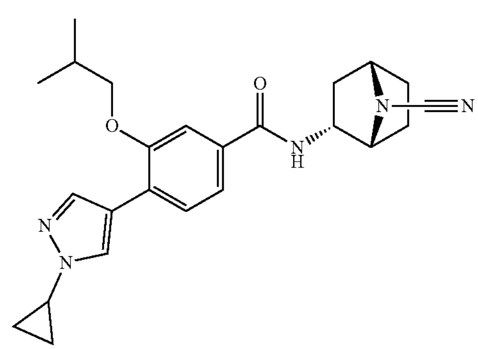 [SMILES: CC(C)COc1cc(C(=O)N[C@@H]2C[C@@H]3CC[C@H]2N3C#N)ccc1-c1cnn(C2CC2)c1] |

-continued

| Ex # | Name[FB-L22] | Structure |
|---|---|---|
| 22-1 | N-((1R,2R,4S)-7-cyano-7-azabicyclo[2.2.1]heptan-2-yl)-1-(6-methyl-2-pyridinyl)-7-(trifluoromethyl)-1H-indazole-5-carboxamide | 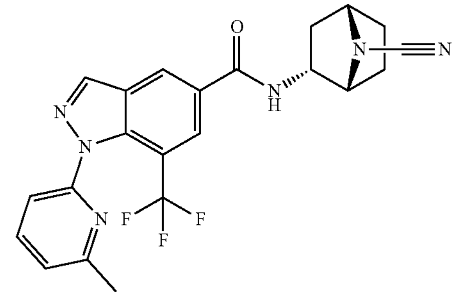 [SMILES: Cc1cccc(-n2ncc3cc(C(=O)N[C@@H]4C[C@@H]5CC[C@H]4N5C#N)cc(C(F)(F)F)c32)n1] |
| 23-7 | N-((1R,2R,4S)-7-cyano-7-azabicyclo[2.2.1]heptan-2-yl)-2-(2,3-dichlorophenyl)-1-pyrrolidinecarboxamide | 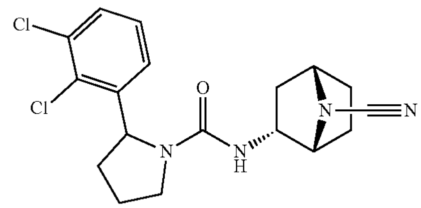 [SMILES: N#CN1[C@H]2CC[C@@H]1[C@H](NC(=O)N1CCCC1c1cccc(Cl)c1Cl)C2] |
| 23-2 | 2-(3-bromo-2-methylphenyl)-N-((1R,2R,4S)-7-cyano-7-azabicyclo[2.2.1]heptan-2-yl)-1-pyrrolidinecarboxamide | 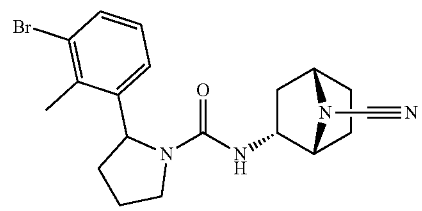 [SMILES: Cc1c(Br)cccc1C1CCCN1C(=O)N[C@@H]1C[C@@H]2CC[C@H]1N2C#N] |
| 23-3 | N-((1R,2R,4S)-7-cyano-7-azabicyclo[2.2.1]heptan-2-yl)-2-(2,3-dichlorophenyl)-1-azetidinecarboxamide | 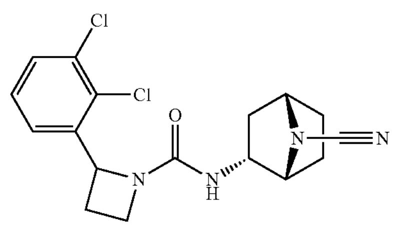 [SMILES: N#CN1[C@H]2CC[C@@H]1[C@H](NC(=O)N1CCC1c1cccc(Cl)c1Cl)C2] |
| 23-4 | 1-((1R,2R,4S)-7-cyano-7-azabicyclo[2.2.1]heptan-2-yl)-3-((-3-(2-propanyl)-2,3-dihydro-1H-inden-1-yl)methyl)urea | 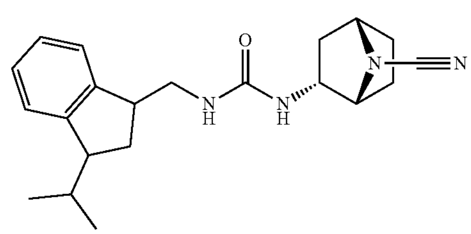 [SMILES: CC(C)C1CC(CNC(=O)N[C@@H]2C[C@@H]3CC[C@H]2N3C#N)c2ccccc21] |
| 23-5 | 1-((1R,2R,4S)-7-cyano-7-azabicyclo[2.2.1]heptan-2-yl)-3-(1-(2,3-dichlorophenyl)ethyl)urea | 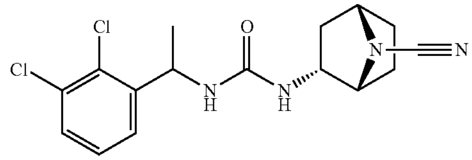 [SMILES: CC(NC(=O)N[C@@H]1C[C@@H]2CC[C@H]1N2C#N)c1cccc(Cl)c1Cl] |
| 23-6 | 1-((7-chloro-1,2,3,4-tetrahydro-1-naphthalenyl)methyl)-3-((1R,2R,4S)-7-cyano-7-azabicyclo[2.2.1]heptan-2-yl)urea | 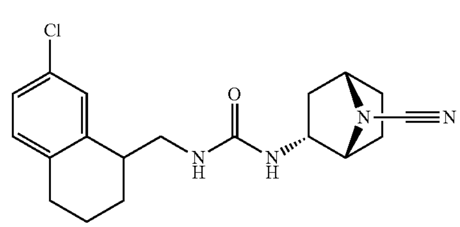 [SMILES: N#CN1[C@H]2CC[C@@H]1[C@H](NC(=O)NCC1CCCc3ccc(Cl)cc31)C2] |

-continued

| Ex # | Name[FB-L22] | Structure |
|---|---|---|
| 23-1 | 1-((1R,2R,4S)-7-cyano-7-azabicyclo[2.2.1]heptan-2-yl)-3-(2-(2,5-dichlorophenyl)ethyl)urea | 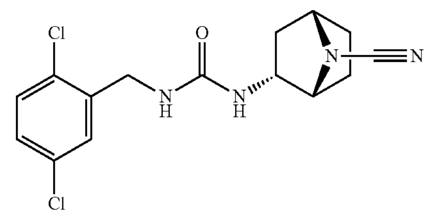 [SMILES: N#CN1[C@H]2CC[C@@H]1[C@H](NC(=O)NCc1cc(Cl)ccc1Cl)C2] |
| 23-8 | 7-chloro-N-((1R,2R,4S)-7-cyano-7-azabicyclo[2.2.1]heptan-2-yl)-2,3-dihydro-1,4-benzoxazepine-4(5H)-carboxamide | 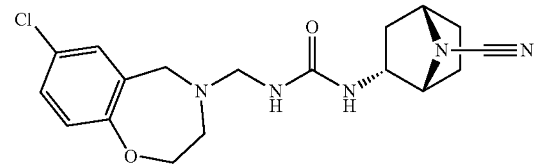 [SMILES: N#CN1[C@H]2CC[C@@H]1[C@H](NC(=O)NCN1CCOc3ccc(Cl)cc3C1)C2] |
| 23-9 | 8-chloro-N-((1R,2R,4S)-7-cyano-7-azabicyclo[2.2.1]heptan-2-yl)-1,3,4,5-tetrahydro-2H-pyrido[4,3-b]indole-2-carboxamide | 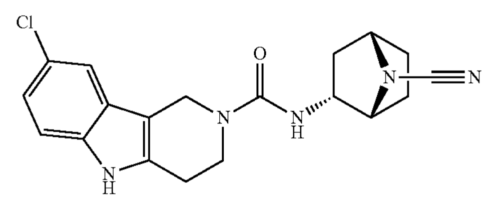 [SMILES: N#CN1[C@H]2CC[C@@H]1[C@H](NC(=O)N1CCc3[nH]c4ccc(Cl)cc4c3C1)C2] |
| 24-1 | N'-((1R,2R,4S)-7-cyano-7-azabicyclo[2.2.1]heptan-2-yl)-N-(2-hydroxyethyl)-N-(tricyclo[3.3.1.1~3,7~]decan-1-ylmethyl)ethanediamide | 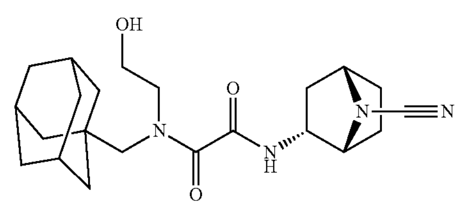 [SMILES: N#CN1[C@H]2CC[C@@H]1[C@H](NC(=O)C(=O)N(CCO)CC13CC4CC(CC(C4)C1)C3)C2] |
| 25-3 | 2-chloro-N-((1R,2R,4S)-7-cyano-7-azabicyclo[2.2.1]heptan-2-yl)-4-(4-(trifluoromethyl)-1H-pyrazol-1-yl)benzamide | 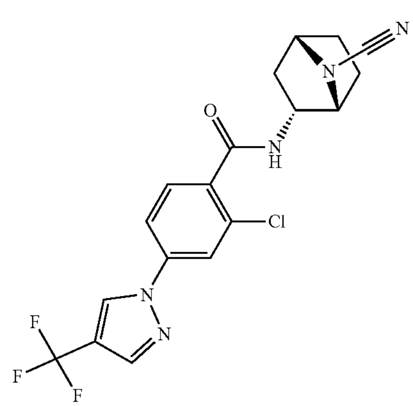 [SMILES: N#CN1[C@H]2CC[C@@H]1[C@H](NC(=O)c1ccc(-n3cc(C(F)(F)F)cn3)cc1Cl)C2] |

-continued

| Ex # | Name[FB-L22] | Structure |
|---|---|---|
| 25-2 | 2-chloro-N-((1R,2R,4S)-7-cyano-7-azabicyclo[2.2.1]heptan-2-yl)-4-(4-(cyanomethyl)-1H-pyrazol-1-yl)benzamide | 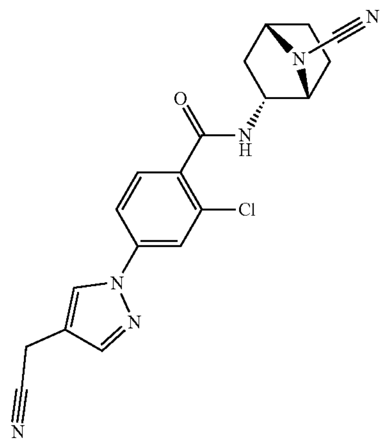 [SMILES: N#CCc1cnn(-c2ccc(C(=O)N[C@@H]3C[C@@H]4CC[C@H]3N4C#N)c(Cl)c2)c1] |
| 25-1 | 2-chloro-N-((1R,2R,4S)-7-cyano-7-azabicyclo[2.2.1]heptan-2-yl)-4-(4-ethyl-1H-pyrazol-1-yl)benzamide | 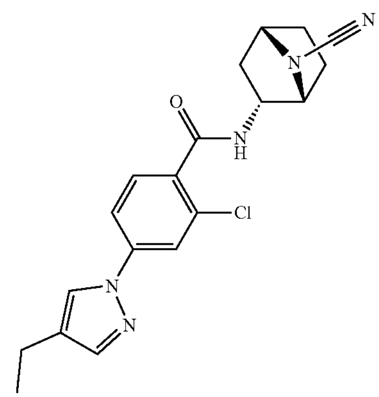 [SMILES: CCc1cnn(-c2ccc(C(=O)N[C@@H]3C[C@@H]4CC[C@H]3N4C#N)c(Cl)c2)c1] |
| 26-1-1 | (3R)-1-(3-chlorophenyl)-N-((1R,2R,4S)-7-cyano-7-azabicyclo[2.2.1]heptan-2-yl)-5-oxo-3-pyrrolidinecarboxamide | |
| 26-1-1 | (3S)-1-(3-chlorophenyl)-N-((1R,2R,4S)-7-cyano-7-azabicyclo[2.2.1]heptan-2-yl)-5-oxo-3-pyrrolidinecarboxamide | |

-continued

| Ex # | Name[FB-L22] | Structure |
|---|---|---|
| 26-3 | (3S)-1-(3-chlorophenyl)-N-((1R,2R,4S)-7-cyano-7-azabicyclo[2.2.1]heptan-2-yl)-3-pyrrolidinecarboxamide | 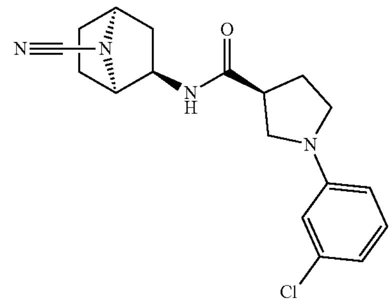 [SMILES: N#CN1[C@H]2CC[C@@H]1[C@H](NC(=O)[C@H]1CCN(c3cccc(Cl)c3)C1)C2] |
| 26-4 | (3R)-1-(3-chlorophenyl)-N-((1R,2R,4S)-7-cyano-7-azabicyclo[2.2.1]heptan-2-yl)-3-pyrrolidinecarboxamide | 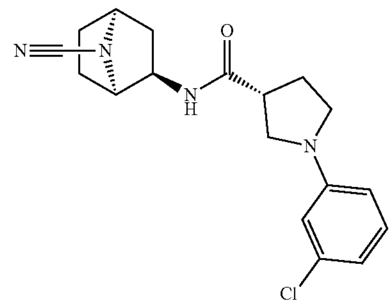 [SMILES: N#CN1[C@H]2CC[C@@H]1[C@H](NC(=O)[C@@H]1CCN(c3cccc(Cl)c3)C1)C2] |
| 26-5 | (2S)-5-bromo-N-((1R,2R,4S)-7-cyano-7-azabicyclo[2.2.1]heptan-2-yl)-2,3-dihydro-1H-indene-2-carboxamide | 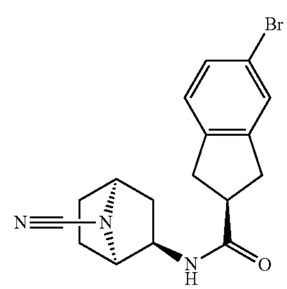 [SMILES: N#CN1[C@H]2CC[C@@H]1[C@H](NC(=O)[C@H]1Cc3ccc(Br)cc3C1)C2] |
| 26-6 | (2R)-5-bromo-N-((1R,2R,4S)-7-cyano-7-azabicyclo[2.2.1]heptan-2-yl)-2,3-dihydro-1H-indene-2-carboxamide | 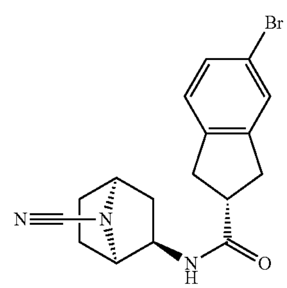 [SMILES: N#CN1[C@H]2CC[C@@H]1[C@H](NC(=O)[C@@H]1Cc3ccc(Br)cc3C1)C2] |
| 27-1 | (3R)-N-((1R,2R,4S)-7-cyano-7-azabicyclo[2.2.1]heptan-2-yl)-1-(4-cyclopropyl-2-pyrimidinyl)-3-pyrrolidinecarboxamide | 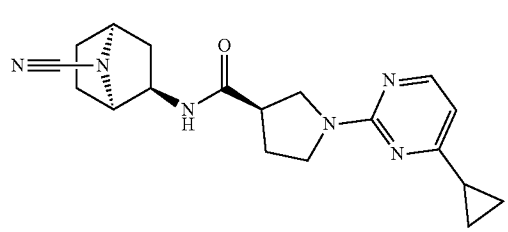 [SMILES: N#CN1[C@H]2CC[C@@H]1[C@H](NC(=O)[C@@H]1CCN(c3nccc(C4CC4)n3)C1)C2] |

| Ex # | Name[FB-L22] | Structure |
|---|---|---|
| 27-2-1 | (3R)-N-((1R,2R,4S)-7-cyano-7-azabicyclo[2.2.1]heptan-2-yl)-1-(6-(trifluoromethyl)-2-pyridinyl)-3-pyrrolidinecarboxamide | 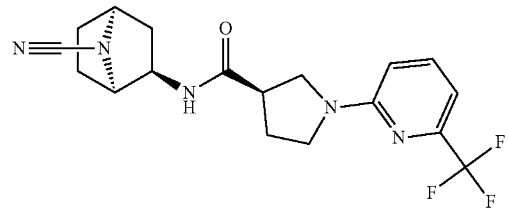 [SMILES: N#CN1[C@H]2CC[C@@H]1[C@H](NC(=O)[C@@H]1CCN(c3cccc(C(F)(F)F)n3)C1)C2] |
| 27-2-3 | (3S)-N-((1R,2R,4S)-7-cyano-7-azabicyclo[2.2.1]heptan-2-yl)-1-(6-(trifluoromethyl)-2-pyridinyl)-3-pyrrolidinecarboxamide | 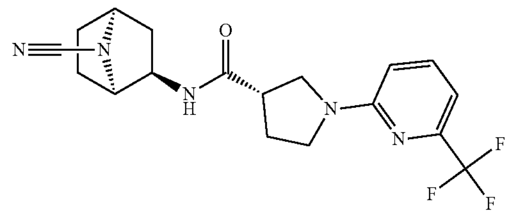 [SMILES: N#CN1[C@H]2CC[C@@H]1[C@H](NC(=O)[C@H]1CCN(c3cccc(C(F)(F)F)n3)C1)C2] |
| 28-1 | (3S)-N-((1R,2R,4S)-7-cyano-7-azabicyclo[2.2.1]heptan-2-yl)-1-(3,5-dichlorophenyl)-3-pyrrolidinecarboxamide | 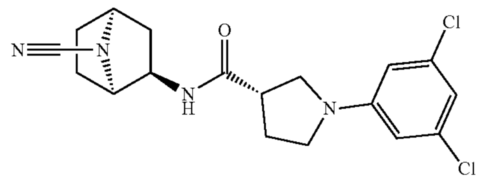 [SMILES: N#CN1[C@H]2CC[C@@H]1[C@H](NC(=O)[C@H]1CCN(c3cc(Cl)cc(Cl)c3)C1)C2] |
| 28-2 | (3S)-1-(5-chloro-2-cyanophenyl)-N-((1R,2R,4S)-7-cyano-7-azabicyclo[2.2.1]heptan-2-yl)-3-pyrrolidinecarboxamide | 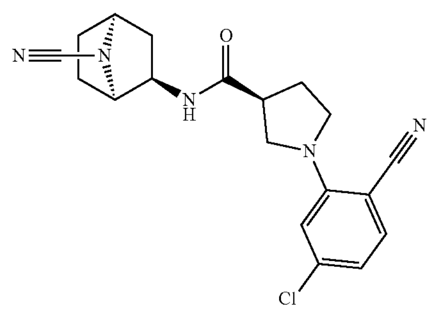 [SMILES: N#Cc1ccc(Cl)cc1N1CC[C@H](C(=O)N[C@@H]2C[C@@H]3CC[C@H]2N3C#N)C1] |
| 29-1 | (3S)-N-((1R,2R,4S)-7-cyano-7-azabicyclo[2.2.1]heptan-2-yl)-1-(6-cyano-4-(trifluoromethyl)-2-pyridinyl)-3-pyrrolidinecarboxamide | 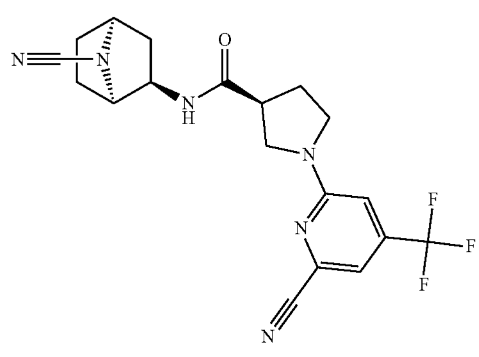 [SMILES: N#Cc1cc(C(F)(F)F)cc(N2CC[C@H](C(=O)N[C@@H]3C[C@@H]4CC[C@H]3N4C#N)C2)n1] |

-continued

| Ex # | Name[FB-L22] | Structure |
|---|---|---|
| 29-2 | (3S)-N-((1R,2R,4S)-7-cyano-7-azabicyclo[2.2.1]heptan-2-yl)-1-(6-cyano-4-methyl-2-pyridinyl)-3-pyrrolidinecarboxamide | 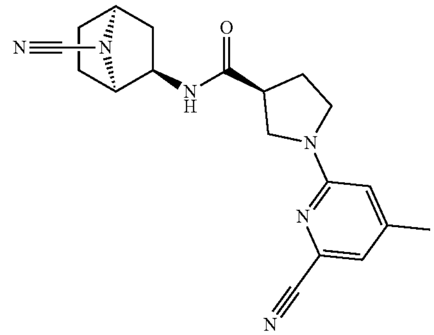 [SMILES: Cc1cc(C#N)nc(N2CC[C@H](C(=O)N[C@@H]3C[C@@H]4CC[C@H]3N4C#N)C2)c1] |
| 29-3 | (3S)-N-(1R,2R,4S)-7-cyano-7-azabicyclo[2.2.1]heptan-2-yl)-1-(4-methyl-6-(trifluoromethyl)-2-pyridinyl)-3-pyrrolidinecarboxamide | 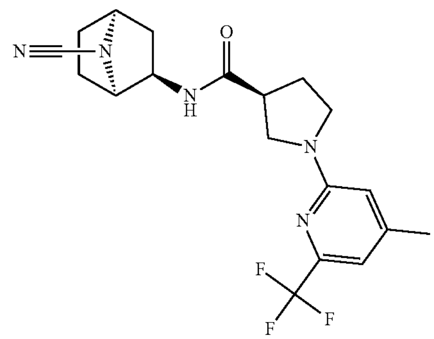 [SMILES: Cc1cc(N2CC[C@H](C(=O)N[C@@H]3C[C@@H]4CC[C@H]3N4C#N)C2)nc(C(F)(F)F)c1] |
| 29-4 | (3S)-N-(1R,2R,4S)-7-cyano-7-azabicyclo[2.2.1]heptan-2-yl)-1-(4-cyano-6-(trifluoromethyl)-2-pyridinyl)-3-pyrrolidinecarboxamide | 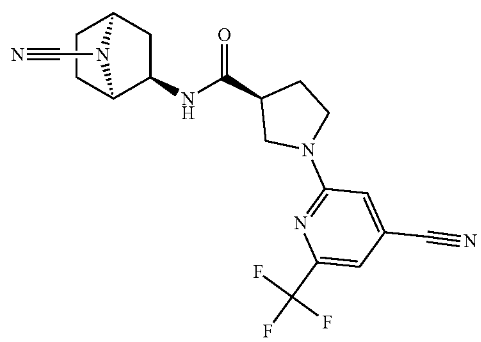 [SMILES: N#Cc1cc(N2CC[C@H](C(=O)N[C@@H]3C[C@@H]4CC[C@H]3N4C#N)C2)nc(C(F)(F)F)c1] |
| 29-5 | (3S)-N-((1R,2R,4S)-7-cyano-7-azabicyclo[2.2.1]heptan-2-yl)-1-(3-cyano-6-(trifluoromethyl)-2-pyridinyl)-3-pyrrolidinecarboxamide | 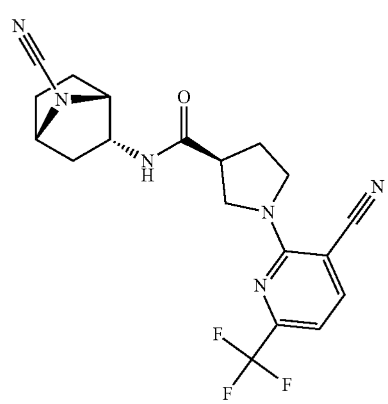 [SMILES: N#Cc1ccc(C(F)(F)F)nc1N1CC[C@H](C(=O)N[C@@H]2C[C@@H]3CC[C@H]2N3C#N)C1] |

-continued

| Ex # | Name[FB-L22] | Structure |
|---|---|---|
| 29-6 | (3S)-N-((1R,2R,4S)-7-cyano-7-azabicyclo[2.2.1]heptan-2-yl)-1-(6-(trifluoromethyl)-2-pyrazinyl)-3-pyrrolidinecarboxamide | 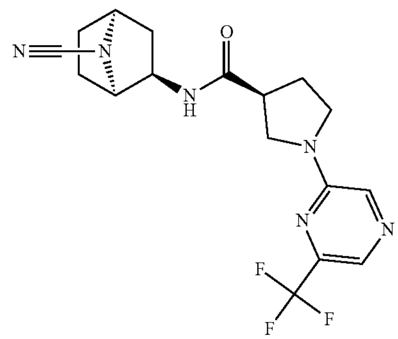 [SMILES: N#CN1[C@H]2CC[C@@H]1[C@H](NC(=O)[C@H]1CCN(c3cncc(C(F)(F)F)n3)C1)C2] |
| 29-7 | (3S)-1-(3-chloro-6-(trifluoromethyl)-2-pyridinyl)-N-((1R,2R,4S)-7-cyano-7-azabicyclo[2.2.1]heptan-2-yl)-3-pyrrolidinecarboxamide | 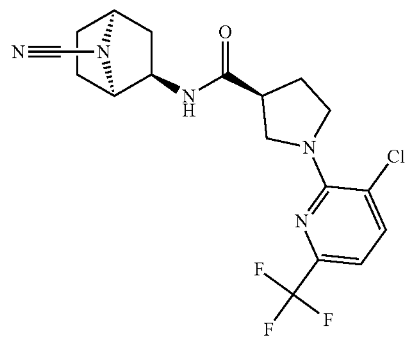 [SMILES: N#CN1[C@H]2CC[C@@H]1[C@H](NC(=O)[C@H]1CCN(c3nc(C(F)(F)F)ccc3Cl)C1)C2] |
| 30-1 | (3S)-N-((1R,2R,4S)-7-cyano-7-azabicyclo[2.2.1]heptan-2-yl)-1-(3-methylphenyl)-3-pyrrolidinecarboxamide | 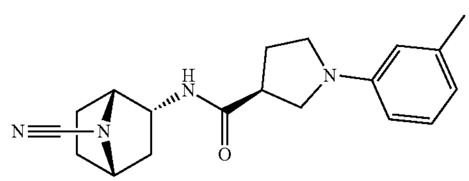 [SMILES: Cc1cccc(N2CC[C@H](C(=O)N[C@@H]3C[C@@H]4CC[C@H]3N4C#N)C2)c1] |
| 30-2 | (3S)-N-((1R,2R,4S)-7-cyano-7-azabicyclo[2.2.1]heptan-2-yl)-1-(3-methoxyphenyl)-3-pyrrolidinecarboxamide | 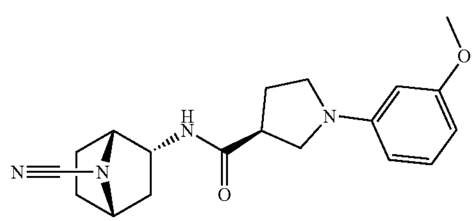 [SMILES: COc1cccc(N2CC[C@H](C(=O)N[C@@H]3C[C@@H]4CC[C@H]3N4C#N)C2)c1] |
| 30-3 | 7-chloro-N-((1R,2R,4S)-7-cyano-7-azabicyclo[2.2.1]heptan-2-yl)-2,3-dihydro-1-benzoxepine-4-carboxamide | 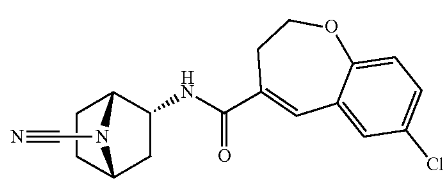 [SMILES: N#CN1[C@H]2CC[C@@H]1[C@H](NC(=O)C1=Cc3cc(Cl)ccc3OCC1)C2] |

-continued

| Ex # | Name[FB-L22] | Structure |
|---|---|---|
| 30-4 | (3S)-N-((1R,2R,4S)-7-cyano-7-azabicyclo[2.2.1]heptan-2-yl)-1-(2,5-dichlorophenyl)-3-pyrrolidinecarboxamide | 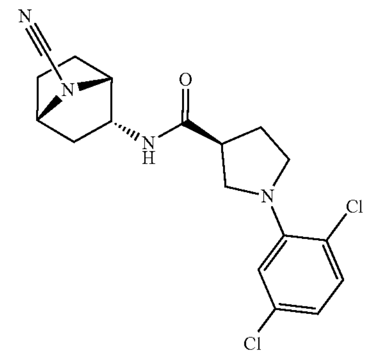 [SMILES: N#CN1[C@H]2CC[C@@H]1[C@H](NC(=O)[C@H]1CCN(c3cc(Cl)ccc3Cl)C1)C2] |
| 30-5 | (3S)-N-((1R,2R,4S)-7-cyano-7-azabicyclo[2.2.1]heptan-2-yl)-1-(3,5-dichloro-4-(trifluoromethoxy)phenyl)-3-pyrrolidinecarboxamide | 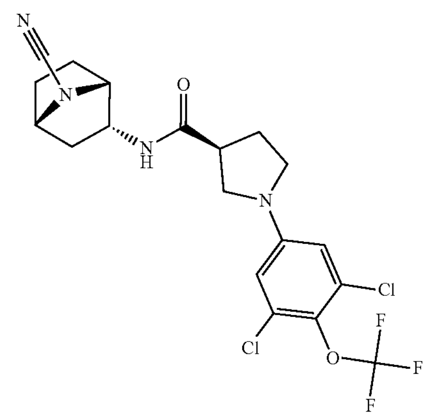 [SMILES: N#CN1[C@H]2CC[C@@H]1[C@H](NC(=O)[C@H]1CCN(c3cc(Cl)c(OC(F)(F)F)c(Cl)c3)C1)C2] |
| 30-6 | (3S)-1-(3-chloro-5-(trifluoromethyl)phenyl)-N-((1R,2R,4S)-7-cyano-7-azabicyclo[2.2.1]heptan-2-yl)-3-pyrrolidinecarboxamide | 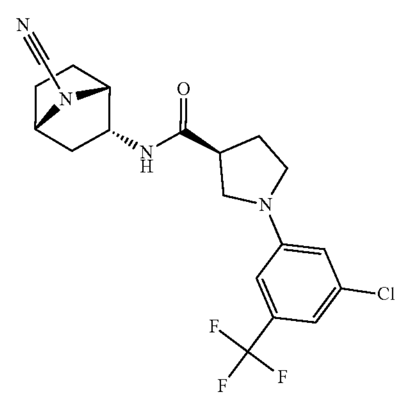 [SMILES: N#CN1[C@H]2CC[C@@H]1[C@H](NC(=O)[C@H]1CCN(c3cc(Cl)cc(C(F)(F)F)c3)C1)C2] |
| 30-7 | (3S)-1-(3-chloro-5-methylphenyl)-N-((1R,2R,4S)-7-cyano-7-azabicyclo[2.2.1]heptan-2-yl)-3-pyrrolidinecarboxamide | 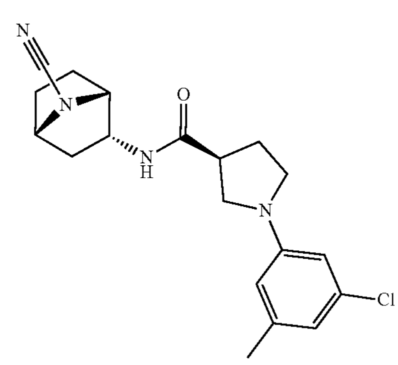 [SMILES: Cc1cc(Cl)cc(N2CC[C@H](C(=O)N[C@@H]3C[C@@H]4CC[C@H]3N4C#N)C2)c1] |

-continued

| Ex # | Name[FB-L22] | Structure |
|---|---|---|
| 30-8 | (3S)-1-(5-chloro-2-methylphenyl)-N-((1R,2R,4S)-7-cyano-7-azabicyclo[2.2.1]heptan-2-yl)-3-pyrrolidinecarboxamide | 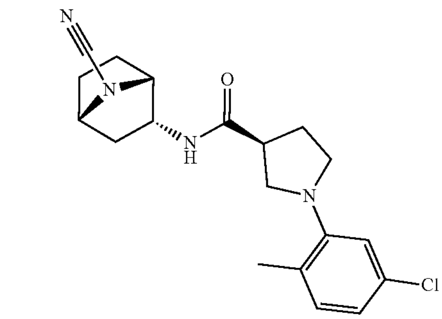 [SMILES: Cc1ccc(Cl)cc1N1CC[C@H](C(=O)N[C@@H]2C[C@@H]3CC[C@H]2N3C#N)C1] |
| 30-9 | 6-(3-chlorophenyl)-N-((1R,2R,4S)-7-cyano-7-azabicyclo[2.2.1]heptan-2-yl)-2-pyridinecarboxamide | 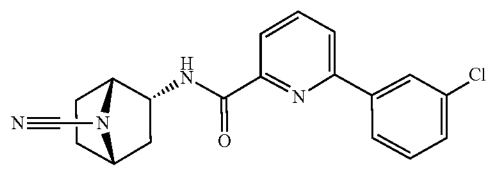 [SMILES: N#CN1[C@H]2CC[C@@H]1[C@H](NC(=O)c1cccc(-c3cccc(Cl)c3)n1)C2] |
| 30-10 | N-((1R,2R,4S)-7-cyano-7-azabicyclo[2.2.1]heptan-2-yl)-4-(2,5-dichlorophenyl)-2-pyridinecarboxamide | 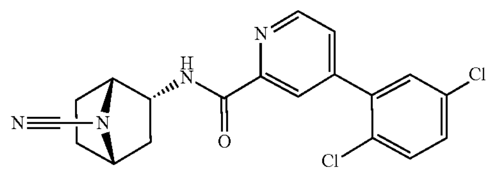 [SMILES: N#CN1[C@H]2CC[C@@H]1[C@H](NC(=O)c1cc(-c3cc(Cl)ccc3Cl)ccn1)C2] |
| 30-11 | N-((1R,2R,4S)-7-cyano-7-azabicyclo[2.2.1]heptan-2-yl)-4-(3,5-dichlorophenyl)-2-pyridinecarboxamide | 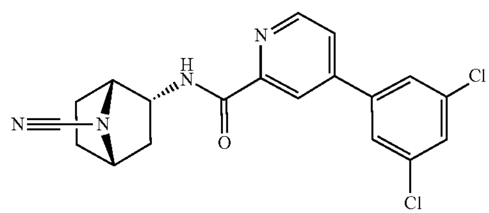 [SMILES: N#CN1[C@H]2CC[C@@H]1[C@H](NC(=O)c1cc(-c3cc(Cl)cc(Cl)c3)ccn1)C2] |
| 30-12 | 4-(3-chlorophenyl)-N-((1R,2R,4S)-7-cyano-7-azabicyclo[2.2.1]heptan-2-yl)-2-pyridinecarboxamide | 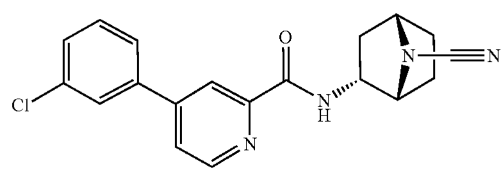 [SMILES: N#CN1[C@H]2CC[C@@H]1[C@H](NC(=O)c1cc(-c3cccc(Cl)c3)ccn1)C2] |
| 30-13 | (3S)-N-((1R,2R,4S)-7-cyano-7-azabicyclo[2.2.1]heptan-2-yl)-1-(3,5-dichloro-4-methoxyphenyl)-3-pyrrolidinecarboxamide | 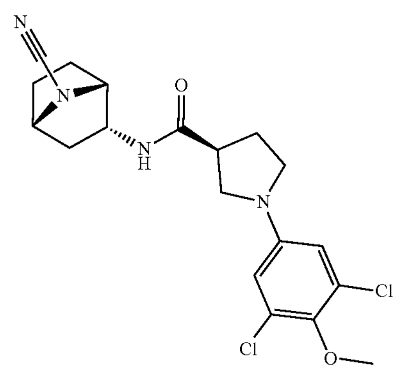 [SMILES: COc1c(Cl)cc(N2CC[C@H](C(=O)N[C@@H]3C[C@@H]4CC[C@H]3N4C#N)C2)cc1Cl] |

-continued

| Ex # | Name[FB-L22] | Structure |
|---|---|---|
| 30-14 | (3S)-N-((1R,2R,4S)-7-cyano-7-azabicyclo[2.2.1]heptan-2-yl)-1-(3,5-dichloro-4-fluorophenyl)-3-pyrrolidinecarboxamide | 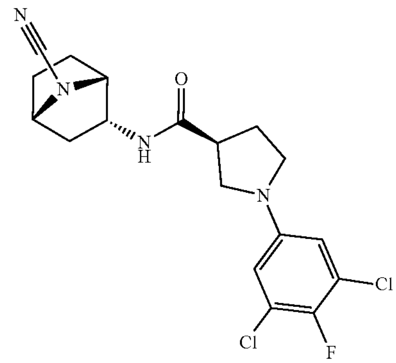 [SMILES: N#CN1[C@H]2CC[C@@H]1[C@H](NC(=O)[C@H]1CCN(c3cc(Cl)c(F)c(Cl)c3)C1)C2] |
| 30-15 | (3S)-N-((1R,2R,4S)-7-cyano-7-azabicyclo[2.2.1]heptan-2-yl)-1-(3-cyclopropylphenyl)-3-pyrrolidinecarboxamide | 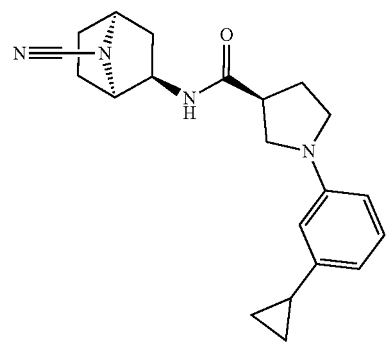 [SMILES: N#CN1[C@H]2CC[C@@H]1[C@H](NC(=O)[C@H]1CCN(c3cccc(C4CC4)c3)C1)C2] |
| 30-16 | N-((1R,2R,4S)-7-cyano-7-azabicyclo[2.2.1]heptan-2-yl)-4-(3,5-dichlorophenyl)-2-morpholinecarboxamide | 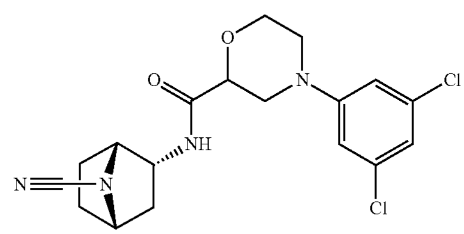 [SMILES: N#CN1[C@H]2CC[C@@H]1[C@H](NC(=O)C1CN(c3cc(Cl)cc(Cl)c3)CCO1)C2] |
| 30-17 | (3S)-N-((1R,2R,4S)-7-cyano-7-azabicyclo[2.2.1]heptan-2-yl)-1-(2,3,5-trichlorophenyl)-3-pyrrolidinecarboxamide | 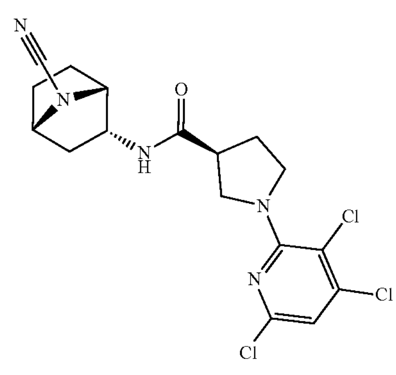 [SMILES: N#CN1[C@H]2CC[C@@H]1[C@H](NC(=O)[C@H]1CCN(c3nc(Cl)cc(Cl)c3Cl)C1)C2] |

-continued

| Ex # | Name[FB-L22] | Structure |
|---|---|---|
| 31-1 | N-((1R,2R,4S)-7-cyano-7-azabicyclo[2.2.1]heptan-2-yl)-1-(3,5-dichlorophenyl)-1H-pyrazole-4-carboxamide | 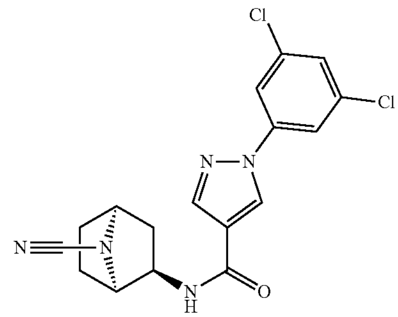 [SMILES: N#CN1[C@H]2CC[C@@H]1[C@H](NC(=O)c1cnn(-c3cc(Cl)cc(Cl)c3)c1)C2] |
| 31-2 | 3-chloro-N-((1R,2R,4S)-7-cyano-7-azabicyclo[2.2.1]heptan-2-yl)-1-(3,5-dichloropheny)-1H-pyrazole-4-carboxamide | 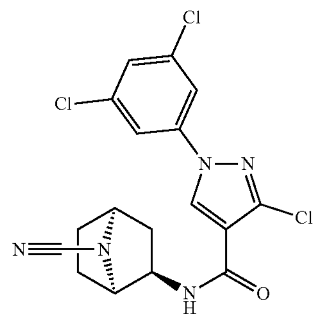 [SMILES: N#CN1[C@H]2CC[C@@H]1[C@H](NC(=O)c1cn(-c3cc(Cl)cc(Cl)c3)nc1Cl)C2] |
| 32-1 | (3S)-1-(3-chloro-5-cyanophenyl)-N-((1R,2R,4S)-7-cyano-7-azabicyclo[2.2.1]heptan-2-yl)-3-pyrrolidinecarboxamide | |
| 32-2 | (3S)-1-(2-chloro-5-cyanophenyl)-N-((1R,2R,4S)-7-cyano-7-azabicyclo[2.2.1]heptan-2-yl)-3-pyrrolidinecarboxamide | |
| 32-3 | (3S)-N-((1R,2R,4S)-7-cyano-7-azabicyclo[2.2.1]heptan-2-yl)-1-(2-oxo-1-(2-propanyl)-5-(trifluoromethyl)-1,2-dihydro-3-pyridinyl)-3-pyrrolidinecarboxamide | 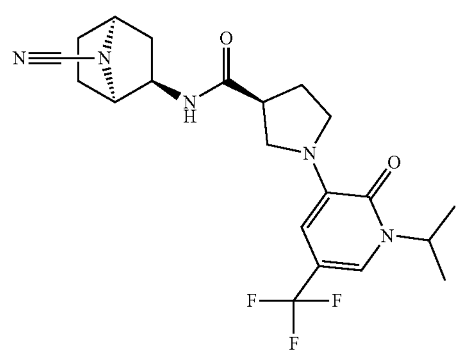 [SMILES: CC(C)n1cc(C(F)(F)F)cc(N2CC[C@H](C(=O)N[C@@H]3C[C@@H]4CC[C@H]3N4C#N)C2)c1=O] |
| 32-4 | (3S)-N-(1R,2R,4S)-7-cyano-7-azabicyclo[2.2.1]heptan-2-yl)-1-(3,4-dichlorophenyl)-3-pyrrolidinecarboxamide | 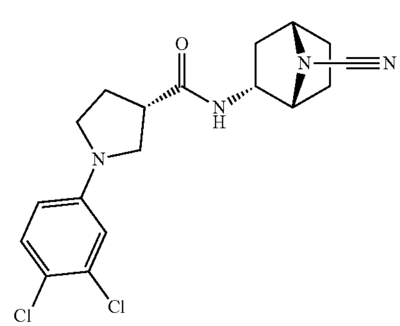 [SMILES: N#CN1[C@H]2CC[C@@H]1[C@H](NC(=O)[C@H]1CCN(c3ccc(Cl)c(Cl)c3)C1)C2] |

-continued

| Ex # | Name[FB-L22] | Structure |
|---|---|---|
| 32-5 | (3S)-N-((1R,2R,4S)-7-cyano-7-azabicyclo[2.2.1]heptan-2-yl)-1-(2,3-dichlorophenyl)-3-pyrrolidinecarboxamide | 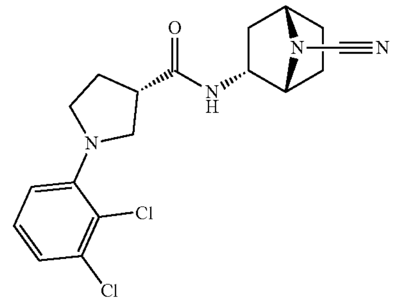 [SMILES: N#CN1[C@H]2CC[C@@H]1[C@H](NC(=O)[C@H]1CCN(c3cccc(Cl)c3Cl)C1)C2] |
| 32-6 | (3S)-1-(2-chloro-5-(trifluoromethyl)phenyl)-N-((1R,2R,4S)-7-cyano-7-azabicyclo[2.2.1]heptan-2-yl)-3-pyrrolidinecarboxamide | 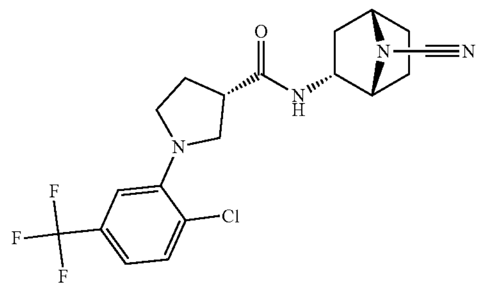 [SMILES: N#CN1[C@H]2CC[C@@H]1[C@H](NC(=O)[C@H]1CCN(c3cc(C(F)(F)F)ccc3Cl)C1)C2] |
| 33-1-1 | (1R,4R,5R)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | 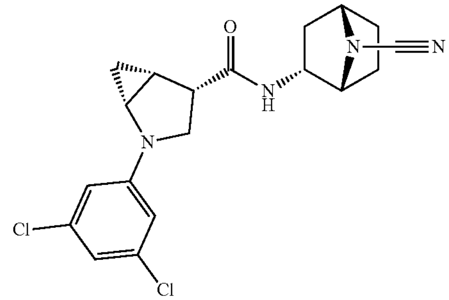 [SMILES: N#CN1[C@H]2CC[C@@H]1[C@H](NC(=O)[C@@H]1CN(c3cc(Cl)cc(Cl)c3)[C@@H]3C[C@@H]31)C2] |
| 33-1-2 | (1R,4R,5R)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | 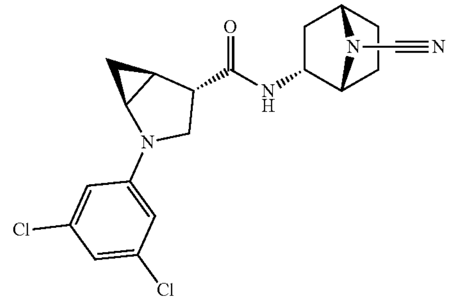 [SMILES: N#CN1[C@H]2CC[C@@H]1[C@H](NC(=O)[C@@H]1CN(c3cc(Cl)cc(Cl)c3)[C@H]3C[C@@H]13)C2] |
| 1-67-1 | (3R)-6-chloro-N-((1R,2R,4S)-7-cyano-7-azabicyclo[2.2.1]heptan-2-yl)-2,3,4,9-tetrahydro-1H-carbazole-3-carboxamide | 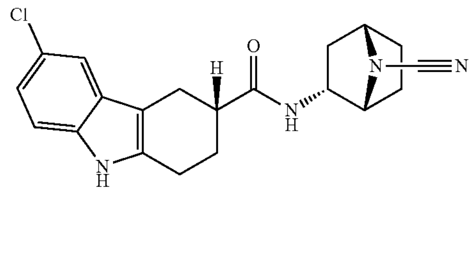 [SMILES: N#CN1[C@H]2CC[C@@H]1[C@H](NC(=O)[C@@H]1CCc3[nH]c4ccc(Cl)cc4c3C1)C2] |

-continued

| Ex # | Name[FB-L22] | Structure |
|---|---|---|
| 12-31-1 | (1S,3S)-N-((1R,2R,4S)-7-cyano-7-azabicyclo[2.2.1]heptan-2-yl)-3-(2,5-dichlorophenyl)cyclopentanecarboxamide | 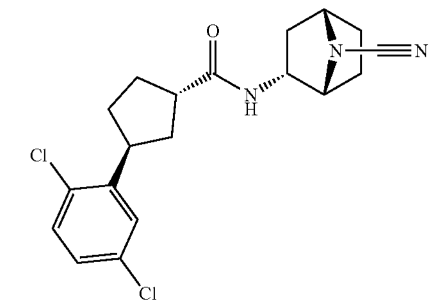 [SMILES: N#CN1[C@H]2CC[C@@H]1[C@H](NC(=O)[C@H]1CC[C@H](c3cc(Cl)ccc3Cl)C1)C2] |
| 12-31-2 | (1R,3R)-N-((1R,2R,4S)-7-cyano-7-azabicyclo[2.2.1]heptan-2-yl)-3-(2,5-dichlorophenyl)cyclopentanecarboxamide | 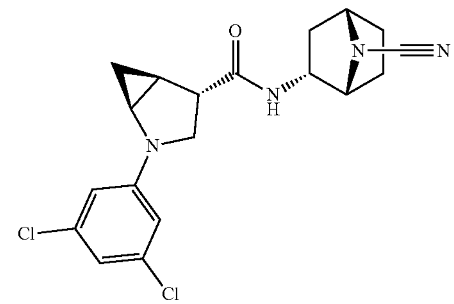 [SMILES: N#CN1[C@H]2CC[C@@H]1[C@H](NC(=O)[C@@H]1CN(c3cc(Cl)cc(Cl)c3)[C@H]3C[C@@H]13)C2] |
| 12-30-3 | (1S,3R)-N-((1R,2R,4S)-7-cyano-7-azabicyclo[2.2.1]heptan-2-yl)-3-(2,5-dichlorophenyl)cyclopentanecarboxamide | 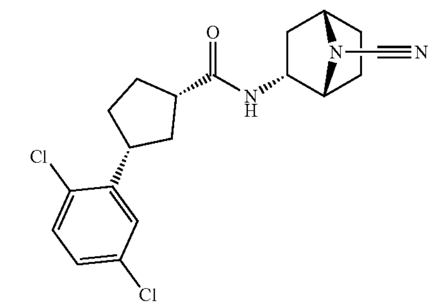 [SMILES: N#CN1[C@H]2CC[C@@H]1[C@H](NC(=O)[C@H]1CC[C@@H](c3cc(Cl)ccc3Cl)C1)C2] |
| 15-15-2 | (5R)-N-((1R,2R,4S)-7-cyano-7-azabicyclo[2.2.1]heptan-2-yl)-1-(6-(1,1-difluoroethyl)-2-pyridinyl)-4,5,6,7-tetrahydro-1H-indazole-5-carboxamide | 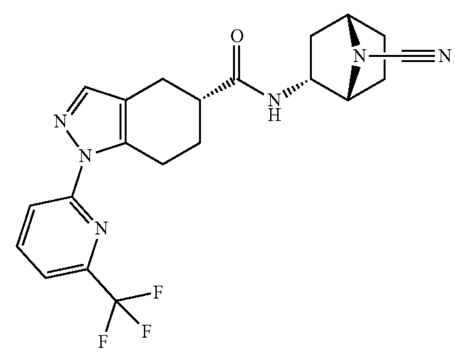 [SMILES: N#CN1[C@H]2CC[C@@H]1[C@H](NC(=O)[C@@H]1CCc3c(cnn3-c3cccc(C(F)(F)F)n3)C1)C2] |
| 15-16-2 | (5R)-N-((1R,2R,4S)-7-cyano-7-azabicyclo[2.2.1]heptan-2-yl)-1-(6-(difluoromethoxy)-2-pyridinyl)-4,5,6,7-tetrahydro-1H-indazole-5-carboxamide | 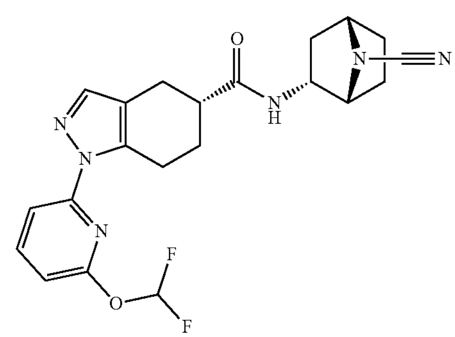 [SMILES: N#CN1[C@H]2CC[C@@H]1[C@H](NC(=O)[C@@H]1CCc3c(cnn3-c3cccc(OC(F)F)n3)C1)C2] |

-continued

| Ex # | Name[FB-L22] | Structure |
|---|---|---|
| 15-16-3 | (5S)-N-((1R,2R,4S)-7-cyano-7-azabicyclo[2.2.1]heptan-2-yl)-2-(6-(1-cyanocyclopropyl)-2-pyridinyl)-4,5,6,7-tetrahydro-2H-indazole-5-carboxamide | |
| 15-15-3 | (5S)-N-((1R,2R,4S)-7-cyano-7-azabicyclo[2.2.1]heptan-2-yl)-2-(6-(1,1-difluoroethyl)-2-pyridinyl)-4,5,6,7-tetrahydro-2H-indazole-5-carboxamide | 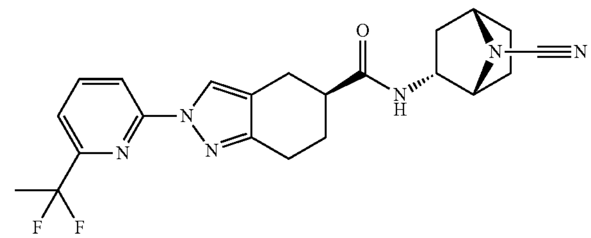 [SMILES: CC(F)(F)c1cccc(-n2cc3c(n2)CC[C@H](C(=O)N[C@@H]2C[C@@H]4CC[C@H]2N4C#N)C3)n1] |
| 15-16-3 | (5S)-N-((1R,2R,4S)-7-cyano-7-azabicyclo[2.2.1]heptan-2-yl)-2-(6-(difluoromethoxy)-2-pyridinyl)-4,5,6,7-tetrahydro-2H-indazole-5-carboxamide | |
| 15-15-4 | (5R)-N-((1R,2R,4S)-7-cyano-7-azabicyclo[2.2.1]heptan-2-yl)-2-(6-(1,1-difluoroethyl)-2-pyridinyl)-4,5,6,7-tetrahydro-2H-indazole-5-carboxamide | 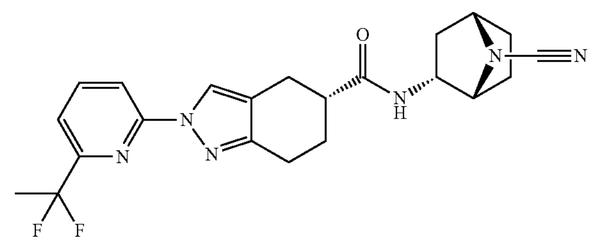 [SMILES: CC(F)(F)c1cccc(-n2cc3c(n2)CC[C@@H](C(=O)N[C@@H]2C[C@@H]4CC[C@H]2N4C#N)C3)n1] |
| 15-16-4 | (5R)-N-((1R,2R,4S)-7-cyano-7-azabicyclo[2.2.1]heptan-2-yl)-2-(6-(difluoromethoxy)-2-pyridinyl)-4,5,6,7-tetrahydro-2H-indazole-5-carboxamide | 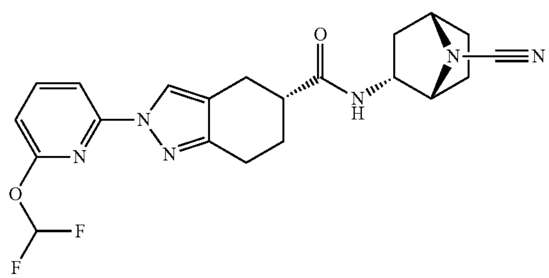 [SMILES: N#CN1[C@H]2CC[C@@H]1[C@H](NC(=O)[C@@H]1CCc3nn(-c4cccc(OC(F)F)n4)cc3C1)C2] |
| 15-17-4 | (5R)-N-((1R,2R,4S)-7-cyano-7-azabicyclo[2.2.1]heptan-2-yl)-2-(6-(difluoromethy))-2-pyridinyl)-4,5,6,7-tetrahydro-2H-indazole-5-carboxamide | 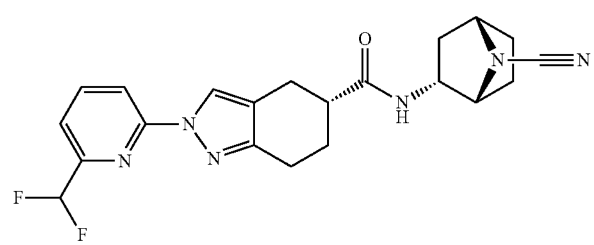 [SMILES: N#CN1[C@H]2CC[C@@H]1[C@H](NC(=O)[C@@H]1CCc3nn(-c4cccc(C(F)F)n4)cc3C1)C2] |

-continued

| Ex # | Name[FB-L22] | Structure |
|---|---|---|
| 17-1 | 7-chloro-N-((1R,2R,4S)-7-cyano-7-azabicyclo[2.2.1]heptan-2-yl)-2,3-dihydrobenzo[f][1,4]oxazepine-4(5H)-carboxamide | 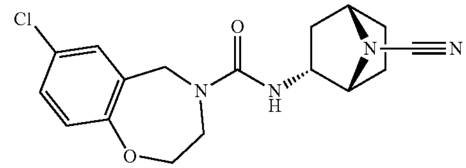 [SMILES: N#CN1[C@H]2CC[C@@H]1[C@H](NC(=O)N1CCOc3ccc(Cl)cc3C1)C2] |
| 18-1 | 7-chloro-N-((1R,2R,4S)-7-cyano-7-azabicyclo[2.2.1]heptan-2-yl)-1,2,3,5-tetrahydro-4H-1,4-benzodiazepine-4-carboxamide | 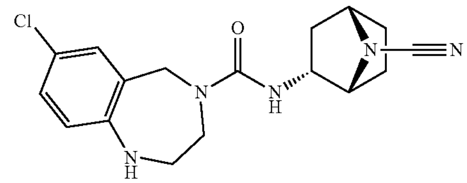 [SMILES: N#CN1[C@H]2CC[C@@H]1[C@H](NC(=O)N1CCNc3ccc(Cl)cc3C1)C2] |
| 19-1 | 1-(6-acetamido-2-pyridinyl)-6-chloro-N-((1R,2R,4S)-7-cyano-7-azabicyclo[2.2.1]heptan-2-yl)-1H-indazole-5-carboxamide | 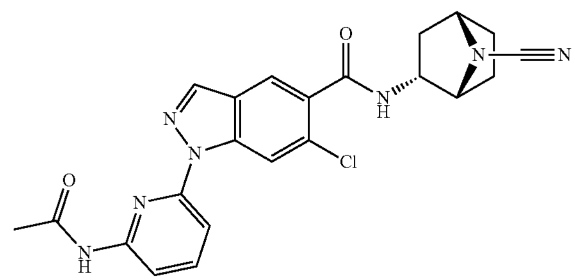 [SMILES: CC(=O)Nc1cccc(-n2ncc3cc(C(=O)N[C@@H]4C[C@@H]5CC[C@H]4N5C#N)c(Cl)cc32)n1] |
| 21-1-1 | (5R)-N-((1R,2R,4S)-7-cyano-7-azabicyclo[2.2.1]heptan-2-yl)-1-(6-methyl-2-pyridinyl)-4,5,6,7-tetrahydro-1H-indazole-5-carboxamide | 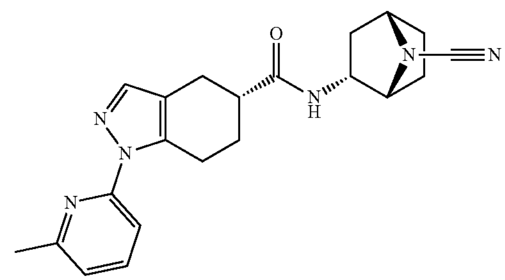 [SMILES: Cc1cccc(-n2ncc3c2CC[C@@H](C(=O)N[C@@H]2C[C@@H]4CC[C@H]2N4C#N)C3)n1] |
| 21-1-2 | (5S)-N-((1R,2R,4S)-7-cyano-7-azabicyclo[2.2.1]heptan-2-yl)-1-(6-methyl-2-pyridinyl)-4,5,6,7-tetrahydro-1H-indazole-5-carboxamide | 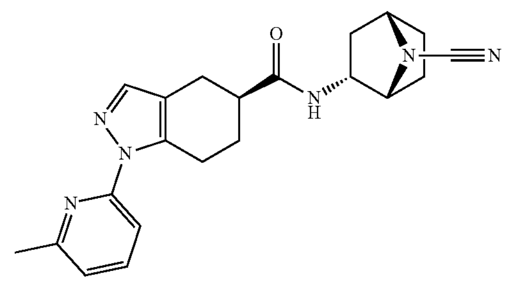 [SMILES: Cc1cccc(-n2ncc3c2CC[C@H](C(=O)N[C@@H]2C[C@@H]4CC[C@H]2N4C#N)C3)n1] |
| 21-1-3 | (5R)-N-((1R,2R,4S)-7-cyano-7-azabicyclo[2.2.1]heptan-2-yl)-2-(6-methyl-2-pyridinyl)-4,5,6,7-tetrahydro-2H-indazole-5-carboxamide | 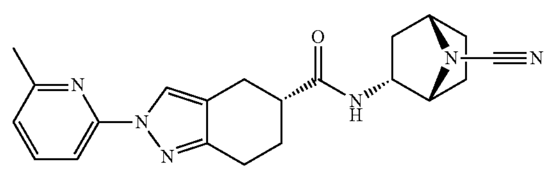 [SMILES: Cc1cccc(-n2cc3c(n2)CC[C@@H](C(=O)N[C@@H]2C[C@@H]4CC[C@H]2N4C#N)C3)n1] |
| 21-1-4 | (5S)-N-((1R,2R,4S)-7-cyano-7-azabicyclo[2.2.1]heptan-2-yl)-2-(6-methyl-2-pyridinyl)-4,5,6,7-tetrahydro-2H-indazole-5-carboxamide | 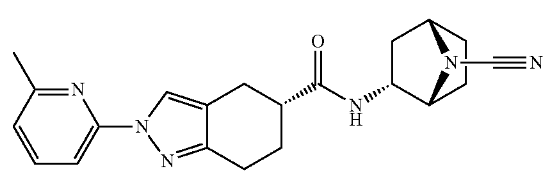 [SMILES: Cc1cccc(-n2cc3c(n2)CC[C@@H](C(=O)N[C@@H]2C[C@@H]4CC[C@H]2N4C#N)C3)n1] |

| Ex # | Name[FB-L22] | Structure |
|---|---|---|
| 21-2-3 | (5S)-N-((1R,2R,4S)-7-cyano-7-azabicyclo[2.2.1]heptan-2-yl)-2-(6-cyclopropyl-2-pyridinyl)-4,5,6,7-tetrahydro-2H-indazole-5-carboxamide | 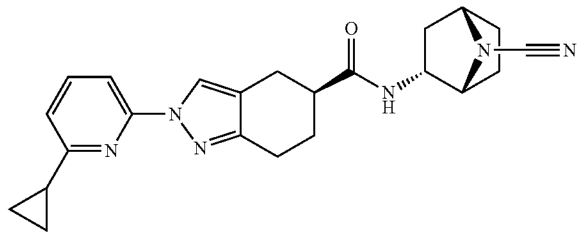 [SMILES: N#CN1[C@H]2CC[C@@H]1[C@H](NC(=O)[C@H]1CCc3nn(-c4cccc(C5CC5)n4)cc3C1)C2] |
| 21-2-4 | (5R)-N-((1R,2R,4S)-7-cyano-7-azabicyclo[2.2.1]heptan-2-yl)-2-(6-cyclopropyl-2-pyridinyl)-4,5,6,7-tetrahydro-2H-indazole-5-carboxamide | 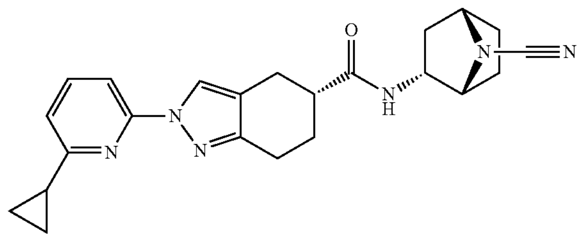 [SMILES: N#CN1[C@H]2CC[C@@H]1[C@H](NC(=O)[C@@H]1CCc3nn(-c4cccc(C5CC5)n4)cc3C1)C2] |
| 20-77 | N-((1R,2R,4S)-7-cyano-7-azabicyclo[2.2.1]heptan-2-yl)-3-(2-methylpropoxy)-4-(3-methyl-1H-pyrazol-1-yl)benzamide | 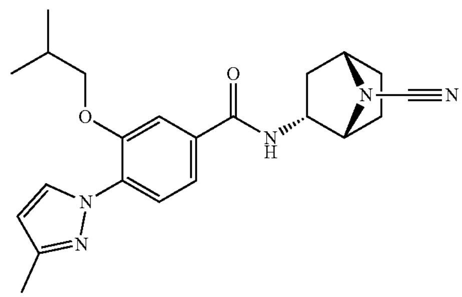 [SMILES: Cc1ccn(-c2ccc(C(=O)N[C@@H]3C[C@@H]4CC[C@H]3N4C#N)cc2OCC(C)C)n1] |

Analytical Data for Experimental Examples:

| Ex # | Name | MS data | 1H NMR |
|---|---|---|---|
| 1-1 | N-((1R,2R,4S)-7-cyano-7-azabicyclo[2.2.1]heptan-2-yl)-2-(1H-pyrrol-1-yl)-1,3-benzothiazole-6-carboxamide | 364 | 1H NMR (500 MHz, DMSO-d6) δ 8.69 (d, J = 5.97 Hz, 1H), 8.57 (d, J = 1.69 Hz, 1H), 7.96-8.00 (m, 1H), 7.93-7.96 (m, 1H), 7.64 (t, J = 2.21 Hz, 2H), 6.44-6.46 (m, 2H), 4.29-4.36 (m, 1H), 4.26 (t, J = 4.54 Hz, 1H), 4.18 (t, J = 4.93 Hz, 1H), 2.19-2.27 (m, 1H), 1.88-1.96 (m, 1H), 1.78-1.88 (m, 1H), 1.65-1.74 (m, 2H), 1.57 (dd, J = 4.67, 12.72 Hz, 1H) |
| 1-2 | racemic-endo 2-methyl-2-propanyl 7-(7-cyano-7-azabicyclo[2.2.1]heptan-2-yl)carbamoyl)-3,4-dihydro-2(1H)-isoquinolinecarboxylate | 397.2 | 1H NMR (600 MHz, DMSO-d6) δ 8.44-8.59 (m, 1H), 7.67 (s, 2H), 7.28 (br d, J = 8.56 Hz, 1H), 4.50-4.60 (m, 2H), 4.25-4.34 (m, 1H), 4.22 (t, J = 4.55 Hz, 1H), 4.08-4.18 (m, 1H), 3.55-3.60 (m, 2H), 3.32 (s, 56H), 2.78-2.86 (m, 2H), 2.16-2.23 (m, 1H), 1.77-1.87 (m, 2H), 1.62-1.73 (m, 2H), 1.50-1.60 (m, 1H), 1.38-1.45 (m, 9H) |
| 1-3 | racemic-endo 2-methyl-2-propanyl 6-(7-cyano-7-azabicyclo[2.2.1]heptan-2-yl)carbamoyl)-3,4-dihydro-2(1H)-isoquinolinecarboxylate | 397.2 | 1H NMR (600 MHz, DMSO-d6) δ 8.49 (d, J = 6.00 Hz, 1H), 7.64-7.70 (m, 2H), 7.27 (d, J = 7.86 Hz, 1H), 4.55 (br s, 2H), 4.24-4.30 (m, 1H), 4.23 (t, J = 4.59 Hz, 1H), 4.16 (t, J = 4.67 Hz, 1H), 3.53-3.60 (m, 2H), 3.32 (s, 37H), 2.82 (br t, J = 5.76 Hz, 2H), 2.17-2.23 (m, 1H), 1.78-1.88 (m, 2H), 1.62-1.72 (m, 2H), 1.55 (dd, J = 4.67, 12.69 Hz, 1H), 1.43 (s, 9H) |
| 1-4 | N-((1R,2R,4S)-7-cyano-7-azabicyclo[2.2.1]heptan-2-yl)-4-((4-cyclopropyl-2-pyrimidinyl)amino)-2,5-difluorobenzamide | 411.2 | 1H NMR (600 MHz, DMSO-d6) δ 9.24 (s, 1H), 8.53 (br d, J = 6.00 Hz, 1H), 8.33 (d, J = 5.06 Hz, 1H), 8.09 (dd, J = 6.42, 12.73 Hz, 1H), 7.44 (dd, J = 6.54. 10.98 Hz, 1H), 6.94 (d, J = 5.06 Hz, 1H), 4.20-4.30 (m, 3H), 4.15 (t, J = 4.75 Hz, 1H), 2.16-2.24 (m, 2H), 2.02-2.08 (m, 1H), 1.87-1.95 (m, 2H), 1.76-1.85 (m, 1H), 1.61-1.73 (m, 3H), 1.40-1.50 (m, 1H), 0.99-1.09 (m, 4H) |
| 1-5 | N-((1R,2R,4S)-7-cyano-7-azabicyclo[2.2.1]heptan-2-yl)-4-((4-cyclopropyl-2-pyrimidinyl)amino)-2,3-difluorobenzamide | 411.2 | 1H NMR (600 MHz, DMSO-d6) δ 9.33 (s, 1H), 8.64 (d, J = 6.15 Hz, 1H), 8.27 (d, J = 5.14 Hz, 1H), 7.72 (t, J = 7.69 Hz, 1H), 7.34 (br t, J = 7.24 Hz, 1H), 6.88 (d, J = 5.06 Hz, 1H), 4.28 (br dd, J = 4.83, 11.13 Hz, 1H), 4.21-4.26 (m, 1H), 4.16 (t, J = 4.79 Hz, 1H), 3.16-3.23 (m, 1H), 2.16-2.24 (m, 1H), 1.99-2.04 (m, 1H), 1.86-1.94 (m, 1H), 1.78-1.85 (m, 1H), 1.60-1.74 (m, 2H), 1.37-1.51 (m, 1H), 0.98-1.06 (m, 4H) |

-continued

| Ex # | Name | MS data | 1H NMR |
|---|---|---|---|
| 1-6 | N-((1R,2R,4S)-7-cyano-7-azabicyclo[2.2.1]heptan-2-yl)-3-phenyl-1H-indazole-6-carboxamide | 358.2 | 1H NMR (600 MHz, DMSO-d6) δ 13.52 (br s, 1H), 8.73 (br d, J = 5.99 Hz, 1H), 8.11 (d, J = 8.81 Hz, 1H), 8.06 (s, 1H), 7.97 (br d, J = 7.24 Hz, 2H), 7.65 (d, J = 8.49 Hz, 1H), 7.50 (t, J = 7.71 Hz, 2H), 7.39 (t, J = 7.60 Hz, 1H), 4.31 (br dd, J = 4.79, 11.02 Hz, 1H), 4.24 (t, J = 4.52 Hz, 1H), 4.14 (t, J = 4.90 Hz, 1H), 2.16-2.23 (m, 1H), 1.84-1.91 (m, 1H), 1.75-1.84 (m, 1H), 1.62-1.72 (m, 2H), 1.57 (dd, J = 4.59, 12.77 Hz, 1H) |
| 1-7 | 2-methyl-2-propanyl (4-(((1R,2R,4S)-7-cyano-7-azabicyclo[2.2.1]heptan-2-yl)carbamoyl)-2-methylphenyl)carbamate | 371.2 | 1H NMR (600 MHz, DMSO-d6) δ 8.61 (s, 1H), 8.39 (d, J = 5.99 Hz, 1H), 7.62 (s, 1H), 7.59 (d, J = 8.53 Hz, 1H), 7.47 (d, J = 8.41 Hz, 1H), 4.19-4.24 (m, 1H), 4.17 (t, J = 4.55 Hz, 1H), 4.11 (t, J = 4.79 Hz, 1H), 2.21 (s, 3H), 2.09-2.18 (m, 1H), 1.71-1.84 (m, 2H), 1.57-1.68 (m, 2H), 1.47-1.55 (m, 1H), 1.43 (s, 9H) |
| 1-8 | N-((1R,2R,4S)-7-cyano-7-azabicyclo[2.2.1]heptan-2-yl)-1-(2,2-dimethylpropanoyl)-2,3-dihydro-1H-indole-5-carboxamide | 367.2 | 1H NMR (600 MHz, DMSO-d6) δ 8.39 (d, J = 5.99 Hz, 1H), 8.08 (d, J = 8.49 Hz, 1H), 7.71 (s, 1H), 7.66 (dd, J = 1.83, 8.52 Hz, 1H), 4.21-4.28 (m, 3H), 4.17 (t, J = 4.52 Hz, 1H), 4.11 (t, J = 4.75 Hz, 1H), 3.10-3.15 (m, 2H), 2.10-2.21 (m, 1H), 1.70-1.87 (m, 2H), 1.58-1.69 (m 2H), 1.52 (dd, J = 4.71, 12.65 Hz, 1H), 1.20-1.28 (m, 9H) |
| 1-9 | N-((1R,2R,4S)-7-cyano-7-azabicyclo[2.2.1]heptan-2-yl)-4-(1,3-thiazol-4-yl)benzamide | 325 | 1H NMR (600 MHz, DMSO-d6) δ 9.28 (d, J = 1.87 Hz, 1H), 8.67 (d, J = 5.92 Hz, 1H), 8.38 (d, J = 1.87 Hz, 1H), 8.12-8.18 (m, J = 8.49 Hz, 2H), 7.97-8.02 (m, J = 8.56 Hz, 2H), 4.32-4.39 (m, 1H), 4.30 (t, J = 4.55 Hz, 1H), 4.22 (t, J = 4.87 Hz, 1H), 2.23-2.29 (m, 1H), 1.82-1.97 (m, 2H), 1.69-1.78 (m, 2H), 1.63 (dd, J = 4.67, 12.69 Hz, 1H) |
| 1-10 | 4-benzamido-N-((1R,2R,4S)-7-cyano-7-azabicyclo[2.2.1]heptan-2-yl)benzamide | 361.2 | 1H NMR (600 MHz, DMSO-d6) δ 10.42 (s, 1H), 8.45 (d, J = 6.07 Hz, 1H), 7.90-7.97 (m, 4H), 7.57 (t, J = 7.59 Hz, 2H), 7.51 (t, J = 7.35 Hz, 3H), 4.22-4.29 (m, 1H), 4.19 (t, J = 4.52 Hz, 1H), 4.12 (t, J = 4.87 Hz, 1H), 2.12-2.20 (m, 1H), 1.73-1.87 (m, 2H), 1.60-1.69 (m, 2H), 1.53 (dd, J = 4.67, 12.69 Hz, 1H) |
| 1-11 | N-(4-(((1R,2R,4S)-7-cyano-7-azabicyclo[2.2.1]heptan-2-yl)carbamoyl)phenyl)-2-pyridinecarboxamide | 362.2 | 1H NMR (600 MHz, DMSO-d6) δ 10.85 (s, 1H), 8.76 (s, 1H), 8.49 (d, J = 5.99 Hz, 1H), 8.18 (d, J = 7.92 Hz, 1H), 8.09 (dt, J = 1.67, 7.69 Hz, 1H), 8.01-8.07 (m, 2H), 7.89 (d, J = 8.72 Hz, 2H), 7.70 (ddd, J = 1.21, 4.75, 7.51 Hz, 1H), 4.26-4.33 (m, 1H), 4.23 (t, J = 4.59 Hz, 1H), 4.16 (t, J = 4.87 Hz, 1H), 2.17-2.24 (m, 1H), 1.77-1.92 (m, 2H), 1.64-1.73 (m, 2H), 1.56 (dd, J = 4.71, 12.73 Hz, 1H) |
| 1-12 | N-((1R,2R,4S)-7-cyano-7-azabicyclo[2.2.1]heptan-2-yl)-4-(phenylethynyl)benzamide | 342.2 | 1H NMR (600 MHz, DMSO-d6) δ 8.67 (d, J = 6.07 Hz, 1H), 7.92 (d, J = 8.49 Hz, 2H), 7.67 (d, J = 8.49 Hz, 2H), 7.59 (td, J = 2.82, 3.93 Hz, 2H), 7.43-7.47 (m, 3H), 4.27-4.33 (m, 1H), 4.24 (t, J = 4.52 Hz, 1H), 4.17 (t, J = 4.87 Hz, 1H), 2.18-2.24 (m, 1H), 1.78-1.91 (m, 2H), 1.64-1.73 (m, 2H), 1.57 (dd, J = 4.67, 12.77 Hz, 1H) |
| 1-13 | 6-(1H-benzimidazol-1-yl)-N-((1R,2R,4S)-7-cyano-7-azabicyclo[2.2.1]heptan-2-yl)-3-pyridinecarboxamide | 359.2 | 1H NMR (600 MHz, DMSO-d6) δ 9.08 (s, 2H), 8.83 (d, J = 5.99 Hz, 1H), 8.46 (dd, J = 2.41, 8.56 Hz, 1H), 8.40 (d, J = 7.86 Hz, 1H), 8.11 (d, J = 8.56 Hz, 1H), 7.80 (d, J = 7.94 Hz, 1H), 7.39-7.45 (m, 1H), 7.34-7.39 (m, 1H), 4.31-4.38 (m, 1H), 4.28 (t, J = 4.44 Hz, 1H), 4.19 (t, J = 4.90 Hz, 1H), 2.22-2.29 (m, 1H), 1.90-1.97 (m, 1H), 1.80-1.89 (m, 1H), 1.66-1.75 (m, 2H), 1.56 (dd, J = 4.67, 12.77 Hz, 1H) |
| 1-14 | 4-((5-chloro-2-pyridinyl)oxy)-N-((1R,2R,4S)-7-cyano-7-azabicyclo[2.2.1]heptan-2-yl)benzamide | 369 | 1H NMR (600 MHz, DMSO-d6) δ 8.57 (d, J = 5.99 Hz, 1H), 8.22 (d, J = 2.72 Hz, 1H), 8.00 (d, J = 9.01 Hz, 1H), 7.91 (d, J = 8.04 Hz, 2H), 7.22-7.27 (m, 2H), 7.17 (d, J = 8.80 Hz, 1H), 4.26-4.32 (m, 1H), 4.24 (t, J = 4.44 Hz, 1H), 4.16 (t, J = 4.87 Hz, 1H), 2.17-2.25 (m, 1H), 1.77-1.91 (m, 2H), 1.63-1.72 (m, 2H), 1.55 (dd, J = 4.71, 12.73 Hz, 1H) |
| 1-15 | N-((1R,2R,4S)-7-cyano-7-azabicyclo[2.2.1]heptan-2-yl)-4-(3,5-dimethyl-1H-pyrazol-1-yl)-3-fluorobenzamide | 354.2 | 1H NMR (600 MHz, DMSO-d6) δ 8.70 (d, J = 5.99 Hz, 1H), 7.86 (dd, J = 1.71, 11.13 Hz, 1H), 7.79 (dd, J = 1.63, 8.25 Hz, 1H), 7.58 (t, J = 7.98 Hz, 1H), 6.06 (s, 1H), 4.22-4.28 (m, 1H), 4.20 (t, J = 4.36 Hz, 1H), 4.13 (t, J = 4.87 Hz, 1H), 2.14-2.20 (m, 1H), 2.13 (s, 3H), 2.09 (s, 3H), 1.74-1.88 (m, 2H), 1.58-1.68 (m, 2H), 1.51 (dd, J = 4.67, 12.77 Hz, 1H) |
| 1-16 | 2-chloro-N-((1R,2R,4S)-7-cyano-7-azabicyclo[2.2.1]heptan-2-yl)-4-(1,1-dioxido-1,2-thiazolidin-2-yl)benzamide | 395 | 1H NMR (600 MHz, DMSO-d6) δ 8.76 (br d, J = 5.76 Hz, 1H), 7.51 (d, J = 8.49 Hz, 1H), 7.29 (d, J = 2.18 Hz, 1H), 7.25 (d, J = 8.56 Hz, 1H), 4.25-4.31 (m, 2H), 4.18 (t, J = 4.94 Hz, 1H), 3.82 (t, J = 6.54 Hz, 2H), 3.61 (t, J = 7.36 Hz, 2H), 2.18-2.29 (m, 1H), 1.97-2.06 (m, 1H), 1.79-1.89 (m, 1H), 1.70-1.79 (m, 1H), 1.58-1.67 (m, 1H), 1.41 (dd, J = 4.01, 12.88 Hz, 1H) |
| 1-17 | 2-methyl-2-propanyl (3-chloro-4-(((1R,2R,4S)-7-cyano-7-azabicyclo[2.2.1]heptan-2-yl)carbamoyl)phenyl)carbamate | 391.2 | 1H NMR (600 MHz, DMSO-d6) δ 9.77 (s, 1H), 8.70 (br d, J = 5.68 Hz, 1H), 7.71 (s, 1H), 7.39-7.48 (m, 2H), 4.26-4.32 (m, 2H), 4.20 (t, J = 4.94 Hz, 1H), 2.21-2.29 (m, 1H), 2.03 (ddd, J = 4.24, 8.99, 12.92 Hz, 1H), 1.80-1.91 (m, 1H), 1.70-1.79 (m, 1H), 1.62-1.68 (m, 1H), 1.54 (s, 8H), 1.44 (dd, J = 4.05, 12.85 Hz, 1H) |

| Ex # | Name | MS data | 1H NMR |
|---|---|---|---|
| 1-18 | N-((1R,2R,4S)-7-cyano-7-azabicyclo[2.2.1]heptan-2-yl)-3-methyl-4-(3-methylbutanamido)benzamide | 355.2 | 1H NMR (600 MHz, DMSO-d6) δ 9.38 (s, 1H), 8.53 (d, J = 5.99 Hz, 1H), 7.76 (s, 1H), 7.71 (dd, J = 1.87, 8.25 Hz, 1H), 7.62 (br d, J = 8.33 Hz, 1H), 4.25-4.36 (m, 2H), 4.22 (t, J = 4.79 Hz, 1H), 2.29-2.35 (m, 5H), 2.23-2.29 (m, 1H), 2.14 (td, J = 6.86, 13.60 Hz, 1H), 1.83-1.95 (m, 2H), 1.68-1.79 (m, 2H), 1.61 (dd, J = 4.67, 12.69 Hz, 1H), 1.02 (d, J = 6.62 Hz, 6H) |
| 1-19 | N-((1R,2R,4S)-7-cyano-7-azabicyclo[2.2.1]heptan-2-yl)-4-(4-methyl-1H-pyrazol-1-yl)benzamide | 322.2 | 1H NMR (600 MHz, DMSO-d6) δ 8.64 (d, J = 5.92 Hz, 1H), 8.43 (s, 1H), 8.03 (d, J = 8.20 Hz, 2H), 7.95 (d, J = 8.22 Hz, 2H), 7.67 (s, 1H), 4.33-4.38 (m, 1H), 4.29 (t, J = 4.52 Hz, 1H), 4.22 (t, J = 4.94 Hz, 1H), 2.21-2.30 (m, 1H), 2.17 (s, 3H), 1.84-1.96 (m, 2H), 1.70-1.78 (m, 2H), 1.62 (dd, J = 4.75, 12.77 Hz, 1H) |
| 1-20 | 4-(1H-benzotriazol-1-yl)-N-((1R,2R,4S)-7-cyano-7-azabicyclo[2.2.1]heptan-2-yl)benzamide | 359.2 | 1H NMR (600 MHz, DMSO-d6) δ 8.76 (d, J = 5.99 Hz, 1H), 8.19 (d, J = 8.41 Hz, 1H), 8.14 (d, J = 7.98 Hz, 2H), 7.99-8.04 (m, 2H), 7.97 (d, J = 8.41 Hz, 1H), 7.68 (ddd, J = 0.93, 7.06, 8.27 Hz, 1H), 7.52 (ddd, J = 0.82, 7.10, 8.19 Hz, 1H), 4.27-4.34 (m, 1H), 4.25 (t, J = 4.32 Hz, 1H), 4.15 (t, J = 4.87 Hz, 1H), 4.05 (br d, J = 5.37 Hz, 1H), 3.11-3.15 (m, 2H), 2.17-2.24 (m, 1H), 1.84-1.91 (m, 1H), 1.76-1.84 (m, 1H), 1.63-1.71 (m, 2H), 1.56 (dd, J = 4.71, 12.73 Hz, 1H) |
| 1-21 | N-((1R,2R,4S)-7-cyano-7-azabicyclo[2.2.1]heptan-2-yl)-3-(4-pyridinyl)benzamide | 319.2 | 1H NMR (600 MHz, DMSO-d6) δ 8.72-8.78 (m, 3H), 8.27 (t, J = 1.52 Hz, 1H), 7.99-8.06 (m, 2H), 7.80-7.85 (m, 2H), 7.69-7.74 (m, 1H), 4.36-4.43 (m, 1H), 4.31-4.36 (m, 1H), 4.24 (t, J = 4.90 Hz, 1H), 2.25-2.36 (m, 1H), 1.93-1.99 (m, 1H), 1.86-1.93 (m, 1H), 1.71-1.78 (m, 2H), 1.63 (dd, J = 4.67, 12.69 Hz, 1H) |
| 1-22 | N-((1R,2R,4S)-7-cyano-7-azabicyclo[2.2.1]heptan-2-yl)-6-(cyclopropylmethoxy)-3-pyridinecarboxamide | 313.2 | 1H NMR (600 MHz, DMSO-d6) δ 8.64 (d, J = 2.49 Hz, 1H), 8.54 (d, J = 5.99 Hz, 1H), 8.12 (dd, J = 2.49, 8.72 Hz, 1H), 6.90 (d, J = 8.72 Hz, 1H), 4.24-4.30 (m, 1H), 4.22 (t, J = 4.40 Hz, 1H), 4.11-4.17 (m, 3H), 2.17-2.23 (m, 1H), 1.77-1.90 (m, 2H), 1.63-1.70 (m, 2H), 1.51 (dd, J = 4.67, 12.69 Hz, 1H), 1.21-1.28 (m, 1H), 0.51-0.60 (m, 2H), 0.32-0.37 (m, 2H) |
| 1-23 | 4-(3-chloro-2-pyridinyl)-N-((1R,2R,4S)-7-cyano-7-azabicyclo[2.2.1]heptan-2-yl)benzamide | 353.2 | 1H NMR (600 MHz, DMSO-d6) δ 8.63-8.66 (m, 1H), 8.61 (s, 1H), 8.03 (dd, J = 1.40, 8.10 Hz, 1H), 7.89-7.94 (m, 2H), 7.71-7.75 (m, 2H), 7.44 (dd, J = 4.59, 8.10 Hz, 1H), 4.24-4.31 (m, 1H), 4.21 (t, J = 4.48 Hz, 1H), 4.12 (t, J = 4.90 Hz, 1H), 2.14-2.20 (m, 1H), 1.82-1.88 (m, 1H), 1.73-1.82 (m, 1H), 1.60-1.68 (m, 2H), 1.53 (dd, J = 4.67, 12.69 Hz, 1H) |
| 1-24 | N-((1R,2R,4S)-7-cyano-7-azabicyclo[2.2.1]heptan-2-yl)-4-(3-pyridinyl)benzamide | 319.2 | 1H NMR (600 MHz, DMSO-d6) δ 8.93 (d, J = 1.71 Hz, 1H), 8.62 (d, J = 6.07 Hz, 1H), 8.58 (dd, J = 1.52, 4.71 Hz, 1H), 8.11 (d, J = 7.89 Hz, 1H), 7.93-7.98 (m, J = 8.49 Hz, 2H), 7.81-7.85 (m, J = 8.49 Hz, 2H), 7.48 (ddd, J = 0.78, 4.75, 7.94 Hz, 1H), 4.24-4.32 (m, 1H), 4.22 (t, J = 4.59 Hz, 1H), 4.13 (t, J = 4.94 Hz, 1H), 2.15-2.21 (m, 1H), 1.75-1.88 (m, 2H), 1.61-1.70 (m, 2H), 1.55 (dd, J = 4.71, 12.73 Hz, 1H) |
| 1-25 | N-((1R,2R,4S)-7-cyano-7-azabicyclo[2.2.1]heptan-2-yl)-4-(3-methyl-1H-pyrazol-1-yl)benzamide | 322.2 | 1H NMR (500 MHz, DMSO-d6) Shift 8.57 (d, J = 6.10 Hz, 1H), 8.47 (d, J = 2.47 Hz, 1H), 7.95-8.01 (m, 2H), 7.88-7.92 (m, 2H), 4.31 (br dd, J = 4.87, 11.09 Hz, 1H), 4.23-4.26 (m, 1H), 4.17 (t, J = 4.87 Hz, 1H), 2.29 (s, 3H), 2.17-2.25 (m, 1H), 1.78-1.92 (m, 2H), 1.69 (ddd, J = 3.70, 8.73, 12.49 Hz, 2H), 1.57 (dd, J = 4.67, 12.72 Hz, 1H) |
| 1-26 | N-((1R,2R,4S)-7-cyano-7-azabicyclo[2.2.1]heptan-2-yl)-4-(4-(trifluoromethyl)-1H-pyrazol-1-yl)benzamide | 376.2 | 1H NMR (600 MHz, DMSO-d6) Shift 9.24 (s, 1H), 8.60 (d, J = 5.99 Hz, 1H), 8.20 (s, 1H), 7.92-8.00 (m, 4H), 4.20-4.28 (m, 1H), 4.18 (t, J = 4.48 Hz, 1H), 4.10 (t, J = 4.90 Hz, 1H), 2.10-2.19 (m, 1H), 1.71-1.85 (m, 2H), 1.57-1.66 (m, 2H), 1.50 (dd, J = 4.67, 12.77 Hz, 1H) |
| 1-27 | N-((1R,2R,4S)-7-cyano-7-azabicyclo[2.2.1]heptan-2-yl)-4-(3-methyl-1H-pyrazolo[3,4-b]pyridin-1-yl)benzamide | 373.2 | 1H NMR (600 MHz, DMSO-d6) Shift 8.68 (dd, J = 1.48, 4.59 Hz, 1H), 8.61 (d, J = 5.99 Hz, 1H), 8.43 (d, J = 8.80 Hz, 2H), 8.37 (dd, J = 1.48, 7.94 Hz, 1H), 8.07 (d, J = 8.80 Hz, 1H), 7.98-8.04 (m, 2H), 7.28-7.42 (m, 2H), 7.03 (dd, J = 8.76, 15.92 Hz, 1H), 4.26-4.33 (m, 1H), 4.24 (t, J = 4.55 Hz, 1H), 4.15 (t, J = 4.90 Hz, 1H), 3.79 (d, J = 6.70 Hz, 1H), 2.60-2.63 (m, 3H), 2.15-2.25 (m, 1H), 1.83-1.96 (m, 1H), 1.75-1.83 (m, 1H), 1.63-1.74 (m, 2H), 1.57 (dd, J = 4.71, 12.81 Hz, 1H) |
| 1-28 | 2-chloro-N-((1R,2R,4S)-7-cyano-7-azabicyclo[2.2.1]heptan-2-yl)-4-(4-methyl-1H-pyrazol-1-yl)benzamide | 356 | 1H NMR (600 MHz, DMSO-d6) Shift 8.77 (br d, J = 5.76 Hz, 1H), 8.37 (s, 1H), 7.91 (d, J = 2.10 Hz, 1H), 7.79 (dd, J = 2.18, 8.41 Hz, 1H), 7.59 (s, 1H), 7.52 (d, J = 8.41 Hz, 1H), 4.17-4.28 (m, 2H), 4.11 (t, J = 4.90 Hz, 1H), 2.11-2.23 (m, 1H), 2.06 (s, 3H), 1.89-2.02 (m, 1H), 1.72-1.85 (m, 1H), 1.64-1.72 (m, 1H), 1.46-1.60 (m, 1H), 1.35 (dd, J = 3.97, 12.77 Hz, 1H) |
| 1-29 | N-((1R,2R,4S)-7-cyano-7-azabicyclo[2.2.1]heptan-2-yl)-2-fluoro-4-(4-methyl-1H-imidazol-1-yl)benzamide | 340 | 1H NMR (600 MHz, DMSO-d6) Shift 8.71 (d, J = 6.15 Hz, 1H), 8.46 (s, 1H), 7.68-7.83 (m, 4H), 4.28-4.37 (m, 2H), 4.21 (t, J = 4.90 Hz, 1H), 2.20-2.31 (m, 1H), 2.16 (s, 3H), 1.93-2.05 (m, 1H), 1.82-1.92 (m, 1H), 1.66-1.80 (m, 2H), 1.50 (dd, J = 4.52, 12.77 Hz, 1H) |

| Ex # | Name | MS data | 1H NMR |
|---|---|---|---|
| 1-30 | N-((1R,2R,4S)-7-cyano-7-azabicyclo[2.2.1]heptan-2-yl)-2-methyl-4-(4-methyl-1H-pyrazol-1-yl)benzamide | 336.2 | 1H NMR (600 MHz, DMSO-d6) Shift 8.65 (d, J = 5.84 Hz, 1H), 8.37 (s, 1H), 7.97 (s, 1H), 7.77 (d, J = 1.71 Hz, 1H), 7.74 (dd, J = 2.10, 8.72 Hz, 2H), 7.52 (d, J = 8.33 Hz, 1H), 4.33-4.38 (m, 1H), 4.28-4.33 (m, 1H), 4.27-4.39 (m, 1H), 4.21 (t, J = 4.87 Hz, 1H), 2.65 (s, 3H), 2.44-2.48 (m, 3H), 2.27 (br s, 1H), 1.96-2.02 (m, 1H), 1.87 (dt, J = 4.01, 7.57 Hz, 1H), 1.74-1.81 (m, 1H), 1.65-1.74 (m, 1H), 1.49 (dd, J = 4.44, 12.69 Hz, 1H), 0.12-0.15 (m, 1H) |
| 1-31 | N-((1R,2R,4S)-7-cyano-7-azabicyclo[2.2.1]heptan-2-yl)-3-fluoro-4-(4-methyl-1H-pyrazol-1-yl)benzamide | 340 | 1H NMR (600 MHz, DMSO-d6) Shift 8.65 (d, J = 5.76 Hz, 1H), 8.04 (s, 1H), 7.86-7.93 (m, 2H), 7.81 (dd, J = 1.71, 8.49 Hz, 1H), 7.64 (s, 1H), 4.18-4.30 (m, 2H), 4.14 (t, J = 4.83 Hz, 1H), 2.12-2.21 (m, 1H), 2.08 (s, 3H), 1.72-1.87 (m, 2H), 1.59-1.71 (m, 2H), 1.52 (dd, J = 4.63, 12.73 Hz, 1H) |
| 1-32 | racemic-endo N-(7-cyano-7-azabicyclo[2.2.1]heptan-2-yl)-5-(4-fluorophenyl)-2-pyridinecarboxamide | 337.2 | $^1$H NMR (500 MHz, DMSO-d$_6$) δ 9.11 (d, J = 6.49 Hz, 1H), 8.94 (d, J = 1.82 Hz, 1H), 8.28 (dd, J = 2.34, 8.17 Hz, 1H), 8.09 (d, J = 8.17 Hz, 1H), 7.87 (t, J = 6.52 Hz, 2H), 7.39 (t, J = 8.21 Hz, 2H), 4.31-4.38 (m, 1H), 4.25 (t, J = 4.61 Hz, 1H), 4.17 (t, J = 4.61 Hz, 1H), 2.14-2.23 (m, 1H), 1.75-1.88 (m, 4H), 1.63-1.73 (m, 1H) |
| 1-33 | racemic-endo 6-(4-chlorophenyl)-N-(7-cyano-7-azabicyclo[2.2.1]heptan-2-yl)-3-pyridinecarboxamide | 353.2 | $^1$H NMR (500 MHz, DMSO-d$_6$) δ 9.09 (d, J = 2.21 Hz, 1H), 8.79 (d, J = 6.10 Hz, 1H), 8.30 (dd, J = 2.21, 8.30 Hz, 1H), 8.12-8.21 (m, 3H), 7.59 (d, J = 8.56 Hz, 2H), 4.24-4.36 (m, 2H), 4.18 (t, J = 4.87 Hz, 1H), 2.20-2.28 (m, 1H), 1.78-1.94 (m, 2H), 1.64-1.73 (m, 2H), 1.55 (dd, J = 4.67, 12.72 Hz, 1H) |
| 1-34 | 6-(4-chlorophenyl)-N-((1R,2R,4S)-7-cyano-7-azabicyclo[2.2.1]heptan-2-yl)-3-pyridinecarboxamide | 353.2 | $^1$H NMR (500 MHz, DMSO-d$_6$) δ 9.10 (s, 1H), 8.79 (br d, J = 5.97 Hz, 1H), 8.31 (dd, J = 1.88, 8.24 Hz, 1H), 8.17-8.21 (m, J = 8.43 Hz, 2H), 8.13 (d, J = 8.30 Hz, 1H), 7.57-7.61 (m, J = 8.56 Hz, 2H), 4.33 (br dd, J = 5.32, 10.90 Hz, 1H), 4.26 (t, J = 4.15 Hz, 1H), 4.18 (t, J = 4.74 Hz, 1H), 2.20-2.28 (m, 1H), 1.87-1.94 (m, 1H), 1.79-1.87 (m, 1H), 1.65-1.74 (m, 2H), 1.55 (dd, J = 4.67, 12.72 Hz, 1H) |
| 1-35 | racemic-endo N-(7-cyano-7-azabicyclo[2.2.1]heptan-2-yl)-2-(3-methylanilino)-5-pyrimidinecarboxamide | 349 | $^1$H NMR (500 MHz, DMSO-d$_6$) δ 10.05 (s, 1H), 8.89 (s, 2H), 8.49 (d, J = 6.10 Hz, 1H), 7.54-7.62 (m, 2H), 7.19 (t, J = 7.79 Hz, 1H), 6.83 (d, J = 7.48 Hz, 1H), 4.25-4.33 (m, 1H), 4.25-4.32 (m, 1H), 4.15-4.32 (m, 1H), 2.16-2.34 (m, 4H), 1.76-1.99 (m, 2H), 1.62-1.72 (m, 2H), 1.50 (dd, J = 4.67, 12.72 Hz, 1H) |
| 1-36 | N-((1R,2R,4S)-7-cyano-7-azabicyclo[2.2.1]heptan-2-yl)-1-(6-cyclopropyl-2-pyridinyl)-6-fluoro-1H-indazole-5-carboxamide | 417.2 | $^1$H NMR (500 MHz, DMSO-d$_6$) δ 8.74 (d, J = 6.36 Hz, 1H), 8.54 (d, J = 0.78 Hz, 1H), 8.37 (d, J = 11.68 Hz, 1H), 8.16 (d, J = 6.88 Hz, 1H), 7.87 (t, J = 7.75 Hz, 1H), 7.76 (dd, J = 0.78, 8.17 Hz, 1H), 7.30 (dd, J = 0.71, 7.59 Hz, 1H), 4.25-4.36 (m, 2H), 4.17 (t, J = 4.93 Hz, 1H), 2.20-2.30 (m, 2H), 1.92-2.03 (m, 1H), 1.78-1.88 (m, 1H), 1.60-1.78 (m, 2H), 1.45 (dd, J = 4.41, 12.72 Hz, 1H), 1.06-1.16 (m, 4H) |
| 1-37 | N-((1R,2R,4S)-7-cyano-7-azabicyclo[2.2.1]heptan-2-yl)-1-(4-cyano-6-methyl-2-pyridinyl)-1H-indazole-5-carboxamide | 398.2 | $^1$H NMR (600 MHz, DMSO-d$_6$) δ 8.80 (d, J = 8.87 Hz, 1H), 8.73 (d, J = 5.92 Hz, 1H), 8.68 (s, 1H), 8.44-8.50 (m, 1H), 8.16 (s, 1H), 8.09 (dd, J = 1.56, 8.88 Hz, 1H), 7.65-7.72 (m, 1H), 4.35 (br dd, J = 4.90, 11.05 Hz, 1H), 4.28 (t, J = 4.48 Hz, 1H), 4.19 (t, J = 4.87 Hz, 1H), 2.67-2.72 (m, 3H), 2.21-2.27 (m, 1H), 1.90-1.97 (m, 1H), 1.81-1.87 (m, 1H), 1.67-1.75 (m, 2H), 1.59 (dd, J = 4.63, 12.73 Hz, 1H) |
| 1-38 | N-((1R,2R,4S)-7-cyano-7-azabicyclo[2.2.1]heptan-2-yl)-1-(4-methyl-2-pyridinyl)-1H-pyrrolo[2,3-b]pyridine-5-carboxamide | 373.2 | $^1$H NMR (600 MHz, DMSO-d$_6$) δ 8.91 (d, J = 2.02 Hz, 1H), 8.72 (d, J = 6.53 Hz, 1H), 8.69 (s, 1H), 8.59 (d, J = 2.18 Hz, 1H), 8.46 (d, J = 3.81 Hz, 1H), 8.41 (d, J = 5.06 Hz, 1H), 7.22 (d, J = 5.53 Hz, 1H), 6.89 (d, J = 3.81 Hz, 1H), 4.32-4.41 (m, 1H), 4.28 (t, J = 4.44 Hz, 1H), 4.19 (t, J = 4.90 Hz, 1H), 2.46-2.49 (m, 3H), 2.22-2.29 (m, 1H), 1.91-1.98 (m, 1H), 1.80-1.88 (m, 1H), 1.66-1.76 (m, 2H), 1.58 (dd, J = 4.71, 12.73 Hz, 1H) |
| 1-39 | N-((1R,2R,4S)-7-cyano-7-azabicyclo[2.2.1]heptan-2-yl)-1-(4-methyl-1,3-thiazol-2-yl)-1H-indazole-5-carboxamide | 379.2 | $^1$H NMR (600 MHz, DMSO-d$_6$) δ 8.75 (d, J = 5.99 Hz, 1H), 8.64 (s, 1H), 8.54 (d, J = 8.80 Hz, 1H), 8.47 (d, J = 0.78 Hz, 1H), 8.12 (dd, J = 1.63, 8.80 Hz, 1H), 7.09 (d, J = 1.09 Hz, 1H), 4.31-4.37 (m, 1H), 4.28 (t, J = 4.48 Hz, 1H), 4.19 (t, J = 4.87 Hz, 1H), 2.44 (d, J = 1.01 Hz, 3H), 2.20-2.28 (m, 1H), 1.90-1.96 (m, 1H), 1.79-1.88 (m, 1H), 1.69-1.73 (m, 2H), 1.59 (dd, J = 4.75, 12.69 Hz, 1H) |

-continued

| Ex # | Name | MS data | 1H NMR |
|---|---|---|---|
| 1-40 | Mixture of two diastereomers: (S)-N-(7-cyano-7-azabicyclo[2.2.1]heptan-2-yl)-1-(6-methyl-2-pyridinyl)-4,5,6,7-tetrahydro-1H-indazole-5-carboxamide and (R)-N-(7-cyano-7-azabicyclo[2.2.1]heptan-2-yl)-1-(6-methyl-2-pyridinyl)-4,5,6,7-tetrahydro-1H-indazole-5-carboxamide | 377.2 | $^1$H NMR (500 MHz, DMSO-d$_6$) δ 8.30 (s, 1H), 8.19-8.24 (m, 1H), 7.79 (t, J = 7.85 Hz, 1H), 7.59-7.62 (m, 1H), 7.11-7.14 (m, 1H), 4.09-4.15 (m, 3H), 2.72-2.85 (m, 2H), 2.60-2.68 (m, 2H), 2.52-2.56 (m, 1H), 2.48 (s, 3H), 2.13-2.23 (m, 1H), 2.01-2.06 (m, 1H), 1.73-1.87 (m, 3H), 1.65-1.69 (m, 1H), 1.58-1.62 (m, 1H), 1.28 (m, 1H) |
| 1-41 | N-((1R,2R,4S)-7-cyano-7-azabicyclo[2.2.1]heptan-2-yl)-3-(4-methyl-2-pyrimidinyl)-1H-indole-6-carboxamide | 373 | $^1$H NMR (600 MHz, DMSO-d$_6$) δ 9.28 (d, J = 0.86 Hz, 1H), 8.75 (d, J = 5.06 Hz, 1H), 8.62 (d, J = 6.23 Hz, 1H), 8.42 (d, J = 3.58 Hz, 1H), 7.72 (d, J = 1.01 Hz, 2H), 7.29 (d, J = 5.06 Hz, 1H), 6.85 (dd, J = 0.70, 3.66 Hz, 1H), 4.36 (br dd, J = 4.87, 11.09 Hz, 1H), 4.28 (t, J = 4.63 Hz, 1H), 4.17 (t, J = 4.90 Hz, 1H), 2.58-2.60 (m, 3H), 2.35-2.39 (m, 1H), 2.18-2.26 (m, 1H), 1.89-1.99 (m, 1H), 1.78-1.86 (m, 1H), 1.66-1.76 (m, 2H), 1.61 (dd, J = 4.71, 12.73 Hz, 1H) |
| 1-42 | N-((1R,2R,4S)-7-cyano-7-azabicyclo[2.2.1]heptan-2-yl)-6-methoxy-1-(4-methyl-2-pyrimidinyl)-1H-indole-5-carboxamide | 403 | $^1$H NMR (600 MHz, DMSO-d$_6$) δ 8.73 (d, J = 4.98 Hz, 1H), 8.55 (s, 1H), 8.38 (d, J = 6.23 Hz, 1H), 8.22 (d, J = 3.66 Hz, 1H), 7.89 (s, 1H), 7.26 (d, J = 5.06 Hz, 1H), 6.78 (d, J = 3.27 Hz, 1H), 4.25-4.36 (m, 2H), 4.16 (t, J = 4.87 Hz, 1H), 3.96 (s, 3H), 2.58-2.64 (m, 3H), 2.21-2.28 (m, 1H), 1.94-2.01 (m, 1H), 1.82 (dt, J = 3.78, 7.65 Hz, 1H), 1.64-1.77 (m, 2H), 1.44 (dd, J = 4.52, 12.77 Hz, 1H) |
| 1-43 | N-((1R,2R,4S)-7-cyano-7-azabicyclo[2.2.1]heptan-2-yl)-1-methyl-3-(6-methyl-2-pyridinyl)-1H-indazole-6-carboxamide | 387 | $^1$H NMR (600 MHz, DMSO-d$_6$) δ 8.70-8.73 (m, 1H), 8.67 (d, J = 8.57 Hz, 1H), 8.18 (s, 1H), 7.92 (d, J = 7.86 Hz, 1H), 7.79 (t, J = 7.81 Hz, 1H), 7.72 (d, J = 8.71 Hz, 1H), 7.24 (d, J = 7.47 Hz, 1H), 4.29-4.38 (m, 2H), 4.18-4.22 (m, 4H), 2.62 (s, 3H), 2.23-2.30 (m, 1H), 1.89-1.98 (m, 1H), 1.80-1.89 (m, 1H), 1.67-1.76 (m, 2H), 1.57-1.64 (m, 1H) |
| 1-44 | N-((1R,2R,4S)-7-cyano-7-azabicyclo[2.2.1]heptan-2-yl)-1-methyl-3-(6-(trifluoromethyl)-2-pyridinyl)-1H-indazole-6-carboxamide | 441.2 | $^1$H NMR (600 MHz, DMSO-d$_6$) δ 8.72 (d, J = 5.99 Hz, 1H), 8.56 (d, J = 8.41 Hz, 1H), 8.40 (d, J = 8.02 Hz, 1H), 8.24 (s, 1H), 8.20 (t, J = 7.85 Hz, 1H), 7.89 (d, J = 7.63 Hz, 1H), 7.80 (dd, J = 1.28, 8.52 Hz, 1H), 4.27-4.38 (m, 2H), 4.25 (s, 3H), 4.20 (t, J = 4.87 Hz, 1H), 2.21-2.30 (m, 1H), 1.89-1.98 (m, 1H), 1.80-1.88 (m, 1H), 1.67-1.75 (m, 2H), 1.59 (dd, J = 4.67, 12.77 Hz, 1H) |
| 1-45 | N-((1R,2R,4S)-7-cyano-7-azabicyclo[2.2.1]heptan-2-yl)-1-methyl-3-phenyl-1H-indazole-6-carboxamide | 372 | $^1$H NMR (600 MHz, DMSO-d$_6$) δ 8.74 (d, J = 5.84 Hz, 1H), 8.20 (s, 1H), 8.15 (d, J = 8.41 Hz, 1H), 7.99 (dd, J = 1.09, 8.17 Hz, 2H), 7.71 (d, J = 1.32, 8.56 Hz, 1H), 7.54 (t, J = 7.75 Hz, 2H), 7.43 (t, J = 7.40 Hz, 1H), 4.27-4.38 (m, 2H), 4.16-4.22 (m, 4H), 2.22-2.29 (m, 1H), 1.89-1.96 (m, 1H), 1.80-1.89 (m, 1H), 1.67-1.76 (m, 2H), 1.61 (dd. J = 4.67, 12.77 Hz, 1H) |
| 1-46 | N-((1R,2R,4S)-7-cyano-7-azabicyclo[2.2.1]heptan-2-yl)-3-((3-fluoro-phenoxy)methyl)benzamide | 366 | $^1$H NMR (600 MHz, DMSO-d6) δ 8.63 (d, J = 5.99 Hz, 1H), 7.93 (s, 1H), 7.83 (d, J = 7.71 Hz, 1H), 7.63 (d, J = 7.63 Hz, 1H), 7.52 (t, J = 7.67 Hz, 1H), 7.27-7.39 (m, 1H), 6.92 (d, J = 11.00 Hz, 1H), 6.88 (d, J = 8.38 Hz, 1H), 6.78 (dt, J = 2.34, 8.49 Hz, 1H), 5.18 (s, 2H), 4.22-4.32 (m, 2H), 4.16 (t, J = 4.87 Hz, 1H), 2.17-2.23 (m, 1H), 1.77-1.90 (m, 2H), 1.63-1.72 (m, 2H), 1.56 (dd, J = 4.71, 12.73 Hz, 1H) |
| 1-47 | N-((1R,2R,4S)-7-cyano-7-azabicyclo[2.2.1]heptan-2-yl)-4-(2-thio-phenylmethoxy)benzamide | 354 | $^1$H NMR (600 MHz, DMSO-d$_6$) δ 8.41 (d, J = 5.99 Hz, 1H), 7.84 (d, J = 8.04 Hz, 2H), 7.56 (dd, J = 1.17, 5.06 Hz, 1H), 7.24 (s, 1H), 7.11 (d, J = 7.99 Hz, 2H), 7.04 (dd, J = 3.46, 5.02 Hz, 1H), 5.37 (s, 2H), 4.19-4.29 (m, 2H), 4.15 (t, J = 4.79 Hz, 1H), 2.15-2.22 (m, 1H), 1.76-1.89 (m, 2H), 1.61-1.72 (m, 2H), 1.54 (dd, J = 4.71, 12.73 Hz, 1H) |
| 1-48 | N-((1R,2R,4S)-7-cyano-7-azabicyclo[2.2.1]heptan-2-yl)-4-((2-methyl-phenyl)sulfanyl)benzamide | 364 | $^1$H NMR (600 MHz, DMSO-d$_6$) δ 8.53 (d, J = 5.99 Hz, 1H), 7.78 (d, J = 7.93 Hz, 2H), 7.35-7.43 (m, 3H), 7.24-7.32 (m, 1H), 7.16 (d, J = 8.00 Hz, 2H), 4.19-4.29 (m, 2H), 4.15 (t, J = 4.79 Hz, 1H), 2.31 (s, 3H), 2.15-2.22 (m, 1H), 1.76-1.87 (m, 2H), 1.61-1.70 (m, 2H), 1.52 (dd, J = 4.67, 12.69 Hz, 1H) |
| 1-49 | N-((1R,2R,4S)-7-cyano-7-azabicyclo[2.2.1]heptan-2-yl)-4-(3-methylbutoxy)benzamide | 328.2 | $^1$H NMR (600 MHz, DMSO-d$_6$) δ 8.39 (d, J = 5.99 Hz, 1H), 7.81-7.85 (m, 2H), 6.98-7.02 (m, J = 8.88 Hz, 2H), 4.18-4.29 (m, 2H), 4.15 (t, J = 4.79 Hz, 1H), 4.05 (t, J = 6.66 Hz, 2H), 2.14-2.22 (m, 1H), 1.74-1.87 (m, 3H), 1.60-1.72 (m, 4H), 1.55 (dd, J = 4.67, 12.69 Hz, 1H), 0.93 (d, J = 6.70 Hz, 6H) |
| 1-50 | N-((1R,2R,4S)-7-cyano-7-azabicyclo[2.2.1]heptan-2-yl)-4-((2-cyano-phenyl)sulfanyl)benzamide | 375 | $^1$H NMR (600 MHz, DMSO-d$_6$) δ 8.64 (d, J = 5.92 Hz, 1H), 7.97 (dd, J = 1.09, 7.71 Hz, 1H), 7.87 (d, J = 7.76 Hz, 2H), 7.71 (dt, J = 1.44, 7.77 Hz, 1H), 7.56 (t, J = 7.61 Hz, 1H), 7.40-7.49 (m, 3H), 4.21-4.31 (m, 2H), 4.16 (t, J = 4.83 Hz, 1H), 2.17-2.23 (m, 1H), 1.77-1.89 (m, 2H), 1.62-1.71 (m, 2H), 1.53 (dd, J = 4.71, 12.81 Hz, 1H) |

| Ex # | Name | MS data | 1H NMR |
|---|---|---|---|
| 1-51 | N-((1R,2R,4S)-7-cyano-7-azabicyclo[2.2.1]heptan-2-yl)-1-(6-cyclopropyl-2-pyridinyl)-3-methyl-1H-indazole-5-carboxamide | 413.2 | $^1$H NMR (600 MHz, DMSO-$d_6$) δ 8.64 (d, J = 6.59 Hz, 1H), 8.60 (d, J = 8.91 Hz, 1H), 8.37 (s, 1H), 8.08 (dd, J = 1.40, 8.87 Hz, 1H), 7.81 (t, J = 7.89 Hz, 1H), 7.69 (d, J = 8.17 Hz, 1H), 7.23 (d, J = 7.47 Hz, 1H), 4.31-4.39 (m, 1H), 4.28 (t, J = 4.59 Hz, 1H), 4.19 (t, J = 4.90 Hz, 1H), 2.60-2.67 (m, 3H), 2.20-2.28 (m, 2H), 1.88-1.97 (m, 1H), 1.80-1.88 (m, 1H), 1.66-1.76 (m, 2H), 1.60 (dd, J = 4.71, 12.73 Hz, 1H), 1.06-1.14 (m, 4H) |
| 1-52 | 6-chloro-N-((1R,2R,4S)-7-cyano-7-azabicyclo[2.2.1]heptan-2-yl)-1-(6-cyclopropyl-2-pyridinyl)-1H-indazole-5-carboxamide | 433 | $^1$H NMR (600 MHz, DMSO-$d_6$) δ 8.85 (d, J = 5.92 Hz, 1H), 8.76 (s, 1H), 8.53 (d, J = 0.78 Hz, 1H), 8.05 (s, 1H), 7.87 (t, J = 8.05 Hz, 1H), 7.75 (d, J = 8.46 Hz, 1H), 7.31 (d, J = 7.01 Hz, 1H), 4.25-4.34 (m, 2H), 4.17 (t, J = 4.90 Hz, 1H), 2.22-2.29 (m, 2H), 2.03 (ddd, J = 4.09, 8.99, 12.85 Hz, 1H), 1.78-1.88 (m, 1H), 1.70-1.78 (m, 1H), 1.50-1.65 (m, 1H), 1.40 (dd, J = 4.16, 12.73 Hz, 1H), 1.07-1.17 (m, 4H) |
| 1-53 | N-((1R,2R,4S)-7-cyano-7-azabicyclo[2.2.1]heptan-2-yl)-1-(6-cyclopropyl-2-pyridinyl)-6-methyl-1H-indazole-5-carboxamide | 413.2 | $^1$H NMR (600 MHz, DMSO-$d_6$) δ 8.69 (d, J = 6.07 Hz, 1H), 8.52 (s, 1H), 8.45 (s, 1H), 7.92 (s, 1H), 7.84 (t, J = 8.14 Hz, 1H), 7.73 (d, J = 8.29 Hz, 1H), 7.26 (d, J = 7.55 Hz, 1H), 4.25-4.36 (m, 2H), 4.11-4.21 (m, 1H), 2.52 (s, 3H), 2.20-2.28 (m, 2H), 1.98 (ddd, J = 4.09, 8.97, 12.79 Hz, 1H), 1.78-1.87 (m, 1H), 1.70-1.78 (m, 1H), 1.61-1.67 (m, 1H), 1.45 (dd, J = 4.48, 12.73 Hz, 1H), 1.09-1.16 (m, 4H) |
| 1-54 | 5-bromo-3-chloro-N-((1R,2R,4S)-7-cyano-7-azabicyclo[2.2.1]heptan-2-yl)-1-methyl-1H-indole-2-carboxamide | 406.8 | 1H NMR (600 MHz, DMSO-d6) Shift 9.02 (d, J = 6.07 Hz, 1H), 7.71-7.75 (m, 1H), 7.59-7.65 (m, 1H), 7.46-7.50 (m, 1H), 4.33-4.39 (m, 1H), 4.30-4.32 (m, 1H), 4.18 (t, J = 4.90 Hz, 1H), 2.23-2.29 (m, 1H), 2.03-2.10 (m, 1H), 1.80-1.89 (m, 1H), 1.70-1.79 (m, 1H), 1.61-1.68 (m, 1H), 1.45-1.49 (m, 1H) |
| 1-55 | Mixture of two diastereomers: (2R)-5-bromo-N-(7-cyano-7-azabicyclo[2.2.1]heptan-2-yl)-2,3-dihydro-1H-indene-2-carboxamide, and (2S)-5-bromo-N-(7-cyano-7-azabicyclo[2.2.1]heptan-2-yl)-2,3-dihydro-1H-indene-2-carboxamide | 360.0 | 1H NMR (600 MHz, DMSO-d6) Shift 8.19-8.27 (m, 1H), 7.38-7.41 (m, 1H), 7.28-7.32 (m, 1H), 7.14-7.17 (m, 1H), 4.08-4.14 (m, 3H), 2.93-3.27 (m, 5H), 2.14-2.21 (m, 1H), 1.78-1.88 (m, 2H), 1.55-1.71 (m, 2H), 1.25-1.30 (m, 1H) |
| 1-56 | 5-bromo-N-((1R,2R,4S)-7-cyano-7-azabicyclo[2.2.1]heptan-2-yl)-3-methyl-1-benzothiophene-2-carboxamide | 390.0 | 1H NMR (600 MHz, DMSO-d6) Shift 8.63-8.72 (m, 1H), 8.11 (d, J = 1.56 Hz, 1H), 8.00 (d, J = 8.56 Hz, 1H), 7.63 (dd, J = 1.87, 8.56 Hz, 1H), 4.28 (br d, J = 4.67 Hz, 2H), 4.17 (t, J = 4.90 Hz, 1H), 2.55 (s, 3H), 2.18-2.26 (m, 1H), 1.63-1.93 (m, 4H), 1.46-1.55 (m, 1H) |
| 1-57 | N-benzyl-3-bromo-N-(2-(((1R,2R,4S)-7-cyano-7-azabicyclo[2.2.1]heptan-2-yl)amino)-2-oxoethyl)benzamide | 467.0 | 1H NMR (500 MHz, CHLOROFORM-d) Shift 7.56-7.67 (m, 2H), 7.26-7.44 (m, 5H), 7.14-7.21 (m, 2H), 6.86-6.96 (m, 1H), 4.63-4.71 (m, 2H), 4.21-4.32 (m, 2H), 3.96-4.10 (m, 3H), 2.30-2.44 (m, 1H), 1.92-2.04 (m, 1H), 1.81-1.90 (m, 2H), 1.45-1.58 (m, 1H), 0.98-1.11 (m, 1H) |
| 1-58 | N-benzyl-3-chloro-N-(2-(((1R,2R,4S)-7-cyano-7-azabicyclo[2.2.1]heptan-2-yl)amino)-2-oxoethyl)benzamide | 423.0 | 1H NMR (600 MHz, DMSO-d6) Shift 8.17 (br d, J = 5.84 Hz, 1H), 7.19-7.57 (m, 10H), 4.44-4.70 (m, 2H), 4.02-4.18 (m, 3H), 3.68-4.02 (m, 2H), 2.07-2.22 (m, 1H), 1.72-1.91 (m, 1H), 1.40-1.68 (m, 3H), 1.03-1.26 (m, 1H) |
| 1-59 | 3-bromo-N-(2-(((1R,2R,4S)-7-cyano-7-azabicyclo[2.2.1]heptan-2-yl)amino)-2-oxoethyl)benzamide | 377.0 | 1H NMR (600 MHz, DMSO-d6) Shift 8.81-8.91 (m, 1H), 8.24-8.30 (m, 1H), 8.03-8.09 (m, 1H), 7.84-7.89 (m, 1H), 7.72-7.78 (m, 1H), 7.43-7.49 (m, 1H), 4.06-4.16 (m, 3H), 3.83-3.92 (m, 2H), 2.12-2.22 (m, 1H), 1.85-1.93 (m, 1H), 1.77-1.84 (m, 1H), 1.54-1.69 (m, 2H), 1.26-1.32 (m, 1H) |
| 1-60 | 3-chloro-N-(2-(((1R,2R,4S)-7-cyano-7-azabicyclo[2.2.1]heptan-2-yl)amino)-2-oxoethyl)benzamide | 333.0 | 1H NMR (600 MHz, DMSO-d6) Shift 8.85-8.91 (m, 1H), 8.28 (br d, J = 6.15 Hz, 1H), 7.90-7.94 (m, 1H), 7.81-7.86 (m, 1H), 7.60-7.65 (m, 1H), 7.49-7.55 (m, 1H), 4.05-4.16 (m, 3H), 3.89 (d, J = 5.84 Hz, 2H), 2.13-2.22 (m, 1H), 1.86-1.93 (m, 1H), 1.76-1.85 (m, 1H), 1.55-1.68 (m, 2H), 1.29 (dd, J = 4.52, 12.69 Hz, 1H) |

| Ex # | Name | MS data | 1H NMR |
|---|---|---|---|
| 1-61 | Mixture of two diastereomers: (3R)-1-(3-chlorophenyl)-N-(7-cyano-7-azabicyclo[2.2.1]heptan-2-yl)-5-oxo-3-pyrrolidinecarboxamide, and (3S)-1-(3-chlorophenyl)-N-(7-cyano-7-azabicyclo[2.2.1]heptan-2-yl)-5-oxo-3-pyrrolidinecarboxamide | 359.0 | 1H NMR (600 MHz, DMSO-d6) Shift 8.38-8.48 (m, 1H), 7.82-7.90 (m, 1H), 7.52-7.59 (m, 1H), 7.36-7.43 (m, 1H), 7.17-7.23 (m, 1H), 4.07-4.18 (m, 3H), 3.98-4.07 (m, 1H), 3.83-3.90 (m, 1H), 3.27 (br s, 1H), 3.17 (d, J = 5.14 Hz, 1H), 2.76 (br dd, J = 9.42, 12.85 Hz, 1H), 2.67 (br dd, J = 6.93, 8.49 Hz, 1H), 2.13-2.24 (m, 1H), 1.77-1.90 (m, 2H), 1.55-1.70 (m, 2H), 1.20-1.30 (m, 1H) |
| 1-62 | Mixture of two diastereomers: (3R)-1-(3-bromophenyl)-N-(7-cyano-7-azabicyclo[2.2.1]heptan-2-yl)-5-oxo-3-pyrrolidinecarboxamide, and (3S)-1-(3-bromophenyl)-N-(7-cyano-7-azabicyclo[2.2.1]heptan-2-yl)-5-oxo-3-pyrrolidinecarboxamide | 403.0 | 1H NMR (600 MHz, DMSO-d6) Shift 8.40-8.44 (m, 1H), 7.99-8.02 (m, 1H), 7.56-7.60 (m, 1H), 7.32-7.36 (m, 2H), 4.08-4.17 (m, 3H), 3.99-4.05 (m, 1H), 3.86 (ddd, J = 5.80, 9.75, 17.93 Hz, 1H), 3.22-3.30 (m, 1H), 2.77 (ddd, J = 9.42, 12.67, 16.99 Hz, 1H), 2.62-2.69 (m, 1H), 2.15-2.25 (m, 1H), 1.78-1.90 (m, 2H), 1.55-1.70 (m, 2H), 1.22-1.29 (m, 1H) |
| 1-63 | Mixture of two diastereomers: (3R)-1-(3-chlorophenyl)-N-(7-cyano-7-azabicyclo[2.2.1]heptan-2-yl)-2-oxo-3-pyrrolidinecarboxamide, and (3S)-1-(3-chlorophenyl)-N-(7-cyano-7-azabicyclo[2.2.1]heptan-2-yl)-2-oxo-3-pyrrolidinecarboxamide | 359.0 | 1H NMR (600 MHz, DMSO-d6) Shift 8.51-8.61 (m, 1H), 7.81-7.88 (m, 1H), 7.53-7.61 (m, 1H), 7.40-7.45 (m, 1H), 7.19-7.26 (m, 1H), 4.04-4.20 (m, 3H), 3.81-3.95 (m, 2H), 3.53-3.60 (m, 1H), 2.15-2.37 (m, 3H), 2.03-2.12 (m, 1H), 1.78-2.11 (m, 1H), 1.77-1.91 (m, 1H), 1.56-1.70 (m, 2H), 1.24-1.37 (m, 1H) |
| 1-64 | 2-(3-chlorophenyl)-N-((1R,2R,4S)-7-cyano-7-azabicyclo[2.2.1]heptan-2-yl)-1,3-thiazole-4-carboxamide | 359.0 | 1H NMR (600 MHz, DMSO-d6) Shift 8.63-8.70 (m, 1H), 8.38-8.42 (m, 1H), 8.18 (t, J = 1.67 Hz, 1H), 7.99-8.03 (m, 1H), 7.55-7.64 (m, 2H), 4.25-4.34 (m, 2H), 4.16-4.21 (m, 1H), 2.18-2.26 (m, 1H), 1.65-1.91 (m, 5H) |
| 2-1-1 | 2-(4-chloro-3-(trifluoromethyl)phenoxy)-N-((endo)-7-cyano-7-azabicyclo[2.2.1]heptan-2-yl)acetamide enantiomer 1 | 374 | $^1$H NMR (500 MHz, DMSO-d$_6$) δ 8.42 (br d, J = 5.58 Hz, 1H), 7.65 (d, J = 8.82 Hz, 1H), 7.38 (d, J = 2.98 Hz, 1H), 7.28 (dd, J = 3.05, 8.89 Hz, 1H), 4.64-4.71 (m, 2H), 4.10-4.16 (m, 3H), 2.13-2.20 (m, 1H), 1.74-1.83 (m, 2H), 1.55-1.67 (m, 2H), 1.36 (dd, J = 4.15, 12.85 Hz, 1H) |
| 2-1-2 | 2-(4-chloro-3-(trifluoromethyl)phenoxy)-N-((endo)-7-cyano-7-azabicyclo[2.2.1]heptan-2-yl)acetamide enantiomer 2 | 374 | $^1$H NMR (500 MHz, DMSO-d$_6$) δ 8.42 (br d, J = 5.58 Hz, 1H), 7.65 (d, J = 8.82 Hz, 1H), 7.38 (d, J = 2.98 Hz, 1H), 7.28 (dd, J = 3.05, 8.89 Hz, 1H), 4.64-4.71 (m, 2H), 4.10-4.16 (m, 3H), 2.13-2.20 (m, 1H), 1.74-1.83 (m, 2H), 1.55-1.67 (m, 2H), 1.36 (dd, J = 4.15, 12.85 Hz, 1H) |
| 3-1-1 | 3-(3-chlorophenyl)-N-((endo)-7-cyano-7-azabicyclo[2.2.1]heptan-2-yl)-1,2-oxazole-5-carboxamide enantiomer 1 | 343.16 | 1H NMR (500 MHz, DMSO-d6) δ 9.30 (d, J = 6.23 Hz, 1H), 8.01 (t, J = 1.69 Hz, 1H), 7.92 (d, J = 7.41 Hz, 1H), 7.77 (s, 1H), 7.56-7.64 (m, 2H), 4.22-4.33 (m, 2H), 4.18 (t, J = 4.80 Hz, 1H), 3.32 (s, 15H), 2.17-2.25 (m, 1H), 1.85-1.92 (m, 1H), 1.77-1.85 (m, 1H), 1.64-1.74 (m, 2H), 1.62 (dd, J = 4.67, 12.85 Hz, 1H) |
| 3-1-2 | 3-(3-chlorophenyl)-N-((endo)-7-cyano-7-azabicyclo[2.2.1]heptan-2-yl)-1,2-oxazole-5-carboxamide enantiomer 2 | 343.16 | 1H NMR (500 MHz, DMSO-d6) δ 9.30 (d, J = 6.23 Hz, 1H), 8.01 (t, J = 1.69 Hz, 1H), 7.92 (d, J = 7.41 Hz, 1H), 7.77 (s, 1H), 7.56-7.64 (m, 2H), 4.22-4.33 (m, 2H), 4.18 (t, J = 4.80 Hz, 1H), 3.32 (s, 15H), 2.17-2.25 (m, 1H), 1.85-1.92 (m, 1H), 1.77-1.85 (m, 1H), 1.64-1.74 (m, 2H), 1.62 (dd, J = 4.67, 12.85 Hz, 1H) |
| 3-3 | Racemic, endo 2-((4-chloro-3-(trifluoromethyl)phenyl)amino)-N-(7-cyano-7-azabicyclo[2.2.1]heptan-2-yl)acetamide | 373 | |

-continued

| Ex # | Name | MS data | 1H NMR |
|---|---|---|---|
| 3-7 | Racemic, endo 3-bromo-N-(1-(7-cyano-7-azabicyclo[2.2.1]heptan-2-yl)amino)-1-oxopropan-2-yl)benzamide | 390.9 | |
| 3-8 | Racemic, endo 3-bromo-N-(1-7-cyano-7-azabicyclo[2.2.1]heptan-2-yl)amino)-2-methyl-1-oxopropan-2-yl)benzamide | 405 | |
| 4-1-1 | (endo)-7-cyano-N-(4-(3-(trifluoromethyl)phenyl)-1,3-thiazol-2-yl)-7-azabicyclo[2.2.1]heptane-2-carboxamide | 393 | $^1$H NMR (500 MHz, DMSO-d$_6$) δ 8.23 (s, 1H), 8.19 (br t, J = 3.57 Hz, 1H), 7.86 (s, 1H), 7.63-7.69 (m, 2H), 4.47 (t, J = 4.74 Hz, 1H), 4.22 (t, J = 4.28 Hz, 1H), 3.30-3.49 (m, 1H), 1.93-2.05 (m, 2H), 1.76-1.85 (m, 1H), 1.64-1.76 (m, 1H), 1.46-1.57 (m, 2H) |
| 4-1-2 | (endo)-7-cyano-N-(4-(3-(trifluoromethyl)phenyl)-1,3-thiazol-2-yl)-7-azabicyclo[2.2.1]heptane-2-carboxamide | 393 | $^1$H NMR (500 MHz, DMSO-d$_6$) δ 8.23 (s, 1H), 8.19 (br t, J = 3.57 Hz, 1H), 7.86 (s, 1H), 7.63-7.69 (m, 2H), 4.47 (t, J = 4.74 Hz, 1H), 4.22 (t, J = 4.28 Hz, 1H), 3.30-3.49 (m, 1H), 1.93-2.05 (m, 2H), 1.76-1.85 (m, 1H), 1.64-1.76 (m, 1H), 1.46-1.57 (m, 2H) |
| 4-1-3 | (exo)-7-cyano-N-(4-(3-(trifluoromethyl)phenyl)-1,3-thiazol-2-yl)-7-azabicyclo[2.2.1]heptane-2-carboxamide | 393 | $^1$H NMR (500 MHz, DMSO-d$_6$) δ 8.24 (s, 1H), 8.17-8.22 (m, 1H), 7.83 (s, 1H), 7.66 (d, J = 4.89 Hz, 2H), 4.44 (d, J = 4.54 Hz, 1H), 4.22 (t, J = 4.48 Hz, 1H), 2.89 (dd, J = 5.13, 9.02 Hz, 1H), 2.15-2.26 (m, 1H), 1.72-1.90 (m, 3H), 1.62-1.71 (m, 1H), 1.51-1.62 (m, 1H) |
| 4-1-4 | (exo)-7-cyano-N-(4-(3-(trifluoromethyl)phenyl)-1,3-thiazol-2-yl)-7-azabicyclo[2.2.1]heptane-2-carboxamide | 393 | $^1$H NMR (500 MHz, DMSO-d$_6$) δ 8.24 (s, 1H), 8.17-8.22 (m, 1H), 7.83 (s, 1H), 7.66 (d, J = 4.89 Hz, 2H), 4.44 (d, J = 4.54 Hz, 1H), 4.22 (t, J = 4.48 Hz, 1H), 2.89 (dd, J = 5.13, 9.02 Hz, 1H), 2.15-2.26 (m, 1H), 1.72-1.90 (m, 3H), 1.62-1.71 (m, 1H), 1.51-1.62 (m, 1H) |
| 4-2-1 | (endo)-2-((5-(2-fluoro-5-methylphenyl)-2,3-dihydro-1H-indol-1-yl)carbonyl)-7-azabicyclo[2.2.1]heptane-7-carbonitrile | 376 | |
| 4-2-2 | (endo)-2-((5-(2-fluoro-5-methylphenyl)-2,3-dihydro-1H-indol-1-yl)carbonyl)-7-azabicyclo[2.2.1]heptane-7-carbonitrile | 376 | 1H NMR (600 MHz, DMSO-d6) δ 8.10 (d, J = 8.41 Hz, 1H), 7.37 (s, 1H), 7.28 (d, J = 8.52 Hz, 1H), 7.24 (d, J = 8.14 Hz, 1H), 7.11 (s, 1H), 7.10 (s, 1H), 4.55 (t, J = 4.32 Hz, 1H), 4.24 (t, J = 8.49 Hz, 2H), 4.18 (t, J = 4.87 Hz, 1H), 3.39-3.45 (m, 1H), 3.15 (br t, J = 8.41 Hz, 2H), 3.11 (br s, 1H), 2.27 (s, 3H), 1.97-2.03 (m, 1H), 1.88-1.97 (m, 1H), 1.71-1.81 (m, 1H), 1.56-1.66 (m, 2H), 1.50-1.56 (m, 1H) |
| 4-2-3 | (exo)-2-((5-(2-fluoro-5-methylphenyl)-2,3-dihydro-1H-indol-1-yl)carbonyl)-7-azabicyclo[2.2.1]heptane-7-carbonitrile | 376.2 | |
| 4-2-4 | (exo)-2-((5-(2-fluoro-5-methylphenyl)-2,3-dihydro-1H-indol-1-yl)carbonyl)-7-azabicyclo[2.2.1]heptane-7-carbonitrile | 376.2 | 1H NMR (600 MHz, DMSO-d6) δ 8.08 (d, J = 8.33 Hz, 1H), 7.37 (s, 1H), 7.30 (d, J = 8.39 Hz, 1H), 7.26 (d, J = 7.69 Hz, 1H), 7.12 (d, J = 7.90 Hz, 2H), 4.38-4.47 (m, 1H), 4.19 (br s, 1H), 4.09-4.17 (m, 1H), 4.02-4.09 (m, 1H), 3.10-3.21 (m, 2H), 2.95 (br dd, J = 5.37, 8.88 Hz, 1H), 2.29 (s, 3H), 2.00-2.11 (m, 1H), 1.85 (br dd, J = 9.23, 11.87 Hz, 1H), 1.76-1.83 (m, 2H), 1.67 (br t, J = 8.64 Hz, 1H), 1.53-1.62 (m, 1H) |
| 5-1 | Racemic, endo N-(7-cyano-7-azabicyclo[2.2.1]heptan-2-yl)-1-(4,6-dimethyl-2-pyrimidinyl)-2,3-dihydro-1H-indole-5-carboxamide | 389 | $^1$H NMR (500 MHz, DMSO-d$_6$) δ 8.42 (d, J = 9.08 Hz, 1H), 8.36 (d, J = 6.10 Hz, 1H), 7.74 (s, 1H), 7.75 (d, J = 6.32 Hz, 1H), 6.74 (s, 1H), 4.26-4.32 (m, 1H), 4.20-4.25 (m, 3H), 4.13-4.19 (m, 1H), 3.18 (t, J = 8.69 Hz, 2H), 2.36-2.43 (m, 6H), 2.19 (br s, 1H), 1.77-1.89 (m, 2H), 1.62-1.72 (m, 2H), 1.56 (dd, J = 4.80, 12.85 Hz, 1H) |
| 5-2 | Racemic, endo N-(7-cyano-7-azabicyclo[2.2.1]heptan-2-yl)-1-(6-cyclopropyl-2-pyridinyl)-2,3-dihydro-1H-indole-5-carboxamide | 400.2 | $^1$H NMR (500 MHz, DMSO-d$_6$) δ 8.29 (d, J = 6.10 Hz, 1H), 8.23 (d, J = 8.43 Hz, 1H), 7.73 (d, J = 8.45 Hz, 1H), 7.70 (s, 1H), 7.58 (t, J = 7.85 Hz, 1H), 6.87 (d, J = 7.40 Hz, 1H), 6.62 (d, J = 8.30 Hz, 1H), 4.13-4.32 (m, 3H), 4.03 (t, J = 8.76 Hz, 2H), 3.18-3.28 (m, 2H), 2.15-2.25 (m, 1H), 2.05-2.11 (m, 1H), 1.77-1.92 (m, 2H), 1.61-1.73 (m, 2H), 1.57 (dd, J = 4.74, 12.78 Hz, 1H), 0.93-1.11 (m, 4H) |

| Ex # | Name | MS data | 1H NMR |
|---|---|---|---|
| 5-3 | Racemic, endo N-(7-cyano-7-azabicyclo[2.2.1]heptan-2-yl)-1-(6-cyclopropyl-2-pyrazinyl)-2,3-dihydro-1H-indole-5-carboxamide | 401.3 | $^1$H NMR (500 MHz, DMSO-d$_6$) δ 8.34 (d, J = 6.10 Hz, 1H), 8.16 (d, J = 8.50 Hz, 1H), 8.14 (s, 1H), 8.07 (s, 1H), 7.77 (d, J = 8.68 Hz, 1H), 7.74 (s, 1H), 4.29 (br dd, J = 4.87, 10.96 Hz, 1H), 4.12-4.23 (m, 4H), 3.23-3.29 (m, 2H), 2.13-2.23 (m, 2H), 1.77-1.90 (m, 2H), 1.62-1.73 (m, 2H), 1.57 (dd, J = 4.67, 12.72 Hz, 1H), 1.00-1.10 (m, 4H) |
| 5-4 | Racemic, endo N-(7-cyano-7-azabicyclo[2.2.1]heptan-2-yl)-1-(3-cyclopropylphenyl)-2,3-dihydro-1H-indole-5-carboxamide | 399.2 | $^1$H NMR (600 MHz, DMSO-d$_6$) δ 8.22-8.33 (m, 1H), 7.70 (s, 1H), 7.64 (d, J = 8.52 Hz, 1H), 7.24 (t, J = 7.86 Hz, 1H), 6.95-7.09 (m, 3H), 6.73 (d, J = 7.63 Hz, 1H), 4.17-4.30 (m, 2H), 4.14 (t, J = 4.71 Hz, 1H), 4.01 (t, J = 8.68 Hz, 2H), 3.10-3.17 (m, 2H), 2.14-2.21 (m, 1H), 1.90-1.97 (m, 1H), 1.76-1.88 (m, 2H), 1.60-1.72 (m, 2H), 1.56 (dd, J = 4.71, 12.65 Hz, 1H), 0.91-0.99 (m, 2H), 0.66-0.73 (m, 2H) |
| 5-5 | Racemic, endo N-(7-cyano-7-azabicyclo[2.2.1]heptan-2-yl)-1-(4-cyclopropyl-2-pyridinyl)-2,3-dihydro-1H-indole-5-carboxamide | 400.2 | $^1$H NMR (600 MHz, DMSO-d$_6$) δ 8.32 (d, J = 6.56 Hz, 1H), 8.28 (d, J = 8.68 Hz, 1H), 8.15 (d, J = 5.22 Hz, 1H), 7.71 (s, 1H), 7.68 (d, J = 8.46 Hz, 1H), 6.63 (s, 1H), 6.58 (dd, J = 0.93, 5.22 Hz, 1H), 4.19-4.30 (m, 2H), 4.15 (t, J = 4.83 Hz, 1H), 4.08 (t, J = 8.76 Hz, 2H), 3.16-3.29 (m, 2H). 2.15-2.22 (m, 1H), 1.92-1.98 (m, 1H), 1.77-1.89 (m, 2H), 1.62-1.73 (m, 2H), 1.56 (dd, J = 4.75, 12.69 Hz, 1H), 0.97-1.09 (m, 2H), 0.78-0.89 (m, 2H) |
| 5-6 | Racemic, endo N-(7-cyano-7-azabicyclo[2.2.1]heptan-2-yl)-1-(4-methoxy-2-pyrimidinyl)-2,3-dihydro-1H-indole-5-carboxamide | 391.2 | $^1$H NMR (600 MHz, DMSO-d$_6$) δ 8.38 (d, J = 5.99 Hz, 1H), 8.34 (s, 1H), 8.33 (s, 1H), 7.74-7.80 (m, 2H), 6.40 (d, J = 5.61 Hz, 1H), 4.20-4.31 (m, 4H), 4.16 (t, J = 4.87 Hz, 1H), 3.99 (s, 3H), 3.16-3.25 (m, 2H), 2.16-2.22 (m, 1H), 1.77-1.90 (m, 2H), 1.63-1.73 (m, 2H), 1.57 (dd, J = 4.75, 12.69 Hz, 1H) |
| 5-7 | Racemic, endo N-(7-cyano-7-azabicyclo[2.2.1]heptan-2-yl)-1-(4-(trifluoromethyl)-2-pyrimidinyl)-2,3-dihydro-1H-indole-5-carboxamide | 429.2 | $^1$H NMR (600 MHz, DMSO-d$_6$) δ 8.97 (d, J = 4.83 Hz, 1H), 8.41 (d, J = 6.86 Hz, 1H), 8.30 (d, J = 9.03 Hz, 1H), 7.80 (s, 1H), 7.81 (d, J = 7.04 Hz, 1H), 7.39 (d, J = 4.90 Hz, 1H), 4.25-4.32 (m, 3H), 4.14-4.25 (m, 2H), 3.23-3.30 (m, 2H), 2.16-2.23 (m, 1H), 1.77-1.91 (m, 2H), 1.63-1.73 (m, 2H), 1.53-1.60 (m, 1H) |
| 5-8 | Racemic, endo N-(7-cyano-7-azabicyclo[2.2.1]heptan-2-yl)-1-(4-(2-methyl-2-propanyl)-2-pyrimidinyl)-2,3-dihydro-1H-indole-5-carboxamide | 417.2 | $^1$H NMR (500 MHz, DMSO-d$_6$) δ 8.54 (d, J = 5.19 Hz, 1H), 8.40 (d, J = 8.28 Hz, 1H), 8.37 (d, J = 5.74 Hz, 1H), 7.78 (d, J = 8.49 Hz, 1H), 7.75 (s, 1H), 7.00 (d, J = 5.32 Hz, 1H), 4.20-4.32 (m, 4H), 4.16 (t, J = 4.87 Hz, 1H), 3.21 (t, J = 8.76 Hz, 2H), 2.15-2.22 (m, 1H), 1.77-1.90 (m, 2H), 1.62-1.72 (m, 2H), 1.57 (dd, J = 4.67, 12.72 Hz, 1H), 1.34 (s, 9H) |
| 5-9 | Racemic, endo N-(7-cyano-7-azabicyclo[2.2.1]heptan-2-yl)-1-(4-(2-propanyl)-2-pyrimidinyl)-2,3-dihydro-1H-indole-5-carboxamide | 403 | $^1$H NMR (500 MHz, DMSO-d$_6$) δ 8.50 (d, J = 5.06 Hz, 1H), 8.40 (d, J = 8.34 Hz, 1H), 8.35 (d, J = 6.23 Hz, 1H), 7.77 (d, J = 8.33 Hz, 1H), 7.75 (s, 1H), 6.88 (d, J = 5.06 Hz, 1H), 4.20-4.31 (m, 4H), 4.15 (t, J = 4.80 Hz, 1H), 3.18-3.26 (m, 2H), 2.97 (quin, J = 6.88 Hz, 1H), 2.16-2.23 (m, 1H), 1.77-1.90 (m, 2H), 1.62-1.73 (m, 2H), 1.57 (dd, J = 4.67, 12.72 Hz, 1H), 1.28 (d, J = 6.88 Hz, 6H) |
| 5-10 | N-((1R,2R,4S)-7-cyano-7-azabicyclo[2.2.1]heptan-2-yl)-1-(4-ethyl-2-pyrimidinyl)-2,3-dihydro-1H-indole-5-carboxamide | 389.2 | $^1$H NMR (500 MHz, DMSO-d$_6$) δ 8.49 (d, J = 5.06 Hz, 1H), 8.33-8.44 (m, 2H), 7.75 (s, 1H), 7.76 (d, J = 6.54 Hz, 1H), 6.86 (d, J = 5.06 Hz, 1H), 4.20-4.32 (m, 4H), 4.15 (t, J = 4.80 Hz, 1H), 3.18-3.25 (m, 2H), 2.69-2.79 (m, 2H), 2.16-2.23 (m, 1H), 1.77-1.91 (m, 2H), 1.62-1.73 (m, 2H), 1.57 (dd, J = 4.67, 12.72 Hz, 1H), 1.28 (t, J = 7.59 Hz, 3H) |
| 5-11 | N-((1R,2R,4S)-7-cyano-7-azabicyclo[2.2.1]heptan-2-yl)-1-(4-cyano-2-pyrimidinyl)-2,3-dihydro-1H-indole-5-carboxamide | 386.2 | $^1$H NMR (500 MHz, DMSO-d$_6$) δ 8.92 (d, J = 4.80 Hz, 1H), 8.43 (d, J = 5.97 Hz, 1H), 8.26 (d, J = 8.43 Hz, 1H), 7.78-7.83 (m, 2H), 7.51 (d, J = 4.80 Hz, 1H), 4.21-4.32 (m, 4H), 4.16 (t, J = 4.74 Hz, 1H), 3.25 (br t, J = 8.63 Hz, 2H), 2.17-2.24 (m, 1H), 1.77-1.92 (m, 2H), 1.63-1.73 (m, 2H), 1.57 (dd, J = 4.80, 12.72 Hz, 1H) |
| 5-12 | N-((1R,2R,4S)-7-cyano-7-azabicyclo[2.2.1]heptan-2-yl)-1-(4-cyano-6-methyl-2-pyrimidinyl)-2,3-dihydro-1H-indole-5-carboxamide | 400.2 | $^1$H NMR (600 MHz, DMSO-d$_6$) δ 8.42 (d, J = 6.07 Hz, 1H), 8.22-8.36 (m, 1H), 7.75-7.84 (m, 2H), 7.44 (s, 1H), 4.20-4.32 (m, 4H), 4.11-4.20 (m, 1H), 3.23 (br t, J = 8.68 Hz, 2H), 2.52-2.55 (s, 3H), 2.16-2.24 (m, 1H), 1.76-1.91 (m, 2H), 1.62-1.74 (m, 2H), 1.56 (br d, J = 12.69 Hz, 1H), 1.57 (br d, J = 12.77 Hz, 1H) |
| 5-13 | N-((1R,2R,4S)-7-cyano-7-azabicyclo[2.2.1]heptan-2-yl)-1-(4-(difluoromethyl)-2-pyrimidinyl)-2,3-dihydro-1H-indole-5-carboxamide | 411.2 | $^1$H NMR (600 MHz, DMSO-d$_6$) δ 8.85 (d, J = 4.91 Hz, 1H), 8.41 (d, J = 6.07 Hz, 1H), 8.36 (d, J = 8.33 Hz, 1H), 7.80 (s, 1H), 7.79 (d, J = 10.62 Hz, 1H), 7.19 (d, J = 4.90 Hz, 1H), 6.96 (t, J = 54.42 Hz, 1H), 4.21-4.33 (m, 4H), 4.16 (t, J = 4.87 Hz, 1H), 3.25 (br t, J = 8.60 Hz, 2H), 2.17-2.23 (m, 1H), 1.77-1.91 (m, 2H), 1.62-1.75 (m, 2H), 1.57 (dd, J = 4.67, 12.69 Hz, 1H) |

| Ex # | Name | MS data | 1H NMR |
|---|---|---|---|
| 5-14 | N-((1R,2R,4S)-7-cyano-7-azabicyclo[2.2.1]heptan-2-yl)-1-(4-methyl-6-(trifluoromethyl)-2-pyrimidinyl)-2,3-dihydro-1H-indole-5-carboxamide | 443.2 | $^1$H NMR (600 MHz, DMSO-d$_6$) δ 8.40 (d, J = 6.07 Hz, 1H), 8.34 (br d, J = 7.86 Hz, 1H), 7.80 (d, J = 10.28 Hz, 1H), 7.79 (s, 1H), 7.33 (s, 1H), 4.21-4.32 (m, 4H), 4.14-4.19 (m, 1H), 3.24 (br t, J = 8.64 Hz, 2H), 2.52-2.58 (m, 3H), 2.17-2.24 (m, 1H), 1.78-1.93 (m, 2H), 1.63-1.73 (m, 2H), 1.54-1.61 (m, 1H) |
| 5-15 | N-((1R,2R,4S)-7-cyano-7-azabicyclo[2.2.1]heptan-2-yl)-1-(3-fluoro-6-methyl-2-pyridinyl)-2,3-dihydro-1H-indole-5-carboxamide | 392.2 | $^1$H NMR (500 MHz, DMSO-d$_6$) δ 8.31 (d, J = 5.97 Hz, 1H), 7.73 (s, 1H), 7.66 (dd, J = 1.82, 8.43 Hz, 1H), 7.61 (dd, J = 8.11, 12.39 Hz, 1H), 7.30 (dd, J = 2.85, 8.43 Hz, 1H), 6.95 (dd, J = 2.79, 8.11 Hz, 1H), 4.28 (br dd, J = 4.80, 11.03 Hz, 1H), 4.17-4.23 (m, 4H), 3.17 (s, 2H), 2.40 (s, 3H), 2.14-2.25 (m, 1H), 1.83-1.88 (m, 1H), 1.79-1.82 (m, 1H), 1.64-1.71 (m, 2H), 1.56 (dd, J = 4.74, 12.65 Hz, 1H) |
| 6-1 | Racemic, endo N-(7-cyano-7-azabicyclo[2.2.1]heptan-2-yl)-1-(4-methyl-2-pyrimidinyl)-1H-indole-5-carboxamide | 373.2 | $^1$H NMR (400 MHz, DMSO-d$_6$) δ 8.81 (d, J = 8.81 Hz, 1H), 8.74 (d, J = 5.08 Hz, 1H), 8.57 (d, J = 5.91 Hz, 1H), 8.36 (d, J = 3.63 Hz, 1H), 8.21 (d, J = 1.66 Hz, 1H), 7.84 (dd, J = 1.76, 8.81 Hz, 1H), 7.28 (d, J = 4.98 Hz, 1H), 6.90 (d, J = 3.63 Hz, 1H), 4.34 (br dd, J = 4.72, 11.14 Hz, 1H), 4.26 (t, J = 4.51 Hz, 1H), 4.17 (t, J = 4.72 Hz, 1H), 2.59 (s, 3H), 2.23 (br s, 1H), 1.87-1.96 (m, 1H), 1.78-1.86 (m, 1H), 1.66-1.75 (m, 2H), 1.60 (dd, J = 4.72, 12.80 Hz, 1H) |
| 6-2 | Racemic, endo N-(7-cyano-7-azabicyclo[2.2.1]heptan-2-yl)-1-(2-pyrimidinyl)-2,3-dihydro-1H-indole-5-carboxamide | 361.2 | $^1$H NMR (500 MHz, DMSO-d$_6$) δ 8.63 (d, J = 4.80 Hz, 2H), 8.39 (d, J = 6.49 Hz, 1H), 8.34 (d, J = 8.38 Hz, 1H), 7.72-7.79 (m, 2H), 6.96 (t, J = 4.80 Hz, 1H), 4.21-4.31 (m, 4H), 4.16 (t, J = 4.74 Hz, 1H), 3.22 (t, J = 8.76 Hz, 2H), 2.16-2.23 (m, 1H), 1.77-1.90 (m, 2H), 1.63-1.73 (m, 2H), 1.57 (dd, J = 4.67, 12.72 Hz, 1H) |
| 6-3 | Racemic, endo N-(7-cyano-7-azabicyclo[2.2.1]heptan-2-yl)-1-(5-methyl-2-pyrimidinyl)-2,3-dihydro-1H-indole-5-carboxamide | 375.2 | $^1$H NMR (500 MHz, DMSO-d$_6$) δ 8.49 (s, 2H), 8.36 (d, J = 5.84 Hz, 1H), 8.29 (d, J = 8.30 Hz, 1H), 7.72-7.77 (m, 2H), 4.13-4.31 (m, 5H), 3.16-3.24 (m, 2H), 2.20 (s, 4H), 1.77-1.90 (m, 2H), 1.62-1.73 (m, 2H), 1.57 (dd, J = 4.61, 12.65 Hz, 1H) |
| 7-1 | N-((1R,2R,4S)-7-cyano-7-azabicyclo[2.2.1]heptan-2-yl)-1-(4-cyclopropyl-2-pyrimidinyl)-N-methyl-2,3-dihydro-1H-indole-5-carboxamide | 415.3 | $^1$H NMR (400 MHz, DMSO-d$_6$) δ 8.37 (d, J = 5.08 Hz, 1H), 8.24 (d, J = 8.19 Hz, 1H), 7.34 (s, 1H), 7.33 (d, J = 9.57 Hz, 1H), 6.89 (d, J = 5.08 Hz, 1H), 4.46 (t, J = 4.30 Hz, 1H), 4.14-4.23 (m, 4H), 3.17 (t, J = 8.81 Hz, 2H), 2.96 (s, 3H), 2.04-2.22 (m, 2H), 1.81-1.90 (m, 2H), 1.66-1.75 (m, 2H), 1.05-1.14 (m, 4H) |
| 7-2 | N-((1S,2S,4R)-7-cyano-7-azabicyclo[2.2.1]heptan-2-yl)-1-(4-cyclopropyl-2-pyrimidinyl)-N-methyl-2,3-dihydro-1H-indole-5-carboxamide (peak 2 derived) | 415.2 | $^1$H NMR (400 MHz, DMSO-d$_6$) δ 8.37 (d, J = 5.08 Hz, 1H), 8.24 (d, J = 8.19 Hz, 1H), 7.34 (s, 1H), 7.33 (d, J = 9.60 Hz, 1H), 6.89 (d, J = 5.18 Hz, 1H), 4.46 (t, J = 4.35 Hz, 1H), 4.15-4.23 (m, 4H), 3.17 (t, J = 8.71 Hz, 2H), 2.96 (s, 3H), 2.13-2.22 (m, 1H), 2.04-2.11 (m, 1H), 1.80-1.89 (m, 2H), 1.64-1.75 (m, 3H), 1.05-1.15 (m, 4H) |
| 8-1 | Racemic, endo N~5~-(7-cyano-7-azabicyclo[2.2.1]heptan-2-yl)-N~1~-cyclopropyl-2,3-dihydro-1H-indole-1,5-dicarboxamide | 366.2 | $^1$H NMR (600 MHz, DMSO-d$_6$) δ 8.32 (d, J = 6.07 Hz, 1H), 7.86 (d, J = 8.33 Hz, 1H), 7.66 (s, 1H), 7.65 (d, J = 7.10 Hz, 1H), 6.84 (d, J = 2.65 Hz, 1H), 4.23-4.29 (m, 1H), 4.20 (t, J = 4.48 Hz, 1H), 4.14 (t, J = 4.79 Hz, 1H), 3.87 (t, J = 8.80 Hz, 2H), 3.12 (t, J = 8.76 Hz, 2H), 2.59 (tdd, J = 3.56, 6.99, 10.41 Hz, 1H), 2.14-2.20 (m, 1H), 1.76-1.87 (m, 2H), 1.61-1.71 (m, 2H), 1.55 (dd, J = 4.67, 12.69 Hz, 1H), 0.58-0.64 (m, 2H), 0.47-0.53 (m, 2H) |
| 8-2 | Racemic, endo 1-(7-cyano-7-azabicyclo[2.2.1]heptan-2-yl)-3-(4-(trifluoromethyl)phenyl)urea | 325.2 | $^1$H NMR (400 MHz, DMSO-d$_6$) δ 8.78 (s, 1H), 7.55-7.61 (m, 4H), 6.79 (d, J = 6.53 Hz, 1H), 4.02-4.22 (m, 3H), 2.21-2.30 (m, 1H), 1.79-1.95 (m, 2H), 1.66-1.76 (m, 1H), 1.54-1.66 (m, 1H), 1.10-1.22 (m, 1H) |
| 9-1 | N-((1R,2R,4S)-7-cyano-7-azabicyclo[2.2.1]heptan-2-yl)-3-methyl-4-(1-methyl-1H-pyrazol-4-yl)benzamide | 336.2 | $^1$H NMR (500 MHz, DMSO-d$_6$) δ 8.49 (d, J = 5.97 Hz, 1H), 8.04 (s, 1H), 7.76 (s, 1H), 7.74 (s, 1H), 7.69 (dd, J = 1.62, 7.98 Hz, 1H), 7.49 (d, J = 8.04 Hz, 1H), 4.22-4.33 (m, 2H), 4.16 (t, J = 4.74 Hz, 1H), 3.90 (s, 3H), 2.44 (s, 3H), 2.17-2.24 (m, 1H), 1.77-1.90 (m, 2H), 1.63-1.73 (m, 2H), 1.57 (dd, J = 4.67, 12.72 Hz, 1H) |
| 9-2 | N-((1R,2R,4S)-7-cyano-7-azabicyclo[2.2.1]heptan-2-yl)-3-(cyclopropylmethoxy)-4-(1-methyl-1H-pyrazol-4-yl)benzamide | 392.0 | $^1$H NMR (500 MHz, CHLOROFORM-d) δ ppm 8.04 (s, 1H), 7.99 (s, 1H), 7.58 (d, J = 7.91 Hz, 1H), 7.43 (d, J = 1.56 Hz, 1H), 7.21 (dd, J = 7.91, 1.69 Hz, 1H), 6.17 (br d, J = 4.54 Hz, 1H), 4.46-4.52 (m, 1H), 4.11 (t, J = 5.00 Hz, 1H), 3.96-4.00 (m, 3H), 2.56 (ddd, J = 4.90, 3.15, 1.43 Hz, 1H), 2.04-2.13 (m, 1H), 1.88-1.99 (m, 2H), 1.53-1.73 (m, 3H), 1.31-1.50 (m, 2H), 1.17 (dd, J = 13.04, 4.09 Hz, 1H), 0.67-0.75 (m, 2H), 0.36-0.46 (m, 2H) |

| Ex # | Name | MS data | 1H NMR |
|---|---|---|---|
| 9-3 | N-((1R,2R,4S)-7-cyano-7-azabicyclo[2.2.1]heptan-2-yl)-4-(1-methyl-1H-pyrazol-4-yl)-3-propoxybenzamide | 380.0 | $^1$H NMR (500 MHz, CHLOROFORM-d) δ ppm 7.94 (d, J = 5.19 Hz, 2H), 7.56 (d, J = 7.92 Hz, 1H), 7.47 (d, J = 1.43 Hz, 1H), 7.19-7.26 (m, 1H), 6.23 (br d, J = 4.80 Hz, 1H), 4.45-4.53 (m, 2H), 4.08-4.13 (m, 3H), 4.01 (s, 1H), 3.96 (s, 3H), 2.48-2.63 (m, 1H), 2.02-2.14 (m, 1H), 1.80-1.98 (m, 5H), 1.58-1.78 (m, 1H), 1.19 (dd, J = 12.98, 4.02 Hz, 1H), 1.10 (t, J = 7.46 Hz, 3H) |
| 9-4 | N-((1R,2R,4S)-7-cyano-7-azabicyclo[2.2.1]heptan-2-yl)-3-ethoxy-4-(1-methyl-1H-pyrazol-4-yl)benzamide | 366.0 | $^1$H NMR (500 MHz, CHLOROFORM-d) δ ppm 7.92 (s, 2H), 7.53 (d, J = 7.92 Hz, 1H), 7.45 (d, J = 1.56 Hz, 1H), 7.23-7.27 (m, 1H), 6.59 (br d, J = 5.06 Hz, 1H), 4.43-4.50 (m, 2H), 4.18 (q, J = 6.92 Hz, 2H), 4.08 (t, J = 5.00 Hz, 1H), 3.94 (s, 3H), 2.60 (s, 2H), 2.45-2.53 (m, 1H), 1.98-2.17 (m, 1H), 1.85-1.98 (m, 2H), 1.59-1.69 (m, 2H), 1.52 (t, J = 6.94 Hz, 3H), 1.23-1.28 (m, 1H) |
| 9-5 | N-((1R,2R,4S)-7-cyano-7-azabicyclo[2.2.1]heptan-2-yl)-4-(1-methyl-1H-pyrazol-4-yl)-3-(2-propanyloxy)benzamide | 380.0 | $^1$H NMR (500 MHz, CHLOROFORM-d) δ ppm 7.94 (s, 2H), 7.55 (d, J = 8.04 Hz, 1H), 7.49 (d, J = 1.56 Hz, 1H), 7.19 (dd, J = 8.04, 1.69 Hz, 1H), 6.22 (br d, J = 4.67 Hz, 1H), 4.78 (dt, J = 12.23, 6.02 Hz, 1H), 4.45-4.53 (m, 2H), 4.11 (t, J = 4.93 Hz, 1H), 3.97 (s, 3H), 2.55 (ddd, J = 4.93, 3.11, 1.43 Hz, 1H), 2.08 (dt, J = 7.69, 4.33 Hz, 1H), 1.88-1.98 (m, 2H), 1.55-1.77 (m, 2H), 1.43 (d, J = 6.10 Hz, 6H), 1.18 (dd, J = 12.98, 4.02 Hz, 1H) |
| 9-6 | N-((1R,2R,4S)-7-cyano-7-azabicyclo[2.2.1]heptan-2-yl)-3-methoxy-4-(1-methyl-1H-pyrazol-4-yl)benzamide | | $^1$H NMR (500 MHz, DMSO-d$_6$) δ 8.51 (d, J = 5.71 Hz, 1H), 8.20 (s, 1H), 7.97 (d, J = 0.65 Hz, 1H), 7.70 (d, J = 8.04 Hz, 1H), 7.50 (d, J = 7.99 Hz, 1H), 7.48 (s, 1H), 4.24-4.34 (m, 2H), 4.17 (t, J = 4.74 Hz, 1H), 3.94 (s, 3H), 3.88 (s, 3H), 2.17-2.26 (m, 1H), 1.78-1.90 (m, 2H), 1.64-1.73 (m, 2H), 1.57 (dd, J = 4.61, 12.78 Hz, 1H) |
| 9-7 | N-((1R,2R,4S)-7-cyano-7-azabicyclo[2.2.1]heptan-2-yl)-4-(1-methyl-1H-pyrazol-4-yl)-3-(trifluoromethoxy)benzamide | 406.2 | $^1$H NMR (500 MHz, DMSO-d$_6$) δ 8.68 (d, J = 5.84 Hz, 1H), 8.20 (s, 1H), 7.85-7.98 (m, 4H), 4.24-4.33 (m, 2H), 4.17 (t, J = 4.74 Hz, 1H), 3.88-3.93 (m, 3H), 2.18-2.26 (m, 1H), 1.79-1.89 (m, 2H), 1.64-1.72 (m, 2H), 1.57 (dd, J = 4.67, 12.85 Hz, 1H) |
| 9-8 | N-((1R,2R,4S)-7-cyano-7-azabicyclo[2.2.1]heptan-2-yl)-4-(1-methyl-1H-pyrazol-4-yl)-3-(trifluoromethyl)benzamide | 390.2 | $^1$H NMR (500 MHz, DMSO-d$_6$) δ 8.79 (d, J = 5.84 Hz, 1H), 8.24 (d, J = 1.69 Hz, 1H), 8.15 (dd, J = 1.69, 8.04 Hz, 1H), 7.98 (s, 1H), 7.67 (d, J = 8.11 Hz, 1H), 7.64 (s, 1H), 4.25-4.34 (m, 2H), 4.18 (t, J = 4.80 Hz, 1H), 3.91 (s, 3H), 2.20-2.27 (m, 1H), 1.79-1.91 (m, 2H), 1.64-1.73 (m, 2H), 1.57 (dd, J = 4.67, 12.85 Hz, 1H) |
| 9-9 | N-((1R,2R,4S)-7-cyano-7-azabicyclo[2.2.1]heptan-2-yl)-3-(6-(trifluoromethyl)-2-pyridinyl)-1H-indazole-6-carboxamide | 427 | $^1$H NMR (600 MHz, DMSO-d$_6$) δ 13.90 (br s, 1H), 8.75 (d, J = 5.99 Hz, 1H), 8.56 (d, J = 8.67 Hz, 1H), 8.46 (d, J = 8.02 Hz, 1H), 8.21 (t, J = 7.86 Hz, 1H), 8.13 (s, 1H), 7.90 (d, J = 7.63 Hz, 1H), 7.77 (dd, J = 1.32, 8.56 Hz, 1H), 4.31-4.41 (m, 1H), 4.28 (t, J = 4.44 Hz, 1H), 4.19 (t, J = 4.87 Hz, 1H), 2.20-2.28 (m, 1H), 1.88-1.99 (m, 1H), 1.79-1.88 (m, 1H), 1.66-1.75 (m, 2H), 1.60 (dd, J = 4.67, 12.69 Hz, 1H) |
| 10-1 | Racemic, endo 2-((3-bromobenzyl)(methyl)amino)-N-(7-cyano-7-azabicyclo[2.2.1]heptan-2-yl)acetamide | 377 | |
| 11-1 | Racemic, endo 2-(4-chloro-2-cyclohexylphenoxy)-N-(7-cyano-7-azabicyclo[2.2.1]heptan-2-yl)acetamide | 388 | |
| 11-2 | N~2~-benzyl-N~2~-(3-bromobenzyl)-N-((1R,2R,4S)-7-cyano-7-azabicyclo[2.2.1]heptan-2-yl)glycinamide | 453.2, 455.2 | 1H NMR (600 MHz, DMSO-d6) Shift 7.51-7.56 (m, 1H), 7.17-7.34 (m, 9H), 4.03-4.12 (m, 2H), 3.96-4.03 (m, 1H), 3.66 (d, J = 6.07 Hz, 3H), 3.63 (d, J = 7.79 Hz, 1H), 2.97-3.06 (m, 2H), 2.04-2.18 (m, 1H), 1.68-1.85 (m, 1H), 1.48-1.66 (m, 3H), 1.18 (dd, J = 4.59, 12.77 Hz, 1H) |
| 11-3 | N~2~-benzyl-N~2~-(3-chlorobenzyl)-N-((1R,2R,4S)-7-cyano-7-azabicyclo[2.2.1]heptan-2-yl)glycinamide | 409.2 | 1H NMR (600 MHz, DMSO-d6) Shift 7.91 (d, J = 6.23 Hz, 1H), 7.31-7.38 (m, 9H), 4.06-4.11 (m, 2H), 4.01-4.05 (m, 1H), 3.71 (d, J = 3.35 Hz, 4H), 3.06 (s, 2H), 2.08-2.15 (m, 1H), 1.72-1.81 (m, 1H), 1.64-1.70 (m, 1H), 1.58-1.64 (m, 1H), 1.52-1.58 (m, 1H), 1.22 (dd, J = 4.63, 12.73 Hz, 1H) |
| 11-4 | N-((1R,2R,4S)-7-cyano-7-azabicyclo[2.2.1]heptan-2-yl)-2-(5,6,7,8-tetrahydro[1]benzothieno[2,3-d]pyrimidin-4-ylsulfanyl)acetamide | 400.2 | 1H NMR (600 MHz, DMSO-d6) Shift 8.76 (s, 1H), 8.67 (br d, J = 6.07 Hz, 1H), 4.15-4.24 (m, 5H), 3.12 (br s, 2H), 2.94 (br s, 2H), 2.23-2.32 (m, 1H), 2.01 (ddd, J = 4.40, 8.76, 12.77 Hz, 1H), 1.87-1.97 (m, 5H), 1.65-1.81 (m, 2H), 1.38 (dd, J = 4.36, 12.69 Hz, 1H) |

-continued

| Ex # | Name | MS data | 1H NMR |
|---|---|---|---|
| 11-5 | N~2~-(3-bromobenzyl)-N-((1R,2R,4S)-7-cyano-7-azabicyclo[2.2.1]heptan-2-yl)-N~2~-(2-methylpropyl)glycinamide | 419.2, 421.2 | 1H NMR (600 MHz, DMSO-d6) Shift 7.84 (br d, J = 6.15 Hz, 1H), 7.50 (s, 1H), 7.40 (d, J = 7.79 Hz, 1H), 7.27-7.30 (m, 1H), 7.22-7.27 (m, 1H), 4.05-4.10 (m, 2H), 4.00-4.05 (m, 1H), 3.61-3.70 (m, 2H), 2.99-3.07 (m, 2H), 2.17-2.26 (m, 2H), 2.09-2.17 (m, 1H), 1.66-1.79 (m, 3H), 1.56-1.64 (m, 1H), 1.48-1.55 (m, 1H), 1.10-1.21 (m, 1H), 0.80 (dd, J = 3.00, 6.58 Hz, 6H) |
| 11-6 | N~2~-(3-chlorobenzyl)-N-((1R,2R,4S)-7-cyano-7-azabicyclo[2.2.1]heptan-2-yl)-N~2~-(4-methoxybenzyl)glycinamide | 439.2 | 1H NMR (600 MHz, DMSO-d6) Shift 7.84 (d, J = 6.31 Hz, 1H), 7.40 (s, 1H), 7.29-7.33 (m, 1H), 7.25-7.29 (m, 2H), 7.22 (d, J = 8.56 Hz, 2H), 6.86 (d, J = 8.64 Hz, 2H), 4.02-4.10 (m, 2H), 3.96-4.02 (m, 1H), 3.69 (s, 3H), 3.59 (s, 2H), 2.94-3.03 (m, 2H), 2.04-2.13 (m, 1H), 1.68-1.81 (m, 1H), 1.60-1.66 (m, 1H), 1.55-1.60 (m, 1H), 1.49-1.55 (m, 1H), 1.19 (dd, J = 4.63, 12.73 Hz, 1H) |
| 11-7 | N-((1R,2R,4S)-7-cyano-7-azabicyclo[2.2.1]heptan-2-yl)-2-(5,7-dichloro-3,4-dihydro-2(1H)-isoquinolinyl)acetamide | 379.2 | 1H NMR (600 MHz, DMSO-d6) Shift 8.08 (br d, J = 6.68 Hz, 1H), 7.40 (d, J = 2.10 Hz, 1H), 7.18 (d, J = 2.02 Hz, 1H), 4.03-4.12 (m, 3H), 3.57-3.68 (m, 2H), 3.06-3.17 (m, 3H), 2.66-2.78 (m, 4H), 2.04-2.13 (m, 1H), 1.68-1.79 (m, 2H), 1.56-1.65 (m, 2H), 1.35 (dd, J = 4.20, 12.69 Hz, 1H) |
| 11-8 | Racemic, endo N-(7-cyano-7-azabicyclo[2.2.1]heptan-2-yl)-2-(2,4-dichloro-5-ethyl-3-methylphenoxy)acetamide | 382 | |
| 11-9 | Racemic, endo 2-((5-chlorobenzo[d]thiazol-2-yl)thio)-N-(7-cyano-7-azabicyclo[2.2.1]heptan-2-yl)acetamide | 378.9 | |
| 12-1 | Racemic, endo 2-(4-((4-chlorophenyl)thio)piperidine-1-carbonyl)-7-azabicyclo[2.2.1]heptane-7-carbonitrile | 376 | |
| 13-1 | Racemic, endo N-(7-cyano-7-azabicyclo[2.2.1]heptan-2-yl)-1-(4-methyl-2-pyrimidinyl)-2,3-dihydro-1H-indole-5-carboxamide | | $^1$H NMR (600 MHz, DMSO-d$_6$) δ 8.97 (d, J = 4.83 Hz, 1H), 8.41 (d, J = 6.86 Hz, 1H), 8.30 (d, J = 9.03 Hz, 1H), 7.80 (s, 1H), 7.81 (d, J = 7.04 Hz, 1H), 7.39 (d, J = 4.90 Hz, 1H), 4.25-4.32 (m, 3H), 4.14-4.25 (m, 2H), 3.23-3.30 (m, 2H), 2.16-2.23 (m, 1H), 1.77-1.91 (m, 2H), 1.63-1.73 (m, 2H), 1.53-1.60 (m, 1H) |
| 13-2 | Racemic, endo N-(7-cyano-7-azabicyclo[2.2.1]heptan-2-yl)-1-(cyclopropylcarbonyl)-2,3-dihydro-1H-indole-5-carboxamide | 351.2 | $^1$H NMR (600 MHz, DMSO-d$_6$) δ 8.42 (d, J = 5.99 Hz, 1H), 8.04 (br s, 1H), 7.75 (s, 1H), 7.70 (br d, J = 8.41 Hz, 1H), 4.34 (br s, 2H), 4.19-4.31 (m, 2H), 4.15 (t, J = 4.75 Hz, 1H), 3.22 (br t, J = 8.29 Hz, 2H), 2.15-2.21 (m, 1H), 1.97 (br s, 1H), 1.76-1.88 (m, 2H), 1.62-1.72 (m, 2H), 1.55 (dd, J = 4.75, 12.69 Hz, 1H), 0.83-0.95 (m, 4H) |
| 13-3 | 6-chloro-N-((1R,2R,4S)-7-cyano-7-azabicyclo[2.2.1]heptan-2-yl)-1-(6-methyl-2-pyridinyl)-1H-indazole-5-carboxamide | 407.0 | $^1$H NMR (500 MHz, CHLOROFORM-d) δ ppm 8.84-8.99 (m, 1H), 8.09-8.21 (m, 1H), 8.04 (s, 1H), 7.79 (br d, J = 7.79 Hz, 1H), 7.72 (br t, J = 7.66 Hz, 1H), 7.05 (br d, J = 7.14 Hz, 1H), 6.69-6.85 (m, 1H), 4.51-4.64 (m, 1H), 4.48 (br s, 1H), 4.10 (br s, 1H), 2.65 (br s, 3H), 2.53 (br s, 1 H), 2.02-2.18 (m, 2H), 1.64-1.76 (m, 2H), 1.19-1.29 (m, 1H) |
| 13-4 | N-((1R,2R,4S)-7-cyano-7-azabicyclo[2.2.1]heptan-2-yl)-1-(6-methyl-2-pyridinyl)-1H-indazole-5-carboxamide | 373.0 | $^1$H NMR (500 MHz, CHLOROFORM-d) δ ppm 8.92 (d, J = 8.82 Hz, 1H), 8.24 (s, 1H), 8.22 (s, 1H), 7.80-7.93 (m, 2H), 7.74 (t, J = 7.85 Hz, 1H), 7.06 (d, J = 7.40 Hz, 1H), 6.34 (br d, J = 5.06 Hz, 1H), 4.47-4.60 (m, 2H), 4.12 (t, J = 4.93 Hz, 1H), 2.66 (s, 3H), 2.04-2.18 (m, 1H), 1.91-2.04 (m, 2H), 1.55-1.65 (m, 2H), 1.18-1.26 (m, 1H) |
| 13-5 | N-((1R,2R,4S)-7-cyano-7-azabicyclo[2.2.1]heptan-2-yl)-6-fluoro-1-(6-methyl-2-pyridinyl)-1H-indazole-5-carboxamide | 391.0 | $^1$H NMR (500 MHz, CHLOROFORM-d) δ ppm 8.65-8.62 (m, 1H), 8.53 (d, J = 7.40 Hz, 1H), 8.25 (s, 1H), 7.84 (br d, J = 8.04 Hz, 1H), 7.74 (br t, J = 7.66 Hz, 1H), 7.07 (br d, J = 7.27 Hz, 1H), 6.82-6.99 (m, 1H), 4.47-4.60 (m, 2H), 4.12 (t, J = 4.93 Hz, 1H), 2.66 (s, 3H), 2.04-2.18 (m, 1H), 1.91- 2.04 (m, 2H), 1.55-1.65 (m, 2H), 1.20 (dd, J = 12.85, 3.89 Hz, 1H) |
| 13-6 | Racemic, endo N-(7-cyano-7-azabicyclo[2.2.1]heptan-2-yl)-4-(4-cyclopropyl-2-pyrimidinyl)-3,4-dihydro-2H-1,4-benzoxazine-7-carboxamide | 417.2 | $^1$H NMR (500 MHz, DMSO-d$_6$) δ 8.41 (d, J = 6.23 Hz, 1H), 8.35 (d, J = 5.06 Hz, 1H), 8.12 (d, J = 8.69 Hz, 1H), 7.42 (s, 1H), 7.39 (d, J = 8.28 Hz, 1H), 6.93 (d, J = 5.06 Hz, 1H), 4.14-4.31 (m, 7H), 2.19 (br s, 1H), 2.02-2.08 (m, 1H), 1.77-1.88 (m, 2H), 1.63-1.72 (m, 2H), 1.57 (dd, J = 4.67, 12.72 Hz, 1H), 1.00-1.06 (m, 4H) |

| Ex # | Name | MS data | 1H NMR |
|---|---|---|---|
| 13-7 | 2-((4-chloro-1-naphthalenyl)oxy)-N-((1R,2R,4S)-7-cyano-7-azabicyclo[2.2.1]heptan-2-yl)acetamide | 356.2 | $^1$H NMR (500 MHz, DMSO-d$_6$) δ 8.52 (br d, J = 5.58 Hz, 1H), 8.34 (d, J = 8.17 Hz, 1H), 8.13 (d, J = 8.43 Hz, 1H), 7.74 (dt, J = 1.23, 7.62 Hz, 1H), 7.64-7.68 (m, 1H), 7.60 (d, J = 8.30 Hz, 1H), 6.89 (d, J = 8.43 Hz, 1H), 4.77 (s, 2H), 4.10-4.23 (m, 3H), 2.14-2.26 (m, 1H), 1.76-1.91 (m, 2H), 1.56-1.72 (m, 2H), 1.34-1.41 (m, 1H) |
| 13-8 | 2-((4-chloro-1-naphthalenyl)oxy)-N-((1R,2R,4S)-7-cyano-7-azabicyclo[2.2.1]heptan-2-yl)acetamide (peak 2 derived) | 356.2 | $^1$H NMR (500 MHz, DMSO-d$_6$) δ 8.52 (br d, J = 5.45 Hz, 1H), 8.34 (d, J = 8.30 Hz, 1H), 8.13 (d, J = 8.30 Hz, 1H), 7.73 (t, J = 7.73 Hz, 1H), 7.66 (t, J = 7.74 Hz, 1H), 7.60 (d, J = 8.18 Hz, 1H), 6.89 (d, J = 8.30 Hz, 1H), 4.73-4.80 (m, 2H), 4.12-4.21 (m, 3H), 2.15-2.23 (m, 1H), 1.76-1.90 (m, 2H), 1.57-1.70 (m, 2H), 1.38 (dd, J = 4.02, 12.85 Hz, 1H) |
| 13-9 | Racemic, endo 2-methyl-2-propanyl 5-((7-cyano-7-azabicyclo[2.2.1]heptan-2-yl)carbamoyl)-2,3-dihydro-1H-indole-1-carboxylate | 383.3 | $^1$H NMR (500 MHz, DMSO-d$_6$) δ 8.38 (d, J = 5.97 Hz, 1H), 7.72 (d, J = 7.07 Hz, 1H), 7.71 (s, 1H), 4.19-4.30 (m, 2H), 4.15 (t, J = 4.80 Hz, 1H), 3.95 (t, J = 8.76 Hz, 2H), 3.10 (t, J = 8.76 Hz, 2H), 2.14-2.22 (m, 1H), 1.76-1.88 (m, 2H), 1.61-1.72 (m, 2H), 1.47-1.57 (m, 10H) |
| 13-10 | Racemic, endo N-(7-cyano-7-azabicyclo[2.2.1]heptan-2-yl)-1-(4-methyl-2-pyrimidinyl)-1H-indazole-5-carboxamide | 374.2 | $^1$H NMR (400 MHz, DMSO-d$_6$) δ 8.80 (d, J = 5.08 Hz, 1H), 8.69-8.75 (m, 2H), 8.61 (d, J = 0.83 Hz, 1H), 8.45 (dd, J = 0.67, 1.61 Hz, 1H), 8.07 (dd, J = 1.66, 8.91 Hz, 1H), 7.37 (d, J = 5.08 Hz, 1H), 4.31-4.40 (m, 1H), 4.28 (t, J = 4.46 Hz, 1H), 4.18 (t, J = 4.82 Hz, 1H), 2.62 (s, 3H), 2.20-2.28 (m, 1H), 1.79-1.99 (m, 2H), 1.65-1.76 (m, 2H), 1.59 (dd, J = 4.66, 12.75 Hz, 1H) |
| 13-11 | Racemic, endo N-(7-cyano-7-azabicyclo[2.2.1]heptan-2-yl)-1-(4-methyl-2-pyrimidinyl)-1H-benzimidazole-5-carboxamide | 374 | $^1$H NMR (500 MHz, DMSO-d$_6$) δ 9.21 (s, 1H), 8.82 (d, J = 5.06 Hz, 1H), 8.69 (d, J = 6.10 Hz, 1H), 8.63 (d, J = 8.69 Hz, 1H), 8.39 (d, J = 1.17 Hz, 1H), 7.97 (dd, J = 1.69, 8.69 Hz, 1H), 7.44 (d, J = 5.06 Hz, 1H), 4.32-4.38 (m, 1H), 4.25-4.29 (m, 1H), 4.18 (t, J = 4.87 Hz, 1H), 2.63 (s, 3H), 2.19-2.26 (m, 1H), 1.80-1.96 (m, 2H), 1.67-1.76 (m, 2H), 1.62 (dd, J = 4.80, 12.72 Hz, 1H) |
| 13-12 | Racemic, endo N-(7-cyano-7-azabicyclo[2.2.1]heptan-2-yl)-1-(4-cyclopropyl-2-pyridinyl)-1H-indazole-5-carboxamide | 399 | $^1$H NMR (500 MHz, DMSO-d$_6$) δ 8.75 (d, J = 8.78 Hz, 1H), 8.72 (d, J = 6.29 Hz, 1H), 8.59 (s, 1H), 8.44 (s, 1H), 8.41 (d, J = 5.69 Hz, 1H), 8.03 (dd, J = 1.56, 8.95 Hz, 1H), 7.76 (s, 1H), 7.05 (d, J = 5.32 Hz, 1H), 4.34 (br dd, J = 5.19, 10.64 Hz, 1H), 4.27 (t, J = 4.54 Hz, 1H), 4.18 (t, J = 4.80 Hz, 1H), 2.19-2.27 (m, 1H), 2.09-2.16 (m, 1H), 1.87-1.96 (m, 1H), 1.79-1.87 (m, 1H), 1.65-1.75 (m, 2H), 1.59 (dd, J = 4.74, 12.65 Hz, 1H), 1.11-1.21 (m, 2H), 0.88-0.94 (m, 2H) |
| 13-13 | Racemic, endo N-(7-cyano-7-azabicyclo[2.2.1]heptan-2-yl)-1-(6-cyclopropyl-2-pyridinyl)-1H-indazole-5-carboxamide | 399 | $^1$H NMR (500 MHz, DMSO-d$_6$) δ 8.68 (d, J = 6.39 Hz, 1H), 8.65 (d, J = 8.70 Hz, 1H), 8.58 (d, J = 0.78 Hz, 1H), 8.44 (s, 1H), 8.09 (dd, J = 1.69, 8.95 Hz, 1H), 7.86 (t, J = 7.77 Hz, 1H), 7.76 (dd, J = 0.78, 8.17 Hz, 1H), 7.30 (dd, J = 0.71, 7.46 Hz, 1H), 4.32-4.39 (m, 1H), 4.27 (t, J = 4.54 Hz, 1H), 4.19 (t, J = 4.87 Hz, 1H), 2.20-2.29 (m, 2H), 1.89-1.99 (m, 1H), 1.79-1.88 (m, 1H), 1.65-1.75 (m, 2H), 1.60 (dd, J = 4.74, 12.65 Hz, 1H), 1.08-1.14 (m, 4H) |
| 13-14 | N-((1R,2R,4S)-7-cyano-7-azabicyclo[2.2.1]heptan-2-yl)-1-(6-cyclopropyl-2-pyridinyl)-1H-indazole-5-carboxamide | 398.9 | $^1$H NMR (500 MHz, DMSO-d$_6$) δ 8.62-8.69 (m, 2H), 8.57 (d, J = 0.65 Hz, 1H), 8.44 (d, J = 1.04 Hz, 1H), 8.09 (dd, J = 1.69, 8.95 Hz, 1H), 7.86 (t, J = 7.72 Hz, 1H), 7.76 (dd, J = 0.71, 8.11 Hz, 1H), 7.30 (d, J = 7.51 Hz, 1H), 4.32-4.39 (m, 1H), 4.27 (t, J = 4.61 Hz, 1H), 4.18 (t, J = 4.93 Hz, 1H), 2.20-2.29 (m, 1H), 1.90-1.97 (m, 1H), 1.79-1.88 (m, 1H), 1.65-1.76 (m, 2H), 1.60 (dd, J = 4.74, 12.78 Hz, 1H), 1.08-1.14 (m, 4H) |
| 13-15 | 3-(4-chloro-3-(trifluoromethyl)phenyl)-N-((1R,2R,4S)-7-cyano-7-azabicyclo[2.2.1]heptan-2-yl)propanamide | 372 | $^1$H NMR (600 MHz, DMSO-d$_6$) δ 8.11 (br d, J = 6.38 Hz, 1H), 7.67 (s, 1H), 7.63 (d, J = 8.32 Hz, 1H), 7.52 (dd, J = 1.71, 8.25 Hz, 1H), 3.97-4.10 (m, 3H), 2.87-2.94 (m, 2H), 2.38-2.48 (m, 2H), 2.08-2.14 (m, 1H), 1.71-1.78 (m, 1H), 1.44-1.56 (m, 3H), 1.09-1.16 (m, 1H) |
| 13-16 | N-((1R,2R,4S)-7-cyano-7-azabicyclo[2.2.1]heptan-2-yl)-1-(6-ethyl-2-pyridinyl)-1H-indazole-5-carboxamide | 387.2 | $^1$H NMR (600 MHz, DMSO-d$_6$) δ 8.86 (d, J = 8.88 Hz, 1H), 8.69 (d, J = 6.07 Hz, 1H), 8.59 (s, 1H), 8.45 (s, 1H), 8.08 (dd, J = 1.63, 8.88 Hz, 1H), 7.93 (t, J = 7.82 Hz, 1H), 7.84 (d, J = 8.10 Hz, 1H), 7.23 (d, J = 7.47 Hz, 1H), 4.32-4.39 (m, 1H), 4.28 (t, J = 4.55 Hz, 1H), 4.19 (t, J = 4.90 Hz, 1H), 2.92 (q, J = 7.55 Hz, 2H), 2.21-2.27 (m, 1H), 1.89-1.98 (m, 1H), 1.80-1.88 (m, 1H), 1.67-1.76 (m, 2H), 1.60 (dd, J = 4.71, 12.73 Hz, 1H), 1.38 (t, J = 7.55 Hz, 3H) |
| 13-17 | N-((1R,2R,4S)-7-cyano-7-azabicyclo[2.2.1]heptan-2-yl)-1-(4-methyl-2-pyrimidiny)-1H-pyrrolo[3,2-b]pyridine-5-carboxamide | 374.2 | $^1$H NMR (600 MHz, DMSO-d$_6$) δ 9.15 (d, J = 8.64 Hz, 1H), 9.02 (d, J = 6.46 Hz, 1H), 8.76 (d, J = 4.98 Hz, 1H), 8.69 (d, J = 3.74 Hz, 1H), 8.05 (d, J = 8.64 Hz, 1H), 7.34 (d, J = 5.06 Hz, 1H), 7.02 (d, J = 3.74 Hz, 1H), 4.31-4.39 (m, 1H), 4.28 (t, J = 4.71 Hz, 1H), 4.18 (t, J = 4.87 Hz, 1H), 2.61 (s, 3H), 2.18-2.24 (m, 1H), 1.77-1.92 (m, 4H), 1.65-1.74 (m, 1H) |

| Ex # | Name | MS data | 1H NMR |
|---|---|---|---|
| 13-18 | N-((1R,2R,4S)-7-cyano-7-azabicyclo[2.2.1]heptan-2-yl)-4-fluoro-1-(4-methyl-2-pyrimidinyl)-1H-indole-5-carboxamide | 391.2 | $^1$H NMR (600 MHz, DMSO-d$_6$) δ 8.75 (d, J = 5.06 Hz, 1H), 8.59-8.66 (m, 2H), 8.37 (d, J = 3.66 Hz, 1H), 7.52 (dd, J = 7.08, 8.56 Hz, 1H), 7.32 (d, J = 5.06 Hz, 1H), 6.95 (d, J = 3.74 Hz, 1H), 4.25-4.37 (m, 2H), 4.17 (t, J = 4.90 Hz, 1H), 2.60 (s, 3H), 2.20-2.27 (m, 1H), 1.98 (ddd, J = 4.28, 8.89, 12.75 Hz, 1H), 1.77-1.88 (m, 1H), 1.63-1.76 (m, 2H), 1.48 (dd, J = 4.59, 12.77 Hz, 1H) |
| 13-19 | N-((1R,2R,4S)-7-cyano-7-azabicyclo[2.2.1]heptan-2-yl)-4-(methyl(4-methyl-2-pyrimidinyl)amino)benzamide | 363.2 | $^1$H NMR (600 MHz, DMSO-d$_6$) δ 8.53 (d, J = 5.99 Hz, 1H), 8.25 (d, J = 4.98 Hz, 1H), 7.82-7.87 (m, 2H), 7.44-7.49 (m, 2H), 6.70 (d, J = 4.98 Hz, 1H), 4.22-4.34 (m, 2H), 4.16 (t, J = 4.87 Hz, 1H), 3.50 (s, 3H), 2.29 (s, 3H), 2.17-2.26 (m, 1H), 1.78-1.91 (m, 2H), 1.64-1.76 (m, 2H), 1.57 (dd, J = 4.67, 12.69 Hz, 1H) |
| 13-20 | N-((1R,2R,4S)-7-cyano-7-azabicyclo[2.2.1]heptan-2-yl)-4-methyl-1-(4-methyl-2-pyrimidinyl)-1H-indole-5-carboxamide | 387.2 | $^1$H NMR (600 MHz, DMSO-d$_6$) δ 8.78 (d, J = 5.06 Hz, 1H), 8.48-8.56 (m, 1H), 8.05 (s, 1H), 7.85 (d, J = 3.43 Hz, 1H), 7.58 (s, 1H), 7.40 (d, J = 5.06 Hz, 1H), 6.84 (d, J = 3.50 Hz, 1H), 4.33 (br dd, J = 4.83, 11.13 Hz, 1H), 4.24-4.28 (m, 1H), 4.15-4.19 (m, 1H), 2.55-2.58 (m, 3H), 2.30-2.34 (m, 3H), 2.16-2.27 (m, 1H), 1.91 (dt, J = 3.78, 8.74 Hz, 1H), 1.78-1.86 (m, 1H), 1.65-1.76 (m, 2H), 1.57-1.64 (m, 1H) |
| 14-1 | Racemic, endo N-(7-cyano-7-azabicyclo[2.2.1]heptan-2-yl)-4-(2-pyrimidinylamino)benzamide | 335.2 | $^1$H NMR (600 MHz, DMSO-d$_6$) δ 9.92 (s, 1H), 8.53 (d, J = 4.75 Hz, 2H), 8.37 (d, J = 5.99 Hz, 1H), 7.83-7.89 (m, J = 8.88 Hz, 2H), 7.78-7.83 (m, J = 8.80 Hz, 2H), 6.91 (t, J = 4.79 Hz, 1H), 4.21-4.30 (m, 2H), 4.15 (t, J = 4.87 Hz, 1H), 2.15-2.23 (m, 1H), 1.77-1.90 (m, 2H), 1.63-1.73 (m, 2H), 1.55 (dd, J = 4.67, 12.69 Hz, 1H) |
| 14-2 | N-((1R,2R,4S)-7-cyano-7-azabicyclo[2.2.1]heptan-2-yl)-6-(3,5-dimethyl-1,2-oxazol-4-yl)-1H-indole-2-carboxamide | 376.2 | $^1$H NMR (500 MHz, DMSO-d$_6$) δ 11.66 (s, 1H), 8.60 (d, J = 6.23 Hz, 1H), 7.73 (d, J = 8.30 Hz, 1H), 7.27 (s, 1H), 7.38 (d, J = 1.43 Hz, 1H), 7.04 (dd, J = 1.36, 8.24 Hz, 1H), 4.30-4.37 (m, 1H), 4.26 (t, J = 4.41 Hz, 1H), 4.19 (t, J = 4.80 Hz, 1H), 2.41 (s, 3H), 2.21-2.28 (m, 4H), 1.80-1.93 (m, 2H), 1.66-1.75 (m, 2H), 1.55 (dd, J = 4.67, 12.72 Hz, 1H) |
| 14-3 | N-((1R,2R,4S)-7-cyano-7-azabicyclo[2.2.1]heptan-2-yl)-1-(4-cyclopropyl-2-pyrimidinyl)-2,3-dihydro-1H-indole-5-carboxamide | 401.2 | $^1$H NMR (500 MHz, DMSO-d$_6$) δ 8.39 (d, J = 5.33 Hz, 1H), 8.36 (d, J = 6.34 Hz, 1H), 8.24 (d, J = 8.43 Hz, 1H), 7.72-7.77 (m, 2H), 6.92 (d, J = 5.06 Hz, 1H), 4.25-4.32 (m, 1H), 4.14-4.24 (m, 4H), 3.15-3.30 (m, 2H), 2.15-2.23 (m, 1H), 2.05-2.11 (m, 1H), 1.77-1.90 (m, 2H), 1.62-1.73 (m, 2H), 1.57 (dd, J = 4.80, 12.72 Hz, 1H), 1.06-1.15 (m, 4H) |
| 14-4 | N-((1R,2R,4S)-7-cyano-7-azabicyclo[2.2.1]heptan-2-yl)-1-(4-cyclopropyl-2-pyrimidinyl)-2,3-dihydro-1H-indole-5-carboxamide | 401.2 | $^1$H NMR (500 MHz, DMSO-d$_6$) δ 8.39 (d, J = 5.31 Hz, 1H), 8.36 (d, J = 6.33 Hz, 1H), 8.24 (d, J = 8.43 Hz, 1H), 7.72-7.77 (m, 2H), 6.92 (d, J = 5.06 Hz, 1H), 4.14-4.31 (m, 5H), 3.18 (t, J = 8.82 Hz, 2H), 2.15-2.23 (m, 1H), 2.05-2.11 (m, 1H), 1.77-1.90 (m, 2H), 1.62-1.73 (m, 2H), 1.57 (dd, J = 4.74, 12.65 Hz, 1H), 1.06-1.15 (m, 4H) |
| 14-5 | N-((1R,2R,4S)-7-cyano-7-azabicyclo[2.2.1]heptan-2-yl)-4-(1-methyl-1H-pyrazol-4-yl)benzamide | 322.2 | $^1$H NMR (500 MHz, DMSO-d$_6$) δ 8.51 (d, J = 5.84 Hz, 1H), 8.25 (s, 1H), 7.95 (s, 1H), 7.84-7.87 (m, J = 8.43 Hz, 2H), 7.65-7.69 (m, J = 8.43 Hz, 2H), 4.26-4.33 (m, 1H), 4.22-4.26 (m, 1H), 4.16 (t, J = 4.74 Hz, 1H), 3.87 (s, 3H), 3.24-3.30 (m, 1H), 2.16-2.24 (m, 1H), 1.78-1.90 (m, 1H), 1.63-1.72 (m, 2H), 1.57 (dd, J = 4.74, 12.65 Hz, 1H) |
| 15-1 | 6-chloro-N-((1R,2R,4S)-7-cyano-7-azabicyclo[2.2.1]heptan-2-yl)-1-(4-methyl-2-pyrimidinyl)-2,3-dihydro-1H-indole-5-carboxamide | 409 | $^1$H NMR (600 MHz, DMSO-d$_6$) δ 8.64 (br d, J = 5.60 Hz, 1H), 8.50 (d, J = 4.98 Hz, 1H), 8.41 (s, 1H), 7.31 (s, 1H), 6.88 (d, J = 4.98 Hz, 1H), 4.21-4.26 (m, 4H), 4.09-4.19 (m, 1H), 3.20 (br s, 1H), 3.16 (t, J = 8.68 Hz, 2H), 2.44 (s, 3H), 2.15-2.24 (m, 1H), 1.99 (ddd, J = 4.17, 8.99, 12.85 Hz, 1H), 1.75-1.86 (m, 1H), 1.66-1.74 (m, 1H), 1.56-1.65 (m, 1H), 1.40 (dd, J = 4.01, 12.81 Hz, 1H) |
| 16-1 | 5-(3-chlorophenyl)-N-((1R,2R,4S)-7-cyano-7-azabicyclo[2.2.1]heptan-2-yl)-4-methyl-1,3-thiazole-2-carboxamide | 373.0 | 1H NMR (500 MHz, CHLOROFORM-d) Shift 7.45-7.46 (m, 1H), 7.39-7.42 (m, 1H), 7.33-7.37 (m, 1H), 7.25-7.28 (m, 1H), 4.48-4.55 (m, 1H), 4.42-4.45 (m, 1H), 4.12-4.16 (m, 1H), 2.51-2.60 (m, 4H), 2.07-2.16 (m, 1H), 1.93-2.05 (m, 2H), 1.68-1.74 (m, 1H), 1.24-1.34 (m, 1H) |
| 16-2 | 5-(3-chlorpheny)-N-((1R,2R,4S)-7-cyano-7-azabicyclo[2.2.1]heptan-2-yl)-1,3-thiazole-2-carboxamide | 359.0 | 1H NMR (500 MHz, CHLOROFORM-d) Shift 8.00-8.02 (m, 1H), 7.61 (td, J = 1.17, 1.82 Hz, 1H), 7.45-7.53 (m, 1H), 7.38-7.43 (m, 2H), 7.23-7.28 (m, 1H), 4.51-4.57 (m, 1H), 4.41-4.45 (m, 1H), 4.14 (t, J = 5.13 Hz, 1H), 2.57 (dddd, J = 2.98, 5.16, 11.13, 13.04 Hz, 1H), 2.07-2.16 (m, 1H), 1.94-2.02 (m, 2H), 1.66-1.72 (m, 1H), 1.24-1.31 (m, 1H) |
| 1-65 | 2-chloro-N-((1R,2R,4S)-7-cyano-7-azabicyclo[2.2.1]heptan-2-yl)-4-((cyclopropylcarbonyl)amino)benzamide | 359.0 | 1H NMR (DMSO-d6) δ 10.49 (s, 1H), 8.68 (br d, J = 5.8 Hz, 1H), 7.85 (d, J = 1.9 Hz, 1H), 7.49 (dd, J = 8.4, 1.9 Hz, 1H), 7.39 (d, J = 8.4 Hz, 1H), 4.20-4.26 (m, 2H), 4.14 (t, J = 4.9 Hz, 1H), 2.15-2.24 (m, 1H), 1.97 (ddd, J = 12.9, 9.0, 4.2 Hz, 1H), 1.79-1.83 (m, 1H), 1.73-1.79 (m, 1H), 1.65-1.73 (m, 1H), 1.56-1.63 (m, 1H), 1.38 (dd, J = 12.8, 4.0 Hz, 1H), 0.80-0.86 (m, 4H) |

-continued

| Ex # | Name | MS data | 1H NMR |
|---|---|---|---|
| 1-66 | 2-chloro-N-((1R,2R,4S)-7-cyano-7-azabicyclo[2.2.1]heptan-2-yl)-4-(1H-indazol-1-yl)benzamide | 390.1 | 1H NMR (DMSO-d6) δ: 8.89 (br d, J = 5.9 Hz, 1H), 8.46 (s, 1H), 7.91-7.97 (m, 3H), 7.88 (dd, J = 8.3, 2.1 Hz, 1H), 7.67 (d, J = 8.3 Hz, 1H), 7.57 (t, J = 7.7 Hz, 1H), 7.33 (t, J = 7.6 Hz, 1H), 4.26-4.31 (m, 2H), 4.12-4.21 (m, 1H), 2.17-2.32 (m, 1H), 2.02 (ddd, J = 12.9, 9.0, 4.0 Hz, 1H), 1.78-1.87 (m, 1H), 1.69-1.78 (m, 1H), 1.57-1.66 (m, 1H), 1.40 (dd, J = 12.7, 4.2 Hz, 1H) |
| 1-68-2 | (3S)-6-chloro-N-((1R,2R,4S)-7-cyano-7-azabicyclo[2.2.1]heptan-2-yl)-2,3,4,9-tetrahydro-1H-carbazole-3-carboxamide | 369.1 | 1H NMR (DMSO-d6) δ: 10.83 (s, 1H), 8.15 (br d, J = 6.0 Hz, 1H), 7.30 (d, J = 1.8 Hz, 1H), 7.17 (d, J = 8.5 Hz, 1H), 6.90 (dd, J = 8.5, 2.0 Hz, 1H), 4.02-4.09 (m, 3H), 2.64-2.74 (m, 3H), 2.57-2.63 (m, 1H), 2.53 (dt, J = 9.4, 2.3 Hz, 1H), 2.05-2.18 (m, 1H), 1.91-2.03 (m, 1H), 1.69-1.84 (m, 3H), 1.56-1.64 (m, 1H), 1.49-1.56 (m, 1H), 1.22 (dd, J = 12.7, 4.5 Hz, 1H) |
| 1-69 | (4R)-7-chloro-N-((1R,2R,4S)-7-cyano-7-azabicyclo[2.2.1]heptan-2-yl)-2,3,4,5-tetrahydro-1-benzoxepine-4-carboxamide | 346.0 | 1H NMR (DMSO-d6) δ: 8.15 (br t, J = 6.1 Hz, 1H), 7.31 (dd, J = 17.3, 2.6 Hz, 1H), 7.17 (dt, J = 8.4, 1.9 Hz, 1H), 6.94 (d, J = 8.5 Hz, 1H), 4.30-4.39 (m, 1H), 4.05-4.15 (m, 3H), 3.58-3.66 (m, 1H), 2.90-2.99 (m, 1H), 2.75 (br d, J = 14.4 Hz, 1H), 2.42-2.48 (m, 1H), 2.13-2.21 (m, 1H), 1.93-2.09 (m, 2H), 1.75-1.90 (m, 2H), 1.52-1.69 (m, 2H), 1.24 (dt, J = 12.7, 4.4 Hz, 1H) |
| 1-70 | 5-chloro-N-((1R,2R,4S)-7-cyano-7-azabicyclo[2.2.1]heptan-2-yl)-1-methyl-3-(6-methyl-2-pyridinyl)-1H-indazole-6-carboxamide | 421.2 | 1H NMR (DMSO-d6) δ: 8.91 (d, J = 6.0 Hz, 1H), 8.69 (s, 1H), 7.90-7.93 (m, 2H), 7.79 (t, J = 7.8 Hz, 1H), 7.26 (d, J = 7.7 Hz, 1H), 4.28-4.34 (m, 2H), 4.13-4.22 (m, 4H), 2.61-2.62 (m, 3H), 2.25 (br d, J = 1.9 Hz, 1H), 2.08 (ddd, J = 12.8, 9.0, 3.9 Hz, 1H), 1.70-1.87 (m, 2H), 1.58-1.65 (m, 1H), 1.41 (dd, J = 12.8, 4.0 Hz, 1H) |
| 1-71 | N-((1R,2R,4S)-7-cyano-7-azabicyclo[2.2.1]heptan-2-yl)-1-(cyclopropylmethyl)-3-(6-methyl-2-pyridinyl)-1H-indazole-6-carboxamide | 427.2 | 1H NMR (DMSO-d6) δ: 8.62-8.73 (m, 2H), 8.24 (s, 1H), 7.94 (d, J = 7.8 Hz, 1H), 7.79 (t, J = 7.7 Hz, 1H), 7.73 (dd, J = 8.4, 1.3 Hz, 1H), 7.25 (d, J = 7.7 Hz, 1H), 4.46 (d, J = 7.0 Hz, 2H), 4.27-4.38 (m, 2H), 4.20 (t, J = 5.0 Hz, 1H), 2.62 (s, 3H), 2.21-2.32 (m, 1H), 1.89-1.99 (m, 1H), 1.80-1.89 (m, 1H), 1.66-1.76 (m, 2H), 1.60 (dd, J = 12.7, 4.5 Hz, 1H), 1.35-1.44 (m, 1H), 0.51-0.57 (m, 2H), 0.45-0.51 (m, 2H) |
| 1-72 | N-((1R,2R,4S)-7-cyano-7-azabicyclo[2.2.1]heptan-2-yl)-1-(2-methylpropyl)-3-(6-methyl-2-pyridinyl)-1H-indazole-6-carboxamide | 429.0 | 1H NMR (DMSO-d6) δ: 8.68 (d, J = 7.8 Hz, 2H), 8.18 (s, 1H), 7.93 (d, J = 7.8 Hz, 1H), 7.78 (t, J = 7.7 Hz, 1H), 7.72 (dd, J = 8.6, 1.2 Hz, 1H), 7.24 (d, J = 7.6 Hz, 1H), 4.29-4.39 (m, 4H), 4.19 (t, J = 4.9 Hz, 1H), 2.62 (s, 3H), 2.32-2.39 (m, 1H), 2.21-2.31 (m, 1H), 1.88-1.96 (m, 1H), 1.80-1.88 (m, 1H), 1.67-1.76 (m, 2H), 1.60 (dd, J = 12.8, 4.6 Hz, 1H), 0.91 (br d, J = 6.6 Hz, 3H), 0.91 (br d, J = 6.6 Hz, 3H) |
| 1-73 | N-((1R,2R,4S)-7-cyano-7-azabicyclo[2.2.1]heptan-2-yl)-3-(6-methyl-2-pyridinyl)-1-(4,4,4-trifluorobutyl)-1H-indazole-6-carboxamide | 482.8 | 1H NMR (DMSO-d6) δ: 8.66-8.73 (m, 2H), 8.21 (s, 1H), 7.94 (d, J = 7.9 Hz, 1H), 7.80 (t, J = 7.7 Hz, 1H), 7.73 (dd, J = 8.5, 1.3 Hz, 1H), 7.26 (d, J = 7.6 Hz, 1H), 4.64 (t, J = 7.0 Hz, 2H), 4.28-4.37 (m, 2H), 4.20 (t, J = 4.9 Hz, 1H), 2.62 (s, 3H), 2.34-2.43 (m, 2H), 2.22-2.30 (m, 1H), 2.12-2.21 (m, 2H), 1.89-1.97 (m, 1H), 1.80-1.88 (m, 1H), 1.67-1.75 (m, 2H), 1.60 (dd, J = 12.7, 4.6 Hz, 1H) |
| 1-74 | N-((1R,2R,4S)-7-cyano-7-azabicyclo[2.2.1]heptan-2-yl)-3-(6-methyl-2-pyridinyl)-1-propyl-1H-indazole-6-carboxamide | 415.0 | 1H NMR (DMSO-d6) δ: 8.64-8.72 (m, 2H), 8.19 (s, 1H), 7.93 (d, J = 7.9 Hz, 1H), 7.78 (t, J = 7.7 Hz, 1H), 7.72 (dd, J = 8.5, 1.3 Hz, 1H), 7.24 (d, J = 7.5 Hz, 1H), 4.51 (t, J = 7.0 Hz, 2H), 4.28-4.37 (m, 2H), 4.20 (t, J = 4.9 Hz, 1H), 2.62 (s, 3H), 2.23-2.31 (m, 1H), 1.90-2.00 (m, 3H), 1.80-1.89 (m, 1H), 1.68-1.76 (m, 2H), 1.60 (dd, J = 12.8, 4.6 Hz, 1H), 0.90 (t, J = 7.4 Hz, 3H) |
| 1-75 | 6-chloro-N-((1R,2R,4S)-7-cyano-7-azabicyclo[2.2.1]heptan-2-yl)-1-(6-(2,2,2-trifluoroethoxy)-2-pyridinyl)-1H-indazole-5-carboxamide | 491.0 | 1H NMR (DMSO-d6) δ: 8.86 (d, J = 6.1 Hz, 1H), 8.65-8.75 (m, 1H), 8.54-8.60 (m, 1H), 8.00-8.09 (m, 2H), 7.65-7.75 (m, 1H), 6.93-7.03 (m, 1H), 5.20 (q, J = 9.0 Hz, 2H), 4.25-4.37 (m, 2H), 4.17 (t, J = 4.9 Hz, 1H), 2.20-2.31 (m, 1H), 2.04 (td, J = 8.6, 4.5 Hz, 1H), 1.79-1.89 (m, 1H), 1.68-1.78 (m, 1H), 1.56-1.65 (m, 1H), 1.40 (dd, J = 12.7, 4.3 Hz, 1H) |
| 1-76 | 6-chloro-N-((1R,2R,4S)-7-cyano-7-azabicyclo[2.2.1]heptan-2-yl)-1-(1,7-naphthyridin-2-yl)-1H-indazole-5-carboxamide | 443.8 | 1H NMR (DMSO-d6) δ: 9.55 (s, 1H), 9.22 (s, 1H), 8.92 (br d, J = 5.9 Hz, 1H), 8.63-8.69 (m, 3H), 8.52 (d, J = 9.0 Hz, 1H), 8.12 (s, 1H), 7.99 (d, J = 5.5 Hz, 1H), 4.28-4.36 (m, 2H), 4.18 (t, J = 4.9 Hz, 1H), 2.22-2.30 (m, 1H), 2.02-2.10 (m, 1H), 1.80-1.88 (m, 1H), 1.71-1.80 (m, 1H), 1.58-1.67 (m, 1H), 1.41 (dd, J = 12.7, 4.0 Hz, 1H) |
| 1-77 | 6-chloro-N-((1R,2R,4S)-7-cyano-7-azabicyclo[2.2.1]heptan-2-yl)-1-(6-(cyanomethyl)-2-pyridinyl)-1H-indazole-5-carboxamide | 432.0 | 1H NMR (DMSO-d6) δ: 9.13 (s, 1H), 8.87 (br d, J = 6.0 Hz, 1H), 8.58 (s, 1H), 8.04-8.08 (m, 2H), 7.98 (d, J = 8.6 Hz, 1H), 7.34 (d, J = 7.8 Hz, 1H), 4.46 (s, 2H), 4.29 (br s, 2H), 4.16 (t, J = 4.7 Hz, 1H), 2.25 (br d, J = 2.9 Hz, 1H), 2.01-2.07 (m, 1H), 1.83 (br d, J = 4.0 Hz, 1H), 1.74 (br s, 1H), 1.61 (br s, 1H), 1.38-1.42 (m, 1H) |

| Ex # | Name | MS data | 1H NMR |
|---|---|---|---|
| 1-78 | 6-chloro-N-((1R,2R,4S)-7-cyano-7-azabicyclo[2.2.1]heptan-2-yl)-1-(1,8-naphthyridin-2-yl)-1H-indazole-5-carboxamide | | 1H NMR (DMSO-d6) δ: 9.31 (s, 1H), 9.12 (dd, J = 4.3, 1.9 Hz, 1H), 8.93 (br d, J = 5.8 Hz, 1H), 8.68 (s, 1H), 8.69 (d, J = 7.7 Hz, 1H), 8.54 (d, J = 8.1, 1.9 Hz, 1H), 8.38 (d, J = 8.8 Hz, 1H), 8.12 (s, 1H), 7.67 (dd, J = 8.0, 4.3 Hz, 1H), 4.29-4.36 (m, 2H), 4.18 (t, J = 4.8 Hz, 1H), 2.23-2.31 (m, 1H), 2.03-2.10 (m, 1H), 1.80-1.88 (m, 1H), 1.71-1.80 (m, 1H), 1.59-1.66 (m, 1H), 1.42 (dd, J = 12.6, 4.2 Hz, 1H). |
| 1-79 | 4-(3-chlorophenyl)-N-((1R,2R,4S)-7-cyano-7-azabicyclo[2.2.1]heptan-2-yl)-1,3-thiazole-2-carboxamide | 359 | 1H NMR (600 MHz, DMSO-d6) d 9.07 (d, J = 6.60 Hz, 1H), 8.56 (s, 1H), 8.18 (s, 1H), 8.05 (d, J = 7.90 Hz, 1H), 7.52 (t, J = 8.03 Hz, 1H), 7.47 (d, J = 8.01 Hz, 1H), 4.29 (br d, J = 4.52 Hz, 2H), 4.19 (s, 1H), 3.21-3.41 (m, 2H), 1.68-1.86 (m, 4H) |
| 1-80 | N-((1R,2R,4S)-7-cyano-7-azabicyclo[2.2.1]heptan-2-yl)-2-(3-thiophenyl)-1,3-thiazole-4-carboxamide | 330.8 | 1H NMR (DMSO-d6, 600 MHz) Shift 8.55 (br d, 1H, J = 6.0 Hz), 8.2-8.3 (m, 2H), 7.75 (dd, 1H, J = 2.9, 5.0 Hz), 7.71 (dd, 1H, J = 1.3, 5.1 Hz), 4.2-4.3 (m, 2H), 4.18 (t, 1H, J = 4.8 Hz), 2.2-2.2 (m, 1H), 1.7-1.9 (m, 3H), 1.7-1.7 (m, 2H) |
| 1-81 | 1-(3-chlorophenyl)-N-((1R,2R,4S)-7-cyano-7-azabicyclo[2.2.1]heptan-2-yl)-1H-pyrazole-3-carboxamide | 341.8 | 1H NMR (DMSO-d6, 600 MHz) δ 8.67 (d, 1H, J = 2.6 Hz), 8.59 (d, 1H, J = 6.1 Hz), 8.11 (t, 1H, J = 2.0 Hz), 7.95 (ddd, 1H, J = 0.8, 2.1, 8.3 Hz), 7.58 (t, 1H, J = 8.1 Hz), 7.45 (d, 1H, J = 8.0 Hz), 6.93 (d, 1H, J = 2.6 Hz), 4.2-4.3 (m, 2H), 4.17 (t, 1H, J = 4.8 Hz), 2.2-2.2 (m, 1H), 1.8-1.9 (m, 1H), 1.7-1.8 (m, 4H) |
| 1-82 | 1-(3-chlorophenyl)-N-((1R,2R,4S)-7-cyano-7-azabicyclo[2.2.1]heptan-2-yl)-5-methyl-1H-pyrazole-3-carboxamide | 355.8 | 1H NMR (DMSO-d6, 600 MHz) δ 8.51 (d, 1H, J = 6.2 Hz), 7.7-7.8 (m, 1H), 7.5-7.6 (m, 3H), 6.68 (d, 1H, J = 0.7 Hz), 4.2-4.3 (m, 1H), 4.20 (t, 1H, J = 4.6 Hz), 4.1-4.2 (m, 1H), 2.3-2.4 (m, 3H), 2.1-2.2 (m, 1H), 1.7-1.9 (m, 3H), 1.6-1.7 (m, 2H) |
| 1-83 | N-((1R,2R,4S)-7-cyano-7-azabicyclo[2.2.1]heptan-2-yl)-3-(2-methyl-1,3-thiazol-4-yl)benzamide | 338.8 | 1H NMR (DMSO-d6, 600 MHz) δ 8.69 (d, 1H, J = 6.0 Hz), 8.36 (t, 1H, J = 1.5 Hz), 8.09 (td, 1H, J = 1.2, 8.0 Hz), 8.02 (s, 1H), 7.80 (td, 1H, J = 1.2, 7.9 Hz), 7.54 (t, 1H, J = 7.7 Hz), 4.2-4.3 (m, 2H), 4.17 (t, 1H, J = 4.9 Hz), 2.74 (s, 3H), 2.2-2.3 (m, 1H), 1.8-1.9 (m, 1H), 1.6-1.7 (m, 2H), 1.58 (dd, 1H, J = 4.7, 12.8 Hz) |
| 1-84 | 7-bromo-N-((1R,2R,4S)-7-cyano-7-azabicyclo[2.2.1]heptan-2-yl)-1-oxo-1,2-dihydro-3-isoquinolinecarboxamide | 386.8 | 1H NMR (DMSO-d6, 600 MHz) δ 11.14 (br s, 1H), 8.90 (br d, 1H, J = 5.4 Hz), 8.31 (d, 1H, J = 2.1 Hz), 7.95 (dd, 1H, J = 2.1, 8.4 Hz), 7.78 (d, 1H, J = 8.5 Hz), 7.29 (s, 1H), 4.15-4.29 (m, 3H), 2.16-2.28 (m, 1H), 1.79-1.96 (m, 2H), 1.64-1.75 (m, 2H), 1.48-1.54 (m, 1H) |
| 1-85 | N-((1R,2R,4S)-7-cyano-7-azabicyclo[2.2.1]heptan-2-yl)-1-phenyl-3-pyrrolidinecarboxamide | 311 | 1H NMR (600 MHz, DMSO-d6) Shift 8.28 (br d, J = 5.60 Hz, 1H), 7.15 (t, J = 7.58 Hz, 2H), 6.59 (t, J = 7.24 Hz, 1H), 6.53 (dd, J = 2.65, 8.25 Hz, 2H), 4.08-4.14 (m, 3H), 3.44 (td, J = 8.62, 16.85 Hz, 1H), 3.30-3.37 (m, 1H), 3.21-3.28 (m, 2H), 3.10 (quin, J = 7.75 Hz, 1H), 2.05-2.21 (m, 3H), 1.78-1.87 (m, 2H), 1.57-1.70 (m, 2H), 1.23-1.30 (m, 1H) |
| 1-86 | N-((1R,2R,4S)-7-cyano-7-azabicyclo[2.2.1]heptan-2-yl)-2-methyl-1-phenyl-3-pyrrolidinecarboxamide | 325 | 1H NMR (600 MHz, DMSO-d6) Shift 8.22 (br d, J = 6.38 Hz, 1H), 7.15 (t, J = 7.57 Hz, 2H), 6.51-6.59 (m, 3H), 4.04-4.20 (m, 4H), 3.32-3.38 (m, 1H), 3.09-3.16 (m, 1H), 3.03 (td, J = 7.16, 12.30 Hz, 1H), 2.31-2.41 (m, 1H), 2.14-2.25 (m, 1H), 1.95-2.06 (m, 1H), 1.79-1.93 (m, 1H), 1.55-1.74 (m, 2H), 1.26 (ddd, J = 4.52, 7.63, 12.46 Hz, 1H), 0.91 (dd, J = 3.11, 6.23 Hz. 3H) |
| 1-87 | (3S)-N-((1R,2R,4S)-7-cyano-7-azabicyclo[2.2.1]heptan-2-yl)-1-(4-cyano-2-fluorophenyl)-3-pyrrolidinecarboxamide | 354 | 1H NMR (600 MHz, DMSO-d6) Shift 8.32 (br t, J = 4.98 Hz, 1H), 7.55 (d, J = 14.32 Hz, 1H), 7.42 (d, J = 8.56 Hz, 1H), 6.75 (dt, J = 4.13, 8.91 Hz, 1H), 4.05-4.14 (m, 3H), 3.61-3.70 (m, 1H), 3.46-3.59 (m, 3H), 3.07 (dquin, J = 2.26, 7.53 Hz, 1H), 2.12-2.21 (m, 2H), 1.99-2.08 (m, 1H), 1.78-1.86 (m, 2H), 1.56-1.69 (m, 2H), 1.22-1.30 (m, 1H) |
| 1-88 | 1-(3-chlorophenyl)-N-((1R,2R,4S)-7-cyano-7-azabicyclo[2.2.1]heptan-2-yl)-3-pyrrolidinecarboxamide | 345.0 | 1H NMR (500 MHz, CHLOROFORM-d) Shift 7.11-7.18 (m, 1H), 6.70 (d, J = 7.79 Hz, 1H), 6.56 (d, J = 1.95 Hz, 1H), 6.46 (dd, J = 2.14, 8.24 Hz, 1H), 5.87 (br s, 1H), 4.30-4.37 (m, 2H), 4.06 (t, J = 5.00 Hz, 1H), 3.45-3.53 (m, 3H), 3.29-3.45 (m, 1H), 2.99-3.07 (m, 1H), 2.42-2.50 (m, 1H), 2.23-2.34 (m, 2H), 2.01-2.10 (m, 1H), 1.91 (br t, J = 12.72 Hz, 1H), 1.71-1.85 (m, 1H), 1.56 (tdd, J = 4.18, 8.50, 12.59 Hz, 1H), 1.03 (dd, J = 4.02, 12.85 Hz, 1H) |
| 1-89 | N-((1R,2R,4S)-7-cyano-7-azabicyclo[2.2.1]heptan-2-yl)-5-phenyl-2-furancarboxamide | 307.8 | 1H NMR (600 MHz, DMSO-d6) Shift 8.49 (br d, J = 5.45 Hz, 1H), 7.90 (br d, J = 7.63 Hz, 2H), 7.49 (br t, J = 7.71 Hz, 2H), 7.37-7.42 (m, 1H), 7.25 (d, J = 3.43 Hz, 1H), 7.11 (d, J = 3.43 Hz, 1H), 4.23-4.30 (m, 2H), 4.18 (t, J = 4.75 Hz, 1H), 2.15-2.31 (m, 1H), 1.79-1.92 (m, 2H), 1.65-1.75 (m, 2H), 1.59 (br dd, J = 4.36, 12.77 Hz, 1H) |
| 1-90 | N-((1R,2R,4S)-7-cyano-7-azabicyclo[2.2.1]heptan-2-yl)-5-(3-(2-propanyl)phenyl)-2-furancarboxamide | 350 | 1H NMR (600 MHz, DMSO-d6) Shift 8.48 (br d, J = 4.98 Hz, 1H), 7.67-7.75 (m, 2H), 7.41 (t, J = 7.63 Hz, 1H), 7.23-7.30 (m, 2H), 7.11 (d, J = 3.43 Hz, 1H), 4.22-4.30 (m, 2H), 4.18 (br t, J = 4.67 Hz, 1H), 2.96 (td, J = 6.75, 13.74 Hz, 1H), 2.23 (br s, 1H), 1.78-1.93 (m, 2H), 1.66-1.75 (m, 2H), 1.58 (br dd, J = 3.89, 12.61 Hz, 1H), 1.26 (d, J = 6.85 Hz, 7H) |

| Ex # | Name | MS data | 1H NMR |
|---|---|---|---|
| 1-91 | N-((1R,2R,4S)-7-cyano-7-azabicyclo[2.2.1]heptan-2-yl)-5-(3-(trifluoromethyl)phenyl)-2-furancarboxamide | 375.8 | 1H NMR (600 MHz, DMSO-d6) Shift 8.58 (br d, J = 4.67 Hz, 1H), 8.18-8.22 (m, 2H), 7.74 (d, J = 4.67 Hz, 2H), 7.35 (d, J = 3.4.3 Hz, 1H), 7.29 (d, J = 3.58 Hz, 1H), 4.27 (br s, 2H), 4.19 (t, J = 4.67 Hz, 1H), 2.25 (br s, 1H), 1.82-1.91 (m, 2H), 1.68-1.73 (m, 2H), 1.58 (br dd, J = 4.05, 12.77 Hz, 1H) |
| 1-92 | 1-(3-chlorophenyl)-N-((1R,2R,4S)-7-cyano-7-azabicyclo[2.2.1]heptan-2-yl)-3-piperidinecarboxamide | 358.8 | 1H NMR (600 MHz, DMSO-d6) Shift 8.12-8.20 (m, 1H), 7.16-7.23 (m, 1H), 6.92-6.95 (m, 1H), 6.87-6.91 (m, 1H), 6.72-6.77 (m, 1H), 4.02-4.16 (m, 3H), 3.60-3.79 (m, 2H), 2.77-2.85 (m, 1H), 2.66-2.75 (m, 1H), 2.12-2.22 (m, 1H), 1.77-1.92 (m, 3H), 1.46-1.75 (m, 5H), 1.21-1.29 (m, 2H) |
| 1-93 | N-((1R,2R,4S)-7-cyano-7-azabicyclo[2.2.1]heptan-2-yl)-1-(4-(trifluoromethyl)-2-pyrimidinyl)-4-piperidinecarboxamide | 394.8 | 1H NMR (600 MHz, DMSO-d6) Shift 8.67 (d, J = 4.83 Hz, 1H), 8.14 (d, J = 6.15 Hz, 1H), 6.99 (d, J = 4.83 Hz, 1H), 4.64 (br d, J = 12.22 Hz, 2H), 4.03-4.14 (m, 3H), 2.99 (br t, J = 12.69 Hz, 2H), 2.45-2.48 (m, 1H), 2.12-2.18 (m, 1H), 1.74-1.85 (m, 4H), 1.55-1.66 (m, 2H), 1.45-1.54 (m, 2H), 1.25 (dd, J = 4.48, 12.65 Hz, 1H) |
| 1-94 | 1-(3-bromophenyl)-N-((1R,2R,4S)-7-cyano-7-azabicyclo[2.2.1]heptan-2-yl)-3-pyrrolidinecarboxamide | 391 | 1H NMR (400 MHz, METHANOL-d4) Shift 7.03-7.09 (m, 1H), 6.67-6.77 (m, 2H), 6.49-6.56 (m, 1H), 4.21-4.29 (m, 2H), 4.07-4.14 (m, 1H), 3.46-3.54 (m, 1H), 3.36-3.44 (m, 2H), 3.29-3.35 (m, 3H), 3.12-3.22 (m, 1H), 2.15-2.40 (m, 2H), 1.89-1.99 (m, 2H), 1.80-1.88 (m, 1H), 1.64-1.73 (m, 1H), 1.27-1.35 (m, 2H) |
| 1-95 | 1-(3-chloro-4-(trifluoromethyl)phenyl)-N-((1R,2R,4S)-7-cyano-7-azabicyclo[2.2.1]heptan-2-yl)-3-pyrrolidinecarboxamide | 413 | 1H NMR (400 MHz, METHANOL-d4) Shift 7.49 (d, J = 8.81 Hz, 1H), 6.68 (s, 1H), 6.55 (br d, J = 8.81 Hz, 1H), 4.21-4.29 (m, 2H), 4.11 (t, J = 4.87 Hz, 1H), 3.35-3.61 (m, 4H), 3.21 (t, J = 7.57 Hz, 1H), 2.19-2.39 (m, 3H), 1.78-2.03 (m, 3H), 1.65-1.78 (m, 1H), 1.31 (dd, J = 4.25, 12.65 Hz, 1H) |
| 1-96 | 6-chloro-N-((1R,2R,4S)-7-cyano-7-azabicyclo[2.2.1]heptan-2-yl)-3,4-dihydro-2H-chromene-3-carboxamide | 332 | 1H NMR (600 MHz, DMSO-d6) Shift 8.42 (br t, J = 5.80 Hz, 1H), 7.16-7.24 (m, 1H), 7.10 (dd, J = 2.41, 8.72 Hz, 1H), 6.79 (dd, J = 3.19, 8.72 Hz, 1H), 4.30-4.37 (m, 1H), 4.06-4.15 (m, 3H), 3.87-3.98 (m, 1H), 2.79-2.98 (m, 3H), 2.14-2.22 (m, 1H), 1.77-1.88 (m, 2H), 1.55-1.69 (m, 2H), 1.25 (dd, J = 4.40, 12.73 Hz, 1H) |
| 1-97 | 2-chloro-N-((1R,2R,4S)-7-cyano-7-azabicyclo[2.2.1]heptan-2-yl)-4-(6-cyclopropyl-2-pyridinyl)benzamide | m/z (ESI): 393.3 (M + H)+. | $^1$H NMR (400 MHz, DMSO-d$_6$): δ ppm 8.85 (d, J = 5.7 Hz, 1H), 8.15 (d, J = 1.6 Hz, 1H), 8.07 (dd, J = 8.0, 1.6 Hz, 1H), 7.72-7.87 (m, 2H), 7.55 (d, J = 8.0 Hz, 1H), 7.33 (dd, J = 7.3, 1.3 Hz, 1H), 4.28 (t, J = 3.8 Hz, 2H), 4.16 (t, J = 4.9 Hz, 1H), 2.13-2.26 (m, 2H), 2.02 (ddd, J = 12.8, 9.1, 3.8 Hz, 1H), 1.67-1.78 (m, 2H), 1.55-1.67 (m, 1H), 1.39 (dd, J = 12.8, 3.9 Hz, 1H), 0.96-1.06 (m, 4H). |
| 2-2 | 1-(3-chlorophenyl)-N-((1R,2R,4S)-7-cyano-7-azabicyclo[2.2.1]heptan-2-yl)-4-piperidinecarboxamide | 359.2 | 1H NMR (600 MHz, DMSO-d6) Shift 8.13 (br d, J = 6.15 Hz, 1H), 7.13-7.24 (m, 1H), 6.93 (s, 1H), 6.89 (d, J = 8.62 Hz, 1H), 6.75 (dd, J = 1.21, 7.82 Hz, 1H), 4.03-4.14 (m, 3H), 3.71-3.79 (m, 2H), 2.68-2.75 (m, 2H), 2.29-2.37 (m, 1H), 2.11-2.20 (m, 1H), 1.69-1.84 (m, 4H), 1.55-1.68 (m, 4H), 1.25 (dd, J = 4.59, 12.69 Hz, 1H) |
| 2-3 | N-((1R,2R,4S)-7-cyano-7-azabicyclo[2.2.1]heptan-2-yl)-1-(3,5-diclilorophenyl)-4-piperidinecarboxamide | 393 | 1H NMR (600 MHz, DMSO-d6) Shift 8.13 (d, J = 6.23 Hz, 1H), 6.93 (d, J = 1.56 Hz, 2H), 6.81 (s, 1H), 4.08-4.12 (m, 2H), 4.06 (br dd, J = 4.75, 11.05 Hz, 1H), 3.81 (br d, J = 12.85 Hz, 2H), 2.77 (br t, J = 12.53 Hz, 2H), 2.33-2.39 (m, 1H), 2.10-2.20 (m, 1H), 1.75-1.82 (m, 3H), 1.72 (br d, J = 14.71 Hz, 2H), 1.55-1.63 (m, 3H), 1.25 (dd, J = 4.52, 12.69 Hz, 1H) |
| 2-4 | (3S)-N-((1R,2R,4S)-7-cyano-7-azabicyclo[2.2.1]heptan-2-yl)-1-(4-methyl-2-pyridinyl)-3-pyrrolidinecarboxamide | 326 | 1H NMR (600 MHz, DMSO-d6) Shift 8.27 (br s, 1H), 7.87-7.95 (m, 1H), 6.36-6.41 (m, 1H), 6.23-6.28 (m, 1H), 4.06-4.15 (m, 4H), 3.58-3.64 (m, 1H), 3.46-3.52 (m, 1H), 3.39-3.44 (m, 1H), 3.02-3.10 (m, 1H), 2.13-2.18 (m, 2H), 2.02-2.12 (m, 1H), 1.78-1.88 (m, 2H), 1.57-1.69 (m, 2H), 1.25-1.28 (m, 1H) |
| 2-5 | (3S)-N-((1R,2R,4S)-7-cyano-7-azabicyclo[2.2.1]heptan-2-yl)-1-(5-cyano-3-pyridinyl)-3-pyrrolidinecarboxamide | 337 | 1H NMR (600 MHz, DMSO-d6) Shift 8.34 (d, J = 6.05 Hz, 1H), 8.16-8.22 (m, 2H), 7.32 (dd, J = 1.83, 2.75 Hz, 1H), 4.07-4.18 (m, 3H), 3.51 (dd, J = 8.16, 9.63 Hz, 1H), 3.39-3.44 (m, 2H), 3.13 (quin, J = 7.57 Hz, 1H), 2.13-2.27 (m, 2H), 2.00-2.13 (m, 1H), 1.76-1.88 (m, 2H), 1.55-1.72 (m, 2H), 1.22-1.31 (m, 1H) |
| 2-6 | (3S)-N-((1R,2R,4S)-7-cyano-7-azabicyclo[2.2.1]heptan-2-yl)-1-(2-methoxy-4-pyridinyl)-3-pyrrolidinecarboxamide | 342 | 1H NMR (600 MHz, DMSO-d6) Shift 8.31 (s, 1H), 7.70-7.78 (m, 2H), 6.20 (dd, J = 2.11, 5.96 Hz, 1H), 5.70-5.76 (m, 1H), 4.05-4.17 (m, 3H), 3.76 (s, 3H), 3.41-3.48 (m, 1H), 3.21-3.38 (m, 3H), 3.06-3.13 (m, 1H), 2.12-2.23 (m, 2H), 2.01-2.10 (m, 1H), 1.79-1.89 (m, 2H), 1.54-1.70 (m, 2H), 1.21-1.30 (m, 1H) |

| Ex # | Name | MS data | 1H NMR |
| --- | --- | --- | --- |
| 2-7 | (3S)-N-((1R,2R,4S)-7-cyano-7-azabicyclo[2.2.1]heptan-2-yl)-1-(6-methyl-2-pyridinyl)-3-pyrrolidinecarboxamide | 326 | 1H NMR (600 MHz, DMSO-d6) Shift 8.27 (d, J = 6.05 Hz, 1H), 7.35 (dd, J = 7.24, 8.34 Hz, 1H), 6.39-6.42 (m, 1H), 6.20-6.23 (m, 1H), 4.07-4.15 (m, 3H), 3.59-3.63 (m, 1H), 3.46-3.51 (m, 1H), 3.38-3.42 (m, 1H), 3.32-3.36 (m, 1H), 3.02-3.10 (m, 1H), 2.27-2.29 (m, 3H), 2.13-2.20 (m, 2H), 2.02-2.09 (m, 1H), 1.78-1.87 (m, 2H), 1.56-1.70 (m, 2H), 1.25-1.29 (m, 1H) |
| 2-8 | (3S)-N-((1R,2R,4S)-7-cyano-7-azabicyclo[2.2.1]heptan-2-yl)-1-(6-methyl-2-pyrazinyl)-3-pyrrolidinecarboxamide | 327 | 1H NMR (600 MHz, DMSO-d6) Shift 8.31 (br d, J = 6.05 Hz, 1H), 7.74 (s, 1H), 7.66 (s, 1H), 4.07-4.14 (m, 3H), 3.65 (dd, J = 7.98, 10.36 Hz, 1H), 3.54 (ddd, J = 4.68, 7.98, 10.09 Hz, 1H), 3.36-3.49 (m, 2H), 3.09 (quin, J = 7.52 Hz, 1H), 2.28 (s, 3H), 2.15-2.27 (m, 2H), 2.08 (br s, 1H), 1.78-1.91 (m, 2H), 1.56-1.70 (m, 2H), 1.21-1.33 (m, 1H) |
| 2-9 | N-((1R,2R,4S)-7-cyano-7-azabicyclo[2.2.1]heptan-2-yl)-1-(3,5-dichlorophenyl)-3-methyl-3-pyrrolidinecarboxamide | 393.2 | 1H NMR (600 MHz, DMSO-d6) Shift 7.91 (br t, J = 5.61 Hz, 1H), 6.66 (d, J = 1.40 Hz, 1H), 6.46 (dd, J = 1.75, 4.01 Hz, 2H), 4.02-4.16 (m, 3H), 3.62-3.69 (m, 1H), 3.08-3.13 (m, 1H), 2.34-2.40 (m, 1H), 2.06-2.17 (m, 1H), 1.87-1.94 (m, 1H), 1.68-1.82 (m, 2H), 1.54-1.66 (m, 2H), 1.41-1.47 (m, 1H), 1.24-1.34 (m, 4H) |
| 2-10 | N-((1R,2R,4S)-7-cyano-7-azabicyclo[2.2.1]heptan-2-yl)-1-(3,5-dichlorophenyl)-3-fluoro-3-pyrrolidinecarboxamide | 397 | 1H NMR (600 MHz, DMSO-d6) Shift 8.77 (br s, 1H), 6.74 (s, 1H), 6.56-6.62 (m, 2H), 4.11-4.18 (m, 3H), 3.56-3.81 (m, 3H), 3.40-3.45 (m, 1H), 2.31-2.38 (m, 1H), 2.07-2.19 (m, 1H), 1.57-1.88 (m, 4H) |
| 2-11 | N-((1R,2R,4S)-7-cyano-7-azabicyclo[2.2.1]heptan-2-yl)-2-(3,5-dichlorophenyl)-2-azabicyclo[3.1.0]hexane-4-carboxamide | 391 | 1H NMR (500 MHz, CHLOROFORM-d) Shift 8.04 (s, 1H), 6.78 (t, J = 1.75 Hz, 1H), 6.67 (d, J = 1.82 Hz, 2H), 4.31-4.40 (m, 2H), 4.06-4.11 (m, 1H), 3.80-3.91 (m, 1H), 3.31-3.50 (m, 2H), 3.02-3.10 (m, 1H), 2.43-2.54 (m, 1H), 2.02-2.14 (m, 1H), 1.78-1.97 (m, 3H), 1.56-1.65 (m, 1H), 1.04-1.13 (m, 1H), 0.76-0.95 (m, 2H) |
| 2-12 | 2-(3-chlorophenyl)-N-((1R,2R,4S)-7-cyano-7-azabicyclo[2.2.1]heptan-2-yl)-1,3-oxazole-5-carboxamide | 341.4 | 1H NMR (600 MHz, DMSO-d6) Shift 8.71-8.83 (m, 1H), 8.12 (t, J = 1.83 Hz, 1H), 8.06-8.09 (m, 1H), 7.97 (s, 1H), 7.62-7.70 (m, 2H), 4.25-4.31 (m, 2H), 4.20 (s, 1H), 2.22-2.30 (m, 1H), 1.81-1.93 (m, 2H), 1.66-1.74 (m, 2H), 1.54-1.59 (m, 1H) |
| 2-13 | (3S)-N-((1R,2R,4S)-7-cyano-7-azabicyclo[2.2.1]heptan-2-yl)-1-(3-(cyanomethyl)phenyl)-3-pyrrolidinecarboxamide | 350 | 1H NMR (600 MHz, DMSO-d6) Shift 8.66-8.69 (m, 1H), 8.03-8.06 (m, 1H), 7.85-7.88 (m, 1H), 7.75-7.79 (m, 1H), 7.44-7.49 (m, 1H), 4.04-4.34 (m, 3H), 2.15-2.27 (m, 1H), 1.77-1.91 (m, 2H), 1.64-1.72 (m, 2H), 1.53-1.59 (m, 1H), 1.23-1.30 (m, 1H) |
| 2-14 | (3S)-1-(3-chloro-5-methoxyphenyl)-N-((1R,2R,4S)-7-cyano-7-azabicyclo[2.2.1]heptan-2-yl)-3-pyrrolidinecarboxamide | 375 | 1H NMR (600 MHz, DMSO-d6) Shift 8.30 (br d, J = 6.18 Hz, 1H), 6.23-6.26 (m, 1H), 6.15 (s, 1H), 5.99 (d, J = 1.91 Hz, 1H), 4.06-4.18 (m, 3H), 3.73 (s, 3H), 3.34-3.50 (m, 2H), 3.21-3.27 (m, 2H), 3.18 (br d, J = 4.63 Hz, 1H), 3.06-3.12 (m, 1H), 2.39 (br s, 1H), 2.18 (b rt, J = 11.94 Hz, 2H), 1.97-2.12 (m, 1H), 1.76-1.87 (m, 1H), 1.55-1.70 (m, 1H), 1.22-1.32 (m, 1H) |
| 2-15 | N-((1R,2R,4S)-7-cyano-7-azabicyclo[2.2.1]heptan-2-yl)-1-(3,5-dichlorophenyl)-L-prolinamide | 379 | 1H NMR (600 MHz, DMSO-d6) Shift 6.72 (td, J = 1.68, 6.68 Hz, 1H), 6.45 (s, 1H), 6.42 (s, 1H), 4.06-4.15 (m, 3H), 4.01 (br dd, J = 4.87, 10.70 Hz, 1H), 3.39-3.55 (m, 1H), 3.23-3.30 (m, 1H), 2.11-2.27 (m, 2H), 1.75-2.08 (m, 4H), 1.58-1.71 (m, 2H), 1.46-1.57 (m, 1H), 1.28-1.36 (m, 1H) |
| 2-16 | 3'-chlor-N-((1R,2R,4S)-7-cyano-7-azabicyclo[2.2.1]heptan-2-yl)[biphenyl]-3-carboxamide | 352 | 1H NMR (600 MHz, DMSO-d6) Shift 8.67 (br d, J = 5.99 Hz, 1H), 8.11 (s, 1H), 7.89 (s, 1H), 7.87 (s, 1H), 7.80 (t, J = 1.71 Hz, 1H), 7.70 (d, J = 8.33 Hz, 1H), 7.59 (t, J = 7.93 Hz, 1H), 7.54 (t, J = 8.04 Hz, 1H), 7.47-7.50 (m, 1H), 4.26-4.34 (m, 2H), 4.18 (t, J = 4.90 Hz, 1H), 2.21-2.26 (m, 1H), 1.86-1.92 (m, 1H), 1.79-1.86 (m, 1H), 1.66-1.72 (m, 2H), 1.57 (dd, J = 4.71, 12.73 Hz, 1H) |
| 2-17 | N-((1R,2R,4S)-7-cyano-7-azabicyclo[2.2.1]heptan-2-yl)-4-(2,5-dichlorophenyl)-5-methyl-2-pyridinecarboxamide | 401 | 1H NMR (600 MHz, DMSO-d6) Shift 9.10 (br d, J = 5.99 Hz, 1H), 8.68 (s, 1H), 7.78 (s, 1H), 7.68 (d, J = 8.63 Hz, 1H), 7.60 (dd, J = 2.63, 8.63 Hz, 1H), 7.55 (s, 1H), 4.34 (br s, 1H), 4.24 (t, J = 4.68 Hz, 1H), 4.17 (t, J = 4.63 Hz, 1H), 2.18 (s, 3H), 1.75-1.89 (m, 4H), 1.68 (br d, J = 9.99 Hz, 1H) |
| 2-18 | 4-(3-chlorophenyl)-N-((1R,2R,4S)-7-cyano-7-azabicyclo[2.2.1]heptan-2-yl)-5-methyl-2-pyridinecarboxamide | 367 | 1H NMR (600 MHz, DMSO-d6) Shift 9.07 (br d, J = 6.36 Hz, 1H), 8.63 (s, 1H), 7.83 (s. 1H), 7.53-7.60 (m, 3H), 7.42-7.47 (m, 1H), 4.34 (br dd, J = 4.90, 11.17 Hz, 1H), 4.24 (t, J = 4.63 Hz, 1H), 4.17 (t, J = 4.68 Hz, 1H), 2.34 (s, 3H), 2.16-2.24 (m, 1H), 1.75-1.88 (m, 4H), 1.68 (br d, J = 9.26 Hz, 1H) |

-continued

| Ex # | Name | MS data | 1H NMR |
|---|---|---|---|
| 2-19 | N-((1R,2R,4S)-7-cyano-7-azabicyclo[2.2.1]heptan-2-yl)-1-(6-(1-cyanocyclopropyl)-2-pyridinyl)-4-piperidinecarboxamide | 391 | 1H NMR (600 MHz, DMSO-d6) Shift 8.10 (d, J = 6.08 Hz, 1H), 7.53 (dd, J = 7.45, 8.45 Hz, 1H), 6.78 (d, J = 7.74 Hz, 1H), 6.74 (d, J = 8.70 Hz, 1H), 4.26 (br d, J = 10.54 Hz, 2H), 4.02-4.15 (m, 3H), 2.81 (br t, J = 12.72 Hz, 2H), 2.38-2.45 (m, 1H), 2.11-2.18 (m, 1H), 1.76-1.84 (m, 2H), 1.45-1.73 (m, 6H), 1.26 (dd, J = 4.54, 12.62 Hz, 1H) |
| 2-20 | N-((1R,2R,4S)-7-cyano-7-azabicyclo[2.2.1]heptan-2-yl)-6-(3-(1-cyanocyclopropyl)phenyl)-3-pyridinecarboxamide | m/z (ESI): 384.1 (M + H)+. | $^1$H NMR (400 MHz, DMSO-d$_6$): δ ppm 9.12 (dd, J = 2.4, 0.9 Hz, 1H), 8.81 (d, J = 6.0 Hz, 1H), 8.31 (dd, J = 8.3, 2.3 Hz, 1H), 8.17 (dd, J = 8.4, 0.9 Hz, 1H), 8.08-8.13 (m, 2H), 7.57 (d, J = 7.8 Hz, 1H), 7.44-7.47 (m, 1H), 4.34 (m, 1H), 4.28 (m, 1H), 4.20 (m, 1H), 2.25 (m, 1H), 1.91-1.96 (m, 1H), 1.79-1.85 (m, 3H), 1.71 (m, 2H), 1.60-1.64 (m, 2H), 1.54 (d, J = 4.7 Hz, 1H). |
| 2-21 | 3-chloro-N-((1R,2R,4S)-7-cyano-7-azabicyclo[2.2.1]heptan-2-yl)-3'-cyclopropyl-5'-fluoro[biphenyl]-4-carboxamide | m/z (ESI): 410.1 (M + H)+. | $^1$H NMR (400 MHz, DMSO-d$_6$): δ ppm 8.85 (d, J = 5.7 Hz, 1H), 7.89 (d, J = 1.8 Hz, 1H), 7.75 (dd, J = 8.0, 1.8 Hz, 1H), 7.52 (d, J = 8.0 Hz, 1H), 7.35 (ddd, J = 10.0, 2.4, 1.5 Hz, 1H), 7.32 (t, J = 1.6 Hz, 1H), 6.93-6.99 (m, 1H), 4.23-4.32 (m, 2H), 4.16 (t, J = 4.9 Hz, 1H), 2.03 (m, 2H), 1.67-1.87 (m, 2H), 1.54-1.65 (m, 1H), 1.39 (dd, J = 12.8, 4.0 Hz, 1H), 1.24 (m, 1H), 0.97-1.06 (m, 2H), 0.79-0.87 (m, 2H). |
| 2-22 | N-((1R,2R,4S)-7-cyano-7-azabicyclo[2.2.1]heptan-2-yl)-6-(1-cyanocyclopropyl)[2,3'-bipyridine]-6'-carboxamide | m/z (ESI): 385.2 (M + H)+. | $^1$H NMR (400 MHz, DMSO-d$_6$): δ ppm 9.34 (dd, J = 2.2, 0.9 Hz, 1H), 9.14 (d, J = 6.7 Hz, 1H), 8.63 (dd, J = 8.2, 2.2 Hz, 1H), 8.13 (dd, J = 8.2, 0.8 Hz, 1H), 8.09 (dd, J = 7.9, 1.0 Hz, 1H), 8.03 (d, J = 7.8 Hz, 1H), 7.61 (dd, J = 7.6, 0.9 Hz, 1H), 4.35 (dt, J = 10.2, 5.0 Hz, 1H), 4.26 (t, J = 4.6 Hz, 1H), 4.18 (t, J = 4.4 Hz, 1H), 2.20 (td, J = 11.5, 4.9 Hz, 1H), 1.75-1.91 (m, 8H), 1.64-1.72 (m, 1H) |
| 2-23 | 2-chloro-N-((1R,2R,4S)-7-cyano-7-azabicyclo[2.2.1]heptan-2-yl)-4-(6-(1-ethynylcyclopropyl)-2-pyridinyl)benzamide | m/z (ESI): 417.1 (M + H)+ | $^1$H NMR (400 MHz, DMSO-d$_6$): δ ppm 8.85 (d, J = 5.8 Hz, 1H), 8.13 (d, J = 1.7 Hz, 1H), 8.06 (dd, J = 8.0, 1.7 Hz, 1H), 7.87-7.95 (m, 2H), 7.81 (dd, J = 6.3, 2.4 Hz, 1H), 7.56 (d, J = 8.0 Hz, 1H), 4.28 (m, 2H), 4.16 (t, J = 4.9 Hz, 1H), 2.23 (m, 1H), 1.92-2.09 (m, 1H), 1.72-1.88 (m, 2H), 1.50-1.74 (m, 4H), 1.46 (m, 2H), 1.38 (dd, J = 12.8, 4.0 Hz, 1H) |
| 2-24-1 | 2-chloro-N-((1R,2R,4S)-7-cyano-7-azabicyclo[2.2.1]heptan-2-yl)-4-((3R)-3-cyano-3-methyl-2,3-dihydro-1H-inden-5-yl)benzamide | m/z (ESI): 431.1 (M + H)+. | $^1$H NMR (400 MHz, DMSO-d$_6$): δ ppm 8.85 (d, J = 5.8 Hz, 1H), 7.88 (dd, J = 10.3, 1.8 Hz, 2H), 7.76 (dd, J = 8.0, 1.8 Hz, 1H), 7.69 (dd, J = 7.9, 1.8 Hz, 1H), 7.54 (d, J = 8.0 Hz, 1H), 7.44 (d, J = 7.9 Hz, 1H), 4.28 (m, 2H), 4.17 (t, J = 4.8 Hz, 1H), 3.04 (t, J = 4.1 Hz, 2H), 2.58-2.65 (m, 1H), 2.22 (dt, J = 12.9, 7.5 Hz, 2H), 2.03 (td, J = 8.6, 4.5 Hz, 1H), 1.82 (dt, J = 9.7, 5.2 Hz, 2H), 1.72 (m, 4H), 1.57-1.66 (m, 1H), 1.40 (dd, J = 12.8, 3.9 Hz, 1H) |
| 2-24-2 | 2-chloro-N-((1R,2R,4S)-7-cyano-7-azabicyclo[2.2.1]heptan-2-yl)-4-((3S)-3-cyano-3-methyl-2,3-dihydro-1H-inden-5-yl)benzamide | m/z (ESI): 431.2 (M + H)+. | $^1$H NMR (400 MHz, DMSO-d$_6$): δ ppm 8.85 (d, J = 5.8 Hz, 1H), 7.88 (dd, J = 10.7, 1.8 Hz, 2H), 7.76 (dd, J = 8.0, 1.8 Hz, 1H), 7.69 (dd, J = 7.9, 1.8 Hz, 1H), 7.54 (d, J = 8.0 Hz, 1H), 7.44 (d, J = 7.9 Hz, 1H), 4.28 (m, 2H), 4.17 (t, J = 4.9 Hz, 1H), 3.04 (t, J = 7.1 Hz, 2H), 2.62 (dt, J = 13.5, 6.8 Hz, 1H), 2.22 (dt, J = 13.0, 7.5 Hz, 2H), 2.03 (td, J = 8.6, 4.4 Hz, 1H), 1.82 (dt, J = 8.3, 4.4 Hz, 1H), 1.72 (m, 4H), 1.61 (td, J = 9.1, 8.7, 4.6 Hz, 1H), 1.40 (dd, J = 12.8, 4.0 Hz, 1H) |
| 2-26 | 2-chloro-N-((1R,2R,4S)-7-cyano-7-azabicyclo[2.2.1]heptan-2-yl)-4-(6-(2-methyl-2-propanyl)-2-pyridinyl)benzamide | m/z (ESI): 409.3 (M + H)+. | $^1$H NMR (400 MHz, DMSO-d$_6$): δ ppm 8.86 (d, J = 5.8 Hz, 1H), 8.22 (d, J = 1.6 Hz, 1H), 8.14 (dd, J = 8.0, 1.7 Hz, 1H), 7.82-7.92 (m, 2H), 7.58 (d, J = 8.0 Hz, 1H), 7.48 (dd, J = 7.0, 1.6 Hz, 1H), 4.29 (m, 2H), 4.17 (t, J = 4.9 Hz, 1H), 2.46 (m, 1H), 2.24 (m, 1H), 1.97-2.08 (m, 1H), 1.75-1.85 (m, 1H), 1.55-1.66 (m, 1H), 1.31-1.46 (m, 1H), 1.39 (s, 9H). |
| 2-27-2 | (1S,6R,7R)-N-((1R,2R,4S)-7-cyano-7-azabicyclo[2.2.1]heptan-2-yl)-3-(3,5-dichlorophenyl)-3-azabicyclo[4.1.0]heptane-7-carboxamide | m/z (ESI): 405.1 (M + H)+. | $^1$H NMR (400 MHz, DMSO-d$_6$): δ ppm 8.31 (d, J = 6.6 Hz, 1H), 6.77 (m, 3H), 4.08 (m, 3H), 3.64 (m, 1H), 3.49 (dd, J = 13.2, 3.3 Hz, 1H), 3.23 (m, 1H), 3.03 (m, 1H), 2.10-2.20 (m, 1H), 2.04 (m, 1H), 1.83 (m, 3H), 1.66 (m, 1H), 1.55 (m, 4H), 1.17 (dd, J = 12.7, 4.6 Hz, 1H). |
| 2-27-1 | (1R,6S,7R)-N-((1R,2R,4S)-7-cyano-7-azabicyclo[2.2.1]heptan-2-yl)-3-(3,5-dichlorophenyl)-3-azabicyclo[4.1.0]heptane-7-carboxamide | m/z (ESI): 405.1 (M + H)+. | $^1$H NMR (400 MHz, DMSO-d$_6$): δ ppm 8.31 (d, J = 6.6 Hz, 1H), 6.77 (m, 3H), 4.08 (m, 3H), 3.64 (m, 1H), 3.49 (dd, J = 13.2, 3.3 Hz, 1H), 3.23 (m, 1H), 3.03 (m, 1H), 2.10-2.20 (m, 1H), 2.04 (m, 1H), 1.83 (m, 3H), 1.66 (m, 1H), 1.55 (m, 4H), 1.17 (dd, J = 12.7, 4.6 Hz, 1H). |
| 2-29 | N-((1R,2R,4S)-7-cyano-7-azabicyclo[2.2.1]heptan-2-yl)-3-(3,5-dichlorophenyl)-3-azabicyclo[4.1.0]heptane-7-carboxamide | m/z (ESI): 405.1 (M + H)+. | $^1$H NMR (400 MHz, DMSO-d$_6$): δ ppm 8.31 (d, J = 6.6 Hz, 1H), 6.79 (t, J = 1.6 Hz, 2H), 6.75 (dt, J = 3.3, 1.7 Hz, 1H), 4.04-4.14 (m, 3H), 3.60-3.66 (m, 1H), 3.49 (dd, J = 13.1, 3.7 Hz, 1H), 3.21 (m, 1H), 2.99-3.08 (m, 1H), 2.15 (m, 1H), 2.06 (m, 1H), 1.83 (m, 3H), 1.51-1.62 (m, 5H), 1.12-1.24 (m, 1H). |

-continued

| Ex # | Name | MS data | 1H NMR |
|---|---|---|---|
| 2-30 | N-((1R,2R,4S)-7-cyano-7-azabicyclo[2.2.1]heptan-2-yl)-1-(6-cyclopropyl-2-pyridinyl)-3-piperidinecarboxamide | m/z (ESI): 366.3 (M + H)+. | $^1$H NMR (400 MHz, DMSO-d$_6$): δ ppm 8.18 (d, J = 5.9 Hz, 1H), 7.36 (ddd, J = 8.5, 7.3, 4.4 Hz, 1H), 6.37-6.65 (m, 2H), 3.61-4.71 (m, 5H), 2.63-2.88 (m, 2H), 2.25-2.41 (m, 1H), 2.06-2.21 (m, 1H), 1.70-1.96 (m, 4H), 1.62 (m, 4 H), 1.29-1.45 (m, 1H), 1.25 (m, 1H), 0.68-0.95 (m, 4H). |
| 2-31-2 | (1S,5S)-N-((1R,2R,4S)-7-cyano-7-azabicyclo[2.2.1]heptan-2-yl)-3-(3,5-dichlorophenyl)-3-azabicyclo[3.1.0]hexane-1-carboxamide | m/z (ESI): 393.0 (M + 2H)+. | $^1$H NMR (400 MHz, DMSO-d$_6$): δ ppm 7.74 (d, J = 5.7 Hz, 1 H), 6.75 (t, J = 1.8 Hz, 1H), 6.56 (d, J = 1.8 Hz, 2H), 4.13 (m, 3H), 3.65 (d, J = 9.7 Hz, 1H), 3.50-3.58 (m, 2H), 3.26-3.32 (m, 1H), 2.14 (m, 2H), 1.74-1.87 (m, 2H), 1.65 (m, 2H), 1.34-1.50 (m, 2H), 0.80 (t, J = 4.7 Hz, 1H), |
| 2-31-2 | (1R,5R)-N-((1R,2S,4S)-7-cyano-7-azabicyclo[2.2.1]heptan-2-yl)-3-(3,5-dichlorophenyl)-3-azabicyclo[3.1.0]hexane-1-carboxamide | m/z (ESI): 393.0 (M + 2H)+. | $^1$H NMR (400 MHz, DMSO-d$_6$): δ ppm 7.74 (d, J = 5.7 Hz, 1H), 6.75 (t, J = 1.8 Hz, 1H), 6.56 (d, J = 1.8 Hz, 2H), 4.13 (m, 3H), 3.65 (d, J = 9.7 Hz, 1H), 3.50-3.58 (m, 2H), 3.26-3.32 (m, 1H), 2.14 (m, 2H), 1.74-1.87 (m, 2H), 1.65 (m, 2H), 1.34-1.50 (m, 2H), 0.80 (t, J = 4.7 Hz, 1H), |
| 2-33 | (1R,5S)-N-((1R,2R,4S)-7-cyano-7-azabicyclo[2.2.1]heptan-2-yl)-3-(3,5-dichlorophenyl)-3-azabicyclo[3.1.0]hexane-1-carboxamide | m/z (ESI): 393.1 (M + 2H)+. | $^1$H NMR (400 MHz, DMSO-d$_6$): δ ppm 7.74 (dd, J = 5.7, 2.6 Hz, 1H), 6.75 (q, J = 1.7 Hz, 1H), 6.56 (d, J = 1.8 Hz, 2H), 4.13 (m, 3H), 3.52-3.66 (m, 3H), 2.14 (m, 2H), 1.83 (m, 2H), 1.60-1.72 (m, 2H), 1.37-1.48 (m, 2H), 0.79 (m, 1H). |
| 2-34 | (3S)-N-((1R,2R,4S)-7-cyano-7-azabicyclo[2.2.1]heptan-2-yl)-1-(6-(1-cyanocyclopropyl)-2-pyridinyl)-3-piperidinecarboxamide | m/z (ESI): 391.3 (M + H)+. | $^1$H NMR (400 MHz, DMSO-d$_6$): δ ppm 8.17 (t, J = 5.6 Hz, 1H), 7.53 (ddd, J = 8.5, 7.4, 5.2 Hz, 1H), 6.41-7.04 (m, 2H), 3.77-4.79 (m, 5H), 2.75-3.03 (m, 2H), 2.26-2.38 (m, 1H), 2.03-2.23 (m, 1H), 1.72-1.95 (m, 3H), 1.38-1.74 (m, 7H), 1.05-1.38 (m, 2H). |
| 2-35 | N-((1R,2R,4S)-7-cyano-7-azabicyclo[2.2.1]heptan-2-yl)-1-cyclopentyl-1H-indazole-3-carboxamide | m/z (ESI): 350.3 (M + H)+. | $^1$H NMR (400 MHz, DMSO-d$_6$): δ ppm 8.46 (d, J = 6.1 Hz, 1H), 8.14 (dt, J = 8.2, 1.0 Hz, 1H), 7.80 (d, J = 8.6 Hz, 1H), 7.45 (ddd, J = 8.4, 6.9, 1.2 Hz, 1H), 7.27 (ddd, J = 7.9, 6.9, 0.9 Hz, 1H), 5.24 (m, 1H), 4.33 (m, 1H), 4.19 (d, J = 4.6 Hz, 1H), 2.07-2.27 (m, 5H), 1.86-1.96 (m, 3H), 1.68-1.82 (m, 6H). |
| 2-36 | N-((1R,2R,4S)-7-cyano-7-azabicyclo[2.2.1]heptan-2-yl)-1-(6-cyclopropyl-2-pyridinyl)-4-piperidinecarboxamide | m/z (ESI): 366.1 (M + H)+. | $^1$H NMR (400 MHz, DMSO-d$_6$): δ ppm 7.35 (dd, J = 8.5, 7.2 Hz, 1H), 6.53 (dd, J = 9.2, 7.8 Hz, 2H), 4.25 (d, J = 13.1 Hz, 2H), 3.96-4.12 (m, 3H), 2.65-2.77 (m, 2H), 2.30-2.46 (m, 2H), 2.14 (t, J = 11.5 Hz, 1H), 1.89 (m, 1H), 1.73-1.82 (m, 2H), 1.55-1.70 (m, 3H), 1.48 (m, 2H), 1.25 (m, 1H), 1.03 (dd, J = 18.1, 6.7 Hz, 1H), 0.71-0.94 (m, 4H). |
| 2-37 | N-((1R,2R,4S)-7-cyano-7-azabicyclo[2.2.1]heptan-2-yl)-1-(3,5-dichloropheny))-1H-1,2,4-triazole-3-carboxamide | m/z (ESI): 377.1 (M + H)+ | $^1$H NMR (400 MHz, DMSO-d$_6$): δ ppm 9.55 (s, 1H), 9.05 (d, J = 6.4 Hz, 1H), 8.09 (d, J = 1.8 Hz, 2H), 7.77 (t, J = 1.8 Hz, 1H), 4.28-4.38 (m, 1H), 4.25 (m, 1H), 4.17 (t, J = 4.4 Hz, 1H), 2.19 (td, J = 12.2, 11.8, 4.5 Hz, 1H), 1.66-1.90 (m, 5H). |
| 2-38 | 2-chloro-N-((1R,2R,4S)-7-cyano-7-azabicyclo[2.2.1]heptan-2-yl)-4-(6-(2-cyano-2-propanyl)-2-pyrazinyl)benzamide | m/z (ESI): 421.1 (M + H)+ | $^1$H NMR (400 MHz, DMSO-d$_6$): δ ppm 8.92 (d, J = 5.7 Hz, 1H), 8.75 (dd, J = 13.8, 2.4 Hz, 2H), 7.69 (d, J = 1.5 Hz, 1H), 7.51-7.61 (m, 2H), 4.29 (m, 2H), 4.17 (t, J = 4.9 Hz, 1H), 2.24 (m, 1H), 2.03 (m, 1H), 1.82 (m, 2H), 1.74 (m, 1H), 1.67 (m, 6H), 1.55-1.64 (m, 1H). |
| 2-39-1 | 2-chloro-N-((1R,2R,4S)-7-cyano-7-azabicyclo[2.2.1]heptan-2-yl)-4-((3S)-3-cyano-1-piperidinyl)benzamide | m/z (ESI): 384.3 (M + H)+. | $^1$H NMR (400 MHz, DMSO-d$_6$): δ ppm 8.55 (d, J = 5.6 Hz, 1H), 7.30 (d, J = 8.6 Hz, 1H), 7.04 (d, J = 2.5 Hz, 1H), 6.97 (dd, J = 8.6, 2.5 Hz, 1H), 4.23 (dp, J = 7.2, 4.0 Hz, 2H), 4.14 (t, J = 4.9 Hz, 1H), 3.53 (d, J = 5.2 Hz, 2H), 3.21-3.32 (m, 2H), 3.07 (dq, J = 7.4, 4.8 Hz, 1H), 2.13-2.25 (m, 1H), 1.75-2.01 (m, 4H), 1.53-1.75 (m, 4H), 1.40 (dd, J = 12.8, 4.0 Hz, 1H). |
| 2-39-2 | 2-chloro-N-((1R,2R,4S)-7-cyano-7-azabicyclo[2.2.1]heptan-2-yl)-4-((3R)-3-cyano-1-piperidinyl)benzamide | m/z (ESI): 384.3 (M + H)+. | $^1$H NMR (400 MHz, DMSO-d$_6$): δ ppm 8.55 (d, J = 5.6 Hz, 1H), 7.30 (d, J = 8.6 Hz, 1H), 7.04 (d, J = 2.5 Hz, 1H), 6.97 (dd, J = 8.6, 2.5 Hz, 1H), 4.23 (dp, J = 7.2, 4.0 Hz, 2H), 4.14 (t, J = 4.9 Hz, 1H), 3.53 (d, J = 5.2 Hz, 2H), 3.21-3.32 (m, 2H), 3.07 (dq, J = 7.4, 4.8 Hz, 1H), 2.13-2.25 (m, 1H), 1.75-2.01 (m, 4H), 1.53-1.75 (m, 4H), 1.40 (dd, J = 12.8, 4.0 Hz, 1H). |

-continued

| Ex # | Name | MS data | 1H NMR |
|---|---|---|---|
| 2-41 | 2-chloro-N-((1R,2R,4S)-7-cyano-7-azabicyclo[2.2.1]heptan-2-yl)-4-((3S)-3-cyano-1-piperidinyl)benzamide | m/z (ESI): 384.3 (M + H)+. | $^1$H NMR (400 MHz, DMSO-d$_6$): δ ppm 8.54 (d, J = 5.6 Hz, 1H), 7.30 (d, J = 8.7 Hz, 1H), 7.04 (d, J = 2.5 Hz, 1H), 6.97 (dd, J = 8.7, 2.5 Hz, 1H), 4.22 (dd, J = 5.5, 3.1 Hz, 2H), 4.14 (t, J = 4.9 Hz, 1H), 3.53 (d, J = 5.2 Hz, 2H), 3.28 (dt, J = 11.1, 3.8 Hz, 2H), 3.07 (dq, J = 10.0, 4.8 Hz, 1H), 2.17 (d, J = 13.0 Hz, 1H), 1.75-1.99 (m, 4H), 1.69 (q, J = 3.9 Hz, 2H), 1.61 (ddt, J = 11.0, 8.8, 4.1 Hz, 2H). 1.39 (dd, J = 12.8, 4.0 Hz, 1H). |
| 2-42 | 2-chloro-N-((1R,2R,4S)-7-cyano-7-azabicyclo[2.2.1]heptan-2-yl)-4-((3R)-3-cyano-3-methyl-2,3-dihydro-1H-inden-5-yl)benzamide | m/z (ESI): 431.2 (M + H)+. | $^1$H NMR (400 MHz, DMSO-d$_6$): δ ppm 8.86 (br s, 1H), 7.83 (dd, J = 16.7, 1.8 Hz, 2H), 7.73 (d, J = 8.0, 1.8 Hz, 1H), 7.66 (dd, J = 7.9, 1.8 Hz, 1H), 7.52 (d, J = 8.0 Hz, 1H), 7.44 (d, J = 7.9 Hz, 1H), 4.26 (q, J = 3.3, 2.1 Hz, 2H), 4.15 (t, J = 4.9 Hz, 1H), 3.03 (t, J = 7.1 Hz, 2H), 2.61 (t, J = 6.6 Hz, 1H), 2.18-2.27 (m, 2H), 2.00 (td, J = 8.6, 4.5 Hz, 1H), 1.78-1.86 (m, 1H), 1.69 (s, 4H), 1.57-1.64 (m, 1H), 1.38 (dd, J = 12.8, 4.0 Hz, 1H). |
| 2-43-1 | 2-chloro-N-((1R,2R,4S)-7-cyano-7-azabicyclo[2.2.1]heptan-2-yl)-4-((1S,2S,5R)-2-cyano-6-azabicyclo[3.2.1]octan-6-yl)benzamide | m/z (ESI): 410.1 (M + H)+. | $^1$H NMR (400 MHz, DMSO-d$_6$): δ ppm 8.43 (d, J = 5.6 Hz, 1H), 7.28 (d, J = 8.6 Hz, 1H), 6.55-6.65 (m, 2H), 4.22 (s, 2H), 4.13 (t, J = 4.9 Hz, 1H), 4.00-4.13 (m, 1H), 3.50 (dd, J = 10.6, 5.2 Hz, 1H), 3.21 (d, J = 10.5 Hz, 1H), 3.13 (dd, J = 12.5, 5.0 Hz, 1H), 2.78 (s, 1H), 2.53-2.58 (m, 1H), 2.43-2.48 (m, 1H), 2.18 (s, 1H), 1.93 (dt, J = 18.5, 12.8 Hz, 2H), 1.57-1.82 (m, 2H), 1.36-1.52 (m, 2H), 1.39 (s, 2H), 1.15-1.26 (m, 1H). |
| 2-44 | N-((1R,2R,4S)-7-cyano-7-azabicyclo[2.2.1]heptan-2-yl)-1-(3-cyanophenyl)-1H-pyrazole-3-carboxamide | m/z (ESI): 333.3 (M + H)+ | $^1$H NMR (400 MHz, DMSO-d$_6$): δ ppm 8.72 (d, J = 2.7 Hz, 1H), 8.61 (d, J = 6.1 Hz, 1H), 8.49 (t, J = 2.0 Hz, 1H), 8.34 (dd, J = 7.8, 2.4 Hz, 1H), 7.87 (d, J = 7.7 Hz, 1H), 7.78 (t, J = 8.0 Hz, 1H), 6.97 (d, J = 2.6 Hz, 1H), 4.28 (dt, J = 14.5, 4.7 Hz, 2H), 4.18 (t, J = 4.7 Hz, 1H), 2.20 (d, J = 12.6 Hz, 1H), 1.64-1.90 (m, 5H) |
| 2-45 | 2-chloro-N-((1R,2R,4S)-7-cyano-7-azabicyclo[2.2.1]heptan-2-yl)-4-(6-(1-cyanocyclobutyl)-2-pyridinyl)benzamide | m/z (ESI): 431.1 (M + H)+ | $^1$H NMR (400 MHz, DMSO-d$_6$): δ ppm 8.88 (d, J = 5.8 Hz, 1H), 8.27 (d, J = 1.7 Hz, 1H), 8.19 (dd, J = 8.0, 1.7 Hz, 1H), 8.10 (dd, J = 7.9, 1.0 Hz, 1H), 8.04 (t, J = 7.8 Hz, 1H), 7.58-7.68 (m, 2H), 4.28 (m, 2H), 4.17 (t, J = 4.9 Hz, 1H), 2.72-2.92 (m, 3H), 2.20-2.36 (m, 1H), 2.12-2.22 (m, 1H), 1.97-2.10 (m, 2H), 1.77-1.90 (m, 3H), 1.53-1.68 (m, 1H), 1.39 (d, J = 12.7, 3.9 Hz, 1H) |
| 2-46-2 | (2S)-N-((1R,2R,4S)-7-cyano-7-azabicyclo[2.2.1]heptan-2-yl)-1-(3,5-dichlorobenzyl)-2-azetidinecarboxamide | m/z (ESI): 379.1 (M + H)+. | $^1$H NMR (400 MHz, DMSO-d$_6$): δ ppm 7.83 (d, J = 5.9 Hz, 1H), 7.49 (d, J = 2.0 Hz, 1H), 7.41 (d, J = 2.0 Hz, 2H), 4.10 (t, J = 4.9 Hz, 1H), 4.05-3.95 (m, 2H), 3.54-3.71 (m, 3H), 3.27 (m, 1H), 2.98 (m, 1H), 2.14-2.26 (m, 1H), 2.08 (m, 2H), 1.65-1.80 (m, 1H), 1.39-1.60 (m, 3H), 1.34 (dd, J = 12.8, 4.1 Hz, 1H) |
| 2-46-3 | (2R)-N-((1R,2R,4S)-7-cyano-7-azabicyclo[2.2.1]heptan-2-yl)-1-(3,5-dichlorobenzyl)-2-azetidinecarboxamide | m/z (ESI): 379.1 (M + H)+. | $^1$H NMR (400 MHz, DMSO-d$_6$): δ ppm 7.87 (d, J = 6.3 Hz, 1H), 7.48 (d, J = 2.0 Hz, 1H), 7.40 (d, J = 2.0 Hz, 2H), 4.10 (t, J = 5.0 Hz, 1H), 4.03 (d, J = 4.4 Hz, 1H), 3.88 (m, 1H), 3.49-3.74 (m, 3H), 3.34 (m, 1H), 3.00 (m, 1H), 2.12-2.24 (m, 1H), 1.93-2.15 (m, 2H), 1.75 (m, 1H), 1.59 (m, 3H), 1.28 (dd, J = 12.7, 4.8 Hz, 1H) |
| 2-48-1 | 2-chloro-N-((1R,2R,4S)-7-cyano-7-azabicyclo[2.2.1]heptan-2-yl)-4-((3S)-3-(cyanomethyl)-1-pyrrolidinyl)benzamide | m/z (ESI): 384.2 (M + H)+. | $^1$H NMR (400 MHz, DMSO-d$_6$): δ ppm 8.43 (d, J = 5.5 Hz, 1H), 7.30 (d, J = 8.4 Hz, 1H), 6.37-6.69 (m, 2H), 4.22 (t, J = 3.4 Hz, 2H), 4.14 (t, J = 5.0 Hz, 1H), 3.41-3.54 (m, 1H), 3.39 (td, J = 5.9, 3.0 Hz, 1H), 3.25-3.31 (m, 1H), 3.02 (dd, J = 9.9, 6.9 Hz, 1H), 2.59-2.81 (m, 3H), 2.19 (dtd, J = 11.8, 7.1, 4.5 Hz, 2H), 1.96 (ddd, J = 11.9, 8.6, 3.9 Hz, 1H), 1.70-1.86 (m, 2H), 1.50-1.67 (m, 2H), 1.42 (dd, J = 12.8, 4.0 Hz, 1H). |
| 2-48-2 | 2-chloro-N-((1R,2R,4S)-7-cyano-7-azabicyclo[2.2.1]heptan-2-yl)-4-((3R)-3-(cyanomethyl)-1-pyrrolidinyl)benzamide | m/z (ESI): 384.2 (M + H)+. | $^1$H NMR (400 MHz, DMSO-d$_6$): δ ppm 8.43 (d, J = 5.5 Hz, 1H), 7.30 (d, J = 8.4 Hz, 1H), 6.37-6.69 (m, 2H), 4.22 (t, J = 3.4 Hz, 2H), 4.14 (t, J = 5.0 Hz, 1H), 3.41-3.54 (m, 1H), 3.39 (td, J = 5.9, 3.0 Hz, 1H), 3.25-3.31 (m, 1H), 3.02 (dd, J = 9.9, 6.9 Hz, 1H), 2.59-2.81 (m, 3H), 2.19 (dtd, J = 11.8, 7.1, 4.5 Hz, 2H), 1.96 (ddd, J = 11.9, 8.6, 3.9 Hz, 1H), 1.70-1.86 (m, 2H), 1.50-1.67 (m, 2H), 1.42 (dd, J = 12.8, 4.0 Hz, 1H). |
| 2-50 | N-((1R,2R,4S)-7-cyano-7-azabicyclo[2.2.1]heptan-2-yl)-1-(3-cyanophenyl)-1H-indazole-3-carboxamide | m/z (ESI): 383.2 (M + H)+. | $^1$H NMR (400 MHz, DMSO-d$_6$): δ ppm 8.92 (d, J = 6.3 Hz, 1H), 8.41 (dd, J = 2.1, 1.5 Hz, 1H), 8.24-8.33 (m, 2H), 7.98 (ddt, J = 7.8, 4.3, 1.1 Hz, 2H), 7.86 (t, J = 8.0 Hz, 1H), 7.61 (ddd, J = 8.5, 6.9, 1.2 Hz, 1H), 7.44 (ddd, J = 7.9, 6.9, 0.8 Hz, 1H), 4.40 (dt, J = 10.0, 4.8 Hz, 1H), 4.33 (t, J = 4.6 Hz, 1H), 4.19 (t, J = 4.7 Hz, 1H), 2.23 (td, J = 11.4, 3.7 Hz, 1H), 1.94 (ddd, J = 12.3, 8.4, 4.5 Hz, 1H), 1.65-1.85 (m, 4H). |

| Ex # | Name | MS data | 1H NMR |
|---|---|---|---|
| 2-51 | (3R)-N-((1R,2R,4S)-7-cyano-7-azabicyclo[2.2.1]heptan-2-yl)-1-(3,5-dichlorobenzyl)-3-pyrrolidinecarboxamide | m/z (ESI): 393.1 (M + H)+ | $^1$H NMR (400 MHz, DMSO-d$_6$): δ ppm 8.08 (dd, J = 6.3, 2.6 Hz, 1H), 7.49 (td, J = 2.0, 0.8 Hz, 1H), 7.36 (d, J = 1.9 Hz, 2H), 4.04-4.11 (m, 3H). 3.58 (d, J = 4.9 Hz, 2H), 2.88 (p, J = 7.4 Hz, 1H), 2.76 (td, J = 8.5, 6.6 Hz, 1H), 2.63 (td, J = 9.4, 7.9, 3.8 Hz, 1H), 2.31-2.46 (m, 2H), 2.06-2.24 (m, 1H), 1.84-2.04 (m, 2H), 1.72-1.87 (m, 2H), 1.51-1.69 (m, 2H), 1.21 (dt, J = 12.6, 4.5 Hz, 1H) |
| 2-52 | (3S)-N-((1R,2R,4S)-7-cyano-7-azabicyclo[2.2.1]heptan-2-yl)-1-(6-(1-cyanocyclopropyl)-2-pyridinyl)-3-pyrrolidinecarboxamide | m/z (ESI): 377.4 (M + H)+ | $^1$H NMR (400 MHz, DMSO-d): δ ppm 8.33 (t, J = 5.2 Hz, 1H), 7.49 (dd, J = 8.4, 7.3 Hz, 1H), 6.75 (d, J = 7.2 Hz, 1H), 6.35 (dd, J = 8.2, 1.9 Hz, 1H), 4.07-4.16 (m, 3H), 3.53-3.63 (m, 1H), 3.38-3.43 (m, 1H), 3.28 (s, 1H), 3.06 (p, J = 7.7 Hz, 1H), 2.14-2.22 (m, 2H), 2.04 (td, J = 9.4, 8.7, 4.2 Hz, 2H), 1.82 (d, J = 7.3 Hz, 2H), 1.55-1.80 (m, 6H), 1.20- 1.30 (m, 1H). |
| 2-43-2 | 2-chloro-N-((1R,2R,4S)-7-cyano-7-azabicyclo[2.2.1]heptan-2-yl)-4-((2R)-2-cyano-6-azabicyclo[3.2.1]octan-6-yl)benzamide | m/z (ESI): 410.1 (M + H)+ | $^1$H NMR (400 MHz, DMSO-d$_6$): δ ppm 8.43 (d, J = 5.6 Hz, 1H), 7.28 (d, J = 8.6 Hz, 1H), 6.55-6.65 (m, 2H), 4.22 (s, 2H), 4.13 (t, J = 4.9 Hz, 1H), 4.00-4.13 (m, 1H), 3.50 (dd, J = 10.6, 5.2 Hz, 1H), 3.21 (d, J = 10.5 Hz, 1H), 3.13 (dd, J = 12.5, 5.0 Hz, 1H), 2.78 (s, 1H), 2.53-2.58 (m, 1H), 2.43-2.48 (m, 1H), 2.18 (s, 1H), 1.93 (dt, J = 18.5, 12.8 Hz, 2H), 1.57-1.82 (m, 2H), 1.36-1.52 (m, 2H), 1.39 (s, 2H), 1.15-1.26 (m, 1H). |
| 2-54 | 2-chloro-N-((1R,2R,4S)-7-cyano-7-azabicyclo[2.2.1]heptan-2-yl)-4-((1-cyanocyclopropyl)methoxy)benzamide | m/z (ESI): 371.1 (M + H)+ | $^1$H NMR (400 MHz, DMSO-d$_6$): δ ppm 8.68 (d, J = 5.6 Hz, 1H), 7.41 (d, J = 8.5 Hz, 1H), 7.13 (d, J = 2.5 Hz, 1H), 7.01 (dd, J = 8.6, 2.5 Hz, 1H), 4.19-4.29 (m, 2H), 4.15 (t, J = 4.9 Hz, 1H), 4.12 (s, 2H), 2.20 (s, 1H), 1.98 (ddd, J = 12.7, 9.1, 4.0 Hz, 1H), 1.78 (m, 2H), 1.60 (ddd, J = 12.3, 9.1, 3.8 Hz, 1H), 1.32-1.43 (m, 3H), 1.10-1.26 (m, 2H) |
| 2-55 | N-((1R,2R,4S)-7-cyano-7-azabicyclo[2.2.1]heptan-2-yl)-4-(6-(1-cyanocyclopropyl)-2-pyridinyl)-2-cyclopropylbenzamide | m/z (ESI): 424.3 (M + H)+ | $^1$H NMR (400 MHz, Chloroform-d): δ ppm 7.73-7.83 (m, 2H), 7.69 (dd, J = 7.8, 0.9 Hz, 1H), 7.57-7.65 (m, 2H), 7.55 (d, J = 8.0 Hz, 1H), 6.14 (d, J = 5.7 Hz, 1H), 4.59 (dt, J = 10.9, 4.9 Hz, 1H), 4.53 (t, J = 4.3 Hz, 1H), 4.13 (t, J = 4.9 Hz, 1H), 2.53-2.65 (m, 1H), 2.24-2.35 (m, 1H), 2.05-2.15 (m, 1H) 1.82-2.07 (m, 4H), 1.75-1.82 (m, 2H), 1.07-1.16 (m, 3H), 0.86 (ddt, J = 7.7, 4.6, 2.6 Hz, 3H) |
| 2-56 | 2-chloro-N-((1R,2R,4S)-7-cyano-7-azabicyclo[2.2.1]heptan-2-yl)-3-((cis-3-cyano-cyclobutyl)oxy)benzamide | m/z (ESI): 371.0 (M + H)+. | $^1$H NMR (400 MHz, DMSO-d6): δ ppm 8.77 (d, J = 5.7 Hz, 1H), 7.33 (dd, J = 8.3, 7.6 Hz, 1H), 7.07 (dd, J = 8.4, 1.4 Hz, 1H), 7.01 (d, J = 7.6, 1.4 Hz, 1H), 5.03-5.15 (m, 1H), 4.24 (s, 2H), 4.14 (t, J = 4.9 Hz, 1H), 3.42-3.53 (m, 1H), 2.86 (dddd, J = 11.4, 7.1, 4.7, 2.6 Hz, 2H), 2.56 (t, J = 1.9 Hz, 2H), 2.20 (s, 1H), 1.98 (ddd, J = 12.6, 9.0, 3.8 Hz, 1H), 1.78 (s, 2H), 1.57 (ddd, J = 11.2, 9.1, 3.7 Hz, 1H), 1.31-1.42 (m, 1H). |
| 2-57 | 2-chloro-N-((1S,2R,4R)-7-cyano-7-azabicyclo[2.2.1]heptan-2-yl)-4-((3R)-3-(cyanomethyl)-1-pyrrolidinyl)benzamide | m/z (ESI): 384.2 (M + H)+. | $^1$H NMR (400 MHz, DMSO-d$_6$): δ ppm 8.43 (d, J = 5.6 Hz, 1H), 7.30 (d, J = 8.5 Hz, 1H), 6.12-6.69 (m, 2H), 4.22 (h, J = 5.4, 4.6 Hz, 2H), 4.14 (t, J = 4.9 Hz, 1H), 3.48 (dd, J = 9.9, 7.2 Hz, 1H), 3.23-3.41 (m, 4H), 3.02 (dd, J = 9.9, 6.8 Hz, 1H), 2.63-2.77 (m, 2H), 2.10-2.25 (m, 1H), 1.96 (ddd, J = 11.9, 8.5, 3.8 Hz, 2H), 1.68-1.87 (m, 2H), 1.55-1.71 (m, 1H), 1.42 (dt, J = 12.7, 4.1 Hz, 1H). |
| 2-58 | 2-chloro-N-((1R,2R,4S)-7-cyano-7-azabicyclo[2.2.1]heptan-2-yl)-4-((cis-3-cyano-cyclobutyl)oxy)benzamide | m/z (ESI): 371.0 (M + H)+. | $^1$H NMR (400 MHz, DMSO-d$_6$): δ ppm 8.66 (d, J = 5.7 Hz, 1H), 7.38 (d, J = 8.5 Hz, 1H), 7.02 (d, J = 2.4 Hz, 1H), 6.91 (dd, J = 8.5, 2.4 Hz, 1H), 5.02-5.14 (m, 1H), 4.19-4.28 (m, J = 4.1 Hz, 2H), 4.14 (t, J = 4.9 Hz, 1H), 3.36-3.52 (m, 1H), 2.83 (dddd, J = 11.6, 7.1, 4.8, 2.5 Hz, 2H), 2.42-2.51 (m, 2H), 2.20 (s, 1H), 1.97 (ddd, J = 12.7, 9.0, 3.9 Hz, 1H), 1.67-1.83 (m, 2H), 1.59 (ddd, J = 12.3, 9.2, 3.8 Hz, 1H), 1.37 (dd, J = 12.8, 4.0 Hz, 1H). |
| 2-59 | 2-chloro-N-((1R,2R,4S)-7-cyano-7-azabicyclo[2.2.1]heptan-2-yl)-4-(6-(1-cyano-3,3-difluorocyclobutyl)-3-pyridinyl)benzamide | m/z (ESI): 468.1 (M + H)+. | $^1$H NMR (400 MHz, DMSO-d$_6$): δ ppm 8.88 (d, J = 5.8 Hz, 1H), 8.27 (d, J = 1.7 Hz, 1H), 8.16 (td, J = 8.2, 1.3 Hz, 2H), 8.08 (t, J = 7.8 Hz, 1H), 7.73 (dd, J = 7.6, 0.9 Hz, 1H), 7.62 (d, J = 8.0 Hz, 1H), 4.28 (t, J = 4.3 Hz, 2H), 4.17 (t, J = 4.9 Hz, 1H), 3.55-3.65 (m, 4H), 2.24 (s, 1H), 2.00-2.06 (m, 1H), 1.82 (d, J = 11.8 Hz, 1H), 1.74 (d, J = 13.0 Hz, 1H), 1.61 (td, J = 9.4, 4.9 Hz, 1H), 1.39 (dd, J = 12.8. 4.0 Hz, 1H) |
| 2-60 | 2-chloro-N-((1R,2R,4S)-7-cyano-7-azabicyclo[2.2.1]heptan-2-yl)-3'-(1-cyanocyclopropyl)[biphenyl]-3-carboxamide | m/z (ESI): 417.1 (M + H)+. | $^1$H NMR (400 MHz, DMSO-d$_6$): δ ppm 8.87 (d, J = 5.9 Hz, 1H), 7.44-7.54 (m, 4H), 7.34-7.39 (m, 3H), 4.27 (q, J = 5.4, 4.2 Hz, 2H), 4.16 (t, J = 4.9 Hz, 1H), 2.21 (d, J = 11.7 Hz, 1H), 2.01 (ddd, J = 12.8, 9.1, 3.9 Hz, 1H), 1.81 (td, J = 4.8, 3.1 Hz, 3H), 1.73 (dd, J = 14.8, 3.7 Hz, 1H), 1.55-1.61 (m, 3H), 1.37 (dd, J = 12.7, 4.0 Hz, 1H) |

-continued

| Ex # | Name | MS data | 1H NMR |
|---|---|---|---|
| 2-61-2 | 2-chloro-N-((1R,2R,4S)-7-cyano-7-azabicyclo[2.2.1]heptan-2-yl)-4-((3S)-3-(cyanomethyl)-1-piperidinyl)benzamide | m/z (ESI): 398.2 (M + H)+. | $^1$H NMR (400 MHz, DMSO-d$_6$): δ ppm 8.52 (d, J = 5.6 Hz, 1H), 7.30 (d, J = 8.6 Hz, 1H), 6.97 (d, J = 2.4 Hz, 1H), 6.91 (dd, J = 8.7, 2.5 Hz, 1H), 4.23 (tq, J = 7.7, 4.7, 4.1 Hz, 2H), 4.14 (t, J = 4.9 Hz, 1H), 3.65-3.84 (m, 2H), 2.79 (td, J = 12.7, 12.2. 3.0 Hz, 1H), 2.63-2.70 (m, 1H), 2.59 (dd, J = 20.4, 3.8 Hz, 2H), 2.46 (t, J = 1.8 Hz, 1H), 2.22 (m, 1H), 1.97 (ddd, J = 12.4, 8.9, 3.9 Hz, 1H), 1.82-1.93 (m, 1H), 1.65-1.82 (m, 2H), 1.47-1.64 (m, 2H), 1.36-1.47 (m, 1H), 1.20-1.35 (m, 1H), 1.06-1.20 (m, 1H). |
| 2-61-1 | 2-chloro-N-((1R,2R,4S)-7-cyano-7-azabicyclo[2.2.1]heptan-2-yl)-4-(3R)-3-(cyanomethyl)-1-piperidinyl)benzamide | m/z (ESI): 398.2 (M + H)+. | $^1$H NMR (400 MHz, DMSO-d$_6$): δ ppm 8.52 (d, J = 5.6 Hz, 1H), 7.30 (d, J = 8.6 Hz, 1H), 6.97 (d, J = 2.4 Hz, 1H), 6.91 (dd, J = 8.7, 2.5 Hz, 1H), 4.23 (tq, J = 7.7, 4.7, 4.1 Hz, 2H), 4.14 (t, J = 4.9 Hz, 1H), 3.65-3.84 (m, 2H), 2.79 (td, J = 12.7, 12.2. 3.0 Hz, 1H), 2.63-2.70 (m, 1H), 2.59 (dd, J = 20.4, 3.8 Hz, 2H), 2.46 (t, J = 1.8 Hz, 1H), 2.22 (m, 1H), 1.97 (ddd, J = 12.4, 8.9, 3.9 Hz, 1H), 1.82-1.93 (m, 1H), 1.65-1.82 (m, 2H), 1.47-1.64 (m, 2H), 1.36-1.47 (m, 1H), 1.20-1.35 (m, 1H), 1.06-1.20 (m, 1H). |
| 2-63 | 3-chloro-N-((1R,2R,4S)-7-cyano-7-azabicyclo[2.2.1]heptan-2-yl)-3'-(1-cyanocyclopropyl)-5'-fluoro[biphenyl]-4-carboxamide | m/z (ESI): 435.1 (M + H)+. | $^1$H NMR (400 MHz, DMSO-d$_6$): δ ppm 8.86 (d, J = 5.8 Hz, 1H), 7.94 (d, J = 1.8 Hz, 1H), 7.79 (dd, J = 7.9, 1.8 Hz, 1H), 7.49-7.66 (m, 2H), 7.47 (t, J = 1.6 Hz, 1H), 7.26 (dt, J = 9.8, 2.0 Hz, 1H), 4.28 (q, J = 6.7, 4.5 Hz, 2H), 4.16 (t, J = 4.9 Hz, 1H), 2.24 (d, J = 9.4 Hz, 1H), 2.01 (ddd, J = 12.6, 9.0, 3.8 Hz, 1H), 1.77-1.90 (m, 3H), 1.63-1.79 (m, 3H), 1.60 (ddd, J = 12.1, 9.3, 3.7 Hz, 1H), 1.39 (dd, J = 12.8, 3.9 Hz, 1H). |
| 2-64 | 2-chloro-N-((1R,2R,4S)-7-cyano-7-azabicyclo[2.2.1]heptan-2-yl)-4-(4,5,6,7-tetrahydro-1H-indazol-1-yl)benzamide | m/z (ESI): 396.1 (M + H)+. | $^1$H NMR (400 MHz, DMSO-d$_6$): δ ppm 8.81 (d, J = 5.7 Hz, 1H), 8.31 (s, 1H), 7.92 (d, J = 2.2 Hz, 1H), 7.80 (dd, J = 8.5, 2.1 Hz, 1H), 7.53 (d, J = 8.5 Hz, 1H), 4.27 (q, J = 5.9, 3.6 Hz, 2H), 4.16 (t, J = 4.9 Hz, 1H), 2.62-2.72 (m, 2H), 2.57 (t, J = 6.1 Hz, 2H), 2.22 (s, 1H), 2.00 (ddd, J = 12.7, 9.0, 3.8 Hz, 1H), 1.79 (q, J = 5.9, 4.9 Hz, 2H), 1.72 (s, 4H), 1.55-1.66 (m, 1H), 1.39 (dd, J = 12.8, 4.0 Hz, 1H). |
| 2-65 | 2-chloro-N-((1R,2R,4S)-7-cyano-7-azabicyclo[2.2.1]heptan-2-yl)-4-(5,6-dihydro-cyclopenta[c]pyrazol-1(4H)-yl)benzamide | m/z (ESI): 382.3 (M + H)+. | $^1$H NMR (400 MHz, DMSO-d$_6$): δ ppm 8.81 (d, J = 5.6 Hz, 1H), 8.23 (s, 1H), 7.92 (d, J = 2.1 Hz, 1H), 7.80 (dd, J = 8.4, 2.2 Hz, 1H), 7.53 (d, J = 8.4 Hz, 1H), 4.27 (q, J = 5.8, 3.5 Hz, 2H), 4.16 (t, J = 4.9 Hz, 1H), 2.68 (dt, J = 14.9, 7.1 Hz, 4H), 2.34-2.44 (m, 2H), 2.22 (s, 1H), 2.00 (ddd, J = 12.8, 9.1, 3.9 Hz, 1H), 1.75 (s, 1H), 1.60 (ddd, J = 12.4, 9.0, 3.7 Hz, 1H), 1.39 (dd, J = 12.8, 4.0 Hz, 1H), 1.15 (t, J = 7.2 Hz, 1H) |
| 2-66 | 2-chloro-N-((1R,2R,4S)-7-cyano-7-azabicyclo[2.2.1]heptan-2-yl)-4-(5,6-dihydro-cyclopenta[c]pyrazol-2(4H)-yl)benzamide | m/z (ESI): 382.1 (M + H)+. | $^1$H NMR (400 MHz, DMSO-d$_6$): δ ppm 8.81 (d, J = 5.7 Hz, 1H), 8.24 (s, 1H), 7.92 (d, J = 1.1 Hz, 1H), 7.80 (dd, J = 8.4, 2.2 Hz, 1H), 7.47-7.61 (m, 1H), 4.27 (q, J = 6.2, 3.5 Hz, 2H), 4.16 (t, J = 4.9 Hz, 1H), 2.89 (d, J = 15.6 Hz, 1H), 2.67 (dt, J = 14.9, 7.2 Hz, 2H), 2.38 (q, J = 7.3 Hz, 1H), 2.10-2.28 (m, 1H), 2.00 (ddd, J = 12.7, 9.0, 3.8 Hz, 1H), 1.65-1.82 (m, 2H), 1.60 (ddd, J = 12.1, 9.1, 3.7 Hz, 1H), 1.25-1.44 (m, 2H), 1.03 (s, 1H). |
| 2-67 | 2-chloro-N-((1R,2R,4S)-7-cyano-7-azabicyclo[2.2.1]heptan-2-yl)-4-((3S)-3-(cyanomethyl)-1-piperidinyl)benzamide | m/z (ESI): 398.2 (M + H)+ | $^1$H NMR (400 MHz, DMSO-d$_6$): δ ppm 8.52 (d, J = 5.6 Hz, 1H), 7.30 (d, J = 8.6 Hz, 1H), 6.97 (d, J = 2.5 Hz, 1H), 6.91 (dd, J = 8.7, 2.5 Hz, 1H), 4.23-4.14 (m, 2H), 3.64-3.84 (m, 2H), 2.78 (ddd, J = 12.7, 11.4, 3.0 Hz, 1H), 2.59-2.71 (m, 2H), 2.53-2.58 (m, 1H), 2.18 (dt, J = 11.3, 7.4 Hz, 1H), 1.80-2.04 (m, 3H), 1.64-1.80 (m, 3H), 1.46-1.63 (m, 2H), 1.22-1.45 (m, 2H). |
| 5-16 | N-((1R,2R,4S)-7-cyano-7-azabicyclo[2.2.1]heptan-2-yl)-1-(3,5-dichlorophenyl)-3-azepanecarboxamide | m/z (ESI): 407.2 (M + H)+ | $^1$H NMR (400 MHz, DMSO-d$_6$): δ ppm 8.24 (t, J = 5.3 Hz, 1H), 6.54-6.87 (m, 3H), 4.10 (dt, J = 19.7, 5.1 Hz, 3H), 3.61-3.84 (m, 2H), 3.38-3.44 (m, 1H), 3.24 (dd, J = 14.2, 8.7 Hz, 1H), 2.71-2.81 (m, 1H), 2.18 (q, J = 13.1, 10.5 Hz, 1H), 1.73-1.98 (m, 4H), 1.45-1.72 (m, 4H), 1.20-1.38 (m, 2H) |
| 7-3 | (3S)-6-chloro-N-((1R,2R,4S)-7-cyano-7-azabicyclo[2.2.1]heptan-2-yl)-N,9-dimethyl-2,3,4,9-tetrahydro-1H-carbazole-3-carboxamide | 397.0 | 1H NMR (DMSO-d6) δ: 7.40 (s, 1H), 7.36 (d, J = 8.6 Hz, 1H), 7.03 (dd, J = 8.6, 2.0 Hz, 1H), 4.39-4.48 (m, 1H), 4.24-4.30 (m, 1H), 4.18 (t, J = 4.8 Hz, 1H), 3.60 (s, 3H), 3.04 (br s, 4H), 2.73-2.88 (m, 3H), 2.50-2.68 (m, 1H), 2.08 (br d, J = 11.6 Hz, 2H), 1.77-1.85 (m, 2H), 1.66-1.75 (m, 4H) |
| 7-4 | N-((1R,2R,4S)-7-cyano-7-azabicyclo[2.2.1]heptan-2-yl)-1-(6-cyclopropyl-2-pyridinyl)-6-fluoro-N-methyl-1H-indazole-5-carboxamide | 431.0 | 1H NMR (DMSO-d6) δ: 8.50 (s, 1H), 8.40 (d, J = 11.0 Hz, 1H), 8.01 (br d, J = 6.5 Hz, 1H), 7.87 (t, J = 8.2 Hz, 1H), 7.76 (d, J = 8.2 Hz, 1H), 7.29 (d, J = 7.6 Hz, 1H), 4.51 (br s, 1H), 4.46 (br s, 1H), 4.24 (br s, 1H), 2.92 (br s, 3H), 2.21-2.29 (m, 1H), 2.17-2.21 (m, 1H), 1.71-1.93 (m, 5H), 1.07-1.19 (m, 4H) |

| Ex # | Name | MS data | 1H NMR |
|---|---|---|---|
| 7-5 | 6-chloro-N-((1R,2R,4S)-7-cyano-7-azabicyclo[2.2.1]heptan-2-yl)-N-methyl-1-(6-methyl-2-pyridinyl)-1H-indazole-5-carboxamide | 420.8 | 1H NMR (DMSO-d6) δ: 8.94 (s, 1H), 8.52 (s, 1H), 7.97 (br s, 1H), 7.92 (t, J = 7.9 Hz, 1H), 7.81 (d, J = 8.3 Hz, 1H), 7.24 (d, J = 7.5 Hz, 1H), 4.56 (br s, 1H), 4.50 (br s, 1H), 4.26 (br s, 1H), 2.82 (s, 3H), 2.62 (s, 3H), 2.14-2.25 (m, 1H), 1.80-1.93 (m, 4H), 1.74 (br d, J = 7.9 Hz, 1H) |
| 7-6 | N-((1R,2R,4S)-7-cyano-7-azabicyclo[2.2.1]heptan-2-yl)-6-fluoro-N-methyl-1-(6-methyl-2-pyridinyl)-1H-indazole-5-carboxamide | 405.0 | 1H NMR (DMSO-d6) δ: 8.61 (d, J = 10.9 Hz, 1H), 8.51 (s, 1H), 8.01 (br d, J = 6.5 Hz, 1H), 7.92 (t, J = 7.8 Hz, 1H), 7.82 (d, J = 8.2 Hz, 1H), 7.23 (d, J = 7.5 Hz, 1H), 4.51 (br s, 1H), 4.46 (br s, 1H), 4.24 (br s, 1H), 2.91 (br s, 3H), 2.62 (s, 3H), 2.52-2.56 (m, 1H), 2.08-2.26 (m, 1H), 1.79-1.92 (m, 3H), 1.65-1.78 (m, 1H) |
| 7-7 | N-((1R,2R,4S)-7-cyano-7-azabicyclo[2.2.1]heptan-2-yl)-N,1-dimethyl-3-(6-methyl-2-pyridinyl)-1H-indazole-6-carboxamide | 400.4 | 1H NMR (DMSO-d6) δ: 8.67 (d, J = 8.5 Hz, 1H), 7.92 (d, J = 7.9 Hz, 1H), 7.81 (s, 1H), 7.78 (t, J = 7.7 Hz, 1H), 7.30 (dd, J = 8.3, 1.2 Hz, 1H), 7.24 (d, J = 7.7 Hz, 1H), 4.45 (br s, 1H), 4.29-4.39 (m, 1H), 4.19-4.25 (m, 1H), 4.17 (s, 3H), 2.96 (s, 3H), 2.61 (s, 3H), 2.19 (br s, 1H), 1.84-1.95 (m, 2H), 1.72-1.84 (m, 3H) |
| 7-8 | (3R)-1-(3-chlorpheny))-N-((1R,2R,4S)-7-cyano-7-azabicyclo[2.2.1]heptan-2-yl)-N-methyl-3-pyrrolidinecarboxamide | 359.2 | 1H NMR (500 MHz, CHLOROFORM-d) Shift 7.14 (t, J = 8.11 Hz, 1H), 6.68 (dd, J = 1.23, 7.85 Hz, 1H), 6.55 (t, J = 2.14 Hz, 1H), 6.45 (dd, J = 1.95, 8.30 Hz, 1H), 4.49-4.56 (m, 1H), 4.32-4.49 (m, 1H), 4.13 (br s, 1H), 3.36-3.57 (m, 4H), 3.10 (br s, 3H), 2.21-2.37 (m, 2H), 2.10 (br s, 1H), 1.94 (br s, 1H), 1.69 (br dd, J = 4.02, 13.10 Hz, 2H), 1.55-1.63 (m, 3H) |
| 7-9 | (3S)-1-(3-chlorophenyl)-N-((1R,2R,4S)-7-cyano-7-azabicyclo[2.2.1]heptan-2-yl)-N-methyl-3-pyrrolidinecarboxamide | 359.2 | 1H NMR (500 MHz, CHLOROFORM-d) Shift 7.14 (t, J = 8.11 Hz, 1H), 6.68 (dd, J = 1.23, 7.85 Hz, 1H), 6.55 (t, J = 2.08 Hz, 1H), 6.45 (dd, J = 2.08, 8.30 Hz, 1H), 4.39-4.55 (m, 2H), 4.13 (br s, 1H), 3.55-3.60 (m, 1H), 3.35-3.53 (m, 4H), 3.03-3.17 (m, 3H), 2.21-2.39 (m, 3H), 2.10 (br s, 1H), 1.83-2.02 (m, 1H), 1.54-1.75 (m, 4H) |
| 7-10 | (3R)-1-(3-chlorophenyl)-N-((1R,2R,4S)-7-cyano-7-azabicyclo[2.2.1]heptan-2-yl)-N-methyl-5-oxo-3-pyrrolidinecarboxamide | 373 | 1H NMR (500 MHz, CHLOROFORM-d) Shift 7.67 (d, J = 1.95 Hz, 1H), 7.55 (ddd, J = 0.78, 2.08, 8.30 Hz, 1H), 7.29-7.33 (m, 1H), 7.17 (ddd, J = 0.91, 1.98, 8.01 Hz, 1H), 4.49-4.59 (m, 1H), 4.37-4.49 (m, 1H), 4.26 (br s, 1H), 4.09-4.21 (m, 1H), 3.91-4.01 (m, 1H), 3.59 (br s, 1H), 3.09 (br s, 3H), 2.82-2.93 (m, 2H), 2.24-2.38 (m, 1H), 2.07-2.16 (m, 1H), 1.91-2.02 (m, 1H), 1.65-1.73 (m, 2H) |
| 7-11 | (3S)-N-((1R,2R,4S)-7-cyano-7-azabicyclo[2.2.1]heptan-2-yl)-1-(3,5-dichlorophenyl)-N-methyl-3-pyrrolidinecarboxamide | 393 | 1H NMR (500 MHz, CHLOROFORM-d) Shift 6.69 (t, J = 1.69 Hz, 1H), 6.44 (d, J = 1.69 Hz, 2H), 4.48-4.54 (m, 1H), 4.46 (br s, 1H), 4.08-4.19 (m, 1H), 3.35-3.56 (m, 4H), 3.10 (br s, 3H), 2.23-2.35 (m, 2H), 2.07 (s, 2H), 1.94 (br s, 1H), 1.52-1.74 (m, 4H) |
| 7-12 | (3S)-N-((1R,2R,4S)-7-cyano-7-azabicyclo[2.2.1]heptan-2-yl)-1-(3-cyano-6-(trifluoromethyl)-2-pyridinyl)-N-methyl-3-pyrrolidinecarboxamide | 419 | 1H NMR (600 MHz, DMSO-d6) Shift 8.25 (d, J = 7.72 Hz, 1H), 7.11 (d, J = 7.81 Hz, 1H), 4.42 (br s, 1H), 4.28 (br s, 1H), 4.20 (br s, 1H), 3.87-3.95 (m, 1H), 3.85 (br s, 1H), 3.75-3.82 (m, 2H), 3.60 (br t, J = 6.86 Hz, 1H), 3.07 (br s, 2H), 2.29 (qd, J = 6.33, 12.34 Hz, 1H), 2.06 (br s, 2H), 1.61-1.80 (m, 4H) |
| 7-13-2 | N-((1R,2R,4S)-7-cyano-7-azabicyclo[2.2.1]heptan-2-yl)-N-methyl-1-(2,3,5-trichlorophenyl)-L-prolinamide | m/z (ESI): 429.1 (M + H)+. | $^1$H NMR (400 MHz, DMSO-$d_6$): δ ppm 7.21 (t, J = 2.5 Hz, 1H), 6.93 (dd, J = 3.5, 2.4 Hz, 1H), 4.41 (m, 1H), 4.20-4.25 (m, 2H), 3.50-3.65 (m, 4H), 3.04 (m, 3H), 1.83-2.17 (m, 3H), 1.73-1.67 (m, 6H). |
| 7-13-1 | N-((1R,2R,4S)-7-cyano-7-azabicyclo[2.2.1]heptan-2-yl)-N-methyl-1-(2,3,5-trichlorophenyl)-D-prolinamide | m/z (ESI): 429.1 (M + H)+. | $^1$H NMR (400 MHz, DMSO-$d_6$): δ ppm 7.21 (t, J = 2.5 Hz, 1H), 6.93 (dd, J = 3.5, 2.4 Hz, 1H), 4.41 (m, 1H), 4.20- 4.25 (m, 2H), 3.50-3.65 (m, 4H), 3.04 (m, 3H), 1.83-2.17 (m, 3H), 1.73-1.67 (m, 6H). |
| 7-15 | 1-((1R,2R,4S)-7-cyano-7-azabicyclo[2.2.1]heptan-2-yl)-3-(2-(2,5-dichlorophenyl)ethyl)-1,3-dimethylurea | [M + 1] 381.2 | |
| 7-16 | 1-(2-(2-bromo-5-chlorophenyl)ethyl)-3-((1R,2R,4S)-7-cyano-7-azabicyclo[2.2.1]heptan-2-yl)-1,3-dimethylurea | [M + 1] 425.3 | |

| Ex # | Name | MS data | 1H NMR |
|---|---|---|---|
| 7-17 | 2-chloro-N-((1R,2R,4S)-7-cyano-7-azabicyclo[2.2.1]heptan-2-yl)-4-(6-(1-cyanocyclopropyl)-2-pyridinyl)-N-methylbenzamide | 432.2 | 1H NMR (500 MHz, DMSO-d6) δ ppm 0.83-0.87 (m, 1H) 1.17 (br t J = 7.14 Hz, 1H) 1.21-1.30 (m, 3H) 1.73 (br d, J = 10.77 Hz, 3H) 1.77-1.90 (m, 19H) 1.96-2.05 (m, 1H) 2.14-2.23 (m, 2H) 2.83 (s, 6H) 3.02-3.07 (m, 1H) 3.31 (s, 5H) 4.17 (br s, 1H) 4.25 (br t, J = 4.28 Hz, 2H) 4.48 (br s, 4H) 7.51 (d, J = 8.04 Hz, 2H) 7.57 (d, J = 7.66 Hz, 3H) 7.95-8.03 (m, 5H) 8.10-8.24 (m, 5H) |
| 7-18 | N-((1R,2R,4S)-7-cyano-7-azabicyclo[2.2.1]heptan-2-yl)-N-methyl-3-(2-methylpropoxy)-4-(1-methyl-1H-pyrazol-4-yl)benzamide | 408.0 | 1H NMR (500 MHz, DMSO-d6) δ ppm 1.03 (d, J = 6.75 Hz, 6H) 1.24 (br s, 1H) 1.69-1.89 (m, 5H) 2.15 (dt, J = 13.20, 6.57 Hz, 1H) 2.94 (s, 3H) 3.32 (s, 3H) 3.85-3.92 (m, 5H) 4.20 (t, J = 4.67 Hz, 1H) 4.24-4.33 (m, 1H) 4.41 (br s, 1H) 7.02 (dd, J = 7.85, 1.36 Hz, 1H) 7.06 (d, J = 1.17 Hz, 1H) 7.63 (d, J = 7.79 Hz, 1H) 7.95 (s, 1H) 8.12 (s, 1H) |
| 9-1 | N-((1R,2R,4S)-7-cyano-7-azabicyclo[2.2.1]heptan-2-yl)-2-methyl-4-(1-methyl-1H-pyrazol-4-yl)-1,3-benzothiazole-7-carboxamide | 393.0 | 1H NMR (500 MHz, DMSO-d6) δ ppm 1.60-1.75 (m, 3H), 1.79-1.92 (m, 2H), 2.24 (br d, J = 3.50 Hz, 1H), 2.85 (s, 3H), 3.81 (s, 1H), 3.94 (s, 3H), 4.19 (t, J = 4.80 Hz, 1H), 4.28 (t, J = 4.54 Hz, 1H), 4.36 (br dd, J = 10.96, 5.13 Hz, 1H), 7.55 (s, 1H), 7.80 (s, 1H), 7.89 (d, J = 8.04 Hz, 1H), 8.13 (d, J = 8.04 Hz, 1H), 8.34 (s, 1H), 8.67 (s, 1H), 8.79 (d, J = 5.84 Hz, 1H) |
| 9-2 | N-((1R,2R,4S)-7-cyano-7-azabicyclo[2.2.1]heptan-2-yl)-5-(2-methylpropoxy)-2,4-bis(1-methyl-1H-pyrazol-4-yl)benzamide | 474.0 | 1H NMR (500 MHz, DMSO-d6) δ ppm 0.99-1.11 (m, 8H) 1.25 (dd, J = 12.65, 4.61 Hz, 1H) 1.44-1.54 (m, 3H) 1.67-1.74 (m, 1H) 2.11-2.19 (m, 2H) 3.32 (s, 6H) 3.81 (s, 7H) 3.84-3.92 (m, 9H) 4.08 (t, J = 4.93 Hz, 1H) 4.20 (t, J = 4.35 Hz, 1H) 4.29 (br d, J = 5.97 Hz, 1H) 6.94 (s, 1H) 7.56 (s, 2H) 7.61 (s, 1H) 7.68 (s, 1H) 7.75 (s, 1H) 7.80 (s, 2H) 7.99 (s, 1H) 8.16 (s, 1H) 8.48 (d, J = 6.88 Hz, 1H) |
| 9-3 | 2-chloro-N-((1R,2R,4S)-7-cyano-7-azabicyclo[2.2.1]heptan-2-yl)-5-(2-methylpropoxy)-4-(1-methyl-1H-pyrazol-4-yl)benzamide | 428.0 | 1H NMR (500 MHz, DMSO-d6) δ ppm 1.02 (d, J = 6.75 Hz, 6H) 1.05-1.10 (m, 2H) 1.21-1.29 (m, 1H) 1.39 (dd, J = 12.85, 4.02 Hz, 1H) 1.57-1.63 (m, 1H) 1.67-1.75 (m, 1H) 1.77-1.85 (m, 1H) 1.98-2.04 (m, 1H) 2.12-2.25 (m, 2H) 3.31 (s, 4H) 3.85-3.92 (m, 6H) 4.15 (t, J = 4.93 Hz, 1H) 4.23-4.28 (m, 2H) 7.07 (s, 1H) 7.71 (s, 1H) 8.00 (s, 1H) 8.18 (s, 1H) 8.71 (d, J = 5.71 Hz, 1H) |
| 9-4 | 3-butoxy-N-((1R,2R,4S)-7-cyano-7-azabicyclo[2.2.1]heptan-2-yl)-4-(1-methyl-1H-pyrazol-4-yl)benzamide | 394.0 | 1H NMR (500 MHz, DMSO-d6) δ ppm 0.97 (t, J = 7.40 Hz, 3H) 1.46-1.53 (m, 2H) 1.57 (dd, J = 12.72, 4.54 Hz, 1H) 1.65-1.72 (m, 2H) 1.79-1.89 (m, 4H) 2.18-2.24 (m, 1H) 3.32 (s, 8H) 3.88 (s, 3H) 4.11-4.18 (m, 3H) 4.24-4.30 (m, 2H) 7.46 (d, J = 1.43 Hz, 1H) 7.48 (dd, J = 8.04, 1.69 Hz, 1H) 7.69 (d, J = 8.04 Hz, 1H) 7.98 (s, 1H) 8.15 (s, 1H) 8.50 (d, J = 5.71 Hz, 1H) |
| 9-5 | N-((1R,2R,4S)-7-cyano-7-azabicyclo[2.2.1]heptan-2-yl)-3-(cyclobutylmethoxy)-4-(1-methyl-1H-pyrazol-4-yl)benzamide | 406.0 | 1H NMR (500 MHz, CHLOROFORM-d) δ ppm 0.90 (t, J = 6.94 Hz, 2H) 1.10 (d, J = 6.75 Hz, 3H) 1.18 (dd, J = 13.04, 3.96 Hz, 3H) 1.23-1.34 (m, 4H) 1.62-1.68 (m, 3H) 1.90-2.12 (m, 23H) 2.16-2.26 (m, 7H) 2.52-2.60 (m, 3H) 2.91 (dt, J = 14.89, 7.54 Hz, 3H) 3.96 (s, 10H) 4.09-4.14 (m, 10H) 4.47-4.53 (m, 7H) 6.18 (br d, J = 4.41 Hz, 3H) 7.17-7.27 (m, 4H) 7.47 (d, J = 1.43 Hz, 3H) 7.56 (d, J = 7.91 Hz, 3H) 7.92 (d, J = 8.82 Hz, 6H) |
| 9-6 | N-((1R,2R,4S)-7-cyano-7-azabicyclo[2.2.1]heptan-2-yl)-3-(2-methylpropoxy)-4-(1-methyl-1H-pyrazol-4-yl)benzamide | 394.0 | 1H NMR (500 MHz, CHLOROFORM-d) δ ppm 1.10 (d, J = 6.62 Hz, 22H) 1.15-1.21 (m, 6H) 1.28 (br dd, J = 6.10, 1.95 Hz, 2H) 1.60-1.66 (m, 5H) 1.92-1.97 (m, 6H) 2.08-2.12 (m, 3H) 2.23 (dt, J = 13.33, 6.63 Hz, 3H) 2.56-2.59 (m, 2H) 3.92-3.98 (m, 18H) 4.12 (t, J = 4.87 Hz, 3H) 4.48-4.52 (m, 7H) 6.12 (br d, J = 3.89 Hz, 3H) 7.20 (dd, J = 7.98, 1.62 Hz, 3H) 7.48 (d, J = 1.43 Hz, 3H) 7.56 (d, J = 7.91 Hz, 3H) 7.94 (d, J = 6.49 Hz, 7H) |
| 12-3 | 6-(5-azaspiro[2.5]octan-5-yl)-N-((1R,2R,4S)-7-cyano-7-azabicyclo[2.2.1]heptan-2-yl)-4-pyrimidinecarboxamide | [M + 1] 353.3 | |
| 12-4 | N-((1R,2R,4S)-7-cyano-7-azabicyclo[2.2.1]heptan-2-yl)-6-(2-methyl-2-phenyl-4-morpholinyl)-4-pyrimidinecarboxamide | [M + 1] 419.3 | |

| Ex # | Name | MS data | 1H NMR |
|---|---|---|---|
| 12-5 | 6-(2-(4-chlorophenyl)-2-methyl-4-morpholinyl)-N-((1R,2R,4S)-7-cyano-7-azabicyclo[2.2.1]heptan-2-yl)-4-pyrimidinecarboxamide | [M + 1] 453.3 | |
| 12-6 | 6-(((1-(4-bromo phenyl)cyclopropyl)methyl)(methyl)amino)-N-((1R,2R,4S)-7-cyano-7-azabicyclo[2.2.1]heptan-2-yl)-4-pyrimidinecarboxamide | [M + 1] 481.2 | |
| 12-7 | 2-chloro-N-(8-cyano-8-azabicyclo[3.2.1]octan-2-yl)-4-(4-methyl-1H-pyrazol-1-yl)benzamide | [M + 1] 370.3 | |
| 12-8 | 3-(6-chloro-2,3-dihydro-1H-indol-1-yl)-N-((1R,2R,4S)-7-cyano-7-azabicyclo[2.2.1]heptan-2-yl)propanamide | [M + 1] 345.3 | |
| 12-9 | (2E)-N-((1R,2R,4S)-7-cyano-7-azabicyclo[2.2.1]heptan-2-yl)-4-(2,5-dichlorophenyl)-2-methyl-2-butenamide | [M + 1] 364.2 | |
| 12-10 | N-((1R,2R,4S)-7-cyano-7-azabicyclo[2.2.1]heptan-2-yl)-4-(2,5-dichlorophenyl)butanamide | 352.2 | |
| 12-11 | N-((1R,2R,4S)-7-cyano-7-azabicyclo[2.2.1]heptan-2-yl)-3-(2,5-dichlorophenyl)cyclopentanecarboxamide | 378.1 | |
| 12-12 | N-((1R,2R,4S)-7-cyano-7-azabicyclo[2.2.1]heptan-2-yl)-3-(4-fluorophenoxy)benzamide | [M + 1] 352.3 | |
| 12-13 | N-((1R,2R,4S)-7-cyano-7-azabicyclo[2.2.1]heptan-2-yl)-3-(4-fluorobenzyl)benzamide | [M + 1] 350.3 | |
| 12-14 | 3-(4-chlorophenoxy)-N-((1R,2R,4S)-7-cyano-7-azabicyclo[2.2.1]heptan-2-yl)benzamide | [M + 1] 368.2 | |
| 12-15 | N-((1R,2R,4S)-7-cyano-7-azabicyclo[2.2.1]heptan-2-yl)-2-(2,5-dichlorobenzyl)cyclopropanecarboxamide | [M + 1] 364.2 | |
| 12-16 | N-((1R,2R,4S)-7-cyano-7-azabicyclo[2.2.1]heptan-2-yl)-3-(4-cyanophenoxy)benzamide | [M + 1] 359.3 | |
| 12-17 | N-((1R,2R,4S)-7-cyano-7-azabicyclo[2.2.1]heptan-2-yl)dibenzo[b,d]furan-3-carboxamide | [M + 1] 332.3 | |
| 12-18 | (2E)-3-(5-chloro-1-ethyl-1H-pyrrolo[2,3-b]pyridin-3-yl)-N-((1R,2R,4S)-7-cyano-7-azabicyclo[2.2.1]heptan-2-yl)-2-propenamide | [M + 1] 570.2 | |
| 12-19 | 2-(3-bromo-2-cyanophenoxy)-N-((1R,2R,4S)-7-cyano-7-azabicyclo[2.2.1]heptan-2-yl)acetamide | [M + 1] 375.1 | |

| Ex # | Name | MS data | 1H NMR |
|---|---|---|---|
| 12-20 | N-(2-(((1R,2R,4S)-7-cyano-7-azabicyclo[2.2.1]heptan-2-yl)amino)-2-oxoethyl)-4,5,6,7-tetrahydro-1-benzothiophene-2-carboxamide | [M + 1] 359.3 | |
| 12-21 | (3E)-N-((1R,2R,4S)-7-cyano-7-azabicyclo[2.2.1]heptan-2-yl)-4-(2,5-dichlorophenyl)-2-methoxy-3-butenamide | [M + 1] 380.3 | |
| 12-22 | (3E)-N-((1R,2R,4S)-7-cyano-7-azabicyclo[2.2.1]heptan-2-yl)-4-(2,5-dichlorophenyl)-N-methyl-3-butenamide | [M + 1] 364.2 | |
| 12-23 | 2',5'-dichloro-N-((1R,2R,4S)-7-cyano-7-azabicyclo[2.2.1]heptan-2-yl)[biphenyl]-3-carboxamide | [M + 1] 386.3 | |
| 12-24 | (3E)-4-(3-chlorophenyl)-N-((1R,2R,4S)-7-cyano-7-azabicyclo[2.2.1]heptan-2-yl)-3-butenamide | [M + 1] 316.2 | |
| 12-25 | (2E)-3-(5-chloro1-ethyl-1H-indol-3-yl)-N-((1R,2R,4S)-7-cyano-7-azabicyclo[2.2.1]heptan-2-yl)-2-methyl-2-propenamide | [M + 1] 383.3 | |
| 12-26 | (3E)-N-((1R,2R,4S)-7-cyano-7-azabicyclo[2.2.1]heptan-2-yl)-4-(2,5-dichlorophenyl)-3-butenamide | [M + 1] 350.2 | |
| 12-27 | N-((1R,2R,4S)-7-cyano-7-azabicyclo[2.2.1]heptan-2-yl)-2,3,4,9-tetrahydro-1H-carbazole-3-carboxamide | [M + 1] 335.3 | |
| 12-28 | (2E)-3-(5-chloro-1-benzothiophen-3-yl)-N-((1R,2R,4S)-7-cyano-7-azabicyclo[2.2.1]heptan-2-yl)-2-methyl-2-propenamide | [M + 1] 372.1 | |
| 12-29 | 3'-bromo-N-((1R,2R,4S)-7-cyano-7-azabicyclo[2.2.1]heptan-2-yl)[biphenyl]-3-carboxamide | [M + 1] 396.1 | |
| 12-30 | (2E)-3-(5-chloro-1H-indazol-3-yl)-N-((1R,2R,4S)-7-cyano-7-azabicyclo[2.2.1]heptan-2-yl)-2-methyl-2-propenamide | [M + 1] 356.3 | |
| 13-21 | N-((1R,2R,4S)-7-cyano-7-azabicyclo[2.2.1]heptan-2-yl)-6-(4-methyl-2-pyrimidinyl)-1H-indole-2-carboxamide | 373.2 | 1H NMR (CHLOROFORM-d) δ: 8.69 (d, J = 4.9 Hz, 1H), 8.60 (s, 1H), 8.55-8.64 (m, 1H), 8.25-8.34 (m, 1H), 7.73 (d, J = 8.4 Hz, 1H), 7.11 (d, J = 4.8 Hz, 1H), 6.94 (s, 1H), 6.90-6.98 (m, 1H), 4.56 (br dd, J = 9.7, 5.0 Hz, 1H), 4.45-4.51 (m, 1H), 4.14 (t, J = 5.1 Hz, 1H), 2.66 (s, 1H), 2.64-2.68 (m, 1H), 2.52-2.63 (m, 1H), 2.12 (br dd, J = 4.3, 2.1 Hz, 1H), 1.92-2.03 (m, 3H), 1.70 (br s, 2H) |
| 13-22 | 5-(3-chlorophenyl)-N-((1R,2R,4S)-7-cyano-7-azabicyclo[2.2.1]heptan-2-yl)-2-furancarboxamide | 341.8 | 1H NMR (600 MHz, DMSO-d6) Shift 8.57 (br d, J = 5.22 Hz, 1H), 7.98 (t, J = 1.71 Hz, 1H), 7.87 (td, J = 1.22, 7.84 Hz, 1H), 7.52 (t, J = 7.90 Hz, 1H), 7.44 (d, J = 8.24 Hz, 1H), 7.21-7.29 (m, 2H), 4.22-4.30 (m, 2H), 4.18 (t, J = 4.79 Hz, 1H), 2.20-2.27 (m, 1H), 1.79-1.91 (m, 2H), 1.66-1.75 (m, 2H), 1.59 (dd, J = 4.28, 12.85 Hz, 1H) |

| Ex # | Name | MS data | 1H NMR |
|---|---|---|---|
| 13-23 | N-((1R,2R,4S)-7-cyano-7-azabicyclo[2.2.1]heptan-2-yl)-1-(4-cyclopropyl-2-pyrimidinyl)-3-pyrrolidinecarboxamide | 353 | 1H NMR (500 MHz, CHLOROFORM-d) Shift 8.08-8.12 (m, 1H), 6.42 (d, J = 5.19 Hz, 1H), 5.82-5.95 (m, 1H), 4.30-4.36 (m, 2H), 4.01-4.11 (m, 1H), 3.75-3.90 (m, 2H), 3.66-3.75 (m, 1H), 3.54 (td, J = 7.77, 11.06 Hz, 1H), 2.96-3.03 (m, 1H), 2.39-2.48 (m, 1H), 2.17-2.31 (m, 2H), 1.97-2.12 (m, 3H), 1.50-1.59 (m, 1H), 0.94-1.12 (m, 5H) |
| 13-24 | N-((1R,2R,4S)-7-cyano-7-azabicyclo[2.2.1]heptan-2-yl)-1-(3-(trifluoromethyl)phenyl)-3-pyrrolidinecarboxamide | 379 | 1H NMR (500 MHz, CHLOROFORM-d) Shift 7.33 (t, J = 7.98 Hz, 1H), 6.94-6.99 (m, 1H), 6.76-6.78 (m, 1H), 6.71-6.74 (m, 1H), 5.82 (br d, J = 4.41 Hz, 1H), 4.32-4.38 (m, 2H), 4.07 (t, J = 5.00 Hz, 1H), 3.49-3.60 (m, 3H), 3.36-3.43 (m, 1H), 3.03-3.10 (m, 1H), 2.43-2.51 (m, 1H), 2.25-2.38 (m, 2H), 2.00-2.11 (m, 1H), 1.87-1.98 (m, 1H), 1.79-1.85 (m, 1H), 1.56 (tdd, J = 3.92, 8.63, 12.46 Hz, 1H), 1.04 (dd, J = 3.57, 13.04 Hz, 1H) |
| 13-25 | N-((1R,2R,4S)-7-cyano-7-azabicyclo[2.2.1]heptan-2-yl)-1-(3,5-dichlorophenyl)-3-pyrrolidinecarboxamide | 379 | 1H NMR (500 MHz, CHLOROFORM-d) d 6.69-6.72 (m, 1H), 6.42-6.45 (m, 2H), 5.59-5.68 (m, 1H), 4.31-4.39 (m, 2H), 4.06-4.10 (m, 1H), 3.44-3.52 (m, 3H), 3.31-3.38 (m, 1H), 2.99-3.07 (m, 1H), 2.45-2.54 (m, 1H), 2.25-2.35 (m, 2H), 2.04-2.13 (m, 1H), 1.89-1.99 (m, 1H), 1.77-1.85 (m, 1H), 1.00-1.06 (m, 1H) |
| 13-26 | N-((1R,2R,4S)-7-cyano-7-azabicyclo[2.2.1]heptan-2-yl)-1-(6-(trifluoromethyl)-2-pyridinyl)-3-pyrrolidinecarboxamide | 380 | 1H NMR (500 MHz, CHLOROFORM-d) Shift 7.56 (t J = 7.91 Hz, 1H), 6.92 (d, J = 7.27 Hz, 1H), 6.52 (d, J = 8.56 Hz, 1H), 5.92-6.04 (m, 1H), 4.28-4.37 (m, 2H), 4.06 (dt, J = 2.34, 4.93 Hz, 1H), 3.77-3.85 (m, 1H), 3.65-3.75 (m, 2H), 3.43-3.53 (m, 1H), 2.99-3.07 (m, 1H), 2.40-2.48 (m, 1H), 2.23-2.38 (m, 2H), 1.99-2.06 (m, 1H), 1.76-1.94 (m, 2H), 1.52-1.64 (m, 1H), 1.04-1.10 (m, 1H) |
| 13-27 | 2-chloro-N-((1R,2R,4S)-7-cyano-7-azabicyclo[2.2.1]heptan-2-yl)-3-(2-methylpropoxy)-4-(1-methyl-1H-pyrazol-4-yl)benzamide | 428.0 | 1H NMR (500 MHz, DMSO-d6) δ ppm 0.86 (br t, J = 6.81 Hz, 1H) 1.00 (d, J = 6.75 Hz, 6H) 1.24 (br s, 1H) 1.37 (br dd, J = 12.85, 3.76 Hz, 1H) 1.53-1.65 (m, 1H) 1.67-1.76 (m, 1H) 1.76-1.87 (m, 1H) 1.95-2.05 (m, 1H) 2.10 (dt, J = 13.23, 6.62 Hz, 1H) 2.16-2.27 (m, 1H) 3.32 (s, 2H) 3.45-3.59 (m, 2H) 3.89 (s, 3H) 4.14 (t, J = 4.80 Hz, 1H) 4.20-4.31 (m, 2H) 7.18 (d, J = 8.04 Hz, 1H) 7.58 (d, J = 8.04 Hz, 1H) 7.90 (s, 1H) 8.11-8.19 (m, 1H) 8.74 (br d, J = 5.58 Hz, 1H) |
| 13-28 | 2-chloro-N-((1R,2R,4S)-7-cyano-7-azabicyclo[2.2.1]heptan-2-yl)-3-(2-methylpropoxy)-4-(4-methyl-1H-pyrazol-1-yl)benzamide | 428.0 | 1H NMR (500 MHz, DMSO-d6) δ ppm 0.86-0.93 (m, 18H) 0.99 (d, J = 6.75 Hz, 1H) 1.37 (dd, J = 12.78, 3.83 Hz, 3H) 1.53-1.66 (m, 2H) 1.67-1.77 (m, 2H) 1.78-1.95 (m, 5H) 2.00 (ddd, J = 12.75, 8.99, 3.83 Hz, 2H) 2.10 (s, 9H) 2.16-2.27 (m, 2H) 2.81 (s, 3H) 3.02 (s, 3H) 3.31 (s, 4H) 3.36-3.42 (m, 6H) 4.15 (t, J = 4.87 Hz, 2H) 4.23-4.31 (m, 4H) 7.21 (d, J = 8.17 Hz, 1H) 7.31 (d, J = 8.30 Hz, 2H) 7.56-7.66 (m, 6H) 7.95-7.99 (m, 3H) 8.84 (br d, J = 5.84 Hz, 2H) |
| 13-29 | N-((1R,2R,4S)-7-cyano-7-azabicyclo[2.2.1]heptan-2-yl)-3-(2-methylpropoxy)-4-(4-methyl-1H-pyrazol-1-yl)benzamide | 394.0 | 1H NMR (500 MHz, DMSO-d6) δ 0.99 (br d, J = 6.10 Hz, 6H), 1.52-1.64 (m, 1H), 1.64-1.77 (m, 2H), 1.77-1.91 (m, 2H), 2.10 (br s, 4H), 2.22 (br s, 1H), 3.95 (br d, J = 5.19 Hz, 2H), 4.17 (br s, 1H), 4.27 (br s, 2H), 7.45-7.69 (m, 3H), 7.77 (br d, J = 7.79 Hz, 1H), 8.06 (br s, 1H), 8.51-8.74 (m, 1H) |
| 13-30 | N-((1R,2R,4S)-7-cyano-7-azabicyclo[2.2.1]heptan-2-yl)-7-methyl-1-(6-methyl-2-pyridinyl)-1H-indazole-5-carboxamide | 387.0 | 1H NMR (500 MHz, DMSO-d6) δ ppm 1.58-1.66 (m, 2H) 1.67-1.76 (m, 5H) 1.79-1.93 (m, 5H) 2.22 (br s, 1H) 2.56-2.76 (m, 28H) 2.80 (br s, 1H) 3.30-3.34 (m, 32H) 4.17 (br s, 4H) 4.26 (br s, 8H) 7.39 (br s, 2H) 7.55 (br s, 2H) 7.99 (br s, 2H) 8.06 (br s, 3H) 8.22 (br s, 2H) 8.61 (br s, 1H) 9.35 (br s, 1H) |
| 15-2 | N-((1R,2R,4S)-7-cyano-7-azabicyclo[2.2.1]heptan-2-yl)-1-(2-quinolinyl)-1H-indazole-5-carboxamide | 409.2 | 1H NMR (DMSO-d6) δ: 9.17 (d, J = 8.9 Hz, 1H), 8.75 (d, J = 6.1 Hz, 1H), 8.69 (s, 1H), 8.59 (d, J = 8.9 Hz, 1H), 8.50 (s, 1H), 8.29 (d, J = 9.0 Hz, 1H), 8.15 (ddd, J = 8.7, 1.6, 1.4 Hz, 2H), 8.05 (d, J = 8.4 Hz, 1H), 7.85 (ddd, J = 8.3, 7.0, 1.4 Hz, 1H), 7.62 (t, J = 7.6 Hz, 1H), 4.37 (br dd, J = 11.1, 4.9 Hz, 1H), 4.29 (t, J = 4.5 Hz, 1H), 4.20 (t, J = 4.9 Hz, 1H), 2.22-2.28 (m, 1H), 1.92-1.98 (m, 1H), 1.81-1.89 (m, 1H), 1.68-1.76 (m, 2H), 1.61 (dd, J = 12.8, 4.8 Hz, 1H) |
| 15-3 | N-((1R,2R,4S)-7-cyano-7-azabicyclo[2.2.1]heptan-2-yl)-1-(6-(1H-imidazol-1-yl)-2-pyridinyl))-1H-indazole-5-carboxamide | 423.2 | 1H NMR (DMSO-d6) δ: 8.65-8.78 (m, 4H), 8.48 (s, 1H), 8.22 (t, J = 8.0 Hz, 1H), 8.18 (dd, J = 8.9, 1.6 Hz, 1H), 8.05-8.12 (m, 1H), 7.98 (d, J = 8.1 Hz, 1H), 7.76 (d, J = 7.9 Hz, 1H), 7.18-7.30 (m, 1H), 4.36 (br dd, J = 10.9, 4.9 Hz, 1H), 4.28 (t, J = 4.6 Hz, 1H), 4.19 (t, J = 4.9 Hz, 1H), 2.20-2.28 (m, 1H), 1.89-1.98 (m, 1H), 1.80-1.88 (m, 1H), 1.66-1.76 (m, 2H), 1.55-1.65 (m, 1H) |

-continued

| Ex # | Name | MS data | 1H NMR |
|---|---|---|---|
| 15-4 | N-((1R,2R,4S)-7-cyano-7-azabicyclo[2.2.1]heptan-2-yl)-1-(6-phenyl-2-pyridinyl)-1H-indazole-5-carboxamide | 435.2 | 1H NMR (DMSO-d6) δ: 8.92 (d, J = 8.9 Hz, 1H), 8.72 (d, J = 6.1 Hz, 1H), 8.65 (s, 1H), 8.49 (d, J = 0.9 Hz, 1H), 8.11-8.23 (m, 4H), 8.01 (d, J = 8.1 Hz, 1H), 7.94 (d, J = 7.7 Hz, 1H), 7.61 (t, J = 7.6 Hz, 2H), 7.49-7.57 (m, 1H), 4.33-4.40 (m, 1H), 4.28 (t, J = 4.6 Hz, 1H), 4.19 (t, J = 4.9 Hz, 1H), 2.20-2.28 (m, 1H), 1.91-1.98 (m, 1H), 1.80-1.88 (m, 1H), 1.67-1.76 (m, 2H), 1.61 (dd, J = 12.7, 4.7 Hz, 1H) |
| 15-5 | N-((1R,2R,4S)-7-cyano-7-azabicyclo[2.2.1]heptan-2-yl)-1-(6-(1H-pyrazol-1-yl)-2-pyridinyl)-1H-indazole-5-carboxamide | 424.0 | 1H NMR (DMSO-d6) δ: 8.80 (d, J = 8.9 Hz, 1H), 8.76 (d, J = 2.3 Hz, 1H), 8.73 (d, J = 6.2 Hz, 1H), 8.67 (s, 1H), 8.49 (s, 1H), 8.16-8.23 (m, 2H), 7.96 (d, J = 8.1 Hz, 1H), 7.92 (d, J = 1.0 Hz, 1H), 7.85 (d, J = 7.9 Hz, 1H), 6.69-6.73 (m, 1H), 4.37 (br dd, J = 11.2, 4.9 Hz, 1H), 4.28 (t, J = 4.5 Hz, 1H), 4.14-4.24 (m, 1H), 2.21-2.28 (m, 1H), 1.80-1.97 (m, 2H), 1.67-1.76 (m, 2H), 1.60 (dd, J = 12.7, 4.6 Hz, 1H) |
| 15-6 | N-((1R,2R,4S)-7-cyano-7-azabicyclo[2.2.1]heptan-2-yl)-1-(6-(1,1-difluoroethyl)-2-pyridinyl)-1H-indazole-5-carboxamide | | 1H NMR (DMSO-d6) δ: 8.78 (d, J = 8.9 Hz, 1H), 8.70 (d, J = 6.1 Hz, 1H), 8.63 (s, 1H), 8.46 (s, 1H), 8.10 (dd, J = 8.9, 1.3 Hz, 1H), 8.04 (t, J = 8.0 Hz, 1H), 7.95 (d, J = 8.2 Hz, 1H), 7.37 (d, J = 7.7 Hz, 1H), 4.35 (br dd, J = 10.9, 4.9 Hz, 1H), 4.23-4.30 (m, 1H), 4.18 (t, J = 4.9 Hz, 1H), 2.19-2.28 (m, 1H), 1.79-2.02 (m, 6H), 1.68-1.72 (m, 1H), 1.60 (dd, J = 12.7, 4.7 Hz, 1H) |
| 15-7 | N-((1R,2R,4S)-7-cyano-7-azabicyclo[2.2.1]heptan-2-yl)-1-(6-(difluoromethoxy)-2-pyridinyl)-1H-indazole-5-carboxamide | 425.2 | 1H NMR (CHLOROFORM-d) δ: 8.65 (d, J = 8.8 Hz, 1H), 8.32 (s, 1H), 8.32 (s, 1H), 7.88-7.96 (m, 3H), 6.86 (dd, J = 7.8, 0.8 Hz, 1H), 6.17 (br s, 1H), 4.51-4.61 (m, 2H), 4.15 (t, J = 5.1 Hz, 1H), 2.58-2.65 (m, 1H), 2.10-2.17 (m, 1H), 1.96-2.03 (m, 2H), 1.64-1.70 (m, 1H), 1.28 (s, 1H), 1.20 (dd, J = 13.0, 4.4 Hz, 1H) |
| 15-8 | N-((1R,2R,4S)-7-cyano-7-azabicyclo[2.2.1]heptan-2-yl)-1-(6-(difluoromethyl)-2-pyridinyl)-1H-indazole-5-carboxamide | 425.2 | 1H NMR (CHLOROFORM-d) δ: 8.91 (d, J = 9.0 Hz, 1H), 8.32 (d, J = 0.8 Hz, 1H), 8.30 (d, J = 0.9 Hz, 1H), 8.23 (dd, J = 8.4, 0.8 Hz, 1H), 8.03 (t, J = 8.0 Hz, 1H), 7.93 (dd, J = 8.9, 1.8 Hz, 1H), 7.54 (d, J = 7.5 Hz, 1H), 6.76 (t, J = 55.5 Hz, 1H), 6.18 (br d, J = 6.0 Hz, 1H), 4.52-4.61 (m, 2H), 4.15 (t, J = 5.1 Hz, 1H), 2.58-2.65 (m, 1H), 2.09-2.18 (m, 1H), 1.97-2.03 (m, 2H), 1.62-1.70 (m, 1H), 1.20 (dd, J = 12.9, 4.5 Hz, 1H) |
| 15-9 | 1-([2,2'-bipyridin]-6-yl)-N-((1R,2R,4S)-7-cyano-7-azabicyclo[2.2.1]heptan-2-yl)-1H-indazole-5-carboxamide | 436.2 | 1H NMR (DMSO-d6) δ: 8.91 (br d, J = 8.8 Hz, 1H), 8.77 (br d, J = 3.8 Hz, 1H), 8.73 (br d, J = 6.1 Hz, 1H), 8.60-8.69 (m, 1H), 8.44-8.53 (m, 2H), 8.33 (d, J = 7.7 Hz, 1H), 8.13-8.23 (m, 2H), 8.04-8.13 (m, 2H), 7.54 (t, J = 6.4 Hz, 1H), 4.32-4.43 (m, 1H), 4.29 (t, J = 4.6 Hz, 1H), 4.19 (t, J = 4.9 Hz, 1H), 2.19-2.30 (m, 1H), 1.90-2.00 (m, 1H), 1.79-1.89 (m, 1H), 1.67-1.77 (m, 2H), 1.62 (dd, J = 2.8, 4.7 Hz, 1H) |
| 15-10 | 3-(3-chlorophenyl)-N-((1R,2R,4S)-7-cyano-7-azabicyclo[2.2.1]heptan-2-yl)-3-azabicyclo[3.1.0]hexane-1-carboxamide | 357 | 1H NMR (500 MHz, METHANOL-d4) d 7.09-7.19 (m, 1H), 6.59-6.71 (m, 2H), 6.50-6.59 (m, 1H), 4.19-4.35 (m, 2H), 4.06-4.16 (m, 1H), 3.70-3.81 (m, 1H), 3.50-3.62 (m, 2H), 3.25-3.30 (m, 1H), 2.19-2.36 (m, 2H), 1.69-2.01 (m, 4H), 1.42-1.52 (m, 2H), 1.26-1.39 (m, 1H), 0.96-1.00 (m, 1H) |
| 15-11 | N-((1R,2R,4S)-7-cyano-7-azabicyclo[2.2.1]heptan-2-yl)-1-(3,5-dichlorophenyl)-1H-pyrazole-3-carboxamide | 376 | 1H NMR (500 MHz, CHLOROFORM-d) Shift 7.94 (d, J = 2.59 Hz, 1H), 7.66 (d, J = 1.69 Hz, 2H), 7.39 (t, J = 1.75 Hz, 1H), 7.05 (d, J = 2.59 Hz, 1H), 6.93-6.97 (m, 1H), 4.45-4.56 (m, 2H), 4.14 (t, J = 5.00 Hz, 1H), 2.51-2.63 (m, 1H), 2.06-2.16 (m, 1H), 1.90-2.04 (m, 2H), 1.72 (ddd, J = 4.54, 8.47, 12.55 Hz, 1H), 1.24-1.33 (m, 1H) |
| 15-12-2 | (1S,4R,5S)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | m/z (ESI): 390.0 (M + H)+. | ¹H NMR (400 MHz, DMSO-d₆): δ ppm 8.40 (d, J = 5.7 Hz, 1H), 6.61-7.42 (m, 3H), 3.94-4.37 (m, 3H), 3.75 (t, J = 9.8 Hz, 1H), 3.42-3.55 (m, 1H), 2.96 (dd, J = 10.3, 8.8 Hz, 1H), 2.19-2.38 (m, 1H), 1.92-2.07 (m, 1H), 1.78-1.92 (m, 1H), 1.56-1.72 (m, 2H), 1.17-1.37 (m 3H), 0.85 (t, J = 6.5 Hz, 1H), 0.56-0.70 (m, 1H). |
| 15-12-1 | (1S,4S,5S)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | m/z. (ESI): 390.0 (M + H)+. | ¹H NMR (400 MHz, DMSO-d₆): δ ppm 8.40 (d, J = 5.7 Hz, 1H), 6.61-7.42 (m, 3H), 3.94-4.37 (m, 3H), 3.75 (t, J = 9.8 Hz, 1H), 3.42-3.55 (m, 1H), 2.96 (dd, J = 10.3, 8.8 Hz, 1H), 2.19-2.38 (m, 1H), 1.92-2.07 (m, 1H), 1.78-1.92 (m, 1H), 1.56-1.72 (m, 2H), 1.47 (m, 1H), 1.17-1.37 (m, 2H), 0.85 (t, J = 6.5 Hz, 1H), 0.56-0.70 (m, 1H). |
| 15-14 | N-((1S,2R,4S)-7-cyano-7-azabicyclo[2.2.1]heptan-2-yl)-1-(3,5-dichlorophenyl)-4-azepanecarboxamide | m/z (ESI): 407.1, 409.1 (M + H)+ | ¹H NMR (400 MHz, DMSO-d₆): δ ppm 8.04 (dd, J = 6.2, 1.9 Hz, 1H), 6.23-7.34 (m, 3H), 3.90-4.37 (m, 3H), 3.40-3.66 (m, 3H), 2.06-2.28 (m, 2H), 1.80-2.07 (m, 2H), 1.40-1.81 (m, 9H), 1.21 (dd, J = 12.7, 4.6 Hz, 1H). |

| Ex # | Name | MS data | 1H NMR |
|---|---|---|---|
| 15-15 | 6-chloro-N-((1R,2R,4S)-7-cyano-7-azabicyclo[2.2.1]heptan-2-yl)-1-(6-cyano-2-pyridinyl)-1H-indazole-5-carboxamide | 417.0 | 1H NMR (600 MHz, DMSO-d6) δ ppm 1.33-1.47 (m, 1H) 1.61 (ddd, J = 12.03, 9.15, 4.05 Hz, 1H) 1.72-1.78 (m, 1H) 1.80-1.87 (m, 1H) 2.04 (ddd, J = 12.96, 9.07, 4.13 Hz, 1H) 2.21-2.29 (m, 1H) 3.32-3.38 (m, 75H) 4.12-4.24 (m, 1H) 4.26-4.37 (m, 2H) 8.01 (d, J = 7.66 Hz, 1H) 8.08-8.20 (m, 1H) 8.27 (t, J = 8.17 Hz, 1H) 8.34 (d, J = 8.52 Hz, 1H) 8.64 (s, 1H) 8.73 (d, J = 0.62 Hz, 1H) 8.89 (br d, J = 5.76 Hz, 1H) |
| 15-16 | 6-chloro-N-((1R,2R,4S)-7-cyano-7-azabicyclo[2.2.1]heptan-2-yl)-1-(4-cyano-2-pyridinyl)-1H-indazole-5-carboxamide | 418.0 | 1H NMR (600 MHz, DMSO-d6) δ ppm 1.40 (dd, J = 12.69, 4.28 Hz, 1H) 1.54-1.67 (m, 1H) 1.67-1.91 (m, 2H) 2.04 (ddd, J = 12.96, 9.07, 4.28 Hz, 1H) 2.20-2.30 (m, 1H) 3.31-3.39 (m, 129H) 4.11-4.21 (m, 1H) 4.25-4.35 (m, 2H) 8.08 (s, 1H) 8.62-8.70 (m, 1H) 8.84 (d, J = 0.62 Hz, 1H) 8.85-8.91 (m, 2H) |
| 16-3 | N-((1R,2R,4S)-7-cyano-7-azabicyclo[2.2.1]heptan-2-yl)-5-(1-methyl-1H-pyrazol-4-yl)-1,3-thiazole-2-carboxamide | 329.0 | 1H NMR (DMSO-d6, 600 MHz) Shift 9.16 (d, 1H, J = 6.5 Hz), 8.23 (s, 1H), 8.13 (s, 1H), 7.89 (d, 1H, J = 0.8 Hz), 4.3-4.3 (m, 1H), 4.21 (t, 1H, J = 4.7 Hz), 4.1-4.2 (m, 1H), 3.87 (s, 3H), 2.1-2.2 (m, 1H), 1.8-1.9 (m, 1H), 1.6-1.8 (m, 4H) |
| 16-4 | N-((1R,2R,4S)-7-cyano-7-azabicyclo[2.2.1]heptan-2-yl)-2-(3-cyanophenyl)-1,3-thiazole-4-carboxamide | 350.0 | 1H NMR (500 MHz, CHLOROFORM-d) Shift 8.34 (t, J = 1.43 Hz, 1H), 8.22 (s, 1H), 8.14 (d, J = 7.81 Hz, 1H), 7.79 (td, J = 1.31, 7.75 Hz, 1H), 7.64 (t, J = 7.85 Hz, 1H), 7.40 (br d, J = 5.84 Hz, 1H), 4.50-4.60 (m, 1H), 4.47 (t, J = 4.22 Hz, 1H), 4.12-4.20 (m, 1H), 2.60 (dddd, J = 3.11, 5.19, 11.11, 13.02 Hz, 1H), 1.94-2.17 (m, 3H), 1.71-1.80 (m, 1H), 1.25-1.38 (m, 1H) |
| 16-5 | N-((1R,2R,4S)-7-cyano-7-azabicyclo[2.2.1]heptan-2-yl)-2-(3-cyclopropylphenyl)-1,3-thiazole-4-carboxamide | 365.1 | 1H NMR (500 MHz, CHLOROFORM-d) Shift 8.12 (s, 1H), 7.72-7.75 (m, 1H), 7.67 (t, J = 1.82 Hz, 1H), 7.46 (br d, J = 5.84 Hz, 1H), 7.38 (t, J = 7.72 Hz, 1H), 7.18 (td, J = 1.18, 7.75 Hz, 1H), 4.47-4.56 (m, 2H), 4.14 (t, J = 5.06 Hz, 1H), 2.58 (dddd, J = 3.05, 5.22, 11.05, 12.99 Hz, 1H), 1.94-2.15 (m, 4H), 1.71 (ddd, J = 4.41, 8.60, 12.55 Hz, 1H), 1.25-1.33 (m, 1H), 1.04-1.10 (m, 2H), 0.76-0.86 (m, 2H) |
| 20-1 | N-((1R,2R,4S)-7-cyano-7-azabicyclo[2.2.1]heptan-2-yl)-7-(4-methyl-2-pyrimidinyl)-1H-indole-3-carboxamide | 373.0 | 1H NMR (DMSO-d6) δ: 8.83 (d, J = 5.1 Hz, 1H), 8.35 (br t, J = 6.6 Hz, 2H), 8.23 (br d, J = 2.8 Hz, 1H), 8.14-8.21 (m, 1H), 7.34 (d, J = 5.0 Hz, 1H), 7.28 (t, J = 7.7 Hz, 1H), 4.31-4.40 (m, 1H), 4.27 (s, 1H), 4.16 (s, 1H), 4.03-4.12 (m, 1H), 2.65 (s, 3H), 2.17-2.30 (m, 1H), 1.90-2.00 (m, 1H), 1.78-1.88 (m, 1H), 1.70 (br s, 2H), 1.53 (br dd, J = 12.7, 4.7 Hz, 1H) |
| 20-2 | N-((1R,2R,4S)-7-cyano-7-a/abicyclo[2.2.1]heptan-2-yl)-7-(6-methyl-2-pyridinyl)-1H-indole-3-carboxamide | 372.0 | 1H NMR (DMSO-d6) δ: 11.77 (br s, 1H), 8.24 (d, J = 7.9 Hz, 1H), 8.20 (d, J = 2.8 Hz, 1H), 8.15 (br d, J = 5.8 Hz, 1H), 7.91 (d, J = 7.9 Hz, 1H), 7.83 (t, J = 7.8 Hz, 1H), 7.80 (d, J = 7.5 Hz, 1H), 7.22-7.27 (m, 2H), 4.31-4.40 (m, 1H), 4.27 (t, J = 4.4 Hz, 1H), 4.16 (t, J = 4.9 Hz, 1H), 2.70 (s, 3H), 2.19-2.28 (m, 1H), 1.89-1.99 (m, 1H), 1.79-1.88 (m, 1H), 1.65-1.74 (m, 2H), 1.53 (br dd, J = 12.7, 4.7 Hz, 1H) |
| 20-3 | 2',3-dichlor-N-((1R,2R,4S)-7-cyano-7-azabicyclo[2.2.1]heptan-2-yl)-3'-(cyanomethyl)[biphenyl]-4-carboxamide | 425.0 | 1H NMR (600 MHz, DMSO-d6) δ ppm 1.07 (s, 1H) 1.24 (s, 1H) 1.41 (dd, J = 12.72, 4.27 Hz, 1H) 1.57-1.66 (m, 1H) 1.69-1.77 (m, 1H) 1.82 (dt, J = 11.97, 3.78 Hz, 1H) 2.02 (ddd, J = 12.92, 9.06, 4.18 Hz, 1H) 2.18-2.27 (m, 1H) 2.51-2.60 (m, 1H) 4.16 (t, J = 5.00 Hz, 1H) 4.18 (s, 2H) 4.24-4.32 (m, 2H) 7.43 (dd, J = 7.67, 1.68 Hz, 1H) 7.46 (dd, J = 7.86, 1.68 Hz, 1H) 7.51 (t, J = 7.67 Hz, 1H) 7.53-7.57 (m, 2H) 7.63 (dd, J = 7.72, 1.63 Hz, 1H) 8.89 (d, J = 6.09 Hz, 1H) |
| 20-4 | 3,3'-dichloro-N-((1R,2R,4S)-7-cyano-7-azabicyclo[2.2.1]heptan-2-yl)-5'-(cyanomethyl)[biphenyl]-4-carboxamide | 425.0 | 1H NMR (600 MHz, DMSO-d6) δ ppm 0.85 (br t, J = 7.04 Hz, 1H) 1.07 (s, 1H) 1.24 (s, 1H) 1.39 (dt, J = 8.45, 4.22 Hz, 1H) 1.55-1.65 (m, 1H) 1.68-1.77 (m, 1H) 1.77-1.87 (m, 1H) 2.01 (ddd, J = 12.90, 8.99, 4.09 Hz, 1H) 2.20-2.27 (m, 1H) 4.13 (s, 2H) 4.15 (t, J = 4.95 Hz, 1H) 4.24-4.31 (m, 2H) 7.51 (t, J = 1.68 Hz, 1H) 7.56 (d, J = 7.90 Hz, 1H) 7.72 (s, 1H) 7.76 (dd, J = 7.99, 1.82 Hz, 1H) 7.82 (t, J = 1.73 Hz, 1H) 7.90 (d, J = 1.73 Hz, 1H) 8.84 (br d, J = 6.00 Hz, 1H) |

| Ex # | Name | MS data | 1H NMR |
|---|---|---|---|
| 20-5 | 2',3-dichlor-N-((1R,2R,4S)-7-cyano-7-azabicyclo[2.2.1]heptan-2-yl)-5'-(cyanomethy])[biphenyl]-4-carboxamide | 425.0 | 1H NMR (600 MHz, DMSO-d6) δ ppm 1.07 (s, 1H) 1.24 (s, 1H) 1.35-1.42 (m, 1H) 1.55-1.64 (m, 1H) 1.68-1.77 (m, 1H) 1.77-1.86 (m, 1H) 2.01 (ddd, J = 12.92, 8.97, 4.09 Hz, 1H) 2.23 (br t, J = 10.99 Hz, 1H) 2.51-2.62 (m, 1H) 4.12-4.17 (m, 3H) 4.24-4.32 (m, 2H) 7.57 (d, J = 7.99 Hz, 1H) 7.66 (d, J = 8.36 Hz, 1H) 7.73 (dd, J = 7.99, 1.73 Hz, 1H) 7.78 (dd, J = 8.40, 2.32 Hz, 1H) 7.85 (d, J = 1.73 Hz, 1H) 7.94 (d, J = 2.27 Hz, 1H) 8.82 (br d, J = 5.90 Hz, 1H) |
| 20-6 | 3,4'-dichloro-N-((1R,2R,4S)-7-cyano-7-azabicyclo[2.2.1]heptan-2-yl)-3'-(cyanomethyl)[biphenyl]-4-carboxamide | 425.0 | 1H NMR (600 MHz, DMSO-d6) δ ppm 1.07 (s, 2H) 1.24 (s, 1H) 1.40 (dd, J = 12.67, 4.31 Hz, 1H) 1.56-1.65 (m, 1H) 1.69-1.77 (m, 1H) 1.78-1.86 (m, 1H) 2.02 (ddd, J = 12.92, 9.06, 4.09 Hz, 1H) 2.18-2.27 (m, 1H) 4.10 (s, 2H) 4.16 (t, J = 4.95 Hz, 1H) 4.24-4.32 (m, 2H) 7.42 (d, J = 2.18 Hz, 1H) 7.45 (dd, J = 8.27, 2.27 Hz, 1H) 7.48 (dd, J = 7.86, 1.68 Hz, 1H) 7.56 (d, J = 7.81 Hz, 1H) 7.59 (d, J = 1.63 Hz, 1H) 7.64 (d, J = 8.27 Hz, 1H) 8.88 (br d, J = 5.99 Hz, 1H) |
| 20-7 | 3-chloro-N-((1R,2R,4S)-7-cyano-7-azabicyclo[2.2.1]heptan-2-yl)-3'-(2-cyano-2-propanyl)[biphenyl]-4-carboxamide | 419.0 | 1H NMR (600 MHz, DMSO-d6) δ ppm 1.07 (s, 1H) 1.24 (s, 1H) 1.34-1.43 (m, 1H) 1.56-1.66 (m, 1H) 1.70-1.76 (m, 1H) 1.77 (s, 6H) 1.82 (td, J = 7.77, 4.18 Hz, 1H) 2.02 (ddd, J = 12.92, 9.01, 4.22 Hz, 1H) 2.18-2.28 (m, 1H) 2.37-2.47 (m, 1H) 4.16 (t, J = 4.90 Hz, 1H) 4.24-4.32 (m, 2H) 7.53-7.57 (m, 2H) 7.57-7.61 (m, 1H) 7.69 (dt, J = 7.56, 1.49 Hz, 1H) 7.74 (dd, J = 7.90, 1.73 Hz, 1H) 7.79 (t, J = 1.73 Hz, 1H) 7.87 (d, J = 1.73 Hz, 1H) 8.81 (br d, J = 6.68 Hz, 1H) |
| 20-8 | 3-chloro-N-((1R,2R,4S)-7-cyano-7-azabicyclo[2.2.1]heptan-2-yl)-3'-(cyanomethyl)-5'-fluoro[biphenyl]-4-carboxamide | 409.0 | 1H NMR (600 MHz, DMSO-d6) δ ppm 1.07 (s, 2H) 1.34-1.42 (m, 1H) 1.56-1.64 (m, 1H) 1.73 (br d, J = 12.17 Hz, 1H) 1.81 (br dd, J = 8.49, 3.95 Hz, 1H) 2.01 (ddd, J = 12.92, 8.97, 4.09 Hz, 1H) 2.23 (br s, 1H) 3.15-3.19 (m, 14H) 4.05-4.12 (m, 6H) 4.15 (t, J = 4.86 Hz, 1H) 4.24-4.31 (m, 1H) 7.41 (t, J = 9.17 Hz, 1H) 7.55 (d, J = 7.99 Hz, 1H) 7.70 (dd, J = 7.95, 1.77 Hz, 1H) 7.76-7.86 (m, 1H) 8.82 (br d, J = 6.00 Hz, 1H) |
| 20-9 | 3-chloro-N-((1R,2R,4S)-7-cyano-7-azabicyclo[2.2.1]heptan-2-yl)-3'-(cyanomethyl)-4'-fluoro[biphenyl]-4-carboxamide | 409.0 | 1H NMR (600 MHz, DMSO-d6) δ ppm 1.07 (s, 2H) 1.34-1.42 (m, 1H) 1.56-1.64 (m, 1H) 1.73 (br d, J = 12.17 Hz, 1H) 1.81 (br dd, J = 8.49, 3.95 Hz, 1H) 2.01 (ddd, J = 12.92, 8.97, 4.09 Hz, 1H) 2.23 (br s, 1H) 3.15-3.19 (m, 14H) 4.05-4.12 (m, 6H) 4.15 (t, J = 4.86 Hz, 1H) 4.24-4.31 (m, 1H) 7.41 (t, J = 9.17 Hz, 1H) 7.55 (d, J = 7.99 Hz, 1H) 7.70 (dd, J = 7.95, 1.77 Hz, 1H) 7.76-7.86 (m, 1H) 8.82 (br d, J = 6.00 Hz, 1H) |
| 20-10 | 3-chloro-N-((1R,2R,4S)-7-cyano-7-azabicyclo[2.2.1]heptan-2-yl)-3'-(cyanomethyl)-2'-fluoro[biphenyl]-4-carboxamide | 409.0 | 1H NMR (600 MHz, DMSO-d6) δ ppm 1.04-1.10 (m, 2H) 1.24 (s, 1H) 1.39 (br dd, J = 12.72, 4.09 Hz, 1H) 1.56-1.65 (m, 1H) 1.73 (br d, J = 12.26 Hz, 1H) 1.78-1.86 (m, 1H) 2.01 (ddd, J = 12.97, 9.06, 4.22 Hz, 1H) 2.16-2.27 (m, 1H) 3.14-3.20 (m, 12H) 3.21-3.24 (m, 1H) 4.08 (qd, J = 5.27, 1.73 Hz, 4H) 4.13 (s, 2H) 4.15 (br t, J = 4.95 Hz, 1H) 4.24-4.32 (m, 2H) 7.37 (t, J = 7.72 Hz, 1H) 7.52-7.61 (m, 3H) 7.69 (s, 1H) 8.86 (br d, J = 6.09 Hz, 1H) |
| 20-11 | 3-chloro-N-((1R,2R,4S)-7-cyano-7-azabicyclo[2.2.1]heptan-2-yl)-5'-(cyanomethyl)-2'-fluoro[biphenyl]-4-carboxamide | 409.0 | 1H NMR (600 MHz, DMSO-d6) δ ppm 1.07 (s, 1H) 1.24 (S, 1H) 1.38 (dd, J = 12.62, 4.36 Hz, 1H) 1.54-1.65 (m, 1H) 1.68-1.77 (m, 1H) 1.82 (td, J = 7.88, 3.95 Hz, 1H) 2.01 (tt, J = 8.65, 4.56 Hz, 1H) 2.16-2.27 (m, 1H) 2.38 (br s, 1H) 2.52 (br s, 1H) 3.14-3.21 (m, 7H) 4.05-4.12 (m, 4H) 4.15 (t, J = 4.95 Hz, 1H) 4.24-4.32 (m, 2H) 7.39 (t, J = 9.49 Hz, 1H) 7.44-7.52 (m, 1H) 7.53-7.63 (m, 3H) 7.70 (s, 1H) 8.85 (br d, J = 6.09 Hz, 1H) |
| 20-12 | 2-chloro-N-((1R,2R,4S)-7-cyano-7-azabicyclo[2.2.1]heptan-2-yl)-4-(6-(2-cyano-2-propanyl)-2-pyridinyl)benzamide | 420.0 | 1H NMR (600 MHz, DMSO-d6) δ ppm 1.07 (s, 1H) 1.24 (s, 1H) 1.34-1.42 (m, 1H) 1.55-1.66 (m, 1H) 1.68-1.77 (m, 1H) 1.77-1.87 (m, 1H) 2.01 (ddd, J = 12.90, 8.99, 4.18 Hz, 1H) 2.18-2.23 (m, 1H) 2.37-2.49 (m, 4H) 3.14-3.24 (m, 1H) 4.02-4.10 (m, 2H) 4.15 (t, J = 5.04 Hz, 1H) 4.24-4.31 (m, 2H) 7.23 (s, 1H) 7.50 (s, 1H) 7.52-7.56 (m, 2H) 7.70 (dd, J = 7.95, 1.77 Hz, 1H) 7.80 (d, J = 1.73 Hz, 1H) 8.81 (br d, J = 5.90 Hz, 1H) |

| Ex # | Name | MS data | 1H NMR |
|---|---|---|---|
| 20-13 | 3-chloro-N-((1R,2R,4S)-7-cyano-7-azabicyclo[2.2.1]heptan-2-yl)-5'-(cyanomethyl)-2'-methyl[biphenyl]-4-carboxamide | 405.0 | 1H NMR (600 MHz, DMSO-d6) δ ppm 1.07 (s, 4H) 1.24 (s, 1H) 1.40 (dd, J = 12.67, 4.31 Hz, 1H) 1.55-1.65 (m, 1H) 1.68-1.77 (m, 1H) 1.78-1.86 (m, 1H) 2.02 (ddd, J = 12.92, 8.97, 4.18 Hz, 1H) 2.21- 2.27 (m, 3H) 2.37-2.47 (m, 1H) 3.17 (d, J = 5.27 Hz, 2H) 3.90 (s, 1H) 4.01-4.08 (m, 2H) 4.16 (t, J = 5.04 Hz, 1H) 4.24-4.32 (m, 1H) 7.18 (d, J = 1.82 Hz, 1H) 7.28-7.33 (m, 1H) 7.33-7.37 (m, 1H) 7.39 (dd, J = 7.81, 1.63 Hz, 1H) 7.47-7.54 (m, 1H) 8.83 (d, J = 5.99 Hz, 1H) |
| 20-14 | 3-chloro-N-((1R,2R,4S)-7-cyano-7-azabicyclo[2.2.1]heptan-2-yl)-3'-(cyanomethyl)-4'-methyl[biphenyl]-4-carboxamide | 405.0 | 1H NMR (600 MHz, DMSO-d6) δ ppm 1.07 (s, 1H) 1.24 (s, 1H) 1.34-1.42 (m, 1H) 1.55-1.66 (m, 1H) 1.68-1.77 (m, 1H) 1.77-1.87 (m, 1H) 2.01 (ddd, J = 12.90, 8.99, 4.18 Hz, 1H) 2.18-2.23 (m, 1H) 2.37-2.49 (m, 4H) 3.14-3.24 (m, 2H) 4.02-4.10 (m, 2H) 4.15 (t, J = 5.04 Hz, 1H) 4.24-4.31 (m, 2H) 7.23 (s, 1H) 7.50 (s, 1H) 7.52-7.56 (m, 2H) 7.70 (dd, J = 7.95, 1.77 Hz, 1H) 7.80 (d, J = 1.73 Hz, 1H) 8.81 (br d , J = 5.90 Hz, 1H) |
| 20-15 | 3-chloro-N-((1R,2R,4S)-7-cyano-7-azabicyclo[2.2.1]heptan-2-yl)-3'-(cyanomethyl)-5'-methyl[biphenyl]-4-carboxamide | 405.0 | 1H NMR (600 MHz, DMSO-d6) δ ppm 1.07 (s, 4H) 1.24 (s, 1H) 1.40 (dd, J = 12.67, 4.31 Hz, 1H) 1.55-1.65 (m, 1H) 1.68-1.77 (m, 1H) 1.78-1.86 (m, 1H) 2.02 (ddd, J = 12.92, 8.97, 4.18 Hz, 1H) 2.21-2.27 (m, 3H) 2.37-2.47 (m, 1H) 3.17 (d, J = 5.27 Hz, 2H) 3.90 (s, 1H) 4.01-4.08 (m, 2H) 4.16 (t, J = 5.04 Hz, 1H) 4.24-4.32 (m, 1H) 7.18 (d, J = 1.82 Hz, 1H) 7.28-7.33 (m, 1H) 7.33-7.37 (m, 1H) 7.39 (dd, J = 7.81, 1.63 Hz, 1H) 7.47-7.54 (m, 1H) 8.83 (d, J = 5.99 Hz, 1H) |
| 20-16 | 3-chloro-N-((1R,2R,4S)-7-cyano-7-azabicyclo[2.2.1]heptan-2-yl)-3'-(cyanomethyl)[biphenyl]-4-carboxamide | 391.0 | 1H NMR (600 MHz, DMSO-d6) δ ppm 1.24 (s, 1H) 1.39 (dd, J = 12.72, 4.27 Hz, 1H) 1.60 (ddd, J = 12.26, 8.72, 4.00 Hz, 1H) 1.77-1.86 (m, 1H) 2.01 (ddd, J = 12.90, 9.04, 4.31 Hz, 1H) 2.23 (br s, 1H) 2.52 (br d, J = 1.82 Hz, 1H) 4.10 (s, 2H) 4.15 (t, J = 4.90 Hz, 1H) 4.24-4.31 (m, 2H) 7.47 (m, J = 8.45 Hz, 2H) 7.53 (d, J = 7.90 Hz, 1H) 7.72 (dd, J = 7.99, 1.73 Hz, 1H) 7.75-7.78 (m, 2H) 7.82 (d, J = 1.73 Hz, 1H) 8.80 (br d, J = 6.09 Hz, 1H) |
| 20-17 | 3-chloro-N-((1R,2R,4S)-7-cyano-7-azabicyclo[2.2.1]heptan-2-yl)-3'-(1-cyanocyclobutyl)[biphenyl]-4-carboxamide | 431.0 | 1H NMR (600 MHz, DMSO-d6) δ ppm 1.07 (s, 2H) 1.24 (br s, 1H) 1.39 (dd, J = 12.62, 4.27 Hz, 1H) 1.60 (ddd, J = 12.38, 8.83, 3.77 Hz, 1H) 1.73 (br d, J = 12.17 Hz, 1H) 1.78-1.87 (m, 1H) 1.98-2.07 (m, 2H) 2.23 (br s, 1H) 2.31 (dt, J = 11.24, 8.78 Hz, 1H) 2.37-2.47 (m, 1H) 2.52 (br s, 1H) 2.70-2.81 (m, 4H) 4.15 (t, J = 4.86 Hz, 1H) 4.23-4.32 (m, 2H) 7.50-7.54 (m, 1H) 7.55 (dd, J = 8.99, 7.90 Hz, 2H) 7.57-7.61 (m, 1H) 7.70 (d, J = 8.07 Hz, 1H) 7.75 (s, 1H) 7.76 (d, J = 6.98 Hz, 1H) 7.89 (d, J = 1.73 Hz, 2H) 8.81 (br d, J = 5.99 Hz, 1H) |
| 20-18 | 2-chloro-N-((1R,2R,4S)-7-cyano-7-azabicyclo[2.2.1]heptan-2-yl)-4-(6-(methoxymethyl)-2-pyridinyl)benzamide | 397.0 | 1H NMR (600 MHz, DMSO-d6) δ ppm 1.24 (s, 1H) 1.40 (dd, J = 12.67, 4.22 Hz, 1H) 1.57-1.68 (m, 1H) 1.68-1.77 (m, 1H) 1.78-1.85 (m, 1H) 2.02 (tt, J = 8.66, 4.55 Hz, 1H) 2.16-2.26 (m, 1H) 2.52 (br d, J = 1.82 Hz, 1H) 4.11-4.21 (m, 1H) 4.21-4.31 (m, 2H) 4.59 (s, 2H) 7.44 (d, J = 7.54 Hz, 1H) 7.57 (d, J = 7.99 Hz, 1H) 7.92-8.00 (m, 2H) 8.12 (dd, J = 7.99, 1.73 Hz, 1H) 8.21 (d, J = 1.64 Hz, 1H) 8.84 (br d, J = 6.27 Hz, 1H) |
| 20-19 | 3-chloro-N-((1R,2R,4S)-7-cyano-7-azabicyclo[2.2.1]heptan-2-yl)-4'-(cyanomethyl)[biphenyl]-4-carboxamide | 391.0 | 1H NMR (600 MHz, DMSO-d6) δ ppm 1.24 (s, 1H) 1.39 (dd, J = 12.72, 4.27 Hz, 1H) 1.60 (ddd, J = 12.26, 8.72, 4.00 Hz, 1H) 1.77-1.86 (m, 1H) 2.01 (ddd, J = 12.90, 9.04, 4.31 Hz, 1H) 2.23 (br s, 1H) 2.52 (br d, J = 1.82 Hz, 1H) 4.10 (s, 2H) 4.15 (t, J = 4.90 Hz, 1H) 4.24-4.31 (m, 2H) 7.47 (m, J = 8.45 Hz, 2H) 7.53 (d, J = 7.90 Hz, 1H) 7.72 (dd, J = 7.99, 1.73 Hz, 1H) 7.75-7.78 (m, 2H) 7.82 (d, J = 1.73 Hz, 1H) 8.80 (br d, J = 6.09 Hz, 1H) |
| 20-20 | 2-chloro-N-((1R,2R,4S)-7-cyano-7-azabicyclo[2.2.1]heptan-2-yl)-4-(5-(1-cyanocyclopropyl)-3-pyridinyl)benzamide | 418.0 | |

-continued

| Ex # | Name | MS data | 1H NMR |
|---|---|---|---|
| 20-21 | 4-(6-(acetyl(methyl)amino)-2-pyridinyl)-2-chloro-N-((1R,2R,4S)-7-cyano-7-azabicyclo[2.2.1]heptan-2-yl)benzamide | 424.0 | |
| 20-22 | 2-chloro-N-((1R,2R,4S)-7-cyano-7-azabicyclo[2.2.1]heptan-2-yl)-4-(5-(cyanomethyl)-3-pyridinyl)benzamide | 392.0 | 1H NMR (500 MHz, DMSO-d6) δ ppm 0.80-0.90 (m, 1H) 1.24 (br s, 3H) 1.39 (dd, J = 12.72, 4.02 Hz, 5H) 1.54-1.66 (m, 5H) 1.68-1.77 (m, 5H) 1.78-1.91 (m, 5H) 2.02 (ddd, J = 12.78, 9.02, 4.02 Hz, 5H) 2.19-2.28 (m, 5H) 3.31 (s, 9H) 4.14-4.18 (m, 15H) 4.24-4.32 (m, 10H) 7.59 (d, J = 7.91 Hz, 5H) 7.80 (dd, J = 7.91, 1.82 Hz, 5H) 7.94 (d, J = 1.69 Hz, 5H) 8.17 (t, J = 2.14 Hz, 5H) 8.62 (d, J = 2.08 Hz, 5H) 8.85 (d, J = 5.84 Hz, 5H) 8.93 (d, J = 2.21 Hz, 5H) |
| 20-23 | 2-chloro-N-((1R,2R,4S)-7-cyano-7-azabicyclo[2.2.1]heptan-2-yl)-4-(4-(cyanomethyl)-2-pyridinyl)benzamide | 392.0 | 1H NMR (500 MHz, DMSO-d6) δ ppm 0.86 (br t, J = 6.88 Hz, 1H) 1.17 (br t, J = 7.07 Hz, 1H) 1.22-1.31 (m, 2H) 1.33-1.46 (m, 5H) 1.54-1.66 (m, 5H) 1.68-1.77 (m, 5H) 1.77-1.88 (m, 5H) 1.95-2.08 (m, 5H) 2.17-2.30 (m, 5H) 3.31 (s, 11H) 4.14-4.23 (m, 13H) 4.24-4.33 (m, 10H) 7.44 (d, J = 4.54 Hz, 4H) 7.54-7.64 (m, 5H) 7.78 (dd, J = 7.98, 1.49 Hz, 1H) 7.93 (d, J = 1.56 Hz, 1H) 8.04-8.15 (m, 8H) 8.21 (d, J = 1.30 Hz, 4H) 8.72 (d, J = 5.06 Hz, 4H) 8.79-8.94 (m, 5H) |
| 20-24 | N-((1R,2R,4S)-7-cyano-7-azabicyclo[2.2.1]heptan-2-yl)-4-(6-(1-cyanocyclopropyl)-2-pyridinyl)-2-methylbenzamide | 398.0 | 1H NMR (500 MHz, DMSO-d6) δ ppm 0.83-0.88 (m, 1H) 1.07 (s, 1H) 1.17 (td, J = 6.81, 1.43 Hz, 1H) 1.22-1.31 (m, 2H) 1.41 (dd, J = 12.65, 4.48 Hz, 1H) 1.58-1.67 (m, 1H) 1.68-1.77 (m, 1H) 1.78-1.87 (m, 5H) 1.89-1.99 (m, 1H) 2.17-2.28 (m, 1H) 2.41 (s, 3H) 3.08 (br s, 1H) 4.15 (t, J = 4.93 Hz, 1H) 4.23-4.33 (m, 2H) 7.45 (d, J = 7.67 Hz, 1H) 7.50-7.56 (m, 1H) 7.86-7.96 (m, 4H) 8.62 (d, J = 6.10 Hz, 1H) |
| 20-25 | 3-chloro-N-((1R,2R,4S)-7-cyano-7-azabicyclo[2.2.1]heptan-2-yl)-3'-(1-cyanocyclopropyl)[biphenyl]-4-carboxamide | 416.4 | 1H NMR (600 MHz, DMSO-d6) δ ppm 1.06-1.08 (m, 5H) 1.35-1.42 (m, 1H) 1.58-1.64 (m, 1H) 1.64-1.68 (m, 1H) 1.69-1.75 (m, 1H) 1.77-1.79 (m, 1H) 1.82 (br dd, J = 7.54, 4.36 Hz, 1H) 2.01 (ddd, J = 12.97, 9.01, 4.27 Hz, 1H) 2.18-2.28 (m, 1H) 2.51-2.60 (m, 1H) 3.90 (s, 1H) 4.15 (t, J = 5.00 Hz, 1H) 4.24-4.32 (m, 1H) 7.45 (d, J = 7.88 Hz, 1H) 7.50-7.57 (m, 2H) 7.66 (dt, J = 8.04, 1.25 Hz, 1H) 7.73 (dd, J = 7.99, 1.73 Hz, 1H) 7.87 (d, J = 1.73 Hz, 1H) 8.81 (br d, J = 5.90 Hz, 1H) |
| 20-26 | 2-chloro-N-((1R,2R,4S)-7-cyano-7-azabicyclo[2.2.1]heptan-2-yl)-4-(2-(cyanomethyl)-3-pyridinyl)benzamide | 392.0 | 1H NMR (600 MHz, DMSO-d6) δ ppm 1.40 (dd, J = 12.72, 4.27 Hz, 1H) 1.57-1.65 (m, 1H) 1.68-1.77 (m, 1H) 1.77-1.87 (m, 1H) 2.02 (ddd, J = 12.97, 9.06, 4.31 Hz, 1H) 2.19-2.27 (m, 1H) 2.51-2.60 (m, 1H) 3.17 (d, J = 5.27 Hz, 1H) 3.23-3.28 (m, 1H) 4.12-4.19 (m, 3H) 4.24-4.32 (m, 2H) 7.47 (dd, J = 7.81, 1.73 Hz, 1H) 7.51 (dd, J = 7.72, 4.81 Hz, 1H) 7.57 (d, J = 8.55 Hz, 1H) 7.63 (d, J = 1.63 Hz, 1H) 7.74 (dd, J = 7.77, 1.68 Hz, 1H) 8.65 (dd, J = 4.81, 1.73 Hz, 1H) 8.86 (d, J = 5.90 Hz, 1H) |
| 20-27 | N-((1R,2R,4S)-7-cyano-7-azabicyclo[2.2.1]heptan-2-yl)-4-(6-(1-cyanocyclopropyl)-2-pyridinyl)-2-(trifluoromethyl)benzamide | 452.0 | 1H NMR (600 MHz, DMSO-d6) δ ppm 1.06-1.09 (m, 2H) 1.24 (s, 1H) 1.32-1.40 (m, 1H) 1.55-1.62 (m, 1H) 1.67-1.77 (m, 1H) 1.79-1.89 (m, 5H) 1.94 (ddd, J = 12.94, 9.04, 4.36 Hz, 1H) 2.18-2.28 (m, 1H) 3.23-3.28 (m, 1H) 4.15 (t, J = 5.00 Hz, 1H) 4.23 (t, J = 4.63 Hz, 1H) 4.26-4.32 (m, 1H) 7.58 (dd, J = 7.81, 0.73 Hz, 1H) 7.69 (d, J = 7.90 Hz, 1H) 8.00 (t, J = 7.81 Hz, 1H) 8.07 (dd, J = 7.90, 0.64 Hz, 1H) 8.42 (d, J = 7.77 Hz, 1H) 8.43 (s, 1H) 8.89 (d, J = 6.36 Hz, 1H) |
| 20-28 | N-((1R,2R,4S)-7-cyano-7-azabicyclo[2.2.1]heptan-2-yl)-4-(6-(1-cyanocyclopropyl)-2-pyridinyl)-2-fluorobenzamide | 402.0 | 1H NMR (600 MHz, DMSO-d6) δ ppm 1.24 (s, 1H) 1.44 (dd, J = 12.76, 4.50 Hz, 1H) 1.60-1.67 (m, 1H) 1.68-1.76 (m, 1H) 1.79-1.89 (m, 5H) 1.94 (ddd, J = 12.85, 8.99, 4.22 Hz, 1H) 2.18-2.29 (m, 1H) 3.22-3.28 (m, 1H) 4.16 (t, J = 4.86 Hz, 1H) 4.24-4.28 (m, 1H) 4.30 (br dd, J = 11.22, 4.95 Hz, 1H) 7.58 (d, J = 7.36 Hz, 1H) 7.68 (t, J = 7.72 Hz, 1H) 7.95-8.02 (m, 4H) 8.72 (br d, J = 6.27 Hz, 1H) |

| Ex # | Name | MS data | 1H NMR |
|---|---|---|---|
| 20-29 | N-((1R,2R,4S)-7-cyano-7-azabicyclo[2.2.1]heptan-2-yl)-4-(1-methyl-1H-pyrazol-3-yl)-2-(trifluoromethyl)benzamide | 390.0 | 1H NMR (600 MHz, DMSO-d6) δ ppm 1.07 (s, 2H) 1.37 (dd, J = 12.72, 4.63 Hz, 1H) 1.55-1.65 (m, 1H) 1.71 (br d, J = 12.62 Hz, 1H) 1.76-1.84 (m, 1H) 1.93 (ddd, J = 13.03, 8.99, 4.13 Hz, 1H) 2.20-2.26 (m, 1H) 3.22-3.28 (m, 1H) 3.89-3.94 (m, 3H) 4.15 (t, J = 4.90 Hz, 1H) 4.22 (t J = 4.68 Hz, 1H) 4.27 (br dd, J = 11.26, 4.72 Hz, 1H) 6.90 (d, J = 2.27 Hz, 1H) 7.58 (d, J = 7.99 Hz, 1H) 7.80 (d, J = 2.27 Hz, 1H) 8.12 (d, J = 8.07 Hz, 1H) 8.84 (d, J = 6.36 Hz, 1H) |
| 20-30 | N-((1R,2R,4S)-7-cyano-7-azabicyclo[2.2.1]heptan-2-yl)-4-(imidazo[1,5-a]pyridin-6-yl)-2-(trifluoromethyl)benzamide | 426.0 | 1H NMR (600 MHz, DMSO-d6) δ ppm 0.99-1.10 (m, 1H) 1.37 (dd, J = 12.72, 4.63 Hz, 1H) 1.55-1.65 (m, 1H) 1.68-1.77 (m, 1H) 1.77-1.86 (m, 1H) 1.95 (ddd, J = 13.06, 9.11, 4.18 Hz, 1H) 2.21-2.28 (m, 1H) 2.51-2.56 (m, 1H) 3.17 (d, J = 5.09 Hz, 1H) 4.16 (t, J = 4.90 Hz, 1H) 4.23 (t, J = 4.68 Hz, 1H) 4.29 (br dd, J = 11.31, 4.68 Hz, 1H) 7.22 (dd, J = 9.45, 1.54 Hz, 1H) 7.42 (s, 1H) 7.67 (br d, J = 7.90 Hz, 1H) 7.69 (br d, J = 9.45 Hz, 1H) 8.06 (dd, J = 7.95, 1.59 Hz, 1H) 8.08 (s, 1H) 8.42 (s, 1H) 8.88 (br d, J = 6.36 Hz, 1H) 8.90 (d, J = 1.36 Hz, 1H) |
| 20-31 | N-((1R,2R,4S)-7-cyano-7-azabicyclo[2.2.1]heptan-2-yl)-2-fluoro-4-(1-methyl-1H-pyrazol-3-yl)benzamide | 340.0 | 1H NMR (600 MHz, DMSO-d6) δ ppm 1.45 (dd, J = 12.72, 4.54 Hz, 1H) 1.62-1.74 (m, 2H) 1.76-1.85 (m, 1H) 1.93 (ddd, J = 12.85, 8.90, 4.31 Hz, 1H) 2.17-2.25 (m, 1H) 3.23-3.28 (m, 1H) 3.90 (s, 3H) 4.15 (t, J = 4.90 Hz, 1H) 4.22-4.26 (m, 1H) 4.26-4.32 (m, 1H) 6.83 (d, J = 2.36 Hz, 1H) 7.59 (t, J = 7.77 Hz, 1H) 7.65 (dd, J = 11.72, 1.45 Hz, 1H) 7.70 (dd, J = 7.99, 1.45 Hz, 1H) 7.78 (d, J = 2.18 Hz, 1H) 8.62 (br d, J = 6.18 Hz, 1H) |
| 20-32 | N-((1R,2R,4S)-7-cyano-7-azabicyclo[2.2.1]heptan-2-yl)-2-fluoro-4-(imidazo[1,5-a]pyridin-6-yl)benzamide | 376.0 | 1H NMR (600 MHz, DMSO-d6) δ ppm 1.45 (dd, J = 12.81, 4.54 Hz, 1H) 1.62-1.75 (m, 2H) 1.78-1.88 (m, 1H) 1.94 (ddd, J = 12.92, 8.97, 4.27 Hz, 1H) 2.18-2.27 (m, 1H) 3.23-3.28 (m, 1H) 3.32-3.43 (m, 1H) 4.16 (t, J = 5.00 Hz, 1H) 4.24-4.28 (m, 1H) 4.28-4.33 (m, 1H) 7.20 (dd, J = 9.54, 1.54 Hz, 1H) 7.41 (s, 1H) 7.63-7.71 (m, 4H) 8.41 (s, 1H) 8.69 (br d, J = 6.18 Hz, 1H) 8.86 (d, J = 1.27 Hz, 1H) |
| 20-33 | 2,6-dichloro-N-((1R,2R,4S)-7-cyano-7-azabicyclo[2.2.1]heptan-2-yl)-4-(1-methyl-1H-pyrazol-3-yl)benzamide | 391.8 | 1H NMR (600 MHz, DMSO-d6) δ ppm 1.05-1.09 (m, 2H) 1.09-1.17 (m, 1H) 1.24 (br s, 1H) 1.33 (dd, J = 12.76, 4.13 Hz, 1H) 1.48-1.60 (m, 1H) 1.66-1.77 (m, 1H) 1.77-1.85 (m, 1H) 2.06 (ddd, J = 12.99, 9.08, 4.18 Hz, 1H) 2.25 (br s, 1H) 2.38 (br s, 1H) 3.18-3.29 (m, 2H) 3.32-3.41 (m, 1H) 3.90 (s, 3H) 4.16 (t, J = 4.90 Hz, 1H) 4.23-4.30 (m, 2H) 6.91 (d, J = 2.27 Hz, 1H) 7.79 (d, J = 2.27 Hz, 1H) 7.89 (s, 2H) 9.03 (br d, J = 6.00 Hz, 1H) |
| 20-34 | 2,6-dichloro-N-((1R,2R,4S)-7-cyano-7-azabicyclo[2.2.1]heptan-2-yl)-4-(imidazo[1,5-a]pyridin-6-yl)benzamide | 427.8 | 1H NMR (600 MHz, DMSO-d6) δ ppm 1.33 (dd, J = 12.67, 4.04 Hz, 1H) 1.53-1.61 (m, 1H) 1.68-1.78 (m, 1H) 1.78-1.87 (m, 1H) 2.07 (ddd, J = 12.94, 9.04, 4.27 Hz, 1H) 2.26 (br t, J = 10.85 Hz, 1H) 3.17 (br d, J = 5.18 Hz, 1H) 3.22-3.29 (m, 2H) 3.32-3.40 (m, 1H) 4.16 (t, J = 4.95 Hz, 1H) 4.24-4.32 (m, 2H) 7.21 (dd, J = 9.54, 1.54 Hz, 1H) 7.41 (s, 1H) 7.67 (d, J = 9.54 Hz, 1H) 7.90 (s, 2H) 8.39 (s, 1H) 8.91 (s, 1H) 9.06 (br d, J = 6.09 Hz, 1H) |
| 20-35 | 2-chloro-N-((1R,2R,4S)-7-cyano-7-azabicyclo[2.2.1]heptan-2-yl)-4-(5-cyano-2-pyrimidinyl)benzamide | 378.8 | 1H NMR (600 MHz, DMSO-d6) δ ppm 0.78-0.89 (m, 1H) 1.24 (s, 2H) 1.28 (s, 1H) 1.33-1.42 (m, 1H) 1.55-1.65 (m, 1H) 1.74 (br d, J = 10.54 Hz, 1H) 1.78-1.87 (m, 1H) 2.02 (ddd, J = 12.92, 9.01, 4.22 Hz, 1H) 2.17-2.28 (m, 1H) 2.52 (br d, J = 1.82 Hz, 1H) 3.23-3.28 (m, 1H) 4.16 (t, J = 4.95 Hz, 1H) 4.25-4.33 (m, 2H) 7.68 (d, J = 7.90 Hz, 1H) 7.73 (br s, 1H) 8.43 (dd, J = 7.95, 1.59 Hz, 1H) 8.46 (d, J = 1.64 Hz, 1H) 8.63 (s, 1H) 8.94 (br d, J = 6.08 Hz, 1H) 9.43 (s, 2H) |
| 20-36 | 2-chloro-N-((1R,2R,4S)-7-cyano-7-azabicyclo[2.2.1]heptan-2-yl)-4-(4-cyano-2-pyrimidinyl)benzamide | 378.8 | 1H NMR (600 MHz, DMSO-d6) δ ppm 1.24 (s, 1H) 1.39 (dd, J = 12.67, 4.31 Hz, 1H) 1.55-1.65 (m, 1H) 1.69-1.78 (m, 1H) 1.78-1.87 (m, 1H) 2.02 (ddd, J = 12.94, 8.99, 4.31 Hz, 1H) 2.24 (br t, J = 11.04 Hz, 1H) 2.51-2.60 (m, 1H) 3.17-3.28 (m, 2H) 4.16 (t, J = 4.95 Hz, 1H) 4.25-4.33 (m, 2H) 7.67 (d, J = 7.99 Hz, 1H) 8.15 (d, J = 4.90 Hz, 1H) 8.38 (dd, J = 7.99, 1.64 Hz, 1H) 8.40 (d, J = 1.63 Hz, 1H) 8.93 (br d, J = 5.99 Hz, 1H) 9.28 (d, J = 4.90 Hz, 1H) |

| Ex # | Name | MS data | 1H NMR |
|---|---|---|---|
| 20-37 | 2-chloro-N-((1R,2R,4S)-7-cyano-7-azabicyclo[2.2.1]heptan-2-yl)-4-(6-methyl-2-pyrazinyl)benzamide | 368.0 | 1H NMR (600 MHz, DMSO-d6) δ ppm 1.24 (br s, 1H) 1.39 (dd, J = 12.72, 4.27 Hz, 1H) 1.55-1.64 (m, 1H) 1.74 (br d, J = 12.44 Hz, 1H) 1.78-1.86 (m, 1H) 2.02 (ddd, J = 12.94, 9.08, 4.22 Hz, 1H) 2.20-2.27 (m, 1H) 2.38 (br s, 1H) 2.57-2.62 (m, 3H) 3.23-3.29 (m, 2H) 3.32-3.43 (m, 1H) 4.16 (t, J = 4.86 Hz, 1H) 4.24-4.32 (m, 2H) 7.60 (d, J = 7.90 Hz, 1H) 8.17 (dd, J = 7.99, 1.73 Hz, 1H) 8.26 (d, J = 1.73 Hz, 1H) 8.58 (s, 1H) 8.87 (br d, J = 5.99 Hz, 1H) 9.15 (s, 1H) |
| 20-38 | 2-chloro-N-((1R,2R,4S)-7-cyano-7-azabicyclo[2.2.1]heptan-2-yl)-4-(5-methyl-2-pyrazinyl)benzamide | 368.0 | 1H NMR (600 MHz, DMSO-d6) δ ppm 1.24 (s, 1H) 1.34-1.42 (m, 1H) 1.55-1.65 (m, 1H) 1.68-1.77 (m, 1H) 1.77-1.86 (m, 1H) 2.02 (ddd, J = 12.97, 9.06, 4.13 Hz, 1H) 2.17-2.27 (m, 1H) 2.56 (s, 3H) 4.16 (t, J = 4.90 Hz, 1H) 4.25-4.32 (m, 2H) 7.59 (d, J = 7.99 Hz, 1H) 8.15 (dd, J = 7.99, 1.63 Hz, 1H) 8.24 (d, J = 1.63 Hz, 1H) 8.65 (d, J = 0.91 Hz, 1H) 8.85 (br d, J = 6.08 Hz, 1H) 9.21 (d, J = 1.45 Hz, 1H) |
| 20-39 | 2-chloro-N-((1R,2R,4S)-7-cyano-7-azabicyclo[2.2.1]heptan-2-yl)-4-(4-cyano-2-pyridinyl)benzamide | 378.0 | 1H NMR (600 MHz, DMSO-d6) δ ppm 1.07 (d, J = 1.00 Hz, 1H) 1.39 (dd, J = 12.90, 4.09 Hz, 1H) 1.56-1.65 (m, 1H) 1.68-1.77 (m, 1H) 1.78-1.86 (m, 1H) 2.02 (ddd, J = 12.97, 9.15, 4.13 Hz, 1H) 2.18-2.27 (m, 1H) 3.23-3.28 (m, 1H) 4.16 (t, J = 5.00 Hz, 1H) 4.24-4.32 (m, 2H) 7.61 (s, 1H) 7.89 (dt, J = 4.97, 1.19 Hz, 1H) 8.20 (d, J = 8.15 Hz, 1H) 8.30 (s, 1H) 8.63 (d, J = 1.00 Hz, 1H) 8.87 (br d, J = 5.81 Hz, 1H) 8.94 (d, J = 5.73 Hz, 1H) |
| 20-40 | 2-chloro-N-((1R,2R,4S)-7-cyano-7-azabicyclo[2.2.1]heptan-2-yl)-4-(6-methyl-2-pyridinyl)benzamide | 367.0 | 1H NMR (600 MHz, DMSO-d6) δ ppm 1.06-1.09 (m, 6H) 1.24 (s, 1H) 1.40 (dd, J = 12.85, 4.13 Hz, 1H) 1.55-1.67 (m, 1H) 1.78-1.86 (m, 1H) 2.02 (ddd, J = 12.97, 9.06, 4.04 Hz, 1H) 2.56 (s, 2H) 3.90 (s, 1H) 4.16 (t, J = 4.90 Hz, 1H) 4.22-4.31 (m, 2H) 7.26-7.32 (m, 1H) 7.55 (d, J = 7.99 Hz, 1H) 7.81 (t, J = 7.72 Hz, 1H) 7.87 (d, J = 7.72 Hz, 1H) 8.11 (dd, J = 7.99, 1.73 Hz, 1H) 8.21 (d, J = 1.64 Hz, 1H) 8.83 (br d, J = 5.90 Hz, 1H) |
| 20-41 | 2-chloro-N-((1R,2R,4S)-7-cyano-7-azabicyclo[2.2.1]heptan-2-yl)-4-(2-methyl-4-pyrimidinyl)benzamide | 368.0 | 1H NMR (600 MHz, DMSO-d6) δ ppm 1.39 (dd, J = 12.72, 4.18 Hz, 1H) 1.55-1.64 (m, 1H) 1.69-1.78 (m, 1H) 1.78-1.86 (m, 1H) 2.01 (ddd, J = 12.81, 8.95, 4.22 Hz, 1H) 2.24 (br t, J = 11.04 Hz, 1H) 2.39-2.48 (m, 1H) 2.71 (s, 3H) 3.27 (s, 1H) 4.16 (t, J = 4.95 Hz, 1H) 4.25-4.32 (m, 2H) 7.62 (d, J = 7.99 Hz, 1H) 8.00 (d, J = 5.36 Hz, 1H) 8.22 (dd, J = 7.99, 1.27 Hz, 1H) 8.32 (d, J = 1.54 Hz, 1H) 8.81 (d, J = 5.36 Hz, 1H) 8.89 (br d, J = 5.90 Hz, 1H) |
| 20-42 | 2-chloro-N-((1R,2R,4S)-7-cyano-7-azabicyclo[2.2.1]heptan-2-yl)-4-(6-methyl-3-pyridazinyl)benzamide | 368.0 | 1H NMR (600 MHz, DMSO-d6) δ ppm 1.24 (s, 1H) 1.39 (dd, J = 12.76, 4.22 Hz, 1H) 1.55-1.64 (m, 1H) 1.69-1.78 (m, 1H) 1.79-1.86 (m, 1H) 2.03 (ddd, J = 12.94, 9.04, 4.18 Hz, 1H) 2.24 (br s, 1H) 2.38 (br d, J = 1.91 Hz, 1H) 2.52-2.57 (m, 1H) 2.68 (s, 3H) 3.22-3.28 (m, 1H) 4.16 (t, J = 4.86 Hz, 1H) 4.26-4.32 (m, 2H) 7.62 (d, J = 7.99 Hz, 1H) 7.71 (d, J = 8.81 Hz, 1H) 8.17 (dd, J = 7.99, 1.64 Hz, 1H) 8.24 (d, J = 8.72 Hz, 1H) 8.27 (d, J = 1.63 Hz, 1H) 8.87 (br d, J = 6.18 Hz, 1H) |
| 20-43 | 2-chloro-N-((1R,2R,4S)-7-cyano-7-azabicyclo[2.2.1]heptan-2-yl)-4-(6-(difluoromethyl)-2-pyridinyl)benzamide | 403.0 | 1H NMR (600 MHz, DMSO-d6) δ ppm 1.04-1.11 (m, 1H) 1.39 (dd, J = 12.72, 4.27 Hz, 1H) 1.57-1.64 (m, 1H) 1.69-1.77 (m, 1H) 1.78-1.86 (m, 1H) 2.02 (ddd, J = 12.83, 8.97, 4.27 Hz, 1H) 2.18-2.28 (m, 1H) 3.21-3.28 (m, 1H) 4.16 (t, J = 5.00 Hz, 1H) 4.24-4.32 (m, 2H) 6.96 (s, 1H) 7.01-7.14 (m, 1H) 7.61 (d, J = 7.99 Hz, 1H) 7.73 (d, J = 7.63 Hz, 1H) 8.11-8.20 (m, 2H) 8.27 (d, J = 9.24 Hz, 1H) 8.26 (s, 1H) 8.87 (br d, J = 6.00 Hz, 1H) |
| 20-44 | 2-chloro-N-((1R,2R,4S)-7-cyano-7-azabicyclo[2.2.1]heptan-2-yl)-4-(6-(cyanomethyl)-2-pyridinyl)benzamide | 392.0 | 1H NMR (600 MHz, DMSO-d6) δ ppm 1.07 (s, 1H) 1.39 (dd, J = 12.76, 4.31 Hz, 1H) 1.56-1.67 (m, 1H) 1.68-1.78 (m, 1H) 1.82 (td, J = 7.86, 3.72 Hz, 1H) 2.02 (ddd, J = 13.06, 9.06, 4.22 Hz, 1H) 2.16-2.27 (m, 1H) 2.37-2.47 (m, 1H) 2.51-2.56 (m, 1H) 3.16-3.28 (m, 1H) 4.16 (t, J = 5.04 Hz, 1H) 4.25-4.33 (m, 4H) 7.46 (d, J = 7.63 Hz, 1H) 7.60 (d, J = 7.99 Hz, 1H) 7.97 (t, J = 7.81 Hz, 1H) 8.06 (d, J = 7.90 Hz, 1H) 8.15 (dd, J = 7.99, 1.73 Hz, 1H) 8.26 (d, J = 1.64 Hz, 1H) 8.85 (br d, J = 6.08 Hz, 1H) |

| Ex # | Name | MS data | 1H NMR |
|---|---|---|---|
| 20-45 | 2-chloro-N-((1R,2R,4S)-7-cyano-7-azabicyclo[2.2.1]heptan-2-yl)-4-(6-(difluoromethoxy)-2-pyridinyl)benzamide | 418.8 | 1H NMR (600 MHz, DMSO-d6) δ ppm 1.07 (s, 1H) 1.13 (br d, J = 7.27 Hz, 1H) 1.24 (s, 1H) 1.39 (dd, J = 12.67, 4.31 Hz, 1H) 1.57-1.64 (m, 1H) 1.74 (br d, J = 12.72 Hz, 1H) 1.78-1.87 (m, 1H) 2.02 (ddd, J = 12.87, 8.97, 4.13 Hz, 1H) 2.24 (br s, 1H) 2.37-2.47 (m, 1H) 2.52 (br d, J = 1.91 Hz, 1H) 3.16-3.28 (m, 2H) 4.16 (t, J = 4.90 Hz, 1H) 4.24-4.32 (m, 2H) 7.11 (d, J = 8.08 Hz, 1H) 7.58 (d, J = 7.99 Hz, 1H) 7.93-7.99 (m, 1H) 8.04 (t, J = 7.93 Hz, 1H) 8.08-8.17 (m, 1H) 8.25 (d, J = 1.64 Hz, 1H) 8.84 (br d, J = 5.72 Hz, 1H) |
| 20-46 | 2-chloro-N-((1R,2R,4S)-7-cyano-7-azabicyclo[2.2.1]heptan-2-yl)-4-(6-(1,1-difluoroethyl)-2-pyridinyl)benzamide | 417.0 | 1H NMR (600 MHz, DMSO-d6) δ ppm 1.07 (s, 4H) 1.24 (s, 1H) 1.39 (dd, J = 12.76, 4.31 Hz, 1H) 1.55-1.65 (m, 1H) 1.69-1.78 (m, 1H) 1.78-1.89 (m, 1H) 2.00-2.07 (m, 2H) 2.08-2.13 (m, 2H) 2.24 (br t, J = 11.26 Hz, 1H) 2.52 (br d, J = 1.82 Hz, 1H) 3.16-3.28 (m, 1H) 3.90 (s, 1H) 4.16 (t, J = 4.90 Hz, 1H) 4.25-4.32 (m, 2H) 7.60 (d, J = 7.99 Hz, 1H) 7.73 (dd, J = 7.72, 0.73 Hz, 1H) 8.12 (t, J = 7.86 Hz, 1H) 8.17 (dd, J = 7.99, 1.64 Hz, 1H) 8.24 (d, J = 10.95 Hz, 1H) 8.24 (s, 1H) 8.86 (br d, J = 6.09 Hz, 1H) |
| 20-47 | 2-chloro-N-((1R,2R,4S)-7-cyano-7-azabicyclo[2.2.1]heptan-2-yl)-4-(6-cyclopropyl-2-pyrazinyl)benzamide | 394.0 | 1H NMR (600 MHz, DMSO-d6) δ ppm 1.06-1.16 (m, 4H) 1.24 (br s, 1H) 1.38 (dd, J = 12.62, 4.18 Hz, 1H) 1.55-1.66 (m, 1H) 1.73 (br d, J = 12.99 Hz, 1H) 1.82 (br dd, J = 7.18, 3.00 Hz, 1H) 2.01 (ddd, J = 12.81, 8.95, 4.31 Hz, 1H) 2.23 (br s, 1H) 2.26-2.31 (m, 1H) 3.27 (br s, 1H) 4.15 (t, J = 4.90 Hz, 1H) 4.24-4.32 (m, 2H) 7.59 (d, J = 7.90 Hz, 1H) 8.12 (dd, J = 7.99, 1.64 Hz, 1H) 8.20 (d, J = 1.54 Hz, 1H) 8.64 (s, 1H) 8.84 (br d, J = 5.90 Hz, 1H) 9.06 (s, 1H) |
| 20-48 | 2-chloro-N-((1R,2R,4S)-7-cyano-7-azabicyclo[2.2.1]heptan-2-yl)-4-(6-cyano-2-pyridinyl)benzamide | 378.0 | 1H NMR (600 MHz, DMSO-d6) δ ppm 1.04-1.11 (m, 1H) 1.39 (dd, J = 12.72, 4.27 Hz, 1H) 1.57-1.64 (m, 1H) 1.69-1.77 (m, 1H) 1.78-1.86 (m, 1H) 2.02 (ddd, J = 12.83, 8.97, 4.27 Hz, 1H) 2.18-2.28 (m, 1H) 3.21-3.28 (m, 1H) 4.16 (t, J = 5.00 Hz, 1H) 4.24-4.32 (m, 2H) 6.96 (s, 1H) 7.01-7.14 (m, 1H) 7.61 (d, J = 7.99 Hz, 1H) 7.73 (d, J = 7.63 Hz, 1H) 8.11-8.20 (m, 2H) 8.27 (d, J = 9.24 Hz, 1H) 8.26 (s, 1H) 8.87 (br d, J = 6.00 Hz, 1H) |
| 20-49 | 2-chloro-N-((1R,2R,4S)-7-cyano-7-azabicyclo[2.2.1]heptan-2-yl)-4-(6-(1-cyanocyclopropyl)-2-pyridinyl)benzamide | 418.0 | 1H NMR (600 MHz, DMSO-d6) δ ppm 1.24 (s, 1H) 1.44 (dd, J = 12.76, 4.50 Hz, 1H) 1.60-1.67 (m, 1H) 1.68-1.76 (m, 1H) 1.79-1.89 (m, 5H) 1.94 (ddd, J = 12.85, 8.99, 4.22 Hz, 1H) 2.18-2.29 (m, 1H) 3.22-3.28 (m, 1H) 4.16 (t, J = 4.86 Hz, 1H) 4.24-4.28 (m, 1H) 4.30 (br dd, J = 11.22, 4.95 Hz, 1H) 7.58 (d, J = 7.36 Hz, 1H) 7.68 (t, J = 7.72 Hz, 1H) 7.95-8.02 (m, 4H) 8.72 (br d, J = 6.27 Hz, 1H) |
| 20-50 | 2-chloro-N-((1R,2R,4S)-7-cyano-7-azabicyclo[2.2.1]heptan-2-yl)-4-(6-(2,2,2-trifluoroethoxy)-2-pyridinyl)benzamide | 451.0 | 1H NMR (500 MHz, CHLOROFORM-d) δ ppm 0.90 (t, J = 6.94 Hz, 4H) 1.18 (dd, J = 12.98, 4.41 Hz, 5H) 1.25-1.34 (m, 9H) 1.60-1.66 (m, 5H) 1.96-2.15 (m, 15H) 2.55-2.61 (m, 5H) 4.11-4.14 (m, 5H) 4.49-4.52 (m, 4H) 4.53-4.59 (m, 5H) 4.89 (q, J = 8.56 Hz, 9H) 6.53 (br d, J = 5.71 Hz, 4H) 6.92 (d, J = 8.30 Hz, 4H) 7.27 (s, 1H) 7.46 (d, J = 7.53 Hz, 5H) 7.77 (t, J = 7.85 Hz, 5H) 7.86 (d, J = 8.17 Hz, 4H) 7.96 (dd, J = 8.17, 1.69 Hz, 4H) 8.06 (d, J = 1.69 Hz, 4H) |
| 20-51 | 2-chloro-N-((1R,2R,4S)-7-cyano-7-azabicyclo[2.2.1]heptan-2-yl)-4-(imidazo[1,2-a]pyridin-6-yl)benzamide | 392.0 | 1H NMR (500 MHz, DMSO-d6) δ ppm 1.40 (dd, J = 12.72, 4.02 Hz, 4H) 1.55-1.65 (m, 4H) 1.68-1.78 (m, 4H) 1.78-1.90 (m, 4H) 1.95-2.10 (m, 5H) 2.18-2.28 (m, 4H) 2.83 (s, 1H) 2.96-3.12 (m, 1H) 3.32-3.36 (m, 1H) 4.16 (t, J = 4.87 Hz, 4H) 4.24-4.32 (m, 8H) 7.57 (d, J = 7.91 Hz, 4H) 7.62-7.78 (m, 17H) 7.90 (d, J = 1.69 Hz, 4H) 7.98 (s, 4H) 8.14 (s, 2H) 8.84 (d, J = 5.97 Hz, 4H) 9.07 (s, 4H) |
| 20-52 | 2-chloro-N-((1R,2R,4S)-7-cyano-7-azabicyclo[2.2.1]heptan-2-yl)-4-(1-methyl-1H-indazol-7-yl)benzamide | 406.0 | 1H NMR (500 MHz, DMSO-d6) δ ppm 1.17 (t, J = 7.14 Hz, 4H) 1.43 (dd, J = 12.72, 4.28 Hz, 3H) 1.58-1.68 (m, 3H) 1.70-1.78 (m, 3H) 1.78-1.88 (m, 3H) 1.96-2.07 (m, 6H) 2.19-2.30 (m, 3H) 3.32 (s, 2H) 3.63-3.66 (m, 8H) 4.03 (q, J = 7.14 Hz, 2H) 4.16 (t, J = 4.93 Hz, 3H) 4.25-4.36 (m, 6H) 5.75 (s, 1H) 7.17-7.27 (m, 6H) 7.49-7.60 (m, 6H) 7.67 (d, J = 1.43 Hz, 3H) 7.80-7.88 (m, 3H) 8.15-8.18 (m, 3H) 8.89 (d, J = 5.97 Hz, 3H) |

| Ex # | Name | MS data | 1H NMR |
|---|---|---|---|
| 20-53 | 2-chloro-N-((1R,2R,4S)-7-cyano-7-azabicyclo[2.2.1]heptan-2-yl)-4-(7-methylimidazo[1,2-a]pyridin-6-yl)benzamide | 406.0 | 1H NMR (500 MHz, DMSO-d6) δ ppm 1.38-1.44 (m, 1H) 1.58-1.65 (m, 1H) 1.69-1.77 (m, 1H) 1.78-1.87 (m, 1H) 1.98-2.05 (m, 1H) 2.25 (br s, 4H) 2.29 (br s, 1H) 2.32-2.37 (m, 1H) 3.31-3.34 (m, 5H) 4.08-4.18 (m, 2H) 4.25-4.33 (m, 3H) 7.48 (br d, J = 7.66 Hz, 5H) 7.54 (br d, J = 7.79 Hz, 3H) 7.62 (s, 2H) 7.87 (br d, J = 8.17 Hz, 1H) 8.48 (br s, 1H) 8.87 (br d, J = 5.71 Hz, 1H) |
| 20-54 | 2-chloro-N-((1R,2R,4S)-7-cyano-7-azabicyclo[2.2.1]heptan-2-yl)-4-(2-methylimidazo[1,2-a]pyridin-6-yl)benzamide | 406.0 | 1H NMR (500 MHz, DMSO-d6) δ 1.36-1.50 (m, 2H), 1.56-1.66 (m, 2H), 1.69-1.78 (m, 2H), 1.78-1.93 (m, 2H), 1.96-2.15 (m, 2H), 2.22-2.47 (m, 14H), 2.52-2.58 (m, 1H), 2.99 (br s, 1H), 3.05 (s, 1H), 3.11-3.25 (m, 3H), 3.35 (br s, 8H), 4.10-4.21 (m, 2H), 4.25-4.34 (m, 4H), 6.80 (td, J = 6.71, 1.10 Hz, 1H), 6.92 (td, J = 6.84, 1.10 Hz, 2H), 7.08-7.21 (m, 2H), 7.29 (ddd, J = 8.99, 6.78, 1.10 Hz, 2H), 7.38-7.44 (m, 11H), 7.50-7.72 (m, 19H), 7.85 (s, 1H), 8.18 (br s, 2H), 8.29 (d, J = 6.74 Hz, 2H), 8.43 (dt, J = 6.75, 1.10 Hz, 1H), 8.80 (d, J = 10.12 Hz, 1H), 8.89 (d, J = 5.97 Hz, 2H) |
| 20-55 | 2-chloro-N-((1R,2R,4S)-7-cyano-7-azabicyclo[2.2.1]heptan-2-yl)-4-(imidazo[1,2-a]pyridin-7-yl)benzamide | 392.0 | 1H NMR (500 MHz, DMSO-d6) δ ppm 1.39 (dd, J = 12.72, 4.02 Hz, 1H) 1.56-1.65 (m, 1H) 1.68-1.87 (m, 2H) 1.95-2.09 (m, 1H) 2.19-2.27 (m, 1H) 3.11-3.26 (m, 1H) 4.16 (t, J = 4.93 Hz, 1H) 4.23-4.34 (m, 2H) 7.34 (dd, J = 7.14, 1.82 Hz, 1H) 7.55 (d, J = 8.04 Hz, 1H) 7.65 (d, J = 1.04 Hz, 1H) 7.87 (dd, J = 8.04, 1.82 Hz, 1H) 7.95-8.04 (m, 3H) 8.65 (dd, J = 7.14, 0.78 Hz, 1H) 8.84 (d, J = 5.97 Hz, 1H) |
| 20-56 | 2-chloro-N-((1R,2R,4S)-7-cyano-7-azabicyclo[2.2.1]heptan-2-yl)-4-(imidazo[1,5-a]pyridin-6-yl)benzamide | 392.0 | 1H NMR (500 MHz, DMSO-d6) δ ppm 1.17 (t, J = 7.07 Hz, 1H) 1.39 (dd, J = 12.72, 4.15 Hz, 1H) 1.57-1.64 (m, 1H) 1.69-1.86 (m, 2H) 1.97-2.04 (m, 2H) 2.19-2.27 (m, 1H) 3.31 (s, 4H) 4.03 (q, J = 7.14 Hz, 1H) 4.16 (t, J = 4.87 Hz, 1H) 4.25-4.32 (m, 2H) 7.18 (dd, J = 9.47, 1.56 Hz, 1H) 7.41 (s, 1H) 7.56 (d, J = 8.04 Hz, 1H) 7.67 (d, J = 9.47 Hz, 1H) 7.74 (dd, J = 8.04, 1.82 Hz, 1H) 7.87 (d, J = 1.69 Hz, 1H) 8.40 (s, 1H) 8.83 (d, J = 5.97 Hz, 1H) 8.85 (d, J = 1.30 Hz, 1H) |
| 20-57 | 2-chloro-N-((1R,2R,4S)-7-cyano-7-azabicyclo[2.2.1]heptan-2-yl)-4-(1-methyl-1H-pyrazol-3-yl)benzamide | 356.0 | 1H NMR (500 MHz, DMSO-d6) δ ppm 1.39 (dd, J = 12.85, 4.02 Hz, 4H) 1.57-1.63 (m, 4H) 1.67-1.75 (m, 4H) 1.77-1.85 (m, 4H) 1.97-2.03 (m, 4H) 2.18-2.25 (m, 4H) 3.01 (s, 1H) 3.31 (s, 15H) 3.58 (s, 1H) 3.90 (s, 13H) 4.15 (t, J = 4.93 Hz, 4H) 4.23-4.30 (m, 8H) 6.83 (d, J = 2.34 Hz, 4H) 7.30 (d, J = 2.21 Hz, 1H) 7.46 (d, J = 8.04 Hz, 7H) 7.74-7.89 (m, 14H) 8.79 (d, J = 5.84 Hz, 4H) |
| 20-58 | 2-chloro-N-((1R,2R,4S)-7-cyano-7-azabicyclo[2.2.1]heptan-2-yl)-4-(1-methyl-1H-pyrazol-5-yl)benzamide | 356.0 | 1H NMR (500 MHz, DMSO-d6) δ ppm 1.17 (t, J = 7.14 Hz, 2H) 1.38 (dd, J = 12.72, 4.15 Hz, 4H) 1.53-1.66 (m, 4H) 1.68-1.77 (m, 4H) 1.78-1.87 (m, 4H) 1.93-2.07 (m, 5H) 2.18-2.27 (m, 4H) 2.82 (s, 1H) 3.03 (s, 1H) 3.31 (s, 8H) 3.88 (s, 12H) 4.03 (d, J = 7.14 Hz, 1H) 4.16 (t, J = 4.93 Hz, 4H) 4.23-4.33 (m, 8H) 6.51 (d, J = 1.95 Hz, 4H) 7.50 (d, J = 1.82 Hz, 5H) 7.53-7.61 (m, 9H) 7.69-7.72 (m, 4H) 8.86 (d, J = 5.97 Hz, 4H) |
| 20-59 | 2-chloro-N-((1R,2R,4S)-7-cyano-7-azabicyclo[2.2.1]heptan-2-yl)-4-(1-cyclopropyl-1H-pyrazol-4-yl)benzamide | 382.0 | 1H NMR (500 MHz, DMSO-d6) δ ppm 0.85 (s, 1H) 0.92-1.10 (m, 17H) 1.17 (t, J = 7.07 Hz, 1H) 1.39 (dd, J = 12.78, 3.96 Hz, 3H) 1.54-1.65 (m, 3H) 1.67-1.76 (m, 3H) 1.76-1.86 (m, 3H) 1.94-2.04 (m, 6H) 2.11-2.25 (m, 3H) 3.32 (s, 4H) 3.65-3.80 (m, 4H) 4.03 (q, J = 7.14 Hz, 2H) 4.14 (t, J = 4.87 Hz, 3H) 4.21-4.31 (m, 6H) 7.41 (d, J = 8.04 Hz, 3H) 7.52 (br s, 1H) 7.55-7.65 (m, 5H) 7.76 (d, J = 1.56 Hz, 3H) 7.90 (s, 1H) 7.96-8.00 (m, 3H) 8.35-8.41 (m, 3H) 8.74 (br d, J = 5.71 Hz, 3H) |
| 20-60 | 2-chloro-N-((1R,2R,4S)-7-cyano-7-azabicyclo[2.2.1]heptan-2-yl)-4-(1-(cyanomethyl)-1H-pyrazol-4-yl)benzamide | 381.0 | 1H NMR (500 MHz, DMSO-d6) δ ppm 1.17 (t, J = 7.07 Hz, 2H) 1.39 (dd, J = 12.78, 3.96 Hz, 3H) 1.54-1.66 (m, 3H) 1.67-1.76 (m, 3H) 1.76-1.86 (m, 3H) 1.92-2.07 (m, 5H) 2.11-2.26 (m, 3H) 3.32 (s, 2H) 4.03 (q, J = 7.14 Hz, 1H) 4.15 (t, J = 4.93 Hz, 3H) 4.21-4.32 (m, 6H) 5.53 (s, 6H) 5.75 (s, 1H) 7.45 (d, J = 7.91 Hz, 3H) 7.64 (dd, J = 7.98, 1.62 Hz, 3H) 7.80 (d, J = 1.56 Hz, 3H) 8.18 (s, 3H) 8.43 (s, 3H) 8.76 (br d, J = 5.84 Hz, 3H) |

| Ex # | Name | MS data | 1H NMR |
|---|---|---|---|
| 20-61 | 2-chloro-N-((1R,2R,4S)-7-cyano-7-azabicyclo[2.2.1]heptan-2-yl)-4-(1-methyl-1H-imidazol-4-yl)benzamide | 356.0 | 1H NMR (500 MHz, DMSO-d6) δ ppm 1.38 (d, J = 4.28 Hz, 2H) 1.40 (d, J = 3.76 Hz, 2H) 1.57-1.63 (m, 4H) 1.70-1.74 (m, 3H) 1.80 (td, J = 7.75, 4.09 Hz, 3H) 2.00 (ddd, J = 12.75, 8.99, 4.09 Hz, 4H) 2.21 (br s, 2H) 3.29-3.33 (m, 31H) 3.64 (s, 1H) 3.69 (s, 13H) 4.14 (t, J = 4.87 Hz, 4H) 4.24-4.28 (m, 8H) 7.42 (d, J = 7.91 Hz, 4H) 7.68 (s, 4H) 7.74 (dd, J = 7.91, 1.56 Hz, 4H) 7.78 (d, J = 1.17 Hz, 4H) 7.83 (d, J = 1.43 Hz, 4H) 8.73 (d, J = 5.84 Hz, 4H) |
| 20-62 | 2-chloro-N-((1R,2R,4S)-7-cyano-7-azabicyclo[2.2.1]heptan-2-yl)-4-(1-methyl-1H-pyrazol-4-yl)benzamide | 356.0 | 1H NMR (500 MHz, DMSO-d6) δ ppm 1.39 (dd, J = 12.78, 3.96 Hz, 1H) 1.54-1.65 (m, 1H) 1.67-1.76 (m, 1H) 1.76-1.86 (m, 1H) 1.91-2.08 (m, 1H) 2.16-2.26 (m, 1H) 3.32 (s, 1H) 3.86 (s, 3H) 4.14 (t, J = 4.93 Hz, 1H) 4.21-4.30 (m, 2H) 7.42 (d, J = 7.91 Hz, 1H) 7.59 (dd, J = 7.98, 1.62 Hz, 1H) 7.74 (d, J = 1.56 Hz, 1H) 7.98 (s, 1H) 8.28 (s, 1H) 8.73 (br d, J = 5.71 Hz, 1H) |
| 20-63 | N-((1R,2R,4S)-7-cyano-7-azabicyclo[2.2.1]heptan-2-yl)-4-(4-cyano-2-pyridinyl)-3-(2-methylpropoxy)benzamide | 416.2 | 1H NMR (600 MHz, DMSO-d6) δ ppm 0.06-0.09 (m, 1H) 0.96-1.03 (m, 6H) 1.59 (dd, J = 12.81, 4.55 Hz, 1H) 1.64-1.74 (m, 2H) 1.79-1.90 (m, 2H) 2.07 (dt, J = 13.12, 6.52 Hz, 1H) 2.36-2.47 (m, 2H) 3.20 (br s, 1H) 3.25-3.30 (m, 2H) 3.97 (d, J = 6.15 Hz, 2H) 4.18 (t, J = 4.83 Hz, 1H) 4.23-4.33 (m, 2H) 7.38 (s, 1H) 7.56 (d, J = 1.48 Hz, 1H) 7.61 (dd, J = 8.02, 1.56 Hz, 1H) 7.85 (dd, J = 4.98, 1.48 Hz, 1H) 7.91 (d, J = 8.02 Hz, 1H) 8.30-8.33 (m, 1H) 8.68 (d, J = 5.92 Hz, 1H) 8.95 (d, J = 4.98, 0.93 Hz, 1H) |
| 20-64 | N-((1R,2R,4S)-7-cyano-7-azabicyclo[2.2.1]heptan-2-yl)-3-(2-methylpropoxy)-4-(5-methyl-2-pyrazinyl)benzamide | 406.0 | 1H NMR (500 MHz, CHLOROFORM-d) δ ppm 1.04 (d, J = 6.75 Hz, 17H) 1.09 (br d, J = 6.75 Hz, 1H) 1.19 (dd, J = 13.10, 3.89 Hz, 4H) 1.34-1.48 (m, 2H) 1.62-1.75 (m, 5H) 1.87-2.02 (m, 6H) 2.05-2.20 (m, 6H) 2.56-2.65 (m, 11H) 3.51 (s, 3H) 3.92 (s, 3H) 3.93 (s, 3H) 4.13 (t, J = 5.00 Hz, 3H) 4.46-4.57 (m, 6H) 6.18 (br d, J = 3.63 Hz, 3H) 7.29-7.39 (m, 5H) 7.48 (s, 2H) 7.52-7.64 (m, 4H) 7.95 (d, J = 7.91 Hz, 3H) 8.56 (s. 3H) 9.17 (d, J = 1.30 Hz, 3H) |
| 20-65 | N-((1R,2R,4S)-7-cyano-7-azabicyclo[2.2.1]heptan-2-yl)-3-(2-methylpropoxy)-4-(6-methyl-2-pyridinyl)benzamide | 405.2 | 1H NMR (600 MHz, DMSO-d6) δ ppm 0.06-0.09 (m, 1H) 0.94-1.00 (m, 6H) 1.24 (br s, 1H) 1.59 (dd, J = 12.69, 4.59 Hz, 1H) 1.65-1.75 (m, 2H) 1.79-1.90 (m, 2H) 2.02 (dt, J = 13.22, 6.51 Hz, 1H) 2.16-2.26 (m, 1H) 2.36-2.47 (m, 1H) 2.52-2.54 (m, 3H) 2.58-2.67 (m, 1H) 3.17 (br s, 1H) 3.90 (d, J = 6.23 Hz, 2H) 4.18 (br t, J = 4.79 Hz, 1H) 4.23-4.32 (m, 2H) 7.21 (d, J = 7.47 Hz, 1H) 7.34-7.46 (m, 1H) 7.51 (d, J = 1.56 Hz, 1H) 7.56 (dd, J = 7.98, 1.60 Hz, 1H) 7.67-7.71 (m, 1H) 7.71-7.75 (m, 1H) 7.81 (d, J = 7.94 Hz, 1H) 8.63 (br d, J = 5.45 Hz, 1H) |
| 20-66 | N-((1R,2R,4S)-7-cyano-7-azabicyclo[2.2.1]heptan-2-yl)-3-(2-methylpropoxy)-4-(4-methyl-2-pyrimidinyl)benzamide | 406.2 | 1H NMR (600 MHz, DMSO-d6) δ ppm 0.91 (d, J = 6.70 Hz, 6H) 1.59 (dd, J = 12.81, 4.63 Hz, 1H) 1.65-1.75 (m, 2H) 1.83 (br dd, J = 7.51, 4.63 Hz, 1H) 1.85-1.94 (m, 2H) 2.19-2.27 (m, 1H) 2.36-2.47 (m, 1H) 2.52-2.57 (m, 1H) 3.84 (d, J = 6.23 Hz, 2H) 4.18 (t, J = 4.83 Hz, 1H) 4.25-4.33 (m, 2H) 7.34 (d, J = 5.14 Hz, 1H) 7.50 (d, J = 1.48 Hz, 1H) 7.55 (dd, J = 7.86, 1.48 Hz, 1H) 7.62 (d, J = 7.86 Hz, 1H) 8.64 (d, J = 5.84 Hz, 1H) 8.73 (d, J = 5.06 Hz, 1H) |
| 20-67 | N-((1R,2R,4S)-7-cyano-7-azabicyclo[2.2.1]heptan-2-yl)-4-(6-(cyanomethyl)-2-pyridinyl)-3-(2-methylpropoxy)benzamide | 430.0 | 1H NMR (500 MHz, DMSO-d6) δ ppm 0.97 (d, J = 6.75 Hz, 6H) 1.07 (s, 3H) 1.59 (dd, J = 12.72, 4.54 Hz, 1H) 1.65-1.74 (m, 2H) 1.79-1.91 (m, 2H) 1.98-2.09 (m, 1H) 2.19-2.27 (m, 1H) 3.31 (s, 16H) 3.90-3.94 (m, 2H) 4.18 (t, J = 4.74 Hz, 1H) 4.25-4.32 (m, 4H) 5.75 (s, 1H) 7.39 (dd, J = 6.49, 2.08 Hz, 1H) 7.53 (d, J = 1.43 Hz, 1H) 7.59 (dd, J = 7.98, 1.49 Hz, 1H) 7.84-7.92 (m, 3H) 8.63 (d, J = 5.71 Hz, 1H) |

-continued

| Ex # | Name | MS data | 1H NMR |
|---|---|---|---|
| 20-68 | N-((1R,2R,4S)-7-cyano-7-azabicyclo[2.2.1]heptan-2-yl)-3-(2-methylpropoxy)-4-(1-methyl-1H-pyrazol-3-yl)benzamide | 394.0 | 1H NMR (500 MHz, DMSO-d6) δ ppm 1.05 (d, J = 6.75 Hz, 14H) 1.17 (t, J = 7.14 Hz, 2H) 1.59 (dd, J = 12.65, 4.48 Hz, 2H) 1.65-1.73 (m, 4H) 1.78-1.90 (m, 5H) 1.99 (s, 2H) 2.10-2.25 (m, 4H) 3.31 (s, 6H) 3.57 (s, 1H) 3.72 (s, 1H) 3.87-3.93 (m, 11H) 4.03 (q, J = 7.14 Hz, 1H) 4.15-4.18 (m, 2H) 4.24-4.31 (m, 4H) 5.75 (s, 1H) 6.81 (d, J = 2.21 Hz, 2H) 6.90 (d, J = 8.69 Hz, 1H) 7.27 (d, J = 8.56 Hz, 1H) 7.43-7.52 (m, 5H) 7.74 (d, J = 2.08 Hz, 2H) 7.98 (s, 1H) 7.98-8.01 (m, 1H) 8.55 (br d, J = 5.58 Hz, 2H) |
| 20-69 | N-((1R,2R,4S)-7-cyano-7-azabicyclo[2.2.1]heptan-2-yl)-3-(2-methylpropoxy)-4-(1-methyl-1H-pyrazol-5-yl)benzamide | 394.0 | 1H NMR (500 MHz, DMSO-d6) δ ppm 0.87 (d, J = 6.62 Hz, 6H) 1.17 (t, J = 7.14 Hz, 2H) 1.58 (dd, J = 12.72, 4.41 Hz, 1H) 1.64-1.74 (m, 2H) 1.81-2.00 (m, 5H) 2.18-2.28 (m, 1H) 3.31 (s, 3H) 3.65 (s, 3H) 3.77- 3.89 (m, 2H) 4.03 (q, J = 7.14 Hz, 1H) 4.14-4.22 (m, 1H) 4.24-4.33 (m, 2H) 5.75 (s, 1H) 6.29 (d, J = 1.69 Hz, 1H) 7.39 (d, J = 7.78 Hz, 1H) 7.44-7.58 (m, 3H) 8.63 (br d, J = 5.58 Hz, 1H) |
| 20-70 | N-((1R,2R,4S)-7-cyano-7-azabicyclo[2.2.1]heptan-2-yl)-4-(1-methyl-1H-imidazol-4-yl)-3-(2-methylpropoxy)benzamide | 394.0 | 1H NMR (500 MHz, DMSO-d6) δ ppm 1.03 (br d, J = 6.62 Hz, 6H) 1.23 (br s, 1H) 1.55 (br dd, J = 12.65, 4.09 Hz, 1H) 1.62-1.73 (m, 2H) 1.77-1.88 (m, 2H) 2.07 (dt, J = 13.10, 6.55 Hz, 1H) 2.21 (br t, J = 10.57 Hz, 1H) 3.38 (br dd, J = 13.82, 6.94 Hz, 1H) 3.49-3.68 (m, 1H) 3.90 (br d, J = 6.23 Hz, 2H) 4.16 (br t, J = 4.54 Hz, 1H) 4.21-4.30 (m, 2H) 4.41 (s, 2H) 6.87 (m, J = 8.43 Hz, 2H) 7.22 (m, J = 8.43 Hz, 2H) 7.40 (d, J = 8.22 Hz, 1H) 7.45 (s, 1H) 7.70 (d, J = 8.17 Hz, 1H) 8.60 (br d, J = 5.19 Hz, 1H) |
| 20-71 | N-((1R,2R,4S)-7-cyano-7-azabicyclo[2.2.1]heptan-2-yl)-4-(6-cyano-2-pyridinyl)-3-(2-methylpropoxy)benzamide | 416.0 | 1H NMR (500 MHz, DMSO-d6) δ ppm 0.97 (d, J = 6.75 Hz, 6H) 1.07 (s, 3H) 1.59 (dd, J = 12.72, 4.54 Hz, 1H) 1.65-1.74 (m, 2H) 1.79-1.91 (m, 2H) 1.98-2.09 (m, 1H) 2.19-2.27 (m, 1H) 3.31 (s, 16H) 3.90-3.94 (m, 2H) 4.18 (t, J = 4.74 Hz, 1H) 4.25-4.32 (m, 4H) 5.75 (s, 1H) 7.39 (dd, J = 6.49, 2.08 Hz, 1H) 7.53 (d, J = 1.43 Hz, 1H) 7.59 (dd, J = 7.98, 1.49 Hz, 1H) 7.84-7.92 (m, 3H) 8.63 (d, J = 5.71 Hz, 1H) |
| 20-72 | N-((1R,2R,4S)-7-cyano-7-azabicyclo[2.2.1]heptan-2-yl)-3-(2-methylpropoxy)-4-(6-methyl-3-pyridazinyl)benzamide | 406.0 | |
| 20-73 | N-((1R,2R,4S)-7-cyano-7-azabicyclo[2.2.1]heptan-2-yl)-3-(2-methylpropoxy)-4-(2-methyl-4-pyrimidinyl)benzamide | 406.0 | 1H NMR (600 MHz, DMSO-d6) δ ppm 0.99 (d, J = 6.79 Hz, 6H) 1.55-1.63 (m, 1H) 1.66-1.74 (m, 2H) 1.80-1.91 (m, 2H) 2.07 (dquin, J = 13.20, 6.60, 6.60, 6.60, 6.60 Hz, 1H) 2.19-2.29 (m, 1H) 2.52-2.58 (m, 1H) 2.66-2.70 (m, 3H) 3.26-3.28 (m, 1H) 3.32-3.42 (m, 2H) 3.95 (d, J = 6.24 Hz, 2H) 4.18 (t, J = 4.86 Hz, 1H) 4.26-4.33 (m, 2H) 7.54 (d, J = 1.47 Hz, 1H) 7.59 (dd, J = 7.98, 1.56 Hz, 1H) 7.81 (d, J = 5.32 Hz, 1H) 7.96 (d, J = 7.89 Hz, 1H) 8.66 (d, J = 5.69 Hz, 1H) 8.74 (d, J = 5.32 Hz, 1H) |
| 20-74 | N-((1R,2R,4S)-7-cyano-7-azabicyclo[2.2.1]heptan-2-yl)-3-(2-methylbutoxy)-4-(1-methyl-1H-pyrazol-4-yl)benzamide | 408.2 | 1H NMR (600 MHz, DMSO-d6) δ ppm 0.94 (t, J = 7.47 Hz, 3H) 1.04 (d, J = 6.70 Hz, 3H) 1.23-1.35 (m, 1H) 1.53-1.61 (m, 2H) 1.64-1.73 (m, 2H) 1.78-1.88 (m, 2H) 1.92-2.00 (m, 1H) 2.17-2.25 (m, 1H) 3.24-3.30 (m, 1H) 3.88 (s, 3H) 3.93 (dd, J = 9.19, 6.46 Hz, 1H) 4.01 (dd, J = 9.19, 5.68 Hz, 1H) 4.17 (t, J = 4.87 Hz, 1H) 4.23-4.31 (m, 2H) 7.45 (d, J = 1.64 Hz, 1H) 7.49 (dd, J = 8.02, 1.63 Hz, 1H) 7.68 (d, J = 8.02 Hz, 1H) 7.97 (d, J = 0.62 Hz, 1H) 8.15 (s, 1H) 8.51 (d, J = 5.76 Hz, 1H) |
| 20-75 | N-((1R,2R,4S)-7-cyano-7-azabicyclo[2.2.1]heptan-2-yl)-4-(1-ethyl-1H-pyrazol-4-yl)-3-(2-methylpropoxy)benzamide | 408.0 | 1H NMR (600 MHz, DMSO-d6) δ ppm 1.05 (dd, J = 6.73, 0.90 Hz, 6H) 1.40 (t, J = 7.28 Hz, 3H) 1.58 (dd, J = 12.69, 4.67 Hz, 1H) 1.63-1.75 (m, 2H) 1.78-1.89 (m, 2H) 2.14-2.25 (m, 2H) 3.16-3.26 (m, 1H) 3.92 (d, J = 6.31 Hz, 2H) 4.13-4.22 (m, 3H) 4.22-4.31 (m, 2H) 7.45 (d, J = 1.63 Hz, 1H) 7.49 (dd, J = 8.02, 1.63 Hz, 1H) 7.70 (d, J = 8.02 Hz, 1H) 7.99 (d, J = 0.62 Hz, 1H) 8.21 (s, 1H) 8.51 (d, J = 5.76 Hz, 1H) |

-continued

| Ex # | Name | MS data | 1H NMR |
|---|---|---|---|
| 20-76 | N-((1R,2R,4S)-7-cyano-7-azabicyclo[2.2.1]heptan-2-yl)-4-(1-cyclopropyl-1H-pyrazol-4-yl)-3-(2-methylpropoxy)benzamide | 420.0 | 1H NMR (600 MHz, DMSO-d6) δ ppm 0.98-1.09 (m, 10H) 1.58 (dd, J = 12.73, 4.63 Hz, 1H) 1.64-1.74 (m, 2H) 1.78-1.88 (m, 2H) 2.14-2.24 (m, 2H) 3.16-3.29 (m, 1H) 3.77 (tt, J = 7.36, 3.78 Hz, 1H) 3.92 (d, J = 6.31 Hz, 2H) 4.17 (t, J = 4.83 Hz, 1H) 4.22-4.31 (m, 2H) 7.45 (d, J = 1.63 Hz, 1H) 7.49 (dd, J = 8.02, 1.64 Hz, 1H) 7.71 (d, J = 8.02 Hz, 1H) 7.99 (d, J = 0.62 Hz, 1H) 8.23 (s, 1H) 8.51 (d, J = 5.76 Hz, 1H) |
| 22-1 | N-((1R,2R,4S)-7-cyano-7-azabicyclo[2.2.1]heptan-2-yl)-1-(6-methyl-2-pyridinyl)-7-(trifluoromethyl)-1H-indazole-5-carboxamide | 441.0 | 1H NMR (DMSO-d6) δ: 9.61 (s, 1H), 8.85 (d, J = 5.8 Hz, 1H), 8.74 (s, 1H), 8.19 (s, 1H), 8.01-8.08 (m, 2H), 7.46 (d, J = 7.3 Hz, 1H), 4.31-4.36 (m, 1H), 4.29 (t, J = 4.4 Hz, 1H), 4.19 (t, J = 4.9 Hz, 1H), 2.62 (s, 3H), 2.21-2.30 (m, 1H), 1.89-1.96 (m, 1H), 1.80-1.89 (m, 1H), 1.66-1.76 (m, 2H), 1.59 (dd, J = 12.7, 4.6 Hz, 1H) |
| 23-1 | N-((1R,2R,4S)-7-cyano-7-azabicyclo[2.2.1]heptan-2-yl)-2-(2,3-dichlorophenyl)-1-pyrrolidinecarboxamide | [M + 1] 379.2 | |
| 23-2 | 2-(3-bromo-2-methylphenyl)-N-((1R,2R,4S)-7-cyano-7-azabicyclo[2.2.1]heptan-2-yl)-1-pyrrolidinecarboxamide | [M + 1] 403.2 | |
| 23-3 | N-((1R,2R,4S)-7-cyano-7-azabicyclo[2.2.1]heptan-2-yl)-2-(2,3-dichlorophenyl)-1-azetidinecarboxamide | [M + 1] 365.1 | |
| 23-4 | 1-((1R,2R,4S)-7-cyano-7-azabicyclo[2.2.1]heptan-2-yl)-3-((-3-(2-propanyl)-2,3-dihydro-1H-inden-1-yl)methyl)urea | [M + 1] 353.3 | |
| 23-5 | 1-((1R,2R,4S)-7-cyano-7-azabicyclo[2.2.1]heptan-2-yl)-3-(1-(2,3-dichlorophenyl)ethyl)urea | [M + 1] 353.1 | |
| 23-6 | 1-((7-chloro-1,2,3,4-tetrahydro-1-naphthalenyl)methyl)-3-((1R,2R,4S)-7-cyano-7-azabicyclo[2.2.1]heptan-2-yl)urea | [M + 1] 359.2 | |
| 23-7 | 1-((1R,2R,4S)-7-cyano-7-azabicyclo[2.2.1]heptan-2-yl)-3-(2-(2,5-dichlorophenyl)ethyl)urea | [M + 1] 353.3 | |
| 23-8 | 7-chloro-N-((1R,2R,4S)-7-cyano-7-azabicyclo[2.2.1]heptan-2-yl)-2,3-dihydro-1,4-benzoxazepine-4(5H)-carboxamide | [M + 1] 347.3 | |
| 23-9 | 8-chloro-N-((1R,2R,4S)-7-cyano-7-azabicyclo[2.2.1]heptan-2-yl)-1,3,4,5-tetrahydro-2H-pyrido[4,3-b]indole-2-carboxamide | [M + 1] 370.2 | |
| 24-1 | N'-((1R,2R,4S)-7-cyano-7-azabicyclo[2.2.1]heptan-2-yl)-N-(2-hydroxyethyl)-N-(tricyclo[3.3.1.1~3,7~]decan-1-ylmethyl)ethanediamide | [M + 1] 401.3 | |
| 25-1 | 2-chloro-N-((1R,2R,4S)-7-cyano-7-azabicyclo[2.2.1]heptan-2-yl)-4-(4-(trifluoromethyl)-1H-pyrazol-1-yl)benzamide | 410.0 | H NMR (600 MHz, DMSO-d6) δ ppm 1.38 (dd, J = 12.67, 4.13 Hz, 1H) 1.55-1.65 (m, 1H) 1.68-1.77 (m, 1H) 1.78-1.86 (m, 1H) 2.00 (ddd, J = 12.90, 8.99, 4.18 Hz, 1H) 2.19-2.27 (m, 1H) 3.16-3.28 (m, 1H) 4.16 (t, J = 5.04 Hz, 1H) 4.24-4.31 (m, 2H) 7.64 (d, J = 8.36 Hz, 1H) 7.96 (dd, J = 8.36, 2.18 Hz, 1H) 8.11 (d, J = 2.18 Hz, 1H) 8.28 (s, 1H) 8.86 (br d, J = 5.90 Hz, 1H) 9.33 (s, 1H) |

| Ex # | Name | MS data | 1H NMR |
|---|---|---|---|
| 25-2 | 2-chloro-N-((1R,2R,4S)-7-cyano-7-azabicyclo[2.2.1]heptan-2-yl)-4-(4-(cyanomethyl)-1H-pyrazol-1-yl)benzamide | 381.0 | |
| 25-3 | 2-chloro-N-((1R,2R,4S)-7-cyano-7-azabicyclo[2.2.1]heptan-2-yl)-4-(4-ethyl-1H-pyrazol-1-yl)benzamide | 370.0 | 1H NMR (600 MHz, DMSO-d6) δ ppm 1.21 (t, J = 7.58 Hz, 3H) 1.24 (br s, 1H) 1.39 (dd, J = 12.67, 4.13 Hz, 1H) 1.56-1.65 (m, 1H) 1.73 (br d, J = 12.35 Hz, 1H) 1.77-1.87 (m, 1H) 2.00 (ddd, J = 12.90, 9.13, 4.13 Hz, 1H) 2.22 (br s, 1H) 2.51-2.55 (m, 2H) 3.19 (br s, 1H) 3.23-3.29 (m, 4H) 3.35-3.46 (m, 3H) 4.15 (t, J = 5.04 Hz, 1H) 4.23-4.30 (m, 2H) 7.56 (d, J = 8.36 Hz, 1H) 7.67 (s, 1H) 7.85 (dd, J = 8.40, 2.13 Hz, 1H) 7.97 (d, J = 2.09 Hz, 1H) 8.43 (s, 1H) 8.79 (br d, J = 5.90 Hz, 1H) |
| 26-1-1 | (3R)-1-(3-chlorophenyl)-N-((1R,2R,4S)-7-cyano-7-azabicyclo[2.2.1]heptan-2-yl)-5-oxo-3-pyrrolidinecarboxamide | 358.8 | 1H NMR (500 MHz, CHLOROFORM-d) Shift 7.67 (t, J = 2.01 Hz, 1H), 7.46-7.52 (m, 1H), 7.29-7.34 (m, 1H), 7.14-7.19 (m, 1H), 6.06 (br s, 1H), 4.36 (br s, 1H), 4.04-4.17 (m, 2H), 3.87-4.01 (m, 1H), 3.16-3.28 (m, 1H), 2.79-2.96 (m, 2H), 2.41-2.52 (m, 1H), 2.01-2.13 (m, 1H), 1.94 (dt, J = 2.40, 12.75 Hz, 1H), 1.82 (ddd, J = 4.54, 8.89, 13.30 Hz, 2H), 1.60 (ddd, J = 4.22, 8.76, 12.59 Hz, 1H), 1.08-1.19 (m, 1H) |
| 26-2-1 | (3S)-1-(3-chlorophenyl)-N-((1R,2R,4S)-7-cyano-7-azabicyclo[2.2.1]heptan-2-yl)-5-oxo-3-pyrrolidinecarboxamide | 358.8 | 1H NMR (500 MHz, CHLOROFORM-d) Shift 7.67 (t, J = 2.08 Hz, 1H), 7.45-7.50 (m, 1H), 7.31 (t, J = 8.11 Hz, 1H), 7.17 (ddd, J = 0.84, 1.91, 8.01 Hz, 1H), 6.26 (br d, J = 4.15 Hz, 1H), 4.32-4.39 (m, 2H), 4.06-4.15 (m, 2H), 3.95 (t, J = 9.08 Hz, 1H), 3.21 (quin, J = 8.50 Hz, 1H), 2.92 (dd, J = 8.63, 17.06 Hz, 1H), 2.81 (dd, J = 9.47, 17.00 Hz, 1H), 2.40-2.51 (m, 1H), 2.00-2.10 (m, 1H), 1.79-1.96 (m, 3H), 1.59 (ddd, J = 4.22, 8.66, 12.55 Hz, 1H), 1.12 (dd, J = 3.96, 12.91 Hz, 1H) |
| 26-3 | (3S)-1-(3-chlorophenyl)-N-((1R,2R,4S)-7-cyano-7-azabicyclo[2.2.1]heptan-2-yl)-3-pyrrolidinecarboxamide | 345 | 1H NMR (600 MHz, DMSO-d6) Shift 8.29 (br d, J = 5.76 Hz, 1H), 7.15 (t, J = 8.10 Hz, 1H), 6.60 (br d, J = 7.79 Hz, 1H), 6.46-6.53 (m, 2H), 4.07-4.17 (m, 3H), 3.40-3.46 (m, 1H), 3.19-3.36 (m, 3H), 3.03-3.18 (m, 1H), 2.14-2.22 (m, 2H), 2.00-2.14 (m, 1H), 1.75-1.90 (m, 2H), 1.54-1.71 (m, 2H), 1.22-1.31 (m, 1H) |
| 26-4 | (3R)-1-(3-chlorophenyl)-N-((1R,2R,4S)-7-cyano-7-azabicyclo[2.2.1]heptan-2-yl)-3-pyrrolidinecarboxamide | 345 | 1H NMR (600 MHz, DMSO-d6) Shift 8.29 (br d, J = 5.29 Hz, 1H), 7.15 (t, J = 8.02 Hz, 1H), 6.60 (br d, J = 7.63 Hz, 1H), 6.52 (s, 1H), 6.48 (d, J = 8.61 Hz, 1H), 4.07-4.16 (m, 3H), 3.46 (br t, J = 8.72 Hz, 1H), 3.20-3.36 (m, 3H), 3.10 (quin, J = 7.55 Hz, 1H), 2.17 (br dd, J = 4.52, 11.83 Hz, 2H), 2.03-2.13 (m, 1H), 1.76-1.90 (m, 2H), 1.63-1.70 (m, 1H), 1.51-1.63 (m, 1H), 1.26 (dd, J = 3.66, 12.69 Hz, 1H) |
| 26-5 | (2S)-5-bromo-N-((1R,2R,4S)-7-cyano-7-azabicyclo[2.2.1]heptan-2-yl)-2,3-dihydro-1H-indene-2-carboxamide | 359.8 | 1H NMR (600 MHz, DMSO-d6) Shift 8.23 (br d, J = 5.61 Hz, 1H), 7.40 (s, 1H), 7.30 (br d, J = 7.94 Hz, 1H), 7.16 (d, J = 7.94 Hz, 1H), 4.08-4.15 (m, 3H), 3.19-3.26 (m, 1H), 3.03-3.12 (m, 3H), 2.93-3.01 (m, 1H), 2.18 (br s, 1H), 1.77-1.88 (m, 2H), 1.55-1.70 (m, 2H), 1.21-1.32 (m, 1H) |
| 26-6 | (2R)-5-bromo-N-((1R,2R,4S)-7-cyano-7-azabicyclo[2.2.1]heptan-2-yl)-2,3-dihydro-1H-indene-2-carboxamide | 359.8 | 1H NMR (600 MHz, DMSO-d6) Shift 8.23 (br d, J = 5.61 Hz, 1H), 7.40 (s, 1H), 7.30 (br d, J = 7.94 Hz, 1H), 7.16 (d, J = 7.94 Hz, 1H), 4.08-4.15 (m, 3H), 3.19-3.26 (m, 1H), 3.03-3.12 (m, 3H), 2.93-3.01 (m, 1H), 2.18 (br s, 1H), 1.77-1.88 (m, 2H), 1.55-1.70 (m, 2H), 1.21-1.32 (m, 1H) |
| 27-1 | (3R)-N-((1R,2R,4S)-7-cyano-7-azabicyclo[2.2.1]heptan-2-yl)-1-(4-cyclopropyl-2-pyrimidinyl)-3-pyrrolidinecarboxamide | 353 | 1H NMR (600 MHz, DMSO-d6) Shift 8.29 (br d, J = 6.15 Hz, 1H), 8.09 (d, J = 4.98 Hz, 1H), 6.52 (d, J = 5.06 Hz, 1H), 4.06-4.16 (m, 2H), 3.66 (dd, J = 7.94, 10.98 Hz, 1H), 3.51-3.60 (m, 1H), 3.34-3.49 (m, 3H), 3.04 (quin, J = 7.55 Hz, 1H), 2.07-2.22 (m, 2H), 2.01 (qd, J = 8.16, 12.27 Hz, 1H), 1.76-1.92 (m, 3H), 1.55-1.71 (m, 2H), 1.20-1.33 (m, 1H), 0.90-1.00 (m, 4H) |
| 27-2 | (3R)-N-((1R,2R,4S)-7-cyano-7-azabicyclo[2.2.1]heptan-2-yl)-1-(6-(trifluoromethyl)-2-pyridinyl)-3-pyrrolidinecarboxamide | 380 | 1H NMR (600 MHz, DMSO-d6) Shift 8.34 (br d, J = 5.99 Hz, 1H), 7.69 (t, J = 7.90 Hz, 1H), 6.96 (d, J = 7.24 Hz, 1H), 6.73 (d, J = 8.56 Hz, 1H), 4.07-4.17 (m, 3H), 3.64 (br t, J = 9.07 Hz, 1H), 3.50-3.58 (m, 1H), 3.36-3.49 (m, 2H), 3.11 (quin, J = 7.47 Hz, 1H), 2.14-2.24 (m, 2H), 2.03-2.13 (m, 1H), 1.77-1.88 (m, 2H), 1.56-1.70 (m, 2H), 1.27 (dd, J = 4.44, 12.69 Hz, 1H) |
| 27-3 | (3S)-N-((1R,2R,4S)-7-cyano-7-azabicyclo[2.2.1]heptan-2-yl)-1-(6-(trifluoromethyl)-2-pyridinyl)-3-pyrrolidinecarboxamide | 380 | 1H NMR (600 MHz, DMSO-d6) Shift 8.34 (br d, J = 5.99 Hz, 1H), 7.69 (t, J = 7.90 Hz, 1H), 6.96 (d, J = 7.24 Hz, 1H), 6.73 (d, J = 8.56 Hz, 1H), 4.07-4.17 (m, 3H), 3.64 (br t, J = 9.07 Hz, 1H), 3.50-3.58 (m, 1H), 3.36-3.49 (m, 2H), 3.11 (quin, J = 7.47 Hz, 1H), 2.14-2.24 (m, 2H), 2.03-2.13 (m, 1H), 1.77-1.88 (m, 2H), 1.56-1.70 (m, 2H), 1.27 (dd, J = 4.44, 12.69 Hz, 1H) |

| Ex # | Name | MS data | 1H NMR |
|---|---|---|---|
| 28-1 | (3S)-N-((1R,2R,4S)-7-cyano-7-azabicyclo[2.2.1]heptan-2-yl)-1-(3,5-dichlorophenyl)-3-pyrrolidinecarboxamide | 379 | 1H NMR (500 MHz, CHLOROFORM-d) Shift 6.69 (t, J = 1.69 Hz, 1H), 6.42 (d, J = 1.69 Hz, 2H), 5.79 (br d, J = 4.54 Hz, 1H), 4.29-4.40 (m, 2H), 4.07 (t, J = 4.93 Hz, 1H), 3.44-3.52 (m, 3H), 3.27-3.39 (m, 1H), 3.04 (quin, J = 7.66 Hz, 1H), 2.43-2.51 (m, 1H), 2.24-2.35 (m, 2H), 2.03-2.12 (m, 1H), 1.87-1.98 (m, 1H), 1.79-1.85 (m, 1H), 1.54-1.61 (m, 1H), 1.05 (dd, J = 4.09, 12.78 Hz, 1H) |
| 28-2 | (3S)-1-(5-chloro-2-cyanophenyl)-N-((1R,2R,4S)-7-cyano-7-azabicyclo[2.2.1]heptan-2-yl)-3-pyrrolidinecarboxamide | 370 | 1H NMR (600 MHz, DMSO-d6) d 8.32-8.39 (m, 1H), 7.55 (dt, J = 1.09, 1.91 Hz, 1H), 6.77-6.82 (m, 1H), 6.72-6.77 (m, 1H), 4.06-4.16 (m, 3H), 3.64-3.77 (m, 2H), 3.52-3.64 (m, 3H), 3.06-3.16 (m, 1H), 2.14-2.28 (m, 2H), 1.99-2.13 (m, 1H), 1.77-1.90 (m, 2H), 1.53-1.73 (m, 1H), 1.20-1.33 (m, 1H) |
| 29-1 | (3S)-N-((1R,2R,4S)-7-cyano-7-azabicyclo[2.2.1]heptan-2-yl)-1-(6-cyano-4-(trifluoromethyl)-2-pyridinyl)-3-pyrrolidinecarboxamide | 405 | 1H NMR (600 MHz, DMSO-d6) Shift 8.53 (br d, J = 4.58 Hz, 1H), 8.30-8.40 (m, 1H), 7.84-7.95 (m, 1H), 7.35-7.43 (m, 1H), 7.21-7.35 (m, 1H), 7.07 (s, 1H), 4.25-4.48 (m, 1H), 4.08-4.19 (m, 3H), 3.44-3.74 (m, 4H), 3.06-3.19 (m, 1H), 2.04-2.30 (m, 3H), 1.78-1.88 (m, 2H), 1.53-1.72 (m, 2H), 1.24-1.32 (m, 1H) |
| 29-2 | (3S)-N-((1R,2R,4S)-7-cyano-7-azabicyclo[2.2.1]heptan-2-yl)-1-(6-cyano-4-methyl-2-pyridinyl)-3-pyrrolidinecarboxamide | 351 | 1H NMR (600 MHz, DMSO-d6) Shift 8.28-8.33 (m, 1H), 6.72-6.76 (m, 1H), 6.67-6.69 (m, 1H), 4.08-4.14 (m, 3H), 3.61-3.66 (m, 2H), 3.49-3.54 (m, 2H), 3.06-3.11 (m, 1H), 2.34 (s, 3H) 2.14-2.22 (m, 1H), 2.04-2.10 (m, 1H), 1.78-1.88 (m, 2H), 1.57-1.69 (m, 2H), 1.23-1.30 (m, 2H) |
| 29-3 | (3S)-N-((1R,2R,4S)-7-cyano-7-azabicyclo[2.2.1]heptan-2-yl)-1-(4-methyl-6-(trifluoromethyl)-2-pyridinyl)-3-pyrrolidinecarboxamide | 394 | 1H NMR (500 MHz, CHLOROFORM-d) d 6.78-6.83 (m, 1H), 6.37-6.43 (m, 1H), 5.85-5.92 (m, 1H), 4.28-4.38 (m, 2H), 4.04-4.10 (m, 1H), 3.78-3.85 (m, 1H), 3.68-3.77 (m, 2H), 3.47-3.56 (m, 1H), 3.02-3.12 (m, 1H), 2.39-2.50 (m, 1H), 2.34-2.38 (m, 2H), 2.24-2.34 (m, 1H), 2.01-2.10 (m, 1H), 1.87-1.96 (m, 1H), 1.55-1.63 (m, 1H), 1.03-1.12 (m, 1H) |
| 29-4 | (3S)-N-((1R,2R,4S)-7-cyano-7-azabicyclo[2.2.1]heptan-2-yl)-1-(4-cyano-6-(trifluoromethyl)-2-pyridinyl)-3-pyrrolidinecarboxamide | 405 | 1H NMR (500 MHz, CHLOROFORM-d) Shift 7.06 (s, 1H), 6.73 (s, 1H), 5.72 (br d, J = 4.67 Hz, 1H), 4.31-4.39 (m, 2H), 4.07-4.17 (m, 1H), 3.69-3.87 (m, 2H), 3.48-3.59 (m, 1H), 3.06 (quin, J = 7.46 Hz, 1H), 2.42-2.53 (m, 1H), 2.28-2.41 (m, 2H), 2.04-2.13 (m, 1H), 1.89-1.99 (m, 1H), 1.76-1.87 (m, 1H), 1.71 (br s, 1H), 1.60 (ddd, J = 4.28, 8.76, 12.65 Hz, 1H), 1.07 (dd, J = 4.28, 12.85 Hz, 1H) |
| 29-5 | (3S)-N-((1R,2R,4S)-7-cyano-7-azabicyclo[2.2.1]heptan-2-yl)-1-(3-cyano-6-(trifluoromethyl)-2-pyridinyl)-3-pyrrolidinecarboxamide | 405 | N/A |
| 29-6 | (3S)-N-((1R,2R,4S)-7-cyano-7-azabicyclo[2.2.1]heptan-2-yl)-1-(6-(trifluoromethyl)-2-pyrazinyl)-3-pyrrolidinecarboxamide | 381 | 1H NMR (600 MHz, DMSO-d6) Shift 8.36 (br d, J = 5.81 Hz, 1H), 8.29 (s, 1H), 8.18 (s. 1H), 4.06-4.17 (m, 3H), 3.72 (dd, J = 7.90, 10.72 Hz, 1H), 3.47-3.65 (m, 3H), 3.10-3.20 (m, 2H), 2.14-2.28 (m, 2H), 2.06-2.14 (m, 1H), 1.78-1.89 (m, 2H), 1.57-1.71 (m, 2H), 1.28 (dd, J = 4.41, 12.76 Hz, 1H) |
| 29-7 | (3S)-1-(3-chloro-6-(trifluoromethyl)-2-pyridinyl)-N-((1R,2R,4S)-7-cyano-7-azabicyclo[2.2.1]heptan-2-yl)-3-pyrrolidinecarboxamide | 414 | 1H NMR (500 MHz, CHLOROFORM-d) Shift 7.59-7.63 (m, J = 7.79 Hz, 1H), 6.90-6.99 (m, J = 7.78 Hz, 1H), 5.95 (br d, J = 4.80 Hz, 1H), 4.31-4.37 (m, 2H), 4.07 (t, J = 5.00 Hz, 1H), 3.88-4.01 (m, 2H), 3.78-3.85 (m, 1H), 2.97 (quin, J = 7.36 Hz, 1H), 2.43-2.50 (m, 1H), 2.19-2.29 (m, 2H), 2.02-2.14 (m, 1H), 1.80-1.97 (m, 2H), 1.52-1.67 (m, 1H), 1.24-1.33 (m, 2H), 1.01-1.09 (m, 1H) |
| 30-1 | (3S)-N-((1R,2R,4S)-7-cyano-7-azabicyclo[2.2.1]heptan-2-yl)-1-(3-methylphenyl)-3-pyrrolidinecarboxamide | 325.1 | 1H NMR (500 MHz, CHLOROFORM-d) Shift 7.12-7.20 (m, 1H), 6.61 (br d, J = 7.40 Hz, 1H), 6.42-6.51 (m, 2H), 6.01 (br s, 1H), 4.30-4.37 (m, 2H), 4.04 (t, J = 4.93 Hz, 1H), 3.43-3.57 (m, 2H), 3.30-3.38 (m, 1H), 3.01-3.08 (m, 1H), 2.38-2.48 (m, 1H), 2.33 (s, 3H), 2.25-2.31 (m, 2H), 1.99-2.06 (m, 1H), 1.85-1.93 (m, 1H), 1.68-1.85 (m, 2H), 1.48-1.56 (m, 1H), 1.28-1.36 (m, 1H), 1.01 (dd, J = 4.02, 12.98 Hz, 1H) |
| 30-2 | (3S)-N-((1R,2R,4S)-7-cyano-7-azabicyclo[2.2.1]heptan-2-yl)-1-(3-methoxyphenyl)-3-pyrrolidinecarboxamide | 341 | 1H NMR (500 MHz, CHLOROFORM-d) Shift 7.18 (t, J = 8.11 Hz, 1H), 6.36 (dd, J = 1.88, 8.11 Hz, 1H), 6.29 (d, J = 7.53 Hz, 1H), 6.17-6.25 (m, 1H), 5.89 (br s, 1H), 4.31-4.37 (m, 2H), 4.05 (t, J = 5.00 Hz, 1H), 3.82 (s, 3H), 3.47-3.57 (m, 2H), 3.33-3.39 (m, 1H), 3.06 (quin, J = 7.14 Hz, 1H), 2.38-2.50 (m, 1H), 2.25-2.35 (m, 2H), 1.97-2.12 (m, 1H), 1.84-1.95 (m, 1H), 1.70-1.83 (m, 1H), 1.52 (ddd, J = 4.35, 8.79, 12.68 Hz, 2H), 1.00 (dd, J = 3.89, 12.98 Hz, 1H) |

| Ex # | Name | MS data | 1H NMR |
|---|---|---|---|
| 30-3 | 7-chloro-N-((1R,2R,4S)-7-cyano-7-azabicyclo[2.2.1]heptan-2-yl)-2,3-dihydro-1-benzoxepine-4-carboxamide | 344 | 1H NMR (500 MHz, CHLOROFORM-d) Shift 7.27 (d, J = 2.59 Hz, 1H), 7.19 (dd, J = 2.60, 8.56 Hz, 1H), 6.91-6.98 (m, 2H), 6.06 (br d, J = 4.80 Hz, 1H), 4.36-4.43 (m, 2H), 4.23-4.31 (m, 2H), 4.09 (t, J = 5.00 Hz, 1H), 2.96 (t, J = 4.41 Hz, 2H), 2.46-2.54 (m, 1H), 2.01-2.13 (m, 1H), 1.86-1.97 (m, 2H), 1.55-1.72 (m, 2H), 1.16 (dd, J = 4.22, 12.78 Hz, 1H) |
| 30-4 | (3S)-N-((1R,2R,4S)-7-cyano-7-azabicyclo[2.2.1]heptan-2-yl)-1-(2,5-dichlorophenyl)-3-pyrrolidinecarboxamide | 379 | 1H NMR (400 MHz, CHLOROFORM-d) d 7.29-7.33 (m, 1H), 6.96-7.07 (m, 2H), 6.73-6.84 (m, 1H), 4.28-4.36 (m, 2H), 4.02-4.07 (m, 1H), 3.64-3.77 (m, 1H), 3.54-3.60 (m, 1H), 3.25-3.33 (m, 1H), 3.03-3.13 (m, 2H), 2.32-2.52 (m, 2H), 2.13-2.24 (m, 1H), 1.96-2.06 (m, 1H), 1.81-1.92 (m, 1H), 1.75-1.81 (m, 1H), 1.49-1.58 (m, 2H), 1.06-1.12 (m, 1H) |
| 30-5 | (3S)-N-((1R,2R,4S)-7-cyano-7-azabicyclo[2.2.1]heptan-2-yl)-1-(3,5-dichloro-4-(trifluoromethoxy)phenyl)-3-pyrrolidinecarboxamide | 462.9 | 1H NMR (600 MHz, DMSO-d6) Shift 8.32 (br d, J = 5.99 Hz, 1H), 6.69 (s, 2H), 4.06-4.17 (m, 3H), 3.42-3.51 (m, 1H), 3.32-3.40 (m, 2H), 3.26-3.30 (m, 1H), 3.07-3.15 (m, 1H), 2.14-2.24 (m, 2H), 2.07 (qd, J = 7.90, 12.27 Hz, 1H), 1.78-1.88 (m, 2H), 1.56-1.71 (m, 2H), 1.27 (dd, J = 4.50, 12.67 Hz, 1H) |
| 30-6 | (3S)-1-(3-chloro-5-(trifluoromethyl)phenyl)-N-((1R,2R,4S)-7-cyano-7-azabicyclo[2.2.1]heptan-2-yl)-3-pyrrolidinecarboxamide | 413 | 1H NMR (600 MHz, DMSO-d6) Shift 8.32 (br d, J = 5.99 Hz, 1H), 6.90 (s, 1H), 6.80 (s, 1H), 6.70 (s, 1H), 4.06-4.16 (m, 3H), 3.50 (t, J = 8.76 Hz, 1H), 3.31-3.42 (m, 3H), 3.08-3.15 (m, 1H), 2.14-2.26 (m, 2H), 2.03-2.14 (m, 1H), 1.78-1.89 (m, 2H), 1.57-1.71 (m, 2H), 1.28 (dd, J = 4.36, 12.72 Hz, 1H) |
| 30-7 | (3S)-1-(3-chloro-5-methylphenyl)-N-((1R,2R,4S)-7-cyano-7-azabicyclo[2.2.1]heptan-2-yl)-3-pyrrolidinecarboxamide | 359 | 1H NMR (600 MHz, DMSO-d6) Shift 8.28 (br d, J = 5.99 Hz, 1H), 6.45 (s, 1H), 6.33 (s, 1H), 6.30 (br s, 1H), 4.07-4.16 (m, 3H), 3.39-3.40 (m, 1H), 3.42 (t, J = 8.63 Hz, 1H), 3.17-3.28 (m, 2H), 3.09 (quin, J = 7.67 Hz, 1H), 2.16-2.25 (m, 5H), 2.06 (qd, J = 7.92, 12.20 Hz, 1H), 1.78-1.88 (m, 2H), 1.57-1.72 (m, 2H), 1.27 (dd, J = 4.59, 12.67 Hz, 1H) |
| 30-8 | (3S)-1-(5-chloro-2-methylphenyl)-N-((1R,2R,4S)-7-cyano-7-azabicyclo[2.2.1]heptan-2-yl)-3-pyrrolidinecarboxamide | 359 | 1H NMR (600 MHz, DMSO-d6) Shift 8.23 (br d, J = 6.09 Hz, 1H), 7.08 (d, J = 7.99 Hz, 1H), 6.81 (d, J = 8.19 Hz, 1H), 6.79 (s, 1H), 4.07-4.17 (m, 3H), 3.32-3.37 (m, 1H), 3.25-3.30 (m, 2H), 3.11-3.22 (m, 1H), 3.03 (quin, J = 7.72 Hz, 1H), 2.10-2.25 (m, 5H), 2.01 (qd, J = 7.55, 12.13 Hz, 1H), 1.76-1.90 (m, 2H), 1.56-1.72 (m, 2H), 1.26 (dd, J = 4.59, 12.67 Hz, 1H) |
| 30-9 | 6-(3-chlorophenyl)-N-((1R,2R,4S)-7-cyano-7-azabicyclo[2.2.1]heptan-2-yl)-2-pyridinecarboxamide | 353 | 1H NMR (400 MHz, CHLOROFORM-d) Shift 8.18 (dd, J = 0.98, 7.62 Hz, 2H), 7.94-8.01 (m, 2H), 7.82-7.91 (m, 2H), 7.44-7.50 (m, 2H), 4.46-4.59 (m, 2H), 4.15 (t, J = 4.98 Hz, 1H), 2.59 (dddd, J = 3.01, 5.18, 11.03, 13.02 Hz, 1H), 2.05-2.17 (m, 1H), 1.92-2.04 (m, 2H), 1.65-1.78 (m, 1H), 1.31 (dd, J = 4.41, 12.91 Hz, 1H) |
| 30-10 | N-((1R,2R,4S)-7-cyano-7-azabicyclo[2.2.1]heptan-2-yl)-4-(2,5-dichlorophenyl)-2-pyridinecarboxamide | 387 | 1H NMR (600 MHz, DMSO-d6) Shift 9.16 (br d, J = 6.54 Hz, 1H), 8.78-8.82 (m, 1H), 8.07-8.10 (m, 1H), 7.74-7.80 (m, 1H), 7.65-7.71 (m, 2H), 7.60 (br dd, J = 2.59, 8.58 Hz, 1H), 4.32-4.39 (m, 1H), 4.24-4.29 (m, 1H), 4.16-4.21 (m, 1H), 2.17-2.26 (m, 1H), 1.61-1.93 (m, 5H) |
| 30-11 | N-((1R,2R,4S)-7-cyano-7-azabicyclo[2.2.1]heptan-2-yl)-4-(3,5-dichlorophenyl)-2-pyridinecarboxamide | 387 | 1H NMR (600 MHz, DMSO-d6) Shift 9.14 (d, J = 6.36 Hz, 1H), 8.77 (d, J = 5.09 Hz, 1H), 8.30 (d, J = 1.27 Hz, 1H), 8.03 (dd, J = 1.91, 5.18 Hz, 1H), 7.96 (d, J = 1.82 Hz, 2H), 7.77 (t, J = 1.82 Hz, 1H), 4.24-4.40 (m, 2H), 4.18 (t, J = 4.54 Hz, 1H), 3.83 (d, J = 5.72 Hz, 1H), 2.39 (br s, 1H), 2.17-2.24 (m, 1H), 1.75-1.89 (m, 2H), 1.57-1.75 (m, 1H) |
| 30-12 | 4-(3-chlorophenyl)-N-((1R,2R,4S)-7-cyano-7-azabicyclo[2.2.1]heptan-2-yl)-2-pyridinecarboxamide | 353 | 1H NMR (600 MHz, DMSO-d6) Shift 9.13 (br d, J = 6.45 Hz, 1H), 8.76 (d, J = 5.09 Hz, 1H), 8.29 (s, 1H), 8.00 (dd, J = 1.32, 5.04 Hz, 1H), 7.95 (s, 1H), 7.81-7.88 (m, 1H), 7.59 (d, J = 5.00 Hz, 2H), 4.36 (br dd, J = 4.86, 11.31 Hz, 1H), 4.27 (t, J = 4.68 Hz, 1H), 4.18 (t, J = 4.68 Hz, 1H), 2.17-2.24 (m, 1H), 1.75-1.92 (m, 4H), 1.69 (br d, J = 10.45 Hz, 1H) |
| 30-13 | (3S)-N-((1R,2R,4S)-7-cyano-7-azabicyclo[2.2.1]heptan-2-yl)-1-(3,5-dichloro-4-niethoxypheny])-3-pyrrolidinecarboxamide | 409 | 1H NMR (400 MHz, CHLOROFORM-d) Shift 6.46 (s, 2H), 5.79 (br d, J = 4.98 Hz, 1H), 4.29-4.38 (m, 2H), 4.07 (t, J = 5.03 Hz, 1H), 3.83 (s, 3H), 3.36-3.47 (m, 3H), 3.22-3.36 (m, 1H), 3.00 (quin, J = 7.57 Hz, 1H), 2.42-2.52 (m, 1H), 2.21-2.34 (m, 2H), 2.01-2.11 (m, 2H), 1.72-1.97 (m, 2H), 1.52-1.58 (m, 1H) |
| 30-14 | (3S)-N-((1R,2R,4S)-7-cyano-7-azabicyclo[2.2.1]heptan-2-yl)-1-(3,5-dichlor-4-fluorophenyl)-3-pyrrolidinecarboxamide | 397 | 1H NMR (400 MHz, CHLOROFORM-d) Shift 6.43 (d, J = 5.29 Hz, 2H), 5.83 (br d, J = 5.29 Hz, 1H), 4.29-4.37 (m, 2H), 4.07 (t, J = 4.98 Hz, 1H), 3.67-3.72 (m, 1H), 3.38-3.50 (m, 2H), 3.22-3.33 (m, 2H), 3.04 (quin, J = 7.62 Hz, 1H), 2.42-2.51 (m, 1H), 2.22-2.35 (m, 2H), 2.00-2.11 (m, 1H), 1.77-1.97 (m, 1H), 1.52-1.61 (m, 2H), 1.05 (dd, J = 4.25, 12.85 Hz, 1H) |

| Ex # | Name | MS data | 1H NMR |
|---|---|---|---|
| 30-15 | (3S)-N-((1R,2R,4S)-7-cyano-7-azabicyclo[2.2.1]heptan-2-yl)-1-(3-cyclopropylphenyl)-3-pyrrolidinecarboxamide | 351 | 1H NMR (600 MHz, DMSO-d6) Shift 8.28 (br d, J = 6.18 Hz, 1H), 7.02 (t, J = 7.81 Hz, 1H), 6.31 (br d, J = 8.08 Hz, 2H), 6.24 (s, 1H), 4.07-4.17 (m, 3H), 3.38-3.52 (m, 2H), 3.21-3.29 (m, 3H), 3.08 (quin, J = 7.77 Hz, 1H), 2.14-2.21 (m, 2H), 2.07 (qd, J = 8.11, 12.09 Hz, 1H), 1.77-1.90 (m, 3H), 1.57-1.71 (m, 2H), 1.24-1.31 (m, 1H), 0.84-0.94 (m, 2H), 0.59-0.67 (m, 2H) |
| 30-16 | N-((1R,2R,4S)-7-cyano-7-azabicyclo[2.2.1]heptan-2-yl)-4-(3,5-dichlorophenyl)-2-morpholinecarboxamide | 394.8 | 1H NMR (600 MHz, DMSO-d6) Shift 8.25 (br t, J = 5.72 Hz, 1H), 6.97 (dd, J = 1.73, 3.09 Hz, 2H), 6.93 (s, 1H), 4.08-4.16 (m, 4H), 4.01 (br d, J = 11.54 Hz, 1H), 3.67-3.76 (m, 2H), 3.58 (br d, J = 12.26 Hz, 1H), 2.81-2.94 (m, 2H), 2.12 (br s, 1H), 1.74-1.84 (m, 2H), 1.61-1.74 (m, 2H), 1.54 (td, J = 4.48, 12.56 Hz, 1H) |
| 30-17 | (3S)-N-((1R,2R,4S)-7-cyano-7-azabicyclo[2.2.1]heptan-2-yl)-1-(2,3,5-trichlorophenyl)-3-pyrrolidinecarboxamide | 413 | 1H NMR (500 MHz, CHLOROFORM-d) d 7.18-7.19 (m, 1H), 6.92-6.93 (m, 1H), 6.45-6.51 (m, 1H), 4.30-4.35 (m, 2H), 4.05-4.08 (m, 1H), 3.64-3.70 (m, 1H), 3.56-3.60 (m, 1H), 3.33-3.38 (m, 1H), 3.14-3.20 (m, 1H), 3.02-3.08 (m, 1H), 2.43-2.51 (m, 1H), 2.31-2.39 (m, 1H), 2.16-2.24 (m, 1H), 2.00-2.08 (m, 2H), 1.85-1.93 (m, 1H), 1.74-1.80 (m, 1H), 1.51-1.55 (m, 1H), 1.05-1.09 (m, 1H) |
| 31-1 | N-((1R,2R,4S)-7-cyano-7-azabicyclo[2.2.1]heptan-2-yl)-1-(3,5-dichlorophenyl)-1H-pyrazole-4-carboxamide | 376 | 1H NMR (600 MHz, DMSO-d6) Shift 9.09 (s, 1H), 8.34 (d, J = 5.99 Hz, 1H), 8.24 (s, 1H), 7.99 (d, J = 1.79 Hz, 2H), 7.62 (s, 1H), 4.20-4.30 (m, 2H), 4.17 (t, J = 4.87 Hz, 1H), 2.20-2.27 (m, 1H), 1.80-1.93 (m, 2H), 1.62-1.72 (m, 2H), 1.44 (dd, J = 4.67, 12.77 Hz, 1H) |
| 31-2 | 3-chloro-N-((1R,2R,4S)-7-cyano-7-azabicyclo[2.2.1]heptan-2-yl)-1-(3,5-dichlorophenyl)-1H-pyrazole-4-carboxamide | 410 | 1H NMR (600 MHz, DMSO-d6) Shift 9.13 (s, 1H), 8.37 (br d, J = 5.68 Hz, 1H), 7.93 (d, J = 1.79 Hz, 2H), 7.68 (t, J = 1.75 Hz, 1H), 4.21-4.29 (m, 2H), 4.18 (t, J = 4.94 Hz, 1H), 2.19-2.28 (m, 1H), 1.96 (ddd, J = 4.40, 8.87, 12.88 Hz, 1H), 1.81-1.90 (m, 1H), 1.61-1.75 (m, 2H), 1.39 (dd, J = 4.24, 12.65 Hz, 1H) |
| 32-1 | (3S)-1-(3-chlor-5-cyanophenyl)-N-((1R,2R,4S)-7-cyano-7-azabicyclo[2.2.1]heptan-2-yl)-3-pyrrolidinecarboxamide | 370 | 1H NMR (600 MHz, DMSO-d6) Shift 8.32 (br d, J = 6.18 Hz, 1H), 7.06 (s, 1H), 6.90 (s, 1H), 6.84 (t, J = 1.95 Hz, 1H), 4.07-4.17 (m, 3H), 3.43-3.52 (m, 1H), 3.21-3.41 (m, 3H), 3.12 (quin, J = 7.52 Hz, 1H), 2.15-2.24 (m, 2H), 2.07 (qd, J = 7.87, 12.26 Hz, 1H), 1.78-1.88 (m, 2H), 1.56-1.71 (m, 2H), 1.27 (dd, J = 4.50, 12.76 Hz, 1H) |
| 32-2 | (3S)-1-(2-chlor-5-cyanophenyl)-N-((1R,2R,4S)-7-cyano-7-azabicyclo[2.2.1]heptan-2-yl)-3-pyrrolidinecarboxamide | 370 | 1H NMR (600 MHz, DMSO-d6) Shift 8.24-8.33 (m, 1H), 7.50 (d, J = 8.08 Hz, 1H), 7.30 (d, J = 1.73 Hz, 1H), 7.22 (dd, J = 1.86, 8.13 Hz, 1H), 4.06-4.17 (m, 3H), 3.46-3.61 (m, 3H), 3.32-3.41 (m, 1H), 3.04 (quin, J = 7.72 Hz, 1H), 2.10-2.22 (m, 2H), 2.02 (qd, J = 7.79, 12.05 Hz, 1H), 1.76-1.90 (m, 2H), 1.55-1.71 (m, 2H), 1.26 (dd, J = 4.54, 12.72 Hz, 1H) |
| 32-3 | (3S)-N-((1R,2R,4S)-7-cyano-7-azabicyclo[2.2.1]heptan-2-yl)-1-(2-oxo-1-(2-propanyl)-5-(trifluoromethyl)-1,2-dihydro-3-pyridinyl)-3-pyrrolidinecarboxamide | 438 | 1H NMR (600 MHz, DMSO-d6) Shift 8.25 (br d, J = 5.99 Hz, 1H), 7.52 (s, 1H), 6.23 (d, J = 2.00 Hz, 1H), 5.06 (td, J = 6.83, 13.58 Hz, 1H), 4.06-4.16 (m, 3H), 3.70 (dd, J = 8.13, 10.40 Hz, 1H), 3.41-3.54 (m, 3H), 2.91-3.05 (m, 1H), 2.13-2.28 (m, 1H), 2.04-2.13 (m, 1H), 1.92-2.04 (m, 1H), 1.75-1.90 (m, 2H), 1.55-1.71 (m, 2H), 1.24-1.36 (m, 7H) |
| 32-4 | (3S)-N-((1R,2R,4S)-7-cyano-7-azabicyclo[2.2.1]heptan-2-yl)-1-(3,4-dichlorophenyl)-3-pyrrolidinecarboxamide | 378.8 | 1H NMR (600 MHz, DMSO-d6) Shift 8.31 (br d, J = 5.99 Hz, 1H), 7.33 (d, J = 8.90 Hz, 1H), 6.69 (d, J = 2.82 Hz, 1H), 6.52 (dd, J = 2.82, 8.90 Hz, 1H), 4.07-4.17 (m, 3H), 3.38-3.52 (m, 2H), 3.22-3.28 (m, 2H), 3.07-3.15 (m, 1H), 2.14-2.23 (m, 2H), 2.07 (qd, J = 7.96, 12.36 Hz, 1H), 1.77-1.88 (m, 2H), 1.55-1.72 (m, 2H), 1.23-1.31 (m, 1H), 1.16 (t, J = 7.27 Hz, 1H) |
| 32-5 | (3S)-N-((1R,2R,4S)-7-cyano-7-azabicyclo[2.2.1]heptan-2-yl)-1-(2,3-dichlorophenyl)-3-pyrrolidinecarboxamide | 378.8 | 1H NMR (600 MHz, DMSO-d6) Shift 8.27 (br d, J = 5.90 Hz, 1H), 7.20 (t, J = 8.08 Hz, 1H), 7.09 (dd, J = 1.32, 7.95 Hz, 1H), 6.96 (dd, J = 1.18, 8.36 Hz, 1H), 4.06-4.18 (m, 3H), 3.19-3.35 (m, 3H), 3.04 (quin, J = 7.74 Hz, 1H), 2.90-2.97 (m, 1H), 2.09-2.21 (m, 2H), 2.02 (qd, J = 7.74, 12.13 Hz, 1H), 1.76-1.89 (m, 2H), 1.56-1.72 (m, 2H), 1.26 (dd, J = 4.50, 12.76 Hz, 1H), 1.17 (t, J = 7.27 Hz, 1H) |
| 32-6 | (3S)-1-(2-chloro-5-(trifluoromethyl)phenyl)-N-((1R,2R,4S)-7-cyano-7-azabicyclo[2.2.1]heptan-2-yl)-3-pyrrolidinecarboxamide | 413 | 1H NMR (600 MHz, DMSO-d6) Shift 8.29 (br d, J = 6.18 Hz, 1H), 7.53 (d, J = 8.17 Hz, 1H), 7.07-7.15 (m, 2H), 4.08-4.16 (m, 3H), 3.49-3.63 (m, 3H), 3.32-3.43 (m, 1H), 3.06 (quin, J = 7.65 Hz, 1H), 2.11-2.21 (m, 2H), 2.03 (qd, J = 7.91, 12.07 Hz, 1H), 1.78-1.88 (m, 2H), 1.56-1.72 (m, 2H), 1.27 (dd, J = 4.59, 12.76 Hz, 1H) |

| Ex # | Name | MS data | 1H NMR |
|---|---|---|---|
| 33-1-1 | (1R,4R,5R)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | 390.8 | 1H NMR (500 MHz, CHLOROFORM-d) Shift 6.77 (t, J = 1.69 Hz, 1H), 6.65 (d, J = 1.69 Hz, 2H), 5.96 (br d, J = 4.67 Hz, 1H), 4.32-4.39 (m, 2H), 4.09 (t, J = 5.00 Hz, 1H), 3.85 (t, J = 9.86 Hz, 1H), 3.33-3.45 (m, 2H), 3.02-3.08 (m, 1H), 2.46-2.54 (m, 1H), 2.04-2.13 (m, 1H), 1.83-1.98 (m, 2H), 1.61 (ddd, J = 4.35, 8.66, 12.55 Hz, 2H), 1.08 (dd, J = 4.15, 12.85 Hz, 1H), 0.79-0.92 (m, 2H) |
| 33-1-2 | (1R,4R,5R)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | 390.8 | 1H NMR (500 MHz, CHLOROFORM-d) Shift 6.78 (t, J = 1.75 Hz, 1H), 6.66 (d, J = 1.69 Hz, 2H), 5.91 (br d, J = 4.80 Hz, 1H), 4.32-4.39 (m, 2H), 4.10 (t, J = 4.93 Hz, 1H), 3.87 (t, J = 9.93 Hz, 1H), 3.45 (dt, J = 5.71, 9.21 Hz, 1H), 3.37 (ddd, J = 2.72, 5.45, 6.49 Hz, 1H), 3.05 (dd, J = 8.95, 10.12 Hz, 1H), 2.47-2.54 (m, 1H), 2.08 (dtd, J = 3.96, 8.09, 12.31 Hz, 1H), 1.80-1.97 (m, 2H), 1.54-1.65 (m, 1H), 1.54-1.64 (m, 1H), 1.09 (dd, J = 4.22, 12.91 Hz, 1H), 0.91 (td, J = 5.69, 8.21 Hz, 1H), 0.79 (dt, J = 2.66, 5.42 Hz, 1H) |
| 1-67-1 | (3R)-6-chloro-N-((1R,2R,4S)-7-cyano-7-azabicyclo[2.2.1]heptan-2-yl)-2,3,4,9-tetrahydro-1H-carbazole-3-carboxamide | 369.1 | 1H NMR (DMSO-d6) δ: 10.82 (s, 1H), 8.13 (br d, J = 6.0 Hz, 1H), 7.31 (d, J = 1.7 Hz, 1H), 7.16 (d, J = 8.5 Hz, 1H), 6.89 (dd, J = 8.5, 2.0 Hz, 1H), 4.00-4.10 (m, 3H), 2.62-2.76 (m, 3H), 2.47-2.59 (m, 2H), 2.03-2.17 (m, 1H), 1.89-2.00 (m, 1H), 1.77-1.84 (m, 1H), 1.69-1.77 (m, 2H), 1.55-1.64 (m, 1H), 1.48-1.55 (m, 1H), 1.20 (dd, J = 12.7, 4.4 Hz, 1H) |
| 12-2-1 | (1S,3S)-N-((1R,2R,4S)-7-cyano-7-azabicyclo[2.2.1]heptan-2-yl)-3-(2,5-dichlorophenyl)cyclopentanecarboxamide | 378.0 | 1H NMR (DMSO-d6) δ: 8.13 (br d, J = 6.0 Hz, 1H), 7.52 (d, J = 2.5 Hz, 1H), 7.45 (d, J = 8.5 Hz, 1H), 7.30 (dd, J = 8.5, 2.5 Hz, 1H), 4.06-4.15 (m, 3H), 3.34-3.45 (m, 1H), 2.79-2.86 (m, 1H), 2.12-2.24 (m, 2H), 1.98-2.06 (m, 1H), 1.85-1.94 (m, 2H), 1.71-1.85 (m, 3H), 1.62-1.71 (m, 2H), 1.56-1.62 (m, 1H), 1.25 (dd, J = 12.7, 4.5 Hz, 1H) |
| 12-2-2 | (1R,3R)-N-((1R,2R,4S)-7-cyano-7-azabicyclo[2.2.1]heptan-2-yl)-3-(2,5-dichlorophenyl)cyclopentanecarboxamide | 378.0 | 1H NMR (DMSO-d6) δ: 8.10 (br d, J = 6.0 Hz, 1H), 7.45 (d, J = 8.5 Hz, 1H), 7.43 (d, J = 2.5 Hz, 1H), 7.30 (dd, J = 8.5, 2.6 Hz, 1H), 4.06-4.14 (m, 3H), 3.45-3.59 (m, 1H), 2.86-2.93 (m, 1H), 2.12-2.20 (m, 2H), 2.00-2.11 (m, 2H), 1.71-1.85 (m, 4H), 1.61-1.71 (m, 2H), 1.53-1.61 (m, 1H), 1.24 (dd, J = 12.7, 4.5 Hz, 1H) |
| 12-2-3 | (1S,3R)-N-((1R,2R,4S)-7-cyano-7-azabicyclo[2.2.1]heptan-2-yl)-3-(2,5-dichlorophenyl)cyclopentanecarboxamide | 378.0 | 1H NMR (DMSO-d6) δ: 8.12 (br d, J = 5.7 Hz, 1H), 7.52 (d, J = 2.5 Hz, 1H), 7.45 (d, J = 8.5 Hz, 1H), 7.30 (dd, J = 8.5, 2.5 Hz, 1H), 4.06-4.14 (m, 3H), 2.79-2.86 (m, 1H), 2.12-2.28 (m, 2H), 1.97-2.05 (m, 1H), 1.83-1.97 (m, 2H), 1.75-1.83 (m, 2H), 1.53-1.75 (m, 4H), 1.25 (dd, J = 12.6, 4.1 Hz, 1H) |
| 15-15-2 | (5R)-N-((1R,2R,4S)-7-cyano-7-azabicyclo[2.2.1]heptan-2-yl)-1-(6-(1,1-difluoroethyl)-2-pyridinyl)-4,5,6,7-tetrahydro-1H-indazole-5-carboxamide | 427.2 | 1H NMR (DMSO-d6) δ: 8.17 (br d, J = 5.9 Hz, 1H), 8.11 (t, J = 7.9 Hz, 1H), 8.00 (d, J = 8.3 Hz, 1H), 7.62 (s, 1H), 7.58 (d, J = 7.5 Hz, 1H), 4.09-4.16 (m, 3H), 3.35 (br s, 2H), 3.01-3.10 (m, 1H), 2.65-2.77 (m, 1H), 2.55-2.63 (m, 2H), 2.13-2.22 (m, 1H), 2.07-2.11 (m, 1H), 1.97-2.07 (m, 1H), 1.72-1.88 (m, 3H), 1.63-1.69 (m, 1H), 1.51-1.63 (m, 1H), 1.19-1.34 (m, 2H) |
| 15-16-2 | (5R)-N-((1R,2R,4S)-7-cyano-7-azabicyclo[2.2.1]heptan-2-yl)-1-(6-(difluoromethoxy)-2-pyridinyl)-4,5,6,7-tetrahydro-1H-indazole-5-carboxamide | 429.0 | 1H NMR (DMSO-d6) δ: 8.18 (br d, J = 5.9 Hz, 1H), 8.04 (t, J = 8.0 Hz, 1H), 7.66-7.72 (m, 1H), 7.61 (s, 1H), 6.95 (d, J = 8.0 Hz, 1H), 4.08-4.16 (m, 3H), 3.34 (br s, 1H), 2.99-3.08 (m, 1H), 2.70 (br dd, J = 14.8, 4.6 Hz, 1H), 2.55-2.62 (m, 2H), 2.14-2.22 (m, 1H), 2.03-2.11 (m, 1H), 1.70-1.88 (m, 3H), 1.57-1.69 (m, 2H), 1.22-1.32 (m, 2H) |
| 15-16-3 | (5S)-N-((1R,2R,4S)-7-cyano-7-azabicyclo[2.2.1]heptan-2-yl)-2-(6-(1-cyanocyclopropyl)-2-pyridinyl)-4,5,6,7-tetrahydro-2H-indazole-5-carboxamide | 428.0 | 1H NMR (DMSO-d6) δ: 8.30 (s, 1H), 8.22 (br d, J = 6.2 Hz, 1H), 7.92-7.98 (m, 1H), 7.69 (d, J = 8.2 Hz, 1H), 7.40-7.44 (m, 1H), 4.07-4.17 (m, 3H), 2.77-2.82 (m, 1H), 2.61-2.76 (m, 3H), 2.52-2.58 (m, 1H), 2.14-2.22 (m, 1H), 2.04 (br d, J = 9.5 Hz, 1H), 1.71-1.87 (m, 7H), 1.64-1.69 (m, 1H), 1.55-1.64 (m, 1H), 1.22-1.31 (m, 1H) |
| 15-15-3 | (5S)-N-((1R,2R,4S)-7-cyano-7-azabicyclo[2.2.1]heptan-2-yl)-2-(6-(1,1-difluoroethyl)-2-pyridinyl)-4,5,6,7-tetrahydro-2H-indazole-5-carboxamide | 427.2 | 1H NMR (DMSO-d6) δ: 8.38 (s, 1H), 8.23 (d, J = 6.0 Hz, 1H), 8.09 (t, J = 7.9 Hz, 1H), 7.93 (d, J = 8.3 Hz, 1H), 7.55 (d, J = 7.6 Hz, 1H), 4.07-4.17 (m, 3H), 2.73-2.89 (m, 2H), 2.62-2.71 (m, 2H), 2.52-2.60 (m, 2H), 2.14-2.22 (m, 1H), 2.04-2.09 (m, 3H), 1.73-1.89 (m, 3H), 1.63-1.70 (m, 1H), 1.57-1.63 (m, 1H), 1.28 (dd, J = 12.8, 4.5 Hz, 1H) |

| Ex # | Name | MS data | 1H NMR |
|---|---|---|---|
| 15-16-3 | (5S)-N-((1R,2R,4S)-7-cyano-7-azabicyclo[2.2.1]heptan-2-yl)-2-(6-(difluoromethoxy)-2-pyridinyl)-4,5,6,7-tetrahydro-2H-indazole-5-carboxamide | 429.0 | 1H NMR (DMSO-d6) δ: 8.41 (s, 1H), 8.21 (br d, J = 6.1 Hz, 1H), 8.01 (t, J = 8.0 Hz, 1H), 7.94 (s, 1H), 7.60 (d, J = 8.0 Hz, 1H), 6.91 (d, J = 8.0 Hz, 1H), 4.09-4.15 (m, 3H), 2.75-2.92 (m, 2H), 2.59-2.70 (m, 2H), 2.55 (tdd, J = 11.2, 5.2, 2.4 Hz, 1H), 2.14-2.22 (m, 1H), 2.00-2.10 (m, 1H), 1.72-1.89 (m, 3H), 1.57-1.70 (m, 2H), 1.22-1.32 (m, 1H) |
| 15-15-4 | (5R)-N-((1R,2R,4S)-7-cyano-7-azabicyclo[2.2.1]heptan-2-yl)-2-(6-(1,1-difluoroethyl)-2-pyridinyl)-4,5,6,7-tetrahydro-2H-indazole-5-carboxamide | 427.2 | 1H NMR (DMSO-d6) δ: 8.39 (s, 1H), 8.21 (br d, J = 6.0 Hz, 1H), 8.09 (t, J = 8.0 Hz, 1H), 7.93 (d, J = 8.3 Hz, 1H), 7.55 (d, J = 7.5 Hz, 1H), 4.09-4.16 (m, 3H), 2.74-2.91 (m, 2H), 2.52-2.68 (m, 4H), 2.14-2.22 (m, 1H), 2.02-2.07 (m, 3H), 1.73-1.88 (m, 3H), 1.52-1.70 (m, 2H), 1.27 (dd, J = 12.6, 4.3 Hz, 1H) |
| 15-16-4 | (5R)-N-((1R,2R,4S)-7-cyano-7-azabicyclo[2.2.1]heptan-2-yl)-2-(6-(difluoromethoxy)-2-pyridinyl)-4,5,6,7-tetrahydro-2H-indazole-5-carboxamide | 429.0 | 1H NMR (DMSO-d6) δ: 8.40 (s, 1H), 8.23 (d, J = 6.1 Hz, 1H), 8.01 (t, J = 8.0 Hz, 1H), 7.94 (t, J = 74.0 Hz, 1H), 7.60 (d, J = 8.0 Hz, 1H), 6.91 (d, J = 8.0 Hz, 1H), 4.07-4.17 (m, 3H), 2.73-2.83 (m, 2H), 2.62-2.71 (m, 2H), 2.53-2.60 (m, 1H), 2.14-2.21 (m, 1H), 2.01-2.09 (m, 1H), 1.73-1.88 (m, 3H), 1.57-1.70 (m, 2H), 1.22-1.31 (m, 1H) |
| 15-17-4 | (5R)-N-((1R,2R,4S)-7-cyano-7-azabicyclo[2.2.1]heptan-2-yl)-2-(6-(difluoromethyl)-2-pyridinyl)-4,5,6,7-tetrahydro-2H-indazole-5-carboxamide | 413.0 | 1H NMR (DMSO-d6) δ: 8.32 (s, 1H), 8.23 (d, J = 6.3 Hz, 1H), 8.11 (t, J = 8.0 Hz, 1H), 7.97 (d, J = 8.3 Hz, 1H), 7.55 (d, J = 7.4 Hz, 1H), 6.96 (t, J = 54.8 Hz, 1H), 4.08-4.15 (m, 3H), 2.73-2.86 (m, 2H), 2.62-2.71 (m, 2H), 2.54-2.60 (m, 1H), 2.15-2.21 (m, 1H), 2.03-2.09 (m, 1H), 1.75-1.88 (m, 3H), 1.63-1.71 (m, 1H), 1.57-1.63 (m, 1H), 1.28 (dd, J = 12.6, 4.6 Hz, 1H) |
| 17-1 | 7-chloro-N-((1R,2R,4S)-7-cyano-7-azabicyclo[2.2.1]heptan-2-yl)-2,3-dihydro-benzo[f][1,4]oxazepine-4(5H)-carboxamide | 347.0 | 1H NMR (DMSO-d6) δ: 7.41 (d, J = 2.4 Hz, 1H), 7.22 (dd, J = 8.5, 2.6 Hz, 1H), 6.98 (d, J = 8.6 Hz, 1H), 6.56 (br d, J = 5.1 Hz, 1H), 4.54 (d, J = 15.7 Hz, 1H), 4.46 (d, J = 15.7 Hz, 1H), 4.03-4.11 (m, 2H), 3.89-4.03 (m, 3H), 3.76-3.84 (m, 1H), 3.61-3.69 (m, 1H), 2.04-2.12 (m, 1H), 1.69-1.78 (m, 1H), 1.52-1.61 (m, 2H), 1.45-1.52 (m, 1H), 1.36 (dd, J = 12.6, 4.7 Hz, 1H) |
| 18-1 | 7-chloro-N-((1R,2R,4S)-7-cyano-7-azabicyclo[2.2.1]heptan-2-yl)-1,2,3,5-tetrahydro-4H-1,4-benzodiazepine-4-carboxamide | 346.0 | 1H NMR (DMSO-d6) δ: 7.25 (br s, 1H), 7.03 (dd, J = 8.5, 1.7 Hz, 1H), 6.80 (d, J = 8.1 Hz, 1H), 6.40 (br d, J = 5.2 Hz, 1H), 5.71 (br s, 1H), 4.41 (d, J = 15.6 Hz, 1H), 4.32 (d, J = 15.6 Hz, 1H), 4.03-4.08 (m, 1H), 4.01 (t, J = 4.5 Hz, 1H), 3.94 (br dd, J = 10.5, 4.8 Hz, 1H), 3.61 (td, J = 6.7, 4.2 Hz, 1H), 3.39-3.48 (m, 1H), 3.04-3.11 (m, 1H), 2.97-3.04 (m, 1H), 2.05-2.12 (m, 1H), 1.70-1.77 (m, 1H), 1.59-1.66 (m, 1H), 1.52-1.58 (m, 1H), 1.46-1.52 (m, 1H), 1.37 (dd, J = 12.6, 4.6 Hz, 1H) |
| 19-1 | 1-(6-acetamido-2-pyridinyl)-6-chloro-N-((1R,2R,4S)-7-cyano-7-azabicyclo[2.2.1]heptan-2-yl)-1H-indazole-5-carboxamide | 450.0 | 1H NMR (DMSO-d6) δ: 10.68-10.74 (m, 1H), 9.14 (s, 1H), 8.82-8.87 (m, 1H), 8.53 (s, 1H), 8.02 (s. 1H), 7.93-8.00 (m, 2H), 7.67-7.71 (m, 1H), 4.26-4.33 (m, 2H), 4.17 (t, J = 4.8 Hz, 1H), 2.11-2.36 (m, 4H), 2.00-2.10 (m, 1H), 1.80-1.87 (m, 1H), 1.70-1.79 (m, 1H), 1.61 (ddd, J = 12.1, 8.9, 3.6 Hz, 1H), 1.41 (dd, J = 12.7, 4.0 Hz, 1H) |
| 21-1-1 | (5R)-N-((1R,2R,4S)-7-cyano-7-azabicyclo[2.2.1]heptan-2-yl)-1-(6-methyl-2-pyridinyl)-4,5,6,7-tetrahydro-1H-indazole-5-carboxamide | 377.0 | 1H NMR (CHLOROFORM-d) δ: 7.59-7.75 (m, 2H), 7.47 (br s, 1H), 6.96-7.09 (m, 1H), 5.92 (br s, 1H), 4.34 (br s, 2H), 4.05 (br s, 1H), 3.36 (br d, J = 13.2 Hz, 1H), 3.20 (br s, 1H), 2.73 (br s, 2H), 2.54 (br s, 3H), 2.45 (br s, 1H), 2.26 (br s, 1H), 2.04 (br s, 2H), 1.82-1.97 (m, 2H), 1.77 (br s, 1H), 1.57 (br s, 1H), 1.07 (br d, J = 9.7 Hz, 1H) |
| 21-1-2 | (5S)-N-((1R,2R,4S)-7-cyano-7-azabicyclo[2.2.1]heptan-2-yl)-1-(6-methyl-2-pyridinyl)-4,5,6,7-tetrahydro-1H-indazole-5-carboxamide | 377.0 | 1H NMR (CHLOROFORM-d) δ: 7.63-7.70 (m, 2H), 7.48 (s, 1H), 7.03 (br d, J = 6.9 Hz, 1H), 5.88 (br s, 1H), 4.29-4.37 (m, 2H), 4.05 (br t, J = 4.3 Hz, 1H), 3.36 (br d, J = 16.9 Hz, 1H), 3.14-3.22 (m, 1H), 2.74-2.78 (m, 1H), 2.54 (s, 3H), 2.44 (br s, 1H), 2.29 (br s, 1H), 2.05 (br s, 2H), 1.95 (br s, 1H), 1.83-1.91 (m, 1H), 1.76-1.83 (m, 1H), 1.51-1.62 (m, 2H), 1.05 (br d, J = 10.8 Hz, 1H) |
| 21-1-3 | (5R)-N-((1R,2R,4S)-7-cyano-7-azabicyclo[2.2.1]heptan-2-yl)-2-(6-methyl-2-pyridinyl)-4,5,6,7-tetrahydro-2H-indazole-5-carboxamide | 377.0 | 1H NMR (CHLOROFORM-d) δ: 8.36 (s, 1H), 7.64-7.70 (m, 2H), 7.00 (d, J = 6.2 Hz, 1H), 5.63 (br d, J = 4.9 Hz, 1H), 4.31-4.41 (m, 2H), 4.06 (t, J = 4.9Hz, 1H), 2.92-3.02 (m, 1H), 2.85-2.91 (m, 2H), 2.78 (ddd, J = 16.7, 11.3, 5.7 Hz, 1H), 2.55 (s, 3H), 2.11-2.22 (m, 1H), 1.97-2.10 (m, 2H), 1.74-1.96 (m, 3H), 1.56 (tt, J = 8.5, 4.4 Hz, 2H), 1.02 (dd, J = 12.8, 4.4 Hz, 1H) |

| Ex # | Name | MS data | 1H NMR |
|---|---|---|---|
| 21-1-4 | (5S)-N-((1R,2R,4S)-7-cyano-7-azabicyclo[2.2.1]heptan-2-yl)-2-(6-methyl-2-pyridinyl)-4,5,6,7-tetrahydro-2H-indazole-5-carboxamide | 377.0 | 1H NMR (CHLOROFORM-d) δ: 8.34 (s, 1H), 7.64-7.68 (m, 2H), 7.00 (dd, J = 5.5, 2.8 Hz, 1H), 5.62 (br s, 1H), 4.33-4.39 (m, 2H), 4.06 (t, J = 4.9 Hz, 1H), 2.94-2.99 (m, 1H), 2.84-2.92 (m, 2H), 2.77 (ddd, J = 16.7, 11.2, 5.8 Hz, 1H), 2.54 (s, 3H), 2.18 (br d, J = 13.1 Hz, 1H), 1.99-2.08 (m, 2H), 1.91 (br t, J = 12.7 Hz, 1H), 1.79 (ddd, J = 13.3, 8.9, 4.5 Hz, 1H), 1.51-1.61 (m, 3H), 1.02 (dd, J = 12.8, 4.0 Hz, 1H) |
| 21-2-3 | (5S)-N-((1R,2R,4S)-7-cyano-7-azabicyclo[2.2.1]heptan-2-yl)-2-(6-cyclopropyl-2-pyridinyl)-4,5,6,7-tetrahydro-2H-indazole-5-carboxamide | 403.2 | 1H NMR (DMSO-d6) δ: 8.27 (s, 1H), 8.22 (d, J = 6.1 Hz, 1H), 7.74 (t, J = 7.8 Hz, 1H), 7.52 (d, J = 8.3 Hz, 1H), 7.17 (d, J = 7.6 Hz, 1H), 4.07-4.17 (m, 3H), 2.74-2.82 (m, 2H), 2.57-2.70 (m, 2H), 2.53-2.55 (m, 1H), 2.14-2.21 (m, 1H), 2.08-2.14 (m, 1H), 1.98-2.06 (m, 1H), 1.78-1.88 (m, 2H), 1.74 (qd, J = 12.3, 5.3 Hz, 1H), 1.62-1.70 (m, 1H), 1.56-1.62 (m, 1H), 1.22-1.31 (m, 1H), 0.95-1.02 (m, 4H) |
| 21-2-4 | (5R)-N-((1R,2R,4S)-7-cyano-7-azabicyclo[2.2.1]heptan-2-yl)-2-(6-cyclopropyl-2-pyridinyl)-4,5,6,7-tetrahydro-2H-indazole-5-carboxamide | 403.2 | 1H NMR (DMSO-d6) δ: 8.21-8.28 (m, 2H), 7.70-7.77 (m, 1H), 7.48-7.57 (m, 1H), 7.12-7.20 (m, 1H), 4.07-4.18 (m, 3H), 2.70-2.83 (m, 2H), 2.59-2.70 (m, 2H), 2.53-2.57 (m, 1H), 2.00-2.22 (m, 3H), 1.56-1.89 (m, 5H), 1.22-1.31 (m, 1H), 0.94-1.04 (m, 4H) |
| 20-77 | N-((1R,2R,4S)-7-cyano-7-azabicyclo[2.2.1]heptan-2-yl)-3-(2-methylpropoxy)-4-(3-methyl-1H-pyrazol-1-yl)benzamide | 394.0 | 1H NMR (500 MHz, CHLOROFORM-d6) δ ppm 1.04 (d, J = 6.75 Hz, 17H) 1.15-1.37 (m, 5H) 1.59-1.69 (m, 3H) 1.87-2.00 (m, 6H) 2.02-2.21 (m, 6H) 2.26 (s, 1H) 2.31-2.40 (m, 13H) 2.45 (s, 1H) 2.49-2.57 (m, 3H) 3.78 (s, 1H) 3.90 (s, 3H) 3.91 (s, 3H) 4.11 (t, J = 4.93 Hz, 3H) 4.41-4.55 (m, 6H) 5.31 (s, 1H) 6.04 (d, J = 10.14 Hz, 1H) 6.09 (s, 1H) 6.17 (s, 1H) 6.25 (d, J = 2.34 Hz, 3H) 6.37 (br d, J = 4.67 Hz, 3H) 7.24-7.31 (m, 5H) 7.49 (d, J = 1.95 Hz, 2H) 7.58 (d, J = 1.82 Hz, 3H) 7.89 (d, J = 8.30 Hz, 3H) 8.18 (d, J = 2.47 Hz, 3H) |

The following examples were purified via chiral chromatography by the method given:

| Ex # | Name | Chiral Purification Conditions |
|---|---|---|
| 1-68-2 | (3S)-6-chloro-N-((1R,2R,4S)-7-cyano-7-azabicyclo[2.2.1]heptan-2-yl)-2,3,4,9-tetrahydro-1H-carbazole-3-carboxamide | SFC = Chiralpak IC 2 × 25 cm, 5 um column (35% methanol, 80 mL/min) |
| 2-24-1 | 2-chloro-N-((1R,2R,4S)-7-cyano-7-azabicyclo[2.2.1]heptan-2-yl)-4-((3R)-3-cyano-3-methyl-2,3-dihydro-1H-inden-5-yl)benzamide | SFC Method: Chiralpak AD-H (250 × 21 mm, 5 μm); mobile phase: 60:40 (A:B), A = liquid CO2, B = methanol, flow rate: 70 ml/min; 20 mg/injection |
| 2-24-2 | 2-chloro-N-((1R,2R,4S)-7-cyano-7-azabicyclo[2.2.1]heptan-2-yl)-4-((3S)-3-cyano-3-methyl-2,3-dihydro-1H-inden-5-yl)benzamide | SFC Method: Chiralpak AD-H (250 × 21 mm, 5 μm); mobile phase: 60:40 (A:B), A = liquid CO2, B = methanol, flow rate: 70 ml/min; 20 mg/injection |
| 2-27-2 | (1S,6R,7R)-N-((1R,2R,4S)-7-cyano-7-azabicyclo[2.2.1]heptan-2-yl)-3-(3,5-dichlorophenyl)-3-azabicyclo[4.1.0]heptane-7-carboxamide | SFC Method: ChiralPak AD-H (250 × 21 mm, 5 μm); mobile phase: 70:30 (A:B), A = liquid CO2, B = methanol, flow rate: 100 mL/min; 25 mg/injection |
| 2-27-1 | (1R,6S,7R)-N-((1R,2R,4S)-7-cyano-7-azabicyclo[2.2.1]heptan-2-yl)-3-(3,5-dichlorophenyl)-3-azabicyclo[4.1.0]heptane-7-carboxamide | SFC Method: ChiralPak AD-H (250 × 21 mm, 5 μm); mobile phase: 70:30 (A:B), A = liquid CO2, B = methanol, flow rate: 100 mL/min; 25 mg/injection |
| 2-31-2 | (1S,5S)-N-((1R,2R,4S)-7-cyano-7-azabicyclo[2.2.1]heptan-2-yl)-3-(3,5-dichlorophenyl)-3-azabicyclo[3.1.0]hexane-1-carboxamide | Chiralpak AD-H (150 × 4.6 mm, 5 μm); mobile phase: 70:30 (A:B), A = liquid CO2, B = methanol, flow rate: 120 ml/min; Sample load: 100 mg/4 mL, 25 mg/injection |
| 2-31-2 | (1R,5R)-N-((1R,2S,4S)-7-cyano-7-azabicyclo[2.2.1]heptan-2-yl)-3-(3,5-dichlorophenyl)-3-azabicyclo[3.1.0]hexane-1-carboxamide | Chiralpak AD-H (150 × 4.6 mm, 5 μm); mobile phase: 70:30 (A:B), A = liquid CO2, B = methanol, flow rate: 120 ml/min; Sample load: 100 mg/4 mL, 25 mg/injection |
| 2-39-1 | 2-chloro-N-((1R,2R,4S)-7-cyano-7-azabicyclo[2.2.1]heptan-2-yl)-4-((3S)-3-cyano-1-piperidinyl)benzamide | SFC Method: ChiralPak AD-H (250 × 21 mm, 5 μm); mobile phase: 60:40 (A:B), A = liquid CO2, B = methanol, flow rate: 80 ml/min; 40 mg/injection |

-continued

| Ex # | Name | Chiral Purification Conditions |
|---|---|---|
| 2-39-2 | 2-chloro-N-((1R,2R,4S)-7-cyano-7-azabicyclo[2.2.1]heptan-2-yl)-4-((3R)-3-cyano-1-piperidinyl)benzamide | SFC Method: ChiralPak AD-H (250 × 21 mm, 5 μm); mobile phase: 60:40 (A:B), A = liquid $CO_2$, B = methanol, flow rate: 80 ml/min; 40 mg/injection |
| 2-43-1 | 2-chloro-N-((1R,2R,4S)-7-cyano-7-azabicyclo[2.2.1]heptan-2-yl)-4-((1S,2S,5R)-2-cyano-6-azabicyclo[3.2.1]octan-6-yl)benzamide | SFC Method: ChiralPak AD-H (250 × 21 mm, 5 μm); mobile phase: 60:40 (A:B), A = liquid $CO_2$, B = methanol, flow rate: 80 ml/min; 40 mg/injection |
| 2-46-2 | (2S)-N-((1R,2R,4S)-7-cyano-7-azabicyclo[2.2.1]heptan-2-yl)-1-(3,5-dichlorobenzyl)-2-azetidinecarboxamide | SFC Method: Chiralpak AS-H (250 × 30 mm, 5 μm); mobile phase: 85:15 (A:B), A = liquid $CO_2$, B = methanol, flow rate: 3 ml/min; Sample load: 80 mg/12 mL, 4 mL/injection |
| 2-46-3 | (2R)-N-((1R,2R,4S)-7-cyano-7-azabicyclo[2.2.1]heptan-2-yl)-1-(3,5-dichlorobenzyl)-2-azetidinecarboxamide | SFC Method: Chiralpak AS-H (250 × 30 mm, 5 μm); mobile phase: 85:15 (A:B), A = liquid $CO_2$, B = methanol, flow rate: 3 ml/min; Sample load: 80 mg/12 mL, 4 mL/injection |
| 2-48-1 | 2-chloro-N-((1R,2R,4S)-7-cyano-7-azabicyclo[2.2.1]heptan-2-yl)-4-((3S)-3-(cyanomethyl)-1-pyrrolidinyl)benzamide | SFC Method: Chiralpak IG (250 × 30 mm, 5μ); mobile phase: 60:40 (A:B), A = liquid $CO_2$, B = methanol, flow rate: 4 ml/min; Sample load: 150 mg/30 mL (THF:MeOH = 1:1), 8 mL/injection |
| 2-48-2 | 2-chloro-N-((1R,2R,4S)-7-cyano-7-azabicyclo[2.2.1]heptan-2-yl)-4-((3R)-3-(cyanomethyl)-1-pyrrolidinyl)benzamide | SFC Method: Chiralpak IG (250 × 30 mm, 5μ); mobile phase: 60:40 (A:B), A = liquid $CO_2$, B = methanol, flow rate: 4 ml/min; Sample load: 150 mg/30 mL (THF:MeOH = 1:1), 8 mL/injection |
| 2-43-2 | 2-chloro-N-((1R,2R,4S)-7-cyano-7-azabicyclo[2.2.1]heptan-2-yl)-4-((2R)-2-cyano-6-azabicyclo[3.2.1]octan-6-yl)benzamide | SFC Method: X-select C-18 (250 × 19 mm, 5 μm); mobile phase: 0.1% ammonia in water: ACN, flow rate: 1 ml/min; Sample load: 20 mg/1 mL, 0.25 mL/injection |
| 2-61-2 | 2-chloro-N-((1R,2R,4S)-7-cyano-7-azabicyclo[2.2.1]heptan-2-yl)-4-((3S)-3-(cyanomethyl)-1-piperidinyl)benzamide | SFC Method: Lux C-4 (250 × 50 mm, 5μ); mobile phase: 50:50 (A:B), A = liquid $CO_2$, B = methanol, flow rate: 180 ml/min; Sample load: 90 mg/10 mL, 5 mL/injection, 19 min runtime. |
| 2-61-1 | 2-chloro-N-((1R,2R,4S)-7-cyano-7-azabicyclo[2.2.1]heptan-2-yl)-4-((3R)-3-(cyanomethyl)-1-piperidinyl)benzamide | SFC Method: Lux C-4 (250 × 50 mm, 5μ); mobile phase: 50:50 (A:B), A = liquid $CO_2$, B = methanol, flow rate: 180 ml/min; Sample load: 90 mg/10 mL, 5 mL/injection, 19 min runtime. |
| 7-13-2 | N-((1R,2R,4S)-7-cyano-7-azabicyclo[2.2.1]heptan-2-yl)-N-methyl-1-(2,3,5-trichlorophenyl)-L-prolinamide | SFC Method: Chiralpak AS-H (250 × 21 mm, 5 μm); mobile phase: 85:15 (A:B), A = liquid $CO_2$, B = methanol, flow rate: 120 ml/min; Sample load: 80 mg/10 mL, 3 mL/injection |
| 7-13-1 | N-((1R,2R,4S)-7-cyano-7-azabicyclo[2.2.1]heptan-2-yl)-N-methyl-1-(2,3,5-trichlorophenyl)-D-prolinamide | SFC Method: Chiralpak AS-H (250 × 21 mm, 5 μm); mobile phase: 85:15 (A:B), A = liquid $CO_2$, B = methanol, flow rate: 120 ml/min; Sample load: 80 mg/10 mL, 3 mL/injection |
| 15-12-2 | (1S,4R,5S)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | SFC Method: Column: Chiralpak AS-H (250 × 30 mm, 5μ); mobile phase: 70:30 (A:B), A = liquid $CO_2$, B = methanol, flow rate: 100 ml/min; Sample load: 50 mg/7 mL injection |
| 15-12-1 | (1S,4S,5S)-N-((1R,2R,4S)-7-cyano-7-azabicyclo[2.2.1]heptan-2-yl)-2-(3,5-dichlorophenyl)-2-azabicyclo[3.1.0]hexane-4-carboxamide | SFC Method: Column: Chiralpak AS-H (250 × 30 mm, 5μ); mobile phase: 70:30 (A:B), A = liquid $CO_2$, B = methanol, flow rate: 100 ml/min; Sample load: 50 mg/7 mL injection |
| 12-2-1 | (1S,3S)-N-((1R,2R,4S)-7-cyano-7-azabicyclo[2.2.1]heptan-2-yl)-3-(2,5-dichlorophenyl)cyclopentanecarboxamide | The sample was purified by SFC via an Chiralpak AY-H 2 × 25 cm, 5 μm column; a mobile phase of 30% isopropanol using a flowrate of 60 mL/min |
| 15-15-2 | (5R)-N-((1R,2R,4S)-7-cyano-7-azabicyclo[2.2.1]heptan-2-yl)-1-(6-(1,1-difluoroethyl)-2-pyridinyl)-4,5,6,7-tetrahydro-1H-indazole-5-carboxamide | The sample was purified by SFC using a Chiralpak AD-H 2 × 25 cm, 5 um column, a mobile phase of 25% methanol using a flowrate of 80 mL/min. to generate <1 mg of peak 1 with an ee of >99%, 3 mg of peak 2 with an ee of >97%, 6 mg of peak 3 with an ee of >99% and 7 mg of peak 4 with an ee of >99%. |

-continued

| Ex # | Name | Chiral Purification Conditions |
|---|---|---|
| 15-16-2 | (5R)-N-((1R,2R,4S)-7-cyano-7-azabicyclo[2.2.1]heptan-2-yl)-1-(6-(difluoromethoxy)-2-pyridinyl)-4,5,6,7-tetrahydro-1H-indazole-5-carboxamide | The sample was purified by SFC using a Chiralcel OJ-H 2 × 25 cm, 5 um column, a mobile phase of 25% methanol using a flowrate of 80 mL/min. to generate 2 mg of peak 1 with an ee of >99%, 3 mg of peak 2 with an ee of >99%, 6 mg of peak 3 with an ee of >97% and 7 mg of peak 4 with an ee of >99% |
| 15-16-3 | (5S)-N-((1R,2R,4S)-7-cyano-7-azabicyclo[2.2.1]heptan-2-yl)-2-(6-(1-cyanocyclopropyl)-2-pyridinyl)-4,5,6,7-tetrahydro-2H-indazole-5-carboxamide | The sample was purified by SFC using Chiralpak AD-H 2 × 25 cm + Chiralpak AD-H 2 × 15 cm, 5 um columns, a mobile phase of 35% methanol using a flowrate of 70 mL/min. |
| 15-17-4 | (5R)-N-((1R,2R,4S)-7-cyano-7-azabicyclo[2.2.1]heptan-2-yl)-2-(6-(difluoromethyl)-2-pyridinyl)-4,5,6,7-tetrahydro-2H-indazole-5-carboxamide | The sample was purified by SFC using a Chiralcel OJ-H 2 × 25 cm, 5 um column, a mobile phase of 30% methanol using a flowrate of 80 mL/min |

USP30 Enzymatic Assay (FP Assay)

Potency of USP30 (ubiquitin specific peptidase 30) inhibitors was measured by their inhibition of human USP30 in a catalytic biochemical assay. Purified human 6×HIS-USP30 (aa 57-517) was incubated with a K11-linked diubiquitin peptide substrate (UbiQ-044; UbiQ). On the N-terminus of the substrate is a fluorescent tag, 5-carboxytetramethylrhodamine, which allows us to measure the cleavage of the substrate by fluorescence polarization. USP30 activity was determined at room temperature in black 384-well microplates (Corning 4514; Corning) in a total reaction volume of 15 µl. Compound in DMSO was plated in a 22-point, 1:2 dose-response curve, across the 384-well plate. Wells 23 and 24 were reserved for positive (enzyme and substrate alone) and negative (substrate alone) reaction controls. Compound, enzyme, and substrate were diluted in assay buffer: 20 mM Tris pH=8.0, 100 mM NaCl, 0.005% Tween-20, and freshly thawed 1 mM DTT. All reagents were prepared at a 3× working concentration. 5 ul of compound was added to the assay plates followed by 5 ul of the enzyme solution and finally, 5 ul of substrate solution. Plates were stored in a dark, humidified environment while the reaction proceeded for 75 minutes at room temperature. To stop the reaction, 5 ul of 80 mM MES, pH=5.0 was added to the assay plates. Fluorescence polarization data was acquired on an EnVision plate reader (Perkin Elmer).

Samples were measured with an excitation wavelength of 531 nm and emission wavelengths of 595Pnm and 595Snm. Fluorescence polarization values (in milliP) were calculated by the EnVision (Perkin Elmer) operating software according to the following formula: mP value=1000*(S−G*P)/(S+G*P), where S=<detector 2 or FP TAMRA Dual(1) channel 2>, P=<detector 1 or FP TAMRA Dual(1) channel 1>, and G=G-factor. Data was then uploaded into Screener software (GeneData AG). The amount of signal generated in the presence of compounds versus that in the presence of DMSO vehicle alone (high control) was calculated using the formula: % control (POC)=(compound−average low)/(average high−average low)*100. For IC50 determinations, data was fitted using Screener based on a general 4-parameter equation (y=A+((B−A)/(1+((x/C)^D))), where A is the minimum y (POC) value, B is the maximum y (POC), C is the x (compound concentration) at the point of inflection and D is the slope factor).

USP30 Enzymatic Assay (Rhodamine Assay)

USP30 inhibition was tested with recombinant human USP30 (Boston Biochem) using the fluorescent substrate Ubiquitin-Rhodamine 110 (UBPBio) in 1536-well format. Compounds in DMSO were dispensed using a Labcyte Echo 550 (50 nl/well). 2 µl of 4 nM USP30 in 25 mM Hepes (pH 7.5) 100 mM NaCl 0.01% Triton X-100 1 mM DTT was added to each well and incubated for 2 hr at room temperature. 6 µl of 53 nM Ubiquitin-Rhodamine 110 in 25 mM Hepes (pH 7.5) 100 mM NaCl 0.01% Triton X-100 4 mM DTT 0.02% BSA was then added to each well and incubated for an additional 2 hr at room temperature. Fluorescence measurements were obtained using an Envision 2105 (Perkin Elmer) with $\lambda_{ex}$=485 nm and $\lambda_{em}$=535 nm. USP30 with DMSO and buffer alone with DMSO were used for normalization of 100% activity and 0% activity, respectively. Apparent $IC_{50}$ values were obtained using Graphpad Prism.

| Ex# | USP30 $IC_{50}$ (µM) |
|---|---|
| 1-1 | 1.3 |
| 1-2 | 55.0 |
| 1-3 | 49.7 |
| 1-4 | 0.4 |
| 1-5 | 1.4 |
| 1-6 | 1.1 |
| 1-7 | 12.5 |
| 1-8 | 1.8 |
| 1-9 | 1.0 |
| 1-10 | 7.2 |
| 1-11 | 3.6 |
| 1-12 | 3.8 |
| 1-13 | 1.3 |
| 1-14 | 5.6 |
| 1-15 | 8.4 |
| 1-16 | 5.3 |
| 1-17 | 0.4 |
| 1-18 | 16.0 |
| 1-19 | 0.5 |
| 1-20 | 0.8 |
| 1-21 | 3.5 |
| 1-22 | 10.1 |
| 1-23 | 2.3 |
| 1-24 | 1.9 |
| 1-25 | 4.3 |
| 1-26 | 8.8 |
| 1-27 | 3.3 |
| 1-28 | 0.3 |
| 1-29 | 1.4 |
| 1-30 | 3.4 |
| 1-31 | 2.7 |
| 1-32 | 1.7 |
| 1-33 | 9.1 |
| 1-34 | 2.0 |
| 1-35 | 13.6 |

| Ex# | USP30 IC$_{50}$ (μM) | Ex# | USP30 IC$_{50}$ (μM) |
|---|---|---|---|
| 1-36 | 0.1 | 13-4 | 0.2 |
| 1-37 | 1.5 | 13-5 | 0.1 |
| 1-38 | 1.1 | 13-6 | 17.2 |
| 1-39 | 0.3 | 13-7 | 28.3 |
| 1-40 | 3.6 | 13-8 | 0.5 |
| 1-41 | 2.0 | 13-9 | 15.0 |
| 1-42 | 0.7 | 13-10 | 1.3 |
| 1-43 | 0.5 | 13-11 | 2.1 |
| 1-44 | 0.4 | 13-12 | 5.8 |
| 1-45 | 1.1 | 13-13 | 0.4 |
| 1-46 | 6.0 | 13-14 | 0.2 |
| 1-47 | 5.9 | 13-15 | 2.4 |
| 1-48 | 8.2 | 13-16 | 0.4 |
| 1-49 | 6.9 | 13-17 | 2.0 |
| 1-50 | 4.7 | 13-18 | 0.6 |
| 1-51 | 1.4 | 13-19 | 8.4 |
| 1-52 | 0.1 | 13-20 | 7.9 |
| 1-53 | 0.2 | 14-1 | 11.7 |
| 1-54 | 5.7 | 14-2 | 39.0 |
| 1-55 | 1.1 | 14-3 | 17.0 |
| 1-56 | 3.1 | 14-4 | 0.1 |
| 1-57 | 0.6 | 14-5 | 1.9 |
| 1-58 | 2.1 | 15-1 | 0.1 |
| 1-59 | 0.2 | 1-65 | 0.59 |
| 1-60 | 0.9 | 1-66 | 0.279 |
| 1-61 | 1.2 | 1-68-2 | 0.02 |
| 1-62 | 0.4 | 1-69 | 2.315 |
| 1-63 | 0.7 | 1-70 | 1.623 |
| 1-64 | 0.5 | 1-71 | 0.126 |
| 2-1-2 | 0.4 | 1-72 | 1.269 |
| 3-1-2 | 12.1 | 1-73 | 0.729 |
| 4-1-4 | 19.8 | 1-74 | 2.947 |
| 4-2-1 | >66.7 | 1-75 | 0.334 |
| 4-2-2 | 26.9 | 1-76 | 0.971 |
| 4-2-3 | 19.0 | 1-77 | 0.026 |
| 4-2-4 | 14.6 | 1-78 | 4.115 |
| 5-1 | 0.2 | 1-79 | 16.4 |
| 5-2 | 0.8 | 1-80 | 18.1 |
| 5-3 | 0.9 | 1-81 | 1.194 |
| 5-4 | 8.2 | 1-82 | 9.37 |
| 5-5 | 3.2 | 1-83 | 23.9 |
| 5-6 | 0.9 | 1-84 | 28.7 |
| 5-7 | 0.3 | 1-85 | 14.5 |
| 5-8 | 16.7 | 1-86 | 29.0 |
| 5-9 | 4.1 | 1-87 | 4.113 |
| 5-10 | 0.2 | 1-88 | 0.421 |
| 5-11 | 0.1 | 1-89 | 25.9 |
| 5-12 | 0.3 | 1-90 | 2.82 |
| 5-13 | 0.3 | 1-91 | 2.083 |
| 5-14 | 0.2 | 1-92 | 3.29 |
| 5-15 | 0.7 | 1-93 | 4.35 |
| 6-1 | 0.7 | 1-94 | 0.798 |
| 6-2 | 0.9 | 1-95 | 3.883 |
| 6-3 | 8.7 | 1-96 | 6.515 |
| 7-1 | 2.1 | 1-97 | 0.061 |
| 7-2 | 2.1 | 2-2 | 2.37 |
| 8-1 | 12.1 | 2-3 | 0.716 |
| 8-2 | 22.5 | 2-4 | 14.5 |
| 9-1 | 25.8 | 2-5 | 9.8 |
| 9-2 | 0.1 | 2-6 | 31.0 |
| 9-3 | 0.4 | 2-7 | 10.5 |
| 9-4 | 1.4 | 2-8 | 36.9 |
| 9-5 | 1.2 | 2-9 | 0.245 |
| 9-6 | 35.0 | 2-10 | 0.987 |
| 9-7 | 4.7 | 2-11 | 0.253 |
| 9-8 | 43.7 | 2-12 | 3.53 |
| 9-9 | 0.5 | 2-13 | 33.868 |
| 11-2 | 0.6 | 2-14 | 0.191 |
| 11-3 | 0.8 | 2-15 | 32.415 |
| 11-4 | 0.4 | 2-16 | 0.392 |
| 11-5 | 0.7 | 2-17 | 0.108 |
| 11-6 | 0.5 | 2-18 | 0.273 |
| 11-7 | 4.8 | 2-19 | 0.157 |
| 13-1 | 0.3 | 2-20 | 0.144 |
| 13-2 | 7.1 | 2-21 | 0.062 |
| 13-3 | 0.1 | 2-22 | 1.470 |

| Ex# | USP30 IC$_{50}$ (μM) |
|---|---|
| 2-23 | 0.078 |
| 2-24-1 | 0.031 |
| 2-24-2 | 0.077 |
| 2-26 | 0.196 |
| 2-27-2 | 1.880 |
| 2-27-1 | 1.270 |
| 2-29 | 1.650 |
| 2-30 | 1.800 |
| 2-31-2 | 0.305 |
| 2-31-2 | 0.091 |
| 2-33 | 0.279 |
| 2-34 | 2.790 |
| 2-35 | 9.840 |
| 2-36 | 0.207 |
| 2-37 | 0.815 |
| 2-38 | 2.690 |
| 2-39-1 | 5.210 |
| 2-39-2 | 5.450 |
| 2-41 | 4.700 |
| 2-42 | 0.046 |
| 2-43-1 | 12.200 |
| 2-44 | 1.660 |
| 2-45 | 0.126 |
| 2-46-2 | 0.604 |
| 2-46-3 | 14.800 |
| 2-48-1 | 2.290 |
| 2-48-2 | 1.510 |
| 2-50 | 2.250 |
| 2-51 | 1.810 |
| 2-52 | 0.161 |
| 2-43-2 | 3.460 |
| 2-54 | 1.210 |
| 2-55 | 0.096 |
| 2-56 | 5.790 |
| 2-57 | 1.190 |
| 2-58 | 4.080 |
| 2-59 | 0.232 |
| 2-60 | 0.444 |
| 2-61-2 | 2.060 |
| 2-61-1 | 2.020 |
| 2-63 | 0.027 |
| 2-64 | 0.083 |
| 2-65 | 0.076 |
| 2-66 | 0.078 |
| 2-67 | 1.580 |
| 5-16 | 0.291 |
| 7-3 | 0.017 |
| 7-4 | 0.064 |
| 7-5 | 0.235 |
| 7-6 | 0.2 |
| 7-7 | 0.557 |
| 7-8 | 1.269 |
| 7-9 | 40.8 |
| 7-10 | 10.7 |
| 7-11 | 0.272 |
| 7-12 | 0.318 |
| 7-13-2 | 0.138 |
| 7-13-1 | 2.080 |
| 7-15 | 0.022 |
| 7-16 | 0.125 |
| 7-17 | 0.037 |
| 7-18 | 0.829 |
| 9-1 | 7.67 |
| 9-2 | 16.7 |
| 9-3 | 4.58 |
| 9-4 | 0.23 |
| 9-5 | 0.286 |
| 9-6 | 0.113 |
| 12-3 | 0.211 |
| 12-4 | 0.417 |
| 12-5 | 0.057 |
| 12-6 | 0.01 |
| 12-7 | 30.4 |
| 12-8 | 0.381 |
| 12-9 | 0.079 |
| 12-10 | 0.064 |
| 12-11 | 0.056 |
| 12-12 | 0.065 |
| 12-13 | 0.274 |
| 12-14 | 0.213 |
| 12-15 | 0.103 |
| 12-16 | 0.165 |
| 12-17 | 0.114 |
| 12-18 | 1.024 |
| 12-19 | 0.151 |
| 12-20 | 0.393 |
| 12-21 | 0.034 |
| 12-22 | 0.192 |
| 12-23 | 0.054 |
| 12-24 | 0.04 |
| 12-25 | 0.026 |
| 12-26 | 0.069 |
| 12-27 | 0.038 |
| 12-28 | 0.044 |
| 12-29 | 0.169 |
| 12-30 | 0.27 |
| 13-21 | 50.529 |
| 13-22 | 0.402 |
| 13-23 | 2.257 |
| 13-24 | 0.762 |
| 13-25 | 0.115 |
| 13-26 | 3.267 |
| 13-27 | 0.923 |
| 13-28 | 6.577 |
| 13-29 | 2.93 |
| 13-30 | 43.6 |
| 15-2 | 3.22 |
| 15-3 | 4.075 |
| 15-4 | 2.335 |
| 15-5 | 4.793 |
| 15-6 | 0.627 |
| 15-7 | 0.196 |
| 15-8 | 0.31 |
| 15-9 | 3.72 |
| 15-10 | 2.937 |
| 15-11 | 2.94 |
| 15-12-2 | 0.048 |
| 15-12-1 | 0.448 |
| 15-14 | 0.257 |
| 15-15 | 0.057 |
| 15-16 | 0.456 |
| 16-3 | 24.8 |
| 16-4 | 1.78 |
| 16-5 | 1.635 |
| 20-1 | 3.26 |
| 20-2 | 2.24 |
| 20-3 | 0.06 |
| 20-4 | 0.055 |
| 20-5 | 0.065 |
| 20-6 | 0.055 |
| 20-7 | 0.028 |
| 20-8 | 0.254 |
| 20-9 | 0.124 |
| 20-10 | 0.194 |
| 20-11 | 0.09 |
| 20-12 | 0.151 |
| 20-13 | 0.105 |
| 20-14 | 0.026 |
| 20-15 | 0.03 |
| 20-16 | 0.047 |
| 20-17 | 0.049 |
| 20-18 | 3.293 |
| 20-19 | 0.407 |
| 20-20 | 0.177 |
| 20-21 | 2.047 |
| 20-22 | 0.519 |
| 20-23 | 0.315 |
| 20-24 | 0.11 |
| 20-25 | 0.041 |
| 20-26 | 2.207 |
| 20-27 | 0.039 |
| 20-28 | 0.088 |

| Ex# | USP30 IC$_{50}$ (μM) |
| --- | --- |
| 20-29 | 1.105 |
| 20-30 | 0.103 |
| 20-31 | 14.9 |
| 20-32 | 0.447 |
| 20-33 | 1.438 |
| 20-34 | 0.783 |
| 20-35 | 1.655 |
| 20-36 | 0.58 |
| 20-37 | 0.703 |
| 20-38 | 0.903 |
| 20-39 | 0.254 |
| 20-40 | 0.204 |
| 20-41 | 2.41 |
| 20-42 | 3.715 |
| 20-43 | 0.247 |
| 20-44 | 0.221 |
| 20-45 | 0.241 |
| 20-46 | 0.235 |
| 20-47 | 0.094 |
| 20-48 | 0.665 |
| 20-49 | 0.027 |
| 20-50 | 0.235 |
| 20-51 | 0.353 |
| 20-52 | 0.117 |
| 20-53 | 0.252 |
| 20-54 | 0.121 |
| 20-55 | 0.201 |
| 20-56 | 0.098 |
| 20-57 | 0.479 |
| 20-58 | 1.284 |
| 20-59 | 0.921 |
| 20-60 | 3.133 |
| 20-61 | 0.86 |
| 20-62 | 1.52 |
| 20-63 | 4.03 |
| 20-64 | 0.136 |
| 20-65 | 0.345 |
| 20-66 | 37.7 |
| 20-67 | 0.192 |
| 20-68 | 0.058 |
| 20-69 | 0.39 |
| 20-70 | 0.328 |
| 20-71 | 1.593 |
| 20-72 | 0.957 |
| 20-73 | 0.311 |
| 20-74 | 0.05 |
| 20-75 | 0.209 |
| 20-76 | 0.141 |
| 22-1 | 6.285 |
| 23-1 | 0.148 |
| 23-2 | 0.121 |
| 23-3 | 0.129 |
| 23-4 | 0.486 |
| 23-5 | 0.212 |
| 23-6 | 0.114 |
| 23-7 | 0.562 |
| 23-8 | 0.118 |
| 23-9 | 0.36 |
| 24-1 | 0.114 |
| 25-1 | 2.04 |
| 25-2 | 1.482 |
| 25-3 | 0.373 |
| 26-1-1 | 9.442 |
| 26-2-1 | 1.293 |
| 26-3 | 0.175 |
| 26-4 | 1.6 |
| 26-5 | 0.194 |
| 26-6 | 2.237 |
| 27-1 | 3.533 |
| 27-2 | 0.774 |
| 27-3 | 9.381 |
| 28-1 | 0.046 |
| 28-2 | 0.054 |
| 29-1 | 0.478 |
| 29-2 | 0.81 |
| 29-3 | 0.097 |
| 29-4 | 0.294 |
| 29-5 | 0.058 |
| 29-6 | 2.09 |
| 29-7 | 0.029 |
| 30-1 | 2.663 |
| 30-2 | 5.89 |
| 30-3 | 0.88 |
| 30-4 | 0.037 |
| 30-5 | 2.155 |
| 30-6 | 0.029 |
| 30-7 | 0.025 |
| 30-8 | 0.128 |
| 30-9 | 8.575 |
| 30-10 | 0.346 |
| 30-11 | 1.95 |
| 30-12 | 0.545 |
| 30-13 | 3.59 |
| 30-14 | 0.062 |
| 30-15 | 0.35 |
| 30-16 | 0.192 |
| 30-17 | 0.054 |
| 31-1 | 5.87 |
| 31-2 | 8.87 |
| 32-1 | 0.044 |
| 32-2 | 0.135 |
| 32-3 | 3.8 |
| 32-4 | 0.133 |
| 32-5 | 0.064 |
| 32-6 | 0.139 |
| 33-1-1 | 1.52 |
| 33-1-2 | 0.062 |
| 1-67-1 | 0.294 |
| 12-2-1 | 0.135 |
| 12-2-2 | 0.324 |
| 12-2-3 | 0.025 |
| 15-15-2 | 4.417 |
| 15-16-2 | 0.701 |
| 15-16-3 | 1.76 |
| 15-15-3 | 8 |
| 15-16-3 | 0.609 |
| 15-15-4 | 0.704 |
| 15-16-4 | 2.647 |
| 15-17-4 | 13.35 |
| 17-1 | 4.16 |
| 18-1 | 0.872 |
| 19-1 | 0.152 |
| 21-1-1 | 1.98 |
| 21-1-2 | 1.84 |
| 21-1-3 | 3.39 |
| 21-1-4 | 0.904 |
| 21-2-3 | 0.52 |
| 21-2-4 | 4.26 |
| 20-77 | 0.05 |

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound or salt thereof, the compound according to the Formula (I):

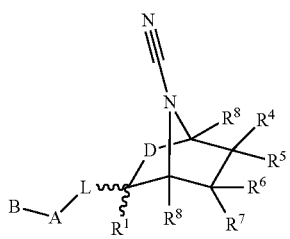

(I)

wherein
D is (CR$^1$R$^2$);
r is 1 or 2;
each of R$^1$, R$^2$, R$^3$, R$^4$, R$^5$, R$^6$ and R$^7$ is independently selected at each occurrence from hydrogen, halogen, C$_1$-C$_4$alkyl, or C$_1$-C$_4$alkoxy;
R$^8$ is independently selected from hydrogen or C$_1$-C$_4$alkyl;
L is a —C(O)N(R$^B$) wherein L is attached to the azanorbornane by the right most atom;
R$^B$ is hydrogen or C$_1$-C$_4$alkyl;
A is a divalent moiety selected from C$_2$-C$_6$alkenylene, phenylene, naphthylene, 5 to 13 member heteroarylene comprising one ring N, O or S atom and 0 or 1 additional ring nitrogen atom, or saturated or partially unsaturated 4 to 13 member monocyclic, bicyclic or tricyclic carbocycle or heterocycle comprising one ring N, O or S atom and 0, 1 or 2 additional ring nitrogen atoms, each of which is optionally substituted with 0 to 4 substituents selected from halogen, hydroxy, oxo, amino, C$_1$-C$_6$alkyl, C$_2$-C$_6$alkenyl, C$_2$-C$_6$alkynyl, C$_1$-C$_6$alkoxy, C$_3$-C$_7$cycloalkyl, C$_3$-C$_7$cycloalkoxy, C$_3$-C$_7$cycloalkylC$_1$-C$_4$alkyl, C$_3$-C$_7$cycloalkylC$_1$-C$_4$alkoxy, haloC$_1$-C$_6$alkyl, haloC$_1$-C$_6$alkoxy;
B is hydrogen, halogen, hydroxy, amino, C$_1$-C$_6$alkyl, haloC$_1$-C$_6$alkyl, hydroxyC$_1$-C$_6$alkyl, cyanoC$_1$-C$_6$alkyl, C$_2$-C$_6$alkenyl, C$_2$-C$_6$alkynyl, C$_1$-C$_6$alkoxy, haloC$_1$-C$_6$alkoxy, C$_3$-C$_7$cycloalkyl, halo C$_3$-C$_7$cycloalkyl, cyanoC$_3$-C$_7$cycloalkyl, C$_3$-C$_7$cycloalkylC$_1$-C$_6$alkyl, cyanoC$_3$-C$_7$cycloalkylC$_1$-C$_6$alkyl, C(O)C$_1$-C$_6$alkyl, C(O)C$_3$-C$_7$cycloalkyl, C(O)C$_1$-C$_6$alkoxy, C(O)C$_3$-C$_7$cycloalkyl, NR$^9$R$^{10}$, OR$^{11}$, C(O)NR$^9$R$^{10}$, N(R$^{10}$)C(O)R$^{12}$, phenyl, aralkyl, heteroaralkyl, 5, 6, 9 or 10 member heteroaryl or 4 to 8 member monocyclic or bicyclic heterocycle, wherein each heteroaryl or heterocycle has one ring N, O or S atom and 0, 1 or 2 additional ring nitrogen atoms, which phenyl, aralkyl, heteroaralkyl, heteroaryl or heterocycle is optionally substituted with 0 to 4 groups independently selected from the group consisting of halogen, hydroxy, amino, mono- and di-C$_1$-C$_6$alkylamino, cyano, C$_1$-C$_6$alkyl, C$_2$-C$_6$alkenyl, C$_2$-C$_6$alkynyl, C$_1$-C$_6$alkoxy, halo C$_1$-C$_6$alkyl, halo C$_1$-C$_6$alkoxy, C$_3$-C$_6$cycloalkyl, phenyl, 5 or 6 member heteroaryl having one ring N, O or S atom and 0, 1 or 2 additional ring nitrogen atoms, —C(O)NR$^9$R$^{10}$, C(O)R$^9$, CO$_2$R$^9$, and S(O)$_n$R$^9$, and where each heterocycle is optionally substituted with oxo;
R$^9$ is hydrogen, C$_1$-C$_6$alkyl, C$_2$-C$_6$alkenyl, C$_2$-C$_6$alkynyl, C$_1$-C$_6$alkoxy, halo C$_1$-C$_6$alkyl, halo C$_1$-C$_6$alkoxy, C$_3$-C$_6$cycloalkyl, aralkyl which aralkyl is substituted with 1 to 4 substituents independently selected from halogen, C$_1$-C$_4$alkyl, C$_3$-C$_6$cycloalkyl or 1,1-cyclopropandiyl;
R$^{10}$ is hydrogen or C$_1$-C$_6$alkyl;

R$^{11}$ is C$_3$-C$_6$cycloalkyl, phenyl or 5 or 6 member heteroaryl having one ring nitrogen atom and 0 or 1 additional ring heteroatoms selected from N, O or S, which phenyl or heteroaryl is optionally substituted with 0, 1, 2, or 3 groups independently selected from halogen, cyano, C$_1$-C$_6$alkyl, C$_2$-C$_6$alkenyl, C$_2$-C$_6$alkynyl, C$_1$-C$_6$alkoxy, halo C$_1$-C$_6$alkyl, halo C$_1$-C$_6$alkoxy, C$_3$-C$_6$cycloalkyl; and
R$^{12}$ is selected from C$_1$-C$_6$alkyl, C$_1$-C$_6$alkoxy, halo C$_1$-C$_6$alkyl, halo C$_1$-C$_6$alkoxy, C$_3$-C$_6$cycloalkyl, phenyl or 5 or 6 member heteroaryl having one ring nitrogen atom and 0 or 1 additional ring heteroatoms selected from N, O or S, which phenyl or heteroaryl is optionally substituted with 0, 1, 2, or 3 groups independently selected from halogen, hydroxy, C$_1$-C$_6$alkyl, C$_2$-C$_6$alkenyl, C$_2$-C$_6$alkynyl, C$_1$-C$_6$alkoxy, halo C$_1$-C$_6$alkyl, halo C$_1$-C$_6$alkoxy, C$_3$-C$_6$cycloalkyl.

2. The compound of claim 1, which compound is represented by Formula Ia:

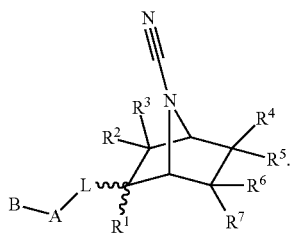

3. The compound of claim 1, wherein the azanorbornane is in endo orientation.

4. The compound of claim 1, represented by Formula II-a or II-b:

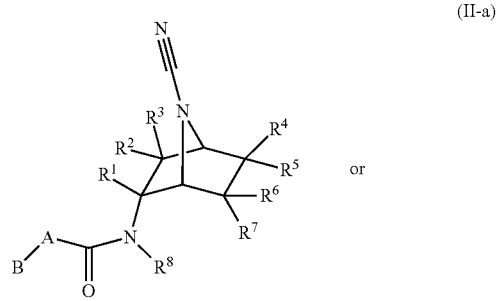

(II-a)

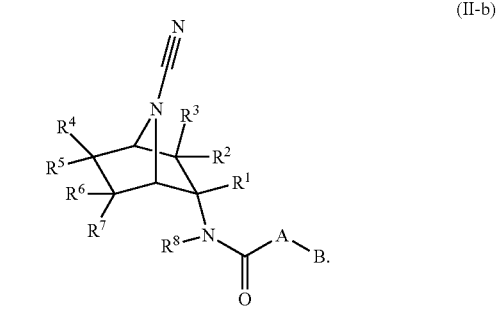

(II-b)

5. The compound of claim 1, in a form of a pharmaceutically acceptable salt.

6. A pharmaceutical composition comprising a pharmaceutically acceptable excipient, carrier or adjuvant and at least one compound of claim 1.

* * * * *